United States Patent
Ohhata et al.

(10) Patent No.: US 7,378,428 B2
(45) Date of Patent: *May 27, 2008

(54) NITROGEN-CONTAINING BICYCLIC COMPOUNDS AND DRUGS CONTAINING THE SAME AS THE ACTIVE INGREDIENT

(75) Inventors: Akira Ohhata, Mishima-gun (JP); Yoshikazu Takaoka, Mishima-gun (JP); Mikio Ogawa, Mishima-gun (JP); Hisao Nakai, Mishima-gun (JP); Susumu Yamamoto, Mishima-gun (JP); Hiroshi Ochiai, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 231 days.

This patent is subject to a terminal disclaimer.

(21) Appl. No.: 10/502,884

(22) PCT Filed: Jan. 30, 2003

(86) PCT No.: PCT/JP03/00877

§ 371 (c)(1),
(2), (4) Date: Jul. 30, 2004

(87) PCT Pub. No.: WO03/064389

PCT Pub. Date: Aug. 7, 2003

(65) Prior Publication Data
US 2005/0222138 A1 Oct. 6, 2005

(30) Foreign Application Priority Data
Jan. 31, 2002 (JP) ............... 2002-023845
Jan. 31, 2002 (JP) ............... 2002-023846

(51) Int. Cl.
*C07D 279/16* (2006.01)
*A61K 31/5415* (2006.01)
*A61K 31/4035* (2006.01)

(52) U.S. Cl. ............ 514/307; 546/18; 546/146
(58) Field of Classification Search ......... 546/18, 546/146; 514/307
See application file for complete search history.

(56) References Cited

U.S. PATENT DOCUMENTS 6,956,033 B2 * 10/2005 Ogawa et al. ......... 514/230.5

FOREIGN PATENT DOCUMENTS

| WO | WO 00/68230 A1 | 11/2000 |
| WO | WO 01/74789 A1 | 10/2001 |
| WO | WO 02/10135 A1 | 2/2002 |
| WO | WO 01/98274 A2 | 12/2002 |

OTHER PUBLICATIONS

Nakata, Clin. Exp. Immunol. 2002 128: 460 (2002).*
Barun et al. Synlett, 2000, No. 5, 653-657.*
Glushkov et al. Chemistry of Heterocyclic Compounds, vol. 37, No. 1, 2001.*
Glushkov, V.A. et al.,, "Synthesis of Monooximies of 3,3-Dialkyl-3,4,Dihydro-1-Isoquinolyl Aryl Ketones and Diketones," Chemistry of Heterocyclic Compounds, 2001, vol. 37, No. pp. 103-108, Plenum Publishing Corporation.

* cited by examiner

Primary Examiner—Kahsay T Habte
(74) Attorney, Agent, or Firm—Sughrue Mion, PLLC

(57) ABSTRACT

A nitrogen-containing bicyclic compound of formula (I) or a pharmaceutically acceptable salt thereof (wherein the symbols have the same meanings as described in the specification).

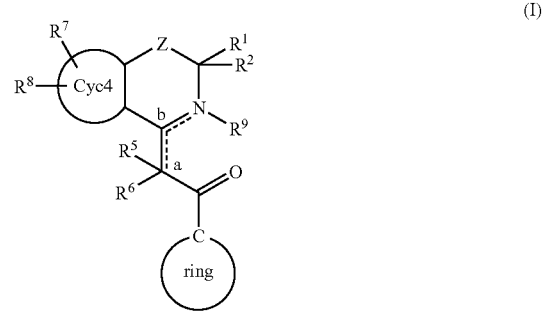

The compound of formula (I) has an inhibitory activity against PDE7 and it is useful for the prevention and/or treatment of various diseases, i.e. autoimmune diseases (ulcerative colitis, Crohn's disease, rheumatism, psoriasis, multiple sclerosis, collagenosis, etc.), inflammatory diseases (obstructive pulmonary disease, sepsis, pancreatitis, sarcoidosis, nephritis, hepatitis, enteritis, etc.), allergic diseases (asthma, allergic rhinitis, allergic conjunctivitis, seasonal conjunctivitis, atopic dermatitis, etc.), rejection of organ transplants, serious graft versus host disease (GVHD), diabetic disease, osteoporosis, bone fracture, restenosis, atherosclerosis, obesity, ischemic reperfusion injury, depression, Parkinson's disease, dementia, leukemia, etc.

9 Claims, No Drawings

NITROGEN-CONTAINING BICYCLIC COMPOUNDS AND DRUGS CONTAINING THE SAME AS THE ACTIVE INGREDIENT

TECHNICAL FIELD

The present invention relates to a nitrogen-containing bicyclic compound or a pharmacologically acceptable salt thereof and a pharmaceutical composition comprising it as active ingredient.

More specifically, the present invention relates to
(1) a compound of formula (I)

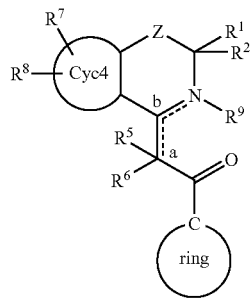

or a pharmacologically acceptable salt thereof,
(2) a method for the preparation thereof, and
(3) a pharmaceutical composition comprising it as active ingredient.

BACKGROUND ART

Cyclic nucleotides such as cyclic adenosine-3',5'-monophosphate (c-AMP) and cyclic guanosine 3',5'-monophosphate (c-GMP) are concerned with intracellular signal transduction molecules as second messengers. These cyclic nucleotides are degraded by a group of hydrolases generally called phosphodiesterase PDE isozyme) into inactive 5'-AMP and 5'-GMP, respectively.

Up to date, the presence of 11 families of PDE1 to PDE11 has been confirmed (see *Current Opinion in Cell Biology*, 12, 174-179 (2000)). PDE isozymes have differences in specificity and affinity to substrates, i.e. c-AMP and c-GMP, cell distribution and tissue distribution, etc., and each isozyme has different function in vivo.

Among these PDEs, PDE7 is a phosphodiesterase which has specific affinity to cAMP, and it is reported that it is not inhibited by rolipram, which is a PDE4 inhibitor specific to PDE4 (see *J. Biol. Chem.*, 268, 12925 (1993)). PDE7 is important in activation of T-cells and it is implied that it is useful for the prevention and treatment of T cell-dependent diseases (see *Science*, 283, 848 (1999)). Also, PDE7 is expressed in airway epitheliocytes, and so it is also implied that it is probable that PDE7 is effective for the diseases in airway (see *Am. J Respir. Cell Mol. Biol.*, 20, 292 (1999)).

Therefore, a drug which inhibits PDE7 is thought to be useful for the prevention and/or treatment of various diseases, i.e. autoimmune diseases (ulcerative colitis, Crohn's diesaes, rheumatism, psoriasis, multiple sclerosis, collagenosis, etc.), inflammatory diseases (obstructive pulmonary diseases, sepsis, pancreatitis, sarcoidosis, nephritis, hepatitis, enteritis, etc.), allergic diseases (asthma, allergic rhinitis, allergic conjunctivitis, seasonal conjunctivitis, atopic dermatitis, etc.), rejection of an organ transplant, graft versus host diseases (GVHD), diabetic diseases, osteoporosis, bone fracture, restenosis, arteriosclerosis, obesity, ischemic reperfusion injury, depression, Parkinson's diseases, dementia, leukemia, etc.

Isoquinoline derivatives are known as follows: for example, in JP63-280069(A), it is disclosed that a compound of formula (A)

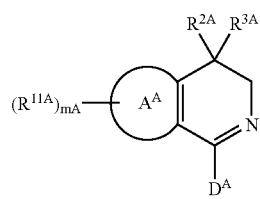

(wherein $A^A$ is benzo or thieno and $R^{2A}$ and $R^{3A}$ are independently hydrogen or (C1-5)alkyl, or taken together with the carbon atom to which they are attached to form 5 or 6 membered carbocycle and $R^{11A}$ is (C1-4)alkyl, halogen, hydroxy and mA is 0, 1, 2 or 3 when $A^A$ is benzo, $D^A$ is $Ib^A$, etc.:

$R^{1A}$ is hydrogen, (C1-10)alkyl etc, $R^{5'A}$ is hydrogen or (C1-4)alkyl, $R^{4A}$ is (C1-4)alkoxy or —$NR^{9A}R^{10A}$ (wherein $R^{9A}$ and $R^{10A}$ are independently hydrogen, C1-12 branched or unbranched alkyl, alkenyl or alkynyl, etc., or $R^{9A}$ and $R^{10A}$ are taken together with the carbon atom to which they are attached to form pyrrolidinyl, piperidinyl, morpholinyl or piperazinyl, etc.)) has heart-protecting activity (groups are extracted for description).

*Khim. Geterotsikl. Soedin.*, 946-949, 7, (1994) discloses a compound of 2-(3,3-dimethyl-3,4-dihydro-(2H)-isoquinoline-1-ylidene)-1-phenylmethan-1-one (Reg No. 163769-77-5).

The specification of WO 02/010135 discloses that a compound of formula (B)

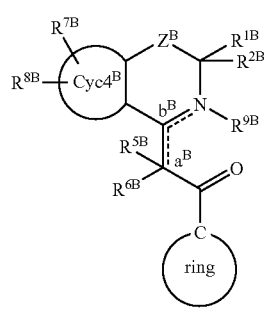

(wherein the explanation of groups are as described in the specification of WO02/010135.) has a cannabinoid (CB) 2 receptor agonizing activity, but no description is found on PDE7 inhibitory activity therein.

DISCLOSURE OF THE INVENTION

In order to find a compound having a PDE7 inhibitory activity, the present inventors have conducted intensive studies and found, as a result, that the objects can be accomplished by nitrogen-containing bicyclic compounds of formula (I) and pharmaceutically acceptable salts thereof, and thus the present invention has been accomplished.

Also, the present inventors have found that some compounds among the compound of formula (I) has cannabinoid (CB)2 receptor agonizing activity, and thus the present invention was accomplished.

Cannabinoid is a generic name of Δ9-tetrahydrocannabinol (abbreviated as Δ9-THC hereafter) which is a main ingredient of marijuana, which is made from hemp, and its analogues (Deway, *Pharmacol. Rev.*, 38, 15-178 (1996)). It is known as a substance which causes euphoria, sleepiness, hallucination, relief from mental tense, etc (Hollister, *Pharmacol. Rev.*, 38, 1-20 (1986)).

Aside from the previous central effects, it is reported that the reactivity of lymphocytes is decreased in habitual users of marijuana (Naha et al., *Science*, 183, 419-420 (1974)), that marijuana or Δ9-THC lowers the ability of leucocytoplania and the function of macrophages, etc. in vitro (Schwartzfarb et al., *J. Clin. Pharmacol.*, 14, 35-41 (1974); Lopez-Capero et al., *J Leuk. Biol.*, 39, 679-686 (1986)), and that it lowers the resistance to virus infection (Morahan et al., *Infect. Immun.*, 23, 670-674 (1979)), etc. These facts implies that cannabinoid acts not only on central nervous system but also on periphery (particularly immune system).

First reported cannabinoid receptor is CB1 receptor, which was cloned from rat cerebral cortex cDNA library in 1990 (Matsuda et al., *Nature.*, 346, 561-564 (1990)). Afterwards, CB2 receptor was cloned from human promyelogenic leukemia cell line HL-60cDNA library (Murano et al., *Nature.*, 365, 61-65 (1993)). It was revealed that CB1 is mainly expressed in brains and CB2 in those cells which are responsible for immunity, e.g. spleens.

It had been conceived to adapt cannabinoid to medical care for a long time (Mechiulan, CRC Press, *Boca Raton.*, 1-20 (1986); Razdan et al., *Med Res. Rev.*, 3, 119-146 (1983)), and some of them are used as pharmaceuticals already such as Cesamet (Ward and Holmes, *Drugs.*, 30, 127-144 (1985)). These are conceived to take effect via CB1.

On the other hand, the physiological roles of CB2 receptor, which is a peripheral receptor, is not revealed enough yet, but it is implied that a compound which acts on CB2 receptor (agonist, antagonist) modulates inflammation and immune. Moreover, it is expected that it is effective for a pain accompanying inflammation (Calignano et al., *Nature.*, 394, 277-281 (1998)).

From these above, a pharmaceutical agent which acts on CB2 receptor specifically, is useful for the prevention and/or treatment of various diseases, that is, asthma, nasal allergy, atopic dermatology, autoimmune diseases (multiple sclerosis, colitis, etc.), rheumatism, arthritis, immune dysfunction (acquired immunodeficiency syndrome etc.), pains (postoperative pain, carcinomatous pain, etc.

That is, the present invention relates to (1) a compound of formula (I)

wherein $R^1$ and $R^2$ are each independently, (1) hydrogen atom, or (2) C1-8 alkyl, or $R^1$ and $R^2$ may be taken together with the carbon atom to which they are attached to form Cyc1, wherein $R^1$ and $R^2$ do not represent hydrogen atom at the same time;

Z is (1) —$CR^3R^4$—, (2) —O—, (3) —S—, or (4) a bond;

$R^3$ and $R^4$ are each independently, (1) hydrogen atom, (2) C1-8 alkyl, (3) C1-8 alkoxy, or (4) hydroxy, or $R^3$ and $R^4$ may be taken together with the carbon atom to which they are attached to form Cyc1 or —C(O)—;

$R^5$ and $R^6$ are each independently, (1) hydrogen atom, or (2) C1-8 alkyl, or $R^5$ and $R^6$ may be taken together with the carbon atom to which they are attached to form Cyc1;

Cyc1, which is represented by $R^1$ and $R^2$, $R^3$ and $R^4$, $R^5$ and $R^6$ is, each independently, (1) C3-10 cycloalkyl, or (2) 3-10 membered monocyclic heterocyclic comprising 1-2 of heteroatom selected from oxygen, nitrogen and sulfur, and Cyc1 may be substituted with $R^{10}$;

$R^{10}$ is (1) C1-8 alkyl, (2) C1-8 alkoxy, (3) hydroxy, (4) —$COOR^{11}$, (5) oxo, (6) —$SO_2R^{12}$, or (7) —$COR^{13}$;

$R^{11}$ is hydrogen atom, or C1-8 alkyl;

$R^{12}$ and $R^{13}$ are (1) C1-8 alkyl, or (2) phenyl which may be substituted with C1-8 alkyl;

$R^7$ and $R^8$ are each independently, (1) hydrogen atom, (2) C1-8 alkyl, (3) C1-8 alkoxy, (4) hydroxy, (5) cyano, (6) halogen atom, (7) —$COOR^{14}$, (8) —$CONR^{15}R^{16}$, (9) Cyc2, (10) C2-8 alkenyl, (11) C2-8 alkynyl, (12) —$NR^{51}R^{52}$, (13) nitro, (14) formyl, (15) C2-8 acyl, (16) C1-8 alkyl substituted with hydroxy, C1-8 alkoxy, Cyc2, —$NR^{51}R^{52}$, or —$NR^{53}$-Cyc2, (17) —$NR^{54}COR^{55}$, (18) —$NR^{56}SO_2R^{57}$, (19) —$SO_2NR^{58}R^{59}$, (20) C2-8 alkenyl substituted with —$COOR^{14}$, (21) —CH═N—OH, (22) —(C1-8 alkylene)-$NR^{60}$—(C1-8 alkylene)-$R^{61}$, (23) C1-8 alkylthio, (24) C1-8 alkyl substituted with 1-3 of halogen atom, (25) C1-8 alkoxy substituted with 1-3 of halogen atom, (26) C1-8 alkoxy substituted with Cyc2, (27) —O-Cyc2, (28) —$OSO_2R^{65}$, or (29) —CH═N—$OR^{137}$;

$R^{14}$ is hydrogen atom, or C1-8 alkyl;

$R^{15}$ and $R^{16}$ are each independently hydrogen atom or C1-8 alkyl;

$R^{51}$ and $R^{52}$, $R^{58}$ and $R^{59}$ are each independently, hydrogen atom, or C1-8 alkyl;

$R^{53}$, $R^{54}$, $R^{56}$ and $R^{60}$ are each independently, hydrogen atom, or C1-8 alkyl;

$R^{55}$ is hydrogen atom, C1-8 alkyl, or C1-8 alkoxy;

$R^{57}$ is C1-8 alkyl;

$R^{61}$ is —$NR^{62}R^{63}$ or hydroxy;

$R^{62}$ and $R^{63}$ are each independently, hydrogen atom, or C1-8 alkyl;

$R^{65}$ is C1-8 alkyl;

$R^{137}$ is C1-8 alkyl;

(hereinafter it is abbreviated as ring;) is Cyc2 wherein the group which attaches to carbonyl is carbon;

$R^7$, $R^8$ and Cyc2 represented by ring are each independently, (1) C3-15 mono-, bi- or tri-cyclic (fused or spiro) carboring, or (2) 3-15 membered mono-, bi- or tri-cyclic (fused or spiro)heterring comprising 1-4 of heteroatom selected from oxygen, nitrogen and sulfur;

Cyc2 may be substituted with 1-5 of $R^{17}$ or $R^{17t}$;

$R^{17}$ is (1) C1-8 alkyl, (2) C2-8 alkenyl, (3) C2-8 alkynyl, (4) C1-8 alkoxy, (5) C1-8 alkylthio, (6) hydroxy, (7) halogen atom, (8) nitro, (9) oxo, (10)carboxy, (11) formyl, (12) cyano, (13) —$NR^{18}R^{19}$, (14) phenyl, phenoxy or phenylthio, which may be substituted with 1-5 of $R^{20}$, (15) C1-8 alkyl, C2-8 alkenyl, C1-8 alkoxy or C1-8 alkylthio, which may be substituted with 1-5 of $R^{21}$ (16) —$OCOR^{22}$, (17) —$CONR^{23}R^{24}$, (18) —$SO_2NR^{25}R^{26}$, (19) —$COOR^{27}$, (20) —$COCOOR^{28}$, (21) —$COR^{29}$, (22) —$COCOR^{30}$, (23) —$NR^{31}COR^{32}$, (24) —$SO_2R^{33}$, (25) —$NR^{34}SO_2R^{35}$, or (26) —$SOR^{64}$;

$R^{18}$ and $R^{19}$, $R^{31}$ and $R^{34}$ are each independently, hydrogen atom, or C1-8 alkyl;

$R^{20}$ and $R^{21}$ are C1-8 alkyl, C1-8 alkoxy, hydroxy, halogen atom, nitro, or —$COOR^{36}$;

$R^{22}$ and $R^{64}$ are each independently C1-8 alkyl;

$R^{23}$, $R^{24}$, $R^{25}$ and $R^{26}$ are each independently hydrogen atom, C1-8 alkyl, or phenyl;

$R^{27}, R^{28}, R^{29}, R^{30}, R^{32}, R^{33}$ and $R^{35}$ are (1) C1-8 alkyl, (2) C2-8 alkenyl, (3) C1-8 alkyl substituted with 1-5 of $R^{37}$, (4) diphenylmethyl, (5) triphenylmethyl, (6) Cyc3, (7) C1-8 alkyl or C2-8 alkenyl substituted with Cyc3, (8) C1-8 alkyl substituted with —O-Cyc3, —S-Cyc3 or —$SO_2$-Cyc3;

$R^{36}$ is hydrogen atom, or C1-8 alkyl;

$R^{37}$ is C1-8 alkoxy, C1-8 alkylthio, benzyloxy, halogen atom, nitro or —$COOR^{38}$;

$R^{38}$ is hydrogen atom, C1-8 alkyl or C2-8 alkenyl;

Cyc3 is (1) C3-15 mono-, bi- or tri-cyclic (fused or spiro)carboring, or (2) 3-15 membered mono-, bi- or tri-cyclic (fused- or spiro)heterring comprising 1-4 of heteroatom selected from oxygen, nitrogen and sulfur;

Cyc3 may be substituted with 1-5 of $R^{39}$;

$R^{39}$ is (1) C1-8 alkyl, (2) C2-8 alkenyl, (3) C2-8 alkynyl, (4) C1-8 alkoxy, (5) C1-8 alkylthio, (6) hydroxy, (7) halogen atom, (8) nitro, (9) oxo, (10) cyano, (11) benzyl, (12) benzyloxy, (13) C1-8 alkyl, C1-8 alkoxy or C1-8 alkylthio substituted with 1-5 of $R^{40}$, (14) phenyl, phenoxy, phenylthio, phenylsulfonyl or benzoyl which may be substituted with 1-5 of $R^{41}$, (15) —$OCOR^{42}$, (16) —$SO_2R^{43}$, (17) —$NR^{44}COR^{45}$, (18) —$SO_2NR^{46}R^{47}$, (19) —$COOR^{48}$, or (20) —$NR^{49}R^{50}$;

$R^{40}$ is halogen atom;

$R^{41}$ is C1-8 alkyl, C1-8 alkoxy, halogen atom, or nitro;

$R^{42}$, $R^{43}$ and $R^{45}$ are C1-8 alkyl;

$R^{44}$ and $R^{48}$ are hydrogen atom or C1-8 alkyl;

$R^{46}$ and $R^{47}$, $R^{49}$ and $R^{50}$ are each independently, hydrogen atom or C1-8 alkyl;

$R^{17'}$ is (1) SH, (2) —$NR^{66}CHO$, (3) Cyc5, (4) C1-8 alkyl, C2-8 alkenyl or C2-8 alkynyl substituted with Cyc5, (5) —CO—(NH-amino acid residue-CO)$_n$—OH, (6) —$NR^{67}CONR^{68}R^{69}$, (7) —$CONR^{70}NR^{71}R^{72}$, (8) —$CONR^{73}R^{74}$, (9) —$CONR^{75}COR^{76}$, (10) —$C(S)NR^{77}R^{78}$, (11) —$CONR^{79}C(S)COOR^{80}$, (12) —$NR^{81}COCOOR^{82}$, (13) —$NR^{83}COOR^{84}$, (14) —$CONR^{85}C(S)R^{86}$, (15) —$OCOR^{87}$, (16) —$SOR^{88}$, (17) —$CONR^{89}R^{90}$, (18) —$SO_2NR^{91}R^{92}$, (19) —$COOR^{93}$, (20) —$COCOOR^{94}$, (21) —$COR^{95}$, (22) —$COCOR^{96}$, (23) —$NR^{97}COR^{98}$, (24) —$SO_2R^{99}$, (25) —$NR^{100}SO_2R^{101}$, or (26) —$NR^{102}R^{103}$;

n is an integer of 1 or 2;

$R^{66}, R^{73}, R^{75}, R^{77}, R^{79}, R^{81}, R^{83}, R^{85}, R^{97}, R^{100}$ and $R^{102}$ are hydrogen atom, or C1-8 alkyl;

$R^{67}$ and $R^{68}$, $R^{70}$ and $R^{71}$ are each independently, hydrogen atom, or C1-8 alkyl;

$R^{89}$ and $R^{91}$ are (1) hydrogen atom, (2) C1-8 alkyl, (3) phenyl, or (4) C1-8 alkyl substituted with cyano or C1-8 alkoxy;

$R^{103}$ is Cyc6;

$R^{69}, R^{72}, R^{74}, R^{76}, R^{78}, R^{80}, R^{82}, R^{84}, R^{86}, R^{87}, R^{88}, R^{90}$ and $R^{92}$ are (1) hydrogen atom, (2) C1-8 alkyl, (3) C2-8 alkenyl, (4) C2-8 alkynyl, (5) C1-8 alkyl substituted with 1-5 of $R^{104}$, (6) diphenylmethyl, (7) triphenylmethyl, (8) Cyc6, (9) C1-8 alkyl or C2-8 alkenyl substituted with Cyc6, or (10) C1-8 alkyl substituted with —O-Cyc6, —S-Cyc6 or —$SO_2$-Cyc6;

$R^{104}$ is (1) C1-8 alkoxy, (2) C1-8 alkylthio, (3)benzyloxy, (4) halogen atom, (5) nitro, (6) —$COOR^{105}$, (7) cyano, (8) —$NR^{106}R^{107}$, (9) —$NR^{108}COR^{109}$, (10) hydroxy, (11) SH, (12) —$SO_3H$, (13) —S(O)OH, (14) —$OSO_3H$, (15) C2-8 alkenyloxy, (16) C2-8 alkynyloxy, (17) —$COR^{110}$, (18) —$SO_2R^{111}$, or (19) C1-8 alkoxy or C1-8 alkylthio substituted with hydroxy;

$R^{105}$ is hydrogen atom, C1-8 alkyl, or C2-8 alkenyl;

$R^{106}$ and $R^{107}$ are each independently, hydrogen atom, or C1-8 alkyl;

$R^{108}$ is hydrogen atom, or C1-8 alkyl;

$R^{109}$ and $R^{111}$ are C1-8 alkyl;

$R^{110}$ is C1-8 alkyl, or halogen atom;

wherein $R^{82}$, $R^{84}$ and $R^{86}$ are not hydrogen atom;

wherein $R^{87}$ and $R^{88}$ are not hydrogen atom and C1-8 alkyl;

wherein $R^{90}$ and $R^{92}$ are not hydrogen atom, C1-8 alkyl or phenyl;

$R^{93}, R^{94}, R^{95}, R^{96}, R^{98}, R^{99}$ and $R^{101}$ are (1) C2-8 alkynyl, (2) C1-8 alkyl substituted with $R^{128}$ which may be substituted with 1-4 of $R^{129}$, (3) Cyc8, (4) C1-8 alkyl or C2-8 alkenyl substituted with Cyc8, or (5) C1-8 alkyl substituted with —O-Cyc8, —S-Cyc8 or —$SO_2$-Cyc8;

$R^{128}$ is (1) cyano, (2) —$NR^{106}R^{107}$, (3) —$NR^{108}COR^{109}$, (4) hydroxy, (5) SH, (6) —$SO_3H$, (7) —S(O)OH, (8) —$OSO_3H$, (9) C2-8 alkenyloxy, (10) C2-8 alkynyloxy, (11) —$COR^{110}$, (12) —$SO_2R^{111}$, or (13) C1-8 alkoxy or C1-8 alkylthio substituted with hydroxy;

$R^{129}$ has the same meaning as $R^{104}$;

Cyc5 and Cyc6 may be substituted with 1-5 of $R^{112}$;

$R^{112}$ is (1) C1-8 alkyl, (2) C2-8 alkenyl, (3) C2-8 alkynyl, (4) C1-8 alkoxy, (5) C1-8 alkylthio, (6) hydroxy, (7) halogen atom, (8) nitro, (9) oxo, (10) cyano, (11) benzyl, (12) benzyloxy, (13) C1-8 alkyl, C1-8 alkoxy or C1-8 alkylthio substituted with 1-5 of $R^{113}$, (14) phenyl, phenoxy, phenylthio or benzoyl, which may be substituted with 1-5 of $R^{114}$, (15) —$COR^{115}$, (16) —$SO_2R^{116}$, (17) —$NR^{117}COR^{118}$, (18) —$SO_2NR^{119}R^{120}$, (19) —$COOR^{121}$, (20) —$NR^{122}R^{123}$, (21) —$COR^{124}$, (22) —$CONR^{125}R^{126}$, (23) SH, (24) C1-8 alkyl substituted with hydroxy or —$NR^{127}$-benzoyl, or (25) Cyc7;

$R^{113}$ is halogen atom;

$R^{114}$ is C1-8 alkyl, C1-8 alkoxy, halogen atom, or nitro;

$R^{115}$, $R^{116}$ and $R^{118}$ are C1-8 alkyl;

$R^{117}$, $R^{121}$, $R^{124}$ and $R^{127}$ are hydrogen atom, or C1-8 alkyl;

$R^{119}$ and $R^{120}$, $R^{122}$ and $R^{123}$, $R^{125}$ and $R^{126}$ are each independently, hydrogen atom or C1-8 alkyl;

Cyc7 may be substituted with 1-5 group selected from (1) C1-8 alkyl, (2) C1-8 alkoxy, (3) halogen atom, or (4) nitro;

Cyc8 may be substituted with $R^{130}$, and it further may be substituted with 1-4 of $R^{131}$;

$R^{130}$ is (1) —$COR^{124}$, (2) —$CONR^{125}R^{126}$, (3) SH, (4) C1-8 alkyl substituted with hydroxy or —$NR^{127}$-benzoyl, or (5) Cyc7;

$R^{131}$ has the same meaning as $R^{112}$;

Cyc5, Cyc6, Cyc7 and Cyc8 are (1) C3-15 mono-, bi- or tri-cyclic (fused or spiro)carboring, or (2) 3-15 membered mono-, bi- or tri-cyclic (fused or spiro)heteroring comprising 1-4 of heteroatom selected from 1-4 of oxygen, nitrogen or sulfur;

wherein when $R^{17'}$ is Cyc5, Cyc5 is not phenyl which may be substituted with 1-5 selected from C1-8 alkyl, C1-8 alkoxy, hydroxy, halogen atom, nitro, —COOH, or —COO—(C1-8 alkyl);

wherein Cyc7 is not phenyl;

Cyc4 is (1) C5-7 monocyclic carboring, or (2) 5-7 membered monocyclic heteroring comprising 1-2 of heteroatom selected from oxygen, nitrogen and sulfur;

$$\overset{a}{=====}$$

(abbreviated as dashed line a hereafter;) and $$\overset{b}{=====}$$

(abbreviated as dashed line b hereafter;) are (1) a bond, or (2) a double bond;

$R^9$ (1) does not exist or (2) is hydrogen atom;
wherein
1) when dashed line a is a bond, dashed line b is a double bond, and $R^9$ does not exist,
2) when dashed line a is a double bond, dashed line b is a bond, and $R^9$ is hydrogen atom and $R^6$ does not exist, and
3) 2-(3,3-dimethyl-3,4-dihydro-(2H)-isoquinolin-1-ylidene)-1-phenylethan-1-one is excluded, or a pharmacologically acceptable salt thereof, (2) the compound according to above (1), wherein Z in formula (I) is —S— or a bond, or a pharmacologically acceptable salt thereof, (3) the compound according to above (1), in formula (I), wherein
   (i) Z is —CR³R⁴—, or —O—, and at least either of $R^7$ or $R^8$ is (24) C1-8 alkyl substituted with 1-3 of halogen atom, (25) C1-8 alkoxy substituted with 1-3 of halogen atom, (26) C1-8 alkoxy substituted with Cyc2, (27) —O-Cyc2, (28) —OSO₂R⁶⁵, or (29) —CH=N—OR¹³⁷, or
   (ii) Z is —CR³R⁴—, or —O—, and at least one Cyc2 which is represented by $R^7$, $R^8$ or ring is substituted with at least one $R^{17'}$ or a pharmacologically acceptable salt thereof, (4) the compound according to above (1), which is represented by formula (I')

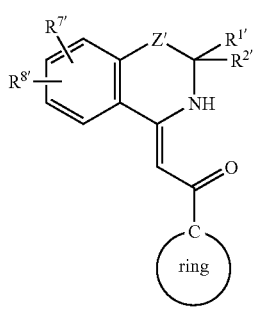

(I')

wherein, $R^{1'}$ and $R^{2'}$ are each independently, C1-8 alkyl, Z' is —CR³'R⁴'—, or —O—, $R^{3'}$ and $R^{4'}$ are each independently, hydrogen atom, C1-8 alkyl, or hydroxy, $R^{7'}$ and $R^{8'}$ are each independently, hydrogen atom, C1-8 alkyl, C1-8 alkoxy, hydroxy, cyano, halogen atom, —COOR¹⁴, —CONR¹⁵R¹⁶, Cyc2, —NR⁵¹R⁵², formyl, hydroxy or C1-8 alkyl substituted with C1-8 alkoxy, or —SO₂NR⁵⁸R⁵⁹;

Cyc2 represented by

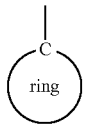

may be substituted with 1-5 of $R^{17''}$;

$R^{17''}$ is C1-8 alkyl, C1-8 alkoxy, hydroxy, halogen atom, nitro, oxo, (10) carboxy, (11) formyl, (12) cyano, (13) —NR¹⁸R¹⁹, (15) C1-8 alkyl substituted with 1-5 of R²¹, (17) —CONR²³R²⁴, (19) —COOR²⁷, (21) —COR²⁹, (23) —NR³¹COR³², or (25) —NR³⁴SO₂R³⁵ and the other symbols have the same meaning as above (1);) or a pharmacologically acceptable salt thereof, (5) a PDE7 inhibitor comprising the compound according to above (1), or a pharmacologically acceptable salt as active ingredient, (6) a pharmaceutical composition for the prevention and/or treatment of autoimmune diseases, inflammatory diseases, allergic diseases, rejection of an organ transplant, graft versus host disease (GVHD), diabetic diseases, osteoporosis, bone fracture, re-stenosis, arteriosclerosis, obesity, ischemic reperfusion injury, depression, Parkinson's diseases, dementia or leukemia, comprising the compound according to above (1) or a pharmacologically acceptable salt thereof as active ingredient, and (7) a pharmaceutical composition for the prevention and/or treatment of asthma, allergy rhinitis, atopic dermatitis, autoimmune diseases, rheumatism, postoperative pain and/or carcinomatous pain, comprising the compound described in above (2) or (3) or a pharmacologically acceptable salt as active ingredient.

In the present specification, C1-8 alkyl is methyl, ethyl, propyl, butyl, pentyl, hexyl, heptyl, octyl and isomers thereof.

In the present specification, C2-8 alkenyl is ethenyl, propenyl, butenyl, pentenyl, hexenyl, heptenyl, octenyl and isomers thereof.

In the present specification, C2-8 alkynyl is ethynyl, propynyl, butynyl, pentynyl, hexynyl, heptynyl, octynyl and isomers thereof.

In the present specification, C1-8 alkoxy is methoxy, ethoxy, propoxy, butoxy, pentyloxy, hexyloxy, heptyloxy, octyloxy and isomers thereof.

In the present specification, C2-8 alkenyloxy is ethenyloxy, propenyloxy, butenyloxy, pentenyloxy, hexenyloxy, heptenyloxy, octenyloxy and isomers thereof.

In the present specification, C2-8 alkynyloxy is ethynyloxy, propynyloxy, butynyloxy, pentynyloxy, hexynyloxy, heptynyloxy, octynyloxy and isomers thereof.

In the present specification, C1-8 alkylthio is methylthio, ethylthio, propylthio, butylthio, pentylthio, hexylthio, heptylthio, octylthio and isomers thereof.

In the present specification, halogen atom is chlorine, bromine, fluorine, iodine.

In the present specification, C3-10 cycloalkyl is cyclopropyl, cyclobutyl, cyclopentyl, cyclohexyl, cycloheptyl, cyclooctyl, cyclononyl, cyclodecyl.

In the present specification, C2-8 acyl is, acetyl, propanoyl, butanoyl, pentanoyl, hexanoyl, heptanoyl, octanoyl and isomers thereof.

In the present specification, C1-8 alkylene is methylene, ethylene, trimethylene, tetramethylene, pentamethylene, hexamethylene, heptamethylene, octamethylene and isomers thereof.

In the present specification, C5-7 monocyclic carboring is, for example, cyclopentane, cyclohexane, cycloheptane, cyclopentene, cyclohexene, cycloheptene, cyclopentadiene, cyclohexadiene, cycloheptadiene, benzene, etc.

In the present specification, 5-7 membered monocyclic heteroring comprising 1-2 of heteroatom selected from oxygen, nitrogen and sulfur includes 5-7 membered monocyclic heteroaryl comprising 1-2 of heteroatom selected from oxygen, nitrogen and sulfur or partially or completely saturated one thereof.

5-7 membered monocyclic heteroaryl comprising 1-2 of heteroatom selected from oxygen, nitrogen and sulfur includes, for example, pyrrole, imidazole, pyrazole, pyridine, pyrazine, pyrimidine, pyridazine, azepine, diazepine, furan, pyran, oxepin, thiophene, thiain (thiopyran), thiepin, oxazole, isoxazole, thiazole, isothiazole, oxazine, oxazepine, thiazine, thiazepine, etc.

Partially or completely saturated 5-7 membered monocyclic heteroring comprising 1-2 of heteroatom selected from oxygen, nitrogen and sulfur includes, for example, pyrroline, pyrrolidine, imidazoline, imidazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, tetrahydrooxazepine, perhydrooxazepine, tetrahydrothiazepine, perhydrothiazepine, morpholine, thiomorpholine, dioxolane, dioxane, dithiolane, dithiane ring, etc.

Above 5-7 membered monocyclic heteroring includes N-oxide compound whose nitrogen is oxidized.

In the present specification, 3-10 membered monocyclic heteroring comprising 1-2 of heteroatom selected from oxygen, nitrogen and sulfur includes, for example, completely saturated 3-10 membered mono-cyclic heteroaryl comprising 1-2 of heteroatom selected from oxygen, nitrogen and sulfur.

Completely saturated 3-10 membered monocyclic heteroaryl comprising 1-2 of heteroatom includes, for example, pyrrolidine, imidazolidine, pyrazolidine, piperidine, piperazine, perhydropyrimidine, perhydropyridazine, perhydroazepine, perhydrodiazepine, tetrahydrofuran, tetrahydropyran, tetrahydrothiophene, tetrahydrothiain (tetrahydrothiopyran), tetrahydrooxazole, tetrahydroisoxazole, tetrahydrothiazole, tetrahydroisothiazole, perhydrooxazepine, perhydrothiazepine, morpholine, thiomorpholine, dioxolane, dioxane, dithiolane, dithiane ring, etc.

Above 3-10 membered mono-cyclic heteroring includes N-oxide compounds whose nitrogen is oxidized.

In the present specification, C3-15 mono-, bi- or tri-cyclic (fused or spiro)carboring, includes, for example, cyclopropane, cyclobutane, cyclopentane, cyclohexane, cycloheptane, cyclooctane, cyclononane, cyclodecane, cycloundecane, cyclododecane, cyclotridodecane, cyclopentene, cyclohexene, cycloheptene, cyclooctene, cyclopentadiene, cyclohexadiene, cycloheptadiene, cyclooctadiene, benzene, indene, naphthalene, indan, tetrahydronaphthalene, bicyclo[3.3.0]octane, bicyclo[4.3.0]nonane, bicyclo[4.4.0]decane, spiro[4.4]nonane, spiro[4.5]decane, spiro[5,5]undecane, fluorene, anthracene, 9,10dihydroanthracene, bicyclo[3.1.1]heptane, bicyclo[3.3.1]-2-heptene, adamantan, noradamantan, bicyclo[2.2.2]octane, etc.

In the present specification, 3-15 membered mono-, bi- or tri-cyclic (fused or spiro)heteroring including 1-4 of heteroatom selected from oxygen, nitrogen and sulfur includes, for example, partially or completely saturated 3-15 membered mono-, bi- or tri-cyclic (fused or spiro)heteroaryl comprising 1-4 of heteroatom selected from oxygen, nitrogen and sulfur.

3-15 membered mono-, bi- or tri-cyclic (fused or spiro) heteroaryl comprising 1-4 of heteroatom selected from oxygen, nitrogen and sulfur includes, for example, pyrrole, imidazole, triazole, tetrazole, pyrazole, pyridine, pyrazine, pyrimidine, pyridazine, azepine, diazepine, furan, pyran, oxepin, thiophene, thiain (thiopyran), thiepin, oxazole, isoxazole, thiazole, isothiazole, furazane, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzoimidazole, pyrazolo[5,4-b]pyridine, benzoxepin, benzooxazepine, benzooxadiazepine, benzothiepin, benzothiazepine, benzothiadiazepine, benzoazepine, benzodiazepine, benzofurazane, benzothiadiazole, benzotriazole, carbazole, acridine, dibenzofuran, dibenzothiophene, phenothiazine, etc.

Partially or completely saturated 3-15 membered mono-, bi- or tri-cyclic (fused or spiro)heteroaryl comprising 1-4 of heteroatom selected from oxygen, nitrogen and sulfur includes, for example, pyrroline, pyrrolidine, imidazoline, imidazolidine, pyrazoline, pyrazolidine, triazoline, triazolidine, tetrazoline, tetrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, dihydrooxadiazole, tetrahydrooxadiazole, dihydrothiodiazole, tetrahydrothiodiazole, tetrahydrooxadiazine, tetrahydrothiadiazine, tetrahydrooxazepine, tetrahydrooxadiazepine, perhydrooxazepine, perhydrooxadiazepine, tetrahydrothiazepine, tetrahydrothiadiazepine, perhydrothiazepine, perhydrothiadiazepine, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzooxazole, perhydrobenzooxazole, dihydrobenzothiazole, perhydrobenzothiazole, dihydrobenzoimidazole, perhydrobenzoimidazole, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithian, benzodioxalane, benzodioxane, benzodithiolane, benzodithian, 2,4,6-trioxaspiro[bicycle[3.3.0]octane-3,1'-cyclohexane]1,3-dioxolano[4,5-g]chromene, 2-oxabicyclo[2.2.1]heptane, etc.

Above 3-15 membered mono-, bi- or tri-cyclic (fused or spiro)heteroring includes N-oxide compounds whose nitrogen is oxidized.

In the present specification, amino acid in —CO—(NH-amino acid residue-CO)$_n$—OH represents natural amino acid or abnormal amino acid, for example, glycine, alanine, valine, leucine, isoleucine, serine, threonine, cysteine, methionine, proline, asparagine, glutamine, phenylalanine, tyrosine, tryptophan, aspartic acid, glutamic acid, lysine, arginine, histidine, β-alanine, cystathionine, cystine, homoserine, isoleucine, lanthionine, norleucine, norvaline, ornithine, sarcosine, thyronine, etc.

Also, —CO—(NH-amino acid residue-CO)$_n$—OH includes a carboxy group esterified by C1-8 alkyl.

Unless otherwise indicated, all isomers are included in the present invention. For example, the alkyl group, the alkoxy group and the alkylene group include straight-chain groups and branched-chain groups. Moreover, isomers in a double bond, a ring, a fused ring (E-, Z-, cis-, trans-isomer), isomers due to the presence of an asymmetric carbon atom(s), etc. (R-, S-isomer, α-, β-isomer, enantiomer, diastereomer), optically active isomers having optical rotation (D-, L-, d-, l-isomer), polar compounds separated by chromatography (more polar compound, less polar compound), equilibrium compounds, mixtures thereof at arbitrary ratios and racemic mixtures are included in the present invention.

According to the present invention, unless otherwise indicated, as is apparent for those skilled in the art, symbol

indicates that it is bound to the behind the sheet (namely α-configuration), symbol

indicates that it is bound to the front of the sheet (namely β-configuration), symbol

indicates that it is α-, β- or a mixture thereof, and symbol

indicates that it is a mixture of α-configuration and β-configuration.

In the compound of formula (I), the compound wherein dashed line a is a double bond, dashed line b is a bond, $R^9$ is hydrogen, and $R^6$ does not exist, i.e. the compound of formula (Ia) and the compound wherein dashed line a is a bond, dashed line b is a double bond, $R^6$ is hydrogen, $R^9$ does not exist, i.e. the compound of formula (Ib) are tautomers.

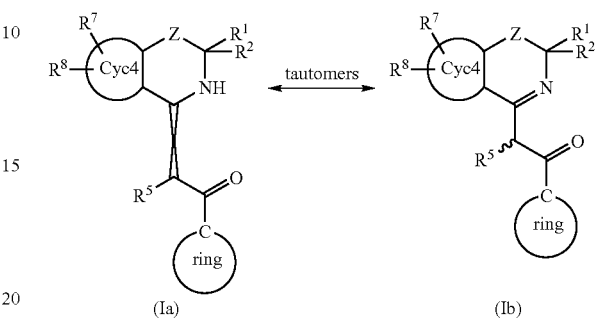

(Ia)                (Ib)

(wherein all symbols have the same meanings as hereinbefore.)

Also, the compound of above formula (Ia) includes the following compound of formula (Ia'), the compound of formula (Ia'') and mixture thereof

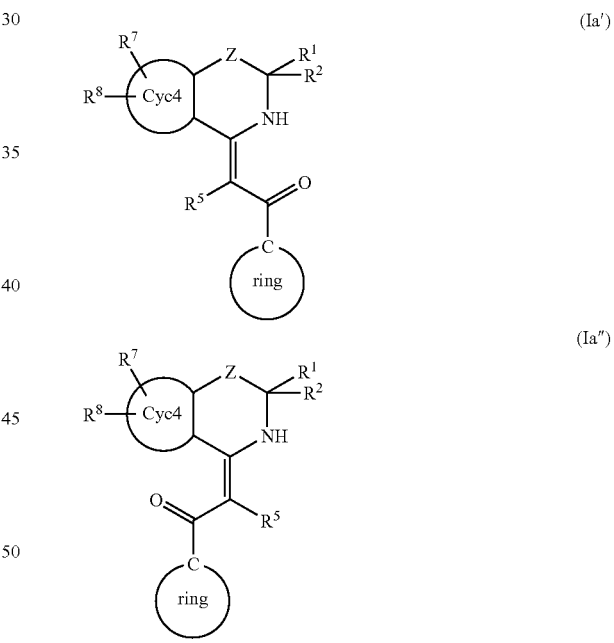

(wherein all symbols have the same meaning as hereinbefore.)

The compound of formula (I) can be converted into a pharmacologically acceptable salt by known methods.

Non-toxic and water-soluble salts are preferable as the pharmacologically acceptable salt.

In the present specification, the nontoxic salt includes alkaline metal (e.g. potassium, sodium, etc.) salts, alkaline earth metal (e.g., calcium, magnesium, etc.) salts, ammonium salts (tetramethylammonium salt, tetrabutylammonium salt, etc.), amine (triethylamine, methylamine, dimethylamine, cyclopentylamine, benzylamine, phenethylamine, piperidine, monoethanolamine, diethanolamine, tris(hydroxymethyl)methylamine, lysine, arguinine, N-methyl-D-glucamine, etc.) salts, acid-addition salts (inorganic acid salts such as hydrochloride, hydrobromate, hydroiodate, sulfate, phosphate, and nitrate; and organic acid salts such as acetate, lactate, tartarate, benzoate, citrate, methane sulfonate, ethane sulfonate, benzene sulfonate, toluene sulfonate, isethionate, glucuronate, and gluconate), and the like.

The salt is preferably non-toxic and water-soluble. Appropriate salts include salts of alkali metals (e.g., potassium, sodium, etc.), salts of alkaline earth metals (e.g., calcium, magnesium, etc.), ammonium salts, and pharmaceutically acceptable organic amines (e.g., tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine, etc.).

The acid-addition salt is preferably nontoxic and water-soluble. Appropriate acid-addition salts include inorganic acid salts such as hydrochloride, hydrobromate, hydroiodate, sulfate, phosphate, and nitrate; and organic acid salts such as acetate, lactate, tartarate, benzoate, citrate, methane sulfonate, ethane sulfonate, benzene sulfonate, toluene sulfonate, isethionate, glucuronate, and gluconate.

Also, the compound of the present invention represented by formula (I) or a salt thereof can be converted into a solvate by known methods.

Pharmacologically acceptable salts include solvates, or solvates of above alkali (alkaline-earth) metal salts, ammonium salts, organic amine salts, acid-addition salts.

The solvates are preferably non-toxic and water-soluble. Appropriate solvates include, for example, solvates of water, alcohols (e.g. ethanol etc.).

In the formula (I), $R^1$ and $R^2$ are preferably, C1-8 alkyl, more preferably methyl.

In the formula (I), Z is preferably, —$CR^3R^4$—, —O— or a bond, more preferably —$CR^3R^4$- or a bond.

In the formula (I), $R^3$ and $R^4$ are preferably, hydrogen or C1-8 alkyl, more preferably hydrogen or methyl.

In the formula (I), $R^5$ and $R^6$ are preferably, hydrogen.

In the formula (I), Cyc4 is preferably, C5-7 monocyclic carbon atom, more preferably benzene.

In the formula (I), ring is preferably C3-15 mono- or bi-cyclic carboring or 3-15 memvered mono- or bi-cyclic heteroring comprising mono- or bi-cyclic heteroring, more preferably benzene, cyclohexane, cycloheptane, adamantan, naphthalene, quinoline, isoquinoline, piperidine or pyridine.

In the compound of formula (I), preferable compounds are the compound of formula (Ia'-1)

(Ia'-1)

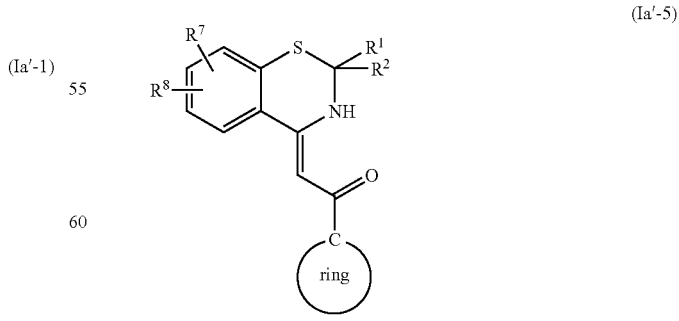

(wherein all symbols have the same meanings as hereinbefore.), the compound of formula (Ia'-2)

(Ia'-2)

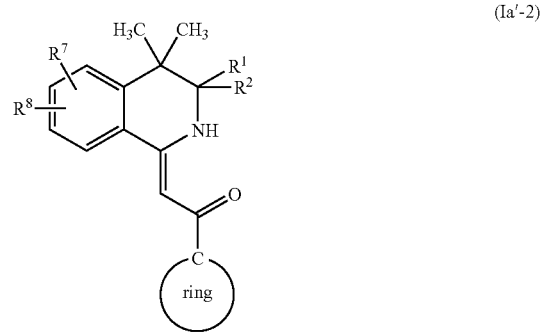

(wherein all symbols have the same meanings as hereinbefore.), the compound of formula (Ia'-3)

(Ia'-3)

(wherein all symbols have the same meanings as hereinbefore.), the compound of formula (Ia'-4)

(Ia'-4)

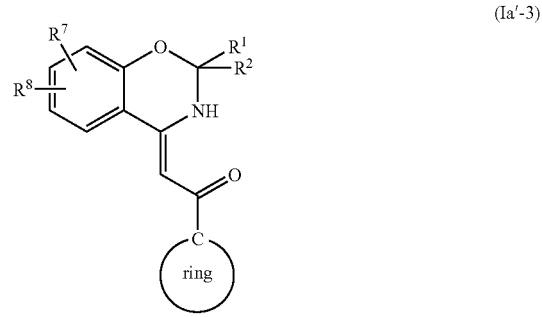

(wherein all symbols have the same meanings as hereinbefore.), the compound of formula (Ia'-5)

(Ia'-5)

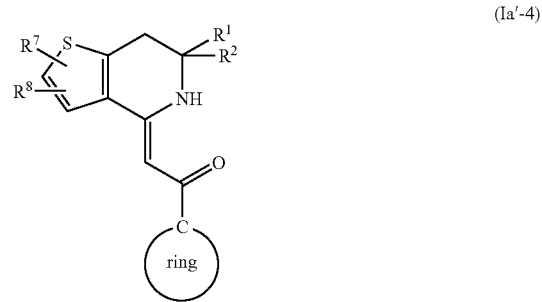

(wherein all symbols have the same meanings as hereinbefore.), and the compound of formula (Ia'-6)

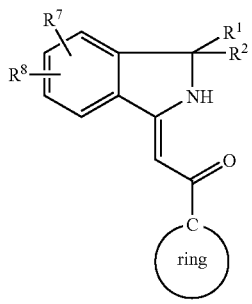

(Ia'-6)

(wherein all symbols have the same meanings as hereinbefore.).

Concretely, the compounds shown in the following tables 1-96, examples and pharmacologically acceptable salts thereof are included in the present invention.

In the following tables, Me is methyl, Et is ethyl, Boc is t-butoxycarbonyl, $R^{132}$ is $R^{17}$ or $R^{17'}$, Ac is acetyl, i-Bu is isobutyl, c-Pr is cyclopropyl, and the other symbols have the same meanings as above.

TABLE 1

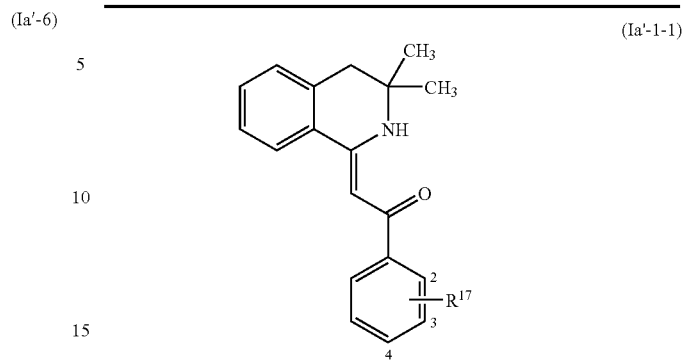

(Ia'-1-1)

| No. | $R^{17}$ |
|---|---|
| 1 | 2-Me |
| 2 | 3-Me |
| 3 | 4-Me |
| 4 | 2-OMe |
| 5 | 3-OMe |
| 6 | 4-OMe |
| 7 | 2-SMe |
| 8 | 3-SMe |
| 9 | 4-SMe |
| 10 | 2-OH |
| 11 | 3-OH |
| 12 | 4-OH |
| 13 | 2-F |
| 14 | 3-F |
| 15 | 4-F |
| 16 | 2-Cl |
| 17 | 3-Cl |
| 18 | 4-Cl |
| 19 | 2-$CF_3$ |
| 20 | 3-$CF_3$ |
| 21 | 4-$CF_3$ |
| 22 | 2-$OCF_3$ |
| 23 | 3-$OCF_3$ |
| 24 | 4-$OCF_3$ |
| 25 | 2-CN |

TABLE 1-continued (Ia'-1-1)

| No. | $R^{17}$ |
|---|---|
| 26 | 3-CN |
| 27 | 4-CN |
| 28 | 2-COOH |
| 29 | 3-COOH |
| 30 | 4-COOH |
| 31 | 2-acetyl |
| 32 | 3-acetyl |
| 33 | 4-acetyl |
| 34 | 2-mesyl |
| 35 | 3-mesyl |
| 36 | 4-mesyl |
| 37 | 2-$NH_2$ |
| 38 | 3-$NH_2$ |
| 39 | 4-$NH_2$ |
| 40 | 2-$NO_2$ |
| 41 | 3-$NO_2$ |
| 42 | 4-$NO_2$ |
| 43 | 2-$CH_2OH$ |
| 44 | 3-$CH_2OH$ |
| 45 | 4-$CH_2OH$ |
| 46 | 2-$CH_2NH_2$ |
| 47 | 3-$CH_2NH_2$ |
| 48 | 4-$CH_2NH_2$ |
| 49 | 2-OEt |
| 50 | 3-OEt |
| 51 | 4-OEt |
| 52 | 2-CHO |
| 53 | 3-CHO |
| 54 | 4-CHO |

TABLE 2

(Ia'-1-2)

| No. | $R^{17}$ |
|---|---|
| 1 | 2-Me |
| 2 | 3-Me |
| 3 | 4-Me |
| 4 | 2-OMe |

TABLE 2-continued (Ia'-1-2)

| No. | R$^{17}$ |
|---|---|
| 5 | 3-OMe |
| 6 | 4-OMe |
| 7 | 2-SMe |
| 8 | 3-SMe |
| 9 | 4-SMe |
| 10 | 2-OH |
| 11 | 3-OH |
| 12 | 4-OH |
| 13 | 2-F |
| 14 | 3-F |
| 15 | 4-F |
| 16 | 2-Cl |
| 17 | 3-Cl |
| 18 | 4-Cl |
| 19 | 2-CF$_3$ |
| 20 | 3-CF$_3$ |
| 21 | 4-CF$_3$ |
| 22 | 2-OCF$_3$ |
| 23 | 3-OCF$_3$ |
| 24 | 4-OCF$_3$ |
| 25 | 2-CN |
| 26 | 3-CN |
| 27 | 4-CN |
| 28 | 2-COOH |
| 29 | 3-COOH |
| 30 | 4-COOH |
| 31 | 2-acetyl |
| 32 | 3-acetyl |
| 33 | 4-acetyl |
| 34 | 2-mesyl |
| 35 | 3-mesyl |
| 36 | 4-mesyl |
| 37 | 2-NH$_2$ |
| 38 | 3-NH$_2$ |
| 39 | 4-NH$_2$ |
| 40 | 2-NO$_2$ |
| 41 | 3-NO$_2$ |
| 42 | 4-NO$_2$ |
| 43 | 2-CH$_2$OH |
| 44 | 3-CH$_2$OH |
| 45 | 4-CH$_2$OH |
| 46 | 2-CH$_2$NH$_2$ |
| 47 | 3-CH$_2$NH$_2$ |
| 48 | 4-CH$_2$NH$_2$ |
| 49 | 2-OEt |
| 50 | 3-OEt |
| 51 | 4-OEt |
| 52 | 2-CHO |
| 53 | 3-CHO |
| 54 | 4-CHO |

TABLE 3

(Ia'-1-3)

| No. | R$^{17}$ |
|---|---|
| 1 | 2-Me |
| 2 | 3-Me |
| 3 | 2-OMe |
| 4 | 3-OMe |
| 5 | 2-SMe |
| 6 | 3-SMe |
| 7 | 2-OH |
| 8 | 3-OH |
| 9 | 2-F |
| 10 | 3-F |
| 11 | 2-Cl |
| 12 | 3-Cl |
| 13 | 2-CF$_3$ |
| 14 | 3-CF$_3$ |
| 15 | 2-OCF$_3$ |
| 16 | 3-OCF$_3$ |
| 17 | 2-CN |
| 18 | 3-CN |
| 19 | 2-COOH |
| 20 | 3-COOH |
| 21 | 2-acetyl |
| 22 | 3-acetyl |
| 23 | 2-mesyl |
| 24 | 3-mesyl |
| 25 | 2-NH$_2$ |
| 26 | 3-NH$_2$ |
| 27 | 2-NO$_2$ |
| 28 | 3-NO$_2$ |
| 29 | 2-CH$_2$OH |
| 30 | 3-CH$_2$OH |
| 31 | 2-CH$_2$NH$_2$ |
| 32 | 3-CH$_2$NH$_2$ |
| 33 | 2-OEt |
| 34 | 3-OEt |
| 35 | 2-CHO |
| 36 | 3-CHO |

TABLE 4

(Ia'-1-4)

| No. | R$^{17}$ |
|---|---|
| 1 | Me |
| 2 | Boc |
| 3 | benzyl ester of acetate (–C(=O)O–CH$_2$–Ph) |
| 4 | acetyl |
| 5 | cyclopentyl methyl ketone (–C(=O)–cyclopentyl) |
| 6 | benzoyl |
| 7 | 2-naphthyl methyl ketone (–C(=O)–2-naphthyl) |
| 8 | 4-pyridyl methyl ketone (–C(=O)–4-pyridyl) |
| 9 | 2-thienyl methyl ketone (–C(=O)–2-thienyl) |
| 10 | 2-furyl methyl ketone (–C(=O)–2-furyl) |
| 11 | phenoxyacetone (–C(=O)–CH$_2$–O–Ph) |
| 12 | benzyl methyl ketone (–C(=O)–CH$_2$–Ph) |
| 13 | cinnamoyl methyl (–C(=O)–CH=CH–Ph) |
| 14 | –C(=O)–CH(Ph)$_2$ |
| 15 | –C(=O)–NMe$_2$ |
| 16 | 1H-indol-3-yl glyoxylyl (–C(=O)–C(=O)–indol-3-yl) |
| 17 | mesyl |
| 18 | 4-methylphenylsulfonyl (tosyl) |

TABLE 4-continued (Ia'-1-4)

[Structure: 3,3-dimethyl-3,4-dihydroisoquinoline with =CH-C(=O)-piperidine-N-R17 substituent]

| No. | R17 |
|-----|-----|
| 19 | methylsulfonyl-naphthalenyl |
| 20 | methylsulfonyl-thienyl |
| 21 | methylsulfonyl-furanyl |
| 22 | methylsulfonyl-styryl |

TABLE 5

(Ia'-1-5)

[Structure: R7-substituted 3,3-dimethyl-3,4-dihydroisoquinoline with =CH-C(=O)-phenyl substituent]

| No. | R7 |
|-----|-----|
| 1 | 6-Me |
| 2 | 7-Me |
| 3 | 6-OMe |
| 4 | 7-OMe |

TABLE 5-continued (Ia'-1-5)

| No. | R7 |
|-----|-----|
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-$CF_3$ |
| 14 | 7-$CF_3$ |
| 15 | 6-$OCF_3$ |
| 16 | 7-$OCF_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-$NH_2$ |
| 26 | 7-$NH_2$ |
| 27 | 6-$NO_2$ |
| 28 | 7-$NO_2$ |
| 29 | 6-$CH_2OH$ |
| 30 | 7-$CH_2OH$ |
| 31 | 6-$CH_2NH_2$ |
| 32 | 7-$CH_2NH_2$ |
| 33 | 6-OEt |
| 34 | 7-OEt |
| 35 | 6-CHO |
| 36 | 7-CHO |

TABLE 6

(Ia'-1-6)

[Structure: R7-substituted 3,3-dimethyl-3,4-dihydroisoquinoline with =CH-C(=O)-cyclohexyl substituent]

| No. | R7 |
|-----|-----|
| 1 | 6-Me |
| 2 | 7-Me |
| 3 | 6-OMe |
| 4 | 7-OMe |

TABLE 6-continued (Ia'-1-6)

| No. | R⁷ |
|---|---|
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF₃ |
| 14 | 7-CF₃ |
| 15 | 6-OCF₃ |
| 16 | 7-OCF₃ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH₂ |
| 26 | 7-NH₂ |
| 27 | 6-NO₂ |
| 28 | 7-NO₂ |
| 29 | 6-CH₂OH |
| 30 | 7-CH₂OH |
| 31 | 6-CH₂NH₂ |
| 32 | 7-CH₂NH₂ |
| 33 | 6-OEt |
| 34 | 7-OEt |
| 35 | 6-CHO |
| 36 | 7-CHO |

TABLE 7

(Ia'-1-7)

| No. | R⁷ |
|---|---|
| 1 | 6-Me |
| 2 | 7-Me |
| 3 | 6-OMe |
| 4 | 7-OMe |

TABLE 7-continued (Ia'-1-7)

| No. | R⁷ |
|---|---|
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF₃ |
| 14 | 7-CF₃ |
| 15 | 6-OCF₃ |
| 16 | 7-OCF₃ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH₂ |
| 26 | 7-NH₂ |
| 27 | 6-NO₂ |
| 28 | 7-NO₂ |
| 29 | 6-CH₂OH |
| 30 | 7-CH₂OH |
| 31 | 6-CH₂NH₂ |
| 32 | 7-CH₂NH₂ |
| 33 | 6-OEt |
| 34 | 7-OEt |
| 35 | 6-CHO |
| 36 | 7-CHO |

TABLE 8

(Ia'-1-8)

| No. | R⁷ |
|---|---|
| 1 | 6-Me |
| 2 | 7-Me |
| 3 | 6-OMe |

TABLE 8-continued (Ia'-1-8)

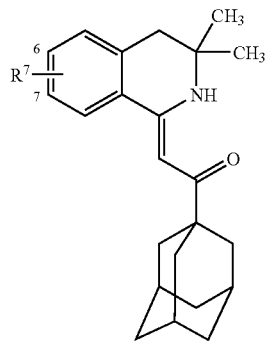

| No. | R⁷ |
|---|---|
| 4 | 7-OMe |
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |

TABLE 9

(Ia'-2-1)

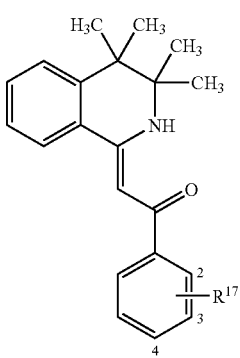

| No. | R¹⁷ |
|---|---|
| 1 | 2-Me |
| 2 | 3-Me |

TABLE 9-continued (Ia'-2-1)

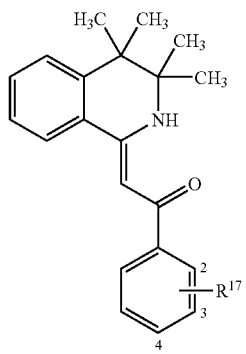

| No. | R¹⁷ |
|---|---|
| 3 | 4-Me |
| 4 | 2-OMe |
| 5 | 3-OMe |
| 6 | 4-OMe |
| 7 | 2-SMe |
| 8 | 3-SMe |
| 9 | 4-SMe |
| 10 | 2-OH |
| 11 | 3-OH |
| 12 | 4-OH |
| 13 | 2-F |
| 14 | 3-F |
| 15 | 4-F |
| 16 | 2-Cl |
| 17 | 3-Cl |
| 18 | 4-Cl |
| 19 | 2-CF$_3$ |
| 20 | 3-CF$_3$ |
| 21 | 4-CF$_3$ |
| 22 | 2-OCF$_3$ |
| 23 | 3-OCF$_3$ |
| 24 | 4-OCF$_3$ |
| 25 | 2-CN |
| 26 | 3-CN |
| 27 | 4-CN |
| 28 | 2-COOH |
| 29 | 3-COOH |
| 30 | 4-COOH |
| 31 | 2-acetyl |
| 32 | 3-acetyl |
| 33 | 4-acetyl |
| 34 | 2-mesyl |
| 35 | 3-mesyl |
| 36 | 4-mesyl |
| 37 | 2-NH$_2$ |
| 38 | 3-NH$_2$ |
| 39 | 4-NH$_2$ |
| 40 | 2-NO$_2$ |
| 41 | 3-NO$_2$ |
| 42 | 4-NO$_2$ |
| 43 | 2-CH$_2$OH |
| 44 | 3-CH$_2$OH |
| 45 | 4-CH$_2$OH |
| 46 | 2-CH$_2$NH$_2$ |
| 47 | 3-CH$_2$NH$_2$ |
| 48 | 4-CH$_2$NH$_2$ |
| 49 | 2-OEt |
| 50 | 3-OEt |
| 51 | 4-OEt |
| 52 | 2-CHO |
| 53 | 3-CHO |
| 54 | 4-CHO |

TABLE 10

(Ia'-2-2)

[Structure: 4,4,3,3-tetramethyl-3,4-dihydroisoquinoline with =CH-C(=O)- linked to cyclohexyl bearing R¹⁷ at positions 2,3,4]

| No. | R¹⁷ |
|---|---|
| 1 | 2-Me |
| 2 | 3-Me |
| 3 | 4-Me |
| 4 | 2-OMe |
| 5 | 3-OMe |
| 6 | 4-OMe |
| 7 | 2-SMe |
| 8 | 3-SMe |
| 9 | 4-SMe |
| 10 | 2-OH |
| 11 | 3-OH |
| 12 | 4-OH |
| 13 | 2-F |
| 14 | 3-F |
| 15 | 4-F |
| 16 | 2-Cl |
| 17 | 3-Cl |
| 18 | 4-Cl |
| 19 | 2-$CF_3$ |
| 20 | 3-$CF_3$ |
| 21 | 4-$CF_3$ |
| 22 | 2-$OCF_3$ |
| 23 | 3-$OCF_3$ |
| 24 | 4-$OCF_3$ |
| 25 | 2-CN |
| 26 | 3-CN |
| 27 | 4-CN |
| 28 | 2-COOH |
| 29 | 3-COOH |
| 30 | 4-COOH |
| 31 | 2-acetyl |
| 32 | 3-acetyl |
| 33 | 4-acetyl |
| 34 | 2-mesyl |
| 35 | 3-mesyl |
| 36 | 4-mesyl |
| 37 | 2-$NH_2$ |
| 38 | 3-$NH_2$ |
| 39 | 4-$NH_2$ |
| 40 | 2-$NO_2$ |
| 41 | 3-$NO_2$ |
| 42 | 4-$NO_2$ |
| 43 | 2-$CH_2OH$ |
| 44 | 3-$CH_2OH$ |
| 45 | 4-$CH_2OH$ |
| 46 | 2-$CH_2NH_2$ |
| 47 | 3-$CH_2NH_2$ |
| 48 | 4-$CH_2NH_2$ |
| 49 | 2-OEt |
| 50 | 3-OEt |
| 51 | 4-OEt |
| 52 | 2-CHO |
| 53 | 3-CHO |
| 54 | 4-CHO |

TABLE 11

(Ia'-2-3)

[Structure: 4,4,3,3-tetramethyl-3,4-dihydroisoquinoline with =CH-C(=O)- linked to pyridin-4-yl bearing R¹⁷ at positions 2,3]

| No. | R¹⁷ |
|---|---|
| 1 | 2-Me |
| 2 | 3-Me |
| 3 | 2-OMe |
| 4 | 3-OMe |
| 5 | 2-SMe |
| 6 | 3-SMe |
| 7 | 2-OH |
| 8 | 3-OH |
| 9 | 2-F |
| 10 | 3-F |
| 11 | 2-Cl |
| 12 | 3-Cl |
| 13 | 2-$CF_3$ |
| 14 | 3-$CF_3$ |
| 15 | 2-$OCF_3$ |
| 16 | 3-$OCF_3$ |
| 17 | 2-CN |
| 18 | 3-CN |
| 19 | 2-COOH |
| 20 | 3-COOH |
| 21 | 2-acetyl |
| 22 | 3-acetyl |
| 23 | 2-mesyl |
| 24 | 3-mesyl |
| 25 | 2-$NH_2$ |
| 26 | 3-$NH_2$ |
| 27 | 2-$NO_2$ |
| 28 | 3-$NO_2$ |
| 29 | 2-$CH_2OH$ |
| 30 | 3-$CH_2OH$ |
| 31 | 2-$CH_2NH_2$ |
| 32 | 3-$CH_2NH_2$ |
| 33 | 2-OEt |
| 34 | 3-OEt |
| 35 | 2-CHO |
| 36 | 3-CHO |

TABLE 12

(Ia'-2-4)

| No. | R$^{17}$ |
|---|---|
| 1 | Me |
| 2 | Boc |
| 3 | -C(=O)-O-CH$_2$-C$_6$H$_5$ (benzyloxycarbonyl) |
| 4 | acetyl |
| 5 | -C(=O)-cyclopentyl |
| 6 | benzoyl |
| 7 | -C(=O)-(2-naphthyl) |
| 8 | -C(=O)-(4-pyridyl) |

TABLE 12-continued (Ia'-2-4)

| No. | R$^{17}$ |
|---|---|
| 9 | -C(=O)-(2-thienyl) |
| 10 | -C(=O)-(2-furyl) |
| 11 | -C(=O)-CH$_2$-O-C$_6$H$_5$ |
| 12 | -C(=O)-CH$_2$-C$_6$H$_5$ |
| 13 | -C(=O)-CH=CH-C$_6$H$_5$ |
| 14 | -C(=O)-CH(Ph)$_2$ |
| 15 | -C(=O)-NMe$_2$ |

TABLE 12-continued (Ia'-2-4)

| No. | R¹⁷ |
|---|---|
| 16 | (1-acetyl-1H-indol-3-yl)methanone-like group (acetyl-indole) |
| 17 | mesyl |
| 18 | 4-methylphenylsulfonylmethyl (mesyl-tolyl) |
| 19 | 1-naphthylsulfonylmethyl |
| 20 | 2-thienylsulfonylmethyl |
| 21 | 2-furylsulfonylmethyl |

TABLE 12-continued (Ia'-2-4)

| No. | R¹⁷ |
|---|---|
| 22 | (E)-2-phenylvinyl methyl sulfone |

TABLE 13

(Ia'-2-5)

| No. | R⁷ |
|---|---|
| 1 | 6-Me |
| 2 | 7-Me |
| 3 | 6-OMe |
| 4 | 7-OMe |
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF₃ |
| 14 | 7-CF₃ |
| 15 | 6-OCF₃ |
| 16 | 7-OCF₃ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH₂ |

TABLE 13-continued (Ia'-2-5)

| No. | R⁷ |
|---|---|
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |

TABLE 14

(Ia'-2-6)

| No. | R⁷ |
|---|---|
| 1 | 6-Me |
| 2 | 7-Me |
| 3 | 6-OMe |
| 4 | 7-OMe |
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |

TABLE 14-continued (Ia'-2-6)

| No. | R⁷ |
|---|---|
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |

TABLE 15

(Ia'-2-7)

| No. | R⁷ |
|---|---|
| 1 | 6-Me |
| 2 | 7-Me |
| 3 | 6-OMe |
| 4 | 7-OMe |
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |
| 19 | 6-COOH |
| 20 | 7-COOH |
| 21 | 6-acetyl |

TABLE 15-continued
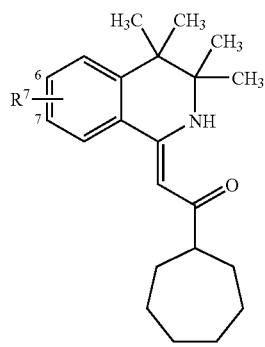
(Ia'-2-7)
| No. | R[7] |
|---|---|
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |
TABLE 16
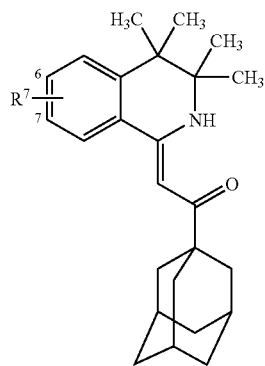
(Ia'-2-8)
| No. | R[7] |
|---|---|
| 1 | 6-Me |
| 2 | 7-Me |
| 3 | 6-OMe |
| 4 | 7-OMe |
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
TABLE 16-continued
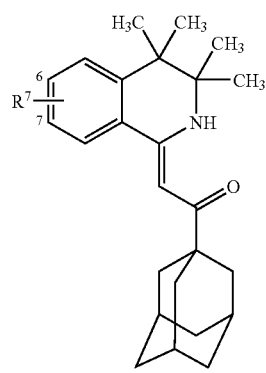
(Ia'-2-8)
| No. | R[7] |
|---|---|
| 16 | 7-OCF$_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |
TABLE 17
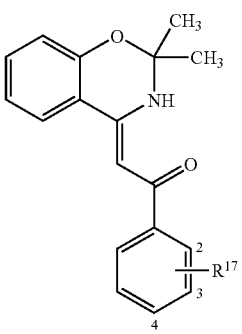
(Ia'-3-1)
| No. | R[17] |
|---|---|
| 1 | 2-Me |
| 2 | 3-Me |
| 3 | 4-Me |
| 4 | 2-OMe |
| 5 | 3-OMe |
| 6 | 4-OMe |
| 7 | 2-S Me |
| 8 | 3-S Me |
| 9 | 4-S Me |
| 10 | 2-OH |

TABLE 17-continued (Ia'-3-1)

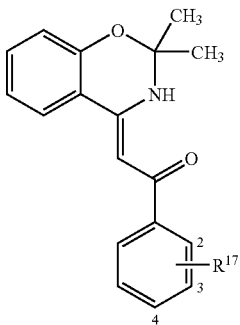

| No. | R17 |
|---|---|
| 11 | 3-OH |
| 12 | 4-OH |
| 13 | 2-F |
| 14 | 3-F |
| 15 | 4-F |
| 16 | 2-Cl |
| 17 | 3-Cl |
| 18 | 4-Cl |
| 19 | 2-CF3 |
| 20 | 3-CF3 |
| 21 | 4-CF3 |
| 22 | 2-OCF3 |
| 23 | 3-OCF3 |
| 24 | 4-OCF3 |
| 25 | 2-CN |
| 26 | 3-CN |
| 27 | 4-CN |
| 28 | 2-COOH |
| 29 | 3-COOH |
| 30 | 4-COOH |
| 31 | 2-acetyl |
| 32 | 3-acetyl |
| 33 | 4-acetyl |
| 34 | 2-mesyl |
| 35 | 3-mesyl |
| 36 | 4-mesyl |
| 37 | 2-NH2 |
| 38 | 3-NH2 |
| 39 | 4-NH2 |
| 40 | 2-NO2 |
| 41 | 3-NO2 |
| 42 | 4-NO2 |
| 43 | 2-CH2OH |
| 44 | 3-CH2OH |
| 45 | 4-CH2OH |
| 46 | 2-CH2NH2 |
| 47 | 3-CH2NH2 |
| 48 | 4-CH2NH2 |
| 49 | 2-OEt |
| 50 | 3-OEt |
| 51 | 4-OEt |
| 52 | 2-CHO |
| 53 | 3-CHO |
| 54 | 4-CHO |

TABLE 18

(Ia'-3-2)

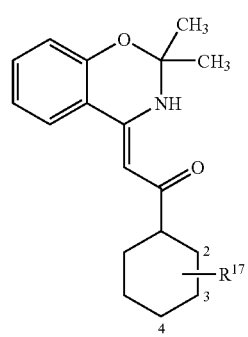

| No. | R17 |
|---|---|
| 1 | 2-Me |
| 2 | 3-Me |
| 3 | 4-Me |
| 4 | 2-OMe |
| 5 | 3-OMe |
| 6 | 4-OMe |
| 7 | 2-S Me |
| 8 | 3-S Me |
| 9 | 4-S Me |
| 10 | 2-OH |
| 11 | 3-OH |
| 12 | 4-OH |
| 13 | 2-F |
| 14 | 3-F |
| 15 | 4-F |
| 16 | 2-Cl |
| 17 | 3-Cl |
| 18 | 4-Cl |
| 19 | 2-CF3 |
| 20 | 3-CF3 |
| 21 | 4-CF3 |
| 22 | 2-OCF3 |
| 23 | 3-OCF3 |
| 24 | 4-OCF3 |
| 25 | 2-CN |
| 26 | 3-CN |
| 27 | 4-CN |
| 28 | 2-COOH |
| 29 | 3-COOH |
| 30 | 4-COOH |
| 31 | 2-acetyl |
| 32 | 3-acetyl |
| 33 | 4-acetyl |
| 34 | 2-mesyl |
| 35 | 3-mesyl |
| 36 | 4-mesyl |
| 37 | 2-NH2 |
| 38 | 3-NH2 |
| 39 | 4-NH2 |
| 40 | 2-NO2 |
| 41 | 3-NO2 |
| 42 | 4-NO2 |
| 43 | 2-CH2OH |
| 44 | 3-CH2OH |
| 45 | 4-CH2OH |
| 46 | 2-CH2NH2 |
| 47 | 3-CH2NH2 |
| 48 | 4-CH2NH2 |
| 49 | 2-OEt |
| 50 | 3-OEt |
| 51 | 4-OEt |
| 52 | 2-CHO |
| 53 | 3-CHO |
| 54 | 4-CHO |

TABLE 19

(Ia'-3-3)

| No. | R17 |
|---|---|
| 1 | 2-Me |
| 2 | 3-Me |
| 3 | 2-OMe |
| 4 | 3-OMe |
| 5 | 2-SMe |
| 6 | 3-SMe |
| 7 | 2-OH |
| 8 | 3-OH |
| 9 | 2-F |
| 10 | 3-F |
| 11 | 2-Cl |
| 12 | 3-Cl |
| 13 | 2-CF$_3$ |
| 14 | 3-CF$_3$ |
| 15 | 2-OCF$_3$ |
| 16 | 3-OCF$_3$ |
| 17 | 2-CN |
| 18 | 3-CN |
| 19 | 2-COOH |
| 20 | 3-COOH |
| 21 | 2-acetyl |
| 22 | 3-acetyl |
| 23 | 2-mesyl |
| 24 | 3-mesyl |
| 25 | 2-NH$_2$ |
| 26 | 3-NH$_2$ |
| 27 | 2-NO$_2$ |
| 28 | 3-NO$_2$ |
| 29 | 2-CH$_2$OH |
| 30 | 3-CH$_2$OH |
| 31 | 2-CH$_2$NH$_2$ |
| 32 | 3-CH$_2$NH$_2$ |
| 33 | 2-OEt |
| 34 | 3-OEt |
| 35 | 2-CHO |
| 36 | 3-CHO |

TABLE 20

(Ia'-3-4)

| No. | R17 |
|---|---|
| 1 | Me |
| 2 | Boc |
| 3 | benzyloxycarbonylmethyl (CH$_2$C(O)OCH$_2$Ph) |
| 4 | acetyl |
| 5 | cyclopentylcarbonylmethyl |
| 6 | benzoyl |
| 7 | 2-naphthoyl |
| 8 | isonicotinoyl |

TABLE 20-continued (Ia'-3-4)

| No. | R17 |
|---|---|
| 9 | 1-(thiophen-2-yl)ethanone-yl |
| 10 | 1-(furan-2-yl)ethanone-yl |
| 11 | phenoxyacetone-yl |
| 12 | phenylacetone-yl |
| 13 | (E)-4-phenylbut-3-en-2-one-yl |
| 14 | 1,1-diphenylpropan-2-one-yl |
| 15 | N,N-dimethylacetamide-yl |
| 16 | 1-(1H-indol-3-yl)propane-1,2-dione-yl |
| 17 | mesyl |
| 18 | 4-methylphenylsulfonyl |
| 19 | naphthalen-1-ylsulfonyl |
| 20 | thiophen-2-ylsulfonyl |
| 21 | furan-2-ylsulfonyl |
| 22 | (E)-styrylsulfonyl |

TABLE 21
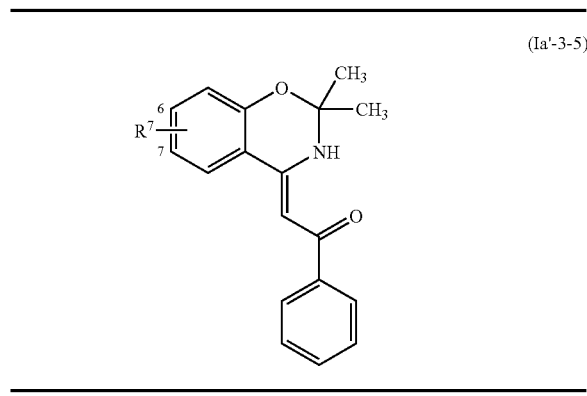
(Ia'-3-5)
| No. | R⁷ |
|---|---|
| 1 | 6-Me |
| 2 | 7-Me |
| 3 | 6-OMe |
| 4 | 7-OMe |
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |
TABLE 22
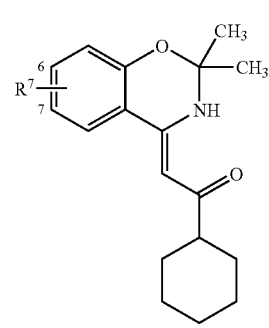
(Ia'-3-6)
| No. | R⁷ |
|---|---|
| 1 | 6-Me |
| 2 | 7-Me |
| 3 | 6-OMe |
| 4 | 7-OMe |
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |

TABLE 23

(Ia'-3-7)

| No. | R⁷ |
|---|---|
| 1 | 6-Me |
| 2 | 7-Me |
| 3 | 6-OMe |
| 4 | 7-OMe |
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |

TABLE 24

(Ia'-3-8)

| No. | R⁷ |
|---|---|
| 1 | 6-Me |
| 2 | 7-Me |
| 3 | 6-OMe |
| 4 | 7-OMe |
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |

TABLE 25

(Ia'-4-1)

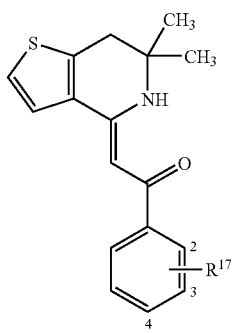

| No. | R$^{17}$ |
|---|---|
| 1 | 2-Me |
| 2 | 3-Me |
| 3 | 4-Me |
| 4 | 2-OMe |
| 5 | 3-OMe |
| 6 | 4-OMe |
| 7 | 2-SMe |
| 8 | 3-SMe |
| 9 | 4-SMe |
| 10 | 2-OH |
| 11 | 3-OH |
| 12 | 4-OH |
| 13 | 2-F |
| 14 | 3-F |
| 15 | 4-F |
| 16 | 2-Cl |
| 17 | 3-Cl |
| 18 | 4-Cl |
| 19 | 2-CF$_3$ |
| 20 | 3-CF$_3$ |
| 21 | 4-CF$_3$ |
| 22 | 2-OCF$_3$ |
| 23 | 3-OCF$_3$ |
| 24 | 4-OCF$_3$ |
| 25 | 2-CN |
| 26 | 3-CN |
| 27 | 4-CN |
| 28 | 2-COOH |
| 29 | 3-COOH |
| 30 | 4-COOH |
| 31 | 2-acetyl |
| 32 | 3-acetyl |
| 33 | 4-acetyl |
| 34 | 2-mesyl |
| 35 | 3-mesyl |
| 36 | 4-mesyl |
| 37 | 2-NH$_2$ |
| 38 | 3-NH$_2$ |
| 39 | 4-NH$_2$ |
| 40 | 2-NO$_2$ |
| 41 | 3-NO$_2$ |
| 42 | 4-NO$_2$ |
| 43 | 2-CH$_2$OH |
| 44 | 3-CH$_2$OH |
| 45 | 4-CH$_2$OH |
| 46 | 2-CH$_2$NH$_2$ |
| 47 | 3-CH$_2$NH$_2$ |
| 48 | 4-CH$_2$NH$_2$ |
| 49 | 2-OEt |
| 50 | 3-OEt |
| 51 | 4-OEt |
| 52 | 2-CHO |
| 53 | 3-CHO |
| 54 | 4-CHO |

TABLE 26

(Ia'-4-2)

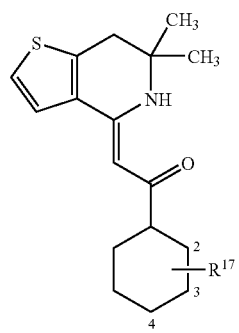

| No. | R$^{17}$ |
|---|---|
| 1 | 2-Me |
| 2 | 3-Me |
| 3 | 4-Me |
| 4 | 2-OMe |
| 5 | 3-OMe |
| 6 | 4-OMe |
| 7 | 2-SMe |
| 8 | 3-SMe |
| 9 | 4-SMe |
| 10 | 2-OH |
| 11 | 3-OH |
| 12 | 4-OH |
| 13 | 2-F |
| 14 | 3-F |
| 15 | 4-F |
| 16 | 2-Cl |
| 17 | 3-Cl |
| 18 | 4-Cl |
| 19 | 2-CF$_3$ |
| 20 | 3-CF$_3$ |
| 21 | 4-CF$_3$ |
| 22 | 2-OCF$_3$ |
| 23 | 3-OCF$_3$ |
| 24 | 4-OCF$_3$ |
| 25 | 2-CN |
| 26 | 3-CN |
| 27 | 4-CN |
| 28 | 2-COOH |
| 29 | 3-COOH |
| 30 | 4-COOH |
| 31 | 2-acetyl |
| 32 | 3-acetyl |
| 33 | 4-acetyl |
| 34 | 2-mesyl |
| 35 | 3-mesyl |
| 36 | 4-mesyl |
| 37 | 2-NH$_2$ |
| 38 | 3-NH$_2$ |
| 39 | 4-NH$_2$ |
| 40 | 2-NO$_2$ |
| 41 | 3-NO$_2$ |
| 42 | 4-NO$_2$ |
| 43 | 2-CH$_2$OH |
| 44 | 3-CH$_2$OH |
| 45 | 4-CH$_2$OH |
| 46 | 2-CH$_2$NH$_2$ |
| 47 | 3-CH$_2$NH$_2$ |
| 48 | 4-CH$_2$NH$_2$ |
| 49 | 2-OEt |
| 50 | 3-OEt |
| 51 | 4-OEt |
| 52 | 2-CHO |
| 53 | 3-CHO |
| 54 | 4-CHO |

TABLE 27

(Ia'-4-3)

| No. | R17 |
|---|---|
| 1 | 2-Me |
| 2 | 3-Me |
| 3 | 2-OMe |
| 4 | 3-OMe |
| 5 | 2-SMe |
| 6 | 3-SMe |
| 7 | 2-OH |
| 8 | 3-OH |
| 9 | 2-F |
| 10 | 3-F |
| 11 | 2-Cl |
| 12 | 3-Cl |
| 13 | 2-CF$_3$ |
| 14 | 3-CF$_3$ |
| 15 | 2-OCF$_3$ |
| 16 | 3-OCF$_3$ |
| 17 | 2-CN |
| 18 | 3-CN |
| 19 | 2-COOH |
| 20 | 3-COOH |
| 21 | 2-acetyl |
| 22 | 3-acetyl |
| 23 | 2-mesyl |
| 24 | 3-mesyl |
| 25 | 2-NH$_2$ |
| 26 | 3-NH$_2$ |
| 27 | 2-NO$_2$ |
| 28 | 3-NO$_2$ |
| 29 | 2-CH$_2$OH |
| 30 | 3-CH$_2$OH |
| 31 | 2-CH$_2$NH$_2$ |
| 32 | 3-CH$_2$NH$_2$ |
| 33 | 2-OEt |
| 34 | 3-OEt |
| 35 | 2-CHO |
| 36 | 3-CHO |

TABLE 28

(Ia'-4-4)

| No. | R17 |
|---|---|
| 1 | Me |
| 2 | Boc |
| 3 | (CH$_3$C(O)CH$_2$-O-phenyl) |
| 4 | acetyl |
| 5 | (cyclopentyl ketone) |
| 6 | benzoyl |
| 7 | (2-naphthyl ketone) |
| 8 | (4-pyridyl ketone) |
| 9 | (2-thienyl ketone) |

TABLE 28-continued
(Ia'-4-4)
| No. | R17 |
|---|---|
| 10 | 2-furyl-C(O)-CH2- |
| 11 | PhO-CH2-C(O)-CH2- |
| 12 | Ph-CH2-C(O)-CH2- |
| 13 | Ph-CH=CH-C(O)-CH2- |
| 14 | Ph2CH-C(O)-CH2- |
| 15 | Me2N-C(O)-CH2- |
| 16 | 3-indolyl-C(O)-C(O)-CH2- |
| 17 | mesyl |
| 18 | 4-Me-C6H4-SO2- |
| 19 | 1-naphthyl-SO2- |
| 20 | 2-thienyl-SO2- |
| 21 | 2-furyl-SO2- |
| 22 | Ph-CH=CH-SO2- |
TABLE 29
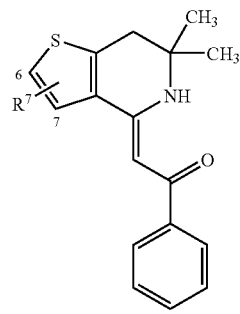
(Ia'-4-5)
| No. | R7 |
|---|---|
| 1 | 6-Me |
| 2 | 7-Me |
| 3 | 6-OMe |
| 4 | 7-OMe |
| 5 | 6-SMe |

TABLE 29-continued

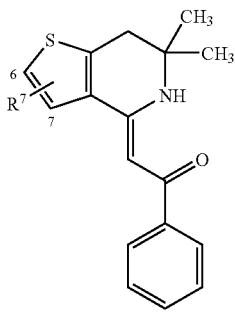

(Ia'-4-5)

| No. | R⁷ |
|---|---|
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |

TABLE 30

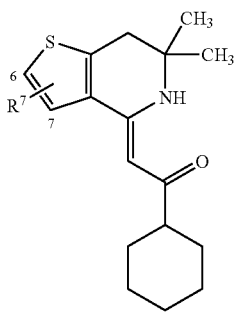

(Ia'-4-6)

| No. | R⁷ |
|---|---|
| 1 | 6-Me |
| 2 | 7-Me |
| 3 | 6-OMe |
| 4 | 7-OMe |
| 5 | 6-SMe |
| 6 | 7-SMe |

TABLE 30-continued

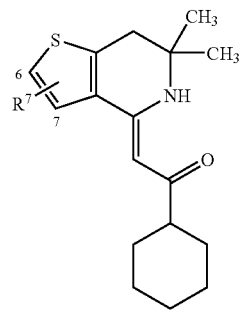

(Ia'-4-6)

| No. | R⁷ |
|---|---|
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |

TABLE 31

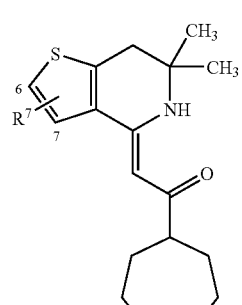

(Ia'-4-7)

| No. | R⁷ |
|---|---|
| 1 | 6-Me |
| 2 | 7-Me |
| 3 | 6-OMe |
| 4 | 7-OMe |
| 5 | 6-SMe |
| 6 | 7-SMe |

TABLE 31-continued (Ia'-4-7)

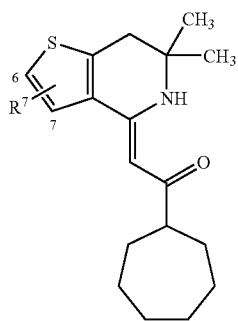

| No. | R⁷ |
|---|---|
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |

TABLE 32

(Ia'-4-8)

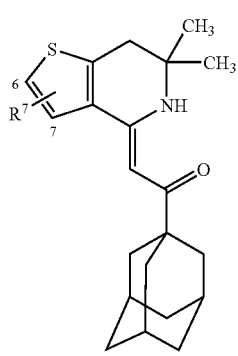

| No. | R⁷ |
|---|---|
| 1 | 6-Me |
| 2 | 7-Me |
| 3 | 6-OMe |
| 4 | 7-OMe |

TABLE 32-continued (Ia'-4-8)

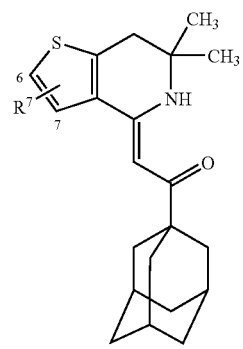

| No. | R⁷ |
|---|---|
| 5 | 6-SMe |
| 6 | 7-SMe |
| 7 | 6-OH |
| 8 | 7-OH |
| 9 | 6-F |
| 10 | 7-F |
| 11 | 6-Cl |
| 12 | 7-Cl |
| 13 | 6-CF$_3$ |
| 14 | 7-CF$_3$ |
| 15 | 6-OCF$_3$ |
| 16 | 7-OCF$_3$ |
| 17 | 6-CN |
| 18 | 8-CN |
| 19 | 6-COOH |
| 20 | 7-COOH |
| 21 | 6-acetyl |
| 22 | 7-acetyl |
| 23 | 6-mesyl |
| 24 | 7-mesyl |
| 25 | 6-NH$_2$ |
| 26 | 7-NH$_2$ |
| 27 | 6-NO$_2$ |
| 28 | 7-NO$_2$ |
| 29 | 6-CH$_2$OH |
| 30 | 7-CH$_2$OH |
| 31 | 6-CH$_2$NH$_2$ |
| 32 | 7-CH$_2$NH$_2$ |
| 33 | 6-OEt |
| 34 | 7-OEt |
| 35 | 6-CHO |
| 36 | 7-CHO |

TABLE 33

(Ia'-1-9)

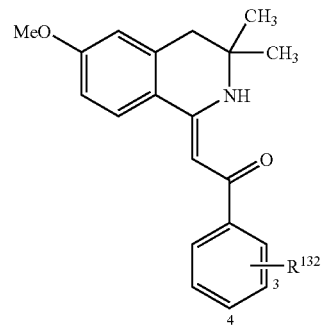

| No. | R¹³² |
|---|---|
| 1 | 3-CN |
| 2 | 3-NHAc |

TABLE 33-continued (Ia'-1-9)

| No. | R$^{132}$ |
|---|---|
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |
| 21 | 4-NHAc |
| 22 | 4-NH$_2$ |
| 23 | 4-MeO |

TABLE 33-continued (Ia'-1-9)

| No. | R$^{132}$ |
|---|---|
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 34

(Ia'-1-10)

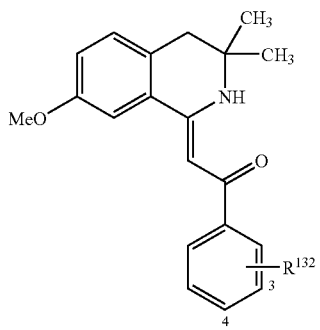

| No. | R[132] |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |
| 21 | 4-NHAc |

TABLE 34-continued (Ia'-1-10)

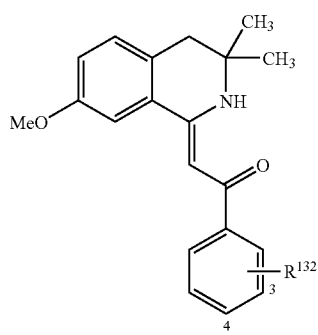

| No. | R[132] |
|---|---|
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 35

(Ia'-1-11)

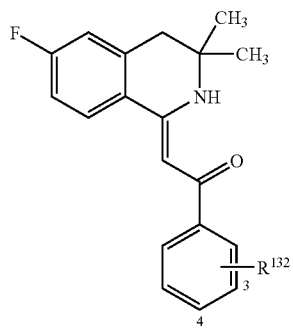

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)-3-pyridyl] |
| 19 | 3-NHCO-[3-(2-chlorophenyl)-5-methylisoxazol-4-yl] |
| 20 | 4-CN |
| 21 | 4-NHAc |

TABLE 35-continued (Ia'-1-11)

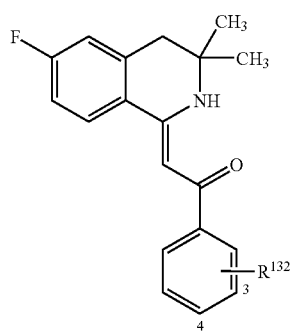

| No. | R¹³² |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)-3-pyridyl] |
| 38 | 4-NHCO-[3-(2-chlorophenyl)-5-methylisoxazol-4-yl] |

TABLE 36

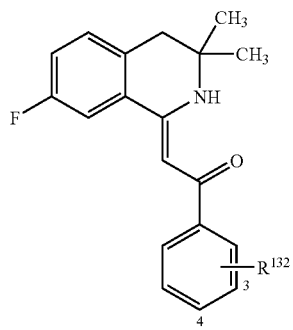

(Ia'-1-12)

| No. | R[132] |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 3- (1,3,4-oxadiazol-2-yl) |
| 14 | 3- (4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |
| 21 | 4-NHAc |

TABLE 36-continued

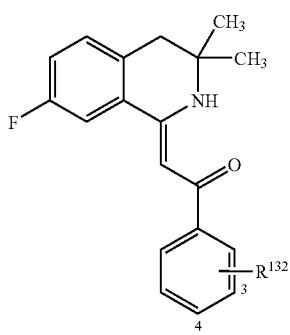

(Ia'-1-12)

| No. | R[132] |
|---|---|
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 4- (1,3,4-oxadiazol-2-yl) |
| 33 | 4- (4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 37

(Ia'-1-13)

[Structure: 6-chloro-3,3-dimethyl-3,4-dihydroisoquinoline with =CH-C(=O)-phenyl-R¹³² substituent]

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |
| 21 | 4-NHAc |
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 38
(Ia'-1-14)
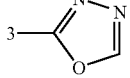
| No. | R[132] |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 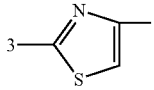 |
| 14 | 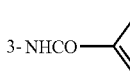 |
| 15 | 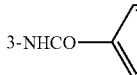 |
| 16 |  |
| 17 |  |
| 18 | 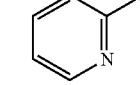 |
| 19 | 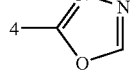 |
| 20 | 4-CN |
| 21 | 4-NHAc |
TABLE 38-continued
(Ia'-1-14)
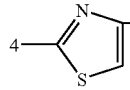
| No. | R[132] |
|---|---|
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 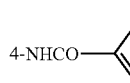 |
| 33 | 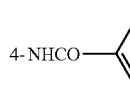 |
| 34 |  |
| 35 | 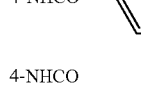 |
| 36 | 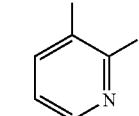 |
| 37 | 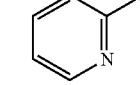 |
| 38 | 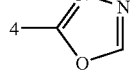 |

TABLE 39

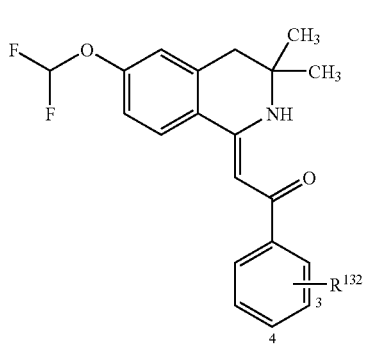

(Ia'-1-15)

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)-3-pyridyl] |
| 19 | 3-NHCO-[3-(2-chlorophenyl)-5-methylisoxazol-4-yl] |
| 20 | 4-CN |
| 21 | 4-NHAc |

TABLE 39-continued

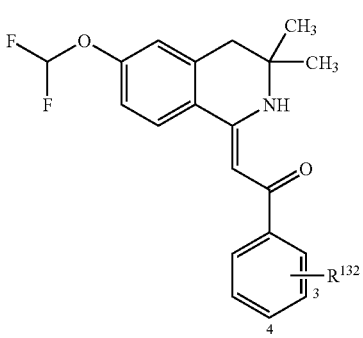

(Ia'-1-15)

| No. | R¹³² |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)-3-pyridyl] |
| 38 | 4-NHCO-[3-(2-chlorophenyl)-5-methylisoxazol-4-yl] |

TABLE 40

(Ia'-1-16)

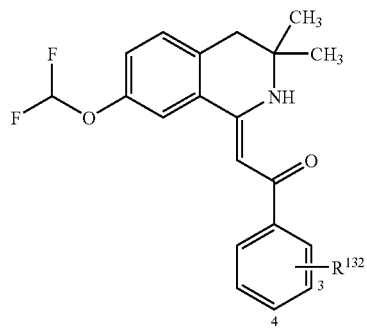

| No. | R132 |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |

13

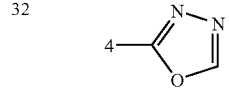

14

15  3-NHCO— (furan)

16  3-NHCO— (pyridine)

17  3-NHCO— (dimethoxyphenyl)

18  3-NHCO— (chlorophenoxy pyridine)

19  3-NHCO— (chlorophenyl methyl isoxazole)

| 20 | 4-CN |
| 21 | 4-NHAc |

TABLE 40-continued (Ia'-1-16)

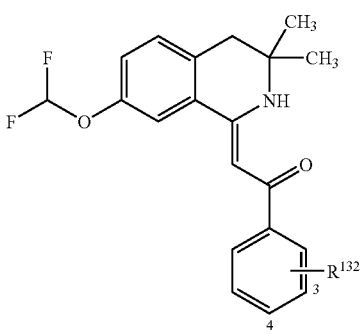

| No. | R132 |
|---|---|
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |

32

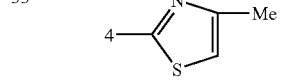

33

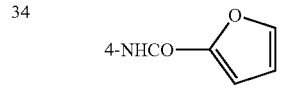

34  4-NHCO— (furan)

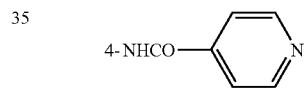

35  4-NHCO— (pyridine)

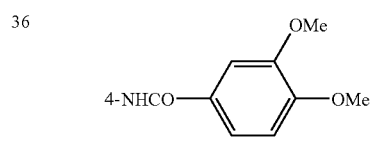

36  4-NHCO— (dimethoxyphenyl)

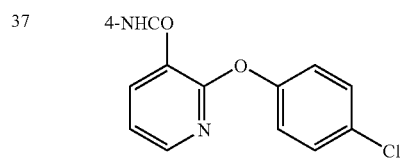

37  4-NHCO— (chlorophenoxy pyridine)

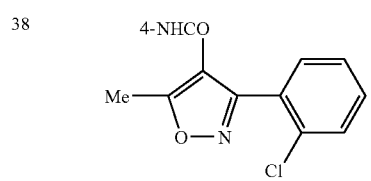

38  4-NHCO— (chlorophenyl methyl isoxazole)

TABLE 41
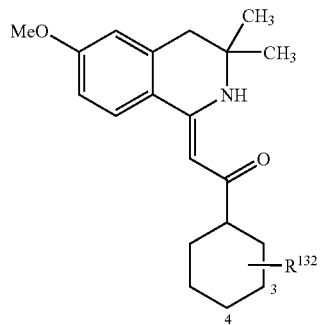
(Ia'-1-17)
| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 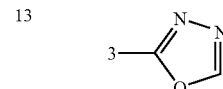 |
| 14 | 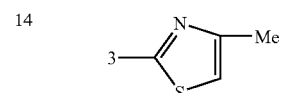 |
| 15 | 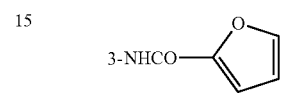 |
| 16 | 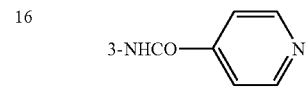 |
| 17 | 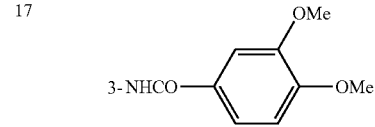 |
| 18 | 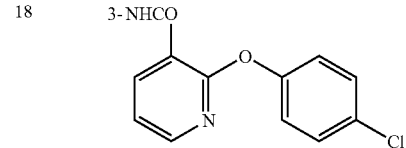 |
| 19 | 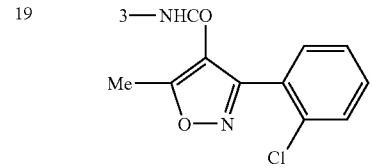 |
| 20 | 4-CN |
| 21 | 4-NHAc |
TABLE 41-continued
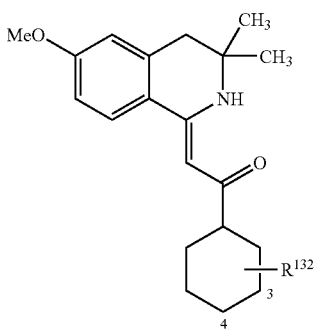
(Ia'-1-17)
| No. | R¹³² |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 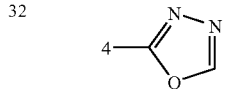 |
| 33 | 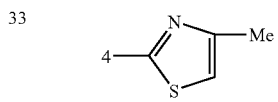 |
| 34 | 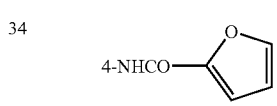 |
| 35 | 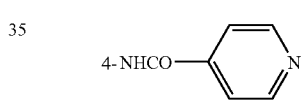 |
| 36 | 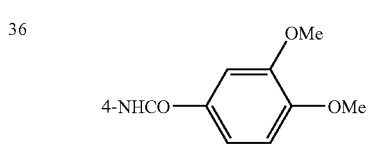 |
| 37 | 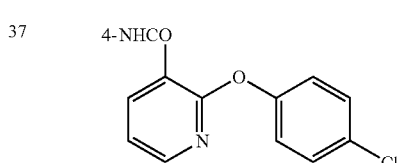 |
| 38 | 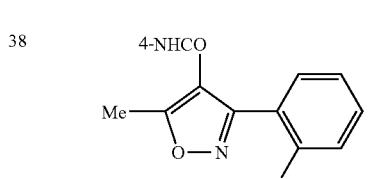 |

TABLE 42

(Ia'-1-18)

[Structure: 7-methoxy-3,3-dimethyl-3,4-dihydroisoquinoline with NH, connected via =CH-C(=O)- to a cyclohexyl group bearing R¹³²]

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[5-methyl-3-(2-chlorophenyl)isoxazol-4-yl] |
| 20 | 4-CN |
| 21 | 4-NHAc |
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[5-methyl-3-(2-chlorophenyl)isoxazol-4-yl] |

TABLE 43

(Ia'-1-19)

| No. | R^132 |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |
| 21 | 4-NHAc |
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 44

(Ia'-1-20)

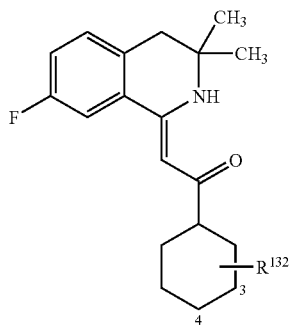

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)-3-pyridyl] |
| 19 | 3-NHCO-[3-(2-chlorophenyl)-5-methylisoxazol-4-yl] |
| 20 | 4-CN |
| 21 | 4-NHAc |

TABLE 44-continued (Ia'-1-20)

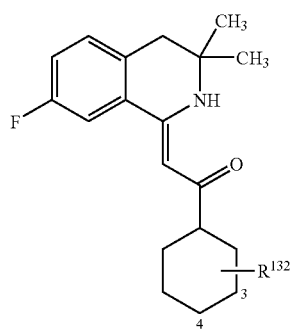

| No. | R¹³² |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)-3-pyridyl] |
| 38 | 4-NHCO-[3-(2-chlorophenyl)-5-methylisoxazol-4-yl] |

TABLE 45

(Ia'-1-21)

[Structure: 6-chloro-3,3-dimethyl-1,2,3,4-tetrahydroisoquinoline with =CH-C(=O)- linked to cyclohexyl bearing R¹³² at position 3 or 4]

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)-3-pyridyl] |
| 19 | 3-NHCO-[3-(2-chlorophenyl)-5-methylisoxazol-4-yl] |
| 20 | 4-CN |
| 21 | 4-NHAc |
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)-3-pyridyl] |
| 38 | 4-NHCO-[3-(2-chlorophenyl)-5-methylisoxazol-4-yl] |

TABLE 46

(Ia'-1-22)

[Structure: 7-chloro-3,3-dimethyl-3,4-dihydroisoquinoline with =CH-C(=O)- linked to a cyclohexyl bearing R$^{132}$ at position 3 or 4]

| No. | R$^{132}$ |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |
| 21 | 4-NHAc |
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 47

(Ia'-1-23)

[Structure: 6-(difluoromethoxy)-3,3-dimethyl-3,4-dihydroisoquinoline with =CH-C(=O)-cyclohexyl-R^132 substituent]

| No. | R^132 |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[5-methyl-3-(2-chlorophenyl)isoxazol-4-yl] |
| 20 | 4-CN |
| 21 | 4-NHAc |
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[5-methyl-3-(2-chlorophenyl)isoxazol-4-yl] |

TABLE 48

(Ia'-1-24)

[Structure: 7-difluoromethoxy-3,3-dimethyl-3,4-dihydroisoquinoline with =CH-C(=O)- linked to cyclohexyl bearing R$^{132}$ at position 3 or 4]

| No. | R$^{132}$ |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |
| 21 | 4-NHAc |
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 49
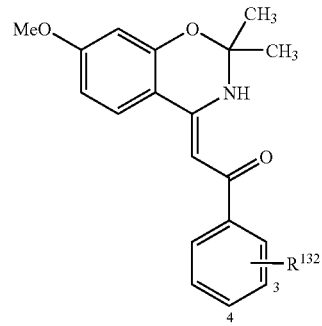
(Ia'-3-9)
| No. | R132 |
|---|---|
| 1 | 3-CN |
| 2 | 3-NHAc |
| 3 | 3-NH2 |
| 4 | 3-MeO |
| 5 | 3-NHCO2Me |
| 6 | 3-NHSO2Me |
| 7 | 3-NHCONH2 |
| 8 | 3-NHCHO |
| 9 | 3-CONHMe |
| 10 | 3-NHCO-i-Bu |
| 11 | 3-NHCO-c-Pr |
| 12 | 3-NHCOCH2OMe |
| 13 | 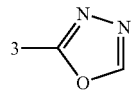 |
| 14 | 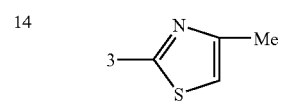 |
| 15 | 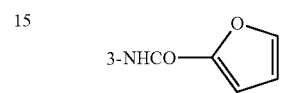 |
| 16 | 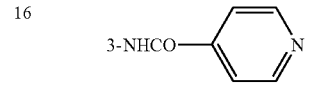 |
| 17 | 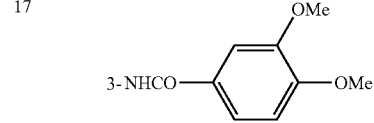 |
| 18 |  |
| 19 | 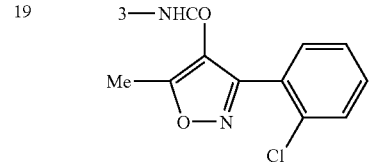 |
| 20 | 4-CN |
| 21 | 4-NHAc |
TABLE 49-continued
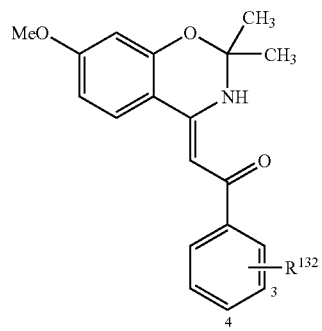
(Ia'-3-9)
| No. | R132 |
|---|---|
| 22 | 4-NH2 |
| 23 | 4-MeO |
| 24 | 4-NHCO2Me |
| 25 | 4-NHSO2Me |
| 26 | 4-NHCONH2 |
| 27 | 4-NHCHO |
| 28 | 4-CONHMe |
| 29 | 4-NHCO-i-Bu |
| 30 | 4-NHCO-c-Pr |
| 31 | 4-NHCOCH2OMe |
| 32 | 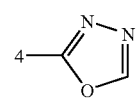 |
| 33 | 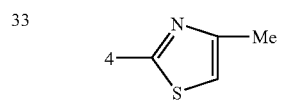 |
| 34 | 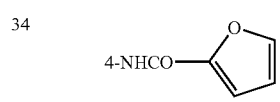 |
| 35 | 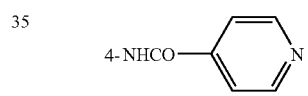 |
| 36 | 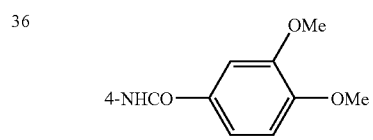 |
| 37 |  |
| 38 | 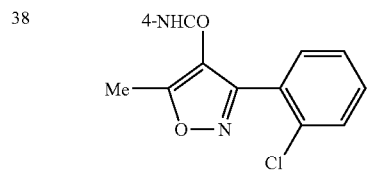 |

TABLE 50

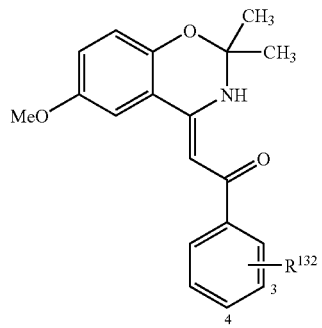

(Ia'-3-10)

| No. | R[132] |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)-3-pyridyl] |
| 19 | 3-NHCO-[3-(2-chlorophenyl)-5-methylisoxazol-4-yl] |
| 20 | 4-CN |
| 21 | 4-NHAc |

TABLE 50-continued

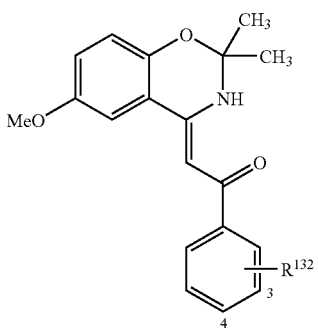

(Ia'-3-10)

| No. | R[132] |
|---|---|
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)-3-pyridyl] |
| 38 | 4-NHCO-[3-(2-chlorophenyl)-5-methylisoxazol-4-yl] |

TABLE 51

(Ia'-3-11)

[Structure: 7-fluoro-2,2-dimethyl-2H-benzo[e][1,3]oxazine with =CH-C(=O)-phenyl-R^132 substituent at position 4; phenyl positions 3 and 4 marked]

| No. | R^132 |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 3-(1,3,4-oxadiazol-2-yl) |
| 14 | 3-(4-methylthiazol-2-yl) |
| 15 | 3-NHCO-(furan-2-yl) |
| 16 | 3-NHCO-(pyridin-4-yl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |
| 21 | 4-NHAc |

TABLE 51-continued (Ia'-3-11)

| No. | R^132 |
|---|---|
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 4-(1,3,4-oxadiazol-2-yl) |
| 33 | 4-(4-methylthiazol-2-yl) |
| 34 | 4-NHCO-(furan-2-yl) |
| 35 | 4-NHCO-(pyridin-4-yl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 52
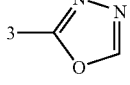
(Ia'-3-12)
| No. | R[132] |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 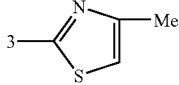 |
| 14 | 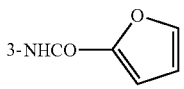 |
| 15 | 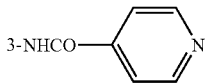 |
| 16 | 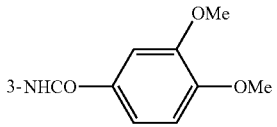 |
| 17 | 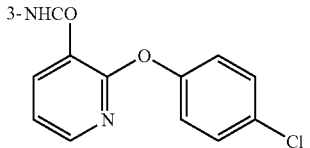 |
| 18 | 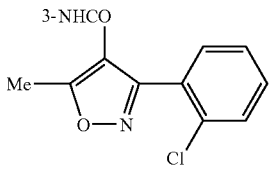 |
| 19 | 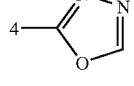 |
| 20 | 4-CN |
| 21 | 4-NHAc |
TABLE 52-continued
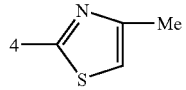
(Ia'-3-12)
| No. | R[132] |
|---|---|
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 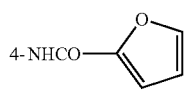 |
| 33 | 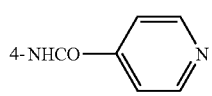 |
| 34 | 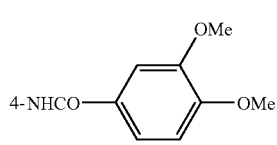 |
| 35 | 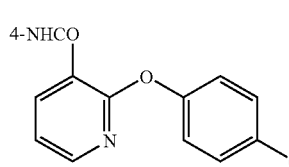 |
| 36 | 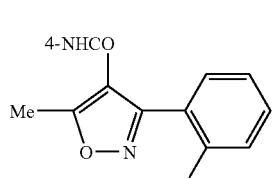 |
| 37 | 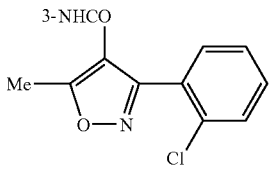 |
| 38 | 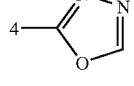 |

TABLE 53

(Ia'-3-13)

[Structure: 7-chloro-2,2-dimethyl-2,3-dihydro-4H-benzo[e][1,3]oxazine with =CH-C(=O)-phenyl-R¹³² substituent]

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |
| 21 | 4-NHAc |
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 54
(Ia'-3-14)
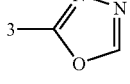
| No. | R^132 |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 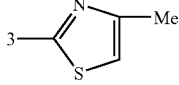 |
| 14 | 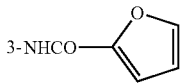 |
| 15 | 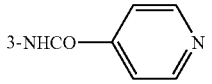 |
| 16 | 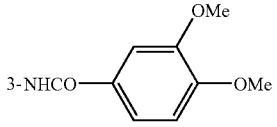 |
| 17 | 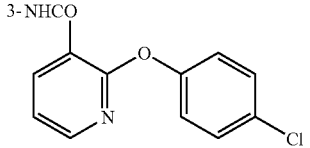 |
| 18 | 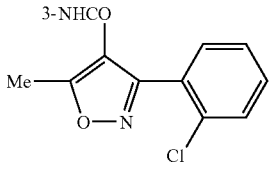 |
| 19 | 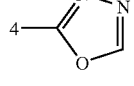 |
| 20 | 4-CN |
| 21 | 4-NHAc |
TABLE 54-continued
(Ia'-3-14)
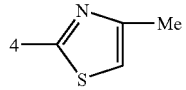
| No. | R^132 |
|---|---|
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 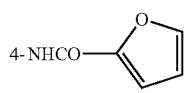 |
| 33 | 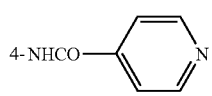 |
| 34 | 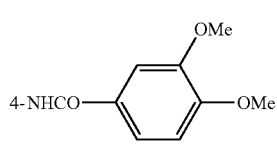 |
| 35 | 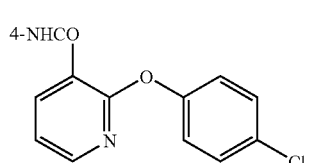 |
| 36 | 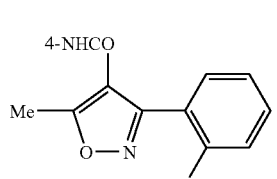 |
| 37 | 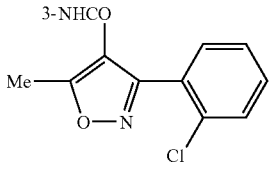 |
| 38 | 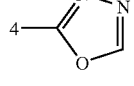 |

TABLE 55

(Ia'-3-15)

[Structure: 7-difluoromethoxy-2,2-dimethyl-2H-benzo[e][1,3]oxazine with =CH-C(=O)-phenyl-R¹³² substituent]

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-(2-(4-chlorophenoxy)pyridin-3-yl) |
| 19 | 3-NHCO-(3-(2-chlorophenyl)-5-methylisoxazol-4-yl) |
| 20 | 4-CN |
| 21 | 4-NHAc |

TABLE 55-continued (Ia'-3-15)

| No. | R¹³² |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-(2-(4-chlorophenoxy)pyridin-3-yl) |
| 38 | 4-NHCO-(3-(2-chlorophenyl)-5-methylisoxazol-4-yl) |

TABLE 56

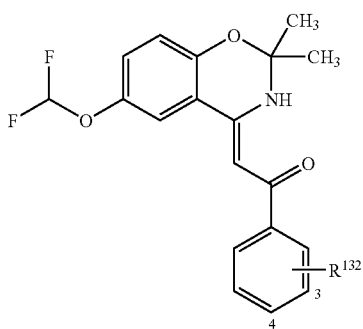

(Ia'-3-16)

| No. | R[132] |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(furan-2-yl) |
| 16 | 3-NHCO-(pyridin-4-yl) |
| 17 | 3-NHCO-(2,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |
| 21 | 4-NHAc |

TABLE 56-continued

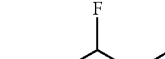

(Ia'-3-16)

| No. | R[132] |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(furan-2-yl) |
| 35 | 4-NHCO-(pyridin-4-yl) |
| 36 | 4-NHCO-(2,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 57
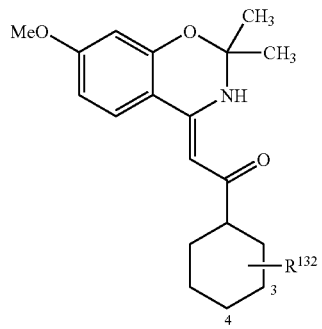
(Ia'-3-17)
| No. | R[132] |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 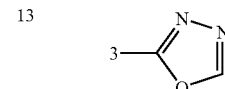 |
| 14 | 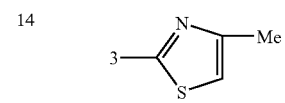 |
| 15 | 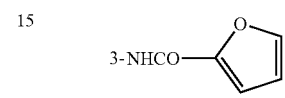 |
| 16 | 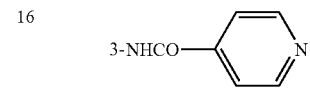 |
| 17 | 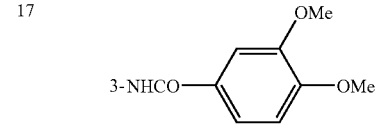 |
| 18 |  |
| 19 | 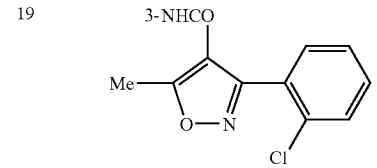 |
| 20 | 4-CN |
| 21 | 4-NHAc |
TABLE 57-continued
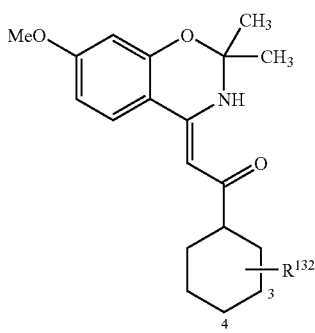
(Ia'-3-17)
| No. | R[132] |
|---|---|
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 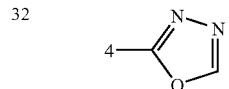 |
| 33 | 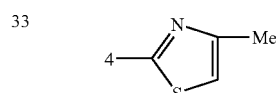 |
| 34 | 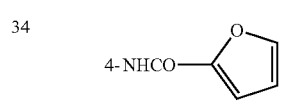 |
| 35 | 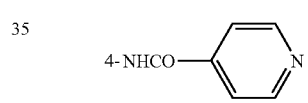 |
| 36 | 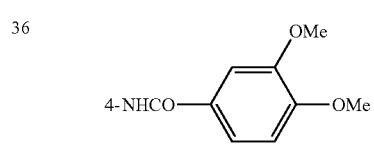 |
| 37 | 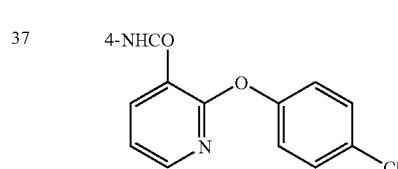 |
| 38 | 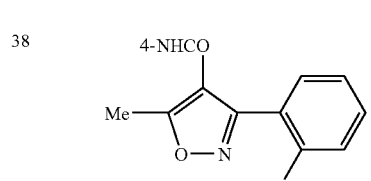 |

TABLE 58
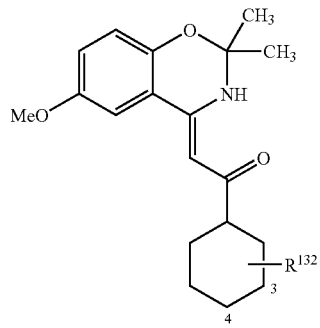
(Ia'-3-18)
| No. | R132 |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 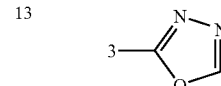 |
| 14 | 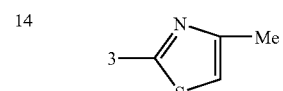 |
| 15 | 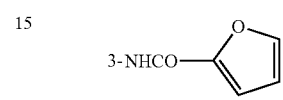 |
| 16 | 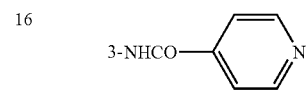 |
| 17 | 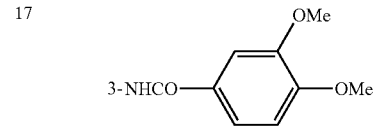 |
| 18 |  |
| 19 | 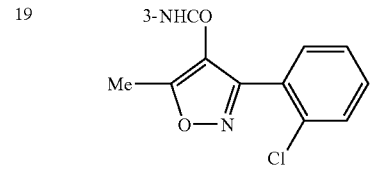 |
| 20 | 4-CN |
| 21 | 4-NHAc |
TABLE 58-continued
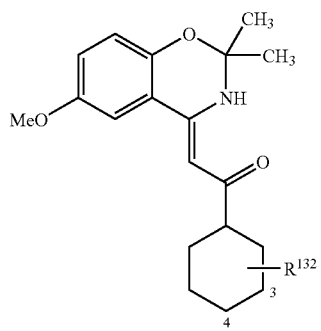
(Ia'-3-18)
| No. | R132 |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 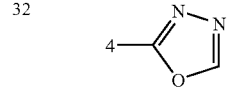 |
| 33 | 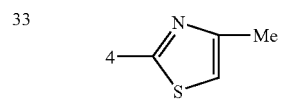 |
| 34 | 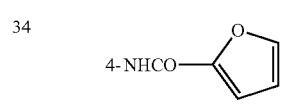 |
| 35 | 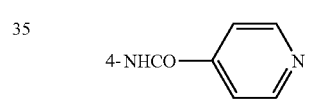 |
| 36 | 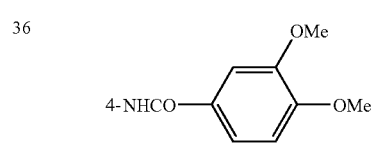 |
| 37 | 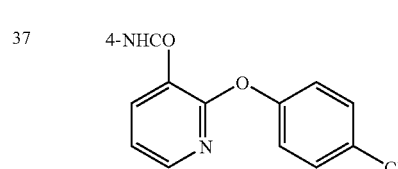 |
| 38 | 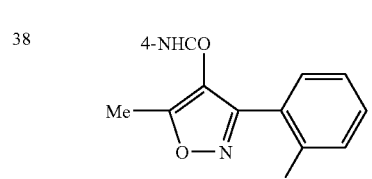 |

TABLE 59

(Ia'-3-19)

[Structure: 7-fluoro-2,2-dimethyl-2H-benzo[e][1,3]oxazine with =CH-C(=O)- linker to cyclohexyl bearing R¹³²]

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[5-methyl-3-(2-chlorophenyl)isoxazol-4-yl] |
| 20 | 4-CN |
| 21 | 4-NHAc |
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[5-methyl-3-(2-chlorophenyl)isoxazol-4-yl] |

TABLE 60
(Ia'-3-20)
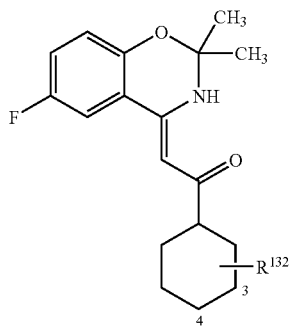
| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 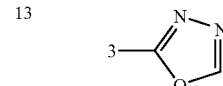 |
| 14 | 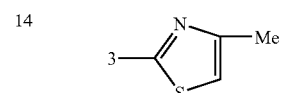 |
| 15 | 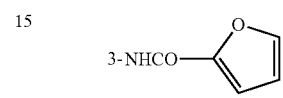 |
| 16 | 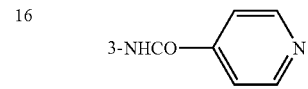 |
| 17 | 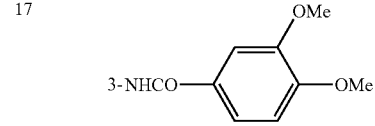 |
| 18 |  |
| 19 | 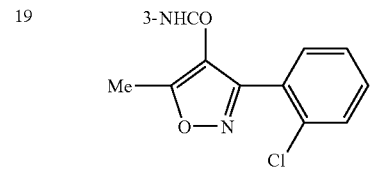 |
| 20 | 4-CN |
| 21 | 4-NHAc |
TABLE 60-continued
(Ia'-3-20)
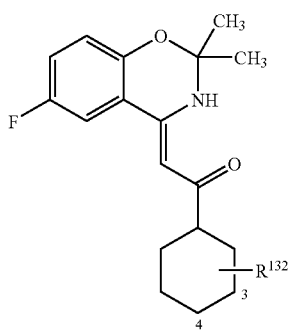
| No. | R¹³² |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 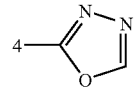 |
| 33 | 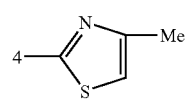 |
| 34 | 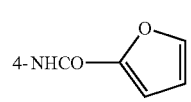 |
| 35 | 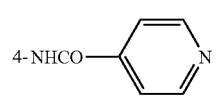 |
| 36 | 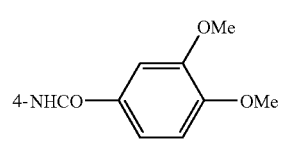 |
| 37 | 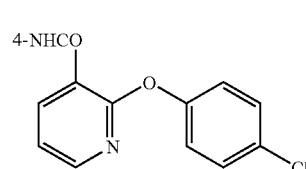 |
| 38 | 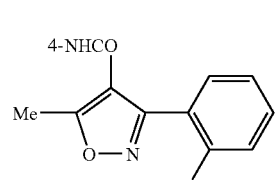 |

TABLE 61
(Ia'-3-21)
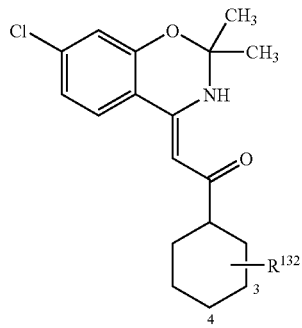
| No. | R132 |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 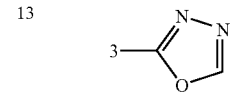 |
| 14 | 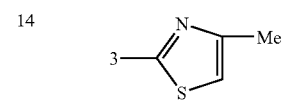 |
| 15 | 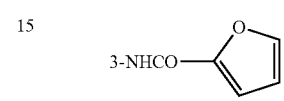 |
| 16 | 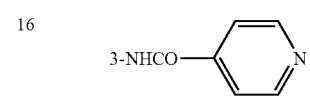 |
| 17 | 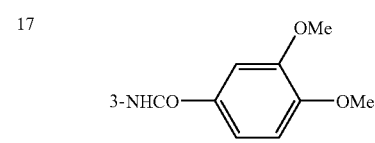 |
| 18 |  |
| 19 | 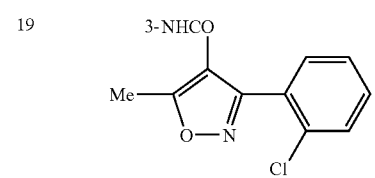 |
| 20 | 4-CN |
TABLE 61-continued
(Ia'-3-21)
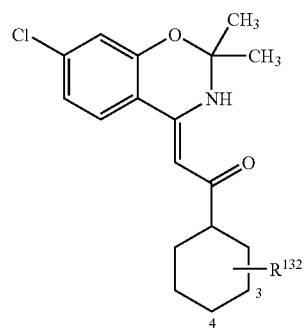
| No. | R132 |
|---|---|
| 21 | 4-NHAc |
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 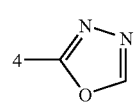 |
| 33 | 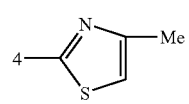 |
| 34 | 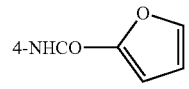 |
| 35 | 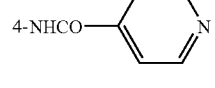 |
| 36 | 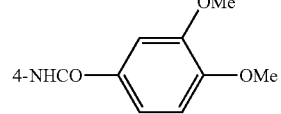 |
| 37 | 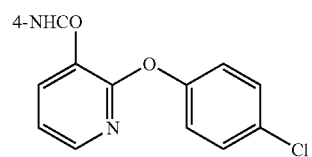 |
| 38 | 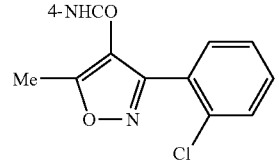 |

TABLE 62
(Ia'-3-22)
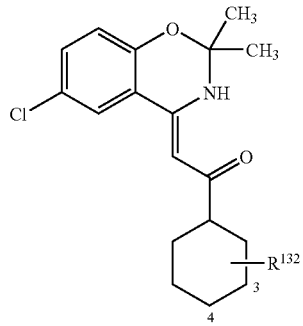
| No. | R132 |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 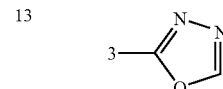 |
| 14 | 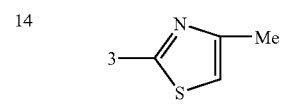 |
| 15 | 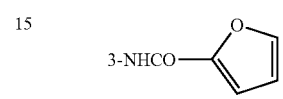 |
| 16 | 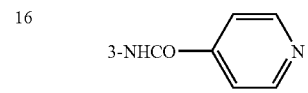 |
| 17 | 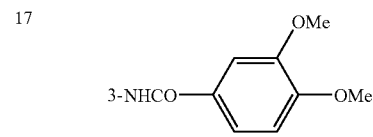 |
| 18 |  |
| 19 | 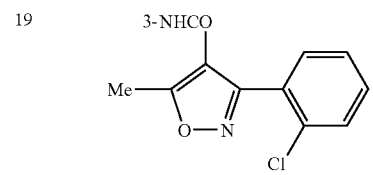 |
| 20 | 4-CN |
TABLE 62-continued
(Ia'-3-22)
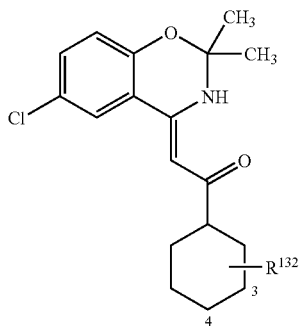
| No. | R132 |
|---|---|
| 21 | 4-NHAc |
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 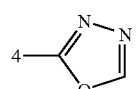 |
| 33 | 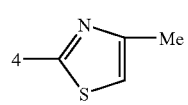 |
| 34 | 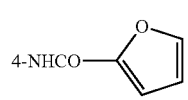 |
| 35 | 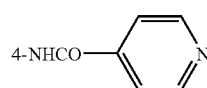 |
| 36 | 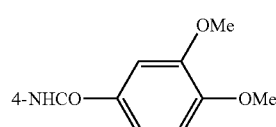 |
| 37 | 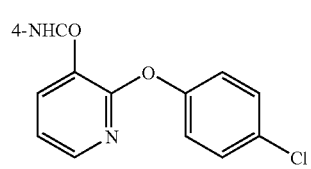 |
| 38 | 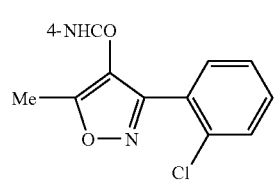 |

TABLE 63
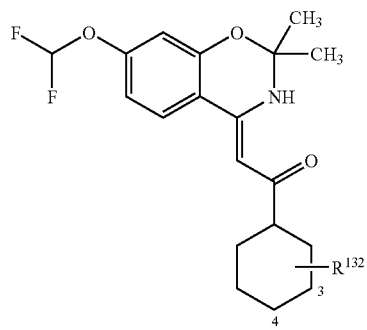
(Ia'-3-23)
| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 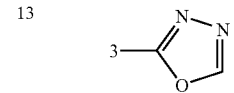 |
| 14 | 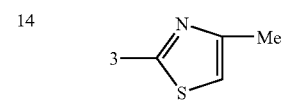 |
| 15 | 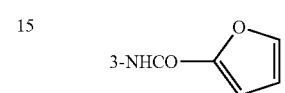 |
| 16 | 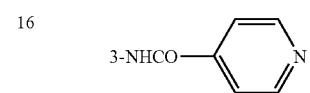 |
| 17 | 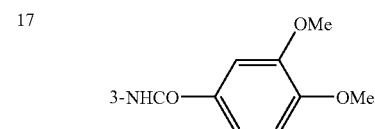 |
| 18 | 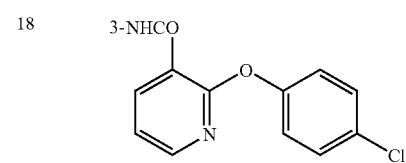 |
| 19 | 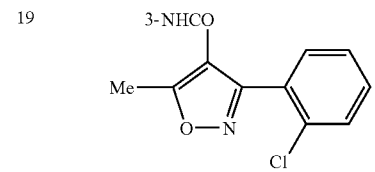 |
| 20 | 4-CN |
TABLE 63-continued
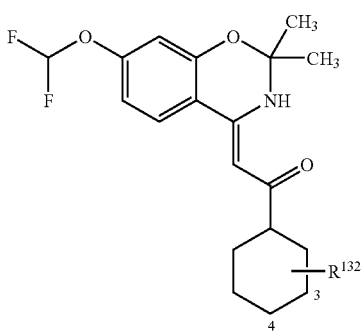
(Ia'-3-23)
| No. | R¹³² |
|---|---|
| 21 | 4-NHAc |
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 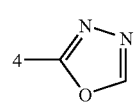 |
| 33 | 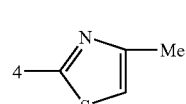 |
| 34 | 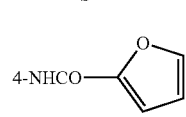 |
| 35 | 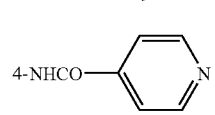 |
| 36 | 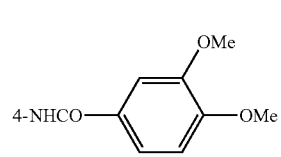 |
| 37 | 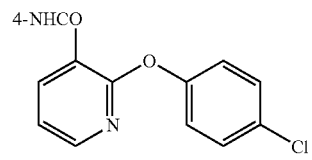 |
| 38 | 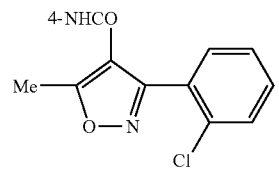 |

TABLE 64
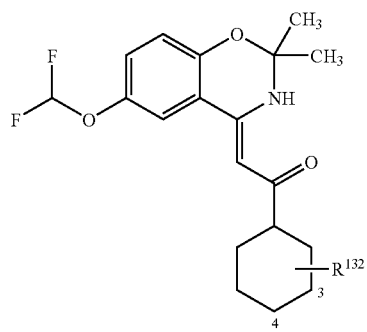
(Ia'-3-24)
| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 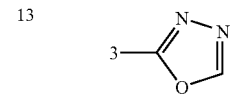 |
| 14 | 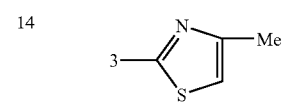 |
| 15 | 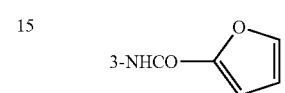 |
| 16 | 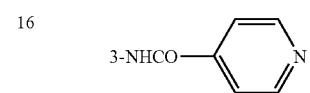 |
| 17 | 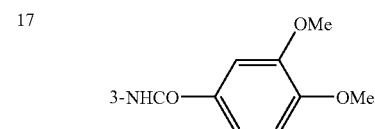 |
| 18 |  |
| 19 | 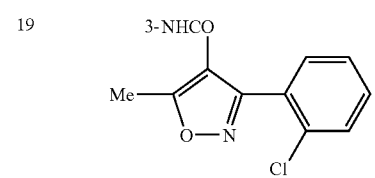 |
| 20 | 4-CN |
TABLE 64-continued
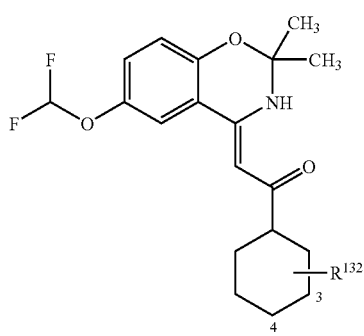
(Ia'-3-24)
| No. | R¹³² |
|---|---|
| 21 | 4-NHAc |
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 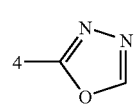 |
| 33 | 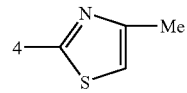 |
| 34 | 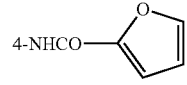 |
| 35 | 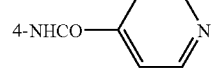 |
| 36 | 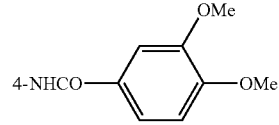 |
| 37 | 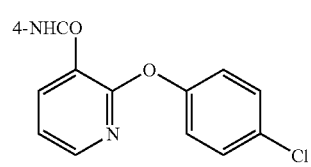 |
| 38 | 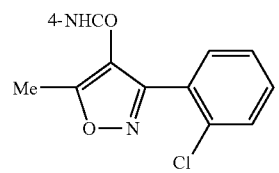 |

TABLE 65
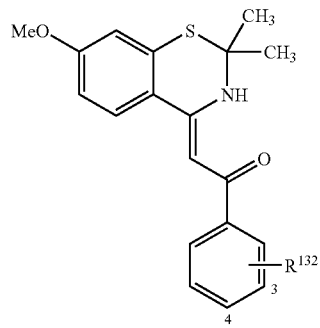
(Ia'-5-9)
| No. | R¹³² |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 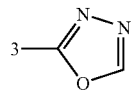 |
| 14 | 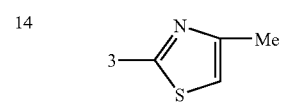 |
| 15 | 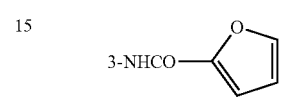 |
| 16 | 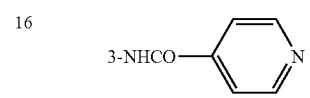 |
| 17 | 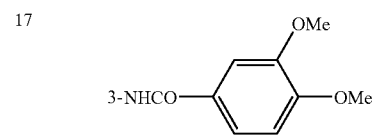 |
| 18 | 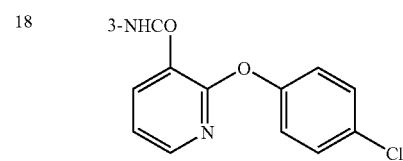 |
| 19 | 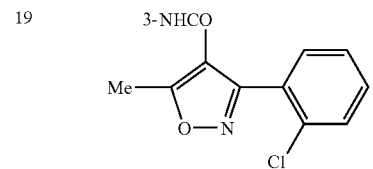 |
| 20 | 4-CN |
TABLE 65-continued
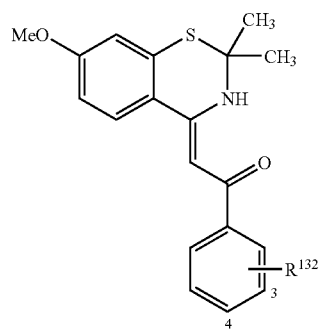
(Ia'-5-9)
| No. | R¹³² |
|---|---|
| 21 | 4-NHAc |
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 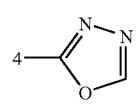 |
| 33 | 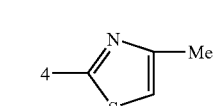 |
| 34 | 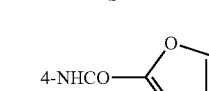 |
| 35 | 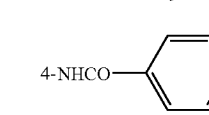 |
| 36 |  |
| 37 | 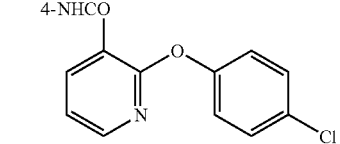 |
| 38 | 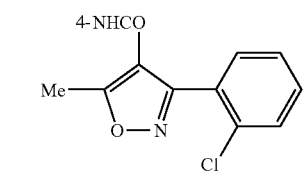 |

TABLE 66
(Ia'-5-10)
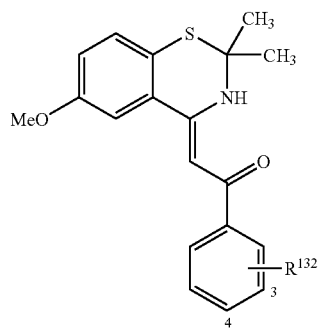
| No. | R132 |
|---|---|
| 1 | 3-CN |
| 2 | 3-NHAc |
| 3 | 3-NH2 |
| 4 | 3-MeO |
| 5 | 3-NHCO2Me |
| 6 | 3-NHSO2Me |
| 7 | 3-NHCONH2 |
| 8 | 3-NHCHO |
| 9 | 3-CONHMe |
| 10 | 3-NHCO-i-Bu |
| 11 | 3-NHCO-c-Pr |
| 12 | 3-NHCOCH2OMe |
| 13 | 3- (1,3,4-oxadiazole) |
| 14 | 3- (4-methylthiazole) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-(2-(4-chlorophenoxy)pyridin-3-yl) |
| 19 | 3-NHCO-(3-(2-chlorophenyl)-5-methylisoxazol-4-yl) |
| 20 | 4-CN |
TABLE 66-continued
(Ia'-5-10)
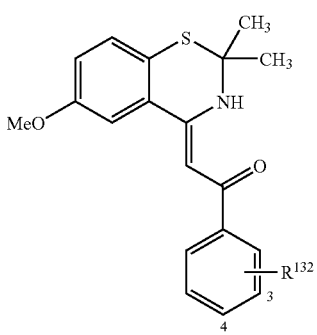
| No. | R132 |
|---|---|
| 21 | 4-NHAc |
| 22 | 4-NH2 |
| 23 | 4-MeO |
| 24 | 4-NHCO2Me |
| 25 | 4-NHSO2Me |
| 26 | 4-NHCONH2 |
| 27 | 4-NHCHO |
| 28 | 4-CONHMe |
| 29 | 4-NHCO-i-Bu |
| 30 | 4-NHCO-c-Pr |
| 31 | 4-NHCOCH2OMe |
| 32 | 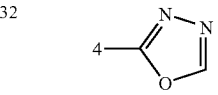 |
| 33 | 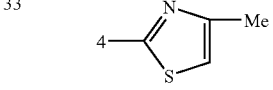 |
| 34 | 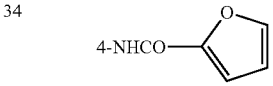 |
| 35 | 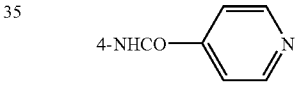 |
| 36 | 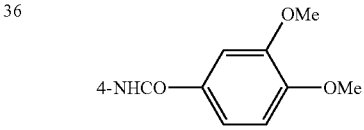 |
| 37 | 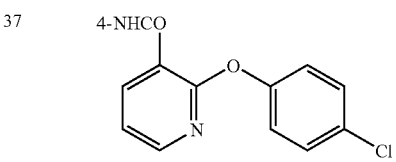 |
| 38 | 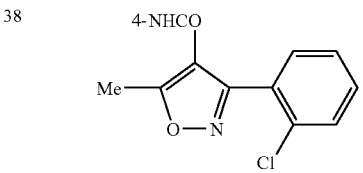 |

TABLE 67

(Ia'-5-11)

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |

TABLE 67-continued (Ia'-5-11)

| No. | R¹³² |
|---|---|
| 21 | 4-NHAc |
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 68

(Ia'-5-12)

[Structure: 6-fluoro-2,2-dimethyl-2,3-dihydro-4H-benzo[1,3]thiazine with =CH-C(=O)-phenyl-R¹³² substituent]

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(furan-2-yl) |
| 16 | 3-NHCO-(pyridin-4-yl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |

TABLE 68-continued (Ia'-5-12)

| No. | R¹³² |
|---|---|
| 21 | 4-NHAc |
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(furan-2-yl) |
| 35 | 4-NHCO-(pyridin-4-yl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 69
(Ia'-5-13)
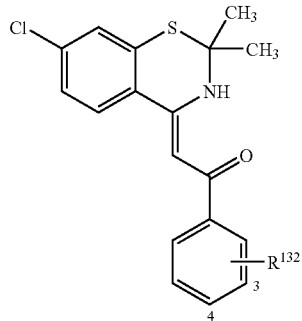
| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 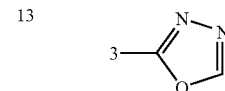 |
| 14 | 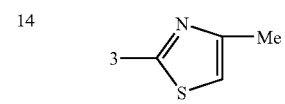 |
| 15 | 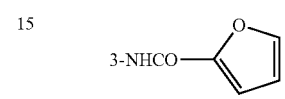 |
| 16 | 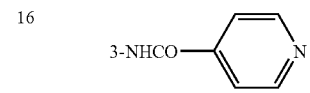 |
| 17 | 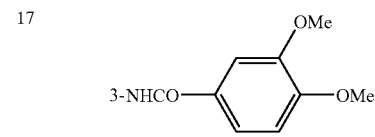 |
| 18 |  |
| 19 | 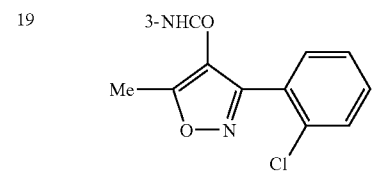 |
| 20 | 4-CN |
TABLE 69-continued
(Ia'-5-13)
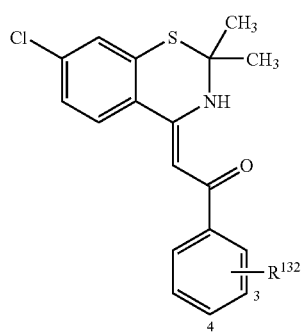
| No. | R¹³² |
|---|---|
| 21 | 4-NHAc |
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 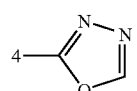 |
| 33 | 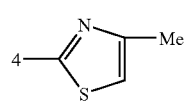 |
| 34 | 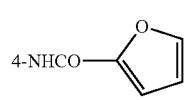 |
| 35 | 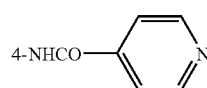 |
| 36 | 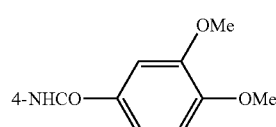 |
| 37 | 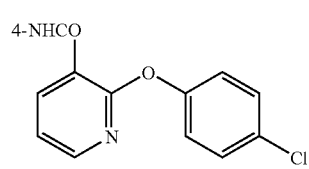 |
| 38 | 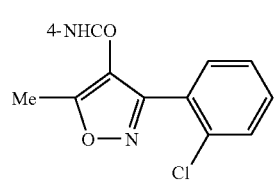 |

TABLE 70
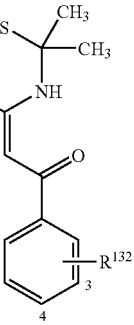
(Ia'-5-14)
| No. | R132 |
|---|---|
| 1 | 3-CN |
| 2 | 3-NHAc |
| 3 | 3-NH2 |
| 4 | 3-MeO |
| 5 | 3-NHCO2Me |
| 6 | 3-NHSO2Me |
| 7 | 3-NHCONH2 |
| 8 | 3-NHCHO |
| 9 | 3-CONHMe |
| 10 | 3-NHCO-i-Bu |
| 11 | 3-NHCO-c-Pr |
| 12 | 3-NHCOCH2OMe |
| 13 | 3- (1,3,4-oxadiazol-2-yl) |
| 14 | 3- (4-methylthiazol-2-yl) |
| 15 | 3-NHCO-(furan-2-yl) |
| 16 | 3-NHCO-(pyridin-4-yl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |
TABLE 70-continued
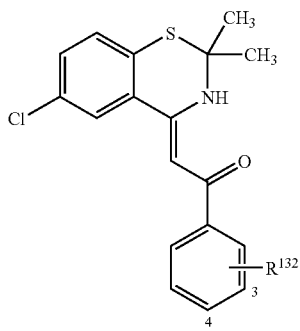
(Ia'-5-14)
| No. | R132 |
|---|---|
| 21 | 4-NHAc |
| 22 | 4-NH2 |
| 23 | 4-MeO |
| 24 | 4-NHCO2Me |
| 25 | 4-NHSO2Me |
| 26 | 4-NHCONH2 |
| 27 | 4-NHCHO |
| 28 | 4-CONHMe |
| 29 | 4-NHCO-i-Bu |
| 30 | 4-NHCO-c-Pr |
| 31 | 4-NHCOCH2OMe |
| 32 | 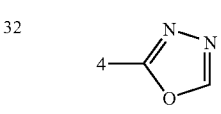 |
| 33 | 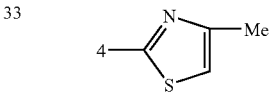 |
| 34 | 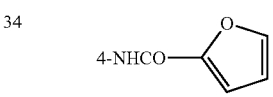 |
| 35 | 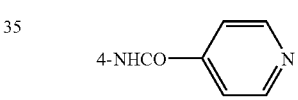 |
| 36 | 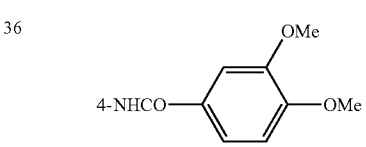 |
| 37 |  |
| 38 | 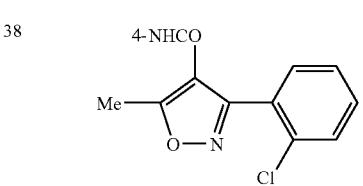 |

TABLE 71

(Ia'-5-15)

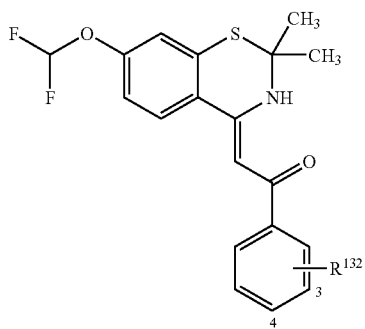

| No. | R132 |
|---|---|
| 1 | 3-CN |
| 2 | 3-NHAc |
| 3 | 3-NH2 |
| 4 | 3-MeO |
| 5 | 3-NHCO2Me |
| 6 | 3-NHSO2Me |
| 7 | 3-NHCONH2 |
| 8 | 3-NHCHO |
| 9 | 3-CONHMe |
| 10 | 3-NHCO-i-Bu |
| 11 | 3-NHCO-c-Pr |
| 12 | 3-NHCOCH2OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)-3-pyridyl] |
| 19 | 3-NHCO-[3-(2-chlorophenyl)-5-methylisoxazol-4-yl] |
| 20 | 4-CN |
| 21 | 4-NHAc |

TABLE 71-continued (Ia'-5-15)

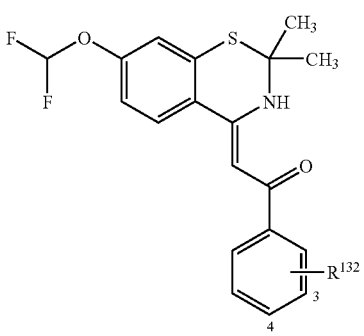

| No. | R132 |
|---|---|
| 22 | 4-NH2 |
| 23 | 4-MeO |
| 24 | 4-NHCO2Me |
| 25 | 4-NHSO2Me |
| 26 | 4-NHCONH2 |
| 27 | 4-NHCHO |
| 28 | 4-CONHMe |
| 29 | 4-NHCO-i-Bu |
| 30 | 4-NHCO-c-Pr |
| 31 | 4-NHCOCH2OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)-3-pyridyl] |
| 38 | 4-NHCO-[3-(2-chlorophenyl)-5-methylisoxazol-4-yl] |

TABLE 72

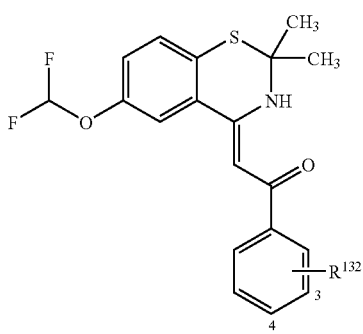

(Ia'-5-16)

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-(2-(4-chlorophenoxy)pyridin-3-yl) |
| 19 | 3-NHCO-(5-methyl-3-(2-chlorophenyl)isoxazol-4-yl) |
| 20 | 4-CN |
| 21 | 4-NHAc |

TABLE 72-continued (Ia'-5-16)

| No. | R¹³² |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-(2-(4-chlorophenoxy)pyridin-3-yl) |
| 38 | 4-NHCO-(5-methyl-3-(2-chlorophenyl)isoxazol-4-yl) |

TABLE 73

(Ia'-5-17)

[Structure: 7-MeO-2,2-dimethyl-benzothiazine with =CH-C(=O)- attached to cyclohexyl bearing R^132]

| No. | R^132 |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |
| 21 | 4-NHAc |
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 74

(Ia'-5-18)

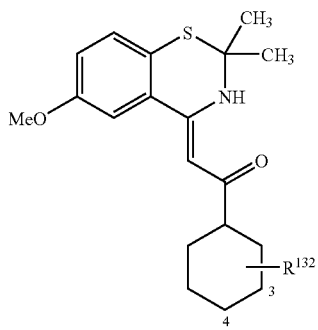

| No. | R[132] |
|-----|--------|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-(2-(4-chlorophenoxy)pyridin-3-yl) |
| 19 | 3-NHCO-(5-methyl-3-(2-chlorophenyl)isoxazol-4-yl) |
| 20 | 4-CN |
| 21 | 4-NHAc |

TABLE 74-continued (Ia'-5-18)

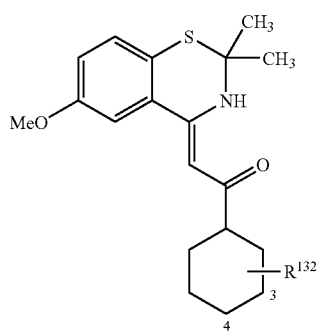

| No. | R[132] |
|-----|--------|
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-(2-(4-chlorophenoxy)pyridin-3-yl) |
| 38 | 4-NHCO-(5-methyl-3-(2-chlorophenyl)isoxazol-4-yl) |

TABLE 75
(Ia'-5-19)
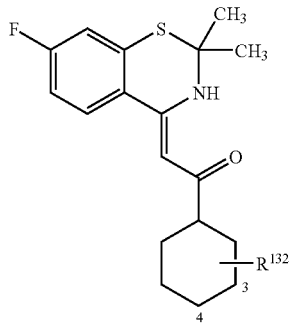
| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 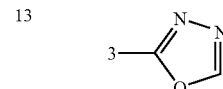 |
| 14 | 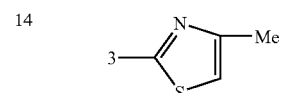 |
| 15 | 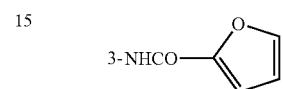 |
| 16 | 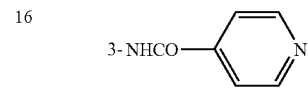 |
| 17 | 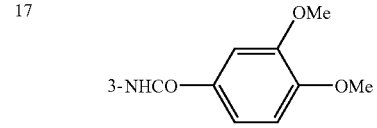 |
| 18 |  |
| 19 | 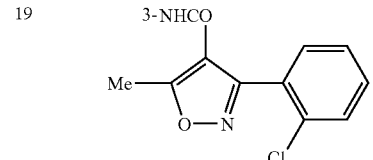 |
| 20 | 4-CN |
| 21 | 4-NHAc |
TABLE 75-continued
(Ia'-5-19)
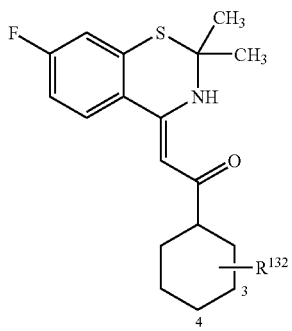
| No. | R¹³² |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 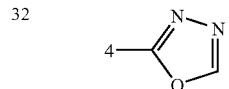 |
| 33 | 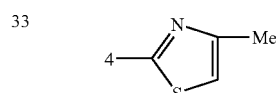 |
| 34 | 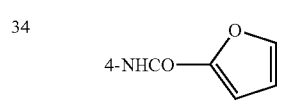 |
| 35 | 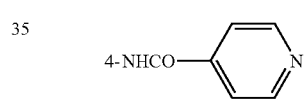 |
| 36 | 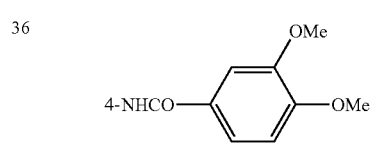 |
| 37 | 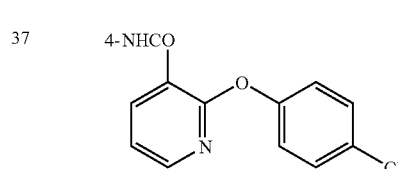 |
| 38 | 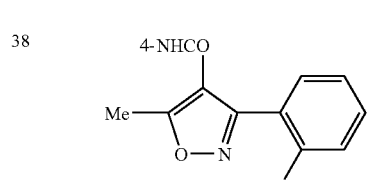 |

TABLE 76

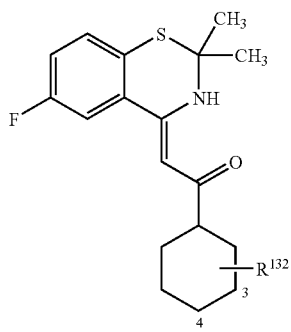
(Ia'-5-20)

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |
| 21 | 4-NHAc |

TABLE 76-continued

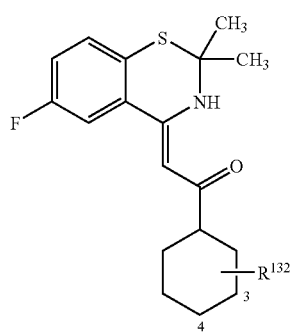
(Ia'-5-20)

| No. | R¹³² |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 77
(Ia'-5-21)
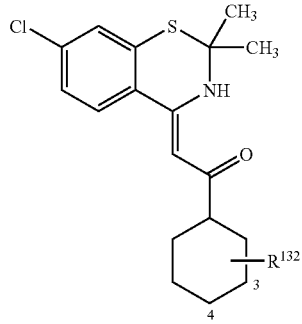
| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 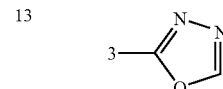 |
| 14 | 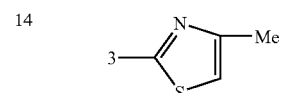 |
| 15 | 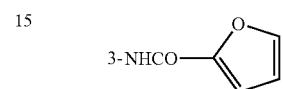 |
| 16 | 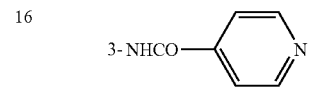 |
| 17 | 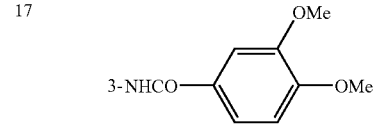 |
| 18 | 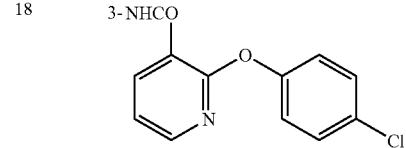 |
| 19 | 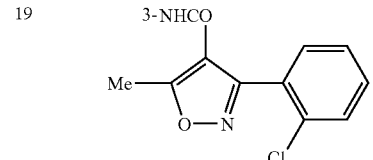 |
| 20 | 4-CN |
| 21 | 4-NHAc |
TABLE 77-continued
(Ia'-5-21)
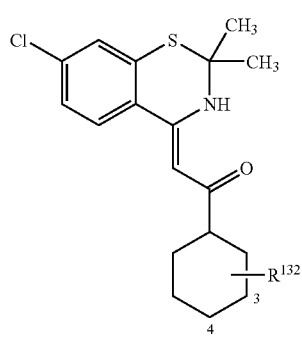
| No. | R¹³² |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 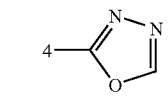 |
| 33 | 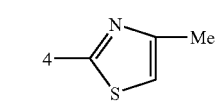 |
| 34 | 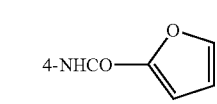 |
| 35 | 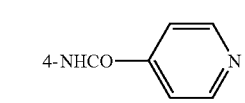 |
| 36 | 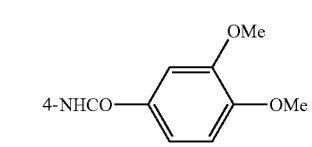 |
| 37 | 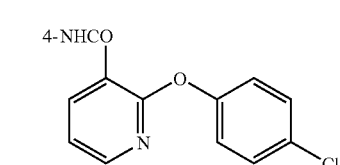 |
| 38 | 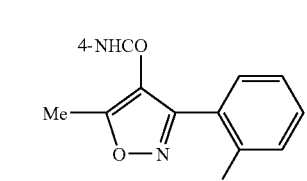 |

TABLE 78
(Ia'-5-22)
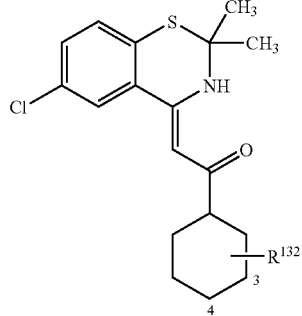
| No. | R¹³² |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 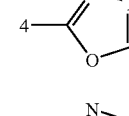 |
| 14 | 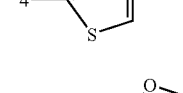 |
| 15 |  |
| 16 |  |
| 17 | 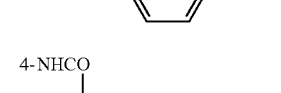 |
| 18 | 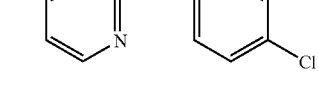 |
| 19 | 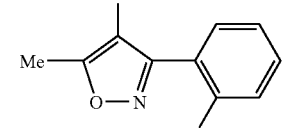 |
| 20 | 4-CN |
| 21 | 4-NHAc |
TABLE 78-continued
(Ia'-5-22)
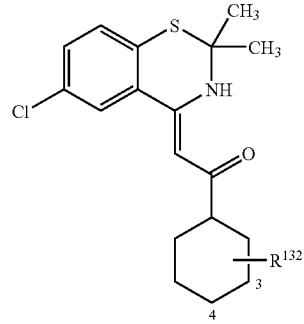
| No. | R¹³² |
|---|---|
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | |
| 33 | |
| 34 | |
| 35 | |
| 36 | |
| 37 | |
| 38 | |

TABLE 79
(Ia'-5-23)
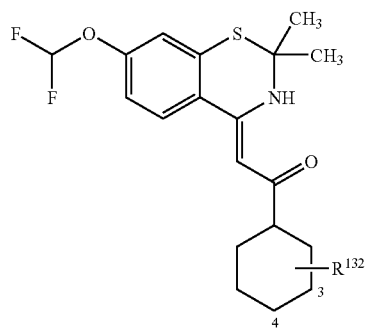
| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 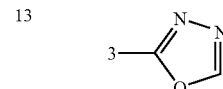 |
| 14 | 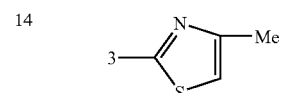 |
| 15 | 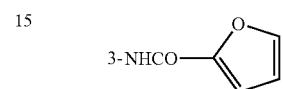 |
| 16 | 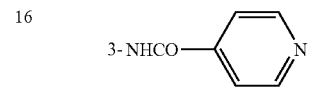 |
| 17 | 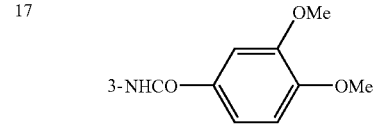 |
| 18 | 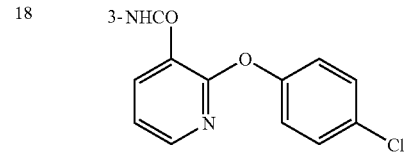 |
| 19 | 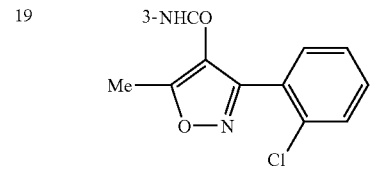 |
| 20 | 4-CN |
| 21 | 4-NHAc |
TABLE 79-continued
(Ia'-5-23)
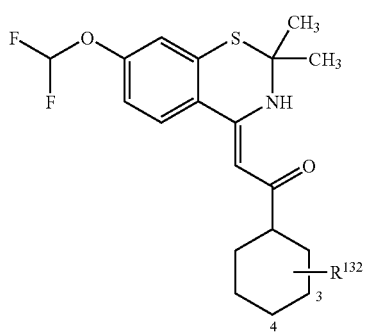
| No. | R¹³² |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 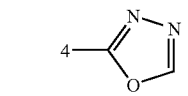 |
| 33 | 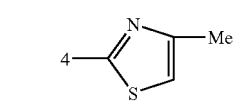 |
| 34 | 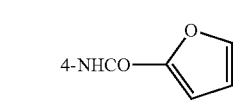 |
| 35 | 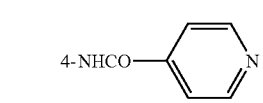 |
| 36 | 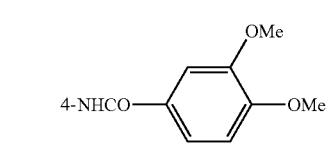 |
| 37 | 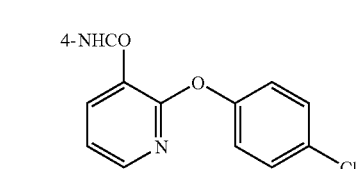 |
| 38 | 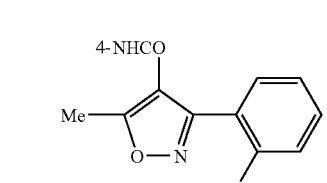 |

TABLE 80

(Ia'-5-24)

[Structure: 6-difluoromethoxy-2,2-dimethyl-2H-1,3-benzothiazine with =CH-C(=O)- linked to cyclohexyl bearing R¹³²]

| No. | R¹³² |
| --- | --- |
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[5-methyl-3-(2-chlorophenyl)isoxazol-4-yl] |
| 20 | 4-CN |
| 21 | 4-NHAc |

TABLE 80-continued (Ia'-5-24)

| No. | R¹³² |
| --- | --- |
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[5-methyl-3-(2-chlorophenyl)isoxazol-4-yl] |

TABLE 81

(Ia'-6-9)

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |
| 21 | 4-NHAc |

TABLE 81-continued (Ia'-6-9)

| No. | R¹³² |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 82
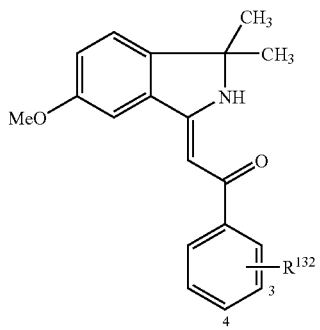
(Ia'-6-10)
| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 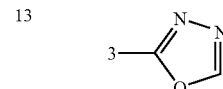 |
| 14 | 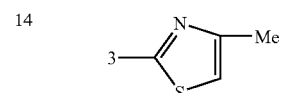 |
| 15 | 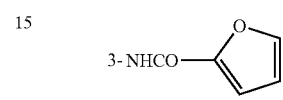 |
| 16 | 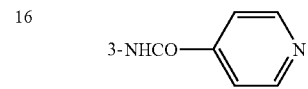 |
| 17 | 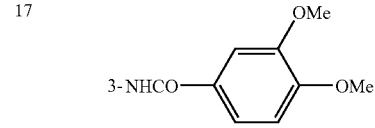 |
| 18 | 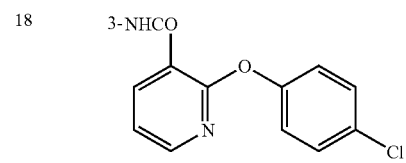 |
| 19 | 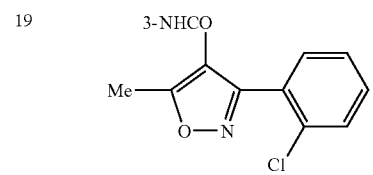 |
| 20 | 4-CN |
| 21 | 4-NHAc |
TABLE 82-continued
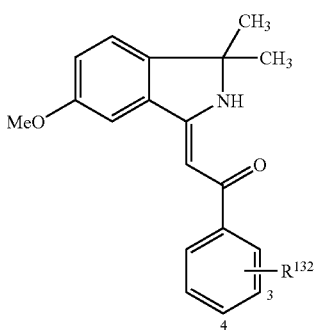
(Ia'-6-10)
| No. | R¹³² |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 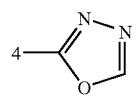 |
| 33 | 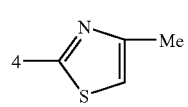 |
| 34 | 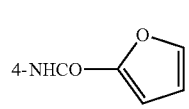 |
| 35 | 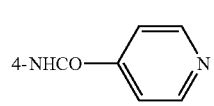 |
| 36 | 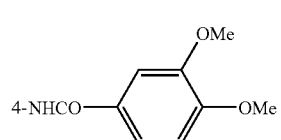 |
| 37 | 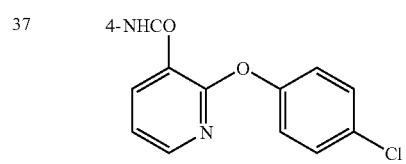 |
| 38 | 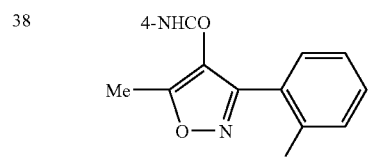 |

TABLE 83

(Ia'-6-11)

| No. | R^132 |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 3-(5-yl-1,3,4-oxadiazole) |
| 14 | 3-(4-methylthiazol-2-yl) |
| 15 | 3-NHCO-(furan-2-yl) |
| 16 | 3-NHCO-(pyridin-4-yl) |
| 17 | 3-NHCO-(3,4-dimethoxyphenyl) |
| 18 | 3-NHCO-(2-(4-chlorophenoxy)pyridin-3-yl) |
| 19 | 3-NHCO-(3-(2-chlorophenyl)-5-methylisoxazol-4-yl) |
| 20 | 4-CN |
| 21 | 4-NHAc |

TABLE 83-continued (Ia'-6-11)

| No. | R^132 |
|---|---|
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 4-(5-yl-1,3,4-oxadiazole) |
| 33 | 4-(4-methylthiazol-2-yl) |
| 34 | 4-NHCO-(furan-2-yl) |
| 35 | 4-NHCO-(pyridin-4-yl) |
| 36 | 4-NHCO-(3,4-dimethoxyphenyl) |
| 37 | 4-NHCO-(2-(4-chlorophenoxy)pyridin-3-yl) |
| 38 | 4-NHCO-(3-(2-chlorophenyl)-5-methylisoxazol-4-yl) |

TABLE 84
(Ia'-6-12)
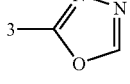
| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 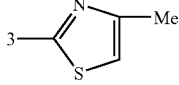 |
| 14 | 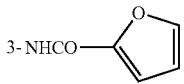 |
| 15 | 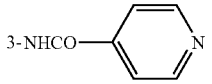 |
| 16 | 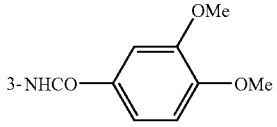 |
| 17 | 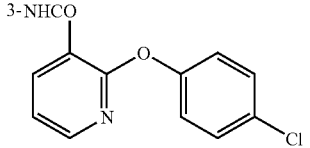 |
| 18 | 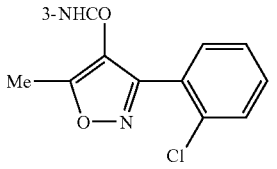 |
| 19 | 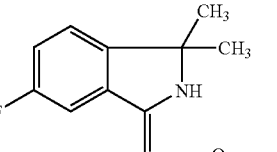 |
| 20 | 4-CN |
| 21 | 4-NHAc |
TABLE 84-continued
(Ia'-6-12)
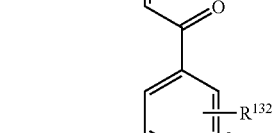
| No. | R¹³² |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 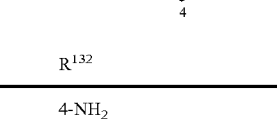 |
| 33 | 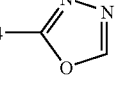 |
| 34 | 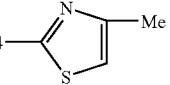 |
| 35 | 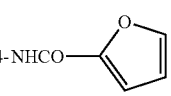 |
| 36 | 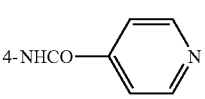 |
| 37 | 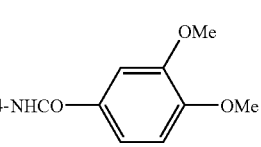 |
| 38 | 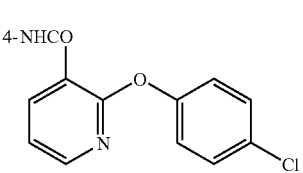 |

TABLE 85

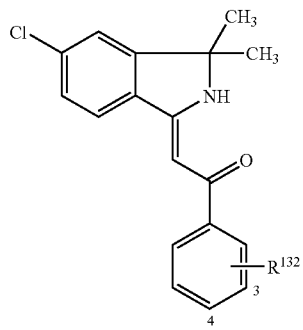

(Ia'-6-13)

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3- (1,3,4-oxadiazol-2-yl) |
| 14 | 3- (4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |
| 21 | 4-NHAc |

TABLE 85-continued

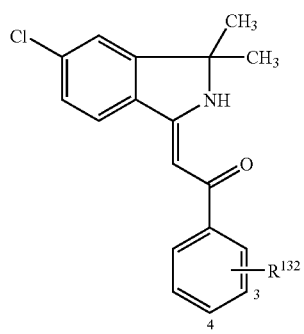

(Ia'-6-13)

| No. | R¹³² |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4- (1,3,4-oxadiazol-2-yl) |
| 33 | 4- (4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 86

(Ia'-6-14)

[Structure: 6-chloro-2,2-dimethyl-2,3-dihydro-1H-isoindole with =CH-C(=O)-phenyl-R¹³² substituent]

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |
| 21 | 4-NHAc |
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 87
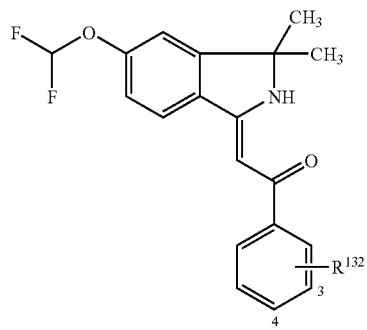
(Ia'-6-15)
| No. | R132 |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 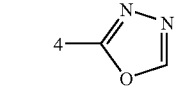 |
| 14 | |
| 15 | |
| 16 | |
| 17 | |
| 18 | |
| 19 | |
| 20 | 4-CN |
| 21 | 4-NHAc |
TABLE 87-continued
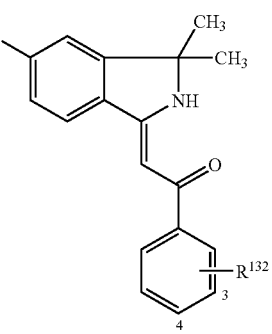
(Ia'-6-15)
| No. | R132 |
|---|---|
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | |
| 33 | |
| 34 | |
| 35 | |
| 36 | |
| 37 | |
| 38 | |

TABLE 88

(Ia'-6-16)

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |
| 21 | 4-NHAc |

TABLE 88-continued (Ia'-6-16)

| No. | R¹³² |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 89
(Ia'-6-17)
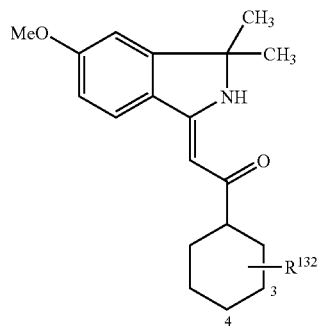
| No. | R132 |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 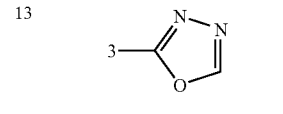 |
| 14 | 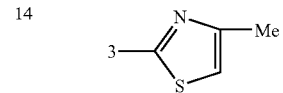 |
| 15 | 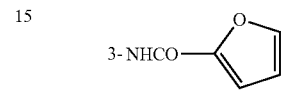 |
| 16 | 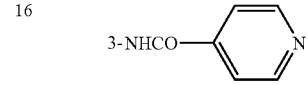 |
| 17 | 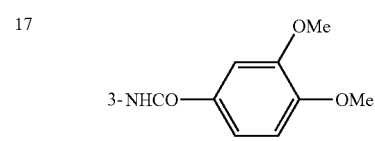 |
| 18 |  |
| 19 | 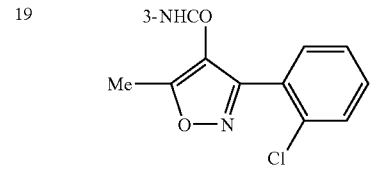 |
| 20 | 4-CN |
| 21 | 4-NHAc |
TABLE 89-continued
(Ia'-6-17)
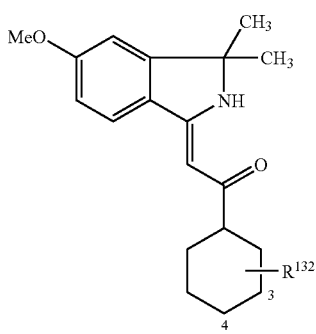
| No. | R132 |
|---|---|
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 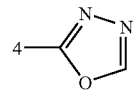 |
| 33 | 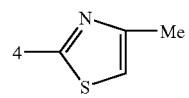 |
| 34 | 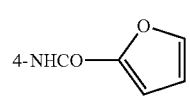 |
| 35 | 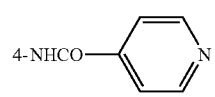 |
| 36 | 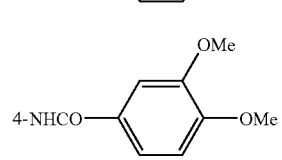 |
| 37 | 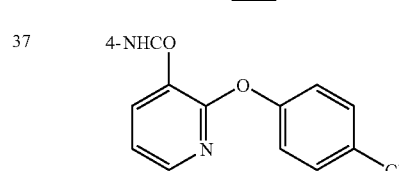 |
| 38 | 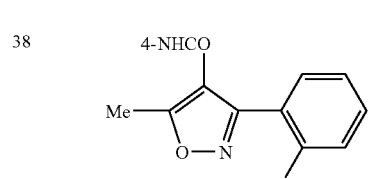 |

TABLE 90
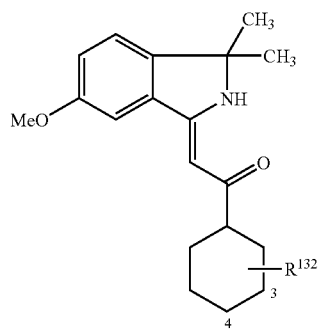
(Ia'-6-18)
| No. | R[132] |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 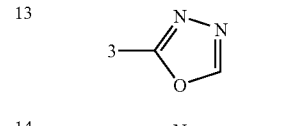 |
| 14 | 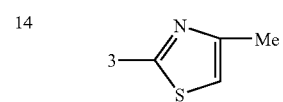 |
| 15 | 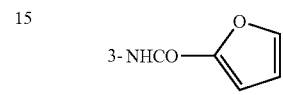 |
| 16 | 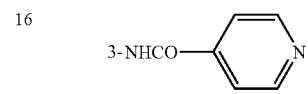 |
| 17 | 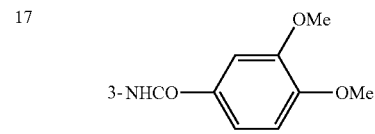 |
| 18 | 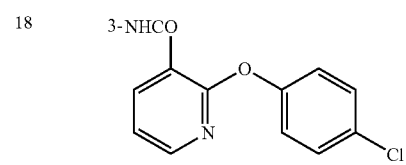 |
| 19 | 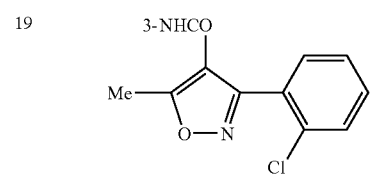 |
| 20 | 4-CN |
| 21 | 4-NHAc |
TABLE 90-continued
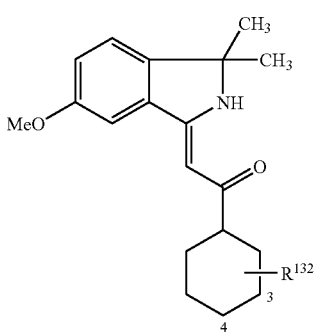
(Ia'-6-18)
| No. | R[132] |
|---|---|
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 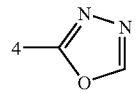 |
| 33 | 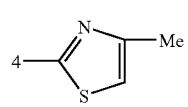 |
| 34 | 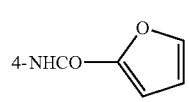 |
| 35 | 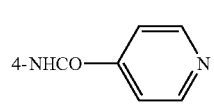 |
| 36 | 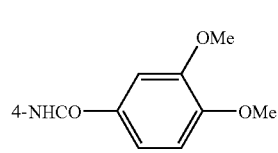 |
| 37 |  |
| 38 | 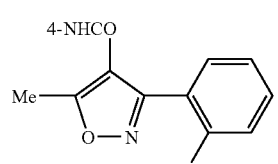 |

TABLE 91

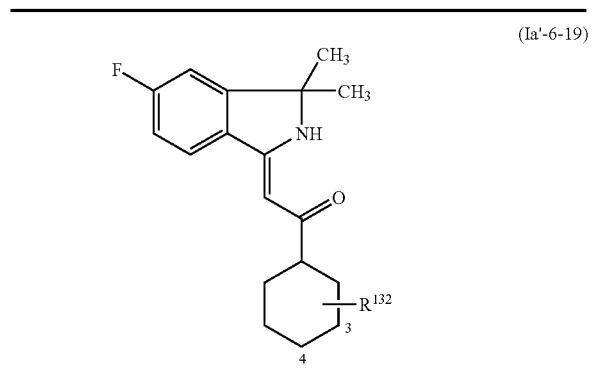

(Ia'-6-19)

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-(2-(4-chlorophenoxy)pyridin-3-yl) |
| 19 | 3-NHCO-(5-methyl-3-(2-chlorophenyl)isoxazol-4-yl) |
| 20 | 4-CN |

TABLE 91-continued

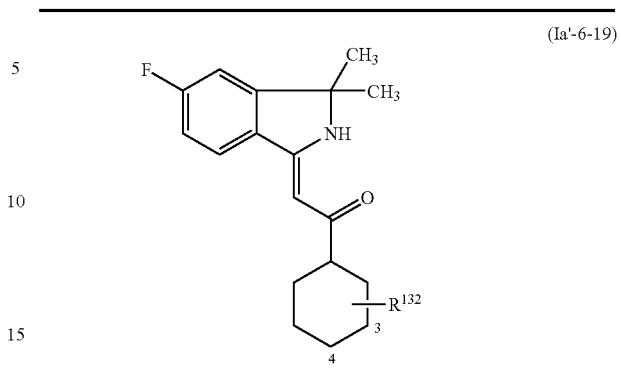

(Ia'-6-19)

| No. | R¹³² |
|---|---|
| 21 | 4-NHAc |
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-(2-(4-chlorophenoxy)pyridin-3-yl) |
| 38 | 4-NHCO-(5-methyl-3-(2-chlorophenyl)isoxazol-4-yl) |

TABLE 92

(Ia'-6-20)

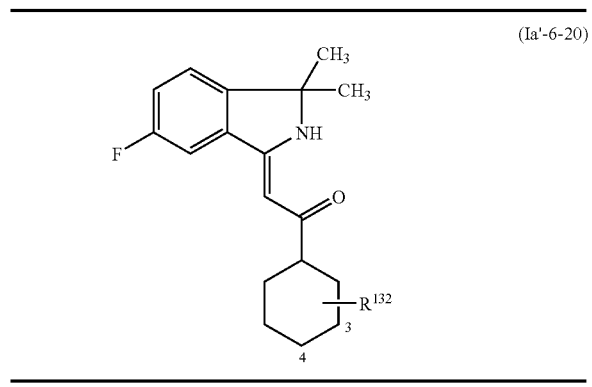

| No. | R[132] |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 3-(1,3,4-oxadiazol-2-yl) |
| 14 | 3-(4-methylthiazol-2-yl) |
| 15 | 3-NHCO-(furan-2-yl) |
| 16 | 3-NHCO-(pyridin-4-yl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |

TABLE 92-continued (Ia'-6-20)

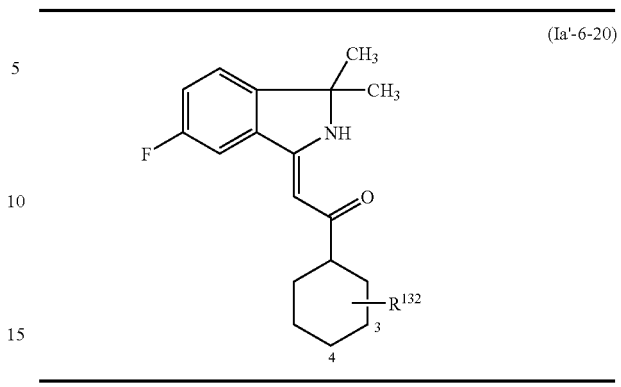

| No. | R[132] |
|---|---|
| 21 | 4-NHAc |
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 4-(1,3,4-oxadiazol-2-yl) |
| 33 | 4-(4-methylthiazol-2-yl) |
| 34 | 4-NHCO-(furan-2-yl) |
| 35 | 4-NHCO-(pyridin-4-yl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 93

(Ia'-6-21)

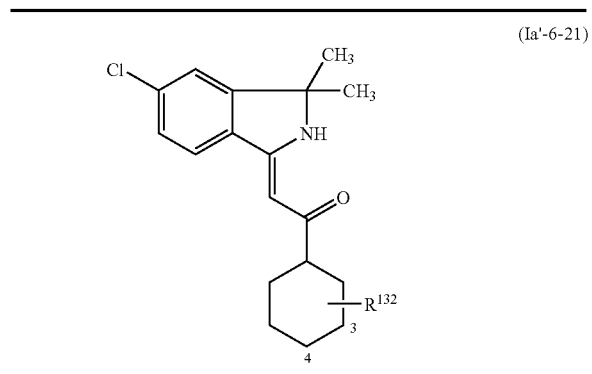

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)pyridin-3-yl] |
| 19 | 3-NHCO-[5-methyl-3-(2-chlorophenyl)isoxazol-4-yl] |
| 20 | 4-CN |

TABLE 93-continued (Ia'-6-21)

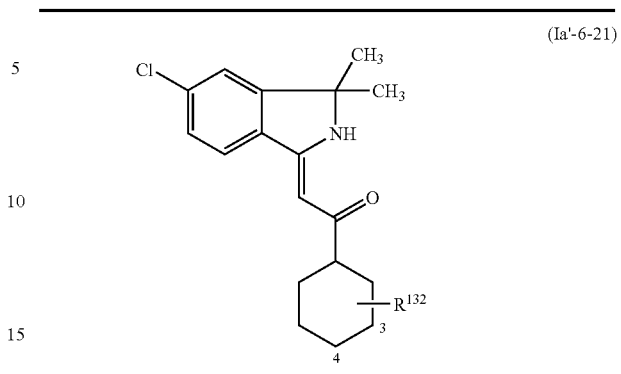

| No. | R¹³² |
|---|---|
| 21 | 4-NHAc |
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)pyridin-3-yl] |
| 38 | 4-NHCO-[5-methyl-3-(2-chlorophenyl)isoxazol-4-yl] |

TABLE 94

(Ia'-6-22)

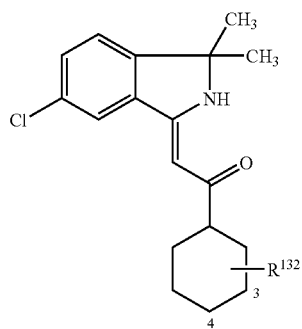

| No. | R[132] |
|---|---|
| 1 | 3-CN |
| 2 | 3-NHAc |
| 3 | 3-NH$_2$ |
| 4 | 3-MeO |
| 5 | 3-NHCO$_2$Me |
| 6 | 3-NHSO$_2$Me |
| 7 | 3-NHCONH$_2$ |
| 8 | 3-NHCHO |
| 9 | 3-CONHMe |
| 10 | 3-NHCO-i-Bu |
| 11 | 3-NHCO-c-Pr |
| 12 | 3-NHCOCH$_2$OMe |
| 13 | 3-(1,3,4-oxadiazol-2-yl) |
| 14 | 3-(4-methylthiazol-2-yl) |
| 15 | 3-NHCO-(furan-2-yl) |
| 16 | 3-NHCO-(pyridin-4-yl) |
| 17 | 3-NHCO-(3,4-dimethoxyphenyl) |
| 18 | 3-NHCO-[2-(4-chlorophenoxy)pyridin-3-yl] |
| 19 | 3-NHCO-[3-(2-chlorophenyl)-5-methylisoxazol-4-yl] |
| 20 | 4-CN |

TABLE 94-continued (Ia'-6-22)

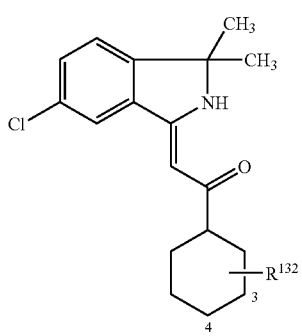

| No. | R[132] |
|---|---|
| 21 | 4-NHAc |
| 22 | 4-NH$_2$ |
| 23 | 4-MeO |
| 24 | 4-NHCO$_2$Me |
| 25 | 4-NHSO$_2$Me |
| 26 | 4-NHCONH$_2$ |
| 27 | 4-NHCHO |
| 28 | 4-CONHMe |
| 29 | 4-NHCO-i-Bu |
| 30 | 4-NHCO-c-Pr |
| 31 | 4-NHCOCH$_2$OMe |
| 32 | 4-(1,3,4-oxadiazol-2-yl) |
| 33 | 4-(4-methylthiazol-2-yl) |
| 34 | 4-NHCO-(furan-2-yl) |
| 35 | 4-NHCO-(pyridin-4-yl) |
| 36 | 4-NHCO-(3,4-dimethoxyphenyl) |
| 37 | 4-NHCO-[2-(4-chlorophenoxy)pyridin-3-yl] |
| 38 | 4-NHCO-[3-(2-chlorophenyl)-5-methylisoxazol-4-yl] |

TABLE 95

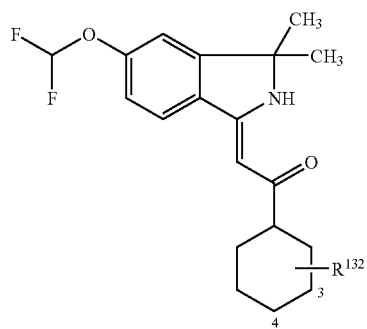

(Ia'-6-23)

| No. | R132 |
|---|---|
| 1 | 3-CN |
| 2 | 3-NHAc |
| 3 | 3-NH2 |
| 4 | 3-MeO |
| 5 | 3-NHCO2Me |
| 6 | 3-NHSO2Me |
| 7 | 3-NHCONH2 |
| 8 | 3-NHCHO |
| 9 | 3-CONHMe |
| 10 | 3-NHCO-i-Bu |
| 11 | 3-NHCO-c-Pr |
| 12 | 3-NHCOCH2OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(3,4-dimethoxyphenyl) |
| 18 | 3-NHCO-[2-(4-chlorophenoxy)-3-pyridyl] |
| 19 | 3-NHCO-[5-methyl-3-(2-chlorophenyl)isoxazol-4-yl] |
| 20 | 4-CN |

TABLE 95-continued

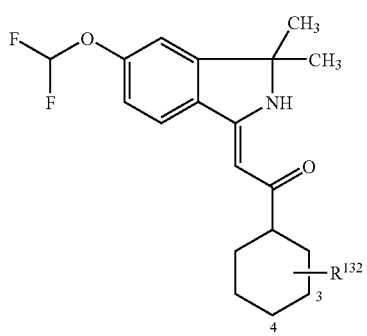

(Ia'-6-23)

| No. | R132 |
|---|---|
| 21 | 4-NHAc |
| 22 | 4-NH2 |
| 23 | 4-MeO |
| 24 | 4-NHCO2Me |
| 25 | 4-NHSO2Me |
| 26 | 4-NHCONH2 |
| 27 | 4-NHCHO |
| 28 | 4-CONHMe |
| 29 | 4-NHCO-i-Bu |
| 30 | 4-NHCO-c-Pr |
| 31 | 4-NHCOCH2OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(3,4-dimethoxyphenyl) |
| 37 | 4-NHCO-[2-(4-chlorophenoxy)-3-pyridyl] |
| 38 | 4-NHCO-[5-methyl-3-(2-chlorophenyl)isoxazol-4-yl] |

TABLE 96

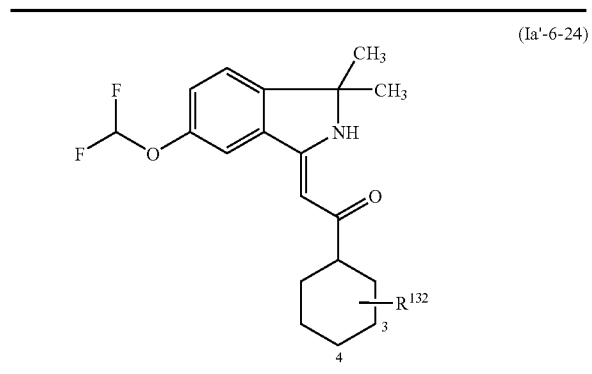

(Ia'-6-24)

| No. | R¹³² |
|---|---|
| 1 | 3-CN |
| 2 | 3-NHAc |
| 3 | 3-NH₂ |
| 4 | 3-MeO |
| 5 | 3-NHCO₂Me |
| 6 | 3-NHSO₂Me |
| 7 | 3-NHCONH₂ |
| 8 | 3-NHCHO |
| 9 | 3-CONHMe |
| 10 | 3-NHCO-i-Bu |
| 11 | 3-NHCO-c-Pr |
| 12 | 3-NHCOCH₂OMe |
| 13 | 3-(1,3,4-oxadiazol-2-yl) |
| 14 | 3-(4-methylthiazol-2-yl) |
| 15 | 3-NHCO-(2-furyl) |
| 16 | 3-NHCO-(4-pyridyl) |
| 17 | 3-NHCO-(2,4-dimethoxyphenyl) |
| 18 | 3-NHCO-[2-(4-chlorophenoxy)-3-pyridyl] |
| 19 | 3-NHCO-[3-(2-chlorophenyl)-5-methylisoxazol-4-yl] |
| 20 | 4-CN |

TABLE 96-continued

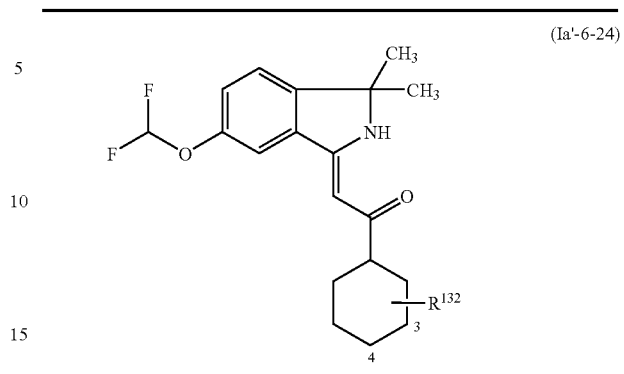

(Ia'-6-24)

| No. | R¹³² |
|---|---|
| 21 | 4-NHAc |
| 22 | 4-NH₂ |
| 23 | 4-MeO |
| 24 | 4-NHCO₂Me |
| 25 | 4-NHSO₂Me |
| 26 | 4-NHCONH₂ |
| 27 | 4-NHCHO |
| 28 | 4-CONHMe |
| 29 | 4-NHCO-i-Bu |
| 30 | 4-NHCO-c-Pr |
| 31 | 4-NHCOCH₂OMe |
| 32 | 4-(1,3,4-oxadiazol-2-yl) |
| 33 | 4-(4-methylthiazol-2-yl) |
| 34 | 4-NHCO-(2-furyl) |
| 35 | 4-NHCO-(4-pyridyl) |
| 36 | 4-NHCO-(2,4-dimethoxyphenyl) |
| 37 | 4-NHCO-[2-(4-chlorophenoxy)-3-pyridyl] |
| 38 | 4-NHCO-[3-(2-chlorophenyl)-5-methylisoxazol-4-yl] |

Methods for the Preparation of the Compound of the Present Invention:

The compound of formula (I) of the present invention may be prepared by the following method or the methods described in the examples.

[1] In the compound of formula (I) of the present invention, the compound wherein $R^6$ is hydrogen, i.e. the compound of formula (IA)

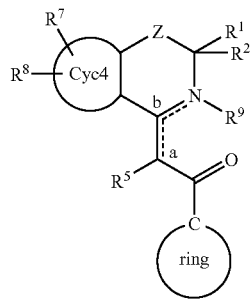
(IA)

(wherein all symbols have the same meaning as hereinbefore.) may be prepared by the method of the following [a], [b] or [c].

[a] The compound of formula (IA) may be prepared by subjecting to a reaction the compound of formula (II)

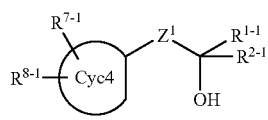
(II)

(wherein $Z^1$ is $-CR^{3-1}R^{4-1}$, $-O-$, $-S-$ or a bond, $R^{1-1}$, $R^{2-1}$, $R^{3-1}$, $R^{4-1}$, $R^{7-1}$ and $R^{8-1}$ are each the same meaning as $R^1$, $R^2$, $R^3$, $R^4$, $R^7$ and $R^8$ respectively, and hydroxy, amino or carboxy included in $R^{1-1}$, $R^{2-1}$, $R^{3-1}$, $R^{4-1}$ and $R^{8-1}$ are protected if necessary.) and the compound of formula (III)

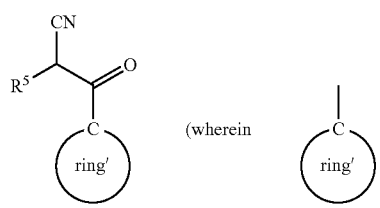
(III) (wherein has the same meaning as ring, and hydroxy, amino or carboxy included in the group represented by ring' are protected if necessary.) to give the compound of formula (IA')

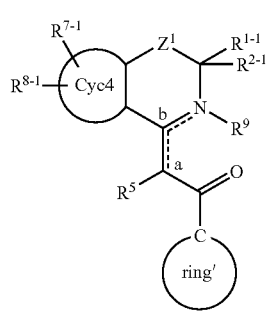
(IA')

(wherein all symbols have the same meaning as hereinbefore.), optionally followed by subjecting it to a deprotection reaction of protective groups.

The reaction of the compound of formula (II) and the compound of formula (III) is known, for example, it is carried out in a concentrated sulfuric acid by subjecting to a reaction the compound of formula (II) and the compound of formula (III) at a temperature between −20 and 100° C.

Deprotection reaction may be carried out by the following methods.

Deprotection reactions of protective groups of carboxy, hydroxy or amino is known, for example, (1) a deprotection reaction under alkaline conditions,
(2) a deprotection reaction under acidic conditions,
(3) a deprotection reaction by hydration,
(4) a deprotection reaction of silyl group, etc are known.

To describe these methods concretely, (1) A deprotection reaction under alkaline conditions is, for example, carried out in an organic solvent (methanol, tetrahydrofuran, dioxane or a mixture thereof, etc.) using a hydroxide of alkali metals (sodium hydroxide, potassium hydroxide, lithium hydroxide, etc.), hydroxide of alkaline earth metals (barium hydroxide, calcium hydroxide, etc.), or carbonates (sodium carbonate, potassium carbonate, etc.) or a solution thereof or a mixture thereof at a temperature between 0 and 40° C.

(2) A deprotection reaction under acidic conditions is, for example, carried out in or without an organic solvent (methylene chloride, chloroform, dioxane, ethyl acetate, anisole, etc.), using an organic acid (acetic acid, trifluoroacetic acid, methanesulfonic acid, etc.) or an inorganic acid (hydrochloric acid, sulfuric acid, etc.) or a mixture thereof (hydrobromic acid/acetic acid, etc.) at a temperature between 0 and 100° C.

(3) A deprotection reaction by hydration is, for example, carried out in a solvent (ethers (tetrahydrofuran, dioxane, dimethoxyethane, diethyl ether, etc.), alcohols (methanol, ethanol, etc.), benzenes (benzene, toluene, etc.), ketones (acetone, methyl ethyl ketone, etc.), nitriles (acetonitrile etc.), amides (dimethylformamide etc.), water, ethyl acetate, acetic acid or a mixture of more than two from above etc.) in the presence of a catalyst (palladium-carbon, palladium black, palladium hydroxide, platinum oxide, Raney nickel, etc.) under atmosphere of hydrogen of normal or suppressed pressure, or in the presence of ammonium formate at a temperature between 0 and 200° C.

(4) A deprotection reaction of silyl group is, for example, carried out in a water-miscible organic solvent (tetrahydrofuran, acetonitrile, etc.) using tetrabutylammonium fluoride at a temperature between 0 and 40° C.

Protective groups for carboxy include, for example, methyl, ethyl, t-butyl and benzyl.

Protective groups for hydroxy include, for example, methoxymethyl, 2-tetrahydropyranyl, t-butyldimethylsilyl, t-butyldiphenylsilyl, acetyl and benzyl.

Protective groups for amino include, for example, benzyloxycarbonyl, t-butoxycarbonyl, trifluoroacetyl and 9-fluorenylmethoxycarbonyl.

Protective groups for carboxy, hydroxy or amino are not limited to above listed, but other groups may also be used instead, if easily and selectively eliminated. For example, the groups described in T. W. Greene, Protective Groups in Organic Synthesis 3rd edition, Wiley, New York, 1999 may be used.

As easily understood by those skilled in the art, the compounds of the present invention may be easily prepared by these reactions.

[b] The compound of formula (IA) may be prepared by subjecting to a reaction the compound of formula (IV)

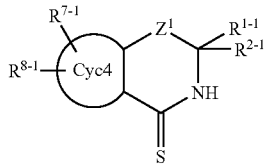
(IV)

(wherein all symbols have the same meaning as hereinbefore.) and the compound of formula (V)

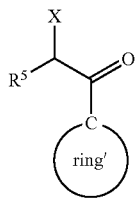
(V)

(wherein X is halogen, and the other symbols have the same meanings hereinbefore.), optionally followed by subjecting to a deprotection reaction of a protective group.

The reaction of the compound of formula (IV) and the compound of formula (V) is known, for example, it is carried out in an organic solvent (xylene, toluene, benzene, acetonitrile, tetrahydrofuran, methylene chloride, chloroform, etc.) in the presence of a phosphine reagent (triphenylphosphine, tributylphosphine, etc.) or phosphate reagents (trimethylphosphite, triethylphosphite, tripropylphosphite, tributylphosphite, etc.) and a base (triethylamine, diisopropylethylamine, dimethylaminopyridine, etc.) at a temperature between 30° C. to refluxing temperature.

Deprotective reactions of protective groups are carried out according to the methods described hereinbefore.

[c] In the compound of formula (IA), the compound wherein $R^5$ is hydrogen, i.e. the compound of formula (IA-1)

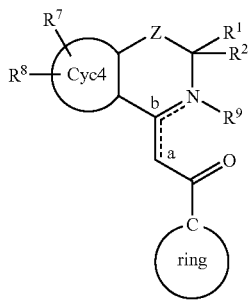
(IA-1)

(wherein all symbols have the same meaning as hereinbefore.) may be prepared by subjecting to a reaction the compound of formula (VI)

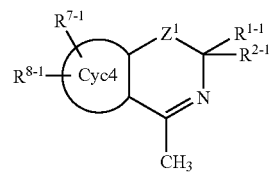
(VI)

(wherein all symbols have the same meaning as hereinbefore) and the compound of formula (VII)

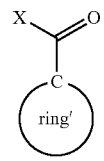
(VII)

(wherein all symbols have the same meaning as hereinbefore.) to give the compound of formula (IA'-1)

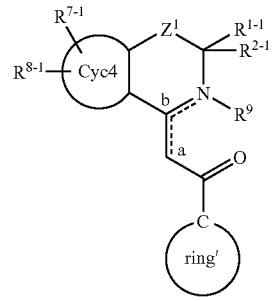
(IA'-1)

(wherein all symbols have the same meaning as hereinbefore), optionally followed by subjecting to a deprotection reaction of protective group.

The reaction of the compound of formula (VI) and the compound of formula (VII) is known, for example, it is carried out in an inert organic solvent (tetrahydrofuran (THF), diethyl ether, benzene, etc.) in the presence of a base (lithium diisopropylamine (LDA), lithium hexamethyldisilazide (LHMDS), n-butyl lithium, t-butyl lithium, etc.) at a temperature between −78° C. and room temperature.

The deprotection reaction of protective groups are carried out by the same method as described hereinbefore.

[2] In the compound of formula (I), the compound wherein $R^5$ and $R^6$ are C1-8 alkyl or taken together with the carbon atom to which they are attached to form Cyc1, i.e. the compound of formula (IB)

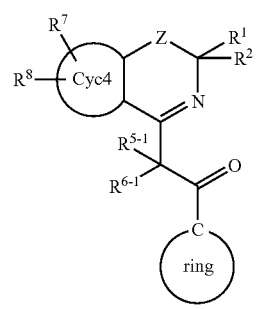
(IB)

(wherein $R^{5-1}$ and $R^{6-1}$ are each independently, C1-8 alkyl, but $R^{5-1}$ and $R^{6-1}$ are taken together with the carbon atom to which they are attached to form Cyc1 and the other symbols have the same meaning as hereinbefore).

The compound of formula (IB) may be prepared by subjecting to a reaction the compound of formula (IA'-1) and the compound of formula (VIII)

$$R^{133}\text{-}X \quad (VIII)$$

(wherein $R^{133}$ is C1-8 alkyl and the other symbols have the same meaning as hereinbefore.) or the compound of formula (IX)

$$X\text{—}Y\text{—}X \quad (IX)$$

(wherein Y is —(CH$_2$)$_m$— (wherein m is an integer of 2-9.) and carbon atom in —(CH$_2$)$_m$— may be replaced by 1-2 of heteroatom selected from oxygen, nitrogen and sulfur and when replaced by nitrogen, the nitrogen atom is protected if necessary. and Y may be substituted with $R^{10-1}$ (wherein $R^{10-1}$ has the same meaning as $R^{10}$, and hydroxy in $R^{10-1}$ is protected if necessary.) to give the compound of formula (IB'), optionally subjecting to deprotection reaction of the protective groups.

The reaction of the compound of formula (IA'-1) and the compound of formula (VIII) or (IX) is known, for example, it is carried out in an inert organic solvent (tetrahydrofuran, diethyl ether, dimethylformamide, benzene, dioxane, etc.) in the presence of a base (sodium hydroxide, LDA, n-butyl lithium, t-butyl lithium, etc.), optionally using potassium iodide, at a temperature between −20° C. and refluxing temperature.

The deprotection reaction of protective groups is carried out by the same method as described hereinbefore.

[3] In the compound of formula (I), the compound wherein $R^7$ is Cyc2, i.e. the compound of formula (IC)

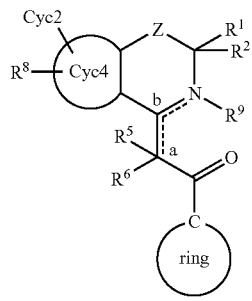

(IC)

(wherein all symbols have the same meaning as hereinbefore.) may also be substituted with the following methods.

The compound of formula (IC) may be prepared by subjecting to a reaction the compound of formula (X)

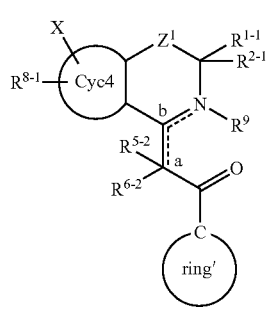

(X)

(wherein $R^{5-2}$ and $R^{6-2}$ have the same meanings as $R^5$ and $R^6$ respectively, and hydroxy or amino included in $R^{5-2}$ and $R^{6-2}$ are protected if necessary, and the other symbols have the same meanings as hereinbefore.) and the compound of formula (XI)

$$\text{Cyc2'-}R^{134} \quad (XI)$$

(wherein $R^{134}$ is —B(OH)$_2$ or —B(C1-8 alkyl)$_2$, Cyc2' has the same meaning as Cyc2, and hydroxy, amino or carboxy included in Cyc2' is protected if necessary.) to give the compound of formula (IC')

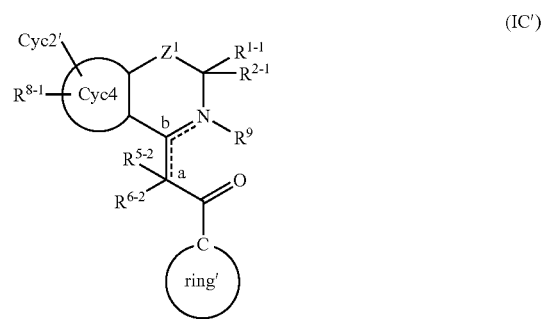

(IC')

(wherein all symbols have the same meanings as hereinbefore,), optionally followed by subjecting to a deprotection reaction of the protective groups.

The reaction of the compound of formula (X) and the compound of formula (XI) is known, for example, it is carried out in an organic solvent (benzene, dimethylformamide, dioxane, tetrahydrofuran, methanol, acetonitrile, dimethoxyethane, acetone, etc.) in the presence of a base (sodium ethylate, sodium hydroxide, potassium hydroxide, triethylamine, sodium carbonate, sodium bicarbonate, potassium carbonate, cesium carbonate, thalium carbonate, tripotassium phosphate, cesium fluoride, barium hydroxide, tetrabutylammonium fluoride, etc.) and a catalyst (tetrakis (triphenylphosphine)palladium (Pd(PPh$_3$)$_4$), bis (triphenylphosphine)palladium dichloride (PdCl$_2$(PPh$_3$)$_2$), palladium acetate (Pd(OAc)$_2$), palladium black, 1,1'-bis (diphenylphosphinoferrocene)dichloropalladium (PdCl$_2$ (dppf)$_2$), diallylpalladium dichloride (PdCl$_2$(allyl)$_2$), phenylbis(triphenylphosphine)palladium (PhPdI(PPh$_3$)$_2$), etc.) at a temperature of between room temperature and 120° C.

The deprotection reaction of protective groups are carried out by the same method as described hereinbefore.

[4] In the compound of formula (I) of the present invention, the compound wherein at least one group selected from ring is amide or a group including amide, i.e. the compound of formula (ID)

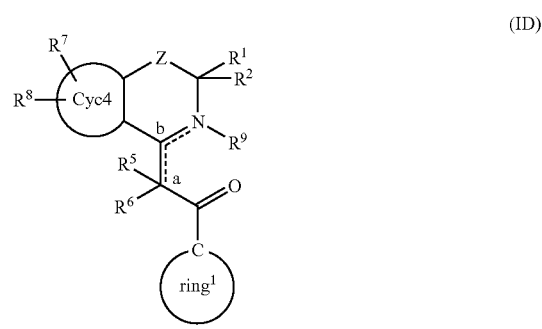

(ID)

(wherein ring1 has the same meaning as ring, and wherein at least one group of ring1 is amide or a group including amide, and the other symbols have the same meaning as hereinbefore.) may be prepared by the following method.

The compound of formula (ID) may be prepared by subjecting to amidation reaction the compound of formula (XII)

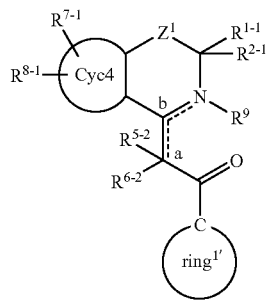

(XII)

(wherein ring1 has the same meaning as ring, and wherein at least one group selected from ring1 is amino or a group including amino, and the other amino, hydroxy or carboxy is protected if necessary.) and a corresponding compound having carboxylic acid or acid halide, optionally followed by subjecting to deprotection reaction of protective groups.

Amidation reactions are known, for example,
(1) a method using acid halide,
(2) a method using mixed anhydride,
(3) a method using a condensing agent, etc.

To explain these methods concretely, (1) The method using acid halide is, for example, carried out by subjecting to a reaction carboxylic acid in an organic solvent (chloroform, methylene chloride, diethyl ether, tetrahydrofuran, etc.) or without a solvent, and acid-halogenating agent (oxalyl chloride, thionyl chloride, etc.) at a temperature between −20° C. and refluxing temperature, and then subjecting to a reaction thus obtained acid halide in the presence of tertiary amine (pyridine, triethylamine, dimethylaniline, dimethylaminopyridine, etc.) at a temperature between 0 and 40° C. And it is also carried out by subjecting to a reaction with an acid halide by using an alkaline aqueous solution (sodium bicarbonate or sodium hydroxide, etc.) in organic solvent (dioxane, tetrahydrofuran, etc.) at a temperature between 0 and 40° C.

(2) The method using mixed anhydride is, for example, carried out by subjecting to a reaction in an organic solvent (chloroform, methylene chloride, diethyl ether, tetrahydrofuran, etc.) or without a solvent, in the presence of tertiary amine (pyridine, triethylamine, dimethylaniline, dimethylaminopyridine, etc.) carboxylic acid with acid halide (pivaloyl chloride, tosyl chloride, mesylchloride, etc.) or acid derivative (chloroethyl formate, chloroisobutyl formate, etc.) at a temperature between −20 and 40° C., and then subjecting to a reaction thus obtained mixed anhydride with amine at a temperature between 0 and 40° C.

(3) The method using a condensing agent is carried out, for example, in an inert organic solvent (chloroform, methylene chloride, dimethylformamide, diethyl ether, tetrahydrofuran, etc.) or without a solvent, in the presence or absence of a tertiary amine (pyridine, triethylamine, dimethylaniline, dimethylaminopyridine, N-methylmorpholine, etc.), using a condensing reagent (1,3-dichlorohexylcarbodiimide (DCC), 1-ethyl-3-[3-(dimethylamino)propyl]carbo diimide (EDC), 1,1'-carbonyldiimizazole (CDI), 2-chloro-1-methylpyridinium iodide, etc.) in the presence or absence of 1-hydroxybenzotriazole, by subjecting to a reaction carboxylic acid and amine at a temperature between 0 and 40° C.

These reactions (1), (2) and (3) are desirably carried out under atmosphere of an inert gas (argon, nitrogen, etc.) under anhydrous conditions.

Deprotection reaction of protective groups may be carried out in the same methods as described hereinbefore described.

[5] In the compound of formula (I), the compound wherein at least one group selected from ring is sulfonamide or a group comprising sulfonamide, i.e. the compound of formula (IE) (wherein ring2 has the same meaning as ring, and wherein at least one group selected from ring2 is sulfonamide or a group including sulfonamide, and the other symbols have the same meaning as hereinbefore.) may also be prepared by the following method.

The compound of formula (IE) may be prepared by subjecting to a sulfonamidation the compound of formula (XIII)

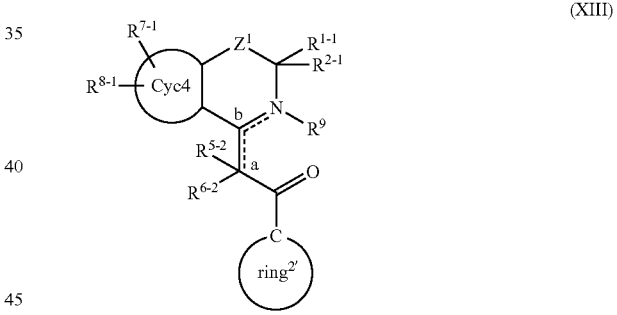

(XIII)

(wherein ring2' has the same meaning as hereinbefore, and wherein at least one of the group represented by ring2' is amino or a group including amino, and the other amino, hydroxy or carboxy is protected if necessary.) and a corresponding compound having sulfonic acid or sulfonyl halide, optionally followed by subjecting to deprotection reaction of protective groups.

Sulfonamidation reaction is known, for example, it is carried out in an inert organic solvent (chloroform, dichloromethane, dichloroethane, diethyl ether, tetrahydrofuran, etc.) or without a solvent, in the presence of acid halide (oxalyl chloride, thionyl chloride, phosphorus pentachloride, phosphorous trichloride, etc.) at a temperature between −20° C. and refluxing temperature, and then subjecting to a reaction thus given sulfonyl halide with amine in the presence of tertiary amine (isopropylethylamine, pyridine, triethylamine, dimethylaniline, dimethylaminopyridine, etc.) in an inert organic solvent (chloroform, dichloromethane, dichloroethane, diethyl ether, tetrahydrofuran, etc.) at a temperature between 0 and 40° C.

The deprotection reaction of protective groups are carried out by the same method as described hereinbefore.

The compounds of formula (II), (III), (IV), (V), (VI), (VII), (VIII), (IX) and (XI), used as starting materials may be prepared by known methods or are commercially available.

For example, the compound of formula (IV) may be prepared according to the method described in the following reaction scheme 1 or 2.

In the reaction schemes 1 and 2, LDA is lithium diisopropylamide, DPPA is diphenylphosphorylazide, Et$_3$N is triethylamine, PPA is polyphosphorous acid, DPPF is 1,1'-bis(diphenylphoshophino)ferrocene, and the other symbols have the same meaning as hereinbefore

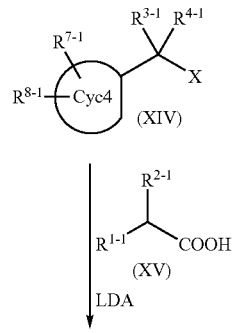

-continued

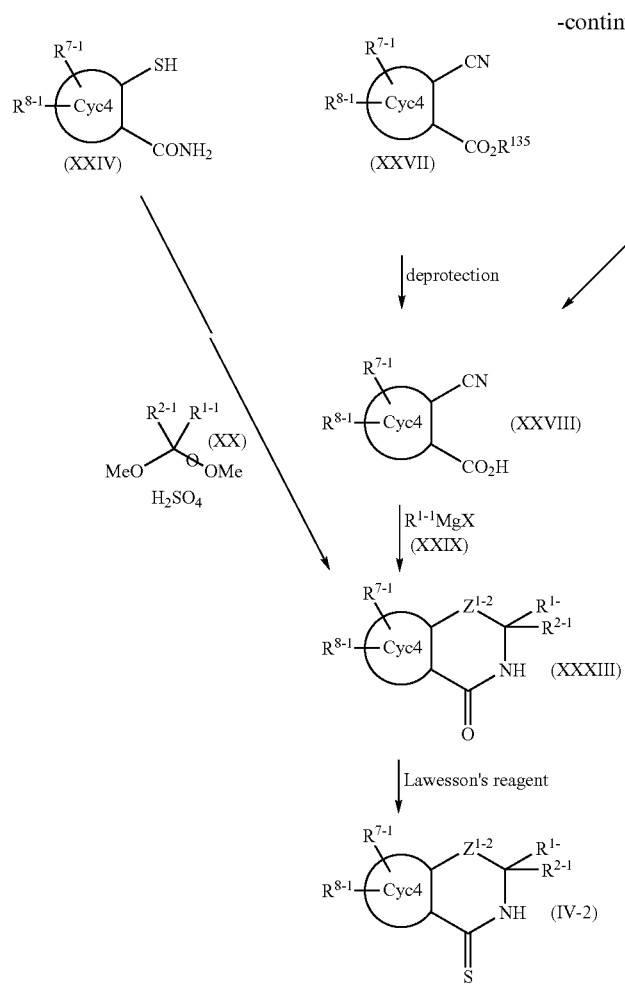
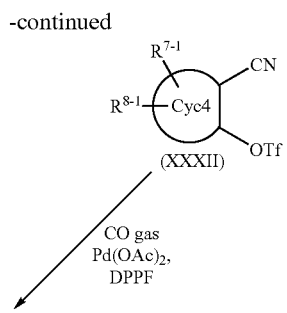

In the reaction schemes 1 and 2, the compounds of formula (XIV), (XV), (XIX), (XX), (XXII), (XXV), (XXIX) and (XXX) are known or may be prepared by known methods easily.

In each reaction in the present invention, the reaction products may be purified by conventional techniques, for example, distillation under normal or reduced pressure, high performance liquid chromatography, thin layer chromatography or column chromatography using silica gel or magnesium silicate. Purification may be carried out after each reaction, or after a series of reactions.

Pharmacological Effect:

It was confirmed by the following experiments that the compound of formula (I) of the present invention has an inhibitory activity against PDE7.

In Vitro Enzyme Assay

Experimental Method:

HuT78 cells (derived from human T cell lymphocyte) were cultured in PRMI1640 medium containing 10% bovine fetus serum. 2 L of cells (approximately $8 \times 10^8$ cells) were collected, and they were homogenized in a buffer [50 mmol/l tris hydrochloric acid buffer containing 1 mmol/l dithiothreitol (DTT), 2 mmol/l ethylenediamine tetraacetate disodium (EDTA-2Na). After centrifugation (50,000 rpm, 4° C., 1 hour), the supernatant was collected, and filtered over 0.22 µm filter and the filtrate was fractionated by column chromatography on MonoQ (Pharmacia, hard negative ion exchange column) using the filtrate as soluble portion. The PDE activity of the fraction eluted by the concentration gradient of NaCl of 0-0.8 mol/L was measured using 1 µmol/l of cAMP as a substrate. Fractions where PDE activity is not inhibited by 10 µmol/l of rolipram (PDE selective inhibitor) are collected. As to the PDE activity of these fractions, substrate-specificity against cAMP and Michaelis-Menten constant were measured and sensitivity to rolipram was confirmed. Then the fractions which show specificity and high affinity to cAMP which are non-sensitive fractions to rolipram were identified as PDE7. The fractions were used as an enzyme liquor for the measurement of PDE inhibitory activity.

PDE7 inhibitory activity of the compound of the present invention of was evaluated by the following method. 70 µl of diluted enzyme solution, 10 µl of the solution of the compound of the present invention (10% in DMSO), 10 µl of reaction buffer solution [50 mmol/l $MgCl_2$, 1 mg/ml bovine serum albumin, 200 mmol/l tris hydrochloric acid buffer (pH 8.0) containing 40 mmol/l 2-mercaptoethanol] in 96 well plate and it was incubated for 30 minutes at room temperature. It was microwaved for 2.5 minutes to terminate the reaction. It was centrifuged (2,000 rpm for 1 minute) and thereto was added 10 µl of 1 mg/ml snake venom (Sigma, cat. V7000) and it was incubated for 30 minutes at room temperature. The serum (50 μl) was applied to alumina column (100 μl). Purified $^3$H-adenosine was eluted with 0.005N hydrochloric acid (80 μl) and its radioactivity of the elute was measured.

PDE7 inhibitory activity of the present invention was evaluated by the activity inhibitory percentage calculated from the following equation.

Activity inhibitory percentage (%)=(1-radioactivity in the presence of the compound of the present invention/radioactivity in the absence of the compound of the present invention)×100

$IC_{50}$ values were calculated as the concentration of the compound of the present invention when it shows 50% inhibition of activity.

The results are shown in table 97.

TABLE 97

| Example No. | $IC_{50}$ (μM) |
| --- | --- |
| 11(35) | 0.15 |
| 11(43) | 0.97 |
| 11(79) | 0.76 |
| 11(162) | 0.37 |
| 12(7) | 0.27 |
| 12(15) | 1.1 |
| 58 | 0.023 |
| 73 | 0.027 |

Inhibitory Effect of IL2 Production:

Experimental Method:

Jurkat cells were cultured in RPMI1640 medium containing 10% bovine fetus serum. Collected cells were prepared to give 1×10$^6$ cells/ml in RPMI1640 medium containing 2% bovine fetus serum and it was added to a 96-well plate 190 μl each. It was allowed to stand for 30 minutes at 37° C. in 5% $CO_2$ incubator and the reaction was initiated by adding 10 μl of stimulating substance solution [0.2 μmol/l phorbol-12-myristate-13-acetate (PMA, Sigma, cat. P8139), 20 μmol/l ionomycin (Sigma, cat 10634), 20 μg/ml anti-CD28 antibody (MBL, cat. IM1376) diluted by RPMI1640 medium containing 2% bovine fetus serum] and after incubating for approximately 20 hours the plate was centrifuged by 300 g for 5 minutes and the supernatant (approximately 100 μl) was collected. The concentration of IL-2 in the supernatant was measured by using human IL-2 ELISA system (DIACLONE, cat. 850010192), according to the attached method of serum.

As a result, the compound of the present invention showed a dose-depending inhibitory effect against IL-2 production.

Mouse Delayed Dermatitis Model

Experimental Method:

The hair of 14-week old BALB/cAnCrj male mice (Nihon Charles River) on abdomen was shaved. The next day to all over the shaved parts was added 0.1 ml of picryl chloride (PC, Tokyo Chemicals industry, cat.C0307) in ethanol (0.1 ml) with pipetman to sensitize. 4 days later, 2% solution of PC in olive oil was applied to front and back of both auricles 0.02 ml/ear each to induce mouse delayed dermatitis. The width of both auricles was measured with dial sickness gauge (Ozaki Mfg. Co., Ltd.) and the auricle edema was evaluated by calculating the average. The compounds of the present invention were administered orally once in a suspension of 0.5% methyl cellulose solution 30 minutes before induction. The compound of the present invention showed an inhibitory activity against auricle edema, almost equivalent effect to cyclosporine A (Wako Pure Chemical Industries, cat. 039-16301; 50 mg) or dexamethasone 21-phosphate (Sigma, cat. D-1159, 3 mg/kg), which were set up as controls.

It was confirmed by the following experiments that the compound of formula (I) has an activity as a CB2 receptor agonist.

In Vitro Signaling Assay

Experimental Method:

Human CB2 receptors expressed CHO cells were used for the assays. Cells were dispersed seeded in 96-well plates in a density of 5×10$^4$ cells/well, and were subjected to experiment the next day. After removing the culture media 1 mM isobutylmethylxanthine (IBMX) solution was added, and cells were incubated for 10 minutes at room temperature. Next, a mixture of 10 μM forskolin and the compound of the present invention was added. After additional incubation for 15 minutes at room temperature, the culture supernatant was discarded and 200 μl of lysis reagent (attached to a cAMP EIA) was added. The amounts of cAMP of the lysate were determined by a cAMP EIA kit (Amersham) under conditions of the forskolin-induced cAMP production. The compound of the present invention was dissolved in DMSO and the solution was diluted to adjust the final concentration of DMSO to 0.1%. $IC_{50}$ values were calculated from the inhibitory ratio of the compound of the present invention toward the amount of the forskolin-induced cAMP production. By the same experiment using CHO cells, it was confirmed that this inhibitory effect toward cAMP production by the compound was mediated via the human CB2 receptors.

The results are shown in table 97.

TABLE 97

| Ex. No. | $IC_{50}$ (nM) |
| --- | --- |
| 46(3) | 5.3 |
| 47(4) | 5.2 |
| 47(6) | 4.1 |
| 57(2) | 3.3 |

Toxicity:

The toxicity of the compound of the present invention of formula (I) is low enough to use as a pharmaceutical.

INDUSTRIAL APPLICABILITY

Application to Pharmaceuticals:

The compound of the present invention inhibits PDE7, and so it is thought to be useful for the prevention and/or treatment of various diseases, i.e. autoimmune diseases (ulcerative colitis, Crohn's disease, rheumatism, psoriasis, multiple sclerosis, collagenosis, etc.), inflammatory diseases (obstructive pulmonary disease, sepsis, pancreatitis, sarcoidosis, nephritis, hepatitis, enteritis, etc.), allergic diseases (asthma, allergic rhinitis, allergic conjunctivitis, seasonal conjunctivitis, atopic dermatitis, etc.), rejection of organ transplants, serious graft versus host disease (GVHD), diabetic disease, osteoporosis, bone fracture, restenosis, atherosclerosis, obesity, ischemic reperfusion injury, depression, Parkinson's disease, dementia, leukemia, etc.

Also, some compounds of the present invention act on CB2 specifically, and therefore, it is thought that the compound of the present invention is useful for the prevention and/or treatment of allergic diseases (asthma, allergic rhinitis, conjunctivitis, urticaria, food allergy, etc.), atopic dermatitis, autoimmune diseases (multiple sclerosis, colitis, etc.), rheumatism, arthritis, immunodeficiency diseases (acquired immunodeficiency syndrome, etc.), pain (postoperative pain, cancer pain, etc.), etc.

The compound of formula (I) or a non-toxic salt thereof may also be administered as a concomitant agent in combination with other agents for 1) supplementing and/or reinforcement of preventive and/or treating effect(s) of the compound,
2) improvement in kinetics and absorption of the compound and reduction of dose and/or
3) reduction of side effect of the compound.

A concomitant agent of the compound of formula (I) with other agents may be administered in a mode of compounded agent in which both components are compounded in a single preparation or in a mode of separate preparations. When administration is conducted using separate preparations, a simultaneous administration and administrations with time difference is included. In the case of administrations with time difference, the compound of formula (I) may be firstly administered and then other drug may be administered, or the other drug may be firstly administered and then the compound of formula (I) may be administered. Each of the methods for the administration may be the same or different.

There is no particular limitation for the diseases for which the above-mentioned concomitant agent achieves the preventive and/or the treating effect but any disease will be acceptable so far as it supplements and/or enforces the preventive and/or treating effect of the compound of formula (I).

For example, examples of the other drug for supplementing and/or reinforcing the preventive and/or treating effect of the compound of formula (I) to atopic dermatitis include, for example, steroidal agents, non-steroidal anti-inflammatory drugs (NSAID), immunosuppressants, prostaglandins, antiallergic drugs, mediator liberation inhibitors, antihistamines, forskolin drugs, other phosphodiesterase inhibitors, etc.

For example, examples of the other drug for supplementing and/or reinforcing the preventive and/or treating effect of the compound of formula (I) to chronic obstructive pulmonary disease and/or asthma include, for example, steroidal agents, β2-adrenergic receptor stimulators, leukotriene receptor antagonists, thromboxane synthase inhibitors, thromboxane A2 receptor antagonists, mediator liberation inhibitors, antihistamines, xanthine derivatives, anticholinergic agents, cytokine inhibitors, prostaglandins, forskolin drugs, other phosphodiesterase inhibitors, elastase inhibitors, metalloproteases, etc.

For example, examples of the other drug for supplementing and/or reinforcing the preventive and/or treating effect of the compound of formula (I) to allergic rhinitis include, for example, steroidal drugs, antihistamines, leukotriene receptor antagonists, prostaglandins, nitric oxide synthase inhibitors, etc.

For example, examples of the other drug for supplementing and/or reinforcing the preventive and/or treating effect of the compound of formula (I) to arthritis and rheumatism include, for example, metalloprotease inhibitors, non-steroidal anti-inflammatory drugs (NSAID), steroid agents, prostaglandins, immunosuppressants, etc.

For example, examples of the other drug for supplementing and/or reinforcing the preventive and/or treating effect of the compound of formula (I) to conjunctivitis include, for example, leukotriene receptor antagonists, antihistamines, non-steroidal anti-inflammatory drugs, prostaglandins, etc.

For example, examples of the other drug for supplementing and/or reinforcing the preventive and/or treating effect of the compound of formula (I) to asthma include, for example, steroidal agents, leukotriene receptor antagonists, prostaglandins, expectorants, etc.

For example, examples of the other drug for supplementing and/or reinforcing the preventive and/or treating effect of the compound of formula (I) to colitis include, for example, steroidal agents, nitric oxide synthase inhibitors, prostaglandins, poly(ADP-ribose)polymerase inhibitors, elastases, interleukin-8 antagonists, etc.

For example, examples of the other drug for supplementing and/or reinforcing the preventive and/or treating effect of the compound of formula (I) to multiple sclerosis include, for example, immunosuppresants.

For example, examples of the other drug for supplementing and/or reinforcing the preventive and/or treating effect of the compound of formula (I) to pain include, for example, prostaglandins, N-type calcium channel inhibitors, nitric oxide synthase inhibitors, etc.

Steroidal agents include the followings.

For example, external medicines include, clobetasol propionate, diflorasone diacetate, fluocinonide, monometasone furoate, betamethasone dipropionate, betamethasone butyrate propionate, betamethasone valerate, difluprednate, budesonide, diflucortolone valerate, amcinonide, halcinonide, dexamethasone, dexamethasone, dexamethasone, dexamethasone, hydrocortisone acetate, hydrocortisone lactate, hydrocortisone lactate propionate, deprodone propionate, prednisolone valerate-acetate, fluocinolone acetonide, beclometasone dipropionate, triamcinoloneacetonide, flumetasone pivalate, alclometasone dipropionate, clobetasone butyrate, prednisolone, beclometasone propionate, fludroxycortide, etc.

For example, internal agents and/or agents for injection include, cortisone acetate, hydrocortisone, hydrocortisone sodium phosphate, hydrocortisone sodium succinate, fludrocortisone acetate, prednisolone, prednisolone acetate, prednisolone sodium succinate, butylprednisolone acetate, prednisolone sodium phosphate, halopredone acetate, methylprednisolone, methylprednisolone acetate, prednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, betamethasone, etc.

For example, inhalant agents include, beclomethasone, fluticasone propionate, Budesonide, flunisolide, triamcinolone, ST-126P, ciclesonide, dexamethasone palmitate, mometasone furoate, prasterone sodium sulfate, deflazacort, methyl predonisolone, methyl predonisolone sodium succinate, etc.

Non-steroidal anti-inflammatory drugs include, for example, sasapyrine (salitylosalitylic acid), sodium salicylate, aspirin, aspirin dialuminate, diflunisal, indomethacin, suprofen, ufenamate, dimethylisopropylazulene, bufexamac, felbinac, dichlofenac, tolmetin sodium, clinoril, fenbufen, nabumetone, proglumetacin maleate, indometacin farnesil, acemetacin, proglumetacin maleate, amfenac sodium, mofezolac, etodolac, ibuprofen, ibuprofenpiconol, naproxen, flurbiprofen, flurbiprofen axetil, ketoprofen, phenoprofen calcium, tiaprofenic acid, oxaprozin, pranoprofen, loxoprofen sodium, alminoprofen, zaltoprofen, mefenamic acid, aluminum mefenamate, tolfenamic acid, floctafenine, ketophenylbutazon, oxyfenbutazon, piroxicam, tenoxicam, ampiroxicam, napageln ointment, epirizole, tiaramide, hydrochloride, tinoridine hydrochloride, emorfazone, sulpyrine, migrenin, saridon, cedes G, amipylo-N, sorbon, pyrine cold preparation, acetoaminofen, fenacetin, dimetotiazine mesilate, simetride, non-pyrine cold preparation, etc.

Immunosuppresants include, for example, Protopic (FK-506), methotrexate, cyslosporin, ascomycin, leflunomide, bucillamine, salazosulfapyridine, etc.

Prostaglandins (abbreviated as PG hereafter.) include, for example, PG receptor agonists, PG receptor antagonists, etc.

PG receptors include, PGE receptor (EP1, EP2, EP3, EP4), PGD receptor (DP), PGF receptor (FP), PGI receptor (IP), TX receptor (TP), etc.

Mediator liberation inhibitors include, for example, tranilast, sodium chromoglicate, amlexanox, repirinast, ibudilast, dazanolast, pemirolast potassium, etc.

Antihistamine agents include, for example, ketotifen fumarate, mequitazine, azelastine hydrochloride, oxatomide, terfenadine, emedastine difumarate, epinastine hydrochloride, astemizole, ebastine, cetirizine hydrochloride, bepotastine, fexofenadine, loratadine, desloratadine, olopatadine hydrochloride, TAK-427, ZCR-2060, NIP-530, mometasone furoate, mizolastine, BP-294, auranofin, etc.

$\beta_2$-Adrenergic receptor agonists include, for example, fenoterol hydrobromide, salbutamol sulfate, terbutaline sulfate, formoterol fumarate, salmeterol xinafoate, isoproterenol sulfate, orciprenaline sulfate, clorprenaline sulfate, epinephrine, trimetoquinol hydrochloride, hexoprenaline sulfate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamine hydrochloride, meluadrine tartrate, AR-C68397, levosalbutamol, R,R-Formoterol, KUR-1246, KUL-7211, AR-C89855, S-1319, etc.

Leukotriene receptor antagonists include, for example, pranlukast hydrate, montelukast, zafirlukast, seratrodast, MCC-847, KCA-757, CS-615, YM-158, L-740515, CP-195494, LM-1484, RS-635, A-93178, S-36496, BIIL-284, ONO-4057, etc.

Thromboxane synthase inhibitors include, for example, ozagrel hydrochloride, imitrodast sodium, etc.

Thromboxane $A_2$ receptor antagonists include, for example, seratrodast, ramatroban, domitroban calcium hydrate, KT-2-962, etc.

Xanthine derivatives include, for example, aminophylline, theophylline, doxophylline, dipamphylline, diprophylline, etc.

Anticholinergic agents include, for example, ipratropium bromide, oxitropium bromide, flutropium bromide, cimetropium bromide, temiverine, tiotropium bromide, revatropate (UK-112166), etc.

Cytokine inhibitors include, for example, suplatast tosylate (product name IPD), etc.

Other phosphodiesterase inhibitors include, for example, PDE4 inhibitors, i.e. rolipram, cilomilast (Produc Name: Alifro), Bay9-8004, NIK-616, cilomilast (BY-217), cipamphiline (BRL-61063), atizolam (CP-80633), SCH-351591, YM-976, V-11294A, PD-168787, D-4396, IC-485, etc.

Non-steroidal anti-inflammatory drugs include, for example, sasapyrine (salitylosalitylic acid), sodium salicylate, aspirin, aspirin dialuminate, diflunisal, indomethacin, suprofen, ufenamate, dimethylisopropylazulene, bufexamac, felbinac, dichlofenac, tolmetin sodium, clinoril, fenbufen, nabumetone, proglumetacin maleate, indometacin farnesil, acemetacin, proglumetacin maleate, amfenac sodium, mofezolac, etodolac, ibuprofen, ibuprofenpiconol, naproxen, flurbiprofen, flurbiprofen axetil, ketoprofen, phenoprofen calcium, tiaprofenic acid, oxaprozin, pranoprofen, loxoprofen sodium, alminoprofen, zaltoprofen, mefenamic acid, aluminum mefenamate, tolfenamic acid, floctafenine, ketophenylbutazon, oxyfenbutazon, piroxicam, tenoxicam, ampiroxicam, napageln ointment, epirizole, tiaramide, hydrochloride, tinoridine hydrochloride, emorfazone, sulpyrine, migrenin, saridon, cedes G, amipylo-N, sorbon, pyrine cold preparation, acetoaminofen, fenacetin, dimetotiazine mesilate, simetride, non-pyrine cold preparation, etc.

There is no limitation for the ratio by weight of the compound of formula (I) to other agent.

With regard to other agents, two or more members of any agent may be administered in combination.

Such other agents which supplement and/or reinforce the preventive and/or treating effect of the compound of formula (I) include not only those which have been found on the basis of the above-mentioned mechanism but also those which will be found in future.

The compound of formula (I) of the present invention, a combination of the compound of the present invention of formula (I) and other drug is generally administered systemically or topically and orally or parenterally when it is used for the above objects.

The dosages are determined depending on age, body weight, symptom, therapeutic effect, administration route, duration of the treatment and the like. Generally, 1 mg to 1000 mg per adult is orally administered once to several times per day, or 1 mg to 100 mg per adult is parenterally administered (preferably by intravenous administration) once to several times per day, or continuously administered from vein for 1 to 24 hours per day.

Since the dose changes depending on various conditions as described above, there are cases in which doses lower than or greater than the above ranges may be used.

The compound of the present invention of formula (I) and concomitant agent of the compound of the present invention of formula (I) and other agent(s) may be administered in the form of solid compositions, liquid compositions and other compositions for oral administration, and injections, liniments, suppositories, eye lotions, inhalants and the like for parenteral administration.

Solid compositions for oral administration include tablets, pills, capsules, dispersible powders, granules and the like.

Capsules include hard capsules and soft capsules.

In such solid compositions, one or more active compound(s) are mixed with at least one inert diluent such as lactose, mannitol, glucose, hydroxypropyl cellulose, microcrystalline cellulose, starch, polyvinyl pyrrolidone or magnesium metasilicate aluminate. The composition may also contain additional substances other than the inert diluent, e.g., lubricants such as magnesium stearate, disintegrating agents such as cellulose calcium glycolate, stabilizing agents such as lactose, and assisting agents for dissolving such as glutamic acid and asparatic acid according to usual methods. If necessary, the tablets or pills may be coated with film of gastric- or enteric-coating agents such as sugar, gelatin, hydroxypropyl cellulose and hydroxypropyl cellulose phthalate, or be coated with two or more films. Furthermore, capsules of absorbable materials such as gelatin are included.

Liquid compositions for oral administration include pharmaceutically acceptable emulsions, solutions, syrups, elixirs and the like. In such liquid compositions, one or more active compound(s) are contained in an inert diluent commonly used (e.g., purified water, ethanol). Furthermore, such compositions may also contain auxiliary material such as wetting agents or suspending agents, sweetening agents, flavoring agents, flavoring agents, and preserving agents.

Other compositions for oral administration include sprays containing one or more active compound(s) which are prepared by known methods. Such compositions may contain stabilizing agents such as sodium hydrogen sulfate, buffering agents to give isotonicity, isotonic solutions such as sodium chloride, sodium citrate or citric acid, in addition to inert diluents. The processes for preparing sprays are described in U.S. Pat. Nos. 2,868,691 and 3,095,355.

Injections for parenteral administration in the present invention include sterile aqueous or non-aqueous solutions, suspensions and emulsions. Aqueous solutions and suspensions include distilled water for injection and physiological saline. Non-aqueous solutions and suspensions include propylene glycol, polyethylene glycol, plant oil such as olive oil, alcohols such as ethanol, POLYSORBATE80 (registered trade mark), and the like. Sterile aqueous and non-aqueous solutions, suspensions and emulsions may be used as a mixture. Such compositions may further contain preserving agents, wetting agents, emulsifying agents, dispersing agents, stabilizing agents (e.g., lactose), auxiliary agents such as solubilizing auxiliary agents (e.g., glutamic acid, aspartic acid). They may be sterilized by filtration through a bacteria-retaining filter, incorporation of a sterilizing agent or irradiation. For example, they may also be manufactured in the form of sterile solid compositions which can be dissolved in sterile water or other sterile diluent for injection before use of the freeze-dried product.

The dosage form of eye-drops for parenteral administration include eye lotions, suspending eye lotions, emulsion eye lotions, eye lotions dissolved when used, and eye ointments.

These eye drops are manufactured according to known methods. For example, the eye drops can be prepared, if necessary, by appropriately selecting isotonizing agents (e.g., sodium chloride, concentrated glycerine, etc.), buffering agents (e.g., sodium phosphate, sodium acetate, etc.), surfactants (e.g., POLYSORBATE80 (product name), polyoxyl 40 stearate, polyoxyethylene hydrogenated castor oil, etc.), stabilizing agents (sodium citrate, sodium edetate, etc.), preserving agents (e.g., benzalkonium chloride, paraben, etc.), and the like. They are sterilized in the final step or prepared by aseptic manipulation.

The inhalants for parenteral administration include aerosols, powders for inhalation, and liquids for inhalation, and the liquid for inhalation may be in the form which is dissolved or suspended in water or an appropriate medium when used.

These inhalations can be produced according to known methods.

For example, the liquids for inhalation can be prepared, if necessary, by appropriately selecting preserving agents (e.g., benzalkonium chloride, paraben, etc.), coloring agents, buffering agents (e.g., sodium phosphate, sodium acetate, etc.), isotonizing agents (e.g., sodium chloride, concentrated glycerine, etc.), thickeners (e.g., carboxyvinyl polymer, etc.), absorbefacients, and the like.

The powders for inhalation can be prepared, if necessary, by appropriately selecting lubricants (e.g., stearic acid, salts thereof, etc.), binding agents (e.g., starch, dextrin, etc.), excipients (e.g., lactose, cellulose, etc.), coloring agents, preserving agents (e.g., benzalkonium chloride, paraben, etc.), absorbefacients, and the like.

When the liquids for inhalation are administered, a sprayer (e.g., atomizer, nebulizer) is usually used. When the powders for inhalation are used, an inhalation administration apparatus for powder agents is usually used.

Other compositions for parenteral administration include liquids for external use, endemic liniments, ointments, suppositories for intrarectal administration, pessaries for intravaginal administration and the like containing one or more active compound(s) which can be prepared by known methods.

BEST MODE FOR CARRYING OUT THE INVENTION

The present invention is explained below in detail based on Reference Examples and Examples; but the present invention is not limited thereto.

The solvents in the parentheses show the developing or eluting solvents and the ratios of the solvents used are by volume in chromatographic separations or TLC. The solvents in the parentheses in NMR show the solvents for measurement.

REFERENCE EXAMPLE 1

3-cyclohexyl-3-oxo-propanenitrile

To a solution of sodium amide (1.87 g) in tetrahydrofuran (10 ml) was added acetonitrile (2.72 ml) dropwise at −50-−40° C. and then thereto was added cyclohexane carboxylic acid, methyl ester (2.86 ml) and the mixture was stirred for 1 hour at −20° C. The reaction mixture was poured into cold hydrochloric acid and the mixture was extracted with ethyl acetate. The extract was washed with water and brine, dried over anhydrous magnesium sulfate and concentrated under reduced pressure. The residue was purified by column chromatography on silica gel (hexane:ethyl acetate=4:1) to give the title compound (0.91 g) having the following physical data.

TLC: Rf0.33 (ethyl acetate:hexane=1:3); NMR (CDCl$_3$): δ 3.50 (s, 2H), 2.55 (m, 1H), 2.00-1.60 (m, 5H), 1.50-1.10 (m, 5H).

EXAMPLE 1

(Z)-2-(3,3-dimethyl-3,4-dihydro-(2H)-isoquinolin-1-ylidene)-1-cyclohexylethan-1-one To a conc. sulfuric acid (2 ml) was added the compound prepared in reference example 1 (890 mg) and to the mixture was added a solution of 2-methyl-1-phenylpropan-2-ol (1061 mg) in benzene (1 ml) dropwise and the mixture was stirred for 30 minutes at 60° C. The reaction mixture was neutralized with an aqueous solution of sodium hydroxide under cooling with ice and it was extracted with ethyl acetate. The residue was purified by column chromatography on silica gel (hexane:ethyl acetate=9:1) to give the compound of the present invention (1170 mg) having the following physical data.

TLC: Rf0.36 (ethyl acetate:hexane=1:5); NMR (CDCl$_3$): δ 11.32 (br, 1H), 7.71 (dd, J=8.0, 1.5 Hz, 1H), 7.39 (ddd, J=8.0, 8.0, 1.5 Hz, 1H), 7.28 (ddd, J=8.0, 8.0, 1.5 Hz, 1H), 7.16 (dd, J=8.0, 1.5 Hz, 1H), 5.64 (s, 1H), 2.84 (s, 2H), 2.39 (m, 1H), 2.00-1.20 (m, 10H), 1.29 (s, 6H).

EXAMPLE 1(1)-EXAMPLE 1(81)

By the same procedure as described in example 1 using the compound prepared in reference example 1 or a corresponding nitrile derivative and 2-methyl-1-phenylpropan-2-ol or a corresponding alcohol derivative, the following compounds of the present invention were given.

EXAMPLE 1(1)

(Z)-2-(3,3-dimethyl-3,4-dihydro-(2H)-isoquinolin-1-ylidene)-1-(4-methoxycarbonylphenyl)ethan-1-one TLC: Rf0.18 (ethyl acetate:hexane=1:5); NMR (CDCl$_3$): δ 11.95 (br, 1H), 8.10 (d, J=8.0 Hz, 2H), 7.99 (d, J=8.0 Hz, 2H), 7.83 (d, J=7.5 Hz, 1H), 7.45 (dd, J=7.5, 7.5 Hz, 1H), 7.35 (dd, J=7.5, 7.5 Hz, 1H), 7.22 (d, J=7.5 Hz, 1H), 6.33 (s, 1H), 3.94 (s, 3H), 2.91 (s, 2H), 1.37 (s, 6H).

EXAMPLE 1(2)

(Z)-2-(3,3-dimethyl-3,4-dihydro-(2H)-isoquinolin-1-ylidene)-1-cyclopentylethan-1-one TLC: Rf0.38 (ethyl acetate:hexane=1:5); NMR (CDCl$_3$): δ 11.27 (br, 1H), 7.70 (m, 1H), 7.45-7.10 (m, 3H), 5.66 (s, 1H), 2.84 (s, 2H), 2.83 (m, 1H), 2.00-1.50 (m, 8H), 1.29 (s, 6H).

EXAMPLE 1(3)

(Z)-2-(3,3-dimethyl-3,4-dihydro-(2H)-isoquinolin-1-ylidene)-1-(2-methylphenyl)ethan-1-one TLC: Rf0.33 (ethyl acetate:hexane=1:4); NMR (CDCl$_3$): δ 11.58 (br, 1H), 7.70 (d, J=8.0 Hz, 1H), 7.50-7.15 (m, 7H), 5.90 (s, 1H), 2.91 (s, 2H), 2.51 (s, 3H), 1.37 (s, 6H).

EXAMPLE 1(4)

(Z)-2-(3,3-dimethyl-3,4-dihydro-(2H)-isoquinolin-1-ylidene)-1-(3-methylphenyl)ethan-1-one TLC: Rf0.33 (ethyl acetate:hexane=1:4); NMR (CDCl$_3$): δ 11.84 (br, 1H), 7.90-7.70 (m, 3H), 7.50-7.15 (m, 5H), 6.32 (s, 1H), 2.90 (s, 2H), 2.42 (s, 3H), 1.36 (s, 6H).

EXAMPLE 1(5)

(Z)-2-(3,3-dimethyl-3,4-dihydro-(2H)-isoquinolin-1-ylidene)-1-(4-methylphenyl)ethan-1-one TLC: Rf0.33 (ethyl acetate:hexane=1:4); NMR (CDCl$_3$): δ 11.80 (br, 1H), 7.86 (d, J=8.0 Hz, 2H), 7.83 (m, 1H), 7.50-7.20 (m, 3H), 7.24 (d, J=8.0 Hz, 2H), 6.33 (s, 1H), 2.90 (s, 2H), 2.40 (s, 3H), 1.36 (s, 6H).

EXAMPLE 1(6)

(Z)-2-(3,3-dimethyl-3,4-dihydro-(2H)-isoquinolin-1-ylidene)-1-(furan-2-yl)ethan-1-one TLC: Rf0.37 (ethyl acetate:hexane=1:3); NMR (CDCl$_3$): δ 11.59 (br, 1H), 7.84 (m, 1H), 7.49 (dd, J=2.0, 1.0 Hz, 1H), 7.50-7.15 (m, 3H), 7.04 (dd, J=3.5, 1.0 Hz, 1H), 6.49 (dd, J=3.5, 2.0 Hz, 1H), 6.30 (s, 1H), 2.90 (s, 2H), 1.34 (s, 6H).

EXAMPLE 1(7)

(Z)-2-(3,3-dimethyl-3,4-dihydro-(2H)-isoquinolin-1-ylidene)-1-(2-chlorophenyl)ethan-1-one TLC: Rf0.25 (hexane:ethyl acetate=5:1); NMR (CDCl$_3$): δ 11.55 (br, 1H), 7.72 (d, J=7.5 Hz, 1H), 7.57-7.52 (m, 1H), 7.45-7.38 (m, 2H), 7.33-7.26 (m, 3H), 7.21 (dd, J=7.5, 1.0 Hz, 1H), 5.97 (s, 1H), 2.92 (s, 2H), 1.38 (s, 6H).

EXAMPLE 1(8)

(Z)-2-(3,3-dimethyl-3,4-dihydro-(2H)-isoquinolin-1-ylidene)-1-(thiophen-2-yl)ethan-1-one TLC: Rf0.54 (ethyl acetate:hexane=1:2); NMR (CDCl$_3$): δ 11.51 (br, 1H), 7.81 (d, J=7.0 Hz, 1H), 7.64 (d, J=3.0 Hz, 1H), 7.50-7.30 (m, 3H), 7.21 (d, J=7.0 Hz, 1H), 7.10 (dd, J=3.0, 3.0 Hz, 1H), 6.21 (s, 1H), 2.89 (s, 2H), 1.34 (s, 6H).

EXAMPLE 1(9)

(Z)-2-(3,3-dimethyl-3,4-dihydro-(2H)-isoquinolin-1-ylidene)-1-(3-chlorophenyl)ethan-1-one TLC: Rf0.46 (hexane:ethyl acetate=3:1); NMR (CDCl$_3$): δ 11.85 (br, 1H), 7.92-7.91 (m, 1H), 7.84-7.80 (m, 2H), 7.47-7.34 (m, 4H), 7.22 (d, J=7.0 Hz, 1H), 6.26 (s, 1H), 2.91 (s, 2H), 1.37 (s, 6H).

EXAMPLE 1(10)

(Z)-2-(3,3-dimethyl-3,4-dihydro-(2H)-isoquinolin-1-ylidene)-1-cyclobutylethan-1-one TLC: Rf0.43 (ethyl acetate:hexane=1:3); NMR (CDCl$_3$): δ 11.34 (br, 1H), 7.69 (d, J=7.0 Hz, 1H), 7.45-7.20 (m, 2H), 7.16 (d, J=7.0 Hz, 1H), 5.56 (s, 1H), 3.26 (m, 1H), 2.84 (s, 2H), 2.45-1.70 (m, 6H), 1.30 (s, 6H).

EXAMPLE 1(11)

(Z)-2-(3,3-dimethyl-3,4-dihydro-(2H)-isoquinolin-1-ylidene)-1-cycloheptylethan-1-one TLC: Rf0.50 (ethyl acetate:hexane=1:3); NMR (CDCl$_3$): δ 11.23 (br, 1H), 6.70 (d, J=8.0 Hz, 1H), 7.45-7.20 (m, 2H), 7.16 (d, J=8.0 Hz, 1H), 5.60 (s, 1H), 2.84 (s, 2H), 2.45 (m, 1H), 2.00-1.30 (m, 12H), 1.29 (s, 6H).

EXAMPLE 1(12)

(Z)-2-(3,3-dimethyl-3,4-dihydro-(2H)-isoquinolin-1-ylidene)-1-(4-chlorophenyl)ethan-1-one TLC: Rf0.48 (hexane:ethyl acetate=3:1); NMR (CDCl$_3$): δ 11.82 (br, 1H), 7.91-7.87 (m, 2H), 7.81 (d, J=8.0 Hz, 1H), 7.47-7.32 (m, 4H), 7.22 (dd, J=7.5, 1.0 Hz, 1H), 6.27 (s, 1H), 2.91 (s, 2H), 1.37 (s, 6H).

EXAMPLE 1(13)

(Z)-2-(3,3-dimethyl-3,4-dihydro-(2H)-isoquinolin-1-ylidene)-1-(adamantan-1-yl)ethan-1-one TLC: Rf0.34 (ethyl acetate:hexane=1:5); NMR (CDCl$_3$): δ 11.48 (br, 1H), 7.72 (d, J=8.0 Hz, 1H), 7.45-7.25 (m, 2H), 7.16 (d, J=8.0 Hz, 1H), 5.79 (s, 1H), 2.84 (s, 2H), 2.05 (m, 3H), 1.91 (m, 6H), 1.75 (m, 6H), 1.29 (s, 6H).

EXAMPLE 1(14)

(Z)-2-(3,3,5-trimethyl-3,4-dihydro-(2H)-isoquinolin-1-ylidene)-1-phenylethan-1-one TLC: Rf0.24 (ethyl acetate:hexane=1:5); NMR (CDCl$_3$): δ 11.92 (br, 1H), 7.95 (m, 2H), 7.71 (d, J=7.5 Hz, 1H), 7.50-7.40 (m, 3H), 7.32 (d, J=7.5 Hz, 1H), 7.23 (dd, J=7.5, 7.5 Hz, 1H), 6.32 (s, 1H), 2.83 (s, 2H), 2.32 (s, 3H), 1.37 (s, 6H).

EXAMPLE 1(15)

(Z)-2-(3,3,6-trimethyl-3,4-dihydro-(2H)-isoquinolin-1-ylidene)-1-phenylethan-1-one TLC: Rf0.27 (ethyl acetate:hexane=1:5); NMR (CDCl$_3$): δ 11.83 (br, 1H), 7.95 (m, 2H), 7.71 (d, J=8.0 Hz, 1H), 7.50-7.40 (m, 3H), 7.13 (d, J=8.0 Hz, 1H), 7.01 (s, 1H), 6.30 (s, 1H), 2.85 (s, 2H), 2.39 (s, 3H), 1.35 (s, 6H).

EXAMPLE 1(16)

(Z)-2-(3,3-dimethyl-3,4-dihydro-(2H)-isoquinolin-1-ylidene)-1-(naphthalen-2-yl)ethan-1-one TLC: Rf0.26 (ethyl acetate:hexane=1:5); NMR (CDCl$_3$): δ 11.95 (br, 1H), 8.46 (s, 1H), 8.07 (dd, J=8.5, 1.0 Hz, 1H), 8.00-7.80 (m, 4H), 7.60-7.20 (m, 5H), 6.49 (s, 1H), 2.93 (s, 2H), 1.39 (s, 6H).

EXAMPLE 1(17)

(Z)-2-(3,3-dimethyl-3,4-dihydro-(2H)-isoquinolin-1-ylidene)-1-(4-methoxyphenyl)ethan-1-one TLC: Rf0.28 (hexane:ethyl acetate=3:1); NMR (CDCl$_3$): δ 11.74 (br, 1H), 7.98-7.91 (m, 2H), 7.83 (d, J=7.0 Hz, 1H), 7.45-7.29 (m, 2H), 7.21 (d, J=7.5 Hz, 1H), 6.97-6.91 (m, 2H), 6.31 (s, 1H), 3.86 (s, 3H), 2.89 (s, 2H), 1.35 (s, 6H).

EXAMPLE 1(18)

(Z)-2-(3,3-dimethyl-3,4-dihydro-(2H)-isoquinolin-1-ylidene)-1-(3-methoxyphenyl)ethan-1-one TLC: Rf0.48 (hexane:ethyl acetate=2:1); NMR (CDCl$_3$): δ 11.83 (br, 1H), 7.83 (d, J=8.0 Hz, 1H), 7.55-7.29 (m, 5H), 7.22 (d, J=7.5 Hz, 1H), 7.03-6.97 (m, 1H), 6.32 (s, 1H), 3.88 (s, 3H), 2.91 (s, 2H), 1.37 (s, 6H).

EXAMPLE 1(19)

(Z)-2-(3,3-dimethyl-3,4-dihydro-(2H)-isoquinolin-1-ylidene)-1-(4-fluorophenyl)ethan-1-one TLC: Rf0.52 (hexane:ethyl acetate=2:1); NMR (CDCl$_3$): δ 11.78 (br, 1H), 7.98-7.91 (m, 2H), 7.81 (d, J=7.5 Hz, 1H), 7.47-7.30 (m, 2H), 7.21 (d, J=7.0 Hz, 1H), 7.14-7.05 (m, 2H), 6.27 (s, 1H), 2.90 (s, 2H), 1.36 (s, 6H).

EXAMPLE 1(20)

(Z)-2-(3,3,7-trimethyl-3,4-dihydro-(2H)-isoquinolin-1-ylidene)-1-phenylethan-1-one TLC: Rf0.38 (ethyl acetate:hexane=1:3); NMR (CDCl$_3$): δ 11.84 (br, 1H), 7.96 (m, 2H), 7.62 (s, 1H), 7.50-7.40 (m, 3H), 7.24 (d, J=7.5 Hz, 1H), 7.10 (d, J=7.5 Hz, 1H), 6.32 (s, 1H), 2.85 (s, 2H), 2.42 (s, 3H), 1.35 (s, 6H).

EXAMPLE 1(21)

(Z)-2-(3,3-dimethyl-3,4-dihydro-(2H)-isoquinolin-1-ylidene)-1-(naphthalen-1-yl)ethan-1-one TLC: Rf0.27 (ethyl acetate:hexane=1:5); NMR (CDCl$_3$): δ 11.78 (br, 1H), 8.50 (m, 1H), 7.90-7.80 (m, 2H), 7.75-7.65 (m, 2H), 7.55-7.15 (m, 6H), 6.09 (s, 1H), 2.94 (s, 2H), 1.41 (s, 6H).

EXAMPLE 1(22)

(Z)-2-(3,3-dimethyl-3,4-dihydro-(2H)-isoquinolin-1-ylidene)-1-(2-methoxyphenyl)ethan-1-one TLC: Rf0.38 (hexane:ethyl acetate=2:1); NMR (CDCl$_3$): δ 11.69 (br, 1H), 7.74 (d, J=8.0 Hz, 1H), 7.67 (dd, J=8.0, 2.0 Hz, 1H), 7.43-7.29 (m, 3H), 7.19 (dd, J=7.0, 0.5 Hz, 1H), 7.03-6.95 (m, 2H), 6.27 (s, 1H), 3.91 (s, 3H), 2.89 (s, 2H), 1.36 (s, 6H).

EXAMPLE 1(23)

(Z)-2-(3,3-dimethyl-3,4-dihydro-(2H)-isoquinolin-1-ylidene)-1-(2-fluorophenyl)ethan-1-one TLC: Rf0.59 (hexane:ethyl acetate=2:1); NMR (CDCl$_3$): δ 11.79 (br, 1H), 7.86 (ddd, J=8.0, 8.0, 2.0 Hz, 1H), 7.79 (d, J=7.0 Hz, 1H), 7.45-7.30 (m, 3H), 7.24-7.18 (m, 2H), 7.10 (ddd, J=11.5, 8.0, 1.0 Hz, 1H), 6.30 (s, 1H), 2.91 (s, 2H), 1.37 (s, 6H).

EXAMPLE 1(24)

(Z)-2-(3,3-dimethyl-3,4-dihydro-(2H)-isoquinolin-1-ylidene)-1-(3-fluorophenyl)ethan-1-one TLC: Rf0.63 (hexane:ethyl acetate=2:1); NMR (CDCl$_3$): δ 11.84 (br, 1H), 7.82 (d, J=8.0 Hz, 1H), 7.72 (d, J=8.0 Hz, 1H), 7.63 (d, J=10.0 Hz, 1H), 7.47-7.33 (m, 3H), 7.22 (d, J=7.5 Hz, 1H), 7.17-7.10 (m, 1H), 6.27 (s, 1H), 2.91 (s, 2H), 1.37 (s, 6H).

EXAMPLE 1(25)

A mixture of (Z)-2-(3,3-dimethyl-3,4-dihydro-(2H)-isoquinolin-1-ylidene)-2-methyl-1-phenylethan-1-one (A) and 2-(3,3-dimethyl-3,4-dihydroisoquinolin-1-yl)-1-phenyl propan-1-one (B), which was given as a mixture of A:B=5:4.

TLC: Rf0.29 (ethyl acetate:hexane=1:5); NMR (CDCl$_3$): δ 13.05 (br, 1H of A), 7.92 (m, 2H of A), 7.81 (m, 1H of A), 7.60-7.10 (m, 6H of A and 9H of B), 4.80 (q, J=7.0 Hz, 1H of B), 2.84 (s, 2H of A), 2.58 (s, 2H of B), 2.56 (d, J=7.0 Hz, 3H of B), 2.10 (s, 3H of A), 1.27 (s, 6H of A), 1.08 (s, 3H of B), 0.97 (s, 3H of B).

EXAMPLE 1(26)

(Z)-2-(spiro[3,4-dihydro-(2H)-isoquinolin-3,1'-cyclohexane]-1-ylidene)-1-phenylethan-1-one TLC: Rf0.58 (hexane:ethyl acetate=3:1); NMR (CDCl$_3$): δ 12.21 (br, 1H), 7.99-7.94 (m, 2H), 7.82 (d, J=7.0 Hz, 1H), 7.47-7.28 (m, 5H), 7.21 (d, J=7.0 Hz, 1H), 6.35 (s, 1H), 2.91 (s, 2H), 1.80-1.30 (m, 10H).

EXAMPLE 1(27)

(Z)-2-(spiro[3,4-dihydro-(2H)-isoquinolin-3,1'-cyclopentan]-1-ylidene)-1-phenylethan-1-one TLC: Rf0.54 (hexane:ethyl acetate=3:1); NMR (CDCl$_3$): δ 12.03 (br, 1H), 7.98-7.93 (m, 2H), 7.82 (d, J=7.5 Hz, 1H), 7.47-7.29 (m, 5H), 7.23 (d, J=7.5 Hz, 1H), 6.34 (s, 1H), 2.98 (s, 2H), 1.95-1.62 (m, 8H).

EXAMPLE 1(28)

(Z)-2-(spiro[3,4-dihydro-(2H)-isoquinolin-3,1'-cycloheptan]-1-ylidene)-1-phenylethan-1-one TLC: Rf0.41 (hexane:ethyl acetate=5:1); NMR (CDCl$_3$): δ 12.16 (br, 1H), 7.99-7.94 (m, 2H), 7.82 (d, J=7.5 Hz, 1H), 7.47-7.29 (m, 5H), 7.20 (d, J=7.0 Hz, 1H), 6.33 (s, 1H), 2.92 (s, 2H), 1.91-1.45 (m, 12H).

EXAMPLE 1(29)

(Z)-2-(3,3-diethyl-3,4-dihydro-(2H)-isoquinolin-1-ylidene)-1-phenylethan-1-one

TLC: Rf0.35 (hexane:ethyl acetate=5:1); NMR (CDCl$_3$): δ 11.98 (br, 1H), 7.99-7.94 (m, 2H), 7.82 (d, J=7.5 Hz, 1H), 7.45-7.29 (m, 5H), 7.21 (d, J=7.0 Hz, 1H), 6.36 (s, 1H), 2.90 (s, 2H), 1.70-1.58 (m, 4H), 0.95 (t, J=7.5 Hz, 6H).

EXAMPLE 1(30)

(Z)-2-(3,3-dimethyl-3,4-dihydro-(2H)-isoquinolin-1-ylidene)-1-(3-methoxycarbonylphenyl)ethan-1-one TLC: Rf0.19 (ethyl acetate:hexane=1:5); NMR (CDCl$_3$): δ 11.91 (br, 1H), 8.60 (dd, J=1.5, 1.5 Hz, 1H), 8.20-8.10 (m, 2H), 7.86 (dd, J=8.5, 1.5 Hz, 1H), 7.60-7.20 (m, 4H), 6.36 (s, 1H), 3.95 (s, 3H), 2.92 (s, 2H), 1.38 (s, 6H).

EXAMPLE 1(31)

(Z)-2-(spiro[3,4-dihydro-(2H)-isoquinolin-3,1'-cyclobutan]-1-ylidene)-1-phenylethan-1-one TLC: Rf0.35 (hexane:ethyl acetate=5:1); NMR (CDCl$_3$): δ 11.99 (br, 1H), 7.97-7.94 (m, 2H), 7.80 (d, J=7.5 Hz, 1H), 7.47-7.41 (m, 4H), 7.37-7.26 (m, 2H), 6.34 (s, 1H), 3.09 (s, 2H), 2.33-2.23 (m, 2H), 2.18-2.09 (m, 2H), 1.96-1.79 (m, 2H).

EXAMPLE 1(32)

(Z)-2-(3,3-dimethyl-3,4-dihydro-(2H)-isoquinolin-1-ylidene)-1-(quinolin-6-yl)ethan-1-one TLC: Rf0.22 (ethyl acetate:hexane=1:1); NMR (CDCl$_3$): δ 11.99 (br, 1H), 8.95 (dd, J=4.0, 1.5 Hz, 1H), 8.44 (d, J=1.5 Hz, 1H), 8.30 (dd, J=9.0, 1.5 Hz, 1H), 8.27 (m, 1H), 8.15 (d, J=9.0 Hz, 1H), 7.90 (m, 1H), 7.50-7.20 (m, 4H), 6.47 (s, 1H), 2.94 (s, 2H), 1.40 (s, 6H).

EXAMPLE 1(33)

(Z)-2-(spiro[3,4-dihydro-(2H)-isoquinolin-3,4'-3,4,5,6-tetrahydropyran]-1-ylidene)-1-phenylethan-1-one TLC: Rf0.49 (hexane:ethyl acetate=1:1); NMR (CDCl$_3$): δ 12.41 (br, 1H), 7.99-7.94 (m, 2H), 7.83 (d, J=7.0 Hz, 1H), 7.48-7.23 (m, 6H), 6.39 (s, 1H), 3.90-3.84 (m, 4H), 2.96 (s, 2H), 1.80-1.73 (m, 4H).

EXAMPLE 1(34)

(Z)-2-(spiro[3,4-dihydro-(2H)-isoquinolin-3,4'-1'-methylpiperidin]-1-ylidene)-1-phenylethan-1-one TLC: Rf0.27 (chloroform:methanol=10:1); NMR (CDCl$_3$): δ 12.22 (br, 1H), 7.98-7.95 (m, 2H), 7.82 (d, J=7.5 Hz, 1H), 7.46-7.41 (m, 4H), 7.34 (t, J=7.5 Hz, 1H), 7.24 (d, J=7.5 Hz, 1H), 6.36 (s, 1H), 2.92 (s, 2H), 2.73-2.69 (m, 2H), 2.53-2.45 (m, 2H), 2.38 (s, 3H), 1.81-1.77 (m, 4H).

EXAMPLE 1(35)

(Z)-2-(3,3-dimethyl-3,4-dihydro-(2H)-isoquinolin-1-ylidene)-1-(2-trifluoromethylphenyl)ethan-1-one TLC: Rf0.19 (ethyl acetate:hexane=1:5); NMR (CDCl$_3$): δ 11.42 (br, 1H), 7.75-7.15 (m, 8H), 5.82 (s, 1H), 2.92 (s, 2H), 1.38 (s, 6H).

EXAMPLE 1(36)

(Z)-2-(3,3-dimethyl-3,4-dihydro-(2H)-isoquinolin-1-ylidene)-1-(3-trifluoromethylphenyl)ethan-1-one TLC: Rf0.47 (ethyl acetate:hexane=1:3); NMR (CDCl$_3$): δ 11.92 (br, 1H), 8.21 (s, 1H), 8.12 (d, J=8.0 Hz, 1H), 7.85 (d, J=7.5 Hz, 1H), 7.70 (d, J=8.0 Hz, 1H), 7.57 (d, J=7.5 Hz, 1H), 7.55-7.20 (m, 3H), 6.31 (s, 1H), 2.93 (s, 2H), 1.39 (s, 6H).

EXAMPLE 1(37)

(Z)-2-(3,3-dimethyl-3,4-dihydro-(2H)-isoquinolin-1-ylidene)-1-(4-trifluoromethylphenyl)ethan-1-one TLC: Rf0.27 (ethyl acetate:hexane=1:5); NMR (CDCl$_3$): δ 11.93 (br, 1H), 8.03 (d, J=8.0 Hz, 2H), 7.83 (m, 1H), 7.69 (d, J=8.0 Hz, 2H), 7.50-7.20 (m, 3H), 6.30 (s, 1H), 2.92 (s, 2H), 1.38 (s, 6H).

EXAMPLE 1(38)

(Z)-2-(3,3,6,8-tetramethyl-3,4-dihydro-(2H)-isoquinolin-1-ylidene)-1-phenylethan-1-one TLC: Rf0.46 (ethyl acetate:hexane=1:3); NMR (CDCl$_3$): δ 12.06 (br, 1H), 7.88 (m, 2H), 7.50-7.35 (m, 3H), 7.03 (s, 1H), 6.86 (s, 1H), 6.11 (s, 1H), 2.79 (s, 2H), 2.65 (s, 3H), 2.34 (s, 3H), 1.30 (s, 6H).

EXAMPLE 1(39)

(Z)-2-(3,3-dimethyl-3,4-dihydro-(2H)-isoquinolin-1-ylidene)-1-(pyridin-3-yl)ethan-1-one TLC: Rf0.36 (ethyl acetate:hexane=2:1); NMR (CDCl$_3$): δ 11.89 (br, 1H), 9.16 (dd, J=2.0, 0.5 Hz, 1H), 8.66 (dd, J=5.0, 2.0 Hz, 1H), 8.22 (ddd, J=8.0, 2.0, 2.0 Hz, 1H), 7.83 (m, 1H), 7.50-7.20 (m, 4H), 6.29 (s, 1H), 2.92 (s, 2H), 1.38 (s, 6H).

EXAMPLE 1(40)

(Z)-2-(3,3-dimethyl-3,4-dihydro-(2H)-isoquinolin-1-ylidene)-1-(pyridin-4-yl)ethan-1-one TLC: Rf0.34 (ethyl acetate:hexane=2:1); NMR (CDCl$_3$): δ 11.98 (br, 1H), 8.72 (d, J=6.0 Hz, 2H), 7.82 (m, 1H), 7.75 (d, J=6.0 Hz, 2H), 7.50-7.20 (m, 3H), 6.29 (s, 1H), 2.92 (s, 2H), 1.38 (s, 6H).

EXAMPLE 1(41)

(Z)-2-(8-methoxy-3,3-dimethyl-3,4-dihydro-(2H)-isoquinolin-1-ylidene)-1-phenylethan-1-one TLC: Rf0.36 (ethyl acetate:hexane=1:3); NMR (CDCl$_3$): δ 12.28 (br, 1H), 7.93 (m, 2H), 7.50-7.35 (m, 3H), 7.35 (dd, J=7.0, 7.0 Hz, 1H), 6.96 (s, 1H), 6.92 (d, J=7.0 Hz, 1H), 6.81 (d, J=7.0 Hz, 1H), 3.97 (s, 3H), 2.85 (s, 2H), 1.34 (s, 6H).

EXAMPLE 1(42)

(Z)-2-(6-methoxy-3,3-dimethyl-3,4-dihydro-(2H)-isoquinolin-1-ylidene)-1-phenylethan-1-one TLC: Rf0.28 (ethyl acetate:hexane=1:3); NMR (CDCl$_3$): δ 11.84 (br, 1H), 7.93 (m, 2H), 7.77 (d, J=9.0 Hz, 1H), 7.50-7.35 (m, 3H), 6.85 (dd, J=9.0, 2.5 Hz, 1H), 6.72 (d, J=2.5 Hz, 1H), 6.25 (s, 1H), 3.87 (s, 3H), 2.86 (s, 2H), 1.36 (s, 6H).

EXAMPLE 1(43)

(Z)-2-(spiro[3,4-dihydro-(2H)-isoquinolin-3,4'-piperidin]-1-ylidene)-1-phenylethan-1-one TLC: Rf0.14 (water:methanol:chloroform=1:10:50); NMR (CDCl$_3$): δ 12.40 (s, 1H), 7.96 (m, 2H), 7.82 (d, J=7.5 Hz, 1H), 7.50-7.20 (m, 6H), 6.39 (s, 1H), 3.12 (m, 4H), 2.96 (s, 2H), 1.83 (m, 4H).

EXAMPLE 1(44)

(Z)-2-(3,3-dimethyl-3,4-dihydro-(2H)-isoquinolin-1-ylidene)-1-(2,6-dimethylphenyl)ethan-1-one TLC: Rf0.24 (ethyl acetate:hexane=1:5); NMR (CDCl$_3$): δ 11.52 (br, 1H), 7.64 (d, J=7.5 Hz, 1H), 7.45-6.95 (m, 6H), 5.71 (s, 1H), 2.92 (s, 2H), 2.33 (s, 6H), 1.38 (s, 6H).

EXAMPLE 1(45)

(Z)-2-(spiro[3,4-dihydro-(2H)-isoquinolin-3,1'-4'-ethoxycarbonylcyclohexane]-1-ylidene)-1-phenylethan-1-one TLC: Rf0.50 (hexane:ethyl acetate=2:1); NMR (CDCl$_3$): δ 12.04 (br, 1H), 7.98-7.93 (m, 2H), 7.82 (d, J=8.0 Hz, 1H), 7.46-7.20 (m, 6H), 6.35 (s, 1H), 4.15 (q, J=7.0 Hz, 2H), 2.98 (s, 2H), 2.55-2.42 (m, 1H), 2.03-1.50 (m, 8H), 1.27 (t, J=7.0 Hz, 3H).

(This compound has two stereoisomers by the existence of a carbon to which ethoxycarbonyl is attached. This compound corresponds to a less polar compound on thin layer silica gel. The more polar compound corresponding to this compound is described in example 1(46).)

EXAMPLE 1(46)

(Z)-2-(spiro[3,4-dihydro-(2H)-isoquinolin-3,1'-4'-ethoxycarbonylcyclohexane]-1-ylidene)-1-phenylethan-1-one TLC: Rf0.36 (hexane:ethyl acetate=2:1); NMR (CDCl$_3$): δ 12.26 (br, 1H), 7.98-7.90 (m, 2H), 7.82 (d, J=7.0 Hz, 1H), 7.57-7.27 (m, 5H), 7.21 (d, J=6.5 Hz, 1H), 6.34 (s, 1H), 4.15 (q, J=7.0 Hz, 2H), 2.89 (s, 2H), 2.34-2.25 (m, 1H), 1.98-1.40 (m, 8H), 1.27 (t, J=7.0 Hz, 3H).

(This compound has two stereoisomers by the existence of a carbon to which ethoxycarbonyl is attached. This compound corresponds to a more polar compound on thin layer silica gel. The less polar compound corresponding to this compound is described in example 1(45).)

EXAMPLE 1(47)

(Z)-2-(3,3-dimethyl-3,4-dihydro-(2H)-isoquinolin-1-ylidene)-1-cyclododecylethan-1-one TLC: Rf0.35 (ethyl acetate:hexane=1:5); NMR (CDCl$_3$): δ 11.32 (br, 1H), 7.72 (m, 1H), 7.45-7.10 (m, 3H), 5.61 (s, 1H), 2.84 (m, 2H), 2.55 (m, 1H), 1.70-1.20 (m, 22H), 1.29 (s, 6H).

EXAMPLE 1(48)

(Z)-2-(3,3-dimethyl-3,4-dihydro-(2H)-isoquinolin-1-ylidene)-1-(4-t-butylphenyl)ethan-1-one TLC: Rf0.26 (ethyl acetate:hexane=1:5); NMR (CDCl$_3$): δ 11.78 (br, 1H), 7.89 (d, J=8.5 Hz, 2H), 7.82 (m, 1H), 7.45 (d, J=8.5 Hz, 2H), 7.45-7.15 (m, 3H), 6.33 (s, 1H), 2.90 (m, 2H), 1.36 (s, 6H), 1.35 (s, 9H).

EXAMPLE 1(49)

(Z)-2-(spiro[3,4-dihydro-(2H)-isoquinolin-3,1'-4'-oxocyclohexane]-1-ylidene)-1-phenylethan-1-one TLC: Rf0.38 (ethyl acetate:hexane=1:1); NMR (CDCl$_3$): δ 12.63 (br, 1H), 7.96 (m, 2H), 7.87 (m, 1H), 7.50-7.20 (m, 6H), 6.45 (s, 1H), 3.04 (s, 2H), 2.77 (m, 2H), 2.39 (m, 2H), 2.17 (m, 2H), 1.93 (m, 2H).

EXAMPLE 1(50)

(Z)-2-(3,3-dimethyl-3,4-dihydro-(2H)-isoquinolin-1-ylidene)-1-(piperidin-4-yl)ethan-1-one TLC: Rf0.18 (water:methanol:chloroform=1:10:50); NMR (CDCl$_3$): δ 11.31 (br, 1H), 7.70 (m, 1H), 7.45-7.15 (m, 3H), 5.64 (s, 1H), 3.17 (dt, J=12.0, 3.5 Hz, 2H), 2.85 (s, 2H), 2.67 (dt, J=3.5, 12.0 Hz, 2H), 2.42 (tt, J=12.0, 4.0 Hz, 1H), 1.86 (m, 2H), 1.68 (m, 2H), 1.30 (s, 6H).

EXAMPLE 1(51)

(Z)-2-(3,3-dimethyl-3,4-dihydro-(2H)-isoquinolin-1-ylidene)-1-(4-isopropylphenyl)ethan-1-one TLC: Rf0.38 (hexane:ethyl acetate=4:1); NMR (CDCl$_3$): δ 11.78 (s, 1H), 7.88 (d, J=8.0 Hz, 2H), 7.86-7.80 (m, 1H), 7.44-7.18 (m, 3H), 7.28 (d, J=8.0 Hz, 2H), 6.32 (s, 1H), 3.02-2.81 (m, 1H), 2.89 (s, 2H), 1.36 (s, 6H), 1.28 (d, J=8.0 Hz, 6H).

EXAMPLE 1(52)

(Z)-2-(3,3-dimethyl-3,4-dihydro-(2H)-isoquinolin-1-ylidene)-1-cyclooctylethan-1-one TLC: Rf0.42 (ethyl acetate:hexane=1:5); NMR (CDCl$_3$): δ 11.21 (br, 1H), 7.71 (d, J=7.5 Hz, 1H), 7.45-7.20 (m, 2H), 7.16 (d, J=7.5 Hz, 1H), 5.60 (s, 1H), 2.84 (s, 2H), 2.51 (m, 1H), 2.00-1.40 (m, 14H), 1.29 (s, 6H).

EXAMPLE 1(53)

(Z)-2-(3,3-dimethyl-3,4-dihydro-(2H)-isoquinolin-1-ylidene)-1-(1-methylcyclohexyl)ethan-1-one TLC: Rf0.44 (ethyl acetate:hexane=1:5); NMR (CDCl$_3$): δ 11.36 (br, 1H), 7.70 (m, 1H), 7.45-7.10 (m, 3H), 5.83 (s, 1H), 2.84 (s, 2H), 2.10-1.95 (m, 2H), 1.65-1.20 (m, 8H), 1.30 (s, 6H), 1.15 (s, 3H).

EXAMPLE 1(54)

(Z)-2-(3,3-dimethyl-3,4-dihydro-(2H)-isoquinolin-1-ylidene)-1-(4-ethylphenyl)ethan-1-one TLC: Rf0.35 (hexane:ethyl acetate=4:1); NMR (CDCl$_3$): δ 11.80 (bs, 1H), 7.90-7.80 (m, 3H), 7.46-7.18 (m, 5H), 6.33 (s, 1H), 2.89 (s, 2H), 2.70 (q, J=7.8 Hz, 2H), 1.36 (s, 6H), 1.27 (t, J=7.8 Hz, 3H).

EXAMPLE 1(55)

(Z)-2-(3,3-dimethyl-3,4-dihydro-(2H)-isoquinolin-1-ylidene)-1-(4-butylphenyl)ethan-1-one TLC: Rf0.20 (hexane:ethyl acetate=4:1); NMR (CDCl$_3$): δ 11.79 (bs, 1H), 7.89-7.81 (m, 3H), 7.46-7.19 (m, 5H), 6.33 (s, 1H), 2.90 (s, 2H), 2.66 (t, J=7.4 Hz, 2H), 1.63 (m, 2H), 1.39 (m, 2H), 1.36 (s, 6H), 0.93 (t, J=7.4 Hz, 3H).

EXAMPLE 1(56)

(Z)-2-(3,3-dimethyl-3,4-dihydro-(2H)-isoquinolin-1-ylidene)-1-(1-phenylcyclohexyl)ethan-1-one TLC: Rf0.37 (ethyl acetate:hexane=1:5); NMR (CDCl$_3$): δ 11.12 (br, 1H), 7.50-7.10 (m, 9H), 5.55 (s, 1H), 2.78 (s, 2H), 2.45-2.30 (m, 2H), 2.15-2.00 (m, 2H), 1.80-1.30 (m, 6H), 1.26 (s, 6H).

EXAMPLE 1(57)

(Z)-2-(3,3-dimethyl-3,4-dihydro-(2H)-isoquinolin-1-ylidene)-1-(4-propylphenyl)ethan-1-one TLC: Rf0.33 (hexane:ethyl acetate=4:1); NMR (CDCl$_3$): δ 11.79 (bs, 1H), 7.87 (d, J=8.0 Hz, 2H), 7.82 (m, 1H), 7.46-7.19 (m, 3H), 7.24 (d, J=8.0 Hz, 2H), 6.33 (s, 1H), 2.90 (s, 2H), 2.64 (t, J=7.4 Hz, 2H), 1.69 (m, 2H), 1.36 (s, 6H), 0.95 (t, J=7.4 Hz, 3).

EXAMPLE 1(58)

2-(3,3-dimethyl-3,4-dihydroisoquinolin-1-yl)-1-phenylbutan-1-one

TLC: Rf0.42 (hexane:ethyl acetate=4:1); NMR (CDCl$_3$): δ 7.95-7.91 (m, 2H), 7.59-7.10 (m, 7H), 4.60 (m, 1H), 2.57 (s, 2H), 2.21 (m, 1H), 1.98 (m, 1H), 1.09 (s, 3H), 1.02 (t, J=8.0 Hz, 3H), 1.00 (s, 3H).

EXAMPLE 1(59)

2-(3,3-dimethyl-3,4-dihydroisoquinolin-1-yl)-1-phenylpentan-1-one

TLC: Rf0.44 (hexane:ethyl acetate=4:1); NMR (CDCl$_3$): δ 8.06-7.91 (m, 3H), 7.59-7.24 (m, 5H), 7.11 (m, 1H), 4.69 (dd, J=7.5, 6.0 Hz, 1H), 2.61 (s, 2H), 2.20 (m, 1H), 1.85 (m, 1H), 1.40 (m, 2H), 1.05 (s, 3H), 1.00 (s, 3H), 0.98 (t, J=8.0 Hz, 3H).

EXAMPLE 1(60)

(Z)-cis(3,3-dimethyl-3,4-dihydro-(2H)-isoquinolin-1-ylidene)-1-(2-methylcyclohexyl)ethan-1-one TLC: Rf0.37 (ethyl acetate:hexane=1:5); NMR (CDCl$_3$): δ 11.25 (br, 1H), 7.70 (m, 1H), 7.45-7.10 (m, 3H), 5.65 (s, 1H), 2.83 (s, 2H), 2.50 (dt, J=11.0, 4.5 Hz, 1H), 2.28 (m, 1H), 1.90-1.10 (m, 8H), 1.29 (s, 3H), 1.28 (s, 3H), 0.90 (d, J=7.0 Hz, 3H).

EXAMPLE 1(61)

(Z)-trans-2-(3,3-dimethyl-3,4-dihydro-(2H)-isoquinolin-1-ylidene)-1-(2-methylcyclohexyl)ethan-1-one TLC: Rf0.35 (ethyl acetate:hexane=1:5); NMR (CDCl$_3$): δ 11.38 (br, 1H), 7.71 (m, 1H), 7.45-7.10 (m, 3H), 5.60 (s, 1H), 2.84 (s, 2H), 2.00-0.90 (m, 10H), 1.30 (s, 6H), 0.88 (d, J=7.5 Hz, 3H).

EXAMPLE 1(62)

(Z)-trans-2-(3,3-dimethyl-3,4-dihydro-(2H)-isoquinolin-1-ylidene)-1-(3-methylcyclohexyl)ethan-1-one TLC: Rf0.39 (ethyl acetate:hexane=1:5); NMR (CDCl$_3$): δ 11.27 (br, 1H), 7.71 (m, 1H), 7.45-7.10 (m, 3H), 5.68 (s, 1H), 2.84 (s, 2H), 2.59 (m, 1H), 2.10-1.10 (m, 9H), 1.29 (s, 6H), 0.98 (d, J=7.0 Hz, 3H).

EXAMPLE 1(63)

(Z)-cis(3,3-dimethyl-3,4-dihydro-(2H)-isoquinolin-1-ylidene)-1-(3-methylcyclohexyl)ethan-1-one TLC: Rf0.34 (ethyl acetate:hexane=1:5); NMR (CDCl$_3$): δ 11.34 (br, 1H), 7.71 (m, 1H), 7.45-7.10 (m, 3H), 5.64 (s, 1H), 2.84 (s, 2H), 2.39 (m, 1H), 1.95-0.80 (m, 9H), 1.29 (s, 6H), 0.92 (d, J=6.5 Hz, 3H).

EXAMPLE 1(64)

(Z)-cis-2-(3,3-dimethyl-3,4-dihydro-(2H)-isoquinolin-1-ylidene)-1-(4-methylcyclohexyl)ethan-1-one TLC: Rf0.43 (ethyl acetate:hexane=1:5); NMR (CDCl$_3$): δ 11.30 (br, 1H), 7.70 (m, 1H), 7.45-7.10 (m, 3H), 5.68 (s, 1H), 2.84 (s, 2H), 2.38 (m, 1H), 2.00-1.30 (m, 9H), 1.29 (s, 6H), 0.97 (d, J=7.0 Hz, 3H).

EXAMPLE 1(65)

(Z)-trans-2-(3,3-dimethyl-3,4-dihydro-(2H)-isoquinolin-1-ylidene)-1-(4-methylcyclohexyl)ethan-1-one TLC: Rf0.37 (ethyl acetate:hexane=1:5); NMR (CDCl$_3$): δ 11.3.3 (br, 1H), 7.70 (m, 1H), 7.45-7.10 (m, 3H), 5.64 (s, 1H), 2.84 (s, 2H), 2.24 (tt, J=12.0, 3.5 Hz, 1H), 2.00-0.90 (m, 9H), 1.29 (s, 6H), 0.90 (d, J=6.5 Hz, 3H).

EXAMPLE 1(66)

(Z)-2-(3,3-dimethyl-3,4-dihydro-(2H)-isoquinolin-1-ylidene)-1-(3,5-dimethylisoxazol-4-yl)ethan-1-one TLC: Rf0.25 (hexane:ethyl acetate=4:1); NMR (CDCl$_3$): δ 11.55 (bs, 1H), 7.68 (d, J=7.8 Hz, 1H), 7.49-7.20 (m, 3H), 5.80 (s, 1H), 2.90 (s, 2H), 2.66 (s, 3H), 2.50 (s, 3H), 1.36 (s, 6H).

EXAMPLE 1(67)

(Z)-2-(3,3-dimethyl-3,4-dihydro-(2H)-isoquinolin-1-ylidene)-1-(4-trifluoromethoxyphenyl)ethan-1-one TLC: Rf0.54 (hexane:ethyl acetate=3:1); NMR (CDCl$_3$): δ 11.83 (br, 1H), 8.00-7.95 (m, 2H), 7.82 (d, J=7.5 Hz, 1H), 7.45 (t, J=7.5 Hz, 1H), 7.35 (t, J=7.5 Hz, 1H), 7.27-7.21 (m, 3H), 6.27 (s, 1H), 2.91 (s, 2H), 1.37 (s, 6H).

EXAMPLE 1(68)

(Z)-2-(6-chloro-3,3-dimethyl-3,4-dihydro-(2H)-isoquinolin-1-ylidene)-1-phenylethan-1-one TLC: Rf0.50 (hexane:ethyl acetate=3:1); NMR (CDCl$_3$): δ 11.82 (br, 1H), 7.95-7.92 (m, 2H), 7.75 (d, J=8.0 Hz, 1H), 7.47-7.40 (m, 3H), 7.32 (dd, J=8.0, 2.0 Hz, 1H), 7.22 (d, J=2.0 Hz, 1H), 6.23 (br, 1H), 2.88 (s, 2H), 1.37 (s, 6H).

EXAMPLE 1(69)

(Z)-2-(5-chloro-3,3-dimethyl-3,4-dihydro-(2H)-isoquinolin-1-ylidene)-1-phenylethan-1-one TLC: Rf0.61 (hexane:ethyl acetate=3:1); NMR (CDCl$_3$): δ 11.83 (br, 1H), 7.96-7.92 (m, 2H), 7.77 (d, J=8.0 Hz, 1H), 7.52 (d, J=8.0 Hz, 1H), 7.48-7.42 (m, 3H), 7.32-7.26 (m, 1H), 6.31 (br, 1H), 3.03 (s, 2H), 1.39 (s, 6H).

EXAMPLE 1(70)

(Z)-2-(7-chloro-3,3-dimethyl-3,4-dihydro-(2H)-isoquinolin-1-ylidene)-1-phenylethan-1-one TLC: Rf0.48 (hexane:ethyl acetate=3:1); NMR (CDCl$_3$): δ 11.81 (br, 1H), 7.97-7.93 (m, 2H), 7.78 (d, J=2.0 Hz, 1H), 7.48-7.43 (m, 3H), 7.41 (dd, J=8.0, 2.0 Hz, 1H), 7.17 (d, J=8.0 Hz, 1H), 6.23 (br, 1H), 2.88 (s, 2H), 1.37 (s, 6H).

EXAMPLE 1(71)

(Z)-2-(3,3-dimethyl-3,4-dihydro-(2H)-isoquinolin-1-ylidene)-1-(5-methyl-2-phenyloxazol-4-yl)ethan-1-one TLC: Rf0.37 (hexane:ethyl acetate=4:1); NMR (CDCl$_3$): δ 11.65 (bs, 1H), 8.11-8.08 (m, 2H), 7.96 (d, J=7.6 Hz, 1H), 7.49-7.36 (m, 5H), 7.20 (d, J=7.6 Hz, 1H), 6.72 (bs, 1H), 2.91 (s, 2H), 2.79 (s, 3H), 1.38 (s, 6H).

EXAMPLE 1(72)

(Z)-2-(7-fluoro-3,3-dimethyl-3,4-dihydro-(2H)-isoquinolin-1-ylidene)-1-phenylethan-1-one TLC: Rf0.45 (hexane:ethyl acetate=3:1); NMR (CDCl$_3$): δ 11.80 (br, 1H), 7.96-7.93 (m, 2H), 7.51 (dd, J=9.5, 2.5 Hz, 1H), 7.48-7.41 (m, 3H), 7.22-7.11 (m, 2H), 6.24 (br, 1H), 2.87 (s, 2H), 1.37 (s, 6H).

EXAMPLE 1(73)

(Z)-2-(6-fluoro-3,3-dimethyl-3,4-dihydro-(2H)-isoquinolin-1-ylidene)-1-phenylethan-1-one TLC: Rf0.45 (hexane:ethyl acetate=3:1); NMR (CDCl$_3$): δ 11.83 (br, 1H), 7.96-7.92 (m, 2H), 7.82 (dd, J=8.5, 5.5 Hz, 1H), 7.48-7.40 (m, 3H), 7.04 (ddd, J=8.5, 8.5, 3.0 Hz, 1H), 6.94 (dd, J=8.5, 3.0 Hz, 1H), 6.23 (br, 1H), 2.90 (s, 2H), 1.38 (s, 6H).

EXAMPLE 1(74)

(Z)-2-(5-fluoro-3,3-dimethyl-3,4-dihydro-(2H)-isoquinolin-1-ylidene)-1-phenylethan-1-one TLC: Rf0.54 (hexane:ethyl acetate=3:1); NMR (CDCl$_3$): δ 11.80 (br, 1H), 7.96-7.93 (m, 2H), 7.65 (d, J=8.0 Hz, 1H), 7.47-7.40 (m, 3H), 7.35-7.30 (m, 1H), 7.19 (dd, J=8.0, 8.0 Hz, 1H), 6.31 (br, 1H), 2.93 (s, 2H), 1.39 (s, 6H).

EXAMPLE 1(75)

(Z)-2-(3,3-dimethyl-3,4-dihydro-(2H)-isoquinolin-1-ylidene)-1-(4-methyl-2-phenylthiazol-5-yl)ethan-1-one TLC: Rf0.37 (hexane:ethyl acetate=4:1); NMR (CDCl$_3$): δ 11.56 (bs, 1H), 8.00-7.97 (m, 2H), 7.77 (d, J=7.8 Hz, 1H), 7.46-7.42 (m, 4H), 7.36 (m, 1H), 7.22 (d, J=7.5 Hz, 1H), 6.08 (s, 1H), 2.91 (s, 2H), 2.85 (s, 3H), 1.37 (s, 6H).

EXAMPLE 1(76)

(Z)-2-(3,3-dimethyl-3,4-dihydro-(2H)-isoquinolin-1-ylidene)-1-(4-pentylbicyclo[2.2.2]octan-1-yl)ethan-1-one TLC: Rf0.54 (hexane:ethyl acetate=4:1); NMR (CDCl$_3$): δ 11.39 (bs, 1H), 7.70 (d, J=7.5 Hz, 1H), 7.36 (m, 1H), 7.28 (m, 1H), 7.16 (d, J=7.5 Hz, 1H), 5.73 (s, 1H), 2.83 (s, 2H), 1.81-1.76 (m, 6H), 1.56 (s, 2H), 1.44-1.38 (m, 6H), 1.28 (s, 6H), 1.23-1.16 (m, 4H), 1.11-1.07 (m, 2H), 0.88 (t, J=7.0 Hz, 3H).

EXAMPLE 1(77)

(Z)-trans-2-(3,3-dimethyl-3,4-dihydro-(2H)-isoquinolin-1-ylidene)-1-(4-t-butylcyclohexyl)ethan-1-one TLC: Rf0.52 (hexane:ethyl acetate=4:1); NMR (CDCl$_3$): δ 11.32 (bs, 1H), 7.71 (d, J=7.8 Hz, 1H), 7.39 (m, 1H), 7.33 (m, 1H), 7.17 (d, J=7.2 Hz, 1H), 5.64 (s, 1H), 2.84 (s, 2H), 2.05 (m, 1H), 1.92 (m, 2H), 1.86 (m, 2H), 1.45 (m, 2H), 1.28 (s, 6H), 1.18-1.01 (m, 3H), 0.86 (s, 9H).

EXAMPLE 1(78)

(Z)-2-(3,3,4,4-tetramethyl-3,4-dihydro-(2H)-isoquinolin-1-ylidene)-1-phenylethan-1-one TLC: Rf0.35 (ethyl acetate:hexane=1:5); NMR (CDCl$_3$): δ 11.80 (br, 1H), 7.96 (m, 2H), 7.81 (m, 1H), 7.55-7.40 (m, 5H), 7.32 (m, 1H), 6.30 (br, 1H), 1.50-1.00 (m, 12H).

EXAMPLE 1(79)

(Z)-2-(spiro[3,3-dimethyl-3,4-dihydro-(2H)-isoquinolin-4,1'-cyclohexane]-1-ylidene)-1-phenylethan-1-one TLC: Rf0.45 (ethyl acetate:hexane=1:5); NMR (CDCl$_3$): δ 12.22 (br, 1H), 7.99 (m, 2H), 7.81 (m, 1H), 7.50-7.40 (m, 5H), 7.32 (m, 1H), 6.32 (br, 1H), 2.20-1.00 (m, 16H).

EXAMPLE 1(80)

(Z)-2-(6,7-dimethoxy-3,3-dimethyl-3,4-dihydro-(2H)-isoquinolin-1-ylidene)-1-phenylethan-1-one TLC: Rf0.59 (hexane:ethyl acetate=1:1); NMR (DMSO-d$_6$): δ 11.91 (br, 1H), 8.00-7.97 (m, 2H), 7.48-7.41 (m, 4H), 6.91 (s, 1H), 6.36 (s, 1H), 3.88 (s, 3H), 3.83 (s, 3H), 2.84 (s, 2H), 1.28 (s, 6H).

EXAMPLE 1(81)

(Z)-2-(spiro[3,3-dimethyl-3,4-dihydro-(2H)-isoquinolin-4,1'-cyclopentan]-1-ylidene)-1-phenylethan-1-one TLC: Rf0.49 (ethyl acetate:hexane=1:3); NMR (CDCl$_3$): δ 11.92 (br, 1H), 7.97 (m, 2H), 7.84 (d, J=8.0 Hz, 1H), 7.55-7.30 (m, 6H), 6.33 (br, 1H), 2.00-1.10 (m, 14H).

EXAMPLE 2

2-(3,3-dimethyl-3,4-dihydroisoquinolin-1-yl)-1-cyclopentylethan-1-one, hydrochloride To a solution of the compound prepared in example 1(2) (1132 mg) in dioxane (5 ml) was added a solution of 4M hydrogen chloride in dioxane (2 ml) at room temperature. The reaction mixture was concentrated under reduced pressure. The residue was washed with hexane to give the compound of the present invention (1212 mg) having the following physical data.

TLC: Rf0.38 (ethyl acetate:hexane=1:5); NMR (CDCl$_3$): δ 14.48 (br, 1H), 7.68 (dd, J=7.5, 7.5 Hz, 1H), 7.62 (d, J=7.5 Hz, 1H), 7.46 (dd, J=7.5, 7.5 Hz, 1H), 7.34 (d, J=7.5 Hz, 1H), 4.35 (br, 2H), 3.26 (m, 1H), 3.06 (s, 2H), 2.20-1.55 (m, 8H), 1.59 (s, 6H).

EXAMPLE 2(1)-EXAMPLE 2(5)

By the same procedure as described in example 2 using the compound prepared in example 1(11), example 1(25), example 1(50), example 1(58) or example 1(59) in place of the compound prepared in example 1(2), the following compounds of the present invention were given.

EXAMPLE 2(1)

2-(3,3-dimethyl-3,4-dihydroisoquinolin-1-yl)-1-cycloheptylethan-1-one hydrochloride TLC: Rf0.40 (ethyl acetate:hexane=1:5); NMR (CDCl$_3$): δ 7.67 (dd, J=7.5, 7.5 Hz, 1H), 7.61 (d, J=7.5 Hz, 1H), 7.45 (dd, J=7.5, 7.5 Hz, 1H), 7.34 (d, J=7.5 Hz, 1H), 4.75 (br, 2H), 3.05 (s, 2H), 2.93 (m, 1H), 2.06 (m, 2H), 1.85-1.50 (m, 10H), 1.58 (s, 6H).

EXAMPLE 2(2)

2-(3,3-dimethyl-3,4-dihydroisoquinolin-1-yl)-1-phenylpropan-1-one hydrochloride

TLC: Rf0.29 (ethyl acetate:hexane=1:5); NMR (CDCl$_3$): δ 8.13 (m, 2H), 7.78 (d, J=8.0 Hz, 1H), 7.60 (ddd, J=8.0, 8.0, 1.0 Hz, 1H), 7.55-7.35 (m, 4H), 7.24 (d, J=8.0 Hz, 1H), 6.31 (q, J=7.0 Hz, 1H), 3.03 (d, J=16.5 Hz, 1H), 2.85 (d, J=16.5 Hz, 1H), 1.81 (d, J=7.0 Hz, 3H), 1.71 (s, 3H), 1.46 (s, 3H).

EXAMPLE 2(3)

(Z)-2-(3,3-dimethyl-3,4-dihydro-(2H)-isoquinolin-1-ylidene)-1-(piperidin-4-yl)ethan-1-one bishydrochloride TLC: Rf0.18 (water:methanol:chloroform=1:10:50); NMR (DMSO-d$_6$): δ 11.19 (br, 1H), 9.02 (br, 1H), 8.75 (br, 1H), 7.80 (d, J=7.5 Hz, 1H), 7.47 (dd, J=7.5, 7.5 Hz, 1H), 7.34 (dd, J=7.5, 7.5 Hz, 1H), 7.29 (d, J=7.5 Hz, 1H), 5.73 (s, 1H), 3.25 (m, 2H), 2.95-2.80 (m, 4H), 2.56 (m, 1H), 1.95-1.65 (m, 4H), 1.22 (s, 6H).

EXAMPLE 2(4)

2-(3,3-dimethyl-3,4-dihydroisoquinolin-1-yl)-1-phenylbutan-1-one hydrochloride

TLC: Rf0.77 (hexane:ethyl acetate=1:1); NMR (CDCl$_3$): δ 8.21-8.16 (m, 2H), 7.87 (d, J=8.0 Hz, 1H), 7.65-7.34 (m, 5H), 7.25 (d, J=8.6 Hz, 1H), 6.20 (dd, J=6.2, 5.8 Hz, 1H), 3.00 (d, J=16.6 Hz, 1H), 2.86 (d, J=16.6 Hz, 1H), 2.56 (m, 1H), 2.13 (m, 1H), 1.70 (s, 3H), 1.48 (s, 3H), 1.15 (t, J=7.4 Hz, 3H).

EXAMPLE 2(5)

2-(3,3-dimethyl-3,4-dihydroisoquinolin-1-yl)-1-phenylpentan-1-one hydrochloride

TLC: Rf0.36 (hexane:ethyl acetate=4:1); NMR (CDCl$_3$): δ 8.20 (m, 2H), 7.88 (d, J=7.6 Hz, 1H), 7.64-7.35 (m, 5H), 7.24 (d, J=7.0 Hz, 1H), 6.24 (dd, J=6.0, 6.2 Hz, 1H), 3.01 (d, J=16.8 Hz, 1H), 2.83 (d, J=16.8 Hz, 1H), 2.48 (m, 1H), 1.99 (m, 1H), 1.80 (m, 1H), 1.71 (s, 3H), 1.45 (s, 3H), 1.35 (m, 1H), 0.99 (t, J=7.4 Hz, 3H).

REFERENCE EXAMPLE 2

1,3,3-trimethyl-3,4-dihydroisoquinoline

To a concentrated sulfuric acid (10 ml) was added a solution of 2-methyl-1-phenylpropan-2-ol (7.0 g) and acetonitrile (1.62 ml) in benzene (7.0 ml) dropwise at 0° C. and the mixture was stirred for 24 hours at room temperature. The reaction mixture was neutralized by adding dropwise to a mixture of ice and a saturated aqueous solution of sodium bicarbonate and the mixture was extracted with ethyl acetate twice. The extract was dried over anhydrous magnesium sulfate and concentrated under reduced pressure. The residue was dissolved in ether and thereto was added a 5N aqueous solution of sodium hydroxide and was extracted with 1N hydrochloric acid and a 2N hydrochloric acid. The extract was washed with ether and thereto was added a 5N aqueous solution of sodium hydroxide and was extracted with ether twice. The extract was washed with water and brine successively, dried over anhydrous magnesium sulfate and concentrated under reduced pressure to give the title compound (2.53 g) having the following physical data.

TLC: Rf0.22 (hexane:ethyl acetate=2:1); NMR (CDCl$_3$): δ 7.48 (dd, J=7.5, 1.5 Hz, 1H), 7.35 (dt, J=1.5, 7.5 Hz, 1H), 7.30-7.25 (m, 1H), 7.14 (d, J=7.5 Hz, 1H), 2.69 (s, 2H), 2.38 (s, 3H), 1.20 (s, 6H).

EXAMPLE 3

(Z)-2-(3,3-dimethyl-3,4-dihydro-(2H)-isoquinolin-1-ylidene)-1-(3-cyanophenyl)ethan-1-one To a solution of diisopropylamine (0.43 ml) in tetrahydrofuran (5 ml) was added n-butyl lithium (1.6M in hexane, 2.15 ml) and the mixture was stirred for 30 minute at 0° C. To the reaction mixture was added a solution of the compound prepared in reference example 2 (478 mg) in tetrahydrofuran (2 ml) dropwise at −78° C. and the mixture was stirred for 90 minutes at −78° C. To the reaction mixture was added 3-cyanobenzoyl chloride (571 mg) in tetrahydrofuran (2 ml) dropwise and then it was stirred under warming to −10° C. over a period of 90 minutes. To the reaction mixture was added water and was extracted with ether twice. The extract was washed with 1N hydrochloric acid, water and a saturated aqueous solution of sodium chloride successively, dried over anhydrous magnesium sulfate and concentrated under reduced pressure. The residue was purified by column chromatography on silica gel (hexane:ethyl acetate=30:1→10:1) to give the compound of the present invention (61 mg) having the following physical data.

TLC: Rf0.49 (hexane:ethyl acetate=2:1); NMR (CDCl$_3$): δ 11.89 (br, 1H), 8.22 (dd, J=1.5, 1.5 Hz, 1H), 8.17 (ddd, J=7.5, 1.5, 1.5 Hz, 1H), 7.83 (d, J=7.0 Hz, 1H), 7.71 (ddd, J=7.5, 1.5, 1.5 Hz, 1H), 7.55 (dd, J=7.5, 7.5 Hz, 1H), 7.47 (t, J=7.0 Hz, 1H), 7.38 (t, J=7.0 Hz, 1H), 7.24 (d, J=7.0 Hz, 1H), 6.25 (s, 1H), 2.93 (s, 2H), 1.38 (s, 6H).

EXAMPLE 3(1)-EXAMPLE 3(4)

By the same procedure as described in example 3, using 4-cyanobenzoyl chloride, 2-trifluoromethoxybenzoyl chloride, 2-cyanobenzoyl chloride or 3-trifluoromethoxy benzoyl chloride, the following compounds of the present invention were given.

EXAMPLE 3(1)

(Z)-2-(3,3-dimethyl-3,4-dihydro-(2H)-isoquinolin-1-ylidene)-1-(4-cyanophenyl)ethan-1-one TLC: Rf0.47 (hexane:ethyl acetate=2:1); NMR (CDCl$_3$): δ 11.96 (br, 1H), 8.02 (d, J=8.5 Hz, 2H), 7.81 (d, J=7.5 Hz, 1H), 7.72 (d, J=8.5 Hz, 2H), 7.47 (t, J=7.5 Hz, 1H), 7.36 (t, J=7.5 Hz, 1H), 7.24 (d, J=7.5 Hz, 1H), 6.28 (s, 1H), 2.92 (s, 2H), 1.38 (s, 6H).

EXAMPLE 3(2)

(Z)-2-(3,3-dimethyl-3,4-dihydro-(2H)-isoquinolin-1-ylidene)-1-(2-trifluoromethoxyphenyl)ethan-1-one TLC: Rf0.69 (hexane:ethyl acetate=2:1); NMR (CDCl$_3$): δ 11.65 (br, 1H), 7.79-7.72 (m, 2H), 7.45-7.25 (m, 5H), 7.21 (d, J=7.5 Hz, 1H), 6.12 (s, 1H), 2.92 (s, 2H), 1.38 (s, 6H).

EXAMPLE 3(3)

(Z)-2-(3,3-dimethyl-3,4-dihydro-(2H)-isoquinolin-1-ylidene)-1-(2-cyanophenyl)ethan-1-one TLC: Rf0.44 (hexane:ethyl acetate=2:1); NMR (CDCl$_3$): δ 11.76 (br, 1H), 7.87 (dd, J=7.5, 1.5 Hz, 1H), 7.81 (d, J=7.0 Hz, 1H), 7.76 (dd, J=7.5, 1.5 Hz, 1H), 7.62 (dt, J=1.5, 7.5 Hz, 1H), 7.52-7.42 (m, 2H), 7.34 (t, J=7.0 Hz, 1H), 7.22 (d, J=7.0 Hz, 1H), 6.21 (s, 1H), 2.92 (s, 2H), 1.39 (s, 6H).

EXAMPLE 3(4)

(Z)-2-(3,3-dimethyl-3,4-dihydro-(2H)-isoquinolin-1-ylidene)-1-(3-trifluoromethoxyphenyl)ethan-1-one TLC: Rf0.53 (hexane:ethyl acetate=3:1); NMR (CDCl$_3$): δ 11.87 (br, 1H), 7.88-7.80 (m, 3H), 7.48-7.43 (m, 2H), 7.36 (t, J=7.5 Hz, 1H), 7.31-7.27 (m, 1H), 7.23 (d, J=7.5 Hz, 1H), 6.27 (s, 1H), 2.92 (s, 2H), 1.38 (s, 6H).

EXAMPLE 4

(Z)-2-(3,3-dimethyl-3,4-dihydro-(2H)-isoquinolin-1-ylidene)-1-(4-carboxyphenyl)ethan-1-one To a solution of the compound prepared in example 1(1) (662 mg) in a mixture of methanol (5 ml) and tetrahydrofuran (5 ml) was added a 2N aqueous solution of sodium hydroxide (5 ml) at room temperature and the mixture was stirred for 3 hours at room temperature. The reaction mixture was neutralized with hydrochloric acid and the mixture was stirred overnight. The precipitate was filtered and dried and washed with a mixture of hexane and ethyl acetate (1/1) to give the compound of the present invention (575 mg) having the following physical data.

TLC: Rf0.29 (methanol:chloroform=1:10); NMR (DMSO-d$_6$): δ 13.12 (br, 1H), 11.94 (s, 1H), 8.09 (d, 7.0 Hz, 1H), 8.09 (d, J=8.5 Hz, 2H), 7.99 (d, J=8.5 Hz, 2H), 7.52 (dd, J=7.0, 7.0 Hz, 1H), 7.39 (dd, J=7.0, 7.0 Hz, 1H), 7.33 (d, J=7.0 Hz, 1H), 6.50 (s, 1H), 2.94 (s, 2H), 1.29 (s, 6H).

EXAMPLE 4(1)-EXAMPLE 4(3)

By the same procedure as described in example 4 using the compound prepared in example 1(30), example 1(45) or example 1(46) in place of the compound prepared in example 1(1), the following compounds of the present invention were given.

EXAMPLE 4(1)

(Z)-2-(3,3-dimethyl-3,4-dihydro-(2H)-isoquinolin-1-ylidene)-1-(3-carboxyphenyl)ethan-1-one TLC: Rf0.37 (methanol:chloroform=1:10); NMR (DMSO-d$_6$): δ 13.10 (br, 1H), 11.90 (s, 1H), 8.47 (dd, J=1.5, 1.5 Hz, 1H), 8.25 (d, J=8.0 Hz, 1H), 8.10-8.00 (m, 2H), 7.65-7.30 (m, 4H), 6.47 (s, 1H), 2.94 (s, 2H), 1.29 (s, 6H).

EXAMPLE 4(2)

(Z)-2-(spiro[3,4-dihydro-(2H)-isoquinolin-3,1'-4'-carboxycyclohexane]-1-ylidene)-1-phenylethan-1-one TLC: Rf0.35 (chloroform:methanol:water=10:1:0.1); NMR (CDCl$_3$): δ 12.08 (br, 1H), 7.97-7.94 (m, 2H), 7.83 (d, J=7.5 Hz, 1H), 7.47-7.41 (m, 4H), 7.35 (t, J=7.5 Hz, 1H), 7.22 (d, J=7.5 Hz, 1H), 6.36 (s, 1H), 2.99 (s, 2H), 2.63-2.56 (m, 1H), 2.06-1.95 (m, 2H), 1.95-1.75 (m, 4H), 1.75-1.60 (m, 2H).

(This compound has two stereoisomers by the existence of a carbon to which carboxy is attached. This compound corresponds to a less polar one on thin layer silica gel. More polar compound of this compound is described in example 4(3).)

EXAMPLE 4(3)

(Z)-2-(spiro[3,4-dihydro-(2H)-isoquinolin-3,1'-4'-carboxycyclohexane]-1-ylidene)-1-phenylethan-1-one TLC: Rf0.32 (chloroform:methanol:water=10:1:0.1); NMR (CDCl$_3$): δ 12.32 (br, 1H), 7.95-7.92 (m, 2H), 7.82 (d, J=7.5 Hz, 1H), 7.44-7.42 (m, 4H), 7.34 (t, J=7.5 Hz, 1H), 7.22 (d, J=7.5 Hz, 1H), 6.33 (s, 1H), 2.90 (s, 2H), 2.40-2.29 (m, 1H), 2.02-1.91 (m, 6H), 1.52-1.43 (m, 2H).

(This compound has two stereoisomers by the existence of a carbon to which carboxy is attached. This compound corresponds to a more polar one on thin layer silica gel. Less polar compound of this compound is described in example 4(2).)

EXAMPLE 5

(Z)-2-(3,3-dimethyl-3,4-dihydro-(2H)-isoquinolin-1-ylidene)-1-(3-hydroxyphenyl)ethan-1-one To the compound prepared in example 1(18) (200 mg) was added a 47% aqueous solution of hydrobromic acid (3 ml) and the mixture was stirred for 1 hour at 115° C. The reaction mixture was allowed to cool and was neutralized by adding a saturated aqueous solution of sodium bicarbonate dropwise, and the mixture was extracted with ethyl acetate twice. The extract was washed with water, dried over anhydrous magnesium sulfate and concentrated under reduced pressure. The residue was purified by column chromatography on silica gel (hexane:ethyl acetate=3:1→1:1) to give the compound of the present invention (147 mg) having the following physical data.

TLC: Rf0.48 (hexane:ethyl acetate=1:1); NMR (CDCl$_3$): δ 11.78 (br, 1H), 7.81 (d, J=8.0 Hz, 1H), 7.53-7.25 (m, 5H), 7.21 (d, J=7.5 Hz, 1H), 6.95 (dd, J=8.0, 3.0 Hz, 1H), 6.30 (s, 1H), 6.13 (br, 1H), 2.90 (s, 2H), 1.36 (s, 6H).

EXAMPLE 5(1)-EXAMPLE 5(3)

By the same procedure as described in example 5 using the compound prepared in example 1(17), example 1(22) or example 1(42) in place of the compound prepared in example 1(18), the following compounds of the present invention were given.

EXAMPLE 5(1)

(Z)-2-(3,3-dimethyl-3,4-dihydro-(2H)-isoquinolin-1-ylidene)-1-(4-hydroxyphenyl)ethan-1-one TLC: Rf0.19 (hexane:ethyl acetate=2:1); NMR (CDCl$_3$): δ 11.72 (br, 1H), 7.91-7.87 (m, 2H), 7.82 (d, J=7.0 Hz, 1H), 7.42 (t, J=7.0 Hz, 1H), 7.33 (t, J=7.0 Hz, 1H), 7.21 (d, J=7.0 Hz, 1H), 6.90-6.85 (m, 2H), 6.29 (s, 1H), 2.89 (s, 2H), 1.35 (s, 6H).

EXAMPLE 5(2)

(Z)-2-(3,3-dimethyl-3,4-dihydro-(2H)-isoquinolin-1-ylidene)-1-(2-hydroxyphenyl)ethan-1-one TLC: Rf0.70 (hexane:ethyl acetate=2:1); NMR (CDCl$_3$): δ 11.34 (br, 1H), 7.83 (d, J=7.0 Hz, 1H), 7.76 (dd, J=8.0, 1.5 Hz, 1H), 7.46 (dt, J=1.5, 8.0 Hz, 1H), 7.40-7.31 (m, 2H), 7.23 (d, J=7.5 Hz, 1H), 6.94 (dd, J=8.0, 1.0 Hz, 1H), 6.83 (dt, J=1.0, 8.0 Hz, 1H), 6.34 (s, 1H), 2.91 (s, 2H), 1.38 (s, 6H).

EXAMPLE 5(3)

(Z)-2-(6-hydroxy-3,3-dimethyl-3,4-dihydro-(2H)-isoquinolin-1-ylidene)-1-phenylethan-1-one TLC: Rf0.18 (ethyl acetate:hexane=1:2); NMR (DMSO-d$_6$): δ 11.84 (s, 1H), 10.15 (s, 1H), 8.00-7.85 (m, 3H), 7.50-7.35 (m, 3H), 6.73 (dd, J=8.5, 2.5 Hz, 1H), 6.67 (d, J=2.5 Hz, 1H), 6.30 (s, 1H), 2.82 (s, 2H), 1.27 (s, 6H).

EXAMPLE 6

2-(3,3-dimethyl-3,4-dihydroisoquinolin-1-yl)-2-methyl-1-phenylpropan-1-one

To a solution of (Z)-2-(3,3-dimethyl-3,4-dihydro-(2H)-isoquinolin-1-ylidene)-1-phenylethan-1-one (277 mg; see Khim. Geterotsikl. Soedin., 7, 946-949 (1994)) in tetrahydrofuran (5 ml) were added at 0° C. 62.7% sodium hydride (77 mg) and methyl iodide (0.14 ml) successively and the mixture was warmed to room temperature and the mixture was stirred for 2 hours. To the reaction mixture were added water and a saturated aqueous solution of ammonium chloride successively and the mixture was extracted with ethyl acetate. The extract was dried over anhydrous magnesium sulfate and concentrated. The residue was purified by column chromatography on silica gel (hexane:ethyl acetate=10:1) to give the compound of the present invention (110 mg) having the following physical data.

TLC: Rf0.62 (ethyl acetate:hexane=1:5); NMR (CDCl$_3$): δ 8.03 (m, 2H), 7.37 (tt, J=7.5, 2.0 Hz, 1H), 7.26 (m, 2H), 7.20-7.00 (m, 4H), 2.65 (s, 2H), 1.64 (s, 6H), 1.23 (s, 6H).

EXAMPLE 6(1)-EXAMPLE 6(3)

By the same procedure as described in example 6 using 1,4-dibromobutane, 1,5-dibromopentane or 2-bromo-1-(2-bromoethoxy)ethane in place of methyl iodide, the following compounds of the present invention were given.

EXAMPLE 6(1)

1-(3,3-dimethyl-3,4-dihydroisoquinolin-1-yl)cyclopentylphenyl ketone

TLC: Rf0.66 (ethyl acetate:hexane=1:5); NMR (CDCl$_3$): δ 7.97 (m, 2H), 7.40-6.90 (m, 7H), 2.57 (s, 2H), 2.70-2.30 (m, 4H), 1.73 (m, 4H), 1.19 (s, 6H).

EXAMPLE 6(2)

1-(3,3-dimethyl-3,4-dihydroisoquinolin-1-yl)cyclohexylphenyl ketone

TLC: Rf0.70 (ethyl acetate:hexane=1:5); NMR (CDCl$_3$): δ 8.09 (m, 2H), 7.40-7.00 (m, 7H), 2.66 (s, 2H), 2.40-2.05 (m, 4H), 1.80-1.30 (m, 6H), 1.24 (s, 6H).

EXAMPLE 6(3)

4-(3,3-dimethyl-3,4-dihydroisoquinolin-1-yl)-3,4,5,6-tetrahydropyran-4-ylphenylketone TLC: Rf0.41 (ethyl acetate:hexane=1:5); NMR (CDCl$_3$): δ 8.11 (m, 2H), 7.45-7.00 (m, 7H), 3.80 (m, 4H), 2.68 (s, 2H), 2.40 (m, 4H), 1.26 (s, 6H).

EXAMPLE 7

(Z)-2-(spiro[3,4-dihydro-(2H)-isoquinolin-3,1'-4'-hydroxycyclohexane]-1-ylidene)-1-phenylethan-1-one To a solution of the compound prepared in example 1(49) (52 mg) in methanol (3 ml) was added sodium borohydride (6 mg) and the mixture was stirred for 10 minutes at room temperature. The reaction mixture was poured into water and was extracted with ethyl acetate. The extract was washed with brine, and dried over anhydrous magnesium sulfate and concentrated under reduced pressure. The residue was purified by thin layer chromatography on silica gel (hexane:ethyl acetate=5:1), to give the compound of the present invention (less polar 11 mg, more polar 33 mg) having the following physical data.

This compound has two stereoisomers by the existence of a carbon to which hydroxy is attached. Less polar means a compound which is in less polar position on thin layer silica gel and more polar means a compound which is in more polar position thereon.

[Less Polar]

TLC: Rf0.33 (ethyl acetate:hexane=2:1); NMR (CDCl$_3$): δ 12.19 (br, 1H), 7.95 (m, 2H), 7.82 (m, 1H), 7.50-7.20 (m, 6H), 6.36 (s, 1H), 4.02 (m, 1H), 2.97 (s, 2H), 2.10-1.55 (m, 8H).

[More Polar]

TLC: Rf0.28 (ethyl acetate:hexane=2:1); NMR (CDCl$_3$): δ 12.34 (br, 1H), 7.96 (m, 2H), 7.83 (m, 1H), 7.50-7.20 (m, 6H), 6.37 (s, 1H), 3.66 (m, 1H), 2.89 (s, 2H), 2.00-1.40 (m, 8H).

EXAMPLE 8

(Z)-2-(3,3-dimethyl-3,4-dihydro-(2H)-isoquinolin-1-ylidene)-1-(1-acetylpiperidin-4-yl)ethan-1-one To a solution of the compound prepared in example 2(3) (77 mg) and triethylamine (0.15 ml) in dichloromethane (5 ml) was added acetyl chloride at room temperature (0.02 ml) and the mixture was stirred for 30 minutes at room temperature. The reaction mixture was poured into water and was extracted with ethyl acetate. The extract was washed with a saturated aqueous solution of sodium bicarbonate, water and brine, dried over anhydrous magnesium sulfate, concentrated under reduced pressure to give the compound of the present invention (65 mg) having the following physical data.

TLC: Rf0.72 (water:methanol:chloroform=1:10:50); NMR (CDCl$_3$): δ 11.33 (br, 1H), 7.69 (m, 1H), 7.45-7.15 (m, 3H), 5.62 (s, 1H), 4.65 (m, 1H), 3.88 (m, 1H), 3.11 (m, 1H), 2.85 (s, 2H), 2.75-2.40 (m, 2H), 2.11 (s, 3H), 2.00-1.60 (m, 4H), 1.31 (s, 6H).

EXAMPLE 8(1)-EXAMPLE 8(3)

By the same procedure as described in example 8 using the compound prepared in example 2(3) or a corresponding amine derivative and a halide derivative corresponding to acetyl chloride, the compounds of the present invention having the following physical data.

EXAMPLE 8(1)

(Z)-2-(spiro[3,4-dihydro-(2H)-isoquinolin-3,4'-1'-acetylpiperidin]-1-ylidene)-1-phenylethan-1-one TLC: Rf0.53 (water:methanol:chloroform=1:10:100); NMR (CDCl$_3$): δ 12.47 (s, 1H), 7.96 (m, 2H), 7.84 (d, J=7.5 Hz, 1H), 7.50-7.20 (m, 6H), 6.42 (s, 1H), 4.35 (m, 1H), 3.80-3.45 (m, 2H), 3.24 (m, 1H), 2.94 (s, 2H), 2.11 (s, 3H), 1.90-1.50 (m, 4H).

EXAMPLE 8(2)

(Z)-2-(3,3-dimethyl-3,4-dihydro-(2H)-isoquinolin-1-ylidene)-1-(1-t-butoxycarbonylpiperidin-4-yl)ethan-1-one TLC: Rf0.34 (ethyl acetate:hexane=1:2); NMR (CDCl$_3$): δ 11.32 (br, 1H), 7.69 (m, 1H), 7.45-7.15 (m, 3H), 5.62 (s, 1H), 4.17 (m, 2H), 2.85 (s, 2H), 2.77 (m, 2H), 2.42 (tt, J=11.5, 3.5 Hz, 1H), 1.84 (m, 2H), 1.66 (m, 2H), 1.47 (s, 9H), 1.30 (s, 6H).

EXAMPLE 8(3)

(Z)-2-(3,3-dimethyl-3,4-dihydro-(2H)-isoquinolin-1-ylidene)-1-(1-mesylpiperidin-4-yl)ethan-1-one TLC: Rf0.34 (ethyl acetate:hexane=2:1); NMR (CDCl$_3$): δ 11.35 (br, 1H), 7.68 (m, 1H), 7.45-7.15 (m, 3H), 5.61 (s, 1H), 3.85 (m, 2H), 2.90-2.70 (m, 2H), 2.86 (s, 2H), 2.81 (s, 3H), 2.42 (m, 1H), 2.05-1.80 (m, 4H), 1.32 (s, 6H).

EXAMPLE 9

(Z)-2-(6-phenyl-3,3-dimethyl-3,4-dihydro-(2H)-isoquinolin-1-ylidene)-1-phenylethan-1-one Under atmosphere of argon, a solution of the compound prepared in example 1(68) (312 mg) in dimethoxyethane (120 ml) was degassed and thereto were added tetrakis(triphenylphosphine)palladium (58 mg), a saturated aqueous solution of sodium bicarbonate (2.5 ml) and benzene boronic acid (183 mg) and the mixture was refluxed for 3 days. The reaction mixture was allowed to cool and thereto was added water and the mixture was extracted with ethyl acetate twice. The extract was washed with water and brine, dried over anhydrous magnesium sulfate, and concentrated under reduced pressure. The residue was purified by column chromatography on silica gel (hexane:ethyl acetate=5:1) to give the compound of the present invention (121 mg) having the following physical data.

TLC: Rf0.39 (hexane:ethyl acetate=3:1); NMR (CDCl$_3$): δ 11.82 (br, 1H), 7.99-7.96 (m, 2H), 7.89 (d, J=8.0 Hz, 1H), 7.66-7.63 (m, 2H), 7.58 (dd, J=8.0, 2.0 Hz, 1H), 7.51-7.38 (m, 7H), 6.36 (br, 1H), 2.98 (s, 2H), 1.41 (s, 6H).

EXAMPLE 9(1)

(Z)-2-(6-(pyridin-3-yl)-3,3-dimethyl-3,4-dihydro-(2H)-isoquinolin-1-ylidene)-1-phenylethan-1-one By the same procedure as described in example 9 using diethyl (3-pyridyl)borane in place of benzene boronic acid, the compound of the present invention having the following physical data was given.

TLC: Rf0.31 (hexane:ethyl acetate=1:1); NMR (CDCl$_3$): δ 11.81 (br, 1H), 8.91 (d, J=1.5 Hz, 1H), 8.65 (dd, J=5.0, 1.5 Hz, 1H), 7.98-7.93 (m, 4H), 7.57 (dd, J=8.0, 2.0 Hz, 1H), 7.48-7.41 (m, 5H), 6.38 (s, 1H), 2.99 (s, 2H), 1.41 (s, 6H).

EXAMPLE 10

(Z)-2-(3,3-dimethyl-3,4-dihydro-(2H)-isoquinolin-1-ylidene)-1-(4-hydroxymethylphenyl)ethan-1-one To a suspension of lithium aluminum hydride (95 mg) in anhydrous tetrahydrofuran (9 ml) was added a solution of the compound prepared in example 1(1) (317 mg) in anhydrous tetrahydrofuran (6 ml) and the mixture was stirred for 1 hour at room temperature. To the reaction mixture was added a saturated aqueous solution of sodium sulfate (1.0 ml) and the mixture was stirred. The reaction mixture was diluted with ether, and the mixture was dried over anhydrous magnesium sulfate and concentrated under reduced pressure. The residue was purified by column chromatography on silica gel (hexane:ethyl acetate=3:1→1:1) to give the compound of the present invention (251 mg) having the following physical data.

TLC: Rf0.33 (hexane:ethyl acetate=1:1); NMR (CDCl$_3$): δ 11.84 (br, 1H), 7.95 (d, J=8.0 Hz, 2H), 7.83 (d, J=7.0 Hz, 1H), 7.46-7.41 (m, 3H), 7.35 (t, J=7.0 Hz, 1H), 7.22 (d, J=7.0 Hz, 1H), 6.33 (s, 1H), 4.76 (s, 2H), 2.91 (s, 2H), 1.75 (br, 1H), 1.37 (s, 6H).

EXAMPLE 10(1)

(Z)-2-(3,3-dimethyl-3,4-dihydro-(2H)-isoquinolin-1-ylidene)-1-(3-hydroxymethylphenyl)ethan-1-one By the same procedure as described in example 10 using the compound prepared in example 1(30) in place of the compound prepared in example 1(1), the compound of the present invention having the following physical data.

TLC: Rf0.33 (hexane:ethyl acetate=1:1); NMR (CDCl$_3$): δ 11.86 (br, 1H), 7.94 (s, 1H), 7.90-7.83 (m, 2H), 7.49-7.41 (m, 3H), 7.35 (t, J=7.0 Hz, 1H), 7.22 (d, J=7.0 Hz, 1H), 6.34 (s, 1H), 4.77 (s, 2H), 2.91 (s, 2H), 1.77 (br, 1H), 1.37 (s, 6H).

REFERENCE EXAMPLE 3

3-(4-isopropylphenyl)-2,2-dimethylpropanoic acid

Diisopropylamine (3.08 ml) was dissolved in tetrahydrofuran (40 ml) and to the mixture was added n-butyl lithium (13.8 ml; 1.6M in hexane) at −78° C. and then was added isobutylacetate (0.93 ml) and the mixture was stirred for 1 hour at 30° C. To the reaction mixture was added a solution of 4-isopropylbenzyl chloride (2.19 g) in tetrahydrofuran (10 ml) at −78° C. and the mixture was stirred for 2 hours at room temperature. The reaction mixture was poured into cool hydrochloric acid and the mixture was extracted with ethyl acetate. The extract was concentrated. The residue was purified by column chromatography on silica gel (hexane: ethyl acetate=5:1) to give the title compound (1.73 g) having the following physical data.

TLC: Rf0.32 (ethyl acetate:hexane=1:4); NMR (CDCl$_3$): δ 7.15-7.05 (m, 4H), 2.88 (m, 1H), 2.86 (s, 2H), 1.23 (d, J=7.0 Hz, 6H), 1.20 (s, 6H).

REFERENCE EXAMPLE 4

2-methyl-1-(4-isopropylphenyl)propan-2-isocyanate

To dioxane (20 ml) were added the compound prepared in reference example 3 (1.71 g), diphenylphosphoryl azide (2.15 g) and triethylamine (1.2 ml) and the mixture was refluxed for 1 hour. The reaction mixture was allowed to cool and was poured into ice-water and was extracted with ether. The extract was washed with brine, dried over anhydrous magnesium sulfate and concentrated to give the title compound (1.70 g, crude). It was used in the next reaction without subjecting to purification.

REFERENCE EXAMPLE 5

3,3-dimethyl-7-isopropyl-3,4-dihydro-(2H)-isoquinolin-1-one

To the compound prepared in reference example 4(1.70 g) was added polyphosphoric acid (100 g) and the mixture was stirred for 2 hours at room temperature. To the reaction mixture was added ice-water and the mixture was extracted with ethyl acetate. The extract was washed with water, a saturated aqueous solution of sodium bicarbonate and brine successively, dried over anhydrous magnesium sulfate and concentrated. The residue was purified by column chromatography on silica gel to give the title compound (60 mg) having the following physical data.

TLC: Rf0.36 (ethyl acetate:hexane=1:1); NMR (CDCl$_3$): δ 7.94 (d, J=2.0 Hz, 1H), 7.31 (dd, J=8.0, 2.0 Hz, 1H), 7.10 (d, J=8.0 Hz, 1H), 5.73 (br, 1H), 2.95 (m, 1H), 2.89 (s, 2H), 1.31 (s, 6H), 1.27 (d, J=7.0 Hz, 6H).

REFERENCE EXAMPLE 6

3,3-dimethyl-7-isopropyl-3,4-dihydro-(2H)-isoquinolin-1-thione

To toluene (5 ml) were added the compound prepared in reference example 5 (52 mg) and Lawesson reagent (48 mg) and the mixture was refluxed for 1 hour. The reaction mixture was allowed to cool and was purified by column chromatography on silica gel (hexane:ethyl acetate=9:1) to give the title compound (48 mg) having the following physical data.

TLC: Rf0.35 (chloroform:hexane=1:4); NMR (CDCl$_3$): δ 8.39 (d, J=2.0 Hz, 1H), 7.97 (br, 1H), 7.33 (dd, J=7.5, 2.0 Hz, 1H), 7.05 (d, J=7.5 Hz, 1H), 2.98 (m, 1H), 2.90 (s, 2H), 1.34 (s, 6H), 1.28 (d, J=7.0 Hz, 6H).

REFERENCE EXAMPLE 7

3,3-dimethyl-4-oxa-3,4-dihydro-(2H)-isoquinolin-1-one

To chloroform (30 ml) were added 2-hydroxybenzamide (2.74 g) and acetone dimethyl acetal (2.6 ml) and thereto was added conc. sulfuric acid (0.6 ml) at room temperature and the mixture was refluxed for 8 hours. The reaction mixture was allowed to cool, and the precipitate was removed. The filtrate was concentrated. To the residue was added ether, and was washed with a 2N aqueous solution of sodium hydroxide, water and brine successively, dried over anhydrous magnesium sulfate and concentrated to give the title compound having the following physical data.

TLC: Rf0.45 (ethyl acetate:hexane=1:1); NMR (CDCl$_3$): δ 7.92 (dd, J=7.5, 1.5 Hz, 1H), 7.45 (ddd, J=8.0, 7.5, 1.5 Hz, 1H), 7.15 (br, 1H), 7.07 (ddd, J=7.5, 7.5, 1.0 Hz, 1H), 6.92 (dd, J=8.0, 1.0 Hz, 1H), 1.66 (s, 6H).

REFERENCE EXAMPLE 8

3,3-dimethyl-4-oxa-3,4-dihydro-(2H)-isoquinolin-1-thione

To toluene (70 ml) were added the compound prepared in reference example 7 (1.20 g) and Lawesson reagent (1.37 g) and the mixture was refluxed for 2 hours. The reaction mixture was purified by column chromatography on silica gel (hexane:ethyl acetate=5:1) to give the title compound (1.34 g) having the following physical data.

TLC: Rf0.45 (ethyl acetate:hexane=1:3); NMR (CDCl$_3$): δ 8.45 (br, 1H), 8.31 (dd, J=8.0, 1.5 Hz, 1H), 7.46 (ddd, J=8.0, 7.5, 1.5 Hz, 1H), 7.07 (ddd, J=8.0, 7.5, 1.0 Hz, 1H), 6.89 (dd, J=8.0, 1.0 Hz, 1H), 1.66 (s, 6H).

EXAMPLE 11

(Z)-2-(7-isopropyl-3,3-dimethyl-3,4-dihydro-(2H)-isoquinolin-1-ylidene)-1-phenylethan-1-one To a solution of the compound prepared in reference example 6 (45 mg) in xylene (5 ml) was added benzoylmethyl bromide (46 mg) and the mixture was stirred for 1.5 hours. To the reaction mixture was added triethylamine (0.04 ml) and the mixture was stirred for 15 minutes. To the reaction mixture was added triphenylphosphine (61 mg) and the mixture was stirred for 15 minutes, and then thereto was added triethylamine (0.04 ml) and the mixture was refluxed for 1 hour. The reaction mixture was allowed to cool and was purified by column chromatography on silica gel (hexane:ethyl acetate=20:1) to give the compound of the present invention (58 mg) having the following physical data.

TLC: Rf0.19 (ethyl acetate:hexane=1:10); NMR (CDCl$_3$): δ 11.88 (br, 1H), 7.96 (m, 2H), 7.64 (d, J=1.5 Hz, 1H), 7.50-7.40 (m, 3H), 7.30 (dd, J=8.0, 1.5 Hz, 1H), 7.14 (d, J=8.0 Hz, 1H), 6.32 (s, 1H), 2.98 (m, 1H), 2.86 (s, 2H), 1.36 (s, 6H), 1.30 (d, J=7.0 Hz, 6H).

EXAMPLE 11(1)-EXAMPLE 11(203)

By the same procedure as described in example 11 using the compound prepared in reference example 6 or a corresponding derivative, and benzoylmethyl bromide or a corresponding derivative, the following compounds were given.

EXAMPLE 11(1)

(Z)-2-(3,3-dimethyl-4-oxa-3,4-dihydro-(2H)-isoquinolin-1-ylidene)-1-phenylethan-1-one TLC: Rf0.22 (chloroform:hexane=1:1); NMR (CDCl$_3$): δ 11.65 (br, 1H), 7.94 (m, 2H), 7.74 (d, J=7.5, 1.5 Hz, 1H), 7.50-7.40 (m, 4H), 7.07 (ddd, J=7.5, 7.5, 1.0 Hz, 1H), 6.96 (dd, J=7.5, 1.0 Hz, 1H), 6.34 (s, 1H), 1.67 (s, 6H).

EXAMPLE 11(2)

(Z)-2-(7-methoxy-3,3-dimethyl-3,4-dihydro-(2H)-isoquinolin-1-ylidene)-1-phenylethan-1-one TLC: Rf0.20 (ethyl acetate:hexane=1:5); NMR (CDCl$_3$): δ 11.82 (br, 1H), 7.94 (m, 2H), 7.50-7.40 (m, 3H), 7.34 (d, J=2.5 Hz, 1H), 7.13 (d, J=8.0 Hz, 1H), 6.98 (dd, J=8.0, 2.5 Hz, 1H), 6.28 (s, 1H), 3.87 (s, 3H), 2.83 (s, 2H), 1.35 (s, 6H).

EXAMPLE 11(3)

(Z)-2-(7-ethyl-3,3-dimethyl-3,4-dihydro-(2H)-isoquinolin-1-ylidene)-1-phenylethan-1-one TLC: Rf0.31 (ethyl acetate:hexane=1:5); NMR (CDCl$_3$): δ 11.86 (br, 1H), 7.96 (m, 2H), 7.63 (s, 1H), 7.50-7.40 (m, 3H), 7.27 (m, 1H), 7.12 (d, J=8.0 Hz, 1H), 6.32 (s, 1H), 2.86 (s, 2H), 2.71 (q, J=7.5 Hz, 2H), 1.36 (s, 6H), 1.29 (t, J=7.5 Hz, 3H).

EXAMPLE 11(4)

(Z)-2-(7-t-butyl-3,3-dimethyl-3,4-dihydro-(2H)-isoquinolin-1-ylidene)-1-phenylethan-1-one TLC: Rf0.37 (ethyl acetate:hexane=1:5); NMR (CDCl$_3$): δ 11.90 (br, 1H), 7.95 (m, 2H), 7.81 (d, J=2.0 Hz, 1H), 7.50-7.40 (m, 4H), 7.14 (d, J=8.0 Hz, 1H), 6.32 (s, 1H), 2.86 (s, 2H), 1.38 (s, 9H), 1.36 (s, 6H).

EXAMPLE 11(5)

(Z)-2-(7-propyl-3,3-dimethyl-3,4-dihydro-(2H)-isoquinolin-1-ylidene)-1-phenylethan-1-one TLC: Rf0.34 (ethyl acetate:hexane=1:5); NMR (CDCl$_3$): δ 11.86 (br, 1H), 7.96 (m, 2H), 7.61 (d, J=1.5 Hz, 1H), 7.50-7.40 (m, 3H), 7.24 (dd, J=8.0, 1.5 Hz, 1H), 7.11 (d, J=8.0 Hz, 1H), 6.32 (s, 1H), 2.86 (s, 2H), 2.65 (t, J=7.5 Hz, 2H), 1.69 (m, 2H), 1.36 (s, 6H), 0.98 (t, J=7.5 Hz, 3H).

EXAMPLE 11(6)

(Z)-2-(7-butyl-3,3-dimethyl-3,4-dihydro-(2H)-isoquinolin-1-ylidene)-1-phenylethan-1-one TLC: Rf0.27 (ethyl acetate:hexane=1:5); NMR (CDCl$_3$): δ 11.86 (br, 1H), 7.96 (m, 2H), 7.61 (d, J=2.0 Hz, 1H), 7.50-7.40 (m, 3H), 7.25 (dd, J=8.0, 2.0 Hz, 1H), 7.11 (d, J=8.0 Hz, 1H), 6.31 (s, 1H), 2.86 (s, 2H), 2.67 (t, J=7.5 Hz, 2H), 1.65 (m, 2H), 1.39 (m, 2H), 1.36 (s, 6H), 0.96 (t, J=7.5 Hz, 3H).

EXAMPLE 11(7)

(Z)-2-(7-bromo-3,3-dimethyl-3,4-dihydro-(2H)-isoquinolin-1-ylidene)-1-phenylethan-1-one TLC: Rf0.27 (ethyl acetate:hexane=1:5); NMR (CDCl$_3$): δ 11.75 (br, 1H), 8.00-7.90 (m, 3H), 7.54 (dd, J=8.0, 2.0 Hz, 1H), 7.50-7.40 (m, 3H), 7.10 (d, J=8.0 Hz, 1H), 6.26 (s, 1H), 2.85 (s, 2H), 1.36 (s, 6H).

EXAMPLE 11(8)

(Z)-2-(7-chloro-3,3-dimethyl-4-oxa-3,4-dihydro-(2H)-isoquinolin-1-ylidene)-1-cycloheptylethan-1-one TLC: Rf0.46 (ethyl acetate:hexane=1:5); NMR (CDCl$_3$): δ 10.98 (br, 1H), 7.56 (d, J=2.5 Hz, 1H), 7.31 (dd, J=8.5, 2.5 Hz, 1H), 6.86 (d, J=2.5 Hz, 1H), 5.55 (s, 1H), 2.49 (m, 1H), 1.95-1.40 (m, 12H), 1.58 (s, 6H).

EXAMPLE 11(9)

(Z)-2-(7-chloro-3,3-dimethyl-4-oxa-3,4-dihydro-(2H)-isoquinolin-1-ylidene)-1-cyclohexylethan-1-one TLC: Rf0.42 (ethyl acetate:hexane=1:5); NMR (CDCl$_3$): δ 11.07 (br, 1H), 7.57 (d, J=2.5 Hz, 1H), 7.32 (dd, J=8.5, 2.5 Hz, 1H), 6.86 (d, J=8.5 Hz, 1H), 5.59 (s, 1H), 2.32 (m, 1H), 1.95-1.15 (m, 10H), 1.59 (s, 6H).

EXAMPLE 11(10)

(Z)-2-(7-chloro-3,3-dimethyl-4-oxa-3,4-dihydro-(2H)-isoquinolin-1-ylidene)-1-(2-methoxyphenyl)ethan-1-one TLC: Rf0.20 (ethyl acetate:hexane=1:5); NMR (CDCl$_3$): δ 11.40 (br, 1H), 7.65 (dd, J=7.5, 2.0 Hz, 1H), 7.60 (d, J=2.5 Hz, 1H), 7.39 (m, 1H), 7.33 (dd, J=8.5, 2.5 Hz, 1H), 7.05-6.95 (m, 2H), 6.89 (d, J=8.5 Hz, 1H), 6.25 (s, 1H), 3.93 (s, 3H), 1.65 (s, 6H).

EXAMPLE 11(11)

(Z)-2-(7-chloro-3,3-dimethyl-4-oxa-3,4-dihydro-(2H)-isoquinolin-1-ylidene)-1-(4-cyanophenyl)ethan-1-one TLC: Rf0.19 (ethyl acetate:hexane=1:5); NMR (CDCl$_3$): δ 11.67 (br, 1H), 8.01 (d, J=9.0 Hz, 2H), 7.75 (d, J=9.0 Hz, 2H), 7.67 (d, J=2.5 Hz, 1H), 7.40 (dd, J=8.5, 2.5 Hz, 1H), 6.93 (d, J=8.5 Hz, 1H), 6.21 (s, 1H), 1.68 (s, 6H).

EXAMPLE 11(12)

(Z)-2-(3,3,7-trimethyl-4-oxa-3,4-dihydro-(2H)-isoquinolin-1-ylidene)-1-cyclohexylethan-1-one TLC: Rf0.39 (ethyl acetate:hexane=1:5); NMR (CDCl$_3$): δ 11.15 (br, 1H), 7.40 (d, J=1.5 Hz, 1H), 7.18 (dd, J=8.5, 1.5 Hz, 1H), 6.81 (d, J=8.5 Hz, 1H), 5.62 (s, 1H), 2.33 (s, 3H), 2.31 (m, 1H), 1.95-1.15 (m, 10H), 1.58 (s, 6H).

EXAMPLE 11(13)

(Z)-2-(7-methoxy-3,3-dimethyl-4-oxa-3,4-dihydro-(2H)-isoquinolin-1-ylidene)-1-cyclohexylethan-1-one TLC: Rf0.31 (ethyl acetate:hexane=1:5); NMR (CDCl$_3$): δ 11.14 (br, 1H), 7.08 (d, J=3.0 Hz, 1H), 6.96 (dd, J=9.0, 3.0 Hz, 1H), 6.85 (d, J=9.0 Hz, 1H), 5.57 (s, 1H), 3.83 (s, 3H), 2.32 (m, 1H), 1.95-1.15 (m, 10H), 1.58 (s, 6H).

EXAMPLE 11(14)

(Z)-2-(7-fluoro-3,3-dimethyl-4-oxa-3,4-dihydro-(2H)-isoquinolin-1-ylidene)-1-cyclohexylethan-1-one TLC: Rf0.41 (ethyl acetate:hexane=1:5); NMR (CDCl$_3$): δ 11.07 (br, 1H), 7.29 (dd, J=9.0, 3.0 Hz, 1H), 7.08 (ddd, J=9.0, 8.0, 3.0 Hz, 1H), 6.88 (dd, J=9.0, 5.0 Hz, 1H), 5.56 (s, 1H), 2.32 (m, 1H), 1.95-1.15 (m, 10H), 1.59 (s, 6H).

EXAMPLE 11(15)

(Z)-2-(3,3,7-trimethyl-4-oxa-3,4-dihydro-(2H)-isoquinolin-1-ylidene)-1-(2-methoxyphenyl)ethan-1-one TLC: Rf0.38 (ethyl acetate:hexane=1:3); NMR (CDCl$_3$): δ 11.48 (br, 1H), 7.64 (dd, J=7.5, 1.5 Hz, 1H), 7.42 (d, J=2.0 Hz, 1H), 7.37 (ddd, J=8.0, 7.5, 1.5 Hz, 1H), 7.19 (dd, J=8.0, 2.0 Hz, 1H), 7.01 (ddd, J=7.5, 7.5, 1.0 Hz, 1H), 6.97 (dd, J=8.0, 1.0 Hz, 1H), 6.83 (d, J=8.0 Hz, 1H), 6.23 (s, 1H), 3.92 (s, 3H), 2.32 (s, 3H), 1.65 (s, 6H).

EXAMPLE 11(16)

(Z)-2-(7-methoxy-3,3-dimethyl-4-oxa-3,4-dihydro-(2H)-isoquinolin-1-ylidene)-1-(2-methoxyphenyl)ethan-1-one TLC: Rf0.31 (ethyl acetate:hexane=1:3); NMR (CDCl$_3$): δ 11.46 (br, 1H), 7.66 (dd, J=7.5, 2.0 Hz, 1H), 7.38 (ddd, J=8.0, 7.5, 2.0 Hz, 1H), 7.12 (d, J=3.0 Hz, 1H), 7.05-6.95 (m, 3H), 6.87 (d, J=8.0 Hz, 1H), 6.23 (s, 1H), 3.91 (s, 3H), 3.81 (s, 3H), 1.64 (s, 6H).

EXAMPLE 11(17)

(Z)-2-(7-fluoro-3,3-dimethyl-4-oxa-3,4-dihydro-(2H)-isoquinolin-1-ylidene)-1-(2-methoxyphenyl)ethan-1-one TLC: Rf0.40 (ethyl acetate:hexane=1:3); NMR (CDCl$_3$): δ 11.40 (br, 1H), 7.67 (dd, J=7.5, 2.0 Hz, 1H), 7.39 (ddd, J=8.0, 7.5, 2.0 Hz, 1H), 7.32 (dd, J=9.0, 3.0 Hz, 1H), 7.10 (ddd, J=9.0, 8.0, 3.0 Hz, 1H), 7.02 (ddd, J=7.5, 7.5, 1.5 Hz, 1H), 6.98 (dd, J=8.0, 1.5 Hz, 1H), 6.90 (dd, J=9.0, 4.5 Hz, 1H), 6.25 (s, 1H), 3.93 (s, 3H), 1.65 (s, 6H).

EXAMPLE 11(18)

(Z)-2-(3,3,7-trimethyl-4-oxa-3,4-dihydro-(2H)-isoquinolin-1-ylidene)-1-cycloheptylethan-1-one TLC: Rf0.49 (ethyl acetate:hexane=1:4); NMR (CDCl$_3$): δ 11.07 (br, 1H), 7.39 (d, J=1.5 Hz, 1H), 7.17 (dd, J=8.0, 1.5 Hz, 1H), 6.81 (d, J=8.0 Hz, 1H), 5.58 (s, 1H), 2.48 (m, 1H), 2.33 (s, 3H), 2.00-1.40 (m, 12H), 1.59 (s, 6H).

EXAMPLE 11(19)

(Z)-2-(7-methoxy-3,3-dimethyl-4-oxa-3,4-dihydro-(2H)-isoquinolin-1-ylidene)-1-cycloheptylethan-1-one TLC: Rf0.43 (ethyl acetate:hexane=1:4); NMR (CDCl$_3$): δ 11.06 (br, 1H), 7.07 (d, J=3.0 Hz, 1H), 6.96 (dd, J=9.0, 3.0 Hz, 1H), 6.85 (d, J=9.0 Hz, 1H), 5.54 (s, 1H), 3.83 (s, 3H), 2.49 (m, 1H), 2.00-1.40 (m, 12H), 1.58 (s, 6H).

EXAMPLE 11(20)

(Z)-2-(7-fluoro-3,3-dimethyl-4-oxa-3,4-dihydro-(2H)-isoquinolin-1-ylidene)-1-cycloheptylethan-1-one TLC: Rf0.53 (ethyl acetate:hexane=1:4); NMR (CDCl$_3$): δ 10.98 (br, 1H), 7.29 (dd, J=9.0, 3.0 Hz, 1H), 7.08 (ddd, J=9.0, 8.0, 3.0 Hz, 1H), 6.87 (dd, J=9.0, 5.0 Hz, 1H), 5.53 (s, 1H), 2.48 (m, 1H), 2.00-1.40 (m, 12H), 1.59 (s, 6H).

EXAMPLE 11(21)

(Z)-2-(3,3,7-trimethyl-4-oxa-3,4-dihydro-(2H)-isoquinolin-1-ylidene)-1-(4-cyanophenyl)ethan-1-one TLC: Rf0.26 (ethyl acetate:hexane=1:5); NMR (CDCl$_3$): δ 11.74 (br, 1H), 8.02 (d, J=8.0 Hz, 2H), 7.74 (d, J=8.0 Hz, 2H), 7.49 (d, J=1.5 Hz, 1H), 7.26 (dd, J=8.0, 1.5 Hz, 1H), 6.87 (d, J=8.0 Hz, 1H), 6.24 (s, 1H), 2.38 (s, 3H), 1.67 (s, 6H).

EXAMPLE 11(22)

(Z)-2-(7-methoxy-3,3-dimethyl-4-oxa-3,4-dihydro-(2H)-isoquinolin-1-ylidene)-1-(4-cyanophenyl)ethan-1-one TLC: Rf0.16 (ethyl acetate:hexane=1:5); NMR (CDCl$_3$): δ 11.72 (br, 1H), 8.00 (d, J=8.0 Hz, 2H), 7.74 (d, J=8.0 Hz, 2H), 7.17 (d, J=3.0 Hz, 1H), 7.04 (dd, J=9.0, 3.0 Hz, 1H), 6.92 (d, J=9.0 Hz, 1H), 6.19 (s, 1H), 3.86 (s, 3H), 1.67 (s, 6H).

EXAMPLE 11(23)

(Z)-2-(7-fluoro-3,3-dimethyl-4-oxa-3,4-dihydro-(2H)-isoquinolin-1-ylidene)-1-(4-cyanophenyl)ethan-1-one TLC: Rf0.24 (ethyl acetate:hexane=1:5); NMR (CDCl$_3$): δ 11.66 (br, 1H), 8.01 (d, J=8.5 Hz, 2H), 7.75 (d, J=8.5 Hz, 2H), 7.40 (dd, J=9.0, 3.0 Hz, 1H), 7.17 (ddd, J=9.0, 8.0, 3.0 Hz, 1H), 6.95 (dd, J=9.0, 4.5 Hz, 1H), 6.18 (s, 1H), 1.68 (s, 6H).

EXAMPLE 11(24)

(Z)-2-(3,3-dimethyl-4-oxa-3,4-dihydro-(2H)-isoquinolin-1-ylidene)-1-(2-methoxyphenyl)ethan-1-one TLC: Rf0.29 (hexane:ethyl acetate=3:1); NMR (CDCl$_3$): δ 11.49 (br, 1H), 7.68-7.63 (m, 2H), 7.42-7.35 (m, 2H), 7.05-6.93 (m, 4H), 6.30 (s, 1H), 3.92 (s, 3H), 1.66 (s, 6H).

EXAMPLE 11(25)

(Z)-2-(3,3-dimethyl-4-oxa-3,4-dihydro-(2H)-isoquinolin-1-ylidene)-1-(4-cyanophenyl)ethan-1-one TLC: Rf0.36 (hexane:ethyl acetate=3:1); NMR (CDCl$_3$): δ 11.75 (br, 1H), 8.03-7.99 (m, 2H), 7.75-7.71 (m, 3H), 7.46 (dt, J=1.5, 8.0 Hz, 1H), 7.09 (t, J=8.0 Hz, 1H), 6.98 (d, J=8.0 Hz, 1H), 6.27 (s, 1H), 1.69 (s, 6H).

EXAMPLE 11(26)

(Z)-2-(3,3-dimethyl-4-oxa-3,4-dihydro-(2H)-isoquinolin-1-ylidene)-1-cycloheptylethan-1-one TLC: Rf0.59 (hexane:ethyl acetate=3:1); NMR (CDCl$_3$): δ 11.08 (br, 1H), 7.61 (dd, J=8.0, 1.5 Hz, 1H), 7.37 (ddd, J=8.0, 7.5, 1.5 Hz, 1H), 7.01 (ddd, J=8.0, 7.5, 1.0 Hz, 1H), 6.91 (dd, J=8.0, 1.0 Hz, 1H), 5.61 (s, 1H), 2.53-2.43 (m, 1H), 1.94-1.85 (m, 2H), 1.82-1.45 (m, 16H).

EXAMPLE 11(27)

(Z)-2-(3,3-dimethyl-4-oxa-3,4-dihydro-(2H)-isoquinolin-1-ylidene)-1-cyclohexylethan-1-one TLC: Rf0.56 (hexane:ethyl acetate=3:1); NMR (CDCl$_3$): δ 11.16 (br, 1H), 7.61 (dd, J=8.0, 1.5 Hz, 1H), 7.37 (ddd, J=8.0, 7.5, 1.5 Hz, 1H), 7.01 (ddd, J=8.0, 7.5, 1.0 Hz, 1H), 6.91 (dd, J=8.0, 1.0 Hz, 1H), 5.64 (s, 1H), 2.31 (tt, J=11.5, 3.5 Hz, 1H), 1.89-1.79 (m, 4H), 1.71-1.67 (m, 1H), 1.61 (s, 6H), 1.49-1.19 (m, 5H).

EXAMPLE 11(28)

(Z)-2-(3,3,7-trimethyl-4-oxa-3,4-dihydro-(2H)-isoquinolin-1-ylidene)-1-phenylethan-1-one TLC: Rf0.35 (ethyl acetate:hexane=1:5); NMR (CDCl$_3$): δ 11.65 (br, 1H), 7.95 (m, 2H), 7.51 (d, J=1.5 Hz, 1H), 7.50-7.40 (m, 3H), 7.23 (m, 1H), 6.86 (d, J=9.0 Hz, 1H), 6.31 (s, 1H), 2.37 (s, 3H), 1.66 (s, 6H).

EXAMPLE 11(29)

(Z)-2-(7-methoxy-3,3-dimethyl-4-oxa-3,4-dihydro-(2H)-isoquinolin-1-ylidene)-1-phenylethan-1-one TLC: Rf0.31 (ethyl acetate:hexane=1:5); NMR (CDCl$_3$): δ 11.62 (br, 1H), 7.94 (m, 2H), 7.50-7.40 (m, 3H), 7.20 (d, J=3.0 Hz, 1H), 7.01 (dd, J=9.0, 3.0 Hz, 1H), 6.90 (d, J=9.0 Hz, 1H), 6.26 (s, 1H), 3.86 (s, 3H), 1.65 (s, 6H).

EXAMPLE 11(30)

(Z)-2-(7-chloro-3,3-dimethyl-4-oxa-3,4-dihydro-(2H)-isoquinolin-1-ylidene)-1-phenylethan-1-one TLC: Rf0.31 (ethyl acetate:hexane=1:5); NMR (CDCl$_3$): δ 11.56 (br, 1H), 7.95 (m, 2H), 7.70 (d, J=2.5 Hz, 1H), 7.50-7.40 (m, 3H), 7.36 (dd, J=8.5, 2.5 Hz, 1H), 6.91 (d, J=8.5 Hz, 1H), 6.28 (s, 1H), 1.66 (s, 6H).

EXAMPLE 11(31)

(Z)-2-(7-fluoro-3,3-dimethyl-4-oxa-3,4-dihydro-(2H)-isoquinolin-1-ylidene)-1-phenylethan-1-one TLC: Rf0.31 (ethyl acetate:hexane=1:5); NMR (CDCl$_3$): δ 11.55 (br, 1H), 7.93 (m, 2H), 7.50-7.40 (m, 3H), 7.41 (dd, J=9.0, 3.0 Hz, 1H), 7.13 (ddd, J=9.0, 8.0, 3.0 Hz, 1H), 6.92 (dd, J=9.0, 4.5 Hz, 1H), 6.25 (s, 1H), 1.66 (s, 6H).

EXAMPLE 11(32)

(Z)-2-(7-methoxy-3,3-dimethyl-3,4-dihydro-(2H)-isoquinolin-1-ylidene)-1-cyclohexylethan-1-one TLC: Rf0.28 (ethyl acetate:hexane=1:5); NMR (CDCl$_3$): δ 11.31 (br, 1H), 7.22 (d, J=2.5 Hz, 1H), 7.08 (d, J=8.5 Hz, 1H), 6.94 (dd, J=8.5, 2.5 Hz, 1H), 5.58 (s, 1H), 3.86 (s, 3H), 2.77 (s, 2H), 2.30 (m, 1H), 1.95-1.20 (m, 10H), 1.28 (s, 6H).

EXAMPLE 11(33)

(Z)-2-(7-methoxy-3,3-dimethyl-3,4-dihydro-(2H)-isoquinolin-1-ylidene)-1-cycloheptylethan-1-one TLC: Rf0.29 (ethyl acetate:hexane=1:5); NMR (CDCl$_3$): δ 11.23 (br, 1H), 7.21 (d, J=2.5 Hz, 1H), 7.08 (d, J=8.5 Hz, 1H), 6.94 (dd, J=8.5, 2.5 Hz, 1H), 5.55 (s, 1H), 3.86 (s, 3H), 2.77 (s, 2H), 2.46 (m, 1H), 2.00-1.40 (m, 12H), 1.28 (s, 6H).

EXAMPLE 11(34)

(Z)-2-(7-methoxy-3,3-dimethyl-3,4-dihydro-(2H)-isoquinolin-1-ylidene)-1-(2-methoxyphenyl)ethan-1-one TLC: Rf0.23 (ethyl acetate:hexane=1:3); NMR (CDCl$_3$): δ 11.67 (br, 1H), 7.67 (dd, J=7.5, 2.0 Hz, 1H), 7.36 (ddd, J=8.0, 7.5, 2.0 Hz, 1H), 7.26 (d, J=2.5 Hz, 1H), 7.11 (d, J=8.0 Hz, 1H), 7.05-6.90 (m, 3H), 6.22 (s, 1H), 3.91 (s, 3H), 3.84 (s, 3H), 2.82 (s, 2H), 1.35 (s, 6H).

EXAMPLE 11(35)

(Z)-2-(7-methoxy-3,3-dimethyl-3,4-dihydro-(2H)-isoquinolin-1-ylidene)-1-(4-cyanophenyl)ethan-1-one TLC: Rf0.29 (ethyl acetate:hexane=1:3); NMR (CDCl$_3$): δ 11.95 (br, 1H), 8.00 (d, J=8.5 Hz, 2H), 7.72 (d, J=8.5 Hz, 2H), 7.31 (d, J=2.5 Hz, 1H), 7.16 (d, J=8.5 Hz, 1H), 7.02 (dd, J=8.5, 2.5 Hz, 1H), 6.21 (s, 1H), 3.88 (s, 3H), 2.85 (s, 2H), 1.37 (s, 6H).

EXAMPLE 11(36)

(Z)-2-(7-t-butyl-3,3-dimethyl-3,4-dihydro-(2H)-isoquinolin-1-ylidene)-1-cyclohexylethan-1-one TLC: Rf0.34 (ethyl acetate:hexane=1:5); NMR (CDCl$_3$): δ 11.41 (br, 1H), 7.69 (d, J=2.0 Hz, 1H), 7.42 (dd, J=8.0, 2.0 Hz, 1H), 7.10 (d, J=8.0 Hz, 1H), 5.61 (s, 1H), 2.79 (s, 2H), 2.33 (m, 1H), 1.95-1.20 (m, 10H), 1.36 (s, 9H), 1.29 (s, 6H).

EXAMPLE 11(37)

(Z)-2-(7-t-butyl-3,3-dimethyl-3,4-dihydro-(2H)-isoquinolin-1-ylidene)-1-cycloheptylethan-1-one TLC: Rf0.34 (ethyl acetate:hexane=1:5); NMR (CDCl$_3$): δ 11.33 (br, 1H), 7.69 (d, J=2.0 Hz, 1H), 7.42 (dd, J=8.0, 2.0 Hz, 1H), 7.09 (d, J=8.0 Hz, 1H), 5.58 (s, 1H), 2.79 (s, 2H), 2.49 (m, 1H), 2.00-1.40 (m, 12H), 1.36 (s, 9H), 1.28 (s, 6H).

EXAMPLE 11(38)

(Z)-2-(7-t-butyl-3,3-dimethyl-3,4-dihydro-(2H)-isoquinolin-1-ylidene)-1-(2-methoxyphenyl)ethan-1-one TLC: Rf0.33 (ethyl acetate:hexane=1:3); NMR (CDCl$_3$): δ 11.71 (br, 1H), 7.77 (d, J=2.0 Hz, 1H), 7.72 (dd, J=7.5, 2.0 Hz, 1H), 7.44 (dd, J=8.0, 2.0 Hz, 1H), 7.37 (ddd, J=8.0, 7.5, 2.0 Hz, 1H), 7.12 (d, J=8.0 Hz, 1H), 7.02 (ddd, J=7.5, 7.5, 1.0 Hz, 1H), 6.98 (dd, J=8.0, 1.0 Hz, 1H), 6.34 (s, 1H), 3.93 (s, 3H), 2.85 (s, 2H), 1.35 (s, 6H), 1.34 (s, 9H).

EXAMPLE 11(39)

(Z)-2-(7-t-butyl-3,3-dimethyl-3,4-dihydro-(2H)-isoquinolin-1-ylidene)-1-(4-cyanophenyl)ethan-1-one TLC: Rf0.40 (ethyl acetate:hexane=1:3); NMR (CDCl$_3$): δ 12.03 (br, 1H), 8.01 (d, J=8.5 Hz, 2H), 7.78 (d, J=2.0 Hz, 1H), 7.74 (d, J=8.5 Hz, 2H), 7.50 (d, J=8.0, 2.0 Hz, 1H), 7.17 (d, J=8.0 Hz, 1H), 6.25 (s, 1H), 2.88 (s, 2H), 1.38 (s, 9H), 1.38 (s, 6H).

EXAMPLE 11(40)

(Z)-2-(7-fluoro-3,3-dimethyl-3,4-dihydro-(2H)-isoquinolin-1-ylidene)-1-(4-cyanophenyl)ethan-1-one TLC: Rf0.33 (hexane:ethyl acetate=2:1); NMR (CDCl$_3$): δ 11.89 (br, 1H), 8.03-7.99 (m, 2H), 7.76-7.72 (m, 2H), 7.50 (dd, J=9.5, 2.5 Hz, 1H), 7.22-7.14 (m, 2H), 6.19 (s, 1H), 2.89 (s, 2H), 1.38 (s, 6H).

EXAMPLE 11(41)

(Z)-2-(7-chloro-3,3-dimethyl-3,4-dihydro-(2H)-isoquinolin-1-ylidene)-1-(4-cyanophenyl)ethan-1-one TLC: Rf0.33 (hexane:ethyl acetate=2:1); NMR (CDCl$_3$): δ 11.89 (br, 1H), 8.04-8.01 (m, 2H), 7.77-7.73 (m, 3H), 7.43 (dd, J=8.0, 2.0 Hz, 1H), 7.19 (d, J=8.0 Hz, 1H), 6.21 (s, 1H), 2.89 (s, 2H), 1.38 (s, 6H).

EXAMPLE 11(42)

(Z)-2-(7-fluoro-3,3-dimethyl-3,4-dihydro-(2H)-isoquinolin-1-ylidene)-1-(2-methoxyphenyl)ethan-1-one TLC: Rf0.40 (hexane:ethyl acetate=2:1); NMR (CDCl$_3$): δ 11.61 (br, 1H), 7.68 (dd, J=8.0, 2.0 Hz, 1H), 7.45-7.34 (m, 2H), 7.19-7.07 (m, 2H), 7.04-6.96 (m, 2H), 6.22 (s, 1H), 3.92 (s, 3H), 2.85 (s, 2H), 1.35 (s, 6H).

EXAMPLE 11(43)

(Z)-2-(7-chloro-3,3-dimethyl-3,4-dihydro-(2H)-isoquinolin-1-ylidene)-1-(2-methoxyphenyl)ethan-1-one TLC: Rf0.40 (hexane:ethyl acetate=2:1); NMR (CDCl$_3$): δ 11.59 (br, 1H), 7.70 (d, J=2.0 Hz, 1H), 7.66 (dd, J=8.0, 2.0 Hz, 1H), 7.40-7.34 (m, 2H), 7.14 (d, J=8.0 Hz, 1H), 7.04-6.96 (m, 2H), 6.22 (s, 1H), 3.92 (s, 3H), 2.85 (s, 2H), 1.35 (s, 6H).

EXAMPLE 11(44)

(Z)-2-(7-fluoro-3,3-dimethyl-3,4-dihydro-(2H)-isoquinolin-1-ylidene)-1-cyclohexylethan-1-one TLC: Rf0.52 (hexane:ethyl acetate=2:1); NMR (CDCl$_3$): δ 11.24 (br, 1H), 7.39 (dd, J=10.0, 2.5 Hz, 1H), 7.16-7.05 (m, 2H), 5.56 (s, 1H), 2.80 (s, 2H), 2.36-2.25 (m, 1H), 1.90-1.79 (m, 4H), 1.71-1.68 (m, 1H), 1.50-1.20 (m, 1H).

EXAMPLE 11(45)

(Z)-2-(7-fluoro-3,3-dimethyl-3,4-dihydro-(2H)-iso-quinolin-1-ylidene)-1-cycloheptylethan-1-one TLC: Rf0.55 (hexane:ethyl acetate=2:1); NMR (CDCl$_3$):
δ 11.16 (br, 1H), 7.39 (dd, J=9.5, 2.5 Hz, 1H), 7.16-7.05 (m, 2H), 5.52 (s, 1H), 2.80 (s, 2H), 2.50-2.42 (m, 1H), 1.95-1.88 (m, 2H), 1.82-1.45 (m, 10H), 1.29 (s, 6H).

EXAMPLE 11(46)

(Z)-2-(7-chloro-3,3-dimethyl-3,4-dihydro-(2H)-iso-quinolin-1-ylidene)-1-cyclohexylethan-1-one TLC: Rf0.52 (hexane:ethyl acetate=2:1); NMR (CDCl$_3$):
δ 11.23 (br, 1H), 7.67 (d, J=2.0 Hz, 1H), 7.35 (dd, J=8.0, 2.0 Hz, 1H), 7.12 (d, J=8.0 Hz, 1H), 5.58 (s, 10H), 2.80 (s, 2H), 2.31 (tt, J=11.5, 3.0 Hz, 1H), 1.90-1.80 (m, 4H), 1.71-1.68 (m, 1H), 1.51-1.20 (m, 1H).

EXAMPLE 11(47)

(Z)-2-(7-chloro-3,3-dimethyl-3,4-dihydro-(2H)-iso-quinolin-1-ylidene)-1-cycloheptylethan-1-one TLC: Rf0.55 (hexane:ethyl acetate=2:1); NMR (CDCl$_3$):
δ 11.15 (br, 1H), 7.67 (d, J=2.0 Hz, 1H), 7.35 (dd, J=8.0, 2.0 Hz, 1H), 7.11 (d, J=8.0 Hz, 1H), 5.54 (s, 1H), 2.80 (s, 2H), 2.48 (tt, J=9.5, 4.0 Hz, 1H), 1.95-1.88 (m, 2H), 1.82-1.47 (m, 10H), 1.28 (s, 6H).

EXAMPLE 11(48)

(Z)-2-(3,3,7-trimethyl-3,4-dihydro-(2H)-isoquinolin-1-ylidene)-1-cyclohexylethan-1-one TLC: Rf0.30 (ethyl acetate:hexane=1:5); NMR (CDCl$_3$):
δ 11.32 (br, 1H), 7.51 (s, 1H), 7.19 (m, 1H), 7.05 (d, J=8.0 Hz, 1H), 5.62 (s, 1H), 2.79 (s, 2H), 2.38 (s, 3H), 2.30 (m, 1H), 1.95-1.20 (m, 10H), 1.28 (s, 6H).

EXAMPLE 11(49)

(Z)-2-(3,3,7-trimethyl-3,4-dihydro-(2H)-isoquinolin-1-ylidene)-1-cycloheptylethan-1-one TLC: Rf0.34 (ethyl acetate:hexane=1:5); NMR (CDCl$_3$):
δ 11.23 (br, 1H), 7.50 (s, 1H), 7.18 (m, 1H), 7.05 (d, J=7.5 Hz, 1H), 5.59 (s, 1H), 2.78 (s, 2H), 2.46 (m, 1H), 2.38 (s, 3H), 2.00-1.40 (m, 12H), 1.28 (s, 6H).

EXAMPLE 11(50)

(Z)-2-(3,3,7-trimethyl-3,4-dihydro-(2H)-isoquinolin-1-ylidene)-1-(2-methoxyphenyl)ethan-1-one TLC: Rf0.34 (ethyl acetate:hexane=1:3); NMR (CDCl$_3$):
δ 11.67 (br, 1H), 7.65 (dd, J=7.5, 2.0 Hz, 1H), 7.54 (s, 1H), 7.35 (ddd, J=8.0, 7.5, 2.0 Hz, 1H), 7.20 (m, 1H), 7.07 (d, J=7.5 Hz, 1H), 7.00 (ddd, J=8.0, 8.0, 1.0 Hz, 1H), 6.96 (dd, J=8.0, 1.0 Hz, 1H), 6.22 (s, 1H), 3.91 (s, 3H), 2.84 (s, 2H), 2.37 (s, 3H), 1.34 (s, 6H).

EXAMPLE 11(51)

(Z)-2-(3,3,7-trimethyl-3,4-dihydro-(2H)-isoquinolin-1-ylidene)-1-(4-cyanophenyl)ethan-1-one TLC: Rf0.40 (ethyl acetate:hexane=1:3); NMR (CDCl$_3$):
δ 11.96 (br, 1H), 8.03 (d, J=8.5 Hz, 2H), 7.73 (d, J=8.5 Hz, 2H), 7.60 (s, 1H), 7.27 (m, 1H), 7.12 (d, J=7.5 Hz, 1H), 6.26 (s, 1H), 2.87 (s, 2H), 2.43 (s, 3H), 1.37 (s, 6H).

EXAMPLE 11(52)

(Z)-2-(3,3-dimethyl-3,4-dihydro-(2H)-isoquinolin-1-ylidene)-1-(2-nitrophenyl)ethan-1-one TLC: Rf0.41 (hexane:ethyl acetate=2:1); NMR (CDCl$_3$):
δ 11.40 (br, 1H), 7.85 (d, J=7.5 Hz, 1H), 7.69 (d, J=7.5 Hz, 1H), 7.64-7.57 (m, 2H), 7.52-7.41 (m, 2H), 7.33-7.27 (m, 1H), 7.21 (d, J=7.5 Hz, 1H), 5.86 (s, 1H), 2.92 (s, 2H), 1.37 (s, 6H).

EXAMPLE 11(53)

(Z)-2-(3,3-dimethyl-3,4-dihydro-(2H)-isoquinolin-1-ylidene)-1-(3-nitrophenyl)ethan-1-one TLC: Rf0.53 (hexane:ethyl acetate=2:1); NMR (CDCl$_3$):
δ 11.94 (br, 1H), 8.77 (dd, J=2.0, 2.0 Hz, 1H), 8.32-8.27 (m, 2H), 7.86 (dd, J=7.5, 1.0 Hz, 1H), 7.62 (dd, J=8.0, 8.0 Hz, 1H), 7.48 (ddd, J=7.5, 7.5, 1.0 Hz, 1H), 7.39 (ddd, J=7.5, 7.5, 1.0 Hz, 1H), 7.27-7.23 (m, 1H), 6.32 (s, 1H), 2.94 (s, 2H), 1.39 (s, 6H).

EXAMPLE 11(54)

(Z)-2-(3,3-dimethyl-3,4-dihydro-(2H)-isoquinolin-1-ylidene)-1-(4-nitrophenyl)ethan-1-one TLC: Rf0.56 (hexane:ethyl acetate=2:1); NMR (CDCl$_3$):
δ 12.00 (br, 1H), 8.30-8.26 (m, 2H), 8.09-8.05 (m, 2H), 7.83 (dd, J=7.5, 1.0 Hz, 1H), 7.48 (ddd, J=7.5, 7.5, 1.0 Hz, 1H), 7.37 (ddd, J=7.5, 7.5, 1.0 Hz, 1H), 7.27-7.23 (m, 1H), 6.30 (s, 1H), 2.93 (s, 2H), 1.39 (s, 6H).

EXAMPLE 11(55)

(Z)-2-(3,3-dimethyl-3,4-dihydro-(2H)-isoquinolin-1-ylidene)-1-(2,5-dimethoxyphenyl)ethan-1-one TLC: Rf0.36 (hexane:ethyl acetate=2:1); NMR (CDCl$_3$):
δ 11.69 (br, 1H), 7.75 (d, J=7.5 Hz, 1H), 7.41 (t, J=7.5 Hz, 1H), 7.33-7.25 (m, 2H), 7.20 (d, J=7.5 Hz, 1H), 6.92-6.91 (m, 2H), 6.37 (s, 1H), 3.88 (s, 3H), 3.81 (s, 3H), 2.90 (s, 2H), 1.36 (s, 6H).

EXAMPLE 11(56)

(Z)-2-(3,3-dimethyl-3,4-dihydro-(2H)-isoquinolin-1-ylidene)-1-(2,4-dimethoxyphenyl)ethan-1-one TLC: Rf0.31 (hexane:ethyl acetate=2:1); NMR (CDCl$_3$):
δ 11.67 (br, 1H), 7.78-7.75 (m, 2H), 7.39 (t, J=7.5 Hz, 1H), 7.33-7.25 (m, 1H), 7.19 (d, J=7.5 Hz, 1H), 6.55 (dd, J=8.5, 2.5 Hz, 1H), 6.50 (d, J=2.5 Hz, 1H), 6.40 (s, 1H), 3.91 (s, 3H), 3.85 (s, 3H), 2.88 (s, 2H), 1.34 (s, 6H).

EXAMPLE 11(57)

(Z)-2-(7-methoxy-3,3-dimethyl-3,4-dihydro-(2H)-isoquinolin-1-ylidene)-1-(naphthalen-1-yl)ethan-1-one TLC: Rf0.22 (ethyl acetate:hexane=1:5); NMR (CDCl$_3$): δ 11.78 (br, 1H), 8.48 (m, 1H), 7.90-7.80 (m, 2H), 7.69 (dd, J=7.0, 1.0 Hz, 1H), 7.55-7.45 (m, 3H), 7.22 (d, J=2.5 Hz, 1H), 7.14 (d, J=8.5 Hz, 1H), 6.98 (dd, J=8.0, 2.5 Hz, 1H), 6.04 (s, 1H), 3.80 (s, 3H), 2.88 (s, 2H), 1.40 (s, 6H).

EXAMPLE 11(58)

(Z)-2-(3,3-dimethyl-3,4-dihydro-(2H)-isoquinolin-1-ylidene)-1-(thiazol-2-yl)ethan-1-one TLC: Rf0.40 (hexane:ethyl acetate=2:1); NMR (CDCl$_3$): δ 11.63 (br, 1H), 7.97-7.92 (m, 2H), 7.52 (d, J=3.0 Hz, 1H), 7.45 (dt, J=1.0, 7.5 Hz, 1H), 7.35 (t, J=7.5 Hz, 1H), 7.21 (d, J=7.5 Hz, 1H), 6.80 (s, 1H), 2.92 (s, 2H), 1.38 (s, 6H).

EXAMPLE 11(59)

(Z)-2-(3,3-dimethyl-3,4-dihydro-(2H)-isoquinolin-1-ylidene)-1-(pyrrol-2-yl)ethan-1-one TLC: Rf0.19 (hexane:ethyl acetate=3:1); NMR (CDCl$_3$): δ 11.14 (br, 1H), 9.42 (br, 1H), 7.80 (dd, J=7.5, 1.0 Hz, 1H), 7.41 (dt, J=1.0, 7.5 Hz, 1H), 7.33 (dt, J=1.0, 7.5 Hz, 1H), 7.20 (dd, J=7.5, 1.0 Hz, 1H), 6.94 (m, 1H), 6.80 (m, 1H), 6.27 (m, 1H), 6.14 (s, 1H), 2.88 (s, 2H), 1.34 (s, 6H).

EXAMPLE 11(60)

(Z)-2-(3,3-dimethyl-3,4-dihydro-(2H)-isoquinolin-1-ylidene)-1-(antracen-9-yl)ethan 1-one TLC: Rf0.28 (hexane:ethyl acetate=3:1); NMR (CDCl$_3$): δ 11.93 (br, 1H), 8.44 (s, 1H), 8.26-8.22 (m, 2H), 8.03-7.98 (m, 2H), 7.59 (d, J=7.5 Hz, 1H), 7.48-7.37 (m, 5H), 7.26-7.17 (m, 2H), 6.03 (s, 1H), 3.01 (s, 2H), 1.49 (s, 6H).

EXAMPLE 11(61)

(Z)-2-(3,3-dimethyl-3,4-dihydro-(2H)-isoquinolin-1-ylidene)-1-(pyrazin-2-yl)ethan-1-one TLC: Rf0.13 (hexane:ethyl acetate=3:1); NMR (CDCl$_3$): δ 11.96 (br, 1H), 9.35 (d, J=1.5 Hz, 1H), 8.63 (d, J=2.5 Hz, 1H), 8.59 (dd, J=2.5, 1.5 Hz, 1H), 7.96 (d, J=7.5 Hz, 1H), 7.46 (t, J=7.5 Hz, 1H), 7.36 (t, J=7.5 Hz, 1H), 7.22 (d, J=7.5 Hz, 1H), 7.02 (s, 1H), 2.93 (s, 2H), 1.40 (s, 6H).

EXAMPLE 11(62)

(Z)-2-(3,3-dimethyl-4-oxa-3,4-dihydro-(2H)-isoquinolin-1-ylidene)-1-(adamantan-1-yl)ethan-1-one TLC: Rf0.60 (hexane:ethyl acetate=3:1); NMR (CDCl$_3$): δ 11.34 (br, 1H), 7.64 (dd, J=8.0, 1.5 Hz, 1H), 7.37 (ddd, J=8.0, 7.5, 1.5 Hz, 1H), 7.02 (ddd, J=8.0, 7.5, 1.0 Hz, 1H), 6.91 (dd, J=8.0, 1.0 Hz, 1H), 5.80 (s, 1H), 2.06 (br, 3H), 1.90-1.89 (m, 6H), 1.74 (br, 6H), 1.60 (s, 6H).

EXAMPLE 11(63)

(Z)-2-(3,3,7-trimethyl-3,4-dihydro-(2H)-isoquinolin-1-ylidene)-1-(adamantan-1-yl)ethan-1-one TLC: Rf0.61 (hexane:ethyl acetate=3:1); NMR (CDCl$_3$): δ 11.51 (br, 1H), 7.51 (s, 1H), 7.20 (d, J=7.5 Hz, 1H), 7.05 (d, J=7.5 Hz, 1H), 5.76 (s, 1H), 2.79 (s, 2H), 2.40 (s, 3H), 2.06 (br, 3H), 1.93 (br, 6H), 1.75 (br, 6H), 1.28 (s, 6H).

EXAMPLE 11(64)

(Z)-2-(7-methoxy-3,3-dimethyl-3,4-dihydro-(2H)-isoquinolin-1-ylidene)-1-(adamantan-1-yl)ethan-1-one TLC: Rf0.50 (hexane:ethyl acetate=3:1); NMR (CDCl$_3$): δ 11.47 (br, 1H), 7.25 (d, J=2.5 Hz, 1H), 7.09 (d, J=8.0 Hz, 1H), 6.94 (dd, J=8.0, 2.5 Hz, 1H), 5.73 (s, 1H), 3.87 (s, 3H), 2.77 (s, 2H), 2.05 (br, 3H), 1.91 (br, 6H), 1.74 (br, 6H), 1.28 (s, 6H).

EXAMPLE 11(65)

(Z)-2-(3,3-dimethyl-3,4-dihydro-(2H)-isoquinolin-1-ylidene)-1-(thiophen-3-yl)ethan-1-one TLC: Rf0.47 (hexane:ethyl acetate=2:1); NMR (CDCl$_3$): δ 11.67 (br, 1H), 7.93 (dd, J=3.0, 1.0 Hz, 1H), 7.80 (d, J=7.5 Hz, 1H), 7.56 (dd, J=5.0, 1.0 Hz, 1H), 7.43 (t, J=7.5 Hz, 1H), 7.37-7.29 (m, 2H), 7.21 (d, J=7.5 Hz, 1H), 6.18 (s, 1H), 2.89 (s, 2H), 1.35 (s, 6H).

EXAMPLE 11(66)

(Z)-2-(3,3-dimethyl-3,4-dihydro-(2H)-isoquinolin-1-ylidene)-1-(5-methylfuran-2-yl)ethan-1-one TLC: Rf0.39 (hexane:ethyl acetate=2:1); NMR (CDCl$_3$): δ 11.54 (br, 1H), 7.84 (dd, J=7.5, 1.0 Hz, 1H), 7.42 (dt, J=1.0, 7.5 Hz, 1H), 7.34 (dt, J=1.0, 7.5 Hz, 1H), 7.20 (dd, J=7.5, 1.0 Hz, 1H), 6.95 (d, J=3.5 Hz, 1H), 6.23 (s, 1H), 6.10 (d, J=3.5 Hz, 1H), 2.88 (s, 2H), 2.39 (s, 3H), 1.34 (s, 6H).

EXAMPLE 11(67)

(Z)-2-(7-fluoro-3,3-dimethyl-4-oxa-3,4-dihydro-(2H)-isoquinolin-1-ylidene)-1-(adamantan-1-yl)ethan-1-one TLC: Rf0.61 (hexane ethyl acetate=3:1); NMR (CDCl$_3$): δ 11.24 (br, 1H), 7.32 (dd, J=9.5, 3.0 Hz, 1H), 7.09 (ddd, J=9.5, 9.0, 3.0 Hz, 1H), 6.88 (dd, J=9.0, 4.5 Hz, 1H), 5.72 (s, 1H), 2.07 (br, 3H), 1.89 (br, 6H), 1.75 (br, 6H), 1.59 (s, 6H).

EXAMPLE 11(68)

(Z)-2-(7-chloro-3,3-dimethyl-4-oxa-3,4-dihydro-(2H)-isoquinolin-1-ylidene)-1-(adamantan-1-yl)ethan-1-one TLC: Rf0.61 (hexane:ethyl acetate=3:1); NMR (CDCl$_3$): δ 11.25 (br, 1H), 7.58 (d, J=2.5 Hz, 1H), 7.32 (dd, J=9.0, 2.5 Hz, 1H), 6.87 (d, J=9.0 Hz, 1H), 5.74 (s, 1H), 2.07 (br, 3H), 1.89 (br, 6H), 1.75 (br, 6H), 1.59 (s, 6H).

EXAMPLE 11(69)

(Z)-2-(7-methoxy-3,3-dimethyl-4-oxa-3,4-dihydro-(2H)-isoquinolin-1-ylidene)-1-(adamantan-1-yl)ethan-1-one TLC: Rf0.56 (hexane:ethyl acetate=3:1); NMR (CDCl$_3$): δ 11.32 (br, 1H), 7.11 (d, J=3.0 Hz, 1H), 6.97 (dd, J=9.0, 3.0 Hz, 1H), 6.85 (d, J=9.0 Hz, 1H), 5.73 (s, 1H), 3.84 (s, 3H), 2.06 (br, 3H), 1.89 (br, 6H), 1.74 (br, 6H), 1.58 (s, 6H).

EXAMPLE 11(70)

(Z)-2-(7-bromo-3,3-dimethyl-3,4-dihydro-(2H)-isoquinolin-1-ylidene)-1-(naphthalen-1-yl)ethan-1-one TLC: Rf0.20 (ethyl acetate:hexane=1:5); NMR (CDCl$_3$): δ 11.70 (br, 1H), 8.46 (m, 1H), 7.90-7.85 (m, 2H), 7.83 (d, J=2.0 Hz, 1H), 7.70 (dd, J=7.0, 1.5 Hz, 1H), 7.55-7.45 (m, 4H), 7.11 (d, J=8.0 Hz, 1H), 6.03 (s, 1H), 2.89 (s, 2H), 1.41 (s, 6H).

EXAMPLE 11(71)

(Z)-2-(3,3,7-trimethyl-4-oxa-3,4-dihydro-(2H)-isoquinolin-1-ylidene)-1-(adamantan-1-yl)ethan-1-one TLC: Rf0.61 (hexane:ethyl acetate=3:1); NMR (CDCl$_3$): δ 11.35 (br, 1H), 7.40 (d, J=2.0 Hz, 1H), 7.18 (dd, J=8.5, 2.0 Hz, 1H), 6.81 (d, J=8.5 Hz, 1H), 5.77 (s, 1H), 2.35 (s, 3H), 2.07 (br, 3H), 1.90 (br, 6H), 1.75 (br, 6H), 1.58 (s, 6H).

EXAMPLE 11(72)

(Z)-2-(6-chloro-3,3-dimethyl-3,4-dihydro-(2H)-isoquinolin-1-ylidene)-1-(4-cyanophenyl)ethan-1-one TLC: Rf0.49 (hexane:ethyl acetate=2:1); NMR (CDCl$_3$): δ 11.90 (br, 1H), 8.00 (d, J=8.5 Hz, 2H), 7.76-7.71 (m, 3H), 7.34 (dd, J=8.5, 2.5 Hz, 1H), 7.24 (d, J=2.5 Hz, 1H), 6.22 (s, 1H), 2.90 (s, 2H), 1.38 (s, 6H).

EXAMPLE 11(73)

(Z)-2-(8-chloro-3,3-dimethyl-3,4-dihydro-(2H)-isoquinolin-1-ylidene)-1-(4-cyanophenyl)ethan-1-one TLC: Rf0.34 (hexane:ethyl acetate=2:1); NMR (CDCl$_3$): δ 12.18 (br, 1H), 7.99 (d, J=8.5 Hz, 2H), 7.72 (d, J=8.5 Hz, 2H), 7.45 (d, J=7.5 Hz, 1H), 7.33 (t, J=7.5 Hz, 1H), 7.15 (d, J=7.5 Hz, 1H), 6.81 (s, 1H), 2.87 (s, 2H), 1.34 (s, 6H).

EXAMPLE 11(74)

(Z)-2-(8-chloro-3,3-dimethyl-3,4-dihydro-(2H)-isoquinolin-1-ylidene)-1-cyclohexylethan-1-one TLC: Rf0.49 (hexane:ethyl acetate=3:1); NMR (CDCl$_3$): δ 11.49 (br, 1H), 7.37 (dd, J=8.0, 1.0 Hz, 1H), 7.24 (t, J=8.0 Hz, 1H), 7.08 (dd, J=8.0, 1.0 Hz, 1H), 6.11 (s, 1H), 2.79 (s, 2H), 2.27 (tt, J=11.5, 3.5 Hz, 1H), 1.91-1.87 (m, 2H), 1.82-1.78 (m, 2H), 1.67 (m, 1H), 1.53-1.25 (m, 1H).

EXAMPLE 11(75)

(Z)-2-(3,3-dimethyl-3,4-dihydro-(2H)-isoquinolin-1-ylidene)-1-(5-methylthiophen-2-yl)ethan-1-one TLC: Rf0.41 (hexane:ethyl acetate=3:1); NMR (CDCl$_3$): δ 11.40 (br, 1H), 7.79 (dd, J=7.5, 1.5 Hz, 1H), 7.46-7.39 (m, 2H), 7.33 (dt, J=1.5, 7.5 Hz, 1H), 7.20 (dd, J=7.5, 1.5 Hz, 1H), 6.76 (dq, J=4.0, 1.0 Hz, 1H), 6.15 (s, 1H), 2.88 (s, 2H), 2.53 (d, J=1.0 Hz, 3H), 1.33 (s, 6H).

EXAMPLE 11(76)

(Z)-2-(3,3-dimethyl-3,4-dihydro-(2H)-isoquinolin-1-ylidene)-1-(2,5-dimethylfuran-3-yl)ethan-1-one TLC: Rf0.45 (hexane:ethyl acetate=3:1); NMR (CDCl$_3$): δ 11.50 (br, 1H), 7.74 (dd, J=7.5, 1.5 Hz, 1H), 7.40 (dt, J=1.5, 7.5 Hz, 1H), 7.31 (dt, J=1.5, 7.5 Hz, 1H), 7.19 (dd, J=7.5, 1.5 Hz, 1H), 6.23 (d, J=1.0 Hz, 1H), 5.92 (s, 1H), 2.87 (s, 2H), 2.61 (s, 3H), 2.26 (d, J=1.0 Hz, 3H), 1.33 (s, 6H).

EXAMPLE 11(77)

(Z)-2-(6-chloro-3,3-dimethyl-4-oxa-3,4-dihydro-(2H)-isoquinolin-1-ylidene)-1-(4-cyanophenyl)ethan-1-one TLC: Rf0.21 (ethyl acetate:hexane=1:5); NMR (CDCl$_3$): δ 11.69 (br, 1H), 7.99 (d, J=9.0 Hz, 2H), 7.74 (d, J=9.0 Hz, 2H), 7.65 (d, J=8.5 Hz, 1H), 7.07 (dd, J=8.5, 2.0 Hz, 1H), 7.01 (d, J=2.0 Hz, 1H), 6.22 (s, 1H), 1.68 (s, 6H).

EXAMPLE 11(78)

(Z)-2-(7-fluoro-3,3-dimethyl-3,4-dihydro-(2H)-isoquinolin-1-ylidene)-1-(adamantan-1-yl)ethan-1-one TLC: Rf0.53 (hexane:ethyl acetate=3:1); NMR (CDCl$_3$): δ 11.41 (br, 1H), 7.41 (dd, J=10.0, 2.5 Hz, 1H), 7.17-7.05 (m, 2H), 5.71 (s, 1H), 2.80 (s, 2H), 2.06 (br, 3H), 1.91 (br, 6H), 1.75 (br, 6H), 1.29 (s, 6H).

EXAMPLE 11(79)

(Z)-2-(7-chloro-3,3-dimethyl-3,4-dihydro-(2H)-isoquinolin-1-ylidene)-1-(adamantan-1-yl)ethan-1-one TLC: Rf0.53 (hexane:ethyl acetate=3:1); NMR (CDCl$_3$): δ 11.42 (br, 1H), 7.67 (d, J=2.0 Hz, 1H), 7.35 (dd, J=8.0, 2.0 Hz, 1H), 7.12 (d, J=8.0 Hz, 1H), 5.72 (s, 1H), 2.80 (s, 2H), 2.07 (br, 3H), 1.91 (br, 6H), 1.75 (br, 6H), 1.29 (s, 6H).

EXAMPLE 11(80)

(Z)-2-(6-chloro-3,3-dimethyl-3,4-dihydro-(2H)-isoquinolin-1-ylidene)-1-(adamantan-1-yl)ethan-1-one TLC: Rf0.57 (hexane:ethyl acetate=3:1); NMR (CDCl$_3$): δ 11.43 (br, 1H), 7.65 (d, J=8.0 Hz, 1H), 7.27 (dd, J=8.0, 2.0 Hz, 1H), 7.17 (d, J=2.0 Hz, 1H), 5.74 (s, 1H), 2.81 (s, 2H), 2.05 (br, 3H), 1.90 (br, 6H), 1.74 (br, 6H), 1.29 (s, 6H).

EXAMPLE 11(81)

(Z)-2-(3,3-dimethyl-3,4-dihydro-(2H)-isoquinolin-1-ylidene)-1-(4-bromophenyl)ethan-1-one TLC: Rf0.45 (hexane:ethyl acetate=3:1); NMR (CDCl$_3$): δ 11.84 (br, 1H), 7.84-7.80 (m, 3H), 7.56 (d, J=8.5 Hz, 2H), 7.44 (t, J=7.5 Hz, 1H), 7.35 (t, J=7.5 Hz, 1H), 7.22 (d, J=7.5 Hz, 1H), 6.27 (s, 1H), 2.91 (s, 2H), 1.37 (s, 6H).

EXAMPLE 11(82)

(Z)-2-(3,3-dimethyl-3,4-dihydro-(2H)-isoquinolin-1-ylidene)-1-(5-cyanothiophen-2-yl)ethan-1-one TLC: Rf0.29 (hexane:ethyl acetate=3:1); NMR (CDCl$_3$): δ 11.63 (br, 1H), 7.78 (d, J=7.5 Hz, 1H), 7.58 (d, J=4.0 Hz, 1H), 7.53 (d, J=4.0 Hz, 1H), 7.48 (t, J=7.5 Hz, 1H), 7.37 (t, J=7.5 Hz, 1H), 7.24 (d, J=7.5 Hz, 1H), 6.15 (s, 1H), 2.92 (s, 2H), 1.36 (s, 6H).

EXAMPLE 11(83)

(Z)-2-(3,3-dimethyl-3,4-dihydro-(2H)-isoquinolin-1-ylidene)-1-(4-methylthiophenyl)ethan-1-one TLC: Rf0.31 (hexane:ethyl acetate=3:1); NMR (CDCl$_3$): δ 11.81 (br, 1H), 7.89 (d, J=8.5 Hz, 2H), 7.83 (d, J=7.5 Hz, 1H), 7.43 (t, J=7.5 Hz, 1H), 7.34 (t, J=7.5 Hz, 1H), 7.28 (d, J=8.5 Hz, 2H), 7.21 (d, J=7.5 Hz, 1H), 6.31 (s, 1H), 2.90 (s, 2H), 2.53 (s, 3H), 1.36 (s, 6H).

EXAMPLE 11(84)

(Z)-2-(6-chloro-3,3-dimethyl-4-oxa-3,4-dihydro-(2H)-isoquinolin-1-ylidene)-1-phenylethan-1-one TLC: Rf0.36 (ethyl acetate:hexane=1:5); NMR (CDCl$_3$): δ 11.59 (br, 1H), 7.93 (m, 2H), 7.66 (d, J=8.5 Hz, 1H), 7.50-7.40 (m, 3H), 7.04 (dd, J=8.5, 2.0 Hz, 1H), 6.98 (d, J=2.0 Hz, 1H), 6.29 (s, 1H), 1.66 (s, 6H).

EXAMPLE 11(85)

(Z)-2-(6-chloro-3,3-dimethyl-4-oxa-3,4-dihydro-(2H)-isoquinolin-1-ylidene)-1-cyclohexylethan-1-one TLC: Rf0.44 (ethyl acetate:hexane=1:5); NMR (CDCl$_3$): δ 11.11 (br, 1H), 7.53 (d, J=8.5 Hz, 1H), 6.98 (dd, J=8.5, 2.0 Hz, 1H), 6.94 (d, J=2.0 Hz, 1H), 5.60 (s, 1H), 2.30 (m, 1H), 1.90-1.20 (m, 10H), 1.66 (s, 6H).

EXAMPLE 11(86)

(Z)-2-(6-chloro-3,3-dimethyl-4-oxa-3,4-dihydro-(2H)-isoquinolin-1-ylidene)-1-cycloheptylethan-1-one TLC: Rf0.60 (ethyl acetate:hexane=1:3); NMR (CDCl$_3$): δ 11.02 (br, 1H), 7.53 (d, J=8.5 Hz, 1H), 6.98 (dd, J=8.5, 2.0 Hz, 1H), 6.93 (d, J=2.0 Hz, 1H), 5.56 (s, 1H), 2.47 (m, 1H), 1.95-1.40 (m, 12H), 1.59 (s, 6H).

EXAMPLE 11(87)

(Z)-2-(3,3-dimethyl-3,4-dihydro-(2H)-isoquinolin-1-ylidene)-1-(4-dimethylaminophenyl)ethan-1-one TLC: Rf0.19 (hexane:ethyl acetate=3:1); NMR (CDCl$_3$): δ 11.65 (br, 1H), 7.91 (d, J=9.0 Hz, 2H), 7.83 (d, J=7.5 Hz, 1H), 7.40 (t, J=7.5 Hz, 1H), 7.33 (t, J=7.5 Hz, 1H), 7.19 (d, J=7.5 Hz, 1H), 6.71 (d, J=9.0 Hz, 2H), 6.32 (s, 1H), 3.04 (s, 6H), 2.88 (s, 2H), 1.34 (s, 6H).

EXAMPLE 11(88)

(Z)-2-(3,3-dimethyl-3,4-dihydro-(2H)-isoquinolin-1-ylidene)-1-(4-mesylphenyl)ethan-1-one TLC: Rf0.32 (hexane:ethyl acetate=1:1); NMR (CDCl$_3$): δ 11.97 (br, 1H), 8.10 (d, J=9.0 Hz, 2H), 8.00 (d, J=9.0 Hz, 2H), 7.83 (d, J=7.5 Hz, 1H), 7.47 (t, J=7.5 Hz, 1H), 7.37 (t, J=7.5 Hz, 1H), 7.24 (d, J=7.5 Hz, 1H), 6.30 (s, 1H), 3.09 (s, 3H), 2.93 (s, 2H), 1.39 (s, 6H).

EXAMPLE 11(89)

(Z)-2-(8-chloro-3,3-dimethyl-3,4-dihydro-(2H)-isoquinolin-1-ylidene)-1-phenylethan-1-one TLC: Rf0.39 (hexane:ethyl acetate=3:1); NMR (CDCl$_3$): δ 12.03 (br, 1H), 7.95-7.91 (m, 2H), 7.44-7.41 (m, 4H), 7.29 (m, 1H), 7.13 (dd, J=7.5, 1.5 Hz, 1H), 6.85 (s, 1H), 2.86 (s, 2H), 1.33 (s, 6H).

EXAMPLE 11(90)

(Z)-2-(6-chloro-3,3-dimethyl-4-oxa-3,4-dihydro-(2H)-isoquinolin-1-ylidene)-1-(adamantan-1-yl)ethan-1-one TLC: Rf0.28 (ethyl acetate:hexane=1:10); NMR (CDCl$_3$): δ 11.28 (br, 1H), 7.56 (d, J=8.5 Hz, 1H), 6.99 (dd, J=8.5, 2.0 Hz, 1H), 6.93 (d, J=2.0 Hz, 1H), 5.76 (s, 1H), 2.06 (m, 3H), 1.88 (m, 6H), 1.74 (m, 6H), 1.59 (s, 6H).

EXAMPLE 11(91)

(Z)-2-(6-chloro-3,3-dimethyl-3,4-dihydro-(2H)-isoquinolin-1-ylidene)-1-(tetrahydropyran-4-yl)ethan-1-one TLC: Rf0.38 (ethyl acetate:hexane=1:1); NMR (CDCl$_3$): δ 11.27 (br, 1H), 7.63 (d, J=8.5 Hz, 1H), 7.27 (dd, J=8.5, 2.0 Hz, 1H), 7.19 (d, J=2.0 Hz, 1H), 5.59 (s, 1H), 4.05 (m, 2H), 3.45 (dt, J=3.0, 11.5 Hz, 2H), 2.82 (s, 2H), 2.51 (m, 1H), 1.90-1.70 (m, 4H), 1.30 (s, 6H).

EXAMPLE 11(92)

(Z)-2-(7-chloro-3,3-dimethyl-3,4-dihydro-(2H)-isoquinolin-1-ylidene)-1-(tetrahydropyran-4-yl)ethan-1-one TLC: Rf0.39 (ethyl acetate:hexane=1:1); NMR (CDCl$_3$): δ 11.24 (br, 1H), 7.66 (d, J=2.0 Hz, 1H), 7.37 (dd, J=8.0, 2.0 Hz, 1H), 7.13 (d, J=8.0 Hz, 1H), 5.58 (s, 1H), 4.05 (m, 2H), 3.46 (dt, J=3.0, 11.5 Hz, 2H), 2.81 (s, 2H), 2.54 (m, 1H), 1.90-1.70 (m, 4H), 1.30 (s, 6H).

EXAMPLE 11(93)

(Z)-2-(7-fluoro-3,3-dimethyl-3,4-dihydro-(2H)-isoquinolin-1-ylidene)-1-(tetrahydropyran-4-yl)ethan-1-one TLC: Rf0.38 (ethyl acetate:hexane=1:1); NMR (CDCl$_3$): δ 11.25 (br, 1H), 7.38 (dd, J=9.5, 2.5 Hz, 1H), 7.20-7.05 (m, 2H), 5.56 (s, 1H), 4.05 (m, 2H), 3.46 (dt, J=3.0, 11.5 Hz, 2H), 2.82 (s, 2H), 2.53 (m, 1H), 1.90-1.70 (m, 4H), 1.30 (s, 6H).

EXAMPLE 11(94)

(Z)-2-(3,3-dimethyl-3,4-dihydro-(2H)-isoquinolin-1-ylidene)-1-(2,4-dichlorophenyl)ethan-1-one TLC: Rf0.29 (hexane:ethyl acetate=5:1); NMR (CDCl$_3$): δ 11.56 (br, 1H), 7.71 (d, J=7.5 Hz, 1H), 7.50 (d, J=8.0 Hz, 1H), 7.46-7.41 (m, 2H), 7.34-7.26 (m, 2H), 7.21 (d, J=7.5 Hz, 1H), 5.94 (s, 1H), 2.92 (s, 2H), 1.38 (s, 6H).

EXAMPLE 11(95)

(Z)-2-(3,3-dimethyl-3,4-dihydro-(2H)-isoquinolin-1-ylidene)-1-(2,5-dichlorothiophen-3-yl)ethan-1-one TLC: Rf0.36 (hexane:ethyl acetate=5:1); NMR (CDCl$_3$): δ 11.61 (br, 1H), 7.76 (d, J=7.5 Hz, 1H), 7.44 (t, J=7.5 Hz, 1H), 7.34 (t, J=7.5 Hz, 1H), 7.21 (d, J=7.5 Hz, 1H), 7.16 (s, 1H), 6.17 (s, 1H), 2.90 (s, 2H), 1.36 (s, 6H).

EXAMPLE 11(96)

(Z)-2-(6-fluoro-3,3-dimethyl-3,4-dihydro-(2H)-isoquinolin-1-ylidene)-1-(adamantan-1-yl)ethan-1-one TLC: Rf0.35 (ethyl acetate:hexane=1:5); NMR (CDCl$_3$): δ 11.48 (br, 1H), 7.72 (dd, J=8.5, 5.5 Hz, 1H), 6.99 (ddd, J=8.5, 8.5, 2.5 Hz, 1H), 6.88 (dd, J=8.5, 2.5 Hz, 1H), 5.72 (s, 1H), 2.82 (s, 2H), 2.05 (m, 3H), 1.91 (m, 6H), 1.74 (m, 6H), 1.30 (s, 6H).

EXAMPLE 11(97)

(Z)-2-(6-fluoro-3,3-dimethyl-3,4-dihydro-(2H)-isoquinolin-1-ylidene)-1-(4-cyanophenyl)ethan-1-one TLC: Rf0.13 (ethyl acetate:hexane=1:5); NMR (CDCl$_3$): δ 11.94 (br, 1H), 8.00 (d, J=8.5 Hz, 2H), 7.82 (dd, J=8.5, 5.5 Hz, 1H), 7.72 (d, J=8.5 Hz, 2H), 7.05 (ddd, J=8.5, 8.5, 2.5 Hz, 1H), 6.95 (dd, J=8.5, 2.5 Hz, 1H), 6.21 (s, 1H), 2.91 (s, 2H), 1.38 (s, 6H).

EXAMPLE 11(98)

(Z)-2-(3,3-dimethyl-3,4-dihydro-(2H)-isoquinolin-1-ylidene)-1-(4-methylnaphthalen-1-yl)ethan-1-one TLC: Rf0.45 (hexane:ethyl acetate=3:1); NMR (CDCl$_3$): δ 11.76 (br, 1H), 8.54 (m, 1H), 8.03 (m, 1H), 7.71 (d, J=7.5 Hz, 1H), 7.61 (d, J=7.0 Hz, 1H), 7.56-7.50 (m, 2H), 7.41 (t, J=7.5 Hz, 1H), 7.35-7.25 (m, 2H), 7.22 (d, J=7.5 Hz, 1H), 6.08 (s, 1H), 2.94 (s, 2H), 2.73 (s, 3H), 1.41 (s, 6H).

EXAMPLE 11(99)

(Z)-2-(3,3-dimethyl-3,4-dihydro-(2H)-isoquinolin-1-ylidene)-1-(4-fluoronaphthalen-1-yl)ethan-1-one TLC: Rf0.46 (hexane:ethyl acetate=3:1); NMR (CDCl$_3$): δ 11.76 (br, 1H), 8.55 (m, 1H), 8.14 (m, 1H), 7.72 (d, J=7.5 Hz, 1H), 7.67 (dd, J=8.0, 5.5 Hz, 1H), 7.60-7.53 (m, 2H), 7.43 (t, J=7.5 Hz, 1H), 7.29 (t, J=7.5 Hz, 1H), 7.23 (d, J=7.5 Hz, 1H), 7.14 (dd, J=10.5, 8.0 Hz, 1H), 6.06 (s, 1H), 2.95 (s, 2H), 1.41 (s, 6H).

EXAMPLE 11(100)

(Z)-2-(7-nitro-3,3-dimethyl-3,4-dihydro-(2H)-isoquinolin-1-ylidene)-1-phenylethan-1-one TLC: Rf0.53 (hexane:ethyl acetate=1:1); NMR (CDCl$_3$): δ 11.78 (brs, 1H), 8.69 (d, J=2.4 Hz, 1H), 8.29 (dd, J=8.4, 2.4 Hz, 1H), 8.00-7.95 (m, 2H), 7.52-7.44 (m, 3H), 7.42 (d, J=8.4 Hz, 1H), 6.40 (s, 1H), 3.01 (s, 2H), 1.39 (s, 6H).

EXAMPLE 11(101)

(Z)-2-(spiro[6-chloro-3,4-dihydro-(2H)-isoquinolin-3,4'-3,4,5,6-tetrahydropyran]-1-ylidene)-1-phenylethan-1-one TLC: Rf0.43 (ethyl acetate:hexane=1:1); NMR (CDCl$_3$): δ 12.35 (br, 1H), 7.94 (m, 2H), 8.76 (d, J=8.5 Hz, 1H), 7.50-7.40 (m, 3H), 7.32 (dd, J=8.5, 2.0 Hz, 1H), 7.25 (d, J=2.0 Hz, 1H), 6.34 (s, 1H), 3.86 (m, 4H), 2.93 (s, 2H), 1.74 (m, 4H).

EXAMPLE 11(102)

(Z)-2-(spiro[6-chloro-3,4-dihydro-(2H)-isoquinolin-3,4'-3,4,5,6-tetrahydropyran]-1-ylidene)-1-(4-cyanophenyl)ethan-1-one TLC: Rf0.35 (ethyl acetate:hexane=1:1); NMR (CDCl$_3$): δ 12.48 (br, 1H), 8.02 (d, J=8.5 Hz, 2H), 7.74 (d, J=8.5 Hz, 2H), 7.74 (d, J=8.5 Hz, 1H), 7.34 (dd, J=8.5, 2.0 Hz, 1H), 7.28 (d, J=2.0 Hz, 1H), 6.28 (s, 1H), 3.86 (m, 4H), 2.95 (s, 2H), 1.76 (m, 4H).

EXAMPLE 11(103)

(Z)-2-(spiro[6-chloro-3,4-dihydro-(2H)-isoquinolin-3,4'-3,4,5,6-tetrahydropyran]-1-ylidene)-1-(adamantan-1-yl)ethan-1-one TLC: Rf0.56 (ethyl acetate:hexane=1:1); NMR (CDCl$_3$): δ 11.92 (br, 1H), 7.64 (d, J=8.5 Hz, 1H), 7.28 (dd, J=8.5, 2.0 Hz, 1H), 7.20 (d, J=2.0 Hz, 1H), 5.79 (s, 1H), 3.80 (m, 4H), 2.86 (s, 2H), 2.06 (m, 3H), 1.91 (m, 6H), 1.80-1.60 (m, 10H).

EXAMPLE 11(104)

(Z)-2-(3,3-dimethyl-3',4-dihydro-(2H)-isoquinolin-1-ylidene)-1-(noradamantan-1-yl)ethan-1-one TLC: Rf0.47 (hexane:ethyl acetate=3:1); NMR (CDCl$_3$): δ 11.35 (br, 1H), 7.70 (dd, J=7.5, 1.0 Hz, 1H), 7.38 (dt, J=1.0, 7.5 Hz, 1H), 7.29 (dt, J=1.0, 7.5 Hz, 1H), 7.17 (dd, J=7.5, 1.0 Hz, 1H), 5.74 (s, 1H), 2.85 (s, 2H), 2.72 (t, J=6.5 Hz, 1H), 2.32 (br, 2H), 2.12-2.07 (m, 2H), 1.89-1.81 (m, 4H), 1.67-1.63 (m, 4H), 1.30 (s, 6H).

EXAMPLE 11(105)

(Z)-2-(6-chloro-3,3-dimethyl-3,4-dihydro-(2H)-isoquinolin-1-ylidene)-1-(noradamantan-1-yl)ethan-1-one TLC: Rf0.50 (hexane:ethyl acetate=3:1); NMR (CDCl$_3$): δ 11.30 (br, 1H), 7.63 (d, J=8.5 Hz, 1H), 7.26 (dd, J=8.5, 2.0 Hz, 1H), 7.18 (d, J=2.0 Hz, 1H), 5.69 (s, 1H), 2.82 (s, 2H), 2.71 (t, J=6.5 Hz, 1H), 2.32 (br, 2H), 2.10-2.05 (m, 2H), 1.88-1.80 (m, 4H), 1.69-1.63 (m, 4H), 1.30 (s, 6H).

EXAMPLE 11(106)

(Z)-2-(6-methoxy-3,3-dimethyl-4-oxa-3,4-dihydro-(2H)-isoquinolin-1-ylidene)-1-(4-cyanophenyl)ethan-1-one TLC: Rf0.26 (hexane:ethyl acetate=3:1); NMR (CDCl$_3$): δ 11.75 (br, 1H), 7.99 (d, J=8.5 Hz, 2H), 7.73 (d, J=8.5 Hz, 2H), 7.63 (d, J=9.0 Hz, 1H), 6.64 (dd, J=9.0, 2.5 Hz, 1H), 6.48 (d, J=2.5 Hz, 1H), 6.17 (s, 1H), 3.85 (s, 3H), 1.69 (s, 6H).

EXAMPLE 11(107)

(Z)-2-(6-methoxy-3,3-dimethyl-4-oxa-3,4-dihydro-(2H)-isoquinolin-1-ylidene)-1-phenylethan-1-one TLC: Rf0.34 (hexane:ethyl acetate=3:1); NMR (CDCl$_3$): δ 11.66 (br, 1H), 7.95-7.92 (m, 2H), 7.65 (d, J=8.5 Hz, 1H), 7.49-7.40 (m, 3H), 6.63 (dd, J=8.5, 2.5 Hz, 1H), 6.46 (d, J=2.5 Hz, 1H), 6.24 (s, 1H), 3.84 (s, 3H), 1.67 (s, 6H).

EXAMPLE 11(108)

(Z)-2-(6-methoxy-3,3-dimethyl-4-oxa-3,4-dihydro-(2H)-isoquinolin-1-ylidene)-1-(adamantan-1-yl)ethan-1-one TLC: Rf0.49 (hexane:ethyl acetate=3:1); NMR (CDCl$_3$): δ 11.37 (br, 1H), 7.55 (d, J=9.0 Hz, 1H), 6.58 (dd, J=9.0, 2.5 Hz, 1H), 6.42 (d, J=2.5 Hz, 1H), 5.70 (s, 1H), 3.82 (s, 3H), 2.05 (br, 3H), 1.89 (br, 6H), 1.74 (br, 6H), 1.60 (s, 6H).

EXAMPLE 11(109)

(Z)-2-(3,3,6-trimethyl-4-oxa-3,4-dihydro-(2H)-isoquinolin-1-ylidene)-1-phenylethan-1-one TLC: Rf0.51 (ethyl acetate:hexane=1:3); NMR (CDCl$_3$): δ 11.63 (br, 1H), 7.94 (m, 2H), 7.62 (d, J=8.0 Hz, 1H), 7.50-7.40 (m, 3H), 6.87 (m, 1H), 6.77 (s, 1H), 6.30 (s, 1H), 2.37 (s, 3H), 1.66 (s, 6H).

EXAMPLE 11(110)

(Z)-2-(3,3,6-trimethyl-4-oxa-3,4-dihydro-(2H)-isoquinolin-1-ylidene)-1-(4-cyanophenyl)ethan-1-one TLC: Rf0.39 (ethyl acetate:hexane=1:3); NMR (CDCl$_3$): δ 11.73 (br, 1H), 8.00 (d, J=8.0 Hz, 2H), 7.73 (d, J=8.0 Hz, 2H), 7.59 (d, J=8.0 Hz, 1H), 6.89 (m, 1H), 6.79 (s, 1H), 6.23 (s, 1H), 2.38 (s, 3H), 1.67 (s, 6H).

EXAMPLE 11(111)

(Z)-2-(3,3,6-trimethyl-4-oxa-3,4-dihydro-(2H)-isoquinolin-1-ylidene)-1-(adamantan-1-yl)ethan-1-one TLC: Rf0.70 (ethyl acetate:hexane=1:3); NMR (CDCl$_3$): δ 11.34 (br, 1H), 7.51 (d, J=8.0 Hz, 1H), 6.82 (m, 1H), 6.73 (s, 1H), 5.76 (s, 1H), 2.35 (s, 3H), 2.05 (m, 3H), 1.90 (m, 6H), 1.74 (m, 6H), 1.59 (s, 6H).

EXAMPLE 11(112)

(Z)-2-(3,3-dimethyl-4-oxa-3,4-dihydro-(2H)-isoquinolin-1-ylidene)-1-(tetrahydropyran-4-yl)ethan-1-one TLC: Rf0.17 (ethyl acetate:hexane=1:3); NMR (CDCl$_3$): δ 11.17 (br, 1H), 7.60 (dd, J=8.0, 1.5 Hz, 1H), 7.39 (ddd, J=8.0, 8.0, 1.5 Hz, 1H), 7.02 (ddd, J=8.0, 8.0, 1.0 Hz, 1H), 6.92 (dd, J=8.0, 1.0 Hz, 1H), 5.64 (s, 1H), 4.05 (m, 2H), 3.46 (m, 2H), 2.54 (m, 1H), 1.90-1.70 (m, 4H), 1.61 (s, 6H).

EXAMPLE 11(113)

(Z)-2-(3,3-dimethyl-3,4-dihydro-(2H)-isoquinolin-1-ylidene)-1-(2-chloro-4-mesylphenyl)ethan-1-one TLC: Rf0.09 (hexane:ethyl acetate=2:1); NMR (CDCl$_3$): δ 11.58 (br, 1H), 8.00 (d, J=1.5 Hz, 1H), 7.86 (dd, J=8.0, 1.5 Hz, 1H), 7.72-7.70 (m, 2H), 7.46 (t, J=7.5 Hz, 1H), 7.32 (t, J=7.5 Hz, 1H), 7.23 (d, J=7.5 Hz, 1H), 5.89 (s, 1H), 3.09 (s, 3H), 2.94 (s, 2H), 1.40 (s, 6H).

EXAMPLE 11(114)

(Z)-2-(6,6-dimethyl-4,5,6,7-tetrahydrothiopheno[3,2-c]pyridin-4-ylidene)-1-phenylethan-1-one TLC: Rf0.44 (hexane:ethyl acetate=3:1); NMR (CDCl$_3$): δ 11.08 (br, 1H), 7.94-7.91 (m, 2H), 7.46-7.40 (m, 3H), 7.32 (d, J=5.0 Hz, 1H), 7.17 (d, J=5.0 Hz, 1H), 6.14 (s, 1H), 3.00 (s, 2H), 1.43 (s, 6H).

EXAMPLE 11(115)

(Z)-2-(6,6-dimethyl-4,5,6,7-tetrahydrothiopheno[3,2-c]pyridin-4-ylidene)-1-(adamantan-1-yl)ethan-1-one TLC: Rf0.58 (hexane:ethyl acetate=3:1); NMR (CDCl$_3$): δ 10.74 (br, 1H), 7.23 (d, J=5.5 Hz, 1H), 7.12 (d, J=5.5 Hz, 1H), 5.59 (s, 1H), 2.93 (s, 2H), 2.05 (br, 3H), 1.89 (br, 6H), 1.73 (br, 6H), 1.36 (s, 6H).

EXAMPLE 11(116)

(Z)-2-(6,6-dimethyl-4,5,6,7-tetrahydrothiopheno[3,2-c]pyridin-4-ylidene)-1-(4-cyanophenyl)ethan-1-one TLC: Rf0.26 (hexane:ethyl acetate=3:1); NMR (CDCl$_3$): δ 11.21 (br, 1H), 7.99 (d, J=8.0 Hz, 2H), 7.72 (d, J=8.0 Hz, 2H), 7.31 (d, J=5.0 Hz, 1H), 7.20 (d, J=5.0 Hz, 1H), 6.07 (s, 1H), 3.02 (s, 2H), 1.45 (s, 6H).

EXAMPLE 11(117)

(Z)-2-(6-methoxy-3,3-dimethyl-3,4-dihydro-(2H)-isoquinolin-1-ylidene)-1-(adamantan-1-yl)ethan-1-one TLC: Rf0.40 (hexane:ethyl acetate=3:1); NMR (CDCl$_3$): δ 11.51 (br, 1H), 7.67 (d, J=8.5 Hz, 1H), 6.81 (dd, J=8.5, 2.5 Hz, 1H), 6.68 (d, J=2.5 Hz, 1H), 5.70 (s, 1H), 3.85 (s, 3H), 2.80 (s, 2H), 2.05 (br, 3H), 1.91 (br, 6H), 1.74 (br, 6H), 1.29 (s, 6H).

EXAMPLE 11(118)

(Z)-2-(6-methoxy-3,3-dimethyl-3,4-dihydro-(2H)-isoquinolin-1-ylidene)-1-(4-cyanophenyl)ethan-1-one TLC: Rf0.18 (hexane:ethyl acetate=3:1); NMR (CDCl$_3$): δ 11.96 (br, 1H), 8.01 (d, J=8.5 Hz, 2H), 7.77-7.70 (m, 3H), 6.87 (dd, J=8.5, 2.5 Hz, 1H), 6.74 (d, J=2.5 Hz, 1H), 6.20 (s, 1H), 3.88 (s, 3H), 2.88 (s, 2H), 1.38 (s, 6H).

EXAMPLE 11(119)

(Z)-2-(7-bromo-6-chloro-3,3-dimethyl-3,4-dihydro-(2H)-isoquinolin-1-ylidene)-1-(adamantan-1-yl)ethan-1-one TLC: Rf0.36 (ethyl acetate:hexane=1:5); NMR (CDCl$_3$): δ 11.39 (br, 1H), 7.91 (s, 1H), 7.28 (s, 1H), 5.69 (s, 1H), 2.76 (s, 2H), 2.07 (m, 3H), 1.91 (m, 6H), 1.75 (m, 6H), 1.29 (s, 6H).

EXAMPLE 11(120)

(Z)-2-(2-chloro-6,6-dimethyl-4,5,6,7-tetrahydrothiopheno[3,2-c]pyridin-4-ylidene)-1-phenylethan-1-one TLC: Rf0.44 (hexane:ethyl acetate=3:1); NMR (CDCl$_3$): δ 10.96 (br, 1H), 7.92-7.89 (m, 2H), 7.46-7.40 (m, 3H), 7.14 (s, 1H), 6.02 (s, 1H), 2.90 (s, 2H), 1.43 (s, 6H).

EXAMPLE 11(121)

(Z)-2-(2-chloro-6,6-dimethyl-4,5,6,7-tetrahydrothiopheno[3,2-c]pyridin-4-ylidene)-1-(adamantan-1-yl)ethan-1-one TLC: Rf0.56 (hexane:ethyl acetate=3:1); NMR (CDCl$_3$): δ 10.62 (br, 1H), 7.05 (s, 1H), 5.47 (s, 1H), 2.82 (s, 2H), 2.05 (br, 3H), 1.87 (br, 6H), 1.73 (br, 6H), 1.36 (s, 6H).

EXAMPLE 11(122)

(Z)-2-(2-chloro-6,6-dimethyl-4,5,6,7-tetrahydrothiopheno[3,2-c]pyridin-4-ylidene)-1-(4-cyanophenyl)ethan-1-one TLC: Rf0.29 (hexane:ethyl acetate=3:1); NMR (CDCl$_3$): δ 11.09 (br, 1H), 7.97 (d, J=8.5 Hz, 2H), 7.72 (d, J=8.5 Hz, 2H), 7.13 (s, 1H), 5.95 (s, 1H), 2.92 (s, 2H), 1.45 (s, 6H).

EXAMPLE 11(123)

(Z)-2-(5-methoxy-3,3-dimethyl-3,4-dihydro-(2H)-isoquinolin-1-ylidene)-1-phenylethan-1-one TLC: Rf0.49 (hexane:ethyl acetate=2:1); NMR (CDCl$_3$): δ 11.84 (brs, 1H), 7.97-7.91 (m, 2H), 7.48-7.40 (m, 4H), 7.30 (t, J=8.1 Hz, 1H), 7.00 (d, J=8.1 Hz, 1H), 6.33 (s, 1H), 3.87 (s, 3H), 2.90 (s, 2H), 1.37 (s, 6H).

EXAMPLE 11(124)

(Z)-2-(3,3,6-trimethyl-3,4-dihydro-(2H)-isoquinolin-1-ylidene)-1-(adamantan-1-yl)ethan-1-one TLC: Rf0.41 (hexane:ethyl acetate=4:1); NMR (CDCl$_3$): δ 11.48 (brs, 1H), 7.61 (d, J=8.1 Hz, 1H), 7.09 (brd, J=8.1 Hz, 1H), 6.97 (brs, 1H), 5.75 (s, 1H), 2.79 (s, 2H), 2.37 (s, 3H), 2.05 (brs, 3H), 1.91 (d, J=3.0 Hz, 6H), 1.74 (d, J=3.0 Hz, 6H), 1.29 (s, 6H).

EXAMPLE 11(125)

(Z)-2-(3,3,6-trimethyl-3,4-dihydro-(2H)-isoquinolin-1-ylidene)-1-(4-cyanophenyl)ethan-1-one TLC: Rf0.13 (hexane:ethyl acetate=4:1); NMR (CDCl$_3$): δ 11.94 (brs, 1H), 8.01 (d, J=8.4 Hz, 2H), 7.72 (d, J=8.4 Hz, 2H), 7.70 (d, J=8.4 Hz, 1H), 7.16 (brd, J=8.4 Hz, 1H), 7.04 (brs, 1H), 6.25 (s, 1H), 2.87 (s, 2H), 2.41 (s, 3H), 1.37 (s, 6H).

EXAMPLE 11(126)

(Z)-2-(7-nitro-3,3-dimethyl-3,4-dihydro-(2H)-isoquinolin-1-ylidene)-1-(4-cyanophenyl)ethan-1-one TLC: Rf0.14 (ethyl acetate:hexane=1:1); NMR (CDCl$_3$).: δ 11.91 (br, 1H), 8.67 (d, J=2.0 Hz, 1H), 8.32 (dd, J=8.0, 2.0 Hz, 1H), 8.05 (d, J=8.5 Hz, 2H), 7.77 (d, J=8.5 Hz, 2H), 7.45 (d, J=8.0 Hz, 1H), 6.34 (s, 1H), 6.04 (s, 2H), 1.41 (s, 6H).

EXAMPLE 11(127)

(Z)-2-(6-chloro-7-nitro-3,3-dimethyl-3,4-dihydro-(2H)-isoquinolin-1-ylidene)-1-cyclohexylethan-1-one TLC: Rf0.29 (ethyl acetate:hexane=1:3); NMR (CDCl$_3$): δ 11.15 (br, 1H), 8.23 (s, 1H), 7.38 (s, 1H), 5.61 (s, 1H), 2.88 (s, 2H), 2.33 (m, 1H), 1.90-1.65 (m, 5H), 1.55-1.20 (m, 5H), 1.31 (s, 6H).

EXAMPLE 11(128)

(Z)-2-(6-chloro-7-nitro-3,3-dimethyl-3,4-dihydro-(2H)-isoquinolin-1-ylidene)-1-cycloheptylethan-1-one TLC: Rf0.30 (ethyl acetate:hexane=1:3); NMR (CDCl$_3$): δ 11.08 (br, 1H), 8.23 (s, 1H), 7.39 (s, 1H), 5.58 (s, 1H), 2.88 (s, 2H), 2.51 (m, 1H), 1.95-1.20 (m, 12H), 1.31 (s, 6H).

EXAMPLE 11(129)

(Z)-2-(6-chloro-7-nitro-3,3-dimethyl-3,4-dihydro-(2H)-isoquinolin-1-ylidene)-1-(4-cyanophenyl)ethan-1-one TLC: Rf0.13 (ethyl acetate:hexane=1:3); NMR (CDCl$_3$): δ 11.83 (br, 1H), 8.34 (s, 1H), 8.01 (d, J=8.5 Hz, 2H), 7.76 (d, J=8.5 Hz, 2H), 7.46 (s, 1H), 6.24 (s, 1H), 2.97 (s, 2H), 1.41 (s, 6H).

EXAMPLE 11(130)

(Z)-2-(6-chloro-7-nitro-3,3-dimethyl-3,4-dihydro-(2H)-isoquinolin-1-ylidene)-1-(adamantan-1-yl)ethan-1-one TLC: Rf0.35 (ethyl acetate:hexane=1:3); NMR (CDCl$_3$): δ 11.36 (br, 1H), 8.22 (s, 1H), 7.39 (s, 1H), 5.75 (s, 1H), 2.88 (s, 2H), 2.07 (m, 3H), 1.90 (m, 6H), 1.75 (m, 6H), 1.32 (s, 6H).

EXAMPLE 11(131)

(Z)-2-(7-dimethylaminomethyl-3,3-dimethyl-3,4-dihydro-(2H)-isoquinolin-1-ylidene)-1-(4-cyanophenyl)ethan-1-one TLC: Rf0.41 (water:methanol:chloroform=1:10:100); NMR (CDCl$_3$): δ 12.01 (br, 1H), 8.03 (d, J=8.0 Hz, 2H), 7.74 (s, 1H), 7.73 (d, J=8.0 Hz, 2H), 7.41 (d, J=7.5 Hz, 1H), 7.19 (d, J=7.5 Hz, 1H), 6.29 (s, 1H), 3.48 (s, 2H), 2.90 (s, 2H), 2.28 (s, 6H), 1.37 (s, 6H).

EXAMPLE 11(132)

(Z)-2-(7-dimethylaminomethyl-3,3-dimethyl-3,4-dihydro-(2H)-isoquinolin-1-ylidene)-1-(adamantan-1-yl)ethan-1-one TLC: Rf0.39 (water:methanol:chloroform=1:10:100); NMR (CDCl$_3$): δ 11.55 (br, 1H), 7.66 (s, 1H), 7.40 (d, J=7.5 Hz, 1H), 7.15 (d, J=7.5 Hz, 1H), 5.80 (s, 1H), 3.55 (br, 2H), 2.82 (s, 2H), 2.33 (s, 6H), 2.06 (m, 3H), 1.92 (m, 6H), 1.75 (m, 6H), 1.29 (s, 6H).

EXAMPLE 11(133)

(Z)-2-(7-amino-6-methoxy-3,3-dimethyl-3,4-dihydro-(2H)-isoquinolin-1-ylidene)-1-(4-cyanophenyl)ethan-1-one TLC: Rf0.35 (hexane:ethyl acetate=1:1); NMR (CDCl$_3$): δ 11.91 (br, 1H), 8.00 (d, J=8.5 Hz, 2H), 7.71 (d, J=8.5 Hz, 2H), 7.13 (s, 1H), 6.59 (s, 1H), 6.12 (s, 1H), 3.92 (s, 3H), 3.88 (br, 2H), 2.80 (s, 2H), 1.37 (s, 6H).

EXAMPLE 11(134)

(Z)-2-(7-amino-6-methoxy-3,3-dimethyl-3,4-dihydro-(2H)-isoquinolin-1-ylidene)-1-(adamantan-1-yl)ethan-1-one TLC: Rf0.56 (hexane:ethyl acetate=1:1); NMR (CDCl$_3$): δ 11.46 (br, 1H), 7.07 (s, 1H), 6.54 (s, 1H), 5.62 (s, 1H), 3.89 (s, 3H), 3.82 (br, 2H), 2.72 (s, 2H), 2.05 (br, 3H), 1.91 (br, 6H), 1.74 (br, 6H), 1.28 (s, 6H).

EXAMPLE 11(135)

(Z)-2-(6-chloro-7-dimethylamino-3,3-dimethyl-3,4-dihydro-(2H)-isoquinolin-1'-ylidene)-1-cyclohexylethan-1-one TLC: Rf0.32 (ethyl acetate:hexane=1:5); NMR (CDCl$_3$): δ 11.33 (br, 1H), 7.36 (s, 1H), 7.17 (s, 1H), 5.54 (s, 1H), 2.86 (s, 6H), 2.74 (s, 2H), 2.32 (m, 1H), 1.95-1.20 (m, 10H), 1.28 (s, 6H).

EXAMPLE 11(136)

(Z)-2-(6-chloro-7-dimethylamino-3,3-dimethyl-3,4-dihydro-(2H)-isoquinolin-1-ylidene)-1-cycloheptylethan-1-one TLC: Rf0.34 (ethyl acetate:hexane=1:5); NMR (CDCl$_3$): δ 11.25 (br, 1H), 7.35 (s, 1H), 7.17 (s, 1H), 5.51 (s, 1H), 2.86 (s, 6H), 2.74 (s, 2H), 2.48 (m, 1H), 1.95-1.40 (m, 12H), 1.28 (s, 6H).

EXAMPLE 11(137)

(Z)-2-(6-chloro-7-dimethylamino-3,3-dimethyl-3,4-dihydro-(2H-isoquinolin-1-ylidene)-1-(4-cyanophenyl)ethan-1-one TLC: Rf0.24 (ethyl acetate:hexane=1:5); NMR (CDCl$_3$): δ 11.95 (br, 1H), 8.00 (d, J=8.5 Hz, 2H), 7.73 (d, J=8.5 Hz, 2H), 7.43 (s, 1H), 7.24 (s, 1H), 6.17 (s, 1H), 2.89 (s, 6H), 2.82 (s, 2H), 1.37 (s, 6H).

EXAMPLE 11(138)

(Z)-2-(6-chloro-7-dimethylamino-3,3-dimethyl-3,4-dihydro-(2H)-isoquinolin-1-ylidene)-1-(adamantan-1-yl)ethan-1-one TLC: Rf0.36 (ethyl acetate:hexane=1:5); NMR (CDCl$_3$): δ 11.51 (br, 1H), 7.36 (s, 1H), 7.16 (s, 1H), 5.69 (s, 1H), 2.86 (s, 6H), 2.73 (s, 2H), 2.06 (m, 3H), 1.91 (m, 6H), 1.74 (m, 6H), 1.28 (s, 6H).

EXAMPLE 11(139)

(Z)-2-(7-dimethylamino-3,3,6-trimethyl-3,4-dihydro-(2H)-isoquinolin-1-ylidene)-1-(4-cyanophenyl)ethan-1-one TLC: Rf0.16 (hexane:ethyl acetate=4:1); NMR (CDCl$_3$): δ 11.98 (brs, 1H), 8.01 (d, J=8.4 Hz, 2H), 7.73 (d, J=8.4 Hz, 2H), 7.40 (s, 1H), 7.01 (s, 1H), 6.19 (s, 1H), 2.81 (s, 2H), 2.76 (s, 6H), 2.37 (s, 3H), 1.37 (s, 6H).

EXAMPLE 11(140)

(Z)-2-(7-dimethylamino-3,3,6-trimethyl-3,4-dihydro-(2H)-isoquinolin-1-ylidene)-1-(adamantan-1-yl)ethan-1-one TLC: Rf0.36 (hexane:ethyl acetate=4:1); NMR (CDCl$_3$): δ 11.55 (brs, 1H), 7.33 (s, 1H), 6.95 (s, 1H), 5.71 (s, 1H), 2.74 (s, 6H), 2.73 (s, 2H), 2.34 (s, 3H), 2.09-2.03 (m, 3H), 1.94-1.90 (m, 6H), 1.77-1.73 (m, 6H), 1.28 (s, 6H).

EXAMPLE 11(141)

(Z)-2-(7-dimethylamino-3,3,6-trimethyl-3,4-dihydro-(2H)-isoquinolin-1-ylidene)-1-cyclohexylethan-1-one TLC: Rf0.39 (hexane:ethyl acetate=4:1); NMR (CDCl$_3$): δ 11.36 (brs, 1H), 7.32 (s, 1H), 6.95 (s, 1H), 5.56 (s, 1H), 2.74 (s, 8H), 2.34 (s, 3H), 2.31 (m, 1H), 1.92-1.20 (m, 10H), 1.28 (s, 6H).

EXAMPLE 11(142)

(Z)-2-(7-dimethylamino-3,3,6-trimethyl-3,4-dihydro-(2H)-isoquinolin-1-ylidene)-1-cycloheptylethan-1-one TLC: Rf0.41 (hexane:ethyl acetate=4:1); NMR (CDCl$_3$): δ 11.29 (brs, 1H), 7.32 (s, 1H), 6.94 (s, 1H), 5.52 (s, 1H), 2.74 (s, 6H), 2.73 (s, 2H), 2.47 (m, 1H), 2.34 (s, 3H), 1.97-1.43 (m, 12H), 1.27 (s, 6H).

EXAMPLE 11(143)

(Z)-2-(7-dimethylaminomethyl-3,3-dimethyl-3,4-dihydro-(2H)-isoquinolin-1-ylidene)-1-cyclohexylethan-1-one TLC: Rf0.44 (water:methanol:chloroform=1:10:100); NMR (CDCl$_3$): δ 11.34 (br, 1H), 7.63 (d, J=1.5 Hz, 1H), 7.34 (dd, J=8.0, 1.5 Hz, 1H), 7.12 (d, J=8.0 Hz, 1H), 5.66 (s, 1H), 3.46 (s, 2H), 2.82 (s, 2H), 2.32 (m, 1H), 2.28 (s, 6H), 1.90-1.20 (m, 10H), 1.28 (s, 6H).

EXAMPLE 11(144)

(Z)-2-(7-dimethylaminomethyl-3,3-dimethyl-3,4-dihydro-(2H)-isoquinolin-1-ylidene)-1-cycloheptyle-than-1-one TLC: Rf0.46 (water:methanol:chloroform=1:10:100); NMR (CDCl$_3$): δ 11.27 (br, 1H), 7.63 (s, 1H), 7.33 (d, J=7.5 Hz, 1H), 7.12 (d, J=7.5 Hz, 1H), 5.62 (s, 1H), 3.45 (s, 2H), 2.82 (s, 2H), 2.48 (m, 1H), 2.27 (s, 6H), 1.95-1.40 (m, 12H), 1.28 (s, 6H).

EXAMPLE 11(145)

(Z)-2-(6-methoxy-7-methylamino-3,3-dimethyl-3,4-dihydro-(2H)-isoquinolin 1-ylidene)-1-(4-cyanophe-nyl)ethan-1-one TLC: Rf0.13 (hexane:ethyl acetate=3:1); NMR (CDCl$_3$): δ 11.97 (br, 1H), 8.00 (d, J=8.5 Hz, 2H), 7.72 (d, J=8.5 Hz, 2H), 6.89 (s, 1H), 6.56 (s, 1H), 6.17 (s, 1H), 4.33 (br, 1H), 3.92 (s, 3H), 2.95 (s, 3H), 2.81 (s, 2H), 1.37 (s, 6H).

EXAMPLE 11(146)

(Z)-2-(6-methoxy-7-methylamino-3,3-dimethyl-3,4-dihydro-(2H)-isoquinolin 1-ylidene)-1-(adamantan-1-yl)ethan-1-one TLC: Rf0.34 (hexane:ethyl acetate=3:1); NMR (CDCl$_3$): δ 11.57 (br, 1H), 6.85 (s, 1H), 6.50 (s, 1H), 5.68 (s, 1H), 4.23 (br, 1H), 3.88 (s, 3H), 2.94 (s, 3H), 2.72 (s, 2H), 2.05 (br, 3H), 1.92 (br, 6H), 1.74 (br, 6H), 1.29 (s, 6H).

EXAMPLE 11(147)

(Z)-2-(7-dimethylamino-6-methoxy-3,3-dimethyl-3,4-dihydro-(2H)-isoquinolin-1-ylidene)-1-cyclohexy-lethan-1-one TLC: Rf0.20 (hexane:ethyl acetate=3:1); NMR (CDCl$_3$): δ 11.37 (br, 1H), 7.23 (s, 1H), 6.60 (s, 1H), 5.51 (s, 1H), 3.93 (s, 3H), 2.82 (s, 6H), 2.76 (s, 2H), 2.30 (tt, J=11.5, 3.5 Hz, 1H), 1.89-1.79 (m, 4H), 1.69 (m, 1H), 1.56-1.20 (m, 1H).

EXAMPLE 11(148)

(Z)-2-(7-dimethylamino-6-methoxy-3,3-dimethyl-3,4-dihydro-(2H)-isoquinolin-1-ylidene)-1-cyclohep-tylethan-1-one TLC: Rf0.20 (hexane:ethyl acetate=3:1); NMR (CDCl$_3$): δ 11.30 (br, 1H), 7.23 (s, 1H), 6.60 (s, 1H), 5.48 (s, 1H), 3.93 (s, 3H), 2.82 (s, 6H), 2.76 (s, 2H), 2.46 (m, 1H), 1.95-1.88 (m, 2H), 1.83-1.45 (m, 10H), 1.29 (s, 6H).

EXAMPLE 11(149)

(Z)-2-(7-dimethylamino-3,3-dimethyl-3,4-dihydro-(2H)-isoquinolin-1-ylidene)-1-(4-cyanophenyl)ethan-1-one TLC: Rf0.14 (hexane:ethyl acetate=4:1); NMR (CDCl$_3$): δ 12.02 (brs, 1H), 8.00 (d, J=8.7 Hz, 2H), 7.72 (d, J=8.7 Hz, 2H), 7.09 (d, J=8.7 Hz, 1H), 7.08 (d, J=2.4 Hz, 1H), 6.86 (dd, J=8.7, 2.4 Hz, 1H), 6.21 (s, 1H), 3.02 (s, 6H), 2.81 (s, 2H), 1.36 (s, 6H).

EXAMPLE 11(150)

(Z)-2-(7-dimethylamino-3,3-dimethyl-3,4-dihydro-(2H)-isoquinolin-1-ylidene)-1-(adamantan-1-yl)ethan-1-one TLC: Rf0.35 (hexane:ethyl acetate=4:1); NMR (CDCl$_3$): δ 11.57 (brs, 1H), 7.05 (d, J=2.4 Hz, 1H), 7.03 (d, J=8.4 Hz, 1H), 6.80 (dd, J=8.4, 2.4 Hz, 1H), 5.73 (s, 1H), 2.99 (s, 6H), 2.73 (s, 2H), 2.08-2.02 (m, 3H), 1.94-1.90 (m, 6H), 1.76-1.72 (m, 6H), 1.28 (s, 6H).

EXAMPLE 11(151)

(Z)-2-(7-amino-6-methoxy-3,3-dimethyl-3,4-dihydro-(2H)-isoquinolin-1-ylidene)-1-cyclohexylethan-1-one TLC: Rf0.26 (hexane:ethyl acetate=2:1); NMR (CDCl$_3$): δ 11.28 (br, 1H), 7.05 (s, 1H), 6.54 (s, 1H), 5.48 (s, 1H), 3.89 (s, 3H), 3.80 (br, 2H), 2.72 (s, 2H), 2.26 (tt, J=11.5, 3.5 Hz, 1H), 1.89-1.79 (m, 4H), 1.68 (m, 1H), 1.56-1.22 (m, 1H).

EXAMPLE 11(152)

(Z)-2-(7-amino-6-methoxy-3,3-dimethyl-3,4-dihydro-(2H)-isoquinolin-1-ylidene)-1-cycloheptylethan-1-one TLC: Rf0.31 (hexane:ethyl acetate=2:1); NMR (CDCl$_3$): δ 11.19 (br, 1H), 7.05 (s, 1H), 6.53 (s, 1H), 5.44 (s, 1H), 3.89 (s, 3H), 3.80 (br, 2H), 2.72 (s, 2H), 2.42 (m, 1H), 1.95-1.87 (m, 2H), 1.82-1.46 (m, 10H), 1.28 (s, 6H).

EXAMPLE 11(153)

(Z)-2-(7-bromo-6-chloro-3,3-dimethyl-3,4-dihydro-(2H)-isoquinolin-1-ylidene)-1-cyclohexylethan-1-one TLC: Rf0.25 (ethyl acetate:hexane=1:5); NMR (CDCl$_3$): δ 11.19 (br, 1H), 7.91 (s, 1H), 7.28 (s, 1H), 5.54 (s, 1H), 2.76 (s, 2H), 2.31 (m, 1H), 1.90-1.20 (m, 10H), 1.29 (s, 6H).

EXAMPLE 11(154)

(Z)-2-(7-bromo-6-chloro-3,3-dimethyl-3,4-dihydro-(2H)-isoquinolin-1-ylidene)-1-cycloheptylethan-1-one TLC: Rf0.24 (ethyl acetate:hexane=1:5); NMR (CDCl$_3$): δ 11.11 (br, 1H), 7.91 (s, 1H), 7.28 (s, 1H), 5.51 (s, 1H), 2.76 (s, 2H), 2.48 (m, 1H), 1.95-1.40 (m, 12H), 1.28 (s, 6H).

EXAMPLE 11(155)

(Z)-2-(7-nitro-3,3-dimethyl-3,4-dihydro-(2H)-iso-quinolin-1-ylidene)-1-cyclohexylethan-1-one TLC: Rf0.67 (ethyl acetate:hexane=2:3); NMR (CDCl$_3$): δ 11.23 (br, 1H), 8.56 (d, J=2.5 Hz, 1H), 8.24 (dd, J=8.0, 2.5 Hz, 1H), 7.37 (d, J=8.0 Hz, 1H), 5.71 (s, 1H), 2.95 (s, 2H), 2.37 (m, 1H), 1.95-1.20 (m, 10H), 1.31 (s, 6H).

EXAMPLE 11(156)

(Z)-2-(7-bromo-6-methoxy-3,3-dimethyl-3,4-dihydro-(2H)-isoquinolin-1-ylidene)-1-(adamantan-1-yl)ethan-1-one TLC: Rf0.28 (hexane:ethyl acetate=3:1); NMR (CDCl$_3$): δ 11.45 (br, 1H), 7.86 (s, 1H), 6.67 (s, 1H), 5.65 (s, 1H), 3.94 (s, 3H), 2.78 (s, 2H), 2.06 (br, 3H), 1.91 (br, 6H), 1.75 (br, 6H), 1.29 (s, 6H).

EXAMPLE 11(157)

(Z)-2-(7-nitro-3,3-dimethyl-3,4-dihydro-(2H)-isoquinolin-1-ylidene)-1-(adamantan-1-yl)ethan-1-one TLC: Rf0.63 (hexane:ethyl acetate=1:1); NMR (CDCl$_3$): δ 11.45 (brs, 1H), 8.56 (d, J=2.1 Hz, 1H), 8.24 (dd, J=8.1, 2.1 Hz, 1H), 7.37 (d, J=8.1 Hz, 1H), 5.85 (s, 1H), 2.94 (s, 2H), 2.12-2.06 (m, 3H), 1.94-1.90 (m, 6H), 1.78-1.74 (m, 6H), 1.31 (s, 6H).

EXAMPLE 11(158)

(Z)-2-(7-dimethylamino-3,3-dimethyl-3,4-dihydro-(2H)-isoquinolin-1-ylidene)-1-cyclohexylethan-1-one TLC: Rf0.24 (hexane:ethyl acetate=4:1); NMR (CDCl$_3$): δ 11.40 (brs, 1H), 7.03 (d, J=8.4 Hz, 1H), 7.03 (d, J=2.4 Hz, 1H), 6.80 (dd, J=8.4, 2.4 Hz, 1H), 5.57 (s, 1H), 2.99 (s, 6H), 2.73 (s, 2H), 2.31 (m, 1H), 1.93-1.10 (m, 10H), 1.28 (s, 6H).

EXAMPLE 11(159)

(Z)-2-(7-dimethylamino-3,3-dimethyl-3,4-dihydro-(2H)-isoquinolin-1-ylidene)-1-cycloheptylethan-1-one TLC: Rf0.26 (hexane:ethyl acetate=4:1); NMR (CDCl$_3$): δ 11.32 (brs, 1H), 7.03 (d, J=8.4 Hz, 1H), 7.02 (d, J=2.4 Hz, 1H), 6.80 (dd, J=8.4, 2.4 Hz, 1H), 5.54 (s, 1H), 2.99 (s, 6H), 2.73 (s, 2H), 2.47 (m, 1H), 1.97-1.40 (m, 12H), 1.28 (s, 6H).

EXAMPLE 11(160)

(Z)-2-(7-methylamino-3,3-dimethyl-3,4-dihydro-(2H)-isoquinolin-1-ylidene)-1-cyclohexylethan-1-one TLC: Rf0.55 (hexane:ethyl acetate=2:1); NMR (CDCl$_3$): δ 11.34 (brs, 1H), 6.98 (d, J=8.1 Hz, 1H), 6.91 (d, J=2.4 Hz, 1H), 6.66 (dd, J=8.1, 2.4 Hz, 1H), 5.56 (s, 1H), 3.76 (brs, 1H), 2.89 (s, 3H), 2.72 (s, 2H), 2.29 (m, 1H), 1.93-1.10 (m, 10H), 1.27 (s, 6H).

EXAMPLE 11(161)

(Z)-2-(7-methylamino-3,3-dimethyl-3,4-dihydro-(2H)-isoquinolin-1-ylidene)-1-cycloheptylethan-1-one TLC: Rf0.59 (hexane:ethyl acetate=2:1); NMR (CDCl$_3$): δ 11.26 (brs, 1H), 6.98 (d, J=8.4 Hz, 1H), 6.91 (d, J=2.4 Hz, 1H), 6.66 (dd, J=8.4, 2.4 Hz, 1H), 5.53 (s, 1H), 3.77 (brs, 1H), 2.89 (s, 3H), 2.71 (s, 2H), 2.45 (m, 1H), 1.97-1.42 (m, 12H), 1.27 (s, 6H).

EXAMPLE 11(162)

(Z)-2-(7-methylamino-3,3-dimethyl-3,4-dihydro-(2H)-isoquinolin-1-ylidene)-1-(4-cyanophenyl)ethan-1-one TLC: Rf0.19 (hexane:ethyl acetate=3:1); NMR (CDCl$_3$): δ 11.97 (br, 1H), 8.00 (d, J=8.7 Hz, 2H), 7.72 (d, J=8.7 Hz, 2H), 7.05 (d, J=8.1 Hz, 1H), 6.99 (d, J=2.4 Hz, 1H), 6.73 (dd, J=8.1, 2.4 Hz, 1H), 6.19 (s, 1H), 3.90 (br, 1H), 2.91 (s, 3H), 2.80 (s, 2H), 1.36 (s, 6H).

EXAMPLE 11(163)

(Z)-2-(7-cyano-6-methoxy-3,3-dimethyl-3,4-dihydro-(2H)-isoquinolin-1-ylidene)-1-(4-cyanophenyl)ethan-1-one TLC: Rf0.23 (hexane:ethyl acetate=1:1); NMR (CDCl$_3$): δ 11.88 (br, 1H), 8.03-8.00 (m, 3H), 7.75 (d, J=8.5 Hz, 2H), 6.82 (s, 1H), 6.16 (s, 1H), 4.02 (s, 3H), 2.95 (s, 2H), 1.39 (s, 6H).

EXAMPLE 11(164)

(Z)-2-(7-methylamino-3,3-dimethyl-3,4-dihydro-(2H)-isoquinolin-1-ylidene)-1-(adamantan-1-yl)ethan-1-one TLC: Rf0.55 (hexane:ethyl acetate=3:1); NMR (CDCl$_3$): δ 11.51 (br, 1H), 6.99 (d, J=8.1 Hz, 1H), 6.94 (d, J=2.4 Hz, 1H), 6.66 (dd, J=8.1, 2.4 Hz, 1H), 5.70 (s, 1H), 3.78 (br, 1H), 2.89 (s, 3H), 2.72 (s, 2H), 2.05 (s, 3H), 1.91 (br, 6H), 1.74 (br, 6H), 1.27 (s, 6H).

EXAMPLE 11(165)

(Z)-2-(7-cyano-6-methoxy-3,3-dimethyl-3,4-dihydro-(2H)-isoquinolin-1-ylidene)-1-(adamantan-1-yl)ethan-1-one TLC: Rf0.23 (hexane:ethyl acetate=2:1); NMR (CDCl$_3$): δ 11.41 (br, 1H), 7.93 (s, 1H), 6.76 (s, 1H), 5.67 (s, 1H), 3.99 (s, 3H), 2.86 (s, 2H), 2.07 (br, 3H), 1.90 (br, 6H), 1.75 (br, 6H), 1.30 (s, 6H).

EXAMPLE 11(166)

(Z)-2-(7-cyano-6-methoxy-3,3-dimethyl-3,4-dihydro-(2H)-isoquinolin-1-ylidene)-1-cyclohexylethan-1-one TLC: Rf0.22 (hexane:ethyl acetate=2:1); NMR (CDCl$_3$): δ 11.25 (br, 1H), 7.91 (s, 1H), 6.76 (s, 1H), 5.53 (s, 1H), 3.98 (s, 3H), 2.87 (s, 2H), 2.30 (m, 1H), 1.89-1.80 (m, 4H), 1.70 (m, 1H), 1.57-1.16 (m, 1H).

EXAMPLE 11(167)

(Z)-2-(7-cyano-6-methoxy-3,3-dimethyl-3,4-dihydro-(2H)-isoquinolin-1-ylidene)-1-cycloheptylethan-1-one TLC: Rf0.26 (hexane:ethyl acetate=2:1); NMR (CDCl$_3$): δ 11.16 (br, 1H), 7.91 (s, 1H), 6.75 (s, 1H), 5.49 (s, 1H), 3.98 (s, 3H), 2.86 (s, 2H), 2.46 (m, 1H), 1.95-1.87 (m, 2H), 1.82-1.47 (m, 10H), 1.30 (s, 6H).

EXAMPLE 11(168)

(Z)-2-(7-bromo-3,3-dimethyl-3,4-dihydro-(2H)-isoquinolin-1-ylidene)-1-(adamantan-1-yl)ethan-1-one TLC: Rf0.36 (hexane:ethyl acetate=4:1); NMR (CDCl$_3$): δ 11.42 (brs, 1H), 7.82 (d, J=1.8 Hz, 1H), 7.50 (dd, J=7.8, 1.8 Hz, 1H), 7.06 (d, J=7.8 Hz, 1H), 5.71 (s, 1H), 2.78 (s, 2H), 2.10-2.04 (m, 3H), 1.93-1.89 (m, 6H), 1.78-1.73 (m, 6H), 1.31 (s, 6H).

EXAMPLE 11(169)

(Z)-2-(7-dimethylaminomethyl-6-methoxy-3,3-dimethyl-3,4-dihydro-(2H)-isoquinolin-1-ylidene)-1-cycloheptylethan-1-one TLC: Rf0.42 (chloroform:methanol=10:1); NMR (CDCl$_3$): δ 11.28 (br, 1H), 7.59 (s, 1H), 6.62 (s, 1H), 5.55 (s, 1H), 3.87 (s, 3H), 3.45 (s, 2H), 2.80 (s, 2H), 2.46 (m, 1H), 2.29 (s, 6H), 1.95-1.87 (m, 2H), 1.82-1.47 (m, 10H), 1.29 (s, 6H).

EXAMPLE 11(170)

(Z)-2-(7-bromo-6-methoxy-3,3-dimethyl-3,4-dihydro-(2H)-isoquinolin-1-ylidene)-1-cyclohexylethan-1-one TLC: Rf0.27 (hexane:ethyl acetate=3:1); NMR (CDCl$_3$): δ 11.24 (br, 1H), 7.86 (s, 1H), 6.67 (s, 1H), 5.51 (s, 1H), 3.94 (s, 3H), 2.79 (s, 2H), 2.29 (tt, J=11.5, 3.5 Hz, 1H), 1.89-1.79 (m, 4H), 1.71-1.20 (m, 12H).

EXAMPLE 11(171)

(Z)-2-(7-dimethylaminomethyl-6-methoxy-3,3-dimethyl-3,4-dihydro-(2H)-isoquinolin-1-ylidene)-1-cyclohexylethan-1-one TLC: Rf0.42 (chloroform:methanol=10:1); NMR (CDCl$_3$): δ 11.35 (br, 1H), 7.60 (s, 1H), 6.63 (s, 1H), 5.58 (s, 1H), 3.87 (s, 3H), 3.45 (s, 2H), 2.81 (s, 2H), 2.37-2.25 (m, 7H), 1.88-1.79 (m, 4H), 1.71-1.20 (m, 12H).

EXAMPLE 11(172)

(Z)-2-(7-nitro-3,3,6-trimethyl-3,4-dihydro-(2H)-isoquinolin-1-ylidene)-1-(adamantan-1-yl)ethan-1-one TLC: Rf0.33 (hexane:ethyl acetate=5:1); NMR (CDCl$_3$): δ 11.42 (br, 1H), 8.33 (s, 1H), 7.16 (s, 1H), 5.79 (s, 1H), 2.86 (s, 2H), 2.64 (s, 3H), 2.07 (br, 3H), 1.91-1.90 (br, 6H), 1.76-1.75 (br, 6H), 1.31 (s, 6H).

EXAMPLE 11(173)

(Z)-2-(6-methoxy-7-methylaminomethyl-3,3-dimethyl-3,4-dihydro-(2H)-isoquinolin-1-ylidene)-1-cyclohexylethan-1-one TLC: Rf0.28 (chloroform:methanol=10:1); NMR (CDCl$_3$): δ 11.31 (br, 1H), 7.57 (s, 1H), 6.62 (s, 1H), 5.58 (s, 1H), 3.88 (s, 3H), 3.75 (s, 2H), 2.80 (s, 2H), 2.47 (s, 3H), 2.29 (tt, J=11.5, 3.5 Hz, 1H), 1.89-1.79 (m, 4H), 1.71-1.20 (m, 12H).

EXAMPLE 11(174)

(Z)-2-(7-dimethylaminomethyl-6-methoxy-3,3-dimethyl-3,4-dihydro-(2H)-isoquinolin-1-ylidene)-1-(4-cyanophenyl)ethan-1-one TLC: Rf0.47 (chloroform:methanol=10:1); NMR (CDCl$_3$): δ 11.99 (br, 1H), 8.02 (d, J=8.5 Hz, 2H), 7.74-7.71 (m, 3H), 6.69 (s, 1H), 6.22 (s, 1H), 3.91 (s, 3H), 3.49 (s, 2H), 2.89 (s, 2H), 2.31 (s, 6H), 1.38 (s, 6H).

EXAMPLE 11(175)

(Z)-2-(7-nitro-3,3,6-trimethyl-3,4-dihydro-(2H)-isoquinolin-1-ylidene)-1-(4-cyanophenyl)ethan-1-one TLC: Rf0.89 (chloroform:methanol=50:1); NMR (CDCl$_3$): δ 11.88 (br, 1H), 8.44 (s, 1H), 8.03 (d, J=8.7 Hz, 2H), 7.76 (d, J=8.7 Hz, 2H), 7.24 (s, 1H), 6.28 (s, 1H), 2.95 (s, 2H), 2.68 (s, 3H), 1.40 (s, 6H).

EXAMPLE 11(176)

(Z)-2-(7-nitro-3,3,6-trimethyl-3,4-dihydro-(2H)-isoquinolin-1-ylidene)-1-cyclohexylethan-1-one TLC: Rf0.25 (hexane:ethyl acetate=4:1); NMR (CDCl$_3$): δ 11.25 (brs, 1H), 8.34 (s, 1H), 7.16 (s, 1H), 5.65 (s, 1H), 2.87 (s, 2H), 2.65 (s, 3H), 2.34 (tt, J=11.4, 3.3 Hz, 1H), 1.93-1.65 (m, 5H), 1.58-1.18 (m, 1H).

EXAMPLE 11(177)

(Z)-2-(7-nitro-3,3,6-trimethyl-3,4-dihydro-(2H)-isoquinolin-1-ylidene)-1-cycloheptylethan-1-one TLC: Rf0.27 (hexane:ethyl acetate=4:1); NMR (CDCl$_3$): δ 11.17 (brs, 1H), 8.34 (s, 1H), 7.16 (s, 1H), 5.62 (s, 1H), 2.86 (s, 2H), 2.65 (s, 3H), 2.51 (tt, J=9.9, 3.9 Hz, 1H), 1.97-1.44 (m, 12H), 1.30 (s, 6H).

EXAMPLE 11(178)

(Z)-2-(7-methylamino-3,3,6-trimethyl-3,4-dihydro-(2H)-isoquinolin-1-ylidene)-1-cyclohexylethan-1-one TLC: Rf0.55 (hexane:ethyl acetate=2:1); NMR (CDCl$_3$): δ 11.37 (brs, 1H), 6.86 (s, 1H), 6.84 (s, 1H), 5.58 (s, 1H), 3.58 (brs, 1H), 2.97 (s, 3H), 2.70 (s, 2H), 2.31 (tt, J=12.0, 3.3 Hz, 1H), 2.15 (s, 3H), 1.92-1.18 (m, 16H).

EXAMPLE 11(179)

(Z)-2-(7-methylamino-3,3,6-trimethyl-3,4-dihydro-(2H)-isoquinolin-1-ylidene)-1-cycloheptylethan-1-one TLC: Rf0.59 (hexane:ethyl acetate=2:1); NMR (CDCl$_3$): δ 11.29 (brs, 1H), 6.86 (s, 1H), 6.84 (s, 1H), 5.55 (s, 1H), 3.58 (brs, 1H), 2.97 (s, 3H), 2.70 (s, 2H), 2.47 (tt, J=9.9, 3.9 Hz, 1H), 2.15 (s, 3H), 1.97-1.43 (m, 12H), 1.28 (s, 6H).

EXAMPLE 11(180)

(Z)-2-(7-methylamino-3,3,6-trimethyl-3,4-dihydro-(2H)-isoquinolin-1-ylidene)-1-(adamantan-1-yl)ethan-1-one TLC: Rf0.61 (hexane:ethyl acetate=2:1); NMR (CDCl₃): δ 11.55 (brs, 1H), 6.88 (s, 1H), 6.84 (s, 1H), 5.74 (s, 1H), 3.58 (brs, 1H), 2.97 (s, 3H), 2.70 (s, 2H), 2.16 (s, 3H), 2.08-2.02 (m, 3H), 1.94-1.90 (m, 6H), 1.76-1.72 (m, 6H), 1.28 (s, 6H).

EXAMPLE 11(181)

(Z)-2-(7-bromo-6-methoxy-3,3-dimethyl-3,4-dihydro-(2H)-isoquinolin-1-ylidene)-1-cycloheptylethan-1-one TLC: Rf0.39 (hexane:ethyl acetate=2:1); NMR (CDCl₃): δ 11.16 (br, 1H), 7.86 (s, 1H), 6.67 (s, 1H), 5.48 (s, 1H), 3.94 (s, 3H), 2.78 (s, 2H), 2.46 (m, 1H), 1.94-1.50 (m, 12H), 1.29 (s, 6H).

EXAMPLE 11(182)

(Z)-2-(6,7-dicyano-3,3-dimethyl-3,4-dihydro-(2H)-isoquinolin-1-ylidene)-1-cyclohexylethan-1-one TLC: Rf0.35 (hexane:ethyl acetate=2:1); NMR (CDCl₃): δ 11.07 (brs, 1H), 8.09 (s, 1H), 7.63 (s, 1H), 5.64 (s, 1H), 2.94 (s, 2H), 2.35 (m, 1H), 1.93-1.75 (m, 5H), 1.56-1.20 (m, 1H).

EXAMPLE 11(183)

(Z)-2-(6,7-dicyano-3,3-dimethyl-3,4-dihydro-(2H)-isoquinolin-1-ylidene)-1-(adamantan-1-yl)ethan-1-one TLC: Rf0.37 (hexane:ethyl acetate=2:1); NMR (CDCl₃): δ 11.22 (brs, 1H), 8.10 (s, 1H), 7.63 (s, 1H), 5.78 (s, 1H), 2.94 (s, 2H), 2.12-2.05 (m, 3H), 1.91-1.87 (m, 6H), 1.83-1.69 (m, 6H), 1.31 (s, 6H).

EXAMPLE 11(184)

(Z)-2-(7-bromo-3,3,6-trimethyl-3,4-dihydro-(2H)-isoquinolin-1-ylidene)-1-(adamantan-1-yl)ethan-1-one TLC: Rf0.33 (hexane:ethyl acetate=9:1); NMR (CDCl₃): δ 11.40 (br, 1H), 7.83 (s, 1H), 7.04 (s, 1H), 5.69 (s, 1H), 2.74 (s, 2H), 2.42 (s, 3H), 2.06 (br, 3H), 1.91-1.90 (br, 6H), 1.76-1.75 (br, 6H), 1.28 (s, 6H).

EXAMPLE 11(185)

(Z)-2-(6,7-dicyano-3,3-dimethyl-3,4-dihydro-(2H)-isoquinolin-1-ylidene) 1-cycloheptylethan-1-one TLC: Rf0.30 (hexane:ethyl acetate=2:1); NMR (CDCl₃): δ 10.98 (brs, 1H), 8.09 (s, 1H), 7.63 (s, 1H), 5.60 (s, 1H), 2.94 (s, 2H), 2.52 (m, 1H), 1.96-1.44 (m, 12H), 1.31 (s, 6H).

EXAMPLE 11(186)

(Z)-2-(6,7-dicyano-3,3-dimethyl-3,4-dihydro-(2H)-isoquinolin-1-ylidene)-1-(4-cyanophenyl)ethan-1-one TLC: Rf0.68 (chloroform:methanol=9:1); NMR (DMSO-d₆): δ 11.77 (brs, 1H), 9.01 (s, 1H), 8.25 (d, J=8.4 Hz, 2H), 8.17 (s, 1H), 7.97 (d, J=8.4 Hz, 2H), 6.75 (s, 1H), 3.09 (s, 2H), 1.30 (s, 6H).

EXAMPLE 11(187)

(Z)-2-(7-methylamino-3,3,6-trimethyl-3,4-dihydro-(2H)-isoquinolin-1-ylidene)-1-(4-cyanophenyl)ethan-1-one TLC: Rf0.50 (hexane:ethyl acetate=1:1); NMR (CDCl₃): δ 11.98 (brs, 1H), 8.01 (d, J=8.7 Hz, 2H), 7.72 (d, J=8.7 Hz, 2H), 6.92 (s, 1H), 6.91 (s, 1H), 6.22 (s, 1H), 3.66 (brs, 1H), 2.99 (s, 3H), 2.78 (s, 2H), 2.19 (s, 3H), 1.36 (s, 6H).

EXAMPLE 11(188)

(Z)-2-(7-bromo-3,3-dimethyl-3,4-dihydro-(2H)-isoquinolin-1-ylidene)-1-cyclohexylethan-1-one TLC: Rf0.41 (hexane:ethyl acetate=4:1); NMR (CDCl₃): δ 11.23 (brs, 1H), 7.81 (d, J=2.1 Hz, 1H), 7.50 (dd, J=8.1, 2.1 Hz, 1H), 7.05 (d, J=8.1 Hz, 1H), 5.57 (s, 1H), 2.78 (s, 2H), 2.31 (tt, J=11.4, 3.3 Hz, 1H), 1.92-1.65 (m, 5H), 1.58-1.18 (m, 1H).

EXAMPLE 11(189)

(Z)-2-(7-bromo-3,3,6-trimethyl-3,4-dihydro-(2H)-isoquinolin-1-ylidene)-1-cyclohexylethan-1-one TLC: Rf0.41 (hexane:ethyl acetate=4:1); NMR (CDCl₃): δ 11.22 (br, 1H), 7.83 (s, 1H), 7.04 (s, 1H), 5.55 (s, 1H), 2.74 (s, 2H), 2.41 (s, 3H), 2.30 (m, 1H), 1.92-1.20 (m, 16H).

EXAMPLE 11(190)

(Z)-2-(6-chloro-7-methylamino-3,3-dimethyl-3,4-dihydro-(2H)-isoquinolin-1-ylidene)-1-cyclohexylethan-1-one TLC: Rf0.34 (ethyl acetate:hexane=1:5); NMR (CDCl₃): δ 11.34 (br, 1H), 7.07 (s, 1H), 6.90 (s, 1H), 5.55 (s, 1H), 4.33 (br, 1H), 2.98 (d, J=4.5 Hz, 3H), 2.69 (s, 2H), 2.31 (m, 1H), 1.90-1.20 (m, 10H), 1.27 (s, 6H).

EXAMPLE 11(191)

(Z)-2-(6-chloro-7-methylamino-3,3-dimethyl-3,4-dihydro-(2H)-isoquinolin-1-ylidene)-1-cycloheptylethan-1-one TLC: Rf0.38 (ethyl acetate:hexane=1:5); NMR (CDCl₃): δ 11.27 (br, 1H), 7.07 (s, 1H), 6.90 (s, 1H), 5.52 (s, 1H), 4.33 (br, 1H), 2.98 (d, J=3.5 Hz, 3H), 2.70 (s, 2H), 2.48 (m, 1H), 1.95-1.40 (m, 12H), 1.27 (s, 6H).

EXAMPLE 11(192)

(Z)-2-(6-chloro-7-methylamino-3,3-dimethyl-3,4-dihydro-(2H)-isoquinolin-1-ylidene)-1-(adamantan-1-yl)ethan-1-one TLC: Rf0.41 (ethyl acetate:hexane=1:5); NMR (CDCl$_3$): δ 11.53 (br, 1H), 7.07 (s, 1H), 6.92 (s, 1H), 5.71 (s, 1H), 4.33 (br, 1H), 2.99 (s, 3H), 2.70 (s, 2H), 2.06 (m, 3H), 1.92 (m, 6H), 1.75 (m, 6H), 1.28 (s, 6H).

EXAMPLE 11(193)

(Z)-2-(7-bromo-3,3-dimethyl-3,4-dihydro-(2H)-isoquinolin-1-ylidene)-1-cycloheptylethan-1-one TLC: Rf0.39 (hexane:ethyl acetate=4:1); NMR (CDCl$_3$): δ 11.14 (brs, 1H), 7.81 (d, J=1.8 Hz, 1H), 7.50 (dd, J=7.8, 1.8 Hz, 1H), 7.05 (d, J=7.8 Hz, 1H), 5.54 (s, 1H), 2.78 (s, 2H), 2.48 (tt, J=9.9, 3.9 Hz, 1H), 1.97-1.43 (m, 12H), 1.28 (s, 6H).

EXAMPLE 11(194)

(Z)-2-(7-bromo-3,3,6-trimethyl-3,4-dihydro-(2H)-isoquinolin-1-ylidene)-1-cycloheptylethan-1-one TLC: Rf0.60 (hexane:ethyl acetate=5:1); NMR (CDCl$_3$): δ 11.15 (br, 1H), 7.83 (s, 1H), 7.04 (s, 1H), 5.52 (s, 1H), 2.74 (s, 2H), 2.41 (s, 3H), 2.46 (m, 1H), 1.96-1.46 (m, 12H), 1.28 (s, 6H).

EXAMPLE 11(195)

(Z)-2-(7-nitro-3,3-dimethyl-3,4-dihydro-(2H)-isoquinolin-1-ylidene)-1-cycloheptylethan-1-one TLC: Rf0.57 (hexane:ethyl acetate=1:1); NMR (CDCl$_3$): δ 11.15 (brs, 1H), 8.56 (d, J=2.1 Hz, 1H), 8.24 (dd, J=8.7, 2.1 Hz, 1H), 7.37 (d, J=8.7 Hz, 1H), 5.68 (s, 1H), 2.94 (s, 2H), 2.53 (tt, J=9.9, 3.9 Hz, 1H), 1.98-1.46 (m, 12H), 1.31 (s, 6H).

EXAMPLE 11(196)

(Z)-2-(7-dimethylsulfamoyl-3,3-dimethyl-3,4-dihydro-(2H)-isoquinolin-1-ylidene)-1-(adamantan-1-yl)ethan-1-one TLC: Rf0.53 (hexane:ethyl acetate=1:1); NMR (CDCl$_3$): δ 11.51 (brs, 1H), 8.08 (d, J=1.8 Hz, 1H), 7.77 (dd, J=7.8, 1.8 Hz, 1H), 7.36 (d, J=1.8 Hz, 1H), 5.79 (s, 1H), 2.92 (s, 2H), 2.77 (s, 6H), 2.10-2.03 (m, 3H), 1.92-1.88 (m, 6H), 1.77-1.72 (m, 6H), 1.31 (s, 6H).

EXAMPLE 11(197)

(Z)-2-(7-butoxycarbonyl-6-chloro-3,3-dimethyl-3,4-dihydro-(2H)-isoquinolin-1-ylidene)-1-(adamantan-1-yl)ethan-1-one TLC: Rf0.40 (hexane:ethyl acetate=4:1); NMR (CDCl$_3$): δ 11.38 (brs, 1H), 8.18 (s, 1H), 7.28 (s, 1H), 5.78 (s, 1H), 4.39 (t, J=6.6 Hz, 2H), 2.83 (s, 2H), 2.10-2.02 (m, 3H), 1.93-1.88 (m, 6H), 1.84-1.72 (m, 8H), 1.61-1.48 (m, 8H), 1.01 (t, J=7.2 Hz, 3H).

EXAMPLE 11(198)

(Z)-2-(7-butoxycarbonyl-6-chloro-3,3-dimethyl-3,4-dihydro-(2H)-isoquinolin-1-ylidene)-1-cycloheptylethan-1-one TLC: Rf0.38 (hexane:ethyl acetate=4:1); NMR (CDCl$_3$): δ 11.12 (brs, 1H), 8.15 (s, 1H), 7.28 (s, 1H), 5.59 (s, 1H), 4.39 (t, J=6.6 Hz, 2H), 2.83 (s, 2H), 2.48 (tt, J=9.9, 3.9 Hz, 1H), 1.96-1.43 (m, 16H), 1.29 (s, 6H), 1.01 (t, J=7.2 Hz, 3H).

EXAMPLE 11(199)

(Z)-2-(7-methylsulfamoyl-3,3-dimethyl-3,4-dihydro-(2H)-isoquinolin-1-ylidene)-1-(adamantan-1-yl)ethan-1-one TLC: Rf0.39 (hexane:ethyl acetate=1:1); NMR (CDCl$_3$): δ 11.50 (brs, 1H), 8.17 (d, J=1.8 Hz, 1H), 7.86 (dd, J=7.8, 1.8 Hz, 1H), 7.35 (d, J=7.8 Hz, 1H), 5.81 (s, 1H), 4.41 (q, J=5.4 Hz, 1H), 2.91 (s, 2H), 2.72 (d, J=5.4 Hz, 3H), 2.10-2.03 (m, 3H), 1.92-1.87 (m, 6H), 1.77-1.73 (m, 6H), 1.31 (s, 6H).

EXAMPLE 11(200)

(Z)-2-(6-chloro-7-methoxy-3,3-dimethyl-3,4-dihydro-(2H)-isoquinolin-1-ylidene)-1-(adamantan-1-yl)ethan-1-one TLC: Rf0.33 (ethyl acetate:hexane=5:1); NMR (CDCl$_3$): δ 11.53 (br, 1H), 7.21 (s, 1H), 7.19 (s, 1H), 5.68 (s, 1H), 3.99 (s, 3H), 2.74 (s, 2H), 2.06 (m, 3H), 1.91 (m, 6H), 1.75 (m, 6H), 1.28 (s, 6H).

EXAMPLE 11(201)

(Z)-2-(7-methoxy-3,3,6-trimethyl-3,4-dihydro-(2H)-isoquinolin-1-ylidene)-1-(adamantan-1-yl)ethan-1-one TLC: Rf0.39 (hexane:ethyl acetate=6:1); NMR (CDCl$_3$): δ 11.54 (br, 1H), 7.10 (s, 1H), 6.93 (s, 1H), 5.69 (s, 1H), 3.91 (s, 3H), 2.73 (s, 2H), 2.24 (s, 3H), 2.06 (br, 3H), 1.92-1.91 (br, 6H), 1.75 (br, 6H), 1.28 (s, 6H).

EXAMPLE 11(202)

(Z)-2-(7-methoxy-3,3,6-trimethyl-3,4-dihydro-(2H)-isoquinolin-1-ylidene)-1-cyclohexylethan-1-one TLC: Rf0.35 (hexane:ethyl acetate=6:1); NMR (CDCl$_3$): δ 11.34 (br, 1H), 7.09 (s, 1H), 6.92 (s, 1H), 5.54 (s, 1H), 3.90 (s, 3H), 2.73 (s, 2H), 2.31 (m, 1H), 2.24 (s, 3H), 1.92-1.18 (m, 16H).

EXAMPLE 11(203)

(Z)-2-(7-methoxy-3,3,6-trimethyl-3,4-dihydro-(2H)-isoquinolin-1-ylidene)-1-cycloheptylethan-1-one TLC: Rf0.31 (hexane:ethyl acetate=6:1); NMR (CDCl$_3$): δ 11.27 (br, 1H), 7.08 (s, 1H), 6.92 (s, 1H), 5.51 (s, 1H), 3.90 (s, 3H), 2.73 (s, 2H), 2.46 (m, 1H), 2.24 (s, 3H), 1.96-1.42 (m, 12H), 1.27 (s, 6H).

EXAMPLE 12-EXAMPLE 12(31)

By the same procedure as described in example 1 using the compound prepared in reference example 1 or a corresponding nitrile derivative, and 2-methyl-1-phenylpropan-2-ol or a corresponding alcohol derivative, the compound of the present invention were given. In example 12(20) and example 12(24), an operation converting to hydrochloride followed it.

EXAMPLE 12

(Z)-2-(6-bromo-3,3-dimethyl-3,4-dihydro-(2H)-isoquinolin-1-ylidene)-1-phenylethan-1-one TLC: Rf0.35 (hexane:ethyl acetate=5:1); NMR (CDCl$_3$): δ 11.78 (br, 1H), 7.95-7.92 (m, 2H), 7.69 (d, J=8.5 Hz, 1H), 7.49-7.38 (m, 5H), 6.28 (br, 1H), 2.87 (s, 2H), 1.37 (s, 6H).

EXAMPLE 12(1)

(Z)-2-(3,3-dimethyl-3,4-dihydro-(2H)-isoquinolin-1-ylidene)-1-(tetrahydropyran-4-yl)ethan-1-one TLC: Rf0.54 (ethyl acetate:hexane=1:1); NMR (CDCl$_3$): δ 11.35 (br, 1H), 7.70 (m, 1H), 7.41 (m, 1H), 7.30 (m, 1H), 7.19 (m, 1H), 5.63 (br, 1H), 4.05 (m, 2H), 3.46 (dt, J=11.5, 3.5 Hz, 2H), 2.86 (s, 2H), 2.54 (m, 1H), 1.90-1.70 (m, 4H), 1.31 (s, 6H).

EXAMPLE 12(2)

(Z)-2-(6-fluoro-3,3-dimethyl-3,4-dihydro-(2H)-isoquinolin-1-ylidene)-1-cyclohexylethan-1-one TLC: Rf0.35 (ethyl acetate:hexane=1:5); NMR (CDCl$_3$): δ 11.31 (br, 1H), 7.70 (dd, J=9.0, 5.5 Hz, 1H), 6.98 (ddd, J=9.0, 9.0, 2.5 Hz, 1H), 6.88 (dd, J=9.0, 2.5 Hz, 1H), 5.57 (s, 1H), 2.82 (s, 2H), 2.28 (m, 1H), 1.95-1.20 (m, 10H), 1.29 (s, 6H).

EXAMPLE 12(3)

(Z)-2-(6-chloro-3,3-dimethyl-3,4-dihydro-(2H)-isoquinolin-1-ylidene)-1-cyclohexylethan-1-one TLC: Rf0.40 (ethyl acetate:hexane=1:5); NMR (CDCl$_3$): δ 11.26 (br, 1H), 7.63 (d, J=9.0 Hz, 1H), 7.26 (dd, J=9.0, 2.5 Hz, 1H), 7.17 (d, J=2.5 Hz, 1H), 5.58 (s, 1H), 2.81 (s, 2H), 2.29 (m, 1H), 1.95-1.20 (m, 10H), 1.29 (s, 6H).

EXAMPLE 12(4)

(Z)-2-(6-fluoro-3,3-dimethyl-3,4-dihydro-(2H)-isoquinolin-1-ylidene)-1-cycloheptylethan-1-one TLC: Rf0.37 (ethyl acetate:hexane=1:5); NMR (CDCl$_3$): δ 11.22 (br, 1H), 7.70 (dd, J=9.0, 5.5 Hz, 1H), 6.97 (ddd, J=9.0, 9.0, 2.5 Hz, 1H), 6.87 (dd, J=9.0, 2.5 Hz, 1H), 5.53 (s, 1H), 2.82 (s, 2H), 2.45 (m, 1H), 2.00-1.40 (m, 12H), 1.29 (s, 6H).

EXAMPLE 12(5)

(Z)-2-(6-chloro-3,3-dimethyl-3,4-dihydro-(2H)-isoquinolin-1-ylidene)-1-cycloheptylethan-1-one TLC: Rf0.42 (ethyl acetate:hexane=1:5); NMR (CDCl$_3$): δ 11.17 (br, 1H), 7.63 (d, J=8.5 Hz, 1H), 7.25 (dd, J=8.5, 2.0 Hz, 1H), 7.17 (d, J=2.0 Hz, 1H), 5.55 (s, 1H), 2.80 (s, 2H), 2.45 (m, 1H), 2.00-1.40 (m, 12H), 1.29 (s, 6H).

EXAMPLE 12(6)

(Z)-2-(8-methoxy-3,3-dimethyl-3,4-dihydro-(2H)-isoquinolin-1-ylidene)-1-cyclohexylethan-1-one TLC: Rf0.42 (ethyl acetate:hexane=1:3); NMR (CDCl$_3$): δ 11.77 (br, 1H), 7.30 (dd, J=7.5, 7.5 Hz, 1H), 6.87 (d, J=7.5 Hz, 1H), 6.77 (d, J=7.5 Hz, 1H), 6.20 (s, 1H), 3.92 (s, 3H), 2.79 (s, 2H), 2.26 (m, 1H), 1.95-1.10 (m, 10H), 1.26 (s, 6H).

EXAMPLE 12(7)

(Z)-2-(6-methoxy-3,3-dimethyl-3,4-dihydro-(2H)-isoquinolin-1-ylidene)-1-cyclohexylethan-1-one TLC: Rf0.32 (ethyl acetate:hexane=1:3); NMR (CDCl$_3$): δ 11.33 (br, 1H), 7.65 (d, J=8.5 Hz, 1H), 6.80 (dd, J=8.5, 2.5 Hz, 1H), 6.67 (d, J=2.5 Hz, 1H), 5.55 (s, 1H), 3.85 (s, 3H), 2.80 (s, 2H), 2.27 (m, 1H), 1.95-1.10 (m, 10H), 1.29 (s, 6H).

EXAMPLE 12(8)

(Z)-2-(8-methoxy-3,3-dimethyl-3,4-dihydro-(2H)-isoquinolin-1-ylidene)-1-cycloheptylethan-1-one TLC: Rf0.46 (ethyl acetate:hexane=1:3); NMR (CDCl$_3$): δ 11.67 (br, 1H), 7.29 (dd, J=7.5, 7.5 Hz, 1H), 6.87 (d, J=7.5 Hz, 1H), 6.76 (d, J=7.5 Hz, 1H), 6.17 (s, 1H), 3.91 (s, 3H), 2.78 (s, 2H), 2.42 (m, 1H), 2.00-1.40 (m, 12H), 1.26 (s, 6H).

EXAMPLE 12(9)

(Z)-2-(6-methoxy-3,3-dimethyl-3,4-dihydro-(2H)-isoquinolin-1-ylidene)-1-cycloheptylethan-1-one TLC: Rf0.37 (ethyl acetate:hexane=1:3); NMR (CDCl$_3$): δ 11.25 (br, 1H), 7.65 (d, J=8.5 Hz, 1H), 6.80 (dd, J=8.5, 3.0 Hz, 1H), 6.67 (d, J=3.0 Hz, 1H), 5.52 (s, 1H), 3.85 (s, 3H), 2.80 (s, 2H), 2.43 (m, 1H), 2.00-1.40 (m, 12H), 1.29 (s, 6H).

EXAMPLE 12(10)

(Z)-2-(3,3,4,4-tetramethyl-3,4-dihydro-(2H)-isoquinolin-1-ylidene)-1-(2-methoxyphenyl)ethan-1-one TLC: Rf0.30 (hexane:ethyl acetate=3:1); NMR (CDCl$_3$): δ 11.63 (br, 1H), 7.74-7.68 (m, 2H), 7.49-7.25 (m, 4H), 7.03-6.95 (m, 2H), 6.26 (s, 1H), 3.92 (s, 3H), 1.31 (br, 12H).

EXAMPLE 12(11)

(Z)-2-(3,3,4,4-tetramethyl-3,4-dihydro-(2H)-isoquinolin-1-ylidene)-1-cyclohexylethan-1-one TLC: Rf0.58 (hexane:ethyl acetate=3:1); NMR (CDCl$_3$): δ 11.25 (br, 1H), 7.69 (dd, J=7.5, 1.0 Hz, 1H), 7.47-7.37 (m, 2H), 7.29-7.24 (m, 1H), 5.59 (s, 1H), 2.35-2.24 (m, 1H), 1.91-1.79 (m, 4H), 1.69-1.64 (m, 1H), 1.55-1.19 (m, 17H).

EXAMPLE 12(12)

(Z)-2-(3,3,4,4-tetramethyl-3,4-dihydro-(2H)-isoquinolin-1-ylidene)-1-cycloheptylethan-1-one TLC: Rf0.57 (hexane:ethyl acetate=3:1); NMR (CDCl$_3$): δ 11.16 (br, 1H), 7.68 (dd, J=8.0, 1.0 Hz, 1H), 7.47-7.37 (m, 2H), 7.29-7.24 (m, 1H), 5.56 (s, 1H), 2.50-2.41 (m, 1H), 1.96-1.90 (m, 2H), 1.83-1.43 (m, 10H), 1.26 (br, 12H).

EXAMPLE 12(13)

(Z)-2-(3,3-dimethyl-3,4-dihydro-(2H)-isoquinolin-1-ylidene)-1-(isoquinolin-1-yl)ethan-1-one TLC: Rf0.30 (hexane:ethyl acetate=2:1); NMR (CDCl$_3$): δ 11.79 (br, 1H), 8.86 (d, J=8.0 Hz, 1H), 8.55 (d, J=5.5 Hz, 1H), 7.88-7.84 (m, 2H), 7.72-7.59 (m, 3H), 7.42 (dt, J=1.0, 7.0 Hz, 1H), 7.33-7.27 (m, 1H), 7.21 (d, J=7.5 Hz, 1H), 6.54 (s, 1H), 2.94 (s, 2H), 1.42 (s, 6H).

EXAMPLE 12(14)

(Z)-2-(3,3-dimethyl-3,4-dihydro-(2H)-isoquinolin-1-ylidene)-1-(quinolin-4-yl)ethan-1-one TLC: Rf0.11 (hexane:ethyl acetate=2:1); NMR (CDCl$_3$): δ 11.84 (br, 1H), 8.96 (d, J=4.5 Hz, 1H), 8.42 (d, J=7.5 Hz, 1H), 8.14 (d, J=8.0 Hz, 1H), 7.75-7.69 (m, 2H), 7.57 (t, J=8.0 Hz, 1H), 7.51 (d, J=4.5 Hz, 1H), 7.45 (t, J=7.5 Hz, 1H), 7.33-7.23 (m, 2H), 6.02 (s, 1H), 2.97 (s, 2H), 1.43 (s, 6H).

EXAMPLE 12(15)

(Z)-2-(6-chloro-3,3-dimethyl-3,4-dihydro-(2H)-isoquinolin-1-ylidene)-1-(2-methoxyphenyl)ethan-1-one TLC: Rf0.44 (hexane:ethyl acetate=2:1); NMR (CDCl$_3$): δ 11.63 (br, 1H), 7.68-7.65 (m, 2H), 7.37 (ddd, J=8.0, 7.5, 2.0 Hz, 1H), 7.29-7.26 (m, 1H), 7.20 (d, J=2.0 Hz, 1H), 7.03-6.95 (m, 2H), 6.23 (s, 1H), 3.91 (s, 3H), 2.86 (s, 2H), 1.36 (s, 6H).

EXAMPLE 12(16)

(Z)-2-(6-chloro-3,3-dimethyl-3,4-dihydro-(2H)-isoquinolin-1-ylidene)-1-(2-chlorophenyl)ethan-1-one TLC: Rf0.38 (hexane:ethyl acetate=3:1); NMR (CDCl$_3$): δ 11.49 (br, 10H), 7.65 (d, J=8.5 Hz, 1H), 7.54-7.51 (m, 1H), 7.42-7.39 (m, 1H), 7.32-7.27 (m, 3H), 7.21 (d, J=2.0 Hz, 1H), 5.93 (s, 10H), 2.89 (s, 2H), 1.38 (s, 6H).

EXAMPLE 12(17)

(Z)-2-(3,3-dimethyl-3,4-dihydro-(2H)-isoquinolin-1-ylidene)-1-(quinolin-8-yl)ethan-1-one TLC: Rf0.17 (hexane:ethyl acetate=1:1); NMR (CDCl$_3$): δ 11.80 (br, 1H), 9.05 (dd, J=4.0, 2.0 Hz, 1H), 8.19 (dd, J=8.0, 2.0 Hz, 1H), 7.98 (dd, J=7.5, 1.5 Hz, 1H), 7.85 (dd, J=8.0, 1.5 Hz, 1H), 7.74 (d, J=7.5 Hz, 1H), 7.58 (dd, J=8.0, 7.5 Hz, 1H), 7.44-7.37 (m, 2H), 7.29-7.24 (m, 1H), 7.20 (d, J=7.5 Hz, 1H), 6.35 (s, 1H), 2.92 (s, 2H), 1.40 (s, 6H).

EXAMPLE 12(18)

(Z)-2-(6,8-dichloro-3,3-dimethyl-3,4-dihydro-(2H)-isoquinolin-1-ylidene)-1-phenylethan-1-one TLC: Rf0.52 (hexane:ethyl acetate=2:1); NMR (CDCl$_3$): δ 11.98 (brs, 1H), 7.93-7.89 (m, 2H), 7.47-7.41 (m, 4H), 7.14 (m, 1H), 6.79 (s, 1H), 2.83 (s, 2H), 1.33 (s, 6H).

EXAMPLE 12(19)

(Z)-2-(3,3-dimethyl-3,4-dihydro-(2H)-isoquinolin-1-ylidene)-1-(2-ethoxyphenyl)ethan-1-one TLC: Rf0.31 (hexane:ethyl acetate=3:1); NMR (CDCl$_3$): δ 11.70 (br, 1H), 7.81 (dd, J=7.5, 2.0 Hz, 1H), 7.77 (d, J=7.5 Hz, 1H), 7.43-7.27 (m, 3H), 7.20 (d, J=7.5 Hz, 1H), 7.01 (dt, J=1.0, 7.5 Hz, 1H), 6.95 (dd, J=7.5, 1.0 Hz, 1H), 6.55 (s, 1H), 4.15 (q, J=7.0 Hz, 2H), 2.90 (s, 2H), 1.49 (t, J=7.0 Hz, 3H), 1.36 (s, 6H).

EXAMPLE 12(20)

2-(3,3-dimethyl-3,4-dihydroisoquinolin-1-yl)-1-(adamantan-1-yl)propan-1-one, hydrochloride TLC: Rf0.40 (ethyl acetate:hexane=1:5); NMR (CDCl$_3$): δ 7.92 (d, J=7.5 Hz, 1H), 7.67 (dd, J=7.5, 7.5 Hz, 1H), 7.42 (dd, J=7.5, 7.5 Hz, 1H), 7.34 (d, J=7.5 Hz, 1H), 5.80 (q, J=7.0 Hz, 1H), 3.03 (s, 2H), 2.02 (m, 3H), 1.87 (m, 6H), 1.80-1.55 (m, 15H).

EXAMPLE 12(21)

(Z)-2-(3,3-dimethyl-3,4-dihydro-(2H)-isoquinolin-1-ylidene)-1-(4-chloro-2-methoxyphenyl)ethan-1-one TLC: Rf0.40 (hexane:ethyl acetate=3:1); NMR (CDCl$_3$): δ 11.70 (br, 1H), 7.73 (d, J=7.5 Hz, 1H), 7.64 (d, J=8.0 Hz, 1H), 7.41 (t, J=7.5 Hz, 1H), 7.31 (t, J=7.5 Hz, 1H), 7.20 (d, J=7.5 Hz, 1H), 6.99 (dd, J=8.0, 2.0 Hz, 1H), 6.94 (d, J=2.0 Hz, 1H), 6.25 (s, 1H), 3.91 (s, 3H), 2.89 (s, 2H), 1.35 (s, 6H).

EXAMPLE 12(22)

(Z)-2-(3,3-dimethyl-3,4-dihydro-(2H)-isoquinolin-1-ylidene)-1-(2-methoxy-4-methylthiophenyl)ethan-1-one TLC: Rf0.20 (hexane:ethyl acetate=3:1); NMR (CDCl$_3$): δ 11.70 (br, 1H), 7.74 (d, J=7.5 Hz, 1H), 7.69 (d, J=8.0 Hz, 1H), 7.40 (t, J=7.5 Hz, 1H), 7.30 (t, J=7.5 Hz, 1H), 7.19 (d, J=7.5 Hz, 1H), 6.87 (dd, J=8.0, 2.0 Hz, 1H), 6.83 (d, J=2.0 Hz, 1H), 6.34 (s, 1H), 3.92 (s, 3H), 2.89 (s, 2H), 2.52 (s, 3H), 1.35 (s, 6H).

EXAMPLE 12(23)

(Z)-2-(3,3-dimethyl-3,4-dihydro-(2H)-isoquinolin-1-ylidene)-1-(2-methoxy-4-mesylphenyl)ethan-1-one TLC: Rf0.15 (hexane:ethyl acetate=1:1); NMR (CDCl$_3$): δ 11.73 (br, 1H), 7.79 (d, J=8.0 Hz, 1H), 7.72 (d, J=7.5 Hz, 1H), 7.57 (dd, J=8.0, 1.5 Hz, 1H), 7.50 (d, J=1.5 Hz, 1H), 7.44 (t, J=7.5 Hz, 1H), 7.32 (t, J=7.5 Hz, 1H), 7.22 (d, J=7.5 Hz, 1H), 6.14 (s, 1H), 3.98 (s, 3H), 3.08 (s, 3H), 2.92 (s, 2H), 1.38 (s, 6H).

EXAMPLE 12(24)

2-(6-fluoro-3,3-dimethyl-3,4-dihydroisoquinolin-1-yl)-1-phenylpropan-1-one, hydrochloride TLC: Rf0.35 (ethyl acetate:hexane=1:3); NMR (CDCl₃):
δ 8.14 (d, J=8.0 Hz, 2H), 7.86 (dd, J=8.5, 5.0 Hz, 1H), 7.54 (m, 1H), 7.46 (m, 2H), 7.05 (ddd, J=8.5, 8.5, 2.5 Hz, 1H), 6.96 (dd, J=8.5, 2.5 Hz, 1H), 6.34 (q, J=6.5 Hz, 1H), 3.04 (d, J=17.0 Hz, 1H), 2.85 (d, J=17.0 Hz, 1H), 1.79 (d, J=6.5 Hz, 3H), 1.71 (s, 3H), 1.46 (s, 3H).

EXAMPLE 12(25)

(Z)-2-(6,7-dichloro-3,3-dimethyl-3,4-dihydro-(2H)-isoquinolin-1-ylidene) 1-phenylethan-1-one TLC: Rf0.23 (hexane:ethyl acetate=5:1); NMR (CDCl₃):
δ 11.72 (br, 1H), 7.96-7.93 (m, 2H), 7.88 (s, 1H), 7.48-7.43 (m, 3H), 7.33 (s, 1H), 6.24 (s, 1H), 2.85 (s, 2H), 1.36 (s, 6H).

EXAMPLE 12(26)

(Z)-2-(3,3-dimethyl-3,4-dihydro-(2H)-isoquinolin-1-ylidene)-1-(4-bromo-2-methoxyphenyl)ethan-1-one TLC: Rf0.29 (hexane:ethyl acetate=3:1); NMR (CDCl₃):
δ 11.70 (br, 1H), 7.72 (d, J=7.5 Hz, 1H), 7.57 (d, J=8.0 Hz, 1H), 7.41 (t, J=7.5 Hz, 1H), 7.31 (t, J=7.5 Hz, 1H), 7.20 (d, J=7.5 Hz, 1H), 7.15 (dd, J=8.0, 2.0 Hz, 1H), 7.10 (d, J=2.0 Hz, 1H), 6.24 (s, 1H), 3.91 (s, 3H), 2.89 (s, 2H), 1.35 (s, 6H).

EXAMPLE 12(27)

(Z)-2-(3,3-dimethyl-3,4-dihydro-(2H)-isoquinolin-1-ylidene)-1-(4-bromo-2-chlorophenyl)ethan-1-one TLC: Rf0.40 (hexane:ethyl acetate=3:1); NMR (CDCl₃):
δ 11.56 (br, 1H), 7.71 (d, J=7.5 Hz, 1H), 7.58 (m, 1H), 7.46-7.41 (m, 3H), 7.31 (t, J=7.5 Hz, 1H), 7.21 (d, J=7.5 Hz, 1H), 5.93 (s, 1H), 2.91 (s, 2H), 1.37 (s, 6H).

EXAMPLE 12(28)

(Z)-2-(6-bromo-3,3-dimethyl-3,4-dihydro-(2H)-isoquinolin-1-ylidene) 1-cyclohexylethan-1-one TLC: Rf0.42 (hexane:ethyl acetate=5:1); NMR (CDCl₃):
δ 11.25 (br, 1H), 7.56 (d, J=8.5 Hz, 1H), 7.42 (dd, J=8.5, 2.0 Hz, 1H), 7.33 (d, J=2.0 Hz, 1H), 5.59 (s, 1H), 2.81 (s, 2H), 2.29 (m, 1H), 1.89-1.79 (m, 4H), 1.69 (m, 1H), 1.55-1.24 (m, 1H).

EXAMPLE 12(29)

(Z)-2-(6-bromo-3,3-dimethyl-3,4-dihydro-(2H)-isoquinolin-1-ylidene)-1-cycloheptylethan-1-one TLC: Rf0.42 (hexane:ethyl acetate=5:1); NMR (CDCl₃):
δ 11.16 (br, 1H), 7.56 (d, J=8.5 Hz, 1H), 7.42 (dd, J=8.5, 2.0 Hz, 1H), 7.33 (d, J=2.0 Hz, 1H), 5.55 (s, 1H), 2.81 (s, 2H), 2.45 (m, 1H), 1.95-1.85 (m, 2H), 1.82-1.45 (m, 10H), 1.29 (s, 6H).

EXAMPLE 12(30)

(Z)-2-(6-bromo-3,3-dimethyl-3,4-dihydro-(2H)-isoquinolin-1-ylidene)-1-(adamantan-1-yl)ethan-1-one TLC: Rf0.41 (hexane:ethyl acetate=5:1); NMR (CDCl₃):
δ 11.42 (br, 1H), 7.58 (d, J=8.5 Hz, 1H), 7.42 (dd, J=8.5, 2.0 Hz, 1H), 7.33 (d, J=2.0 Hz, 1H), 5.74 (s, 1H), 2.81 (s, 2H), 2.05 (br, 3H), 1.90 (br, 6H), 1.74 (br, 6H), 1.29 (s, 6H).

EXAMPLE 12(31)

(Z)-2-(6-bromo-3,3-dimethyl-3,4-dihydro-(2H)-isoquinolin-1-ylidene)-1-(pyridin-3-yl)ethan-1-one TLC: Rf0.25 (hexane:ethyl acetate=1:1); NMR (CDCl₃):
δ 11.82 (br, 1H), 9.13 (dd, J=2.0, 1.0 Hz, 1H), 8.67 (dd, J=5.0, 2.0 Hz, 1H), 8.20 (ddd, J=8.0, 2.0, 2.0 Hz, 1H), 7.69 (d, J=8.5 Hz, 1H), 7.50 (dd, J=8.5, 2.0 Hz, 1H), 7.40-7.35 (m, 2H), 6.24 (s, 1H), 2.89 (s, 2H), 1.38 (s, 6H).

EXAMPLE 13

(Z)-2-(6-formyl-3,3-dimethyl-3,4-dihydro-(2H)-isoquinolin-1-ylidene)-1-phenylethan-1-one To a solution of the compound prepared in example 12 (356 mg) in ether (10 ml) was added n-butyl lithium (1.4 ml, 1.6M in hexane) dropwise and ten minutes later it was warmed to 0° C. and the mixture was stirred for 30 minutes. To the reaction mixture was added dimethylformamide (0.20 ml) at −78° C. and was stirred for 30 minutes at 0° C. To the reaction mixture was added a saturated aqueous solution of ammonium chloride and was extracted with ethyl acetate. The extract was washed with water and brine, dried over anhydrous magnesium sulfate and concentrated. The residue was purified by column chromatography on silica gel (hexane:ethyl acetate=20:1→5:1) to give the compound of the present invention (165 mg) having the following physical data.

TLC: Rf0.34 (hexane:ethyl acetate=3:1); NMR (CDCl₃):
δ 11.75 (br, 1H), 10.07 (s, 1H), 8.01-7.94 (m, 3H), 7.85 (d, J=8.0 Hz, 1H), 7.74 (s, 1H), 7.48-7.42 (m, 3H), 6.38 (s, 1H), 2.99 (s, 2H), 1.38 (s, 6H).

EXAMPLE 13-EXAMPLE 13(16)

By the same procedure as described in example 13, using the compound prepared in example 11(7), example 11(70), example 11(81), example 12(26), example 11(119), example 11(153), example 11(154), example 11(156), example 11(168), example 11(170), example 11(181), example 11(184), example 11(188), example 11(189), example 11(193) or example 11(194) in place of the compound prepared in example 12, the following compounds of the present invention were given.

EXAMPLE 13(1)

(Z)-2-(7-formyl-3,3-dimethyl-3,4-dihydro-(2H)-isoquinolin-1-ylidene)-1-phenylethan-1-one TLC: Rf0.24 (hexane:ethyl acetate=3:1); NMR (CDCl₃):
δ 11.82 (br, 1H), 10.08 (s, 1H), 8.34 (d, J=1.5 Hz, 1H), 7.99-7.93 (m, 3H), 7.49-7.40 (m, 4H), 6.42 (s, 1H), 2.99 (s, 2H), 1.38 (s, 6H).

EXAMPLE 13(2)

(Z)-2-(7-formyl-3,3-dimethyl-3,4-dihydro-(2H)-isoquinolin-1-ylidene)-1-(naphthalen-1-yl)ethan-1-one TLC: Rf0.31 (ethyl acetate:hexane=1:3); NMR (CDCl₃):
δ 11.76 (br, 1H), 10.00 (s, 1H), 8.48 (m, 1H), 8.22 (d, J=1.5 Hz, 1H), 7.95-7.85 (m, 3H), 7.72 (dd, J=7.0, 1.5 Hz, 1H), 7.55-7.45 (m, 3H), 7.42 (d, J=8.0 Hz, 1H), 6.19 (s, 1H), 3.04 (s, 2H), 1.44 (s, 6H).

EXAMPLE 13(3)

(Z)-2-(3,3-dimethyl-3,4-dihydro-(2H)-isoquinolin-1-ylidene)-1-(4-formylphenyl)ethan-1-one TLC: Rf0.26 (hexane:ethyl acetate=3:1), NMR (CDCl$_3$): δ 11.99 (br, 1H), 10.08 (s, 1H), 8.08 (d, J=8.5 Hz, 2H), 7.95 (d, J=8.5 Hz, 2H), 7.84 (d, J=7.5 Hz, 1H), 7.46 (t, J=7.5 Hz, 1H), 7.37 (t, J=7.5 Hz, 1H), 7.24 (d, J=7.5 Hz, 1H), 6.34 (s, 1H), 2.93 (s, 2H), 1.39 (s, 6H).

EXAMPLE 13(4)

(Z)-2-(3,3-dimethyl-3,4-dihydro-(2H)-isoquinolin-1-ylidene)-1-(4-formyl-2-methoxyphenyl)ethan-1-one TLC: Rf0.26 (hexane:ethyl acetate=2:1); NMR (CDCl$_3$): δ 11.76 (br, 1H), 10.02 (s, 1H), 7.79 (d, J=7.5 Hz, 1H), 7.73 (d, J=7.5 Hz, 1H), 7.51 (dd, J=7.5, 1.0 Hz, 1H), 7.48 (d, J=1.0 Hz, 1H), 7.43 (t, J=7.5 Hz, 1H), 7.31 (t, J=7.5 Hz, 1H), 7.21 (d, J=7.5 Hz, 1H), 6.20 (s, 1H), 3.89 (s, 3H), 2.91 (s, 2H), 1.37 (s, 6H).

EXAMPLE 13(5)

(Z)-2-(6-chloro-7-formyl-3,3-dimethyl-3,4-dihydro-(2H)-isoquinolin-1-ylidene)-1-(adamantan-1-yl)ethan-1-one TLC: Rf0.28 (ethyl acetate:hexane=1:5); NMR (CDCl$_3$): δ 11.43 (br, 1H), 10.47 (s, 1H), 8.25 (s, 1H), 7.30 (s, 1H), 5.83 (s, 1H), 2.87 (s, 2H), 2.06 (m, 3H), 1.90 (m, 6H), 1.76 (m, 6H), 1.30 (s, 6H).

EXAMPLE 13(6)

(Z)-2-(6-chloro-7-formyl-3,3-dimethyl-3,4-dihydro-(2H)-isoquinolin-1-ylidene)-1-cyclohexylethan-1-one TLC: Rf0.36 (ethyl acetate:hexane=1:3); NMR (CDCl$_3$): δ 11.19 (br, 1H), 10.46 (s, 1H), 8.25 (s, 1H), 7.29 (s, 1H), 5.70 (s, 1H), 2.87 (s, 2H), 2.35 (m, 1H), 1.90-1.20 (m, 10H), 1.30 (s, 6H).

EXAMPLE 13(7)

(Z)-2-(6-chloro-7-formyl-3,3-dimethyl-3,4-dihydro-(2H)-isoquinolin-1-ylidene)-1-cycloheptylethan-1-one TLC: Rf0.38 (ethyl acetate:hexane=1:3); NMR (CDCl$_3$): δ 11.11 (br, 1H), 10.45 (s, 1H), 8.24 (s, 1H), 7.29 (s, 1H), 5.66 (s, 1H), 2.86 (s, 2H), 2.48 (m, 1H), 1.95-1.40 (m, 12H), 1.28 (s, 6H).

EXAMPLE 13(8)

(Z)-2-(7-formyl-6-methoxy-3,3-dimethyl-3,4-dihydro-(2H)-isoquinolin-1-ylidene)-1-(adamantan-1-yl)ethan-1-one TLC: Rf0.22 (hexane:ethyl acetate=2:1); NMR (CDCl$_3$): δ 11.52 (br, 1H), 10.45 (s, 1H), 8.20 (s, 1H), 6.78 (s, 1H), 5.80 (s, 1H), 3.99 (s, 3H), 2.87 (s, 2H), 2.05 (br, 3H), 1.91 (br, 6H), 1.75 (br, 6H), 1.30 (s, 6H).

EXAMPLE 13(9)

(Z)-2-(7-formyl-3,3-dimethyl-3,4-dihydro-(2H)-isoquinolin-1-ylidene)-1-(adamantan-1-yl)ethan-1-one TLC: Rf0.64 (hexane:ethyl acetate=1:1); NMR (CDCl$_3$): δ 11.49 (brs, 1H), 10.06 (s, 1H), 8.22 (d, J=1.5 Hz, 1H), 7.90 (dd, J=7.8, 1.5 Hz, 1H), 7.36 (d, J=7.8 Hz, 1H), 5.87 (s, 1H), 2.93 (s, 2H), 2.11-2.04 (m, 3H), 1.94-1.90 (m, 6H), 1.78-1.73 (m, 6H), 1.31 (s, 6H).

EXAMPLE 13(10)

(Z)-2-(7-formyl-6-methoxy-3,3-dimethyl-13,4-dihydro-(2H)-isoquinolin-1-ylidene)-1-cyclohexylethan-1-one TLC: Rf0.10 (hexane:ethyl acetate=3:1); NMR (CDCl$_3$): δ 11.27 (br, 1H), 10.44 (s, 1H), 8.19 (s, 1H), 6.77 (s, 1H), 5.67 (s, 1H), 3.99 (s, 3H), 2.87 (s, 2H), 2.31 (m, 1H), 1.90-1.79 (m, 4H), 1.70 (m, 1H), 1.56-1.20 (m, 1H).

EXAMPLE 13(11)

(Z)-2-(7-formyl-6-methoxy-3,3-dimethyl-3,4-dihydro-(2H)-isoquinolin-1-ylidene) 1-cycloheptylethan-1-one TLC: Rf0.21 (hexane:ethyl acetate=2:1); NMR (CDCl$_3$): δ 11.20 (br, 1H), 10.44 (s, 1H), 8.19 (s, 1H), 6.77 (s, 1H), 5.64 (s, 1H), 3.99 (s, 3H), 2.87 (s, 2H), 2.47 (m, 1H), 1.94-1.45 (m, 12H), 1.30 (s, 6H).

EXAMPLE 13(12)

(Z)-2-(7-formyl-3,3,6-trimethyl-3,4-dihydro-(2H)-isoquinolin-1-ylidene)-1-(adamantan-1-yl)ethan-1-one TLC: Rf0.20 (hexane:ethyl acetate=6:1); NMR (CDCl$_3$): δ 11.48 (br, 1H), 10.31 (s, 1H), 8.13 (s, 1H), 7.09 (s, 1H), 5.84 (s, 1H), 2.86 (s, 2H), 2.70 (s, 3H), 2.07-2.06 (br, 3H), 1.93-1.92 (br, 6H), 1.75 (br, 6H), 1.30 (s, 6H).

EXAMPLE 13(13)

(Z)-2-(7-formyl-3,3-dimethyl-3,4-dihydro-(2H)-isoquinolin-1-ylidene)-1-cyclohexylethan-1-one TLC: Rf0.19 (hexane:ethyl acetate=4:1); NMR (CDCl$_3$): δ 11.27 (brs, 1H), 10.04 (s, 1H), 8.22 (d, J=1.5 Hz, 1H), 7.90 (dd, J=7.5, 1.5 Hz, 1H), 7.36 (d, J=7.5 Hz, 1H), 5.73 (s, 1H), 2.93 (s, 2H), 2.34 (tt, J=11.7, 3.3 Hz, 1H), 1.94-1.66 (m, 5H), 1.58-1.24 (m, 1H).

EXAMPLE 13(14)

(Z)-2-(7-formyl-3,3,6-trimethyl-3,4-dihydro-(2H)-isoquinolin-1-ylidene)-1-cyclohexylethan-1-one TLC: Rf0.27 (hexane:ethyl acetate=5:1); NMR (CDCl$_3$): δ 11.26 (br, 1H), 10.29 (s, 1H), 8.13 (s, 1H), 7.09 (s, 1H), 5.71 (s, 1H), 2.86 (s, 2H), 2.70 (s, 3H), 2.33 (m, 1H), 1.90-1.27 (m, 16H).

EXAMPLE 13(15)

(Z)-2-(7-formyl-3,3-dimethyl-3,4-dihydro-(2H)-isoquinolin-1-ylidene)-1-cycloheptylethan-1-one TLC: Rf0.41 (hexane:ethyl acetate=2:1); NMR (CDCl$_3$): δ 11.19 (brs, 1H), 10.05 (s, 1H), 8.21 (d, J=1.5 Hz, 1H), 7.89 (dd, J=7.5, 1.5 Hz, 1H), 7.36 (d, J=7.5 Hz, 1H), 5.70 (s, 1H), 2.93 (s, 2H), 2.51 (tt, J=9.9, 3.9 Hz, 1H), 1.98-1.46 (m, 12H), 1.31 (s, 6H).

EXAMPLE 13(16)

(Z)-2-(7-formyl-3,3,6-trimethyl-3,4-dihydro-(2H)-isoquinolin-1-ylidene)-1-cycloheptylethan-1-one TLC: Rf0.26 (hexane:ethyl acetate=5:1); NMR (CDCl$_3$): δ 11.18 (br, 1H), 10.29 (s, 1H), 8.13 (s, 1H), 7.08 (s, 1H), 5.67 (s, 1H), 2.86 (s, 2H), 2.70 (s, 3H), 2.50 (m, 1H), 1.98-1.54 (m, 12H), 1.30 (s, 6H).

EXAMPLE 14

(Z)-2-(3,3-dimethyl-3,4-dihydro-(2H)-isoquinolin-1-ylidene)-1-(4-aminophenyl)ethan-1-one To a suspension of the compound prepared in example 11(54) (312 mg) in acetic acid (10 ml) was added steel powder (1.35 g) and the mixture was stirred for 40 minutes at 70° C. The reaction mixture was allowed to cool and thereto were added ice and 1N hydrochloric acid and filtered over celite. The filtrate was extracted. The organic layer was extracted with 2N hydrochloric acid. The combined aqueous layer was alkalified with a 5N aqueous solution of sodium hydroxide and extracted with t-butyl methyl ether. The extract was washed with water and brine, dried over anhydrous magnesium sulfate and concentrated to give the compound of the present invention (229 mg) having the following physical data.

TLC: Rf0.15 (hexane:ethyl acetate=2:1); NMR (CDCl$_3$): δ 11.67 (br, 1H), 7.86-7.81 (m, 3H), 7.41 (t, J=7.5 Hz, 1H), 7.33 (t, J=7.5 Hz, 1H), 7.20 (d, J=7.5 Hz, 1H), 6.71-6.67 (m, 2H), 6.29 (s, 1H), 4.02-3.84 (br, 2H), 2.88 (s, 2H), 1.34 (s, 6H).

EXAMPLE 14(1)-EXAMPLE 14(15)

By the same procedure as described in example 14 using the compound prepared in example 11(52), example 11(53), example 11(100), example 11(126) to 11(130), example 11(150), example 11(157), example 11(195), example 11(172) or example 11(175) to 11(177) in place of the compound prepared in example 11(54), the following compounds of the present invention were given.

EXAMPLE 14(1)

(Z)-2-(3,3-dimethyl-3,4-dihydro-(2H)-isoquinolin-1-ylidene)-1-(2-aminophenyl)ethan-1-one TLC: Rf0.14 (chloroform:methanol=10:1); NMR (CDCl$_3$): δ 8.43 (dd, J=8.0, 1.5 Hz, 1H), 7.62-7.56 (m, 2H), 7.48-7.32 (m, 5H), 6.35 (s, 1H), 2.82 (br, 2H), 1.43 (s, 6H).

EXAMPLE 14(2)

(Z)-2-(3,3-dimethyl-3,4-dihydro-(2H)-isoquinolin-1-ylidene)-1-(3-aminophenyl)ethan-1-one TLC: Rf0.26 (hexane:ethyl acetate=1:1); NMR (CDCl$_3$): δ 11.80 (br, 1H), 7.82 (d, J=7.5 Hz, 1H), 7.43 (t, J=7.5 Hz, 1H), 7.36-7.27 (m, 3H), 7.24-7.19 (m, 2H), 6.78 (ddd, J=8.0, 2.5, 1.0 Hz, 1H), 6.29 (s, 1H), 3.79 (br, 2H), 2.90 (s, 2H), 1.36 (s, 6H).

EXAMPLE 14(3)

(Z)-2-(7-amino-3,3-dimethyl-3,4-dihydro-(2H)-isoquinolin-1-ylidene)-1-phenylethan-1-one TLC: Rf0.36 (hexane:ethyl acetate=1:1); NMR (CDCl$_3$): δ 11.81 (brs, 1H), 7.97-7.92 (m, 2H), 7.46-7.41 (m, 3H), 7.14 (d, J=2.7 Hz, 1H), 7.00 (d, J=7.8 Hz, 1H), 6.77 (dd, J=7.8, 2.7 Hz, 1H), 6.24 (s, 1H), 3.74 (brs, 2H), 2.78 (s, 2H), 1.35 (s, 6H).

EXAMPLE 14(4)

(Z)-2-(7-amino-3,3-dimethyl-3,4-dihydro-(2H)-isoquinolin-1-ylidene)-1-(4-cyanophenyl)ethan-1-one TLC: Rf0.44 (ethyl acetate:hexane=1:1); NMR (CDCl$_3$): δ 11.93 (br, 1H), 8.01 (d, J=8.5 Hz, 2H), 7.71 (d, J=8.5 Hz, 2H), 7.11 (d, J=2.5 Hz, 1H), 7.02 (d, J=8.0 Hz, 1H), 6.80 (dd, J=8.0, 2.5 Hz, 1H), 6.18 (s, 1H), 3.77 (br, 2H), 2.79 (s, 2H), 1.36 (s, 6H).

EXAMPLE 14(5)

(Z)-2-(7-amino-6-chloro-3,3-dimethyl-3,4-dihydro-(2H)-isoquinolin-1-ylidene)-1-cyclohexylethan-1-one TLC: Rf0.58 (ethyl acetate:hexane=1:2); NMR (CDCl$_3$): δ 11.26 (br, 1H), 7.11 (s, 1H), 7.06 (s, 1H), 5.51 (s, 1H), 4.06 (br, 2H), 2.69 (s, 2H), 2.27 (m, 1H), 1.95-1.20 (m, 10H), 1.27 (s, 6H).

EXAMPLE 14(6)

(Z)-2-(7-amino-6-chloro-3,3-dimethyl-3,4-dihydro-(2H)-isoquinolin-1-ylidene)-1-cycloheptylethan-1-one TLC: Rf0.63 (ethyl acetate:hexane=1:2); NMR (CDCl$_3$): δ 11.17 (br, 1H), 7.10 (s, 1H), 7.06 (s, 1H), 5.47 (s, 1H), 4.06 (br, 2H), 2.69 (s, 2H), 2.44 (m, 1H), 2.00-1.40 (m, 12H), 1.27 (s, 6H).

EXAMPLE 14(7)

(Z)-2-(7-amino-6-chloro-3,3-dimethyl-3,4-dihydro-(2H)-isoquinolin-1-ylidene)-1-(4-cyanophenyl)ethan-1-one TLC: Rf0.40 (ethyl acetate:hexane=1:2); NMR (CDCl$_3$): δ 11.90 (br, 1H), 8.00 (d, J=8.5 Hz, 2H), 7.72 (d, J=8.5 Hz, 2H), 7.19 (s, 1H), 7.13 (s, 1H), 6.14 (s, 1H), 4.14 (br, 2H), 2.78 (s, 2H), 1.36 (s, 6H).

EXAMPLE 14(8)

(Z)-2-(7-amino-6-chloro-3,3-dimethyl-3,4-dihydro-(2H)-isoquinolin-1-ylidene)-1-(adamantan-1-yl)ethan-1-one TLC: Rf0.68 (ethyl acetate:hexane=1:2); NMR (CDCl$_3$): δ 11.43 (br, 1H), 7.12 (s, 1H), 7.07 (s, 1H), 5.65 (s, 1H), 4.08 (br, 2H), 2.69 (s, 2H), 2.05 (m, 3H), 1.90 (m, 6H), 1.74 (m, 6H), 1.27 (s, 6H).

EXAMPLE 14(9)

(Z)-2-(7-amino-3,3-dimethyl-3,4-dihydro-(2H)-isoquinolin-1-ylidene) 1-cyclohexylethan-1-one TLC: Rf0.15 (ethyl acetate:hexane=1:3); NMR (CDCl$_3$): δ 11.29 (br, 1H), 7.02 (d, J=2.5 Hz, 1H), 6.95 (d, J=8.0 Hz, 1H), 6.73 (dd, J=8.0, 2.5 Hz, 1H), 5.54 (s, 1H), 3.69 (br, 2H), 2.71 (s, 2H), 2.28 (m, 1H), 1.95-1.20 (m, 10H), 1.27 (s, 6H).

EXAMPLE 14(10)

(Z)-2-(7-amino-3,3-dimethyl-3,4-dihydro-(2H)-isoquinolin-1-ylidene)-1-(adamantan 1-yl)ethan-1-one TLC: Rf0.57 (hexane:ethyl acetate=1:1); NMR (CDCl$_3$): δ 11.46 (brs, 1H), 7.04 (d, J=2.4 Hz, 1H), 6.95 (d, J=8.4 Hz, 1H), 6.73 (dd, J=8.4, 2.4 Hz, 1H), 5.69 (s, 1H), 3.72 (brs, 2H), 2.71 (s, 2H), 2.05 (brs, 3H), 1.93-1.89 (m, 6H), 1.77-1.72 (m, 6H), 1.27 (s, 6H).

EXAMPLE 14(11)

(Z)-2-(7-amino-3,3-dimethyl-3,4-dihydro-(2H)-isoquinolin-1-ylidene)-1-cycloheptylethan-1-one TLC: Rf0.57 (hexane:ethyl acetate=1:1); NMR (CDCl$_3$): δ 11.20 (brs, 1H), 7.02 (d, J=2.4 Hz, 1H), 6.95 (d, J=7.8 Hz, 1H), 6.73 (dd, J=7.8, 2.4 Hz, 1H), 5.51 (s, 1H), 3.69 (brs, 2H), 2.71 (s, 2H), 2.44 (m, 1H), 1.97-1.42 (m, 12H), 1.27 (s, 6H).

EXAMPLE 14(12)

(Z)-2-(7-amino-3,3,6-trimethyl-3,4-dihydro-(2H)-isoquinolin-1-ylidene)-1-(adamantan-1-yl)ethan-1-one TLC: Rf0.21 (ethyl acetate:hexane=1:4); NMR (CDCl$_3$): δ 11.45 (br, 1H), 7.02 (s, 1H), 6.84 (s, 1H), 5.67 (s, 1H), 3.66 (br, 2H), 2.69 (s, 2H), 2.19 (s, 3H), 2.05 (br, 3H), 1.92-1.91 (br, 6H), 1.75-1.74 (br, 6H), 1.27 (s, 6H).

EXAMPLE 14(13)

(Z)-2-(7-amino-3,3,6-trimethyl-3,4-dihydro-(2H)-isoquinolin-1-ylidene)-1-(4-cyanophenyl)ethan-1-one TLC: Rf0.31 (hexane:ethyl acetate=3:2); NMR (CDCl$_3$): δ 11.91 (br, 1H), 8.01 (d, J=8.7 Hz, 2H), 7.72 (d, J=8.7 Hz, 2H), 7.09 (s, 1H), 6.91 (s, 1H), 6.17 (s, 1H), 3.71 (br, 2H), 2.78 (s, 2H), 2.22 (s, 3H), 1.36 (s, 6H).

EXAMPLE 14(14)

(Z)-2-(7-amino-3,3,6-trimethyl-3,4-dihydro-(2H)-isoquinolin-1-ylidene)-1-cyclohexylethan-1-one TLC: Rf0.37 (hexane:ethyl acetate=2:1); NMR (CDCl$_3$): δ 11.28 (brs, 1H), 7.01 (s, 1H), 6.84 (s, 1H), 5.53 (s, 1H), 3.62 (brs, 2H), 2.69 (s, 2H), 2.27 (tt, J=12.0, 3.3 Hz, 1H), 2.19 (s, 3H), 1.92-1.18 (m, 16H).

EXAMPLE 14(15)

(Z)-2-(7-amino-3,3,6-trimethyl-3,4-dihydro-(2H)-isoquinolin-1-ylidene)-1-cycloheptylethan-1-one TLC: Rf0.40 (hexane:ethyl acetate=2:1); NMR (CDCl$_3$): δ 11.19 (brs, 1H), 7.00 (s, 1H), 6.84 (s, 1H), 5.49 (s, 1H), 3.62 (brs, 2H), 2.69 (s, 2H), 2.43 (tt, J=9.9, 3.6 Hz, 1H), 2.19 (s, 3H), 1.96-1.42 (m, 12H), 1.27 (s, 6H).

EXAMPLE 15

(Z)-2-(6-carboxy-3,3-dimethyl-3,4-dihydro-(2H)-isoquinolin-1-ylidene)-1-phenylethan-1-one To a solution of the compound prepared in example 12 (356 mg) in ether (10 ml) was added t-butyl lithium (2.2 ml, 1.5M in pentane) dropwise and five minutes later carbon dioxide gas was bubbled to it. The reaction mixture was allowed to warm to room temperature and thereto were added water and ethyl acetate and extracted. The organic layer was extracted with water. The combined aqueous layer was azeotroped. To the given solid was added ethanol and filtered and the filtrate was concentrated. The residue was purified by column chromatography on silica gel (hexane: ethyl acetate=1:1) to give the compound of the present invention (19 mg) having the following physical data.

TLC: Rf0.25 (hexane:ethyl acetate=1:1); NMR (CDCl$_3$): δ 11.76 (br, 1H), 8.06 (dd, J=8.0, 1.5 Hz, 1H), 7.97-7.92 (m, 4H), 7.49-7.42 (m, 3H), 6.38 (s, 1H), 2.98 (s, 2H), 1.39 (s, 6H).

EXAMPLE 15(1)-EXAMPLE 15(14)

By the same procedure as described in example 15 using the compound of example 11(7), example 11(168), example 12(28), example 12(29), example 11(188), example 11(193), example 11(181), example 11(156), example 11(189), example 11(170), example 11(184), example 111(194), example 12(30) or example 12(31) in place of the compound prepared in example 12, the compounds of the present invention were given.

EXAMPLE 15(1)

(Z)-2-(7-carboxy-3,3-dimethyl-3,4-dihydro-(2H)-isoquinolin-1-ylidene)-1-phenylethan-1-one TLC: Rf0.13 (hexane:ethyl acetate=1:1); NMR (CDCl$_3$): δ 11.84 (br, 1H), 8.57 (d, J=2.0 Hz, 1H), 8.16 (dd, J=8.0, 2.0 Hz, 1H), 8.00-7.96 (m, 2H), 7.48-7.44 (m, 3H), 7.35 (d, J=8.0 Hz, 1H), 6.43 (s, 1H), 2.99 (s, 2H), 1.39 (s, 6H).

EXAMPLE 15(2)

(Z)-2-(7-carboxy-3,3-dimethyl-3,4-dihydro-(2H)-isoquinolin-1-ylidene)-1-(adamantan-1-yl)ethan-1-one TLC: Rf0.27 (chloroform:methanol=10:1); NMR (CDCl$_3$): δ 11.52 (br, 1H), 8.45 (d, J=1.5 Hz, 1H), 8.12 (dd, J=8.0, 1.5 Hz, 1H), 7.31 (d, J=8.0 Hz, 1H), 5.87 (s, 1H), 2.92 (s, 2H), 2.08 (br, 3H), 1.93 (br, 6H), 1.77 (br, 6H), 1.31 (s, 6H).

EXAMPLE 15(3)

(Z)-2-(6-carboxy-3,3-dimethyl-3,4-dihydro-(2H)-isoquinolin-1-ylidene)-1-cyclohexylethan-1-one TLC: Rf0.36 (chloroform:methanol=10:1); NMR (CDCl$_3$): δ 11.25 (br, 1H), 8.01 (dd, J=8.0, 1.5 Hz, 1H), 7.92 (d, J=1.5 Hz, 1H), 7.81 (d, J=8.0 Hz, 1H), 5.69 (s, 1H), 2.91 (s, 2H), 2.33 (m, 1H), 1.91-1.80 (m, 4H), 1.72 (m, 1H), 1.50-1.20 (m, 1H).

EXAMPLE 15(4)

(Z)-2-(6-carboxy-3,3-dimethyl-3,4-dihydro-(2H)-isoquinolin-1-ylidene)-1-cycloheptylethan-1-one TLC: Rf0.39 (chloroform:methanol=10:1); NMR (CDCl$_3$): δ 11.16 (br, 1H), 8.02 (dd, J=8.5, 1.5 Hz, 1H), 7.92 (d, J=1.5 Hz, 1H), 7.81 (d, J=8.5 Hz, 1H), 5.66 (s, 1H), 2.91 (s, 2H), 2.50 (m, 1H), 1.97-1.90 (m, 2H), 1.84-1.45 (m, 10H), 1.31 (s, 6H).

EXAMPLE 15(5)

(Z)-2-(7-carboxy-3,3-dimethyl-3,4-dihydro-(2H)-isoquinolin-1-ylidene)-1-cyclohexylethan-1-one TLC: Rf0.24 (hexane:ethyl acetate=1:1); NMR (CDCl$_3$): δ 11.29 (brs, 1H), 8.45 (d, J=1.8 Hz, 1H), 8.11 (dd, J=7.8, 1.8 Hz, 1H), 7.30 (d, J=7.8 Hz, 1H), 5.73 (s, 1H), 2.92 (s, 2H), 2.35 (m, 1H), 1.95-1.65 (m, 5H), 1.54-1.20 (m, 1H).

EXAMPLE 15(6)

(Z)-2-(7-carboxy-3,3-dimethyl-3,4-dihydro-(2H)-isoquinolin-1-ylidene)-1-cycloheptylethan-1-one TLC: Rf0.30 (hexane:ethyl acetate=1:1); NMR (CDCl$_3$): δ 11.22 (brs, 1H), 8.45 (d, J=1.8 Hz, 1H), 8.12 (dd, J=7.8, 1.8 Hz, 1H), 7.30 (d, J=7.8 Hz, 1H), 5.71 (s, 1H), 2.92 (s, 2H), 2.52 (tt, J=9.9, 3.6 Hz, 1H), 1.99-1.45 (m, 12H), 1.31 (s, 6H).

EXAMPLE 15(7).

(Z)-2-(7-carboxy-6-methoxy-3,3-dimethyl-3,4-dihydro-(2H)-isoquinolin-1-ylidene)-1-cycloheptylethan-1-one TLC: Rf0.09 (hexane:ethyl acetate=1:1); NMR (CDCl$_3$): δ 11.17 (br, 1H), 10.40 (br, 1H), 8.54 (s, 1H), 6.85 (s, 1H), 5.67 (s, 1H), 4.13 (s, 3H), 2.89 (s, 2H), 2.49 (tt, J=10.0, 4.0 Hz, 1H), 1.94-1.87 (m, 2H), 1.83-1.48 (m, 10H), 1.30 (s, 6H).

EXAMPLE 15(8)

(Z)-2-(7-carboxy-6-methoxy-3,3-dimethyl-3,4-dihydro-(2H)-isoquinolin-1-ylidene)-1-(adamantan-1-yl)ethan-1-one TLC: Rf0.10 (hexane:ethyl acetate=1:1); NMR (CDCl$_3$): δ 11.50 (br, 1H), 10.40 (br, 1H), 8.55 (s, 1H), 6.85 (s, 1H), 5.83 (s, 1H), 4.14 (s, 3H), 2.89 (s, 2H), 2.06 (br, 3H), 1.91 (br, 6H), 1.75 (br, 6H), 1.31 (s, 6H).

EXAMPLE 15(9)

(Z)-2-(7-carboxy-3,3,6-trimethyl-3,4-dihydro-(2H)-isoquinolin-1-ylidene)-1-cyclohexylethan-1-one TLC: Rf0.16 (hexane:ethyl acetate=3:1); NMR (CDCl$_3$): δ 11.29 (br, 1H), 8.41 (s, 1H), 7.10 (s, 1H), 5.69 (s, 1H), 2.85 (s, 2H), 2.68 (s, 3H), 2.34 (m, 1H), 1.91-1.20 (m, 16H).

EXAMPLE 15(10)

(Z)-2-(7-carboxy-6-methoxy-3,3-dimethyl-3,4-dihydro-(2H)-isoquinolin-1-ylidene)-1-cyclohexylethan-1-one TLC: Rf0.07 (hexane:ethyl acetate=1:1); NMR (CDCl$_3$): δ 11.23 (br, 1H), 10.40 (br, 1H), 8.54 (s, 1H), 6.85 (s, 1H), 5.71 (s, 1H), 4.13 (s, 3H), 2.89 (s, 2H), 2.32 (tt, J=11.5, 3.5 Hz, 1H), 1.89-1.79 (m, 4H), 1.70 (m, 1H), 1.56-1.21 (m, 1H).

EXAMPLE 15(11)

(Z)-2-(7-carboxy-3,3,6-trimethyl-3,4-dihydro-(2H)-isoquinolin-1-ylidene)-1-(adamantan-1-yl)ethan-1-one TLC: Rf0.25 (hexane:ethyl acetate=2:1); NMR (CDCl$_3$): δ 11.51 (br, 1H), 8.41 (s, 1H), 7.10 (s, 1H), 5.83 (s, 1H), 2.85 (s, 2H), 2.69 (s, 3H), 2.07-2.05 (br, 3H), 1.93-1.92 (br, 6H), 1.76-1.75 (br, 6H), 1.31 (s, 6H).

EXAMPLE 15(12)

(Z)-2-(7-carboxy-3,3,6-trimethyl-3,4-dihydro-(2H)-isoquinolin-1-ylidene)-1-cycloheptylethan-1-one TLC: Rf0.13 (hexane:ethyl acetate=3:1); NMR (CDCl$_3$): δ 11.22 (br, 1H), 8.42 (s, 1H), 7.10 (s, 1H), 5.66 (s, 1H), 2.85 (s, 2H), 2.69 (s, 3H), 2.50 (m, 1H), 1.98-1.64 (m, 12H), 1.31 (s, 6H).

EXAMPLE 15(13)

(Z)-2-(6-carboxy-3,3-dimethyl-3,4-dihydro-(2H)-isoquinolin-1-ylidene)-1-(adamantan-1-yl)ethan-1-one TLC: Rf0.08 (hexane:ethyl acetate=2:1); NMR (CDCl$_3$): δ 11.39 (br, 1H), 7.99 (br, 1H), 7.88 (s, 1H), 7.78 (br, 1H), 5.82 (s, 1H), 2.86 (s, 2H), 2.06 (br, 3H), 1.91 (br, 6H), 1.74 (br, 6H), 1.28 (s, 6H).

EXAMPLE 15(14)

(Z)-2-(6-carboxy-3,3-dimethyl-3,4-dihydro-(2H)-isoquinolin-1-ylidene)-1-(pyridin-3-yl)ethan-1-one TLC: Rf0.31 (methylene chloride:methanol=10:1); NMR (CDCl$_3$+a few drops of CD$_3$OD): δ 9.17 (d, J=1.5 Hz, 1H), 8.67 (dd, J=4.5, 1.5 Hz, 1H), 8.27 (ddd, J=8.5, 1.5, 1.5 Hz, 1H), 8.06 (dd, J=8.5, 2.0 Hz, 1H), 7.94-7.91 (m, 2H), 7.44 (dd, J=8.5, 4.5 Hz, 1H), 6.35 (s, 1H), 2.98 (s, 2H), 1.39 (s, 6H).

EXAMPLE 16-EXAMPLE 16(6)

By the same procedure as described in example 5 using the compound prepared in example 12(10), example 11(57), example 11(2), example 11(123), example 11(200), example 11(64) or example 11(32) in place of the compound prepared in example 1(18), the compounds of the present invention were given.

EXAMPLE 16

(Z)-2-(3,3,4,4-tetramethyl-3,4-dihydro-(2H)-isoquinolin-1-ylidene)-1-(2-hydroxyphenyl)ethan-1-one TLC: Rf0.60 (hexane:ethyl acetate=3:1); NMR (CDCl$_3$): δ 13.65 (s, 1H), 11.29 (br, 1H), 7.81 (d, J=7.5 Hz, 1H), 7.76 (dd, J=8.0, 1.5 Hz, 1H), 7.54-7.49 (m, 1H), 7.44 (dd, J=8.0, 1.5 Hz, 1H), 7.38-7.30 (m, 2H), 6.94 (dd, J=7.0, 1.5 Hz, 1H), 6.83 (dt, J=1.5, 7.5 Hz, 1H), 6.30 (s, 1H), 1.31 (br, 12H).

EXAMPLE 16(1)

(Z)-2-(7-hydroxy-3,3-dimethyl-3,4-dihydro-(2H)-isoquinolin-1-ylidene)-1-(naphthalen-1-yl)ethan-1-one TLC: Rf0.44 (ethyl acetate:hexane=1:2); NMR (CDCl$_3$): δ 11.70 (br, 1H), 8.45 (m, 1H), 7.90-7.80 (m, 2H), 7.62 (dd, J=7.0, 1.0 Hz, 1H), 7.50-7.40 (m, 2H), 7.38 (dd, J=8.0, 7.0 Hz, 1H), 7.10 (d, J=2.5 Hz, 1H), 7.00 (d, J=8.5 Hz, 1H), 6.85 (dd, J=8.5, 2.5 Hz, 1H), 6.04 (br, 1H), 5.94 (br, 1H), 2.79 (s, 2H), 1.34 (s, 6H).

EXAMPLE 16(2)

(Z)-2-(7-hydroxy-3,3-dimethyl-3,4-dihydro-(2H)-isoquinolin-1-ylidene)-1-phenylethan-1-one TLC: Rf0.14 (ethyl acetate:hexane=1:5); NMR (CDCl$_3$): δ 11.76 (br, 1H), 7.91 (m, 2H), 7.50-7.35 (m, 3H), 7.26 (d, J=2.5 Hz, 1H), 7.05 (d, J=8.5 Hz, 1H), 6.93 (dd, J=8.5, 2.5 Hz, 1H), 6.24 (s, 1H), 5.95 (s, 1H), 2.78 (s, 2H), 1.30 (s, 6H).

EXAMPLE 16(3)

(Z)-2-(5-hydroxy-3,3-dimethyl-3,4-dihydro-(2H)-isoquinolin-1-ylidene)-1-phenylethan-1-one TLC: Rf0.25 (hexane:ethyl acetate=2:1); NMR (DMSO-d$_6$): δ 11.87 (brs, 1H), 9.80 (s, 1H), 7.98-7.93 (m, 2H), 7.52 (d, J=8.4 Hz, 1H), 7.48-7.40 (m, 3H), 7.18 (t, J=8.4 Hz, 1H), 7.01 (d, J=8.4 Hz, 1H), 6.39 (s, 1H), 2.81 (s, 2H), 1.28 (s, 6H).

EXAMPLE 16(4)

(Z)-2-(6-chloro-7-hydroxy-3,3-dimethyl-3',4-dihydro-(2H)-isoquinolin-1-ylidene) 1-(adamantan-1-yl)ethan-1-one TLC: Rf0.28 (ethyl acetate:hexane=5:1); NMR (CDCl$_3$): δ 11.38 (br, 1H), 7.39 (s, 1H), 7.14 (s, 1H), 5.70 (s, 1H), 5.60 (br, 1H), 2.73 (s, 2H), 2.04 (m, 3H), 1.89 (m, 6H), 1.73 (m, 6H), 1.28 (s, 6H).

EXAMPLE 16(5)

(Z)-2-(7-hydroxy-3,3-dimethyl-3,4-dihydro-(2H)-isoquinolin-1-ylidene)-1-(adamantan-1-yl)ethan-1-one TLC: Rf0.18 (ethyl acetate:hexane=1:4); NMR (CDCl$_3$): δ 11.42 (br, 1H), 7.21 (d, J=2.4 Hz, 1H), 7.04 (d, J=8.1 Hz, 1H), 6.88 (dd, J=2.4, 8.1 Hz, 1H), 5.71 (s, 1H), 5.16 (br, 1H), 2.75 (s, 2H), 2.05 (br, 3H), 1.91-1.90 (br, 6H), 1.73 (br, 6H), 1.27 (s, 6H).

EXAMPLE 16(6)

(Z)-2-(7-hydroxy-3,3-dimethyl-3,4-dihydro-(2H)-isoquinolin-1-ylidene)-1-cyclohexylethan-1-one TLC: Rf0.13 (ethyl acetate:hexane=1:4); NMR (CDCl$_3$): δ 11.27 (br, 1H), 7.19 (d, J=2.4 Hz, 1H), 7.03 (d, J=8.1 Hz, 1H), 6.89 (dd, J=2.4, 8.1 Hz, 1H), 5.57 (s, 1H), 2.75 (s, 2H), 2.28 (m, 1H), 1.92-1.18 (m, 16H).

EXAMPLE 17-EXAMPLE 17(1)

By the same procedure as described in example 9 using the compound prepared in example 11(7) in place of the compound prepared in example 1(68) and benzeneboronic acid or pyridin-3-ylboronic acid instead, the compounds of the present invention were given.

EXAMPLE 17

(Z)-2-(7-phenyl-3,3-dimethyl-3,4-dihydro-(2H)-isoquinolin-1-ylidene)-1-phenylethan-1-one TLC: Rf0.44 (hexane:ethyl acetate=3:1); NMR (CDCl$_3$): δ 11.88 (br, 1H), 8.01 (d, J=2.0 Hz, 1H), 7.97-7.94 (m, 2H), 7.66-7.62 (m, 3H), 7.52-7.40 (m, 6H), 7.30 (d, J=8.0 Hz, 1H), 6.39 (s, 1H), 2.95 (s, 2H), 1.40 (s, 6H).

EXAMPLE 17(1)

(Z)-2-(7-(pyridin-3-yl)-3,3-dimethyl-3,4-dihydro-(2H)-isoquinolin-1-ylidene) 1-phenylethan-1-one TLC: Rf0.32 (hexane:ethyl acetate=1:1); NMR (CDCl$_3$): δ 11.87 (br, 1H), 8.90 (d, J=1.5 Hz, 1H), 8.65 (dd, J=5.0, 1.5 Hz, 1H), 8.00-7.91 (m, 4H), 7.64 (dd, J=8.0, 1.5 Hz, 1H), 7.46-7.41 (m, 4H), 7.35 (d, J=7.5 Hz, 1H), 6.38 (s, 1H), 2.96 (s, 2H), 1.41 (s, 6H).

EXAMPLE 18

(Z)-2-(6-(morpholin-4-yl)-3,3-dimethyl-3,4-dihydro-(2H)-isoquinolin-1-ylidene)-1-phenylethan-1-one To a solution of the compound prepared in example 12 (180 mg) in toluene (5 ml) were added morpholine (0.060 ml) and sodium t-butyrate (70.5 mg) and it was degassed and thereto was added dichlorobis(tri-O-tolylphosphine)palladium(II) (12 mg) and the mixture was stirred for 8 hours at 100° C. To the reaction mixture was added dichlorobis(tri-O-tolylphosphine)palladium(II) (12 mg) and the mixture was stirred for 2 hours. The mixture was allowed to cool and it was diluted with t-butyl methyl ether and it was washed with water and brine successively, dried over anhydrous magnesium sulfate and concentrated. The residue was purified by column chromatography on silica gel (hexane:ethyl acetate=4:1) to give the compound of the present invention (65 mg) having the following physical data.

TLC: Rf0.30 (hexane:ethyl acetate=1:1); NMR (CDCl$_3$): δ 11.81 (brs, 1H), 7.98-7.90 (m, 2H), 7.73 (d, J=8.7 Hz, 1H), 7.45-7.39 (m, 3H), 6.81 (dd, J=8.7, 2.7 Hz, 1H), 6.65 (d, J=2.7 Hz, 1H), 6.24 (s, 1H), 3.88 (t, J=4.8 Hz, 4H), 3.29 (t, J=4.8 Hz, 4H), 2.83 (s, 2H), 1.36 (s, 6H).

EXAMPLE 18(1)

(Z)-2-(7-(morpholin-4-yl)-3,3-dimethyl-3,4-dihydro-(2H)-isoquinolin-1-ylidene)-1-phenylethan-1-one By the same procedure as described in example 18 using the compound prepared in example 11(7) in place of the compound prepared in example 12, the compound of the present invention having the following physical data was given.

TLC: Rf0.44 (hexane:ethyl acetate=1:1); NMR (CDCl$_3$): δ 11.87 (brs, 1H), 7.97-7.90 (m, 2H), 7.48-7.41 (m, 3H), 7.32 (d, J=2.4 Hz, 1H), 7.12 (d, J=8.1 Hz, 1H), 7.00 (dd, J=8.1, 2.4 Hz, 1H), 6.25 (s, 1H), 3.91 (t, J=4.8 Hz, 4H), 3.21 (t, J=4.8 Hz, 4H), 2.82 (s, 2H), 1.35 (s, 6H).

EXAMPLE 19

(Z)-2-(6-chloro-7-propoxycarbonyl-3,3-dimethyl-3,4-dihydro-(2H)-isoquinolin-1-ylidene)-1-cyclohexylethan-1-one A solution of the compound prepared in example 11(153) (198 mg), dichloro bis(triphenylphosphine)palladium(II) (35 mg) and triethylamine (0.14 ml) in n-propanol (5 ml) was stirred overnight at 100° C. under atmosphere of carbon monooxide. To the reaction mixture were added dichlorobis(triphenylphosphine)palladium(II) (315 mg) and triethylamine (0.84 ml) and the mixture was stirred overnight at 100° C. The reaction mixture was filtered over celite. The filtrate was added to water and the mixture was extracted with ethyl acetate. The extract was washed with a saturated aqueous solution of sodium chloride, dried over anhydrous magnesium sulfate and concentrated. The residue was purified by column chromatography on silica gel (hexane:chloroform=3:2→2:3) to give the compound of the present invention (140 mg) having the following physical data.

TLC: Rf0.31 (ethyl acetate:hexane=1:5); NMR (CDCl$_3$): δ 11.22 (br, 1H), 8.16 (s, 1H), 7.28 (s, 1H), 5.63 (s, 1H), 4.35 (t, J=6.5 Hz, 2H), 2.83 (s, 2H), 2.32 (m, 1H), 1.90-1.20 (m, 12H), 1.29 (s, 6H), 1.07 (t, J=7.5 Hz, 3H).

EXAMPLE 20

(Z)-2-(3,3-dimethyl-3,4-dihydro-(2H)-isoquinolin-1-ylidene)-1-(4-methylsulfinylphenyl)ethan-1-one To a solution of the compound prepared in example 11(83) (296 mg) in acetone (4 ml) was added a suspension of Oxone (844 mg, product name) in water/a saturated aqueous solution of sodium bicarbonate/acetone (2 ml/2 ml/2 ml) and the mixture was stirred for 45 minutes at 0° C. To the reaction mixture was added water and was extracted with ethyl acetate. The extract was washed with water and brine successively, dried over anhydrous magnesium sulfate and concentrated. The residue was purified crudely by column chromatography on silica gel (hexane:ethyl acetate=3:1→1:2) and then purified crudely by column chromatography on silica gel (chloroform:methanol=100:0→100:1) and then washed with t-butyl methyl ether/hexane to give the compound of the present invention (20 mg) having the following physical data.

TLC: Rf0.07 (hexane:ethyl acetate=1:2); NMR (CDCl$_3$): δ 11.91 (br, 1H), 8.09 (d, J=8.5 Hz, 2H), 7.84 (d, J=7.5 Hz, 1H), 7.71 (d, J=8.5 Hz, 2H), 7.46 (t, J=7.5 Hz, 1H), 7.36 (t, J=7.5 Hz, 1H), 7.23 (d, J=7.5 Hz, 1H), 6.31 (s, 1H), 2.92 (s, 2H), 2.76 (s, 3H), 1.38 (s, 6H).

EXAMPLE 21

(Z)-2-(6-cyano-3,3-dimethyl-3,4-dihydro-(2H)-isoquinolin-1-ylidene)-1-phenylethan-1-one To a solution of the compound prepared in example 1(68) (312 mg) in N-methylpyrrolidone (3 ml) was added copper cyanide (448 mg) at room temperature and the mixture was stirred for 19 hours at 180-190° C. The reaction mixture was allowed to cool and thereto was added a saturated aqueous solution of sodium bicarbonate and was extracted with ethyl acetate. The extract was washed with water and brine successively, dried over anhydrous magnesium sulfate and concentrated. The residue was purified by column chromatography on silica gel (hexane:ethyl acetate=20:1→15:1) to give the compound of the present invention (45 mg) having the following physical data.

TLC: Rf0.43 (hexane:ethyl acetate=3:1); NMR (CDCl$_3$): δ 11.75 (br, 1H), 7.95-7.91 (m, 3H), 7.64 (d, J=8.0 Hz, 1H), 7.53 (s, 1H), 7.49-7.41 (m, 3H), 6.33 (br, 1H), 2.94 (s, 2H), 1.38 (s, 6H).

EXAMPLE 22

(Z)-2-(7-(1-hydroxy-1-methylethyl)-3,3-dimethyl-3,4-dihydro-(2H)-isoquinolin-1-ylidene)-1-phenylethan-1-one To a solution of the compound prepared in example 11(7) (186 mg) in ether (4 ml) was added n-butyl lithium (1.4 ml; 1.5M in hexane) dropwise and the mixture was stirred for 90 minutes at 0° C. Thereto was added acetone (0.23 ml) at 0° C. and the mixture was stirred for 45 minutes at 0° C. To the reaction mixture was added water and the mixture was extracted with ethyl acetate. The extract was washed with water and brine successively, dried over anhydrous magnesium sulfate and concentrated. The residue was purified crudely by column chromatography on silica gel (hexane:ethyl acetate=4:1→2.5:1) and then washed with ethyl acetate to give the compound of the present invention (91 mg) having the following physical data.

TLC: Rf0.16 (hexane:ethyl acetate=3:1); NMR (CDCl$_3$): δ 11.89 (br, 1H), 7.98-7.94 (m, 3H), 7.53 (dd, J=8.0, 2.0 Hz, 1H), 7.47-7.42 (m, 3H), 7.19 (d, J=8.0 Hz, 1H), 6.35 (s, 1H), 2.88 (s, 2H), 1.80 (br, 1H), 1.64 (s, 6H), 1.36 (s, 6H).

EXAMPLE 22(1)-EXAMPLE 22(2)

By the same procedure as described in example 22 using the compound prepared in example 11(188) or example 11(168) in place of the compound prepared in example 11(7), the following compounds of the present invention were given.

EXAMPLE 22(1)

(Z)-2-(7-(1-hydroxy-1-methylethyl)-3,3-dimethyl-3,4-dihydro-(2H)-isoquinolin-1-ylidene)-1-cyclohexylethan-1-one TLC: Rf0.26 (hexane:ethyl acetate=3:1); NMR (CDCl$_3$): δ 11.36 (br, 1H), 7.86 (d, J=2.0 Hz, 1H), 7.48 (dd, J=8.0, 2.0

Hz, 1H), 7.14 (d, J=8.0 Hz, 1H), 5.66 (s, 1H), 2.82 (s, 2H), 2.32 (tt, J=11.5, 3.5 Hz, 1H), 1.90-1.76 (m, 5H), 1.71-1.20 (m, 18H).

EXAMPLE 22(2)

(Z)-2-(7-(1-hydroxy-1-methylethyl)-3,3-dimethyl-3,4-dihydro-(2H)-isoquinolin-1-ylidene)-1-(adamantan-1-yl)ethan-1-one TLC: Rf0.31 (hexane:ethyl acetate=3:1); NMR (CDCl$_3$): δ 11.59 (br, 1H), 7.87 (d, J=2.0 Hz, 1H), 7.47 (dd, J=8.0, 2.0 Hz, 1H), 7.14 (d, J=8.0 Hz, 1H), 5.80 (s, 1H), 2.81 (s, 2H), 2.06 (br, 3H), 1.92 (br, 6H), 1.80 (s, 1H), 1.75 (br, 6H), 1.63 (s, 6H), 1.29 (s, 6H).

EXAMPLE 23

(Z)-2-(6-acetyl-3,3-dimethyl-3,4-dihydro-(2H)-isoquinolin-1-ylidene)-1-phenylethan-1-one To a solution of the compound prepared in example 12 (356 mg) in ether (10 ml) was added n-butyl lithium (1.6 ml, 1.6 M in hexane) dropwise at −78° C. and the mixture was stirred for 30 minutes at 0° C. and thereto carbon dioxide gas was bubbled. The reaction mixture was stirred for 20 minutes at 0° C. and thereto was added methyl magnesium bromide (3.0 ml, 0.9M in tetrahydrofuran) dropwise and the mixture was stirred for 2 hours at 0° C. To the reaction mixture were added tetrahydrofuran, water and ethyl acetate, and filtered and the filtrate was washed with a saturated aqueous solution of ammonium chloride and ethyl acetate successively, and extracted with ethyl acetate. The combined organic layer was washed with water and brine, dried over anhydrous magnesium sulfate and concentrated. The residue was purified by column chromatography on silica gel (hexane:ethyl acetate=10:1→3:1) to give the compound of the present invention (84 mg) having the following physical data.

TLC: Rf0.27 (hexane:ethyl acetate=3:1); NMR (CDCl$_3$): δ 11.74 (br, 1H), 7.97-7.93 (m, 2H), 7.91-7.88 (m, 2H), 7.80 (s, 1H), 7.48-7.42 (m, 3H), 6.37 (s, 1H), 2.97 (s, 2H), 2.65 (s, 3H), 1.37 (s, 6H).

EXAMPLE 24

(Z)-2-(7-hydroxyiminomethyl-3,3-dimethyl-3,4-dihydro-(2H)-isoquinolin-1-ylidene)-1-phenylethan-1-one To a solution of the compound prepared in example 13(1) (209 mg) in formic acid (4 ml) was added hydroxylamine hydrochloride (62 mg) and the mixture was stirred for 1 hour at 100° C. The reaction mixture was allowed to cool, and then it was added to a 2N aqueous solution of sodium hydroxide and the mixture was extracted with ethyl acetate. The extract was washed with water and brine successively, dried over anhydrous magnesium sulfate and concentrated. The residue was purified by column chromatography on silica gel (hexane:ethyl acetate=3:1) to give the compound of the present invention (84 mg) having the following physical data.

TLC: Rf0.49 (hexane:ethyl acetate=1:1); NMR (CDCl$_3$): δ 11.83 (brs, 1H), 8.20 (s, 1H), 8.03 (d, J=1.5 Hz, 1H), 7.98-7.93 (m, 2H), 7.64 (dd, J=8.1, 1.5 Hz, 1H), 7.48-7.43 (m, 3H), 7.41 (brs, 1H), 7.25 (d, J=8.1 Hz, 1H), 6.35 (s, 1H), 2.92 (s, 2H), 1.37 (s, 6H).

EXAMPLE 24(1)-EXAMPLE 24(10)

By the same procedure as described in example 24 using the compound prepared in example 13, example 13(8), example 13(10), example 13(9), example 13(11), example 13(13), example 13(12), example 13(15), example 13(14) or example 13(16) in place of the compound prepared in example 13(1), the following compounds of the present invention were given.

EXAMPLE 24(1)

(Z)-2-(6-hydroxyiminomethyl-3,3-dimethyl-3,4-dihydro-(2H)-isoquinolin-1-ylidene)-1-phenylethan-1-one TLC: Rf0.51 (hexane:ethyl acetate=1:1); NMR (CDCl$_3$): δ 11.78 (brs, 1H), 8.15 (s, 1H), 7.97-7.92 (m, 2H), 7.84 (d, J=8.1 Hz, 1H), 7.53 (dd, J=8.1, 1.5 Hz, 1H), 7.50-7.40 (m, 4H), 6.34 (s, 1H), 2.92 (s, 2H), 1.37 (s, 6H).

EXAMPLE 24(2)

(Z)-2-(7-hydroxyiminomethyl-6-methoxy-3,3-dimethyl-3,4-dihydro-(2H)-isoquinolin-1-ylidene)-1-(adamantan-1-yl)ethan-1-one TLC: Rf0.30 (hexane:ethyl acetate=2:1); NMR (CDCl$_3$): δ 11.54 (br, 1H), 8.49 (s, 1H), 8.08 (s, 1H), 7.55 (br, 1H), 6.68 (s, 1H), 5.75 (s, 1H), 3.91 (s, 3H), 2.82 (s, 2H), 2.05 (br, 3H), 1.91 (br, 6H), 1.74 (br, 6H), 1.30 (s, 6H).

EXAMPLE 24(3)

(Z)-2-(7-hydroxyiminomethyl-6-methoxy-3,3-dimethyl-3,4-dihydro-(2H)-isoquinolin-1-ylidene)-1-cyclohexylethan-1-one TLC: Rf0.45 (hexane:ethyl acetate=1:1); NMR (CDCl$_3$): δ 11.31 (br, 1H), 8.49 (s, 1H), 8.08 (s, 1H), 7.38 (br, 1H), 6.68 (s, 1H), 5.61 (s, 1H), 3.91 (s, 3H), 2.83 (s, 2H), 2.29 (m, 1H), 1.88-1.79 (m, 4H), 1.70-1.20 (m, 12H).

EXAMPLE 24(4)

(Z)-2-(7-hydroxyiminomethyl-3,3-dimethyl-3,4-dihydro-(2H)-isoquinolin-1-ylidene)-1-(adamantan-1-yl)ethan-1-one TLC: Rf0.16 (hexane:ethyl acetate=4:1).

EXAMPLE 24(5)

(Z)-2-(7-hydroxyiminomethyl-6-methoxy-3,3-dimethyl-3,4-dihydro-(2H)-isoquinolin-1-ylidene)-1-cycloheptylethan-1-one TLC: Rf0.57 (hexane:ethyl acetate=1:1).

EXAMPLE 24(6)

(Z)-2-(7-hydroxyiminomethyl-3,3-dimethyl-3,4-dihydro-(2H)-isoquinolin-1-ylidene)—cyclohexylethan-1-one TLC: Rf0.34 (hexane:ethyl acetate=2:1).

EXAMPLE 24(7)

(Z)-2-(7-hydroxyiminomethyl-3,3,6-trimethyl-3,4-dihydro-(2H)-isoquinolin-1-ylidene)-1-(adamantan-1-yl)ethan-1-one TLC: Rf0.56 (hexane:ethyl acetate=3:1).

EXAMPLE 24(8)

(Z)-2-(7-hydroxyiminomethyl-3,3-dimethyl-3,4-dihydro-(2H)-isoquinolin-1-ylidene)-1-cycloheptylethan-1-one TLC: Rf0.31 (hexane:ethyl acetate=2:1).

EXAMPLE 24(9)

(Z)-2-(7-hydroxyiminomethyl-3,3,6-trimethyl-3,4-dihydro-(2H)-isoquinolin-1-ylidene)-1-cyclohexylethan-1-one TLC: Rf0.47 (hexane:ethyl acetate=3:1).

EXAMPLE 24(10)

(Z)-2-(7-hydroxyiminomethyl-3,3,6-trimethyl-3,4-dihydro-(2H)-isoquinolin-1-ylidene)-1-cycloheptylethan-1-one TLC: Rf0.39 (hexane:ethyl acetate=3:1); NMR (CDCl$_3$): δ 11.22 (br, 1H), 8.41 (s, 1H), 8.01 (s, 1H), 7.00 (s, 1H), 5.62 (s, 1H), 2.80 (s, 2H), 2.50-2.44 (m, 4H), 1.96-1.42 (m, 12H), 1.28 (s, 6H).

EXAMPLE 25

(Z)-2-(6-aminomethyl-3,3-dimethyl-3,4-dihydro-(2H)-isoquinolin-1-ylidene) 1-phenylethan-1-one To the compound prepared in example 24(1) (360 mg) were added ethanol (16 ml) and a 50% aqueous solution of acetic acid (4 ml) and to the mixture was added 10% palladium carbon (30 mg), and under atmosphere of hydrogen the mixture was vigorously stirred for 7 hours. The reaction mixture was filtered over celite. The filtrate was concentrated and azeotroped with ethanol. The residue was purified by column chromatography on silica gel (chloroform:methanol=19:1→4:1) to give the compound of the present invention (240 mg) having the following physical data.

TLC: Rf0.22 (chloroform:methanol=4:1); NMR (CDCl$_3$): δ 11.82 (brs, 1H), 7.97-7.91 (m, 2H), 7.79 (d, J=7.8 Hz, 1H), 7.46-7.40 (m, 3H), 7.28 (brd, J=7.8 Hz, 1H), 7.18 (brs, 1H), 6.32 (s, 1H), 3.93 (s, 2H), 2.89 (s, 2H), 1.36 (s, 6H).

EXAMPLE 25(1)-EXAMPLE 25(10)

By the same procedure as described in example 25 using the compound prepared in example 24, example 24(2) to example 24(5), example 24(7), example 24(6) or example 24(8)-example 24(10) in place of the compound prepared in example 24(1), the following compounds of the present invention were given.

EXAMPLE 25(1)

(Z)-2-(7-aminomethyl-3,3-dimethyl-3,4-dihydro-(2H)-isoquinolin-1-ylidene)-1-phenylethan-1-one TLC: Rf0.15 (hexane:ethyl acetate:isopropylamine=10:2:1); NMR (CDCl$_3$): δ 11.86 (br, 1H), 7.98-7.94 (m, 2H), 7.77 (s, 1H), 7.46-7.38 (m, 4H), 7.19 (d, J=7.5 Hz, 1H), 6.35 (s, 1H), 3.95 (s, 2H), 2.89 (s, 2H), 1.36 (s, 6H).

EXAMPLE 25(2)

(Z)-2-(7-aminomethyl-6-methoxy-3,3-dimethyl-3,4-dihydro-(2H)-isoquinolin-1-ylidene)-1-(adamantan-1-yl)ethan-1-one TLC: Rf0.16 (chloroform:methanol=10:1); NMR (CDCl$_3$): δ 11.52 (br, 1H), 7.56 (s, 1H), 6.63 (s, 1H), 5.71 (s, 1H), 3.90 (s, 3H), 3.85 (s, 2H), 2.80 (s, 2H), 2.06 (br, 3H), 1.92 (br, 6H), 1.75 (br, 6H), 1.29 (s, 6H).

EXAMPLE 25(3)

(Z)-2-(7-aminomethyl-6-methoxy-3,3-dimethyl-3,4-dihydro-(2H)-isoquinolin-1-ylidene)-1-cyclohexylethan-1-one TLC: Rf0.10 (chloroform:methanol=10:1); NMR (CDCl$_3$): δ 11.31 (br, 1H), 7.57 (s, 1H), 6.62 (s, 1H), 5.58 (s, 1H), 3.89 (s, 3H), 3.84 (s, 2H), 2.81 (s, 2H), 2.29 (tt, J=11.5, 3.5 Hz, 1H), 1.90-1.79 (m, 4H), 1.70-1.16 (m, 12H).

EXAMPLE 25(4)

(Z)-2-(7-aminomethyl-3,3-dimethyl-3,4-dihydro-(2H)-isoquinolin-1-ylidene)-1-(adamantan-1-yl)ethan-1-one TLC: Rf0.27 (chloroform:methanol=9:1); NMR (CDCl$_3$): δ 11.53 (brs, 1H), 7.64 (s, 1H), 7.35 (brd, J=7.8 Hz, 1H), 7.14 (d, J=7.8 Hz, 1H), 5.79 (s, 1H), 3.92 (s, 2H), 2.82 (s, 2H), 2.09-2.02 (m, 3H), 1.94-1.90 (m, 6H), 1.77-1.72 (m, 6H), 1.29 (s, 6H).

EXAMPLE 25(5)

(Z)-2-(7-aminomethyl-6-methoxy-3,3-dimethyl-3,4-dihydro-(2H)-isoquinolin-1-ylidene)-1-cycloheptylethan-1-one TLC: Rf0.25 (chloroform:methanol=10:1); NMR (CDCl$_3$) δ 11.23 (br, 1H), 7.57 (s, 1H), 6.62 (s, 1H), 5.55 (s, 1H), 3.89 (s, 3H), 3.84 (s, 2H), 2.80 (s, 2H), 2.45 (tt, J=10.0, 4.0 Hz, 1H), 1.95-1.88 (m, 2H), 1.83-1.46 (m, 10H), 1.29 (s, 6H).

EXAMPLE 25(6)

(Z)-2-(7-aminomethyl-3,3,6-trimethyl-3,4-dihydro-(2H)-isoquinolin-1-ylidene)-1-(adamantan-1-yl)ethan-1-one TLC: Rf0.28 (hexane:ethyl acetate:isopropylamine=10:1:0.5); NMR (CDCl$_3$): δ 11.52 (br, 1H), 7.63 (s, 1H), 6.96 (s, 1H), 5.78 (s, 1H), 3.90 (s, 2l), 2.78 (s, 2H), 2.37 (s, 3H), 2.06 (br, 3H), 1.93-1.92 (br, 6H), 1.76-1.75 (br, 6H), 1.28 (s, 6H).

EXAMPLE 25(7)

(Z)-2-(7-aminomethyl-3,3-dimethyl-3,4-dihydro-(2H)-isoquinolin-1-ylidene)-1-cyclohexylethan-1-one TLC: Rf0.23 (chloroform:methanol=9:1); NMR (CDCl$_3$): δ 11.32 (brs, 1H), 7.66 (brs, 1H), 7.34 (dd, J=7.8, 1.8 Hz, 1H), 7.14 (d, J=7.8 Hz, 1H), 5.65 (s, 1H), 3.92 (s, 2H), 2.82 (s, 2H), 2.31 (tt, J=12.0, 3.3 Hz, 1H), 1.93-1.18 (m, 16H).

EXAMPLE 25(8)

(Z)-2-(7-aminomethyl-3,3-dimethyl-3,4-dihydro-(2H)-isoquinolin-1-ylidene)-1-cycloheptylethan-1-one TLC: Rf0.28 (chloroform:methanol=9:1); NMR (CDCl$_3$): δ 11.24 (brs, 1H), 7.66 (d, J=1.8 Hz, 1H), 7.34 (dd, J=7.8, 1.8 Hz, 1H), 7.14 (d, J=7.8 Hz, 1H), 5.62 (s, 1H), 3.92 (s, 2H), 2.82 (s, 2H), 2.48 (tt, J=9.9, 3.3 Hz, 1H), 1.97-1.43 (m, 12H), 1.28 (s, 6H).

EXAMPLE 25(9)

(Z)-2-(7-aminomethyl-3,3,6-trimethyl-3,4-dihydro-(2H)-isoquinolin-1-ylidene)-1-cyclohexylethan-1-one TLC: Rf0.17 (hexane:ethyl acetate:isopropylamine=10:1:0.5); NMR (CDCl$_3$): δ 11.31 (br, 1H), 7.65 (s, 1H), 6.96 (s, 1H), 5.65 (s, 1H), 3.89 (s, 2H), 2.78 (s, 2H), 2.36 (s, 3H), 2.30 (m, 1H), 1.86 (m, 4H), 1.68 (m, 1H), 1.50-1.28 (m, 1H).

EXAMPLE 25(10)

(Z)-2-(7-aminomethyl-3,3,6-trimethyl-3,4-dihydro-(2H)-isoquinolin-1-ylidene)-1-cycloheptylethan-1-one TLC: Rf0.49 (hexane:ethyl acetate:isopropylamine=10:1:1); NMR (CDCl$_3$): δ 11.23 (br, 1H), 7.64 (s, 1H), 6.96 (s, 1H), 5.61 (s, 1H), 3.89 (s, 2H), 2.78 (s, 2H), 2.46 (m, 1H), 2.36 (s, 3H), 1.96-1.46 (m, 12H), 1.28 (s, 6H).

EXAMPLE 26

(Z)-2-(7-cyano-3,3-dimethyl-3,4-dihydro-(2H)-isoquinolin-1-ylidene)-1-(adamantan-1-yl)ethan-1-one To a solution of the compound prepared in example 24(4) (214 mg) in methylene chloride (6 ml) were added trifluoromethanesulfonic anhydride (0.11 ml) and triethylamine (0.11 ml) and the mixture was stirred for 3 hours at room temperature. To the reaction mixture was added a saturated aqueous solution of sodium bicarbonate and the mixture was extracted with ethyl acetate. The extract was washed with brine, dried over anhydrous magnesium sulfate and concentrated. The residue was crudely purified by column chromatography on silica gel (hexane:ethyl acetate=4:1), and it was dissolved in a mixture of ethanol (6 ml) and tetrahydrofuran (3 ml) and thereto was added sodium borohydride (75 mg) under cooling with ice and the mixture was stirred overnight. To the reaction mixture was added water and was extracted with methylene chloride. The extract was purified by column chromatography on silica gel (hexane:ethyl acetate=4:1) to give the compound of the present invention (52 mg) having the following physical data.

TLC: Rf0.23 (hexane:ethyl acetate=4:1); NMR (CDCl$_3$): δ 11.36 (brs, 1H), 8.00 (s, 1H), 7.65 (dd, J=7.8, 1.5 Hz, 1H), 7.30 (d, J=7.8 Hz, 1H), 5.76 (s, 1H), 2.90 (s, 2H), 2.12-2.04 (m, 3H), 1.93-1.88 (m, 6H), 1.78-1.73 (m, 6H), 1.30 (s, 6H).

EXAMPLE 26(1)-EXAMPLE 26(2)

By the same procedure as described in example 26 using the compound prepared in example 24(6) or example 24(8) in place of the compound prepared in example 24(4), the compounds of the present invention were given.

EXAMPLE 26(1)

(Z)-2-(7-cyano-3,3-dimethyl-3,4-dihydro-(2H)-isoquinolin-1-ylidene)-1-cyclohexylethan-1-one TLC: Rf0.36 (hexane:ethyl acetate=2:1); NMR (CDCl$_3$): δ 11.21 (brs, 1H), 7.99 (d, J=1.5 Hz, 1H), 7.65 (dd, J=7.5, 1.5 Hz, 1H), 7.31 (d, J=7.5 Hz, 1H), 5.62 (s, 1H), 2.90 (s, 2H), 2.33 (tt, J=11.4, 3.6 Hz, 1H), 1.94-1.66 (m, 5H), 1.52-1.18 (m, 1H).

EXAMPLE 26(2)

(Z)-2-(7-cyano-3,3-dimethyl-3,4-dihydro-(2H)-isoquinolin-1-ylidene)-1'-cycloheptylethan-1-one TLC: Rf0.42 (hexane:ethyl acetate=2:1); NMR (CDCl$_3$): δ 11.12 (brs, 1H), 7.98 (d, J=1.8 Hz, 1H), 7.65 (dd, J=8.1, 1.8 Hz, 1H), 7.30 (d, J=8.1 Hz, 1H), 5.58 (s, 1H), 2.90 (s, 2H), 2.50 (tt, J=9.9, 3.9 Hz, 1H), 1.97-1.43 (m, 12H), 1.30 (s, 6H).

EXAMPLE 27

(Z)-2-(7-(morpholin-4-yl)methyl-3,3-dimethyl-3,4-dihydro-(2H)-isoquinolin-1-ylidene)-1-(naphthalen-1-yl)ethan-1-one To a solution of the compound prepared in example 13(2) (206 mg) in tetrahydrofuran (5 ml) was added morpholine (0.065 ml) dropwise and the mixture was stirred for 2 hours at room temperature. To the reaction mixture was added sodium triacetoxyborohydride (167 mg) and the mixture was stirred for 3 hours. To the reaction mixture was added sodium triacetoxyborohydride (30 mg) and the mixture was stirred for 1 hour. The reaction mixture was added to a cold saturated aqueous solution of sodium bicarbonate and the mixture was extracted with ethyl acetate. The extract was washed with water and brine successively, dried over anhydrous magnesium sulfate and concentrated. The residue was purified by column chromatography on silica gel (hexane:ethyl acetate=1:1→2:3) to give the compound of the present invention (250 mg) having the following physical data.

TLC: Rf0.17 (ethyl acetate:hexane=1:1); NMR (CDCl$_3$): δ 11.80 (br, 1H), 8.47 (m, 1H), 7.90-7.85 (m, 2H), 7.70 (dd, J=7.0, 1.0 Hz, 1H), 7.64 (s, 1H), 7.55-7.45 (m, 3H), 7.40 (dd, J=8.0, 1.5 Hz, 1H), 7.17 (d, J=8.0 Hz, 1H), 6.08 (s, 1H), 3.68 (t, J=7.5 Hz, 4H), 3.47 (s, 2H), 2.92 (s, 2H), 2.41 (t, J=7.5 Hz, 4H), 1.41 (s, 6H).

EXAMPLE 27(1)-EXAMPLE 27(27)

By the same procedure as described in example 27 using the compound prepared in example 13(1), example 13, example 13(1), example 13(8), example 13(9), example 13(11), example 11(119), example 13(12), example 13(5), example 13(13), example 13(7), example 13(14), example 13(15), example 13(14), example 13(6) or example 13(16) and morpholine or a corresponding amine derivative instead, the compounds of the present invention were given.

EXAMPLE 27(1)

(Z)-2-(7-(morpholin-4-yl)methyl-3,3-dimethyl-3,4-dihydro-(2H)-isoquinolin-1-ylidene)-1-phenylethan-1-one TLC: Rf0.32 (hexane:ethyl acetate=1:4); NMR (CDCl$_3$): δ 11.87 (brs, 1H), 7.99-7.93 (m, 2H), 7.75 (brs, 1H), 7.48-7.39 (m, 4H), 7.17 (d, J=7.8 Hz, 1H), 6.33 (s, 1H), 3.74 (t, J=4.8 Hz, 4H), 3.55 (s, 2H), 2.88 (s, 2H), 2.48 (t, J=4.8 Hz, 4H), 1.36 (s, 6H).

EXAMPLE 27(2)

(Z)-2-(7-(piperidin-1-yl)methyl-3,3-dimethyl-3,4-dihydro-(2H)-isoquinolin-1-ylidene)-1-phenylethan-1-one TLC: Rf0.49 (chloroform:methanol=9:1); NMR (CDCl$_3$): δ 11.87 (brs, 1H), 7.99-7.93 (m, 2H), 7.74 (brs, 1H), 7.48-7.39 (m, 4H), 7.16 (d, J=7.8 Hz, 1H), 6.34 (s, 1H), 3.52 (s, 2H), 2.88 (s, 2H), 2.41 (brs, 4H), 1.60 (quintet, J=5.4 Hz, 4H), 1.46 (m, 2H), 1.36 (s, 6H).

EXAMPLE 27(3)

(Z)-2-(7-(N-methyl-N-(2-dimethylaminoethyl)aminomethyl)-3,3-dimethyl-3,4-dihydro-(2H)-isoquinolin-1-ylidene)-1-phenylethan-1-one TLC: Rf0.13 (chloroform:methanol=9:1); NMR (CDCl$_3$): δ 11.87 (brs, 1H), 7.99-7.93 (m, 2H), 7.76 (brs, 1H), 7.47-7.38 (m, 4H), 7.16 (d, J=7.8 Hz, 1H), 6.34 (s, 1H), 3.57 (s, 2H), 2.88 (s, 2H), 2.55-2.44 (m, 4H), 2.28 (s, 3H), 2.23 (s, 6H), 1.36 (s, 6H).

EXAMPLE 27(4)

(Z)-2-(7-(N-(2-hydroxyethyl)-N-methylaminomethyl)-3,3-dimethyl-3,4-dihydro-(2H)-isoquinolin-1-ylidene)-1-phenylethan-1-one TLC: Rf0.40 (chloroform:methanol=9:1); NMR (CDCl$_3$): δ 11.86 (brs, 1H), 7.99-7.93 (m, 2H), 7.71 (brs, 1H), 7.47-7.38 (m, 4H), 7.18 (d, J=7.8 Hz, 1H), 6.32 (s, 1H), 3.67 (t, J=5.4 Hz, 2H), 3.63 (s, 2H), 2.89 (s, 2H), 2.64 (t, J=5.4 Hz, 2H), 2.42 (m, 1H), 2.28 (s, 3H), 1.36 (s, 6H).

EXAMPLE 27(5)

(Z)-2-(7-(N-cyclohexylaminomethyl)-3,3-dimethyl-3,4-dihydro-(2H)-isoquinolin-1-ylidene)-1-phenylethan-1-one TLC: Rf0.36 (chloroform:methanol=9:1); NMR (CDCl$_3$): δ 11.85 (brs, 1H), 7.99-7.93 (m, 2H), 7.76 (brs, 1H), 7.47-7.38 (m, 4H), 7.17 (d, J=7.8 Hz, 1H), 6.34 (s, 1H), 3.87 (s, 2H), 2.88 (s, 2H), 2.53 (m, 1H), 2.01-1.91 (m, 2H), 1.82-1.71 (m, 2H), 1.62 (m, 1H), 1.38-1.08 (m, 6H), 1.36 (s, 6H).

EXAMPLE 27(6)

(Z)-2-(6-(morpholin-4-yl)methyl-3,3-dimethyl-3,4-dihydro-(2H)-isoquinolin-1-ylidene)-1-phenylethan-1-one TLC: Rf0.28 (hexane:ethyl acetate=1:4); NMR (CDCl$_3$): δ 11.82 (brs, 1H), 7.97-7.92 (m, 2H), 7.78 (d, J=8.4 Hz, 1H), 7.47-7.40 (m, 3H), 7.30 (brd, J=8.4 Hz, 1H), 7.19 (brs, 1H), 6.32 (s, 1H), 3.74 (t, J=4.8 Hz, 4H), 3.53 (s, 2H), 2.89 (s, 2H), 2.48 (t, J=4.8 Hz, 4H), 1.36 (s, 6H).

EXAMPLE 27(7)

(Z)-2-(6-dimethylaminomethyl-3,3-dimethyl-3,4-dihydro-(2H)-isoquinolin-1-ylidene)-1-phenylethan-1-one TLC: Rf0.31 (chloroform:methanol=9:1); NMR (CDCl$_3$): δ 11.82 (brs, 1H), 7.98-7.92 (m, 2H), 7.78 (d, J=8.4 Hz, 1H), 7.47-7.40 (m, 3H), 7.27 (m, 1H), 7.19 (brs, 1H), 6.32 (s, 1H), 3.46 (s, 2H), 2.89 (s, 2H), 2.28 (s, 6H), 1.36 (s, 6H).

EXAMPLE 27(8)

(Z)-2-(6-methylaminomethyl-3,3-dimethyl-3,4-dihydro-(2H)-isoquinolin-1-ylidene)-1-phenylethan-1-one TLC: Rf0.23 (chloroform:methanol=4:1); NMR (CDCl$_3$): δ 11.82 (brs, 1H), 7.98-7.91 (m, 2H), 7.79 (d, J=8.4 Hz, 1H), 7.47-7.40 (m, 3H), 7.28 (m, 1H), 7.20 (brs, 1H), 6.32 (s, 1H), 3.80 (s, 2H), 2.89 (s, 2H), 2.50 (s, 3H), 1.36 (s, 6H).

EXAMPLE 27(9)

(Z)-2-(7-dimethylaminomethyl-3,3-dimethyl-3,4-dihydro-(2H)-isoquinolin-1-ylidene)-1-phenylethan-1-one TLC: Rf0.53 (hexane:ethyl acetate:isopropylamine=10:2:1); NMR (CDCl$_3$): δ 11.88 (br, 1H), 7.98-7.95 (m, 2H), 7.74 (d, J=1.5 Hz, 1H), 7.46-7.42 (m, 3H), 7.39 (dd, J=8.0, 1.5 Hz, 1H), 7.17 (d, J=8.0 Hz, 1H), 6.34 (s, 1H), 3.47 (s, 2H), 2.89 (s, 2H), 2.28 (s, 6H), 1.36 (s, 6H).

EXAMPLE 27(10)

(Z)-2-(7-dimethylaminomethyl-6-methoxy-3,3-dimethyl-3,4-dihydro-(2H)-isoquinolin-1-ylidene)-1-(adamantan-1-yl)ethan-1-one TLC: Rf0.22 (chloroform:methanol=10:1); NMR (CDCl$_3$): δ 11.58 (br, 1H), 7.58 (s, 1H), 6.63 (s, 1H), 5.71 (s, 1H), 3.88 (s, 3H), 3.46 (s, 2H), 2.80 (s, 2H), 2.30 (s, 6H), 2.06 (br, 3H), 1.92 (br, 6H), 1.74 (br, 6H), 1.29 (s, 6H).

EXAMPLE 27(11)

(Z)-2-(6-methoxy-7-methylaminomethyl-3,3-dimethyl-3,4-dihydro-(2H)-isoquinolin-1-ylidene)-1-(adamantan-1-yl)ethan-1-one TLC: Rf0.35 (hexane:ethyl acetate:isopropylamine=10:1:1); NMR (CDCl$_3$): δ 11.53 (br, 1H), 7.56 (s, 1H), 6.63 (s, 1H), 5.71 (s, 1H), 3.88 (s, 3H), 3.76 (s, 2H), 2.80 (s, 2H), 2.48 (s, 3H), 2.06 (br, 3H), 1.92 (br, 6H), 1.75 (br, 6H), 1.29 (s, 6H).

EXAMPLE 27(12)

(Z)-2-(7-methylaminomethyl-3,3-dimethyl-3,4-dihydro-(2H)-isoquinolin-1-ylidene) 1-(adamantan-1-yl)ethan-1-one TLC: Rf0.28 (chloroform:methanol=9:1); NMR (CDCl$_3$): δ 11.54 (brs, 1H), 7.64 (d, J=1.5 Hz, 1H), 7.36 (dd, J=7.5, 1.5 Hz, 1H), 7.13 (d, J=7.5 Hz, 1H), 5.79 (s, 1H), 3.79 (s, 2H), 2.82 (s, 2H), 2.50 (s, 3H), 2.09-2.03 (m, 3H), 1.94-1.90 (m, 6H), 1.77-1.72 (m, 6H), 1.28 (s, 6H).

EXAMPLE 27(13)

(Z)-2-(6-methoxy-7-methylaminomethyl-3,3-dimethyl-3,4-dihydro-(2H)-isoquinolin-1-ylidene)-1-cycloheptylethan-1-one TLC: Rf0.24 (chloroform:methanol=10:1); NMR (CDCl$_3$): δ 11.24 (br, 1H), 7.57 (s, 1H), 6.62 (s, 1H), 5.54 (s, 1H), 3.88 (s, 3H), 3.75 (s, 2H), 2.80 (s, 2H), 2.49-2.40 (m, 4H), 1.95-1.87 (m, 2H), 1.82-1.46 (m, 10H), 1.29 (s, 6H).

EXAMPLE 27(14)

(Z)-2-(6-chloro-7-dimethylaminomethyl-3,3-dimethyl-3,4-dihydro-(2H)-isoquinolin-1-ylidene)-1-(adamantan-1-yl)ethan-1-one TLC: Rf0.16 (ethyl acetate:hexane=1:5); NMR (CDCl$_3$): δ 11.52 (br, 1H), 7.73 (s, 10H), 7.18 (s, 1H), 5.76 (s, 1H), 3.57 (s, 2H), 2.78 (s, 2H), 2.34 (s, 6H), 2.05 (m, 3H), 1.91 (m, 6H), 1.74 (m, 6H), 1.28 (s, 6H).

EXAMPLE 27(15)

(Z)-2-(7-methylaminomethyl-3,3,6-trimethyl-3,4-dihydro-(2H)-isoquinolin-1-ylidene)-1-(adamantan-1-yl)ethan-1-one TLC: Rf0.18 (chloroform:methanol=50:1); NMR (CDCl$_3$): δ 11.53 (br, 10H), 7.59 (s, 1H), 6.96 (s, 1H), 5.77 (s, 1H), 3.75 (s, 2H), 2.77 (s, 2H), 2.55 (s, 3H), 2.38 (s, 3H), 2.06 (br, 3H), 1.93-1.92 (br, 6H), 1.76-1.75 (br, 6H), 1.28 (s, 6H).

EXAMPLE 27(16)

(Z)-2-(7-dimethylaminomethyl-3,3,6-trimethyl-3,4-dihydro-(2H)-isoquinolin-1-ylidene)-1-(adamantan-1-yl)ethan-1-one TLC: Rf0.21 (hexane:ethyl acetate=3:1); NMR (CDCl$_3$): δ 11.56 (br, 1H), 7.53 (s, 1H), 6.96 (s, 1H), 5.75 (s, 1H), 3.41 (s, 2H), 2.77 (s, 2H), 2.39 (s, 3H), 2.27 (s, 6H), 2.06 (br, 3H), 1.93-1.92 (br, 6H), 1.76-1.75 (br, 6H), 1.28 (s, 6H).

EXAMPLE 27(17)

(Z)-2-(6-chloro-7-methylaminomethyl-3,3-dimethyl-3,4-dihydro-(2H)-isoquinolin-1-ylidene)-1-(adamantan-1-yl)ethan-1-one TLC: Rf0.35 (water:methanol:chloroform=1:10:100); NMR (CDCl$_3$): δ 11.45 (br, 1H), 7.79 (s, 1H), 7.20 (s, 1H), 5.81 (s, 1H), 3.94 (s, 2H), 2.79 (s, 2H), 2.53 (s, 3H), 2.06 (m, 3H), 1.91 (m, 6H), 1.74 (m, 6H), 1.28 (s, 6H).

EXAMPLE 27(18)

(Z)-2-(7-methylaminomethyl-3,3-dimethyl-3,4-dihydro-(2H)-isoquinolin-1-ylidene)-1-cyclohexylethan-1-one TLC: Rf0.21 (chloroform:methanol=9:1); NMR (CDCl$_3$): δ 11.31 (brs, 1H), 7.67 (brs, 1H), 7.36 (dd, J=7.5, 1.5 Hz, 1H), 7.13 (d, J=7.5 Hz, 1H), 5.66 (s, 1H), 3.79 (s, 2H), 2.82 (s, 2H), 2.49 (s, 3H), 2.31 (tt, J=11.4, 3.6 Hz, 1H), 1.94-1.64 (m, 5H), 1.54-1.18 (m, 11H).

EXAMPLE 27(19)

(Z)-2-(6-chloro-7-methylaminomethyl-3,3-dimethyl-3,4-dihydro-(2H)-isoquinolin-1-ylidene)-1-cycloheptylethan-1-one TLC: Rf0.47 (water:methanol:chloroform=1:10:100); NMR (CDCl$_3$): δ 11.19 (br, 1H), 7.71 (s, 1H), 7.19 (s, 1H), 5.59 (s, 1H), 3.87 (s, 2H), 2.79 (s, 2H), 2.52 (s, 3H), 2.47 (m, 1H), 1.95-1.40 (m, 12H), 1.28 (s, 6H).

EXAMPLE 27(20)

(Z)-2-(6-chloro-7-dimethylaminomethyl-3,3-dimethyl-3,4-dihydro-(2H)-isoquinolin-1-ylidene)-1-cycloheptylethan-1-one TLC: Rf0.24 (ethyl acetate:hexane=1:3); NMR (CDCl$_3$): δ 11.24 (br, 1H), 7.73 (s, 1H), 7.18 (s, 1H), 5.58 (s, 1H), 3.55 (s, 2H), 2.78 (s, 2H), 2.48 (m, 1H), 2.33 (s, 6H), 1.95-1.40 (m, 12H), 1.28 (s, 6H).

EXAMPLE 27(21)

(Z)-2-(7-methylaminomethyl-3,3,6-trimethyl-3,4-dihydro-(2H)-isoquinolin-1-ylidene)-1-cyclohexylethan-1-one TLC: Rf0.20 (chloroform:methanol=20:1); NMR (CDCl$_3$): δ 11.31 (br, 1H), 7:61 (s, 1H), 6.96 (s, 1H), 5.63 (s, 1H), 3.75 (s, 2H), 2.77 (s, 2H), 2.54 (s, 3H), 2.37 (s, 3H), 2.34-2.26 (m, 1H), 1.90-1.79 (m, 4H), 1.71 (m, 1H), 1.55-1.28 (m, 11H).

EXAMPLE 27(22)

(Z)-2-(7-methylaminomethyl-3,3-dimethyl-3,4-dihydro-(2H)-isoquinolin-1-ylidene)-1-cycloheptylethan-1-one TLC: Rf0.28 (chloroform:methanol=9:1); NMR (CDCl$_3$): δ 11.24 (brs, 1H), 7.65 (d, J=1.8 Hz, 1H), 7.34 (dd, J=7.8, 1.8 Hz, 1H), 7.13 (d, J=7.8 Hz, 1H), 5.62 (s, 1H), 3.78 (s, 2H), 2.82 (s, 2H), 2.49 (s, 3H), 2.47 (m, 1H), 1.97-1.43 (m, 12H), 1.28 (s, 6H).

EXAMPLE 27(23)

(Z)-2-(7-dimethylaminomethyl-3,3,6-trimethyl-3,4-dihydro-(2H)-isoquinolin 1-ylidene)-1-cyclohexylethan-1-one TLC: Rf0.22 (hexane:ethyl acetate=1:2); NMR (CDCl$_3$): δ 11.34 (br, 1H), 7.55 (s, 1H), 6.95 (s, 1H), 5.62 (s, 1H), 3.39 (s, 2H), 2.77 (s, 2H), 2.38 (s, 3H), 2.30 (m, 1H), 2.27 (s, 6H), 1.89-1.79 (m, 4H), 1.70 (m, 1H), 1.54-1.28 (m, 1H).

EXAMPLE 27(24)

(Z)-2-(6-chloro-7-methylaminomethyl-3,3-dimethyl-3,4-dihydro-(2H)-isoquinolin-1-ylidene)-1-cyclohexylethan-1-one TLC: Rf0.43 (water:methanol:chloroform=1:10:100); NMR (CDCl$_3$): δ 11.27 (br, 1H), 7.71 (s, 1H), 7.19 (s, 1H), 5.62 (s, 1H), 3.87 (s, 2H), 2.79 (s, 2H), 2.51 (s, 3H), 2.31 (m, 1H), 1.90-1.20 (m, 10H), 1.28 (s, 6H).

EXAMPLE 27(25)

(Z)-2-(6-chloro-7-dimethylaminomethyl-3,3-dimethyl-3,4-dihydro-(2H)-isoquinolin-1-ylidene)-1-cyclohexylethan-1-one TLC: Rf0.59 (water:methanol:chloroform=1:10:100); NMR (CDCl$_3$): δ 11.31 (br, 1H), 7.74 (s, 1H), 7.18 (s, 1H), 5.62 (s, 1H), 3.55 (s, 2H), 2.79 (s, 2H), 2.33 (s, 6H), 2.32 (m, 1H), 1.90-1.20 (m, 10H), 1.28 (s, 6H).

EXAMPLE 27(26)

(Z)-2-(7-methylaminomethyl-3,3,6-trimethyl-3,4-dihydro-(2H)-isoquinolin-1-ylidene)-1-cycloheptylethan-1-one TLC: Rf0.27 (chloroform:methanol=10:1); NMR (CDCl$_3$): δ 11.23 (br, 1H), 7.61 (s, 1H), 6.96 (s, 1H), 5.60 (s, 1H), 3.75 (s, 2H), 2.77 (s, 2H), 2.54 (s, 3H), 2.46 (m, 1H), 2.37 (s, 3H), 1.96-1.44 (m, 12H), 1.27 (s, 6H).

EXAMPLE 27(27)

(Z)-2-(7-dimethylaminomethyl-3,3,6-trimethyl-3,4-dihydro-(2H)-isoquinolin-1-ylidene)-1-cycloheptylethan-1-one TLC: Rf0.29 (hexane:ethyl acetate=1:2); NMR (CDCl$_3$): δ 11.27 (br, 1H), 7.55 (s, 1H), 6.95 (s, 1H), 5.58 (s, 1H), 3.40 (s, 2H), 2.77 (s, 2H), 2.48 (m, 1H), 2.38 (s, 3H), 2.27 (s, 6H), 1.96-1.44 (m, 12H), 1.28 (s, 6H).

EXAMPLE 28

(Z)-2-(6-hydroxymethyl-3,3-dimethyl-3,4-dihydro-(2H)-isoquinolin-1-ylidene)-1-phenylethan-1-one To a solution of the compound prepared in example 13(85 ing) in methanol (4 ml) and tetrahydrofuran (1 ml) was added sodium borohydride (20 mg) and 10 minutes later thereto was added water and the mixture was extracted with ethyl acetate. The extract was dried over anhydrous magnesium sulfate and concentrated. The residue was purified by column chromatography on silica gel (hexane:ethyl acetate=3:1→1:1) to give the compound of the present invention (90 mg) having the following physical data.

TLC: Rf0.34 (hexane:ethyl acetate=1:1); NMR (CDCl$_3$): δ 11.81 (br, 1H), 7.96-7.93 (m, 2H), 7.82 (d, J=8.0 Hz, 1H), 7.46-7.41 (m, 3H), 7.32 (d, J=8.0 Hz, 1H), 7.23 (s, 1H), 6.33 (s, 1H), 4.76 (brd, 2H), 2.90 (s, 2H), 1.86 (brt, 1H), 1.36 (s, 6H).

EXAMPLE 28(1)-EXAMPLE 28(13)

By the same procedure as described in example 28 using the compound prepared in example 13, example 13(5)-example 13(16) in place of the compound prepared in example 13, the following compounds of the present invention were given.

EXAMPLE 28(1)

(Z)-2-(7-hydroxymethyl-3,3-dimethyl-3,4-dihydro-(2H)-isoquinolin-1-ylidene)-1-phenylethan-1-one TLC: Rf0.12 (hexane:ethyl acetate=3:1); NMR (CDCl$_3$): δ 11.83 (br, 1H), 7.97-7.94 (m, 2H), 7.83 (s, 1H), 7.47-7.42 (m, 4H), 7.22 (d, J=7.5 Hz, 1H), 6.35 (s, 1H), 4.77 (s, 2H), 2.90 (s, 2H), 1.80 (br, 1H), 1.36 (s, 6H).

EXAMPLE 28(2)

(Z)-2-(6-chloro-7-hydroxymethyl-3,3-dimethyl-3,4-dihydro-(2H)-isoquinolin-1-ylidene)-1-(adamantan-1-yl)ethan-1-one TLC: Rf0.38 (ethyl acetate:hexane=1:3); NMR (CDCl$_3$): δ 11.46 (br, 1H), 7.83 (s, 1H), 7.20 (s, 1H), 5.78 (s, 1H), 4.83 (s, 2H), 2.82 (s, 2H), 2.06 (m, 3H), 1.91 (m, 6H), 1.74 (m, 6H), 1.29 (s, 6H).

EXAMPLE 28(3)

(Z)-2-(6-chloro-7-hydroxymethyl-3,3-dimethyl-3,4-dihydro-(2H)-isoquinolin-1-ylidene)-1-cyclohexylethan-1-one TLC: Rf0.29 (ethyl acetate:hexane=1:3); NMR (CDCl$_3$): δ 11.25 (br, 1H), 7.84 (s, 1H), 7.19 (s, 1H), 5.65 (s, 1H), 4.82 (d, J=6.0 Hz, 2H), 2.80 (s, 2H), 2.31 (m, 1H), 1.90-1.20 (m, 10H), 1.29 (s, 6H).

EXAMPLE 28(4)

(Z)-2-(6-chloro-7-hydroxymethyl-3,3-dimethyl-3,4-dihydro-(2H)-isoquinolin-1-ylidene)-1-cycloheptylethan-1-one TLC: Rf0.31 (ethyl acetate:hexane=1:3); NMR (CDCl$_3$): δ 11.16 (br, 1H), 7.83 (s, 1H), 7.17 (s, 1H), 5.61 (s, 1H), 4.81 (s, 2H), 2.79 (s, 2H), 2.46 (m, 1H), 1.95-1.40 (m, 12H), 1.27 (s, 6H).

EXAMPLE 28(5)

(Z)-2-(7-hydroxymethyl-6-methoxy-3,3-dimethyl-3,4-dihydro-(2H)-isoquinolin-1-ylidene)-1-(adamantan-1-yl)ethan-1-one TLC: Rf0.44 (hexane:ethyl acetate=1:1); NMR (CDCl$_3$): δ 11.50 (br, 1H), 7.64 (s, 1H), 6.65 (s, 1H), 5.72 (s, 1H), 4.72 (d, J=6.0 Hz, 2H), 3.92 (s, 3H), 2.82 (s, 2H), 2.18 (t, J=6.0 Hz, 1H), 2.06 (br, 3H), 1.91 (br, 6H), 1.75 (br, 6H), 1.29 (s, 6H).

EXAMPLE 28(6)

(Z)-2-(7-hydroxymethyl-3,3-dimethyl-3,4-dihydro-(2H)-isoquinolin-1-ylidene)-1-(adamantan-1-yl)ethan-1-one TLC: Rf0.50 (hexane:ethyl acetate=1:1); NMR (CDCl$_3$): δ 11.51 (brs, 1H), 7.71 (brs, 1H), 7.40 (dd, J=7.8, 1.8 Hz, 1H), 7.17 (d, J=7.8 Hz, 1H), 5.80 (s, 1H), 4.75 (d, J=5.4 Hz, 2H), 2.83 (s, 2H), 2.09-2.03 (m, 3H), 1.94-1.90 (m, 6H), 1.78-1.72 (m, 6H), 1.29 (s, 6H).

EXAMPLE 28(7)

(Z)-2-(7-hydroxymethyl-6-methoxy-3,3-dimethyl-3,4-dihydro-(2H)-isoquinolin-1-ylidene)-1-cyclohexylethan-1-one TLC: Rf0.10 (hexane:ethyl acetate=3:1); NMR (CDCl$_3$): δ 11.29 (br, 1H), 7.64 (s, 1H), 6.65 (s, 1H), 5.58 (s, 1H), 4.71 (d, J=6.0 Hz, 2H), 3.91 (s, 3H), 2.82 (s, 2), 2.29 (tt, J=11.5, 3.5 Hz, 1H), 2.16 (t, J=6.0 Hz, 1H), 1.89-1.78 (m, 4H), 1.69 (m, 1H), 1.56-1.20 (m, 1H).

EXAMPLE 28(8)

(Z)-2-(7-hydroxymethyl-6-methoxy-3,3-dimethyl-3,4-dihydro-(2H)-isoquinolin-1-ylidene)-1-cycloheptylethan-1-one TLC: Rf0.41 (hexane:ethyl acetate=1:1); NMR (CDCl$_3$): δ 11.21 (br, 1H), 7.64 (s, 1H), 6.65 (s, 1H), 5.55 (s, 1H), 4.71 (d, J=6.5 Hz, 2H), 3.91 (s, 3H), 2.82 (s, 2H), 2.45 (m, 1H), 2.16 (t, J=6.5 Hz, 1H), 1.95-1.88 (m, 2H), 1.82-1.46 (m, 10H), 1.29 (s, 6H).

EXAMPLE 28(9)

(Z)-2-(7-hydroxymethyl-3,3,6-trimethyl-3,4-dihydro-(2H)-isoquinolin-1-ylidene)-1-(adamantan-1-yl)ethan-1-one TLC: Rf0.17 (hexane:ethyl acetate=5:1); NMR (CDCl$_3$): δ 11.50 (br, 10H), 7.69 (s, 1H), 6.99 (s, 1H), 5.78 (s, 1H), 4.75 (d, J=5.7 Hz, 2H), 2.79 (s, 2H), 2.39 (s, 3H), 2.06 (br, 3H), 1.92-1.91 (br, 6H), 1.76-1.75 (br, 6H), 1.28 (s, 6H).

EXAMPLE 28(10)

(Z)-2-(7-hydroxymethyl-3,3-dimethyl-3,4-dihydro-(2H)-isoquinolin-1-ylidene)-1-cyclohexylethan-1-one TLC: Rf0.49 (hexane:ethyl acetate=1:1); NMR (CDCl$_3$): δ 11.30 (brs, 1H), 7.72 (brs, 1H), 7.39 (dd, J=7.8, 1.8 Hz, 1H), 7.17 (d, J=7.8 Hz, 1H), 5.66 (s, 1H), 4.74 (s, 2H), 2.83 (s, 2H), 2.30 (tt, J=11.4, 3.6 Hz, 1H), 1.93-1.18 (m, 16H).

EXAMPLE 28(11)

(Z)-2-(7-hydroxymethyl-3,3,6-trimethyl-3,4-dihydro-(2H)-isoquinolin-1-ylidene)-1-cyclohexylethan-1-one TLC: Rf0.21 (hexane:ethyl acetate=3:1); NMR (CDCl$_3$): δ 11.29 (br, 10H), 7.70 (s, 1H), 6.98 (s, 1H), 5.64 (s, 1H), 4.74 (d, J=5.1 Hz, 2H), 2.79 (s, 2H), 2.37 (s, 3H), 2.30 (m, 1H), 1.92-1.76 (m, 4H), 1.69 (m, 1H), 1.55-1.28 (m, 1H).

EXAMPLE 28(12)

(Z)-2-(7-hydroxymethyl-3,3-dimethyl-3,4-dihydro-(2H)-isoquinolin-1-ylidene)-1-cycloheptylethan-1-one TLC: Rf0.21 (hexane:ethyl acetate=2:1); NMR (CDCl$_3$): δ 11.22 (brs, 1H), 7.71 (brs, 1H), 7.39 (dd, J=7.8, 1.8 Hz, 1H), 7.16 (d, J=7.8 Hz, 1H), 5.62 (s, 1H), 4.74 (s, 2H), 2.83 (s, 2H), 2.46 (tt, J=9.9, 3.3 Hz, 1H), 1.99-1.42 (m, 12H), 1.28 (s, 6H).

EXAMPLE 28(13)

(Z)-2-(7-hydroxymethyl-3,3,6-trimethyl-3,4-dihydro-(2H)-isoquinolin-1-ylidene)-1-cycloheptylethan-1-one TLC: Rf0.34 (hexane:ethyl acetate=3:1); NMR (CDCl$_3$): δ 11.21 (br, 1H), 7.70 (s, 1H), 6.98 (s, 1H), 5.61 (s, 1H), 4.74 (d, J=4.8 Hz, 2H), 2.79 (s, 2H), 2.46 (m, 1H), 2.37 (s, 3H), 1.96-1.86 (m, 2H), 1.84-1.56 (m, 10H), 1.28 (s, 6H).

EXAMPLE 29-EXAMPLE 29(11)

By the same procedure as described in example 8 using the compound prepared in example 2(3) or example 14, example 14(2), example 14(3), example 14(10), example 14(3) or example 14(10), and acetyl chloride or a corresponding halide derivative, the following compounds of the present invention were given.

EXAMPLE 29

(Z)-2-(3,3-dimethyl-3,4-dihydro-(2H)-isoquinolin-1-ylidene)-1-(1-phenylsulfonylpiperidin-4-yl)ethan-1-one TLC: Rf0.47 (hexane:ethyl acetate=1:1); NMR (CDCl$_3$): δ 11.29 (br, 1H), 7.81-7.77 (m, 2H), 7.64-7.51 (m, 4H), 7.40 (t, J=7.5 Hz, 1H), 7.31-7.26 (m, 1H), 7.17 (d, J=7.5 Hz, 1H), 5.54 (s, 1H), 3.88-3.85 (m, 2H), 2.84 (s, 2H), 2.41-2.33 (m, 2H), 2.24-2.14 (m, 1H), 1.97-1.76 (m, 4H), 1.29 (s, 6H).

EXAMPLE 29(1)

(Z)-2-(3,3-dimethyl-3,4-dihydro-(2H)-isoquinolin-1-ylidene)-1-(1-ethylsulfonylpiperidin-4-yl)ethan-1-one TLC: Rf0.26 (hexane:ethyl acetate=1:1); NMR (CDCl$_3$): δ 11.32 (br, 1H), 7.69 (d, J=7.5 Hz, 1H), 7.41 (t, J=7.5 Hz, 1H), 7.30 (t, J=7.5 Hz, 1H), 7.19 (d, J=7.5 Hz, 1H), 5.62 (s, 1H), 3.88-3.84 (m, 2H), 3.01-2.86 (m, 6H), 2.46-2.35 (m, 1H), 1.99-1.93 (m, 2H), 1.89-1.78 (m, 2H), 1.38 (t, J=7.0 Hz, 3H), 1.31 (s, 6H).

EXAMPLE 29(2)

(Z)-2-(3,3-dimethyl-3,4-dihydro-(2H)-isoquinolin-1-ylidene)-1-(1-propylsulfonylpiperidin-4-yl)ethan-1-one TLC: Rf0.34 (hexane:ethyl acetate=1:1); NMR (CDCl$_3$): δ 11.32 (br, 1H), 7.69 (d, J=7.5 Hz, 1H), 7.41 (t, J=7.5 Hz, 1H), 7.30 (t, J=7.5 Hz, 1H), 7.19 (d, J=7.5 Hz, 1H), 5.62 (s, 1H), 3.87-3.83 (m, 2H), 2.93-2.83 (m, 6H), 2.44-2.35 (m, 1H), 1.99-1.75 (m, 6H), 1.31 (s, 6H), 1.06 (t, J=7.5 Hz, 3H).

EXAMPLE 29(3)

(Z)-2-(3,3-dimethyl-3,4-dihydro-(2H)-isoquinolin-1-ylidene)-1-(1-butylsulfonylpiperidin-4-yl)ethan-1-one TLC: Rf0.10 (hexane:ethyl acetate=3:1); NMR (CDCl$_3$): δ 11.33 (br, 1H), 7.69 (dd, J=7.5, 1.0 Hz, 1H), 7.41 (dt, J=1.0, 7.5 Hz, 1H), 7.30 (dt, J=1.0, 7.5 Hz, 1H), 7.19 (dd, J=7.5, 1.0 Hz, 1H), 5.62 (s, 1H), 3.87-3.83 (m, 2H), 2.95-2.83 (m, 6H), 2.45-2.34 (m, 1H), 2.00-1.93 (m, 2H), 1.90-1.76 (m, 4H), 1.51-1.40 (m, 2H), 1.31 (s, 6H), 0.96 (t, J=7.5 Hz, 3H).

EXAMPLE 29(4)

(Z)-2-(3,3-dimethyl-3,4-dihydro-(2H)-isoquinolin-1-ylidene)-1-(1-octyldulfonylpiperidin-4-yl)ethan-1-one TLC: Rf0.22 (hexane:ethyl acetate=3:1); NMR (CDCl$_3$): δ 11.33 (br, 1H), 7.69 (d, J=7.5 Hz, 1H), 7.41 (t, J=7.5 Hz, 1H), 7.30 (t, J=7.5 Hz, 1H), 7.19 (d, J=7.5 Hz, 1H), 5.61 (s, 1H), 3.87-3.83 (m, 2H), 2.94-2.82 (m, 6H), 2.44-2.34 (m, 1H), 1.98-1.93 (m, 2H), 1.87-1.76 (m, 4H), 1.44-1.22 (m, 16H), 0.88 (brt, 3H).

EXAMPLE 29(5)

(Z)-2-(3,3-dimethyl-3,4-dihydro-(2H)-isoquinolin-1-ylidene)-1-(4-acetylaminophenyl)ethan-1-one TLC: Rf0.09 (hexane:ethyl acetate=1:1); NMR (CDCl$_3$): δ 11.80 (br, 1H), 7.94 (d, J=8.5 Hz, 2H), 7.83 (d, J=7.5 Hz, 1H), 7.58 (d, J=8.5 Hz, 2H), 7.43 (t, J=7.5 Hz, 1H), 7.37-7.32 (m, 2H), 7.21 (d, J=7.5 Hz, 1H), 6.31 (s, 1H), 2.90 (s, 2H), 2.21 (s, 3H), 1.36 (s, 6H).

EXAMPLE 29(6)

(Z)-2-(3,3-dimethyl-3,4-dihydro-(2H)-isoquinolin-1-ylidene)-1-(3-acetylaminophenyl)ethan-1-one TLC: Rf0.12 (hexane:ethyl acetate=1:1); NMR (CDCl$_3$): δ 11.83 (br, 1H), 7.87-7.82 (m, 3H), 7.69 (d, J=8.0 Hz, 1H), 7.46-7.32 (m, 4H), 7.22 (d, J=7.5 Hz, 1H), 6.31 (s, 1H), 2.91 (s, 2H), 2.21 (s, 3H), 1.37 (s, 6H).

EXAMPLE 29(7)

(Z)-2-(3,3-dimethyl-3,4-dihydro-(2H)-isoquinolin-1-ylidene)-1-(3-mesylaminophenyl)ethan-1-one TLC: Rf0.24 (hexane:ethyl acetate=1:1); NMR (CDCl$_3$): δ 11.86 (br, 1H), 7.82 (d, J=7.5 Hz, 1H), 7.78-7.73 (m, 2H), 7.48-7.40 (m, 3H), 7.36 (t, J=7.5 Hz, 1H), 7.21 (d, J=7.5 Hz, 1H), 6.54 (br, 1H), 6.29 (s, 1H), 3.02 (s, 3H), 2.91 (s, 2H), 1.37 (s, 6H).

EXAMPLE 29(8)

(Z)-2-(7-acetylamino-3,3-dimethyl-3,4-dihydro-(2H)-isoquinolin-1-ylidene)-1-phenylethan-1-one TLC: Rf0.23 (hexane:ethyl acetate=1:1); NMR (CDCl$_3$): δ 11.81 (br, 1H), 7.96-7.91 (m, 3H), 7.64 (dd, J=8.0, 2.0 Hz, 1H), 7.45-7.39 (m, 4H), 7.17 (d, J=8.0 Hz, 1H), 6.29 (s, 1H), 2.84 (s, 2H), 2.23 (s, 3H), 1.33 (s, 6H).

EXAMPLE 29(9)

(Z)-2-(7-acetylamino-3,3-dimethyl-3,4-dihydro-(2H)-isoquinolin-1-ylidene)-1-(adamantan-1-yl)ethan-1-one TLC: Rf0.38 (hexane:ethyl acetate=1:1); NMR (CDCl$_3$): δ 11.48 (br, 1H), 7.78 (d, J=2.0 Hz, 1H), 7.62 (dd, J=8.0, 2.0 Hz, 1H), 7.27 (br, 1H), 7.13 (d, J=8.0 Hz, 1H), 5.74 (s, 1H), 2.79 (s, 2H), 2.22 (s, 3H), 2.05 (br, 3H), 1.91 (br, 6H), 1.74 (br, 6H), 1.28 (s, 6H).

EXAMPLE 29(10)

(Z)-2-(7-mesylamino-3,3-dimethyl-3,4-dihydro-(2H)-isoquinolin-1-ylidene)-1-phenylethan-1-one TLC: Rf0.14 (hexane:ethyl acetate=2:1); NMR (CDCl$_3$): δ 11.80 (br, 1H), 7.96-7.92 (m, 2H), 7.64 (d, J=2.0 Hz, 1H), 7.47-7.42 (m, 3H), 7.35 (dd, J=8.0, 2.0 Hz, 1H), 7.22 (d, J=8.0 Hz, 1H), 6.54 (br, 1H), 6.27 (s, 1H), 3.06 (s, 3H), 2.88 (s, 2H), 1.36 (s, 6H).

EXAMPLE 29(11)

(Z)-2-(7-mesylamino-3,3-dimethyl-3,4-dihydro-(2H)-isoquinolin-1-ylidene)-1-(adamantan-1-yl)ethan-1-one TLC: Rf0.20 (hexane:ethyl acetate=2:1); NMR (CDCl$_3$): δ 11.46 (br, 1H), 7.51 (d, J=2.0 Hz, 1H), 7.34 (dd, J=8.0, 2.0 Hz, 1H), 7.18 (d, J=8.0 Hz, 1H), 6.46 (br, 1H), 5.72 (s, 1H), 3.05 (s, 3H), 2.81 (s, 2H), 2.06 (br, 3H), 1.90 (br, 6H), 1.74 (br, 6H), 1.29 (s, 6H).

EXAMPLE 30

(Z)-2-(6-methylcarbamoyl-3,3-dimethyl-3,4-dihydro-(2H)-isoquinolin-1-ylidene)-1-phenylethan-1-one To a solution of the compound prepared in example 15 (100 mg) in tetrahydrofuran (3 ml) were added triethylamine (0.09 ml) and isobutyl chlorocarbonate (0.08 ml) under cooling with ice and the mixture was stirred for 30 minutes at room temperature. The precipitate was removed. The filtrate was added to a solution of a 40% aqueous solution of methylamine (0.120 ml) in tetrahydrofuran (2 ml) under cooling with ice and the mixture was stirred overnight at room temperature. The reaction mixture was concentrated. The residue was purified by column chromatography on silica gel (hexane:ethyl acetate=1:1) to give the compound of the present invention (92 mg) having the following physical data.

TLC: Rf0.46 (ethyl acetate); NMR (CDCl$_3$): δ 11.76 (brs, 1H), 7.97-7.92 (m, 2H), 7.87 (d, J=9.0 Hz, 1H), 7.69-7.63 (m, 2H), 7.48-7.42 (m, 3H), 6.34 (s, 1H), 6.20 (brs, 1H), 3.05 (d, J=4.8 Hz, 3H), 2.94 (s, 2H), 1.36 (s, 6H).

EXAMPLE 30(1)-EXAMPLE 30(11)

By the same procedure as described in example 30 using the compound prepared in example 15 or example 15(1)-example 15(4) or example 15(13) and methylamine or a corresponding amine derivative, the following compounds of the present invention were given.

EXAMPLE 30(1)

(Z)-2-(6-dimethylcarbamoyl-3,3-dimethyl-3,4-dihydro-(2H)-isoquinolin-1-ylidene)-1-phenylethan-1-one TLC: Rf0.40 (ethyl acetate); NMR (CDCl$_3$): δ 11.78 (brs, 1H), 7.97-7.92 (m, 2H), 7.86 (d, J=8.1 Hz, 1H), 7.48-7.41 (m, 3H), 7.37 (dd, J=8.1, 1.5 Hz, 1H), 7.29 (d, J=1.5 Hz, 1H), 6.34 (s, 1H), 3.14 (s, 3H), 3.01 (s, 3H), 2.92 (s, 2H), 1.37 (s, 6H).

EXAMPLE 30(2)

(Z)-2-(6-carbamoyl-3,3-dimethyl-3,4-dihydro-(2H)-isoquinolin-1-ylidene) 1-phenylethan-1-one TLC: Rf0.36 (chloroform:methanol=9:1); NMR (CDCl$_3$): δ 11.76 (brs, 1H), 7.98-7.88 (m, 3H), 7.75-7.69 (m, 2H), 7.49-7.41 (m, 3H), 6.35 (s, 1H), 6.12 (brs, 1H), 5.71 (brs, 1H), 2.95 (s, 2H), 1.37 (s, 6H).

EXAMPLE 30(3)

(Z)-2-(7-carbamoyl-3,3-dimethyl-3,4-dihydro-(2H)-isoquinolin-1-ylidene) 1-phenylethan-1-one TLC: Rf0.07 (hexane:ethyl acetate=1:1); NMR (CDCl$_3$): δ 11.82 (br, 1H), 8.31 (d, J=1.5 Hz, 1H), 7.98-7.94 (m, 2H), 7.83 (dd, J=8.0, 1.5 Hz, 1H), 7.48-7.42 (m, 3H), 7.31 (d, J=8.0 Hz, 1H), 6.39 (s, 1H), 6.10 (br, 1H), 5.67 (br, 1H), 2.95 (s, 2H), 1.37 (s, 6H).

EXAMPLE 30(4)

(Z)-2-(7-methylcarbamoyl-3,3-dimethyl-3,4-dihydro-(2H)-isoquinolin-1-ylidene)-1-phenylethan-1-one TLC: Rf0.14 (hexane:ethyl acetate=1:1); NMR (CDCl$_3$): δ 11.81 (br, 1H), 8.24 (d, J=2.0 Hz, 1H), 7.98-7.94 (m, 2H), 7.78 (dd, J=8.0, 2.0 Hz, 1H), 7.48-7.41 (m, 3H), 7.28 (d, J=8.0 Hz, 1H), 6.39 (s, 1H), 6.20 (br, 1H), 3.07 (d, J=5.0 Hz, 3H), 2.94 (s, 2H), 1.36 (s, 6H).

EXAMPLE 30(5)

(Z)-2-(7-dimethylcarbamoyl-3,3-dimethyl-3,4-dihydro-(2H)-isoquinolin-1-ylidene)-1-phenylethan-1-one TLC: Rf0.12 (hexane:ethyl acetate=1:1); NMR (CDCl$_3$): δ 11.79 (br, 1H), 7.96-7.91 (m, 3H), 7.49-7.40 (m, 4H), 7.26 (m, 1H), 6.33 (s, 1H), 3.16 (br, 3H), 3.04 (br, 3H), 2.93 (s, 2H), 1.37 (s, 6H).

EXAMPLE 30(6)

(Z)-2-(7-carbamoyl-3,3-dimethyl-3,4-dihydro-(2H)-isoquinolin-1-ylidene)-1-(adamantan-1-yl)ethan-1-one TLC: Rf0.34 (hexane:ethyl acetate=1:1); NMR (CDCl$_3$): δ 11.51 (br, 1H), 8.19 (d, J=1.2 Hz, 1H), 7.77 (dd, J=1.2, 7.5 Hz, 1H), 7.27 (d, J=7.5 Hz, 1H), 5.84 (s, 1H), 2.89 (s, 2H), 2.06 (br, 3H), 1.92-1.91 (br, 6H), 1.76-1.75 (br, 6H), 1.30 (s, 6H).

EXAMPLE 30(7)

(Z)-2-(7-methylcarbamoyl-3,3-dimethyl-3,4-dihydro-(2H)-isoquinolin-1-ylidene)-1-(adamantan-1-yl)ethan-1-one TLC: Rf0.40 (hexane:ethyl acetate=1:1); NMR (CDCl$_3$): δ 11.49 (br, 1H), 8.14 (d, J=1.2 Hz, 1H), 7.70 (dd, J=1.2, 7.8 Hz, 1H), 7.23 (d, J=7.8 Hz, 1H), 6.14 (br, 1H), 5.84 (s, 1H), 3.06 (d, J=7.8 Hz, 3H), 2.87 (s, 2H), 2.06 (br, 3H), 1.92-1.91 (b r, 6H), 1.75 (s, 6H), 1.29 (s, 6H).

EXAMPLE 30(8)

(Z)-2-(7-dimethylcarbamoyl-3,3-dimethyl-3,4-dihydro-(2H)-isoquinolin-1-ylidene)-1-(adamantan-1-yl)ethan-1-one TLC: Rf0.50 (chloroform:methanol=50:1); NMR (CDCl$_3$): δ 11.45 (br, 1H), 7.81 (d, J=1.2 Hz, 1H), 7.41 (dd, J=1.2, 7.8 Hz, 1H), 7.20 (d, J=7.8 Hz, 1H), 5.78 (s, 1H), 3.15 (br, 3H), 3.02 (br, 3H), 2.86 (s, 2H), 2.05 (br, 3H), 1.90-1.89 (br, 6H), 1.74 (br, 6H), 1.30 (s, 6H).

EXAMPLE 30(9)

(Z)-2-(6-carbamoyl-3,3-dimethyl-3,4-dihydro-(2H)-isoquinolin-1-ylidene)-1-cyclohexylethan-1-one TLC: Rf0.12 (hexane:ethyl acetate=1:1); NMR (CDCl$_3$): δ 11.24 (br, 1H), 7.78 (d, J=8.0 Hz, 1H), 7.70-7.66 (m, 2H), 6.14 (br, 1H), 5.83 (br, 1H), 5.66 (s, 1H), 2.89 (s, 2H), 2.30 (tt, J=11.5, 3.5 Hz, 1H), 1.90-1.80 (m, 4H), 1.70 (m, 1H), 1.50-1.20 (m, 1H).

EXAMPLE 30(10)

(Z)-2-(6-carbamoyl-3,3-dimethyl-3,4-dihydro-(2H)-isoquinolin-1-ylidene)-1-cycloheptylethan-1-one TLC: Rf0.12 (hexane:ethyl acetate=1:1); NMR (CDCl$_3$): δ 11.15 (br, 1H), 7.78 (d, J=8.0 Hz, 1H), 7.69-7.66 (m, 2H), 6.08 (br, 1H), 5.75 (br, 1H), 5.63 (s, 1H), 2.89 (s, 2H), 2.48 (tt, J=10.0, 4.0 Hz, 1H), 1.95-1.88 (m, 2H), 1.82-1.45 (m, 10H), 1.29 (s, 6H).

EXAMPLE 30(11)

(Z)-2-(6-carbamoyl-3,3-dimethyl-3,4-dihydro-(2H)-isoquinolin-1-ylidene)-1-(adamantan-1-yl)ethan-1-one TLC: Rf0.13 (hexane:ethyl acetate=1:1); NMR (CDCl$_3$): δ 11.40 (br, 1H), 7.79 (d, J=8.0 Hz, 1H), 7.70-7.66 (m, 2H), 6.05 (br, 1H), 5.81 (s, 1H), 5.76 (br, 1H), 2.89 (s, 2H), 2.06 (br, 3H), 1.91 (br, 6H), 1.75 (br, 6H), 1.30 (s, 6H).

EXAMPLE 31

(Z)-2-(3,3-dimethyl-3,4-dihydro-(2H)-isoquinolin-1-ylidene)-1-(4-cyano-2-methoxyphenyl)ethan-1-one To a suspension of the compound prepared in example 13(4) (423 mg) in formic acid (10 ml) was added hydroxylamine chloride (1.05 g) and the mixture was stirred for 30 minutes at 130° C. The reaction mixture was allowed to cool and thereto were added ice and water, and the precipitate was collected and was dissolved in ethyl acetate, washed with water and a saturated aqueous solution of sodium chloride successively, dried over anhydrous magnesium sulfate and concentrated. The residue was crudely purified by column chromatography on silica gel (hexane:ethyl acetate=5:1→2:1) and then washed with t-butyl methyl ether to give the compound of the present invention (65 mg) having the following physical data.

TLC: Rf0.32 (hexane:ethyl acetate=2:1); NMR (CDCl$_3$): δ 11.73 (br, 1H), 7.73-7.70 (m, 2H), 7.44 (dt, J=1.0, 7.5 Hz, 1H), 7.34-7.29 (m, 2H), 7.23-7.19 (m, 2H), 6.16 (s, 1H), 3.94 (s, 3H), 2.91 (s, 2H), 1.37 (s, 6H).

EXAMPLE 31(1)-EXAMPLE 31(3)

By the same procedure as described in example 31 using the compound prepared in example 13(1), example 13(12) or example 13(14) in place of the compound prepared in 13(4), the following compounds of the present invention were given.

EXAMPLE 31(1)

(Z)-2-(7-cyano-3,3-dimethyl-3,4-dihydro-(2H)-isoquinolin-1-ylidene)-1-phenylethan-1-one TLC: Rf0.49 (hexane:ethyl acetate=1:1); NMR (CDCl$_3$): δ 11.73 (brs, 1H), 8.11 (d, J=1.5 Hz, 1H), 7.99-7.93 (m, 2H), 7.70 (dd, J=8.1, 1.5 Hz, 1H), 7.51-7.44 (m, 3H), 7.35 (d, J=8.1 Hz, 1H), 6.31 (s, 1H), 2.97 (s, 2H), 1.37 (s, 6H).

EXAMPLE 31(2)

(Z)-2-(7-cyano-3,3,6-trimethyl-3,4-dihydro-(2H)-isoquinolin-1-ylidene)-1-(adamantan-1-yl)ethan-1-one TLC: Rf0.50 (methylene chloride); NMR (CDCl$_3$): δ 11.37 (br, 1H), 7.94 (s, 1H), 7.14 (s, 1H), 5.73 (s, 1H), 2.84 (s, 2H), 2.57 (s, 3H), 2.07 (br, 3H), 1.91-1.90 (br, 6H), 1.76 (br, 6H), 1.29 (s, 6H).

EXAMPLE 31(3)

(Z)-2-(7-cyano-3,3,6-trimethyl-3,4-dihydro-(2H)-isoquinolin-1-ylidene)-1-cyclohexylethan-1-one TLC: Rf0.45 (methylene chloride); NMR (CDCl$_3$): δ 11.21 (br, 1H), 7.92 (s, 1H), 7.14 (s, 1H), 5.58 (s, 1H), 2.84 (s, 2H), 2.57 (s, 3H), 2.36-2.28 (m, 1H), 1.92-1.29 (m, 16H).

EXAMPLE 32

(Z)-2-(6-ethynyl-3,3-dimethyl-3,4-dihydro-(2H)-isoquinolin-1-ylidene)-1-phenylethan-1-one To a suspension of (bromomethyl)triphenylphosphonium bromide (371 mg) in tetrahydrofuran (3 ml) was added -potassium t-butoxide (2.55 ml, 1.0M in THF) at −78° C. and the mixture was stirred for 30 minutes at 0° C. To the mixture was added a solution of the compound prepared in example 13 (200 mg) in tetrahydrofuran (5 ml) dropwise and the mixture was stirred for 90 minutes at 0° C. and for 60 minute at room temperature. To the reaction mixture was added ice-water and the mixture was extracted with ethyl acetate. The extract was washed with water and a saturated aqueous solution of sodium chloride successively, dried over anhydrous magnesium sulfate and concentrated. The residue was purified by column chromatography on silica gel (hexane:ethyl acetate=20:1→10:1) to give the compound of the present invention (127 mg) having the following physical data.

TLC: Rf0.46 (hexane:ethyl acetate=3:1); NMR (CDCl$_3$): δ 11.76 (br, 1H), 7.96-7.92 (m, 2H), 7.78 (d, J=8.0 Hz, 1H), 7.47-7.41 (m, 4H), 7.35 (d, J=1.0 Hz, 1H), 6.31 (s, 1H), 3.22 (s, 1H), 2.88 (s, 2H), 1.36 (s, 6H).

EXAMPLE 32(1)-EXAMPLE 32(2)

By the same procedure as described in example 32 using the compound prepared in example 13(1) or example 13(3) in place of the compound prepared in example 13, the following compounds of the present invention were given.

EXAMPLE 32(1)

(Z)-2-(7-ethynyl-3,3-dimethyl-3,4-dihydro-(2H)-isoquinolin-1-ylidene)-1-phenylethan-1-one TLC: Rf0.48 (hexane:ethyl acetate=3:1); NMR (CDCl$_3$): δ 11.79 (br, 1H), 7.97-7.94 (m, 3H), 7.54 (dd, J=8.0, 1.5 Hz, 1H), 7.47-7.42 (m, 3H), 7.19 (d, J=8.0 Hz, 1H), 6.31 (s, 1H), 3.14 (s, 1H), 2.90 (s, 2H), 1.36 (s, 6H).

EXAMPLE 32(2)

(Z)-2-(3,3-dimethyl-3,4-dihydro-(2H)-isoquinolin-1-ylidene)-1-(4-ethynylphenyl)ethan-1-one TLC: Rf0.39 (hexane:ethyl acetate=3:1); NMR(CDCl$_3$): δ 11.88 (br, 1H), 7.91 (d, J=8.5 Hz, 2H), 7.82 (d, J=7.5 Hz, 1H), 7.55 (d, J=8.5 Hz, 2H), 7.44 (t, J=7.5 Hz, 1H), 7.35 (t, J=7.5 Hz, 1H), 7.22 (d, J=7.5 Hz, 1H), 6.31 (s, 1H), 3.17 (s, 1H), 2.91 (s, 2H), 1.37 (s, 6H).

EXAMPLE 33

(Z)-2-(6-((E)-2-carboxyethenyl)-3,3-dimethyl-3,4-dihydro-(2H)-isoquinolin-1-ylidene)-1-phenylethan-1-one To a solution of the compound prepared in example 13 (200 mg) in pyridine (5 ml) was added piperidine (2 drops) at room temperature and then thereto was added malonic acid (122 mg) and the mixture was stirred for 20 minutes at room temperature, for 30 minutes at 85° C. and for 3.5 hours at 100° C. and overnight at 80° C. The reaction mixture was allowed to cool and was extracted with ethyl acetate. The organic layer was washed with a saturated aqueous solution of ammonium chloride, water and brine successively, dried over anhydrous magnesium sulfate and concentrated. The residue was purified by column chromatography on silica gel (hexane:ethyl acetate=2:1→ethyl acetate) to give the compound of the present invention (173 mg) having the following physical data.

TLC: Rf0.16 (hexane:ethyl acetate=1:1); NMR (CDCl$_3$): δ 11.76 (br, 1H), 7.97-7.93 (m, 2H), 7.87 (d, J=8.0 Hz, 1H), 7.78 (d, J=16.0 Hz, 1H), 7.52 (dd, J=8.0, 1.5 Hz, 1H), 7.48-7.41 (m, 3H), 7.40 (d, J=1.5 Hz, 1H), 6.54 (d, J=16.0 Hz, 1H), 6.35 (s, 1H), 2.93 (s, 2H), 1.38 (s, 6H).

EXAMPLE 34

(Z)-2-(6-((E)-2-methoxycarbonylethenyl)-3,3-dimethyl-3,4-dihydro-(2H)-isoquinolin-1-ylidene)-1-phenylethan-1-one To a solution of the compound prepared in example 33 (90 mg) in dimethylformamide (2 ml) was added potassium carbonate (30 mg) at room temperature and thereto was added methyl iodide (0.033 ml) and the mixture was stirred overnight at room temperature. To the reaction mixture was added water and the precipitate was collected. It was dissolved in ethyl acetate and the mixture was washed with water and brine, dried over anhydrous magnesium sulfate and concentrated to give the compound of the present invention (94 mg) having the following physical data.

TLC: Rf0.68 (hexane:ethyl acetate=1:1); NMR (CDCl$_3$): δ 11.76 (br, 1H), 7.96-7.93 (m, 2H), 7.85 (d, J=8.0 Hz, 1H), 7.69 (d, J=16.0 Hz, 1H), 7.51-7.41 (m, 4H), 7.36 (s, 1H), 6.52 (d, J=16.0 Hz, 1H), 6.34 (s, 1H), 3.83 (s, 3H), 2.92 (s, 2H), 1.38 (s, 6H).

EXAMPLE 34(1)-EXAMPLE 34(2)

By the same procedure as described in example 34 using the compound prepared in example 15 or example 15(1) in place of the compound prepared in example 33, the following compounds of the present invention were given.

EXAMPLE 34(1)

(Z)-2-(6-methoxycarbonyl-3,3-dimethyl-3,4-dihydro-(2H)-isoquinolin-1-ylidene)-1-phenylethan-1-one TLC: Rf0.43 (hexane:ethyl acetate=3:1); NMR (CDCl$_3$): δ 11.75 (br, 1H), 8.01-7.94 (m, 3H), 7.90-7.88 (m, 2H), 7.48-7.41 (m, 3H), 6.37 (s, 1H), 3.96 (s, 3H), 2.95 (s, 2H), 1.37 (s, 6H).

EXAMPLE 34(2)

(Z)-2-(7-methoxycarbonyl-3,3-dimethyl-3,4-dihydro-(2H)-isoquinolin-1-ylidene)-1-phenylethan-1-one TLC: Rf0.25 (hexane:ethyl acetate=3:1); NMR (CDCl$_3$): δ 11.83 (br, 1H), 8.49 (d, J=2.0 Hz, 1H), 8.10 (dd, J=8.0, 2.0 Hz, 1H), 7.99-7.96 (m, 2H), 7.49-7.44 (m, 3H), 7.31 (d, J=8.0 Hz, 1H), 6.40 (s, 1H), 3.98 (s, 3H), 2.96 (s, 2H), 1.37 (s, 6H).

EXAMPLE 35

(Z)-2-(7-carboxy-6-chloro-3,3-dimethyl-3,4-dihydro-(2H)-isoquinolin-1-ylidene)-1-cyclohexylethan-1-one To a solution of the compound prepared in example 19 (58 mg) in tetrahydrofuran (1 ml) and methanol (1 ml) was added a 2N aqueous solution of sodium hydroxide and the mixture was stirred overnight at room temperature. The reaction mixture was neutralized with 1N hydrochloric acid and the mixture was extracted with ethyl acetate. The extract was washed with brine, dried over anhydrous magnesium sulfate and concentrated. The residue was washed with a mixture of hexane and ethyl acetate to give the compound of the present invention (45 mg) having the following physical data.

TLC: Rf0.40 (water:methanol:chloroform=1:10:100); NMR (CDCl$_3$): δ 11.24 (br, 1H), 8.35 (s, 1H), 7.33 (s, 1H), 5.66 (s, 1H), 2.86 (s, 2H), 2.34 (m, 1H), 1.95-1.65 (m, 5H), 1.55-1.20 (m, 5H), 1.31 (s, 6H).

EXAMPLE 35(1)-EXAMPLE 35(2)

By the same procedure as described in example 35 using the compound prepared in example 11(197) or example 11(198) in place of the compound prepared in example 19, the following compounds of the present invention were given.

EXAMPLE 35(1)

(Z)-2-(7-carboxy-6-chloro-3,3-dimethyl-3,4-dihydro-(2H)-isoquinolin-1-ylidene)-1-(adamantan-1-yl)ethan-1-one TLC: Rf0.28 (hexane:ethyl acetate=1:1); NMR (CDCl$_3$): δ 11.44 (brs, 1H), 8.33 (s, 1H), 7.33 (s, 1H), 5.80 (s, 1H), 2.86 (s, 2H), 2.10-2.03 (m, 3H), 1.93-1.89 (m, 6H), 1.77-1.72 (m, 6H), 1.31 (s, 6H).

EXAMPLE 35(2)

(Z)-2-(7-carboxy-6-chloro-3,3-dimethyl-3,4-dihydro-(2H)-isoquinolin-1-ylidene)-1-cycloheptylethan-1-one TLC: Rf0.28 (hexane:ethyl acetate=1:1); NMR (CDCl$_3$): δ 11.16 (brs, 1H), 8.34 (s, 1H), 7.32 (s, 1H), 5.63 (s, 1H), 2.85 (s, 2H), 2.50 (tt, J=9.9, 3.9 Hz, 1H), 1.97-1.42 (m, 12H), 1.31 (s, 6H).

EXAMPLE 36

(Z)-2-(3,3,4,4-tetramethyl-3,4-dihydro-(2H)-isoquinolin-1-ylidene)-1-(4-cyanophenyl)ethan-1-one By the same procedure as described in example 3 using 1,3,3,4,4-pentamethyl-3,4-dihydroisoquinoline in place of the compound prepared in reference example 2, and 4-cyanobenzoyl chloride in place of 3-cyanobenzoyl chloride, the present invention having the following physical data was given.

TLC: Rf0.48 (hexane:ethyl acetate=2:1); NMR (CDCl$_3$): δ 11.90 (br, 1H), 8.03 (d, J=8.5 Hz, 2H), 7.79 (dd, J=7.5, 1.0 Hz, 1H), 7.72 (d, J=8.5 Hz, 2H), 7.52 (dt, J=1.0, 7.5 Hz, 1H), 7.45 (dd, J=7.5, 1.0 Hz, 1H), 7.34 (dt, J=1.0, 7.5 Hz, 1H), 6.25 (s, 1H), 1.31 (br, 12H).

EXAMPLE 37

(Z)-2-(7-formylamino-3,3-dimethyl-3,4-dihydro-(2H)-isoquinolin-1-ylidene)-1-phenylethan-1-one To a mixture of acetic anhydride (0.50 ml) and formic acid (5 ml) was added the compound prepared in example 14(3) (151 mg) and the mixture was stirred for 1 hour at 70° C. The reaction mixture was allowed to cool and to the mixture was added ice and it was neutralized with a saturated aqueous solution of sodium bicarbonate and it was extracted with ethyl acetate. The extract was washed with a saturated aqueous solution of sodium bicarbonate, water and brine, dried over anhydrous magnesium sulfate and concentrated. The residue was purified by column chromatography on silica gel (hexane:ethyl acetate=2:1) to give the compound of the present invention (131 mg) having the following physical data.

TLC: Rf0.21 (hexane:ethyl acetate=1:1); NMR (DMSO-d$_6$): δ 11.74 (brs, 1H), 10.26 (brs, 1H), 8.13 (d, J=1.8 Hz, 1H), 7.89-7.84 (m, 2H), 7.74 (dd, J=8.1, 1.8 Hz, 1H), 7.50-7.43 (m, 3H), 7.28 (d, J=8.1 Hz, 1H), 7.26 (s, 1H), 6.24 (s, 1H), 2.87 (s, 2H), 1.27 (s, 6H).

EXAMPLE 37(1)

(Z)-2-(6-formylamino-3,3-dimethyl-3,4-dihydro-(2H)-isoquinolin-1-ylidene)-1-phenylethan-1-one By the same procedure as described in example 37 using the compound prepared in example 40 in place of the compound prepared in example 14(3), the compound of the present invention having the following physical data was given.

TLC: Rf0.40 (hexane:ethyl acetate=1:4); NMR (CDCl$_3$): δ 11.79 (brs, 1H), 8.43 (s, 1H), 7.97-7.92 (m, 2H), 7.80 (d, J=8.4 Hz, 1H), 7.63 (d, J=2.1 Hz, 1H), 7.47-7.39 (m, 3H), 7.37 (dd, J=8.4, 2.1 Hz, 1H), 6.27 (s, 1H), 2.89 (s, 2H), 1.36 (s, 6H).

EXAMPLE 38

(Z)-2-(7-methylamino-3,3-di methyl-3,4-dihydro-(2H)-isoquinolin-1-ylidene)-1-phenylethan-1-one To a suspension of lithium aluminum hydride (77 mg) in tetrahydrofuran (1 ml) was added the compound prepared in example 37 (131 mg) in tetrahydrofuran (4 ml) and the mixture was stirred for 4 hours at room temperature. To the reaction mixture was added a saturated aqueous solution of sodium sulfate and the mixture was filtered over celite. The filtrate was concentrated. The residue was purified by column chromatography on silica gel (hexane:ethyl acetate=4:1) to give the compound of the present invention (73 mg) having the following physical data.

TLC: Rf0.41 (hexane:ethyl acetate=2:1); NMR (CDCl$_3$): δ 11.85 (brs, 1H), 7.97-7.91 (m, 2H), 7.46-7.40 (m, 3H), 7.03 (d, J=8.1 Hz, 1H), 7.03 (d, J=2.4 Hz, 1H), 6.71 (dd, J=8.1, 2.4 Hz, 1H), 6.25 (s, 1H), 2.91 (s, 3H), 2.78 (s, 2H), 1.35 (s, 6H).

EXAMPLE 38(1)-EXAMPLE 38(2)

By the same procedure as described in example 38 using the compound prepared in example 37(1) or example 30(4) in place of the compound prepared in example 37, the following compounds of the present invention were given.

EXAMPLE 38(1)

(Z)-2-(6-methylamino-3,3-dimethyl-3,4-dihydro-(2H)-isoquinolin-1-ylidene)-1-phenylethan-1-one TLC: Rf0.69 (hexane:ethyl acetate=1:4); NMR (CDCl$_3$): δ 11.85 (brs, 1H), 7.97-7.91 (m, 2H), 7.66 (d, J=8.7 Hz, 1H), 7.44-7.38 (m, 3H), 6.51 (dd, J=8.7, 2.4 Hz, 1H), 6.35 (d, J=2.4 Hz, 1H), 6.21 (s, 1H), 4.14 (brs, 1H), 2.91 (s, 3H), 2.80 (s, 2H), 1.36 (s, 6H).

EXAMPLE 38(2)

(Z)-2-(7-methylaminomethyl-3,3-dimethyl-3,4-dihydro-(2H)-isoquinolin-1-ylidene)-1-phenylethan-1-one TLC: Rf0.29 (hexane:ethyl acetate:isopropylamine=10:2:1); NMR (CDCl$_3$): δ 11.86 (br, 1H), 7.98-7.95 (m, 2H), 7.77 (s, 1H), 7.47-7.37 (m, 4H), 7.18 (d, J=8.0 Hz, 1H), 6.35 (s, 1H), 3.81 (s, 2H), 2.89 (s, 2H), 2.50 (s, 3H), 1.36 (s, 6H).

EXAMPLE 39

(Z)-2-(6-t-butoxycarbonylamino-3,3-dimethyl-3,4-dihydro-(2H)-isoquinolin-1-ylidene)-1-phenylethan-1-one To a suspension of the compound prepared in example 15 (965 mg) in t-butanol (15 ml) were added triethylamine (0.460 ml) and diphenylphosphorylazide (0.710 ml) and the mixture was stirred for 3 hours at 100° C. The reaction mixture was allowed to cool and diluted with ethyl acetate and the mixture was washed with water, a saturated aqueous solution of sodium bicarbonate and brine, dried over anhydrous magnesium sulfate and concentrated. The residue was purified by column chromatography on silica gel (hexane:ethyl acetate=9:1) to give the compound of the present invention (1.04 g) having the following physical data.

TLC: Rf0.58 (hexane:ethyl acetate=1:1); NMR (CDCl$_3$): δ 11.81 (brs, 1H), 7.96-7.91 (m, 2H), 7.74 (d, J=8.7 Hz, 1H), 7.46-7.40 (m, 4H), 7.16 (dd, J=8.7, 2.7 Hz, 1H), 6.64 (brs, 1H), 6.26 (s, 1H), 2.87 (s, 2H), 1.54 (s, 9H), 1.35 (s, 6H).

EXAMPLE 39(1)-EXAMPLE 39(4)

By the same procedure as described in example 39 using the compound prepared in example 15(3), example 15(4), example 15(13) or example 15(14) in place of the compound prepared in example 15, the following compounds of the present invention were given.

EXAMPLE 39(1)

(Z)-2-(6-t-butoxycarbonylamino-3,3-dimethyl-3,4-dihydro-(2H)-isoquinolin-1-ylidene)-1-cyclohexylethan-1-one TLC: Rf0.17 (hexane:ethyl acetate=5:1); NMR (CDCl$_3$): δ 11.30 (br, 1H), 7.62 (d, J=8.5 Hz, 1H), 7.38 (d, J=2.0 Hz, 1H), 7.12 (dd, J=8.5, 2.0 Hz, 1H), 6.61 (br, 1H), 5.56 (s, 1H), 2.80 (s, 2H), 2.26 (m, 1H), 1.89-1.78 (m, 4H), 1.68 (m, 1H), 1.58-1.24 (m, 20H).

EXAMPLE 39(2)

(Z)-2-(6-t-butoxycarbonylamino-3,3-dimethyl-3,4-dihydro-(2H)-isoquinolin-1-ylidene)-1-cycloheptylethan-1-one TLC: Rf0.42 (hexane:ethyl acetate=3:1).

EXAMPLE 39(3)

(Z)-2-(6-t-butoxycarbonylamino-3,3-dimethyl-3,4-dihydro-(2H)-isoquinolin-1-ylidene)-1-(adamantan-1-yl)ethan-1-one TLC: Rf0.42 (hexane:ethyl acetate=3:1); NMR (CDCl$_3$): δ 11.48 (br, 1H), 7.64 (d, J=9.0 Hz, 1H), 7.42 (d, J=2.0 Hz, 1H), 7.10 (dd, J=9.0, 2.0 Hz, 1H), 6.60 (br, 1H), 5.71 (s, 1H), 2.80 (s, 2H), 2.05 (br, 3H), 1.91 (br, 6H), 1.74 (br, 6H), 1.53 (s, 9H), 1.28 (s, 6H).

EXAMPLE 39(4)

(Z)-2-(6-t-butoxycarbonylamino-3,3-dimethyl-3,4-dihydro-(2H)-isoquinolin-1-ylidene)-1-(pyridin-3-yl)ethan-1-one TLC: Rf0.41 (methylene chloride:methanol=10:1); NMR (CDCl$_3$): δ 11.84 (br, 1H), 9.14 (d, J=1.5 Hz, 1H), 8.65 (dd, J=5.0, 1.5 Hz, 1H), 8.21 (ddd, J=8.5, 1.5, 1.5 Hz, 1H), 7.74 (d, J=8.5 Hz, 1H), 7.49 (d, J=2.0 Hz, 1H), 7.36 (dd, J=8.5, 5.0 Hz, 1H), 7.17 (dd, J=8.5, 2.0 Hz, 1H), 6.67 (s, 1H), 6.21 (s, 1H), 2.88 (s, 2H), 1.54 (s, 9H), 1.37 (s, 6H).

EXAMPLE 40

(Z)-2-(6-amino-3,3-dimethyl-3,4-dihydro-(2H)-isoquinolin-1-ylidene)-1-phenylethan-1-one To the compound prepared in example 39 (1.04 g) was added a 4N solution of hydrogen chloride in dioxane (20 ml) and the mixture was stirred for 2 hours at room temperature. To the reaction mixture was added methanol until homogeneous and the mixture was stirred for 1 hour at 50° C. To the reaction mixture was added a saturated aqueous solution of sodium bicarbonate and was extracted with a mixture of ethyl acetate and tetrahydrofuran. The extract was washed with brine, dried over anhydrous magnesium sulfate and concentrated. The residue was purified by column chromatography on silica gel (hexane:ethyl acetate=3:1→chloroform) to give the compound of the present invention (458 mg) having the following physical data.

TLC: Rf0.29 (hexane:ethyl acetate=1:1); NMR (CDCl$_3$): δ 11.84 (brs, 1H), 7.96-7.91 (m, 2H), 7.64 (d, J=8.4 Hz, 1H), 7.44-7.39 (m, 3H), 6.59 (dd, J=8.4, 2.4 Hz, 1H), 6.46 (d, J=2.4 Hz, 1H), 6.21 (s, 1H), 4.00 (brs, 2H), 2.78 (s, 2H), 1.35 (s, 6H).

EXAMPLE 40(1)-EXAMPLE 40(4)

By the same procedure as described in example 40 using the compound prepared in example 39(1)-example 39(4) in place of the compound prepared in example 39, the compounds of the present invention were given.

EXAMPLE 40(1)

(Z)-2-(6-amino-3,3-dimethyl-3,4-dihydro-(2H)-isoquinolin-1-ylidene)-1-cyclohexylethan-1-one TLC: Rf0.11 (hexane:ethyl acetate=3:1); NMR (CDCl$_3$): δ 11.33 (br, 1H), 7.52 (d, J=8.5 Hz, 1H), 6.55 (dd, J=8.5, 2.5 Hz, 1H), 6.42 (d, J=2.5 Hz, 1H), 5.50 (s, 1H), 3.94 (br, 2H), 2.72 (s, 2H), 2.25 (tt, J=11.5, 3.5 Hz, 1H), 1.89-1.78 (m, 4H), 1.68 (m, 1H), 1.58-1.20 (m, 1H).

EXAMPLE 40(2)

(Z)-2-(6-amino-3,3-dimethyl-3,4-dihydro-(2H)-isoquinolin-1-ylidene)-1-cycloheptylethan-1-one TLC: Rf0.14 (hexane:ethyl acetate=3:1); NMR (CDCl$_3$): δ 11.25 (br, 1H), 7.51 (d, J=8.5 Hz, 1H), 6.55 (dd, J=8.5, 2.5 Hz, 1H), 6.42 (d, J=2.5 Hz, 1H), 5.47 (s, 1H), 3.93 (br, 2H), 2.71 (s, 2H), 2.41 (tt, J=9.5, 4.0 Hz, 1H), 1.94-1.88 (m, 2H), 1.82-1.45 (m, 10H), 1.28 (s, 6H).

EXAMPLE 40(3)

(Z)-2-(6-amino-3,3-dimethyl-3,4-dihydro-(2H)-isoquinolin-1-ylidene)-1-(adamantan-1-yl)ethan-1-one TLC: Rf0.12 (hexane:ethyl acetate=3:1); NMR (CDCl$_3$): δ 11.51 (br, 1H), 7.54 (d, J=8.5 Hz, 1H), 6.56 (dd, J=8.5, 2.5 Hz, 1H), 6.42 (d, J=2.5 Hz, 1H), 5.65 (s, 1H), 3.94 (br, 2H), 2.71 (s, 2H), 2.05 (br, 3H), 1.91 (br, 6H), 1.74 (br, 6H), 1.28 (s, 6H).

EXAMPLE 40(4)

(Z)-2-(6-amino-3,3-dimethyl-3,4-dihydro-(2H)-isoquinolin-1-ylidene)-1-(pyridin-3-yl)ethan-1-one TLC: Rf0.39 (methylene chloride:methanol=10:1); NMR (CDCl$_3$): δ 11.86 (br, 1H), 9.13 (dd, J=2.0, 1.0 Hz, 1H), 8.64 (dd, J=4.5, 2.0 Hz, 1H), 8.21 (ddd, J=8.0, 2.0, 2.0 Hz, 1H), 7.63 (d, J=8.5 Hz, 1H), 7.35 (ddd, J=8.0, 4.5, 1.0 Hz, 1H), 6.61 (dd, J=8.5, 2.5 Hz, 1H), 6.47 (d, J=2.5 Hz, 1H), 6.16 (s, 1H), 4.04 (br, 2H), 2.80 (s, 2H), 1.37 (s, 6H).

EXAMPLE 41

(Z)-2-(7-dimethylamino-3,3-dimethyl-3,4-dihydro-(2H)-isoquinolin-1-ylidene)-1-phenylethan-1-one To a solution of the compound prepared in example 38 (49 mg) in tetrahydrofuran (2 ml) were added acetic acid (0.10 ml), a 35% aqueous solution of formaldehyde (0.14 ml) and sodium borotriacetoxyhydride (340 mg) and the mixture was stirred overnight at room temperature. The reaction mixture was added to a saturated aqueous solution of sodium bicarbonate and the mixture was extracted with ethyl acetate. The extract was washed with brine, dried over anhydrous magnesium sulfate and concentrated. The residue was purified by column chromatography on silica gel (hexane:ethyl acetate=9:1) to give the compound of the present invention (25 mg) having the following physical data.

TLC: Rf0.54 (hexane:ethyl acetate=2:1); NMR (CDCl$_3$): δ 11.90 (brs, 1H), 7.97-7.90 (m, 2H), 7.46-7.41 (m, 3H), 7.13 (d, J=2.7 Hz, 1H), 7.07 (d, J=8.4 Hz, 1H), 6.84 (dd, J=8.4, 2.7 Hz, 1H), 6.28 (s, 1H), 3.01 (s, 6H), 2.79 (s, 2H), 1.35 (s, 6H).

EXAMPLE 41(1)-EXAMPLE 41(2)

By the same procedure as described in example 41 using the compound prepared in example 11(133) or example 11(134) in place of the compound prepared in example 38, the following compounds of the present invention were given.

EXAMPLE 41(1)

(Z)-2-(7-dimethylamino-6-methoxy-3,3-dimethyl-3,4-dihydro-(2H)-isoquinolin-1-ylidene)-1-(4-cyanophenyl)ethan-1-one TLC: Rf0.26 (hexane:ethyl acetate=1:1); NMR (CDCl$_3$): δ 11.97 (br, 1H), 8.00 (d, J=8.5 Hz, 2H), 7.72 (d, J=8.5 Hz, 2H), 7.30 (s, 1H), 6.66 (s, 1H), 6.14 (s, 1H), 3.96 (s, 3H), 2.85 (s, 8H), 1.38 (s, 6H).

EXAMPLE 41(2)

(Z)-2-(7-dimethylamino-6-methoxy-3,3-dimethyl-3,4-dihydro-(2H)-isoquinolin-1-ylidene)-1-(adamantan-1-yl)ethan-1-one TLC: Rf0.47 (hexane:ethyl acetate=1:1); NMR (CDCl$_3$): δ 11.56 (br, 1H), 7.25 (s, 1H), 6.60 (s, 1H), 5.66 (s, 1H), 3.93 (s, 3H), 2.83 (s, 6H), 2.76 (s, 2H), 2.06 (br, 3H), 1.92 (br, 6H), 1.75 (br, 6H), 1.30 (s, 6H).

REFERENCE EXAMPLE 9

4-bromo-3,3-dimethyl-3,4-dihydro-(2H)-isoquinolin-1-one

To a solution of 3,3-dimethyl-3,4-dihydro-(2H)-isoquinolin-1-one (200 mg) and N-bromosuccinimide (223 mg) in carbon tetrachloride (5 ml) was added benzoylperoxide (24 mg) and the mixture was stirred overnight at room temperature, and refluxed for 1 hour. The reaction mixture was allowed to cool and the precipitate was removed. The filtrate was washed with a mixture of hexane and ethyl acetate (4/1) to give the compound of the present invention (196 mg) having the following physical data.

TLC: Rf0.37 (ethyl acetate:hexane=1:1); NMR (CDCl$_3$): δ 8.10 (dd, J=7.5, 1.5 Hz, 1H), 7.54 (ddd, J=7.5, 7.5, 1.5 Hz, 1H), 7.46 (ddd, J=7.5, 7.5, 1.5 Hz, 1H), 7.39 (dd, J=7.5, 1.5 Hz, 1H), 5.98 (br, 1H), 5.11 (s, 1H), 1.59 (s, 3H), 1.37 (s, 3H).

REFERENCE EXAMPLE 10

4-hydroxy-3,3-dimethyl-3,4-dihydro-(2H)-isoquinolin 1-one

To a solution of the compound prepared in reference example 9 (6.57 g) and sodium acetate (21.2 g) in dioxane (100 ml) and water (20 ml) and the mixture was refluxed for 3 days. To the reaction mixture was added potassium carbonate (10.6 g) and the mixture was stirred overnight at room temperature. The reaction mixture was concentrated. To the residue was added ethyl acetate and the precipitate was removed. The aqueous layer of the filtrate was extracted with ethyl acetate. The combined organic layer was washed with brine, dried over anhydrous magnesium sulfate and concentrated. The residue was purified by column chromatography on silica gel (hexane:ethyl acetate=3:2) to give the compound of the present invention (2 g) having the following physical data.

TLC: Rf0.28 (ethyl acetate:hexane=1:1).

REFERENCE EXAMPLE 11

4-t-butyldimethylsilyloxy-3,3-dimethyl-3,4-dihydro-(2H)-isoquinolin-1-one

To a solution of the compound prepared in reference example 10 (1.0 g) and t-butyldimethylsilyl chloride (784 mg) in methylene chloride (10 ml) was added imidazole (708 mg) and the mixture was stirred for 2 hours at room temperature. To the reaction mixture were added methylene chloride (10 ml), dimehylformamide (5 ml) and triethylamine (0.5 ml) and the mixture was stirred overnight. The reaction mixture was poured into water and extracted with a mixture of hexane and ethyl acetate (1/3). The extract was washed with water and brine successively, dried over anhydrous magnesium sulfate and concentrated. The residue was purified by column chromatography on silica gel (hexane:ethyl acetate=3:1) to give the compound of the present invention (632 mg) having the following physical data.

TLC: Rf0.61 (ethyl acetate:hexane=1:1); NMR (CDCl$_3$): δ 8.02 (dd, J=7.5, 1.5 Hz, 1H), 7.52 (ddd, J=7.5, 7.5, 1.5 Hz, 1H), 7.45-7.35 (m, 2H), 5.80 (br, 1H), 4.65 (s, 1H), 1.26 (s, 3H), 1.18 (s, 3H), 0.93 (s, 9H), 0.14 (s, 3H), 0.00 (s, 3H).

REFERENCE EXAMPLE 12

(Z)-2-(4-t-butyldimethylsilyloxy-3,3-dimethyl-3,4-dihydro-(2H)-isoquinolin-1-ylidene)-1-phenylethan-1-one By the same procedure as described in reference example 6→example 11 using the compound prepared in reference example 11 in place of the compound prepared in reference example 5, the compound of the present invention was given.

TLC: Rf0.56 (chloroform:hexane=1:5); NMR (CDCl$_3$): δ 11.66 (br, 1H), 7.95 (m, 2H), 7.79 (d, J=8.0 Hz, 1H), 7.55-7.30 (m, 6H), 6.32 (s, 1H), 4.65 (s, 1H), 1.36 (s, 3H), 1.15 (s, 3H), 0.95 (s, 9H), 0.15 (s, 3H), 0.06 (s, 3H).

EXAMPLE 42

(Z)-2-(3,3-dimethyl-4-hydroxy-3,4-dihydro-(2H)-isoquinolin-1-ylidene)-1-phenylethan-1-one To a solution of the compound prepared in reference example 12 (810 mg) in tetrahydrofuran (10 ml) was added tetrabutylammonium fluoride (4.0 ml, 1.0 M in tetrahydrofuran) at 0° C. and the mixture was stirred for 3 hours at room temperature. The reaction mixture was poured into ice-water and the mixture was extracted with ethyl acetate. The extract was washed with hydrochloric acid, a saturated aqueous solution of sodium bicarbonate, water and brine successively, dried over anhydrous magnesium sulfate and concentrated. The residue was purified by column chromatography on silica gel (hexane:ethyl acetate=4:1→3:2) to give the compound of the present invention (566 mg) having the following physical data.

TLC: Rf0.52 (ethyl acetate:hexane=1:1); NMR (CDCl$_3$): δ 11.65 (br, 1H), 7.94 (m, 2H), 7.85 (d, J=8.0 Hz, 1H), 7.60-7.40 (m, 6H), 6.37 (s, 1H), 4.55 (d, J=7.5 Hz, 1H), 2.11 (d, J=7.5 Hz, 1H), 1.37 (s, 3H), 1.33 (s, 3H).

EXAMPLE 43

(Z)-2-(3,3-dimethyl-4-oxo-3,4-dihydro-(2H)-isoquinolin-1-ylidene)-1-phenylethan-1-one To a solution of the compound prepared in example 42 (428 mg) in methylene chloride (40 ml) was added pyridinium chlorochromate (2793 mg) at room temperature and the mixture was stirred for 6 hours at room temperature. The reaction mixture was filtered. The filtrate was concentrated. The residue was purified by column chromatography on silica gel (hexane:ethyl acetate=9:1→5:1) to give the compound of the present invention (137 mg) having the following physical data.

TLC: Rf0.31 (ethyl acetate:hexane=1:5); NMR (CDCl$_3$): δ 12.22 (br, 1H), 8.17 (dd, J=7.5, 1.5 Hz, 1H), 8.06 (m, 1H), 7.97 (m, 2H), 7.76 (ddd, J=7.5, 7.5, 1.5 Hz, 1H), 7.68 (ddd, J=7.5, 7.5, 1.5 Hz, 1H), 7.55-7.40 (m, 3H), 6.60 (s, 1H), 1.60 (s, 6H).

EXAMPLE 44

EXAMPLE 44(4)

By converting the compounds prepared in example 11(80) or example 14(8) to corresponding salts by a conventional method, the following compounds of the present invention were given.

EXAMPLE 44

(Z)-2-(6-chloro-3,3-dimethyl-3,4-dihydroisoquinolin-1-yl)-1-(adamantan-1-yl)ethan-1-one, hydrochloride TLC: Rf0.25 (ethyl acetate:hexane=1:10); NMR (CDCl$_3$): δ 7.50 (d, J=8.0 Hz, 1H), 7.35 (dd, J=8.0, 2.0 Hz, 1H), 7.28 (d, J=2.0 Hz, 1H), 4.6 (br, 2H), 2.95 (s, 2H), 2.09 (m, 3H), 1.95 (m, 6H), 1.75 (m, 6H), 1.49 (s, 6H).

EXAMPLE 44(1)

(Z)-2-(6-chloro-3,3-dimethyl-3,4-dihydroisoquinolin-1-yl)-1-(adamantan-1-yl)ethan 1-one, methanesulfonate TLC: Rf0.25 (ethyl acetate:hexane=1:10); NMR (CDCl$_3$): δ 7.47 (d, J=8.5 Hz, 1H), 7.39 (dd, J=8.5, 2.0 Hz, 1H), 7.33 (s, 1H), 4.6 (br, 2H), 3.02 (s, 2H), 2.85 (s, 3H), 2.12 (m, 3H), 1.96 (m, 6H), 1.76 (m, 6H), 1.55 (s, 6H).

EXAMPLE 44(2)

(Z)-2-(7-amino-6-chloro-3,3-dimethyl-3,4-dihydroisoquinolin-1-yl)-1-(adamantan-1-yl)ethan-1-one, bishydrochloride TLC: Rf0.68 (ethyl acetate:hexane=1:2); NMR (CDCl$_3$): δ 7.22 (s, 1H), 6.80 (s, 1H), 2.91 (s, 2H), 2.12 (m, 3H), 1.98 (m, 6H), 1.76 (m, 6H), 1.59 (s, 6H).

EXAMPLE 44(3)

(Z)-2-(7-amino-6-chloro-3,3-dimethyl-3,4-dihydroisoquinolin-1-yl)-1-(adamantan-1-yl)ethan-1-one, bismethanesulfonate TLC: Rf0.68 (ethyl acetate:hexane=1:2); NMR (CDCl$_3$): δ 7.58 (s, 1H), 7.30 (s, 1H), 4.94 (br, 6H), 2.99 (s, 2H), 2.85 (s, 6H), 2.09 (m, 3H), 1.95 (m, 6H), 1.74 (m, 6H), 1.53 (s, 6H).

EXAMPLE 44(4)

(Z)-2-(7-amino-6-chloro-3,3-dimethyl-3,4-dihydroisoquinolin-1-yl)-1-(adamantan-1-yl)ethan-1-one methanesulfonate TLC: Rf0.68 (ethyl acetate:hexane=1:2); NMR (CDCl$_3$): δ 7.34 (s, 1H), 7.15 (s, 1H), 4.81 (br, 2H), 3.46 (br, 3H), 2.86 (s, 2H), 2.83 (s, 3H), 2.05 (m, 3H), 1.96 (m, 6H), 1.73 (m, 6H), 1.46 (s, 6H).

EXAMPLE 45

(Z)-2-(6-cyano-3,3-dimethyl-3,4-dihydro-(2H)-isoquinolin-1-ylidene)-1-cyclohexylethan-1-one To a solution of the compound prepared in example 30(9) (488 mg) in 1,4-dioxane (10 ml) was added pyridine (0.36 ml) at room temperature and to the mixture was added trifluoroacetic anhydride (0.32 ml) under cooling with ice and the mixture was stirred for 15 minutes. To the reaction mixture was added water and the mixture was extracted with ethyl acetate. The extract was washed with water and brine successively, dried over anhydrous magnesium sulfate and concentrated. The residue was purified by column chromatography on silica gel (hexane:ethyl acetate=15:1→13:1) to give the compound of the present invention (305 mg) having the following physical data.

TLC: Rf0.44 (hexane:ethyl acetate=3:1); NMR (CDCl$_3$): δ 11.18 (br, 1H), 7.80 (d, J=8.5 Hz, 1H), 7.58 (dd, J=8.5, 1.5 Hz, 1H), 7.48 (d, J=1.5 Hz, 1H), 5.64 (s, 1H), 2.87 (s, 2H), 2.31 (tt, J=11.5, 3.5 Hz, 1H), 1.89-1.80 (m, 4H), 1.70 (m, 1H), 1.51-1.20 (m, 11H).

EXAMPLE 45(1)-EXAMPLE 45(2)

By the same procedure as described in example 45 using the compound prepared in example 30(10) or example 30(11) in place of the compound prepared in example 30(9), the following compounds of the present invention were given.

EXAMPLE 45(1)

(Z)-2-(6-cyano-3,3-dimethyl-3,4-dihydro-(2H)-isoquinolin-1-ylidene)-1-cycloheptylethan-1-one TLC: Rf0.45 (hexane:ethyl acetate=3:1); NMR (CDCl$_3$): δ 11.09 (br, 1H), 7.79 (d, J=8.0 Hz, 1H), 7.58 (dd, J=8.0, 1.5 Hz, 1H), 7.47 (d, J=1.5 Hz, 1H), 5.61 (s, 1H), 2.87 (s, 2H), 2.48 (tt, J=10.0, 4.0 Hz, 1H), 1.94-1.87 (m, 2H), 1.83-1.45 (m, 10H), 1.29 (s, 6H).

EXAMPLE 45(2)

(Z)-2-(6-cyano-3,3-dimethyl-3,4-dihydro-(2H)-isoquinolin-1-ylidene)-1-(adamantan-1-yl)ethan-1-one TLC: Rf0.48 (hexane:ethyl acetate=3:1); NMR (CDCl$_3$): δ 11.34 (br, 1H), 7.81 (d, J=8.0 Hz, 1H), 7.59 (dd, J=8.0, 1.5 Hz, 1H), 7.48 (d, J=1.5 Hz, 1H), 5.80 (s, 1H), 2.87 (s, 2H), 2.06 (br, 3H), 1.90 (br, 6H), 1.74 (br, 6H), 1.30 (s, 6H).

EXAMPLE 46

EXAMPLE 46(5)

By the same procedure as described in example II using a derivative corresponding to the compound prepared in reference example 6 and a derivative corresponding to benzoylmethyl bromide, the compounds of the present invention were given.

EXAMPLE 46

(Z)-2-(7-t-butylsulfamoyl-3,3-dimethyl-3,4-dihydro-(2H)-isoquinolin-1-ylidene)-1-(adamantan-1-yl)ethan-1-one TLC: Rf0.33 (hexane:ethyl acetate=2:1); NMR (CDCl$_3$): δ 11.46 (brs, 1H), 8.20 (d, J=1.8 Hz, 1H), 7.88 (dd, J=8.1, 1.8 Hz, 1H), 7.30 (d, J=8.1 Hz, 1H), 5.79 (s, 1H), 4.53 (brs, 1H), 2.89 (s, 2H), 2.09-2.03 (m, 3H), 1.92-1.88 (m, 6H), 1.77-1.72 (m, 6H), 1.29 (s, 6H), 1.27 (s, 9H).

EXAMPLE 46(1)

(Z)-2-(7-bromo-6-methoxy-3,3-dimethyl-3,4-dihydro-(2H)-isoquinolin-1-ylidene)-1-(tetrahydropyran-4-yl)ethan-1-one TLC: Rf0.26 (hexane:ethyl acetate=1:1); NMR (CDCl$_3$): δ 11.25 (brs, 1H), 7.85 (s, 1H), 6.68 (s, 1H), 5.51 (s, 1H), 4.05 (ddd, J=11.4, 4.2, 2.4 Hz, 2H), 3.95 (s, 3H), 3.46 (dt, J=3.0, 11.4 Hz, 2H), 2.80 (s, 2H), 2.52 (tt, J=11.1, 4.5 Hz, 1H), 1.92-1.72 (m, 4H), 1.31 (s, 6H).

EXAMPLE 46(2)

(Z)-2-(7-hydroxymethyl-6-methoxy-3,3-dimethyl-3,4-dihydro-(2H)-isoquinolin 1-ylidene)-1-(6-chloropyridin-3-yl)ethan-1-one TLC: Rf0.20 (hexane:ethyl acetate=1:1); NMR (CDCl$_3$): δ 11.86 (br, 1H), 8.92 (dd, J=2.5, 0.5 Hz, 1H), 8.17 (dd, J=8.5, 2.5 Hz, 1H), 7.75 (s, 1H), 7.38 (dd, J=8.5, 0.5 Hz, 1H), 6.71 (s, 1H), 6.16 (s, 1H), 4.74 (d, J=6.5 Hz, 2H), 3.94 (s, 3H), 2.90 (s, 2H), 2.20 (t, J=6.5 Hz, 1H), 1.38 (s, 6H).

EXAMPLE 46(3)

(Z)-2-(6,7-dicyano-3,3-dimethyl-3,4-dihydro-(2H)-isoquinolin-1-ylidene)-1-(tetrahydropyran-4-yl)ethan-1-one TLC: Rf0.37 (ethyl acetate:hexane=1:1); NMR (CDCl$_3$): δ 11.09 (br, 1H), 8.08 (s, 1H), 7.64 (s, 1H), 5.63 (s, 1H), 4.06 (m, 2H), 3.47 (m, 2H), 2.95 (s, 2H), 2.59 (m, 1H), 1.90-1.70 (m, 4H), 1.32 (s, 6H).

EXAMPLE 46(4)

(Z)-2-(7-t-butylsulfamoyl-3,3-dimethyl-3,4-dihydro-(2H)-isoquinolin-1-ylidene)-1-(tetrahydropyran-4-yl)ethan-1-one TLC: Rf0.28 (hexane:ethyl acetate=1:1); NMR (CDCl$_3$) δ 11.25 (brs, 1H), 8.21 (d, J=2.0 Hz, 1H), 7.90 (dd, J=8.0, 2.0 Hz, 1H), 7.32 (d, J=8.0 Hz, 1H), 5.67 (s, 1H), 4.57 (s, 1H), 4.05 (m, 2H), 3.48 (dt, J=11.5, 3.0 Hz, 2H), 2.91 (s, 2H), 2.57 (m, 1H), 1.90-1.70 (m, 4H), 1.31 (s, 6H), 1.26 (s, 9H).

EXAMPLE 46(5)

(Z)-2-(7-bromo-3,3-dimethyl-3,4-dihydro-(2H)-isoquinolin-1-ylidene)-1-(4-cyanophenyl)ethan-1-one TLC: Rf0.57 (hexane:ethyl acetate=1:1); NMR (CDCl$_3$): δ 11.88 (brs, 1H), 8.02 (d, J=8.7 Hz, 2H), 7.91 (d, J=2.1 Hz, 1H), 7.74 (d, J=8.7 Hz, 2H), 7.58 (dd, J=8.1, 2.1 Hz, 1H), 7.13 (d, J=8.1 Hz, 1H), 6.20 (s, 1H), 2.87 (s, 2H), 1.37 (s, 6H).

EXAMPLE 47-EXAMPLE 47(6)

By the same procedure as described in example 5 using the compound prepared in example 12(7), 12(9), 11(117), 11(201)-11(203) in place of the compound prepared in example 1(18), the compounds of the present invention were given.

EXAMPLE 47

(Z)-2-(7-hydroxy-3,3-dimethyl-3,4-dihydro-(2H)-isoquinolin-1-ylidene)-1-cycloheptylethan-1-one TLC: Rf0.28 (hexane:ethyl acetate=5:1); NMR (CDCl$_3$): δ 11.17 (br, 1H), 7.18 (d, J=2.4 Hz, 1H), 7.04 (d, J=7.8 Hz, 1H), 6.88 (dd, J=2.4, 7.8 Hz, 1H), 5.53 (s, 1H), 2.75 (s, 2H), 2.44 (m, 1H), 1.92-1.42 (m, 12H), 1.27 (s, 6H).

EXAMPLE 47(1)

(Z)-2-(6-hydroxy-3,3-dimethyl-3,4-dihydro-(2H)-isoquinolin-1-ylidene)-1-cyclohexyl ethan-1-one TLC: Rf0.16 (hexane:ethyl acetate=3:1); NMR (CDCl$_3$): δ 11.34 (br, 1H), 7.61 (d, J=8.4 Hz, 1H), 6.76 (dd, J=2.4, 8.4 Hz, 1H), 6.66 (d, J=2.4 Hz, 1H), 5.55 (s, 1H), 2.77 (s, 2H), 2.26 (m, 1H), 1.92-1.22 (m, 16H).

EXAMPLE 47(2)

(Z)-2-(6-hydroxy-3,3-dimethyl-3,4-dihydro-(2H)-isoquinolin-1-ylidene)-1-cycloheptylethan-1-one TLC: Rf0.18 (hexane:ethyl acetate=3:1); NMR (CDCl$_3$): δ 11.25 (br, 1H), 7.60 (d, J=8.7 Hz, 1H), 6.75 (dd, J=2.4, 8.7 Hz, 1H), 6.64 (d, J=2.4 Hz, 1H), 5.51 (s, 1H), 2.77 (s, 2H), 2.43 (m, 1H), 1.96-1.40 (m, 12H), 1.28 (s, 6H).

EXAMPLE 47(3)

(Z)-2-(6-hydroxy-3,3-dimethyl-3,4-dihydro-(2H)-isoquinolin-1-ylidene)-1-(adamantan-1-yl)ethan-1-one TLC: Rf0.09 (hexane:ethyl acetate=5:1); NMR (CDCl$_3$): δ 11.50 (br, 1H), 7.63 (d, J=8.4 Hz, 1H), 6.76 (dd, J=2.4, 8.4 Hz, 1H), 6.64 (d, J=2.4 Hz, 1H), 5.69 (s, 1H), 5.53 (br, 1H), 2.77 (s, 2H), 2.05 (br, 3H), 1.91-1.90 (m, 6H), 1.74 (br, 6H), 1.28 (s, 6H).

EXAMPLE 47(4)

(Z)-2-(7-hydroxy-3,3,6-trimethyl-3,4-dihydro-(2H)-isoquinolin-1-ylidene)-1-(adamantan-1-yl)ethan-1-one TLC: Rf0.30 (hexane:ethyl acetate=5:1); NMR (CDCl$_3$): δ 11.42 (br, 1H), 7.14 (s, 1H), 6.91 (s, 1H), 5.67 (s, 1H), 4.98 (s, 1H), 2.71 (s, 2H), 2.28 (s, 3H), 2.04 (br, 3H), 1.90 (br, 6H), 1.73 (br, 6H), 1.26 (s, 6H).

EXAMPLE 47(5)

(Z)-2-(7-hydroxy-3,3,6-trimethyl-3,4-dihydro-(2H)-isoquinolin-1-ylidene)-1-cyclohexylethan-1-one TLC: Rf0.16 (hexane:ethyl acetate=5:1); NMR (CDCl$_3$): δ 11.24 (br, 1H), 7.11 (s, 1H), 6.90 (s, 1H), 5.53 (s, 1H), 5.19-5.15 (br, 1H), 2.71 (s, 2H), 2.32-2.20 (m, 4H), 1.92-1.20 (m, 16H).

EXAMPLE 47(6)

(Z)-2-(7-hydroxy-3,3,6-trimethyl-3,4-dihydro-(2H)-isoquinolin-1-ylidene)-1-cycloheptylethan-1-one TLC: Rf0.21 (hexane:ethyl acetate=5:1); NMR (CDCl$_3$): δ 11.16 (br, 1H), 7.11 (s, 1H), 6.91 (s, 1H), 5.49 (s, 1H), 4.86 (br, 1H), 2.71 (s, 2H), 2.43 (m, 1H), 2.27 (s, 3H), 1.96-1.42 (m, 12H), 1.26 (s, 6H).

EXAMPLE 48

(Z)-2-(7-(1-hydroxy-1-methylethyl)-6-methoxy-3,3-dimethyl-3,4-dihydro-(2H)-isoquinolin-1-ylidene)-1-cycloheptylethan-1-one By the same procedure as described in example 22 using the compound prepared in example 11(181) in place of the compound prepared in example 11(7), the compound of the present invention having the following physical data was given.

TLC: Rf0.21 (ethyl acetate:hexane=1:5); NMR (CDCl$_3$): δ 11.28 (br, 1H), 7.68 (s, 1H), 6.68 (s, 1H), 5.52 (s, 1H), 3.95 (s, 3H), 3.65 (s, 1H), 2.79 (s, 2H), 2.46 (m, 1H), 2.00-1.40 (m, 12H), 1.65 (s, 6H), 1.29 (s, 6H).

EXAMPLE 49

(Z)-2-(7-formyl-6-methoxy-3,3-dimethyl-3,4-dihydro-(2H)-isoquinolin-1-ylidene)-1-(tetrahydropyran-4-yl)ethan-1-one By the same procedure as described in example 13 using the compound prepared in example 46(1) in place of the compound prepared in example 12, the compound of the present invention having the following physical data was given.

TLC: Rf0.49 (hexane:ethyl acetate=1:4).

EXAMPLE 50

(Z)-2-(7-hydroxymethyl-6-methoxy-3,3-dimethyl-3,
4-dihydro-(2H)-isoquinolin-1-ylidene)-1-(tetrahydropyran-4-yl)ethan-1-one By the same procedure as described in example 28 using the compound prepared in example 49 in place of the compound prepared in example 13, the compound of the present invention having the following physical data was given.

TLC: Rf0.34 (hexane:ethyl acetate=1:4); NMR (CDCl$_3$):
δ 11.30 (brs, 1H), 7.64 (s, 1H), 6.66 (s, 1H), 5.59 (s, 1H), 4.71 (d, J=6.0 Hz, 2H), 4.05 (m, 2H), 3.92 (s, 3H), 3.46 (dt, J=3.0, 11.4 Hz, 2H), 2.83 (s, 2H), 2.51 (tt, J=10.8, 4.5 Hz, 1H), 2.16 (t, J=6.0 Hz, 1H), 1.92-1.72 (m, 4H), 1.31 (s, 6H).

EXAMPLE 51

(Z)-2-(7-(1-hydroxyethyl)-6-methoxy-3,3-dimethyl-3,4-dihydro-(2H)-isoquinolin-1-ylidene)-1-cycloheptylethan-1-one To a solution of the compound prepared in example 13(11) (140 mg) in tetrahydrofuran (5 ml) was added methyl lithium (1.7 μL, 1.04 M in ether) at −78° C. and the mixture was stirred for 10 minutes at −78° C. To the reaction mixture was added a saturated aqueous solution of ammonium chloride and the mixture was extracted with ethyl acetate. The extract was washed with water and brine successively, dried over anhydrous magnesium sulfate and concentrated. The residue was washed with a mixture of hexane and ethyl acetate (20/1) to give the compound of the present invention (95 mg) having the following physical data.

TLC: Rf0.25 (ethyl acetate:hexane=1:2); NMR (CDCl$_3$):
δ 11.24 (br, 1H), 7.71 (s, 1H), 6.63 (s, 1H), 5.56 (s, 1H), 5.13 (m, 1H), 3.90 (s, 3H), 2.80 (s, 2H), 2.46 (m, 1H), 2.36 (d, J=5.0 Hz, 1H), 2.00-1.40 (m, 12H), 1.53 (d, J=3.5 Hz, 3H), 1.29 (s, 3H), 1.28 (s, 3H).

EXAMPLE 52

(Z)-2-(7-bromomethyl-3,3-dimethyl-3,4-dihydro-(2H)-isoquinolin-1-ylidene)-1-(adamantan-1-yl)ethan-1-one To a solution of the compound prepared in example 28(6) (400 mg) in methylene chloride (10 ml) were added triphenylphosphine (349 mg) and carbon tetrabromide (550 mg) and the mixture was stirred for 1 hour at room temperature. To the reaction mixture were added triphenylphosphine (350 mg) and carbon tetrabromide (546 mg) and the mixture was stirred for 10 minutes at room temperature. To the reaction mixture were added a saturated aqueous solution of sodium bicarbonate and t-butyl methyl ether and the mixture was washed with water and brine successively, dried over anhydrous magnesium sulfate and then to the mixture was added a 4N solution of hydrogen chloride in ethyl acetate (1 ml) and the mixture was concentrated. The residue was purified by column chromatography on silica gel (hexane:ethyl acetate=9:1) to give the compound of the present invention (220 mg) having the following physical data.

TLC: Rf0.61 (hexane:ethyl acetate=2:1); NMR (CDCl$_3$):
δ 11.49 (brs, 1H), 7.70 (d, J=1.5 Hz, 1H), 7.42 (dd, J=7.8, 1.5 Hz, 1H), 7.18 (d, J=7.8 Hz, 1H), 5.78 (s, 1H), 4.64 (s, 2H), 2.83 (s, 2H), 2.10-2.03 (m, 3H), 1.94-1.90 (m, 6H), 1.78-1.73 (m, 6H), 1.29 (s, 6H).

EXAMPLE 53

(Z)-2-(7-methoxymethyl-3,3-dimethyl-3,4-dihydro-(2H)-isoquinolin-1-ylidene) 1-(adamantan-1-yl)ethan-1-one To a suspension of sodium hydride (54 mg) in dimethylformamide (3 ml) was added methanol (0.25 ml) under cooling with ice and the mixture was stirred for 30 minutes at room temperature. The reaction mixture was again cooled with ice and to the mixture was added a solution of the compound prepared in example 52 (220 mg) in tetrahydrofuran (3 ml) and the mixture was stirred for 3 hours at room temperature. To the reaction mixture was added ice and the mixture was extracted with a mixture of hexane and ethyl acetate. The extract was washed with water and brine, dried over anhydrous magnesium sulfate and concentrated. The residue was purified by column chromatography on silica gel (hexane:ethyl acetate=9:1) to give the compound of the present invention (56 mg) having the following physical data.

TLC: Rf0.42 (hexane:ethyl acetate=4:1); NMR (CDCl$_3$):
δ 11.52 (brs, 1H), 7.66 (brs, 1H), 7.37 (dd, J=7.8, 1.8 Hz, 1H), 7.16 (d, J=7.8 Hz, 1H), 5.79 (s, 1H), 4.49 (s, 2H), 3.44 (s, 3H), 2.83 (s, 2H), 2.09-2.03 (m, 3H), 1.94-1.90 (m, 6H), 1.77-1.73 (m, 6H), 1.28 (s, 6H).

EXAMPLE 54

(Z)-2-(7-hydroxymethyl-6-methoxy-3,3-dimethyl-3,4-dihydro-(2H)-isoquinolin-1-ylidene)-1-(pyridin-3-yl)ethan-1-one To a suspension of the compound prepared in example 46(2) (55 mg) and sodium acetate (17 mg) in methanol (5.5 ml) was added 1% palladium carbon under atmosphere of argon at room temperature, and under atmosphere of hydrogen the mixture was stirred for 6 hours. The reaction mixture was filtered over celite. The filtrate was concentrated. To the residue was added ethyl acetate and the mixture was washed with a saturated aqueous solution of sodium bicarbonate, water and brine successively and concentrated. The residue was purified by column chromatography on silica gel (hexane:ethyl acetate=1:1→ethyl acetate) to give the compound of the present invention (35 mg) having the following physical data.

TLC: Rf0.06 (hexane:ethyl acetate=1:2); NMR (CDCl$_3$):
δ 11.85 (br, 1H), 9.15 (dd, J=2.0, 1.0 Hz, 1H), 8.65 (dd, J=4.5, 2.0 Hz, 1H), 8.21 (ddd, J=7,5, 2.0, 2.0 Hz, 1H), 7.77 (s, 1H), 7.36 (ddd, J=7.5, 4.5, 1.0 Hz, 1H), 6.70 (s, 1H), 6.23 (s, 1H), 4.74 (s, 2H), 3.94 (s, 3H), 2.90 (s, 2H), 2.32 (br, 1H), 1.38 (s, 6H).

EXAMPLE 55

(Z)-2-(7-sulfamoyl-3,3-dimethyl-3,4-dihydro-(2H)-isoquinolin-1-ylidene)-1-(adamantan-1-yl)ethan-1-one To a solution of the compound prepared in example 46 (369 mg) in methanol (12 ml) was added concentrated hydrochloric acid (6 ml) and the mixture was refluxed for 8 hours at 100° C. The mixture was allowed to cool to room temperature and the reaction mixture was cooled with ice and it was neutralized with a 5N aqueous solution of sodium hydroxide, and was extracted with a mixture of ethyl acetate, tetrahydrofuran and methanol. The extract was washed with brine, dried over anhydrous magnesium sulfate and concentrated. The residue was washed with t-butyl methyl ether to give the compound of the present invention (295 mg) having the following physical data.

TLC: Rf0.32 (hexane:ethyl acetate=1:1); NMR (DMSO-$d_6$): δ 11.45 (brs, 1H), 8.18 (d, J=1.8 Hz, 1H), 7.86 (dd, J=7.8, 1.8 Hz, 1H), 7.49 (s, 2H), 7.48 (d, J=7.8 Hz, 1H), 5.80 (s, 1H), 2.94 (s, 2H), 2.04-1.97 (m, 3H), 1.83-1.78 (m, 6H), 1.75-1.63 (m, 6H), 1.22 (s, 6H).

EXAMPLE 55(1)

(Z)-2-(7-sulfamoyl-3,3-dimethyl-3,4-dihydro-(2H)-isoquinolin-1-ylidene)-1-(tetrahydropyran-4-yl)ethan-1-one By the same procedure as described in example 55 using the compound prepared in example 46(4) in place of the compound prepared in example 46, the compound of the present invention having the following physical data was given.

TLC: Rf0.14 (ethyl acetate:hexane=1:1); NMR ($CDCl_3$): δ 11.23 (br, 1H), 8.25 (d, J=2.0 Hz, 1H), 7.94 (dd, J=8.0, 2.0 Hz, 1H), 7.36 (d, J=8.0 Hz, 1H), 5.68 (s, 1H), 4.91 (br, 2H), 4.05 (m, 2H), 3.47 (m, 2H), 2.95 (s, 2H), 2.59 (m, 1H), 1.90-1.70 (m, 4H), 1.32 (s, 6H).

REFERENCE EXAMPLE 13

2-bromo-5-methoxybenzoic acid, methyl ester

To a solution of 2-bromo-5-methoxybenzoic acid (15.0 g) in dimethylformamide (100 ml) were added potassium bicarbonate (7.83 g) and methyl iodide (8.12 ml) and the mixture was stirred for 20 hours at room temperature. The reaction mixture was diluted with water and was extracted with a mixture of ethyl acetate and hexane (1/1). The extract was washed with water, dried over anhydrous magnesium sulfate and concentrated. The residue was purified by column chromatography on silica gel (hexane:ethyl acetate=8:1) to give the title compound (16.3 g) having the following physical data.

TLC: Rf0.80 (hexane:ethyl acetate=2:1); NMR ($CDCl_3$): δ 7.53 (d, J=9.0 Hz, 1H), 7.31 (d, J=3.0 Hz, 1H), 6.89 (dd, J=9.0, 3.0 Hz, 1H), 3.93 (s, 3H), 3.82 (s, 3H).

REFERENCE EXAMPLE 14

2-cyano-5-methoxybenzoic acid, methyl ester

In 1-methylpyrrolidin-2-one (60 ml) was dissolved the compound prepared in reference example 13 (5.07 g) and thereto was added copper cyanide (2.79 g) and the mixture was stirred for 3 hours at 150° C. The mixture was cooled to room temperature and thereto was added water and t-butyl ethyl ether. The precipitate was collected, and it was suspended in water (200 ml) and to the mixture was added sodium cyanide (10.9 g) and the mixture was stirred for 2 hours at room temperature. The reaction mixture was filtered over celite. The filtrate was extracted with ethyl acetate. The extract was washed with water, dried over anhydrous magnesium sulfate and concentrated to give the title compound (2.71 g) having the following physical data.

TLC: Rf0.49 (hexane:ethyl acetate=4:1); NMR ($CDCl_3$): δ 7.72 (d, J=8.4 Hz, 1H), 7.62 (d, J=2.7 Hz, 1H), 7.13 (dd, J=8.4, 2.7 Hz, 1H), 4.00 (s, 3H), 3.92 (s, 3H).

REFERENCE EXAMPLE 15

2-cyano-5-methoxybenzoic acid

To a solution of the compound prepared in reference example 14 (2.48 g) in methanol (10 ml) and a 2N aqueous solution of sodium hydroxide (9.75 ml) and the mixture was stirred for 2 hours at room temperature. The reaction mixture was neutralized with 2N hydrochloric acid (9.75 ml) and the mixture was concentrated. The residue was washed with water and ether to give the title compound (1.50 g) having the following physical data.

TLC: Rf0.24 (chloroform:methanol=10:1); NMR (DMSO-$d_6$): δ 7.89 (d, J=8.4 Hz, 1H), 7.53 (d, J=2.7 Hz, 1H), 7.32 (dd, J=8.4, 2.7 Hz, 1H), 3.89 (s, 3H), 3.31 (brs, 1H).

REFERENCE EXAMPLE 16

6-methoxy-3,3-dimethylisoindolin-1-one

Under atmosphere of argon, to a solution of the compound prepared in reference example 15 (1.00 g) in tetrahydrofuran (20 ml) was added methyl magnesium chloride (28.3 ml; 3.0 M in tetrahydrofuran) at −78° C. dropwise and the mixture was stirred for 12 hours at room temperature. The reaction mixture was poured into a 1N hydrochloric acid at 0° C. and the mixture was extracted with ethyl acetate. The extract was washed with water, dried over anhydrous magnesium sulfate and concentrated. The residue was purified by column chromatography on silica gel (hexane:ethyl acetate=2:1→1:1→ethyl acetate) to give the title compound (146 mg) having the following physical data.

TLC: Rf0.62 (ethyl acetate); NMR ($CDCl_3$): δ 7.29 (d, J=2.4 Hz, 1H), 7.28 (d, J=8.4 Hz, 1H), 7.12 (dd, J=8.4, 2.4 Hz, 1H), 6.60 (br, s, 1H), 3.86 (s, 3H), 1.54 (s, 6H).

REFERENCE EXAMPLE 17

6-methoxy-3,3-dimethylisoindolin-1-thione

To a solution of the compound prepared in reference example 16 (146 mg) in toluene (3.0 ml) was added Lawesson reagent (2,4-bis(4-methoxyphenyl)-1,3-dithia-2,4-diphosphethan-2,4-disulfide) (155 mg) and the mixture was refluxed for 1 hour. The reaction mixture was cooled to room temperature and purified by column chromatography on silica gel (hexane:ethyl acetate=5:1→3:1) to give the title compound (106 mg) having the following physical data.

TLC: Rf0.67 (hexane:ethyl acetate=2:1); NMR ($CDCl_3$): δ 8.17 (br, s, 1H), 7.49 (d, J=2.4 Hz, 1H), 7.26 (d, J=8.4 Hz, 1H), 7.15 (dd, J=8.4, 2.4 Hz, 1H), 3.90 (s, 3H), 1.56 (s, 6H).

EXAMPLE 56

(Z)-2-(6-methoxy-3,3-dimethyl-2,3-dihydro-(2H)-isoindol-1-ylidene)-1-(4-nitrophenyl)ethan-1-one To m-xylene were added the compound prepared in reference example 17 (246 mg) and 4-nitrophenacyl bromide (307 mg) and the mixture was stirred for 15 hours at room temperature. To the reaction mixture were added triethylamine (0.22 ml), triphenylphosphine (330 mg) and triethylamine (0.22 ml) successively and the mixture was refluxed for 1 hour. The reaction mixture was allowed to cool to room temperature and it was purified by column chromatography on silica gel (hexane:ethyl acetate=4:1→2:

1→1:1) to give the compound of the present invention having the following physical data.

TLC: Rf0.55 (hexane:ethyl acetate=2:1); NMR (CDCl$_3$): δ 10.60 (br, s, 1H), 8.30 (d, J=9.0 Hz, 2H), 8.12 (d, J=9.0 Hz, 2H), 7.33 (d, J=8.4 Hz, 1H), 7.22 (d, J=2.1 Hz, 1H), 7.13 (dd, J=8.4, 2.1 Hz, 1H), 6.30 (s, 1H), 3.91 (s, 3H), 1.60 (s, 6H).

EXAMPLE 56(1)-EXAMPLE 56(4)

By the same procedure as described in example 56 using a corresponding derivative in place of 4-nitrophenacyl bromide, the following compounds of the present invention were given.

EXAMPLE 56(1)

(Z)-2-(6-methoxy-3,3-dimethyl-2,3-dihydro-(2H)-isoindol-1-ylidene)-1-(4-cyanophenyl)ethan-1-one TLC: Rf0.50 (hexane:ethyl acetate=2:1); NMR (CDCl$_3$): δ 10.56 (br, s, 1H), 8.07 (d, J=8.4 Hz, 2H), 7.75 (d, J=8.4 Hz, 2H), 7.33 (d, J=8.4 Hz, 1H), 7.21 (d, J=2.4 Hz, 1H), 7.12 (dd, J=8.4, 2.4 Hz, 1H), 6.28 (s, 1H), 3.91 (s, 3H), 1.59 (s, 6H).

EXAMPLE 56(2)

(Z)-2-(6-methoxy-3,3-dimethyl-2,3-dihydro-(2H)-isoindol-1-ylidene)-1-(4-methoxyphenyl)ethan-1-one TLC: Rf0.35 (hexane:ethyl acetate=2:1); NMR (CDCl$_3$): δ 10.33 (br, s, 1H), 7.99 (d, J=8.7 Hz, 2H), 7.29 (d, J=8.1 Hz, 1H), 7.21 (d, J=2.1 Hz, 1H), 7.08 (dd, J=8.1, 2.1 Hz, 1H), 6.96 (d, J=8.7 Hz, 2H), 6.29 (s, 1H), 3.90 (s, 3H), 3.87 (s, 3H), 1.56 (s, 6H).

EXAMPLE 56(3)

(Z)-2-(6-methoxy-3,3-dimethyl-2,3-dihydro-(2H)-isoindol-1-ylidene)-1-(2-methoxyphenyl)ethan-1-one TLC: Rf0.42 (hexane:ethyl acetate=2:1); NMR (CDCl$_3$): δ 10.29 (br, s, 1H), 7.70 (dd, J=7.8, 2.1 Hz, 1H), 7.37 (m, 1H), 7.29 (d, J=8.1 Hz, 1H), 7.14 (d, J=2.4 Hz, 1H), 7.06 (dd, J=8.1, 2.4 Hz, 1H), 7.05-6.95 (m, 2H), 6.25 (s, 1H), 3.92 (s, 3H), 3.86 (s, 3H), 1.57 (s, 6H).

EXAMPLE 56(4)

(Z)-2-(6-methoxy-3,3-dimethyl-2,3-dihydro-(2H)-isoindol-1-ylidene)-1-cyclohexylethan-1-one TLC: Rf0.68 (hexane:ethyl acetate=2:1); NMR (CDCl$_3$): δ 9.96 (br, s, 1H), 7.25 (d, J=8.4 Hz, 1H), 7.10 (d, J=2.4 Hz, 1H), 7.04 (dd, J=8.4, 2.4 Hz, 1H), 5.63 (s, 1H), 3.87 (s, 3H), 2.34 (m, 1H), 1.95-1.80 (m, 4H), 1.69 (m, 1H), 1.51 (s, 6H), 1.55-1.20 (m, 5H).

REFERENCE EXAMPLE 18

2-cyano-4-methoxyphenol

To a solution of 2-hydroxy-5-methoxybenzaldehyde (4.00 g) in formic acid (30 ml) were added hydroxylamine hydrochloride (2.01 g) and sodium formate (3.22 g) at room temperature and the mixture was refluxed for 2 hours. The reaction mixture was concentrated. the residue was diluted with water and was extracted with t-butyl methyl ether. The extract was washed with water, dried over anhydrous magnesium sulfate and concentrated. The residue was washed with a mixture of t-butyl methyl ether and hexane to give the title compound (2.02 g) having the following physical data.

TLC: Rf0.53 (hexane:ethyl acetate=2:1); NMR (CDCl$_3$): δ 7.06 (dd, J=9.0, 3.0 Hz, 1H), 6.94 (d, J=3.0 Hz, 1H), 6.91 (d, J=9.0 Hz, 1H), 5.60 (br, s, 1H), 3.78 (s, 3H).

REFERENCE EXAMPLE 19

2-cyano-4-methoxyphenyl trifluoromethanesulfonate

To a solution of the compound prepared in reference example 18 (1.00 g) in a mixture of acetonitrile (10 ml) and triethylamine (1.87 ml) was added N-phenylbistrifluoromethane sulfonimide (2.40 g) at 0° C. and the mixture was stirred for 2.5 hours at 0° C. The reaction mixture was diluted with water and the mixture was extracted with ethyl acetate. The extract was washed with water, dried over anhydrous magnesium sulfate and concentrated. The residue was purified by column chromatography on silica gel (hexane:ethyl acetate=10:1→6:1→4:1) to give the title compound (2.36 g) having the following physical data.

TLC: Rf0.54 (hexane:ethyl acetate=4:1); NMR (CDCl$_3$): δ 7.38 (dd, J=8.4, 1.5 Hz, 1H), 7.20 (d, J=1.5 Hz, 1H), 7.18 (d, J=8.4 Hz, 1H), 3.87 (s, 3H).

REFERENCE EXAMPLE 20

2-cyano-4-methoxybenzoic acid

To a solution of the compound prepared in reference example 19 (2.36 g) in dimethylformamide (15 ml) were added palladium acetate (75.3 mg), 1,1'-bis(diphenylphosphino)ferrocene (372 mg, DPPF) and potassium acetate (3.29 g) and under atmosphere of carbon monooxide the mixture was stirred for 5 hours at 60° C. The reaction mixture was diluted with a dilute hydrochloric acid. The mixture was extracted with ethyl acetate. The extract was washed with brine, dried over anhydrous magnesium sulfate and concentrated. The residue was dissolved in toluene, and it was subjected to back extraction. The aqueous layer was neutralized with 1N hydrochloric acid. The precipitate was washed with water to give the title compound (600 mg) having the following physical data.

TLC: Rf0.37 (chloroform:methanol=10:1); NMR (DMSO-d$_6$): δ 8.03 (d, J=9.0 Hz, 1H), 7.52 (d, J=3.0 Hz, 1H), 7.33 (dd, J=9.0, 3.0 Hz, 1H), 3.88 (s, 3H), 3.31 (br, s, 1H).

EXAMPLE 57-EXAMPLE 57(4)

By the same procedure as described in reference example 16→reference example 17→example 56 using the compound prepared in reference example 20 in place of the compound prepared in reference example 15, and a corresponding derivative in place of 4-nitrophenacyl bromide, the following compounds of the present invention were given.

EXAMPLE 57

(Z)-2-(5-methoxy-3,3-dimethyl-2,3-dihydro-(2H)-isoindol-1-ylidene)-1-phenylethan-1-one TLC: Rf0.42 (hexane:ethyl acetate=2:1); NMR (CDCl$_3$): δ 10.40 (br, s, 1H), 8.01-7.96 (m, 2H), 7.67 (d, J=8.4 Hz, 1H), 7.50-7.40 (m, 3H), 6.96 (dd, J=8.4, 2.4 Hz, 1H), 6.88 (d, J=2.4 Hz, 1H), 6.29 (s, 1H), 3.90 (s, 3H), 1.58 (s, 6H).

EXAMPLE 57(1)

(Z)-2-(5-methoxy-3,3-dimethyl-2,3-dihydro-(2H)-isoindol-1-ylidene)-1-(4-cyanophenyl)ethan-1-one TLC: Rf0.31 (hexane:ethyl acetate=2:1); NMR (CDCl$_3$): δ 10.51 (br, s, 1H), 8.05 (d, J=8.4 Hz, 2H), 7.73 (d, J=8.4 Hz, 2H), 7.68 (d, J=8.4 Hz, 1H), 6.98 (dd, J=8.4, 2.4 Hz, 1H), 6.90 (d, J=2.4 Hz, 1H), 6.24 (s, 1H), 3.91 (s, 3H), 1.60 (s, 6H).

EXAMPLE 57(2)

(Z)-2-(5-methoxy-3,3-dimethyl-2,3-dihydro-(2H)-isoindol-1-ylidene)-1-(2-methoxyphenyl)ethan-1-one TLC: Rf0.29 (hexane:ethyl acetate=2:1); NMR (CDCl$_3$): δ 10.27 (br, s, 1H), 7.71 (dd, J=7.5, 1.8 Hz, 1H), 7.59 (d, J=8.7 Hz, 1H), 7.36 (m, 1H), 7.10-6.90 (m, 3H), 6.86 (d, J=2.1 Hz, 1H), 6.22 (s, 1H), 3.92 (s, 3H), 3.89 (s, 3H), 1.58 (s, 6H).

EXAMPLE 57(3)

(Z)-2-(5-methoxy-3,3-dimethyl-2,3-dihydro-(2H)-isoindol-1-ylidene)-1-cyclohexylethan-1-one TLC: Rf0.48 (hexane:ethyl acetate=2:1); NMR (CDCl$_3$): δ 9.96 (br, s, 1H), 7.55 (d, J=8.4 Hz, 1H), 6.91 (dd, J=8.4, 2.1 Hz, 1H), 6.83 (d, J=2.1 Hz, 1H), 5.59 (s, 1H), 3.88 (s, 3H), 2.31 (m, 1H), 1.95-1.85 (m, 2H), 1.85-1.75 (m, 2H), 1.70 (m, 1H), 1.56 (s, 6H), 1.55-1.35 (m, 2H), 1.45-1.20 (m, 3H).

EXAMPLE 57(4)

(Z)-2-(5-methoxy-3,3-dimethyl-2,3-dihydro-(2H)-isoindol-1-ylidene)-1-(4-methoxyphenyl)ethan-1-one TLC: Rf0.27 (hexane:ethyl acetate=2:1); NMR (CDCl$_3$): δ 10.31 (br, s, 1H), 7.98 (d, J=9.0 Hz, 2H), 7.67 (d, J=8.7 Hz, 1H), 7.00-6.85 (m, 4H), 6.26 (s, 1H), 3.90 (s, 3H), 3.87 (s, 3H), 1.57 (s, 6H).

EXAMPLE 58

(Z)-2-(6-methoxy-3,3-dimethyl-2,3-dihydro-(2H)-isoindol-1-ylidene)-1-(4-aminophenyl)ethan-1-one A solution of the compound prepared in example 56 (350 mg) in acetic acid (5.5 ml) and water (0.5 ml) was stirred and to the mixture was added steel (465 mg) and the mixture was stirred for 2 hours at 70° C. The reaction mixture was filtered. The filtrate was diluted with ethyl acetate, washed with a saturated aqueous solution of sodium bicarbonate, water and brine successively, dried over anhydrous sodium sulfate and concentrated. The residue was purified by column chromatography on silica gel (hexane:ethyl acetate=1:1→ethyl acetate) to give the compound of the present invention (217 mg) having the following physical data.

TLC: Rf0.53 (hexane:ethyl acetate=1:1); NMR (CDCl$_3$): δ 10.26 (br, s, 1H), 7.88 (d, J=8.4 Hz, 2H), 7.28 (d, J=8.4 Hz, 1H), 7.20 (d, J=2.4 Hz, 1H), 7.06 (dd, J=8.4, 2.4 Hz, 1H), 6.71 (d, J=8.4 Hz, 2H), 6.27 (s, 1H), 3.94 (br, s, 2H), 3.90 (s, 3H), 1.55 (s, 6H).

EXAMPLE 59

(Z)-2-(6-methoxy-3,3-dimethyl-2,3-dihydro-(2H)-isoindol-1-ylidene)-1-(4-acetylaminophenyl)ethan-1-one A solution of the compound prepared in example 58 (68.0 mg) in pyridine (0.5 ml) and acetic anhydride (0.5 ml) was stirred for 3 hours at room temperature. The reaction mixture was diluted with water. The precipitate was collected and was washed with isopropyl ether to give the compound of the present invention (52.7 mg) having the following physical data.

TLC: Rf0.16 (hexane:ethyl acetate=1:1); NMR (CDCl$_3$): δ 10.39 (br, s, 1H), 7.99 (d, J=8.7 Hz, 2H), 7.60 (d, J=8.7 Hz, 2H), 7.30 (d, J=8.1 Hz, 1H), 7.35-7.25 (br, 1H), 7.21 (d, J=2.4 Hz, 1H), 7.09 (dd, J=8.1, 2.4 Hz, 1H), 6.30 (s, 1H), 3.91 (s, 3H), 2.21 (s, 3H), 1.56 (s, 6H).

EXAMPLE 59(1)-EXAMPLE 59(2)

By the same procedure as described in example 59 using an acid anhydride corresponding to acetic anhydride, the following compounds of the present invention were given.

EXAMPLE 59(1)

(Z)-2-(6-methoxy-3,3-dimethyl-2,3-dihydro-(2H)-isoindol-1-ylidene)-1-(4-butanoylaminophenyl)ethan-1-one TLC: Rf0.44 (hexane:ethyl acetate=1:1); NMR (CDCl$_3$): δ 10.39 (br, s, 1H), 7.99 (d, J=8.7 Hz, 2H), 7.62 (d, J=8.7 Hz, 2H), 7.30 (d, J=8.4 Hz, 1H), 7.35-7.20 (br, 1H), 7.22 (d, J=2.1 Hz, 1H), 7.08 (dd, J=8.4, 2.1 Hz, 1H), 6.30 (s, 1H), 3.91 (s, 3H), 2.37 (t, J=7.5 Hz, 2H), 1.79 (sextet, J=7.5 Hz, 2H), 1.56 (s, 6H), 1.03 (t, J=7.5 Hz, 3H).

EXAMPLE 59(2)

(Z)-2-(6-methoxy-3,3-dimethyl-2,3-dihydro-(2H)-isoindol-1-ylidene)-1-(4-hexanoylaminophenyl)ethan-1-one TLC: Rf0.55 (hexane:ethyl acetate=1:1); NMR (CDCl$_3$): δ 10.39 (br, s, 1H), 7.99 (d, J=8.7 Hz, 2H), 7.61 (d, J=8.7 Hz, 2H), 7.30 (d, J=8.4 Hz, 1H), 7.24 (br, s, 1H), 7.22 (d, J=2.1 Hz, 1H), 7.08 (dd, J=8.4, 2.1 Hz, 1H), 6.30 (s, 1H), 3.91 (s, 3H), 2.39 (t, J=7.5 Hz, 2H), 1.75 (m, 2H), 1.56 (s, 6H), 1.45-1.30 (m, 4H), 0.92 (t, J=6.9 Hz, 3H).

EXAMPLE 60

EXAMPLE 60(29)

By the same procedure as described in example II using a corresponding derivative in place of the compound prepared in reference example 6 and a corresponding derivative in place of benzoylmethyl bromide, the following compounds of the present invention were given.

EXAMPLE 60

(Z)-2-(7-bromo-3,3-dimethyl-3,4-dihydro-(2H)-isoquinolin-1-ylidene)-1-(2-methoxyphenyl)ethan-1-one TLC: Rf0.58 (hexane:ethyl acetate=2:1); NMR (CDCl$_3$): δ 11.57 (br, 1H), 7.85 (d, J=2.1 Hz, 1H), 7.66 (dd, J=7.5, 1.8 Hz, 1H), 7.51 (dd, J=8.0, 2.1 Hz, 1H), 7.37 (ddd, J=8.2, 7.5, 1.8 Hz, 1H), 7.08 (d, J=8.0 Hz, 1H), 7.01 (m, 1H), 6.97 (d, J=8.2 Hz, 1H), 6.21 (s, 1H), 3.92 (s, 3H), 2.84 (s, 2H), 1.35 (s, 6H).

EXAMPLE 60(1)

(Z)-2-(7-methoxy-3,3-dimethyl-3,4-dihydro-(2H)-isoquinolin-1-ylidene)-1-(4-fluorophenyl)ethan-1-one TLC: Rf0.56 (hexane:ethyl acetate=2:1); NMR (CDCl$_3$): δ 11.78 (br, 1H), 7.94 (m, 2H), 7.32 (d, J=2.6 Hz, 1H), 7.13 (m, 2H), 7.09 (d, J=8.4 Hz, 1H), 6.99 (dd, J=8.4, 2.6 Hz, 1H), 6.21 (s, 1H), 3.88 (s, 3H), 2.83 (s, 2H), 1.35 (s, 6H).

EXAMPLE 60(2)

(Z)-2-(7-methoxy-3,3-dimethyl-3,4-dihydro-(2H)-isoquinolin-1-ylidene)-1-(4-chlorophenyl)ethan-1-one TLC: Rf0.60 (hexane:ethyl acetate=2:1); NMR (CDCl$_3$): δ 11.82 (br, 1H), 7.88 (d, J=8.4 Hz, 2H), 7.40 (d, J=8.4 Hz, 2H), 7.32 (d, J=2.5 Hz, 1H), 7.14 (d, J=8.5 Hz, 1H), 6.99 (dd, J=8.5, 2.5 Hz, 1H), 6.21 (s, 1H), 3.88 (s, 3), 2.83 (s, 2H), 1.35 (s, 6H).

EXAMPLE 60(3)

(Z)-2-(7-methoxy-3,3-dimethyl-3,4-dihydro-(2H)-isoquinolin-1-ylidene)-1-(4-methylphenyl)ethan-1-one TLC: Rf0.54 (hexane:ethyl acetate=2:1); NMR (CDCl$_3$): δ 11.78 (br, 1H), 7.85 (d, J=7.8 Hz, 2H), 7.34 (d, J=2.5 Hz, 1H), 7.24 (d, J=7.8 Hz, 2H), 7.13 (d, J=8.1 Hz, 1H), 6.98 (dd, J=8.1, 2.5 Hz, 1H), 6.27 (s, 1H), 3.88 (s, 3H), 2.83 (s, 2H), 2.40 (s, 3H), 1.35 (s, 6H).

EXAMPLE 60(4)

(Z)-2-(7-methoxy-3,3-dimethyl-3,4-dihydro-(2H)-isoquinolin-1-ylidene)-1-(4-methoxyphenyl)ethan-1-one TLC: Rf0.44 (hexane:ethyl acetate=2:1); NMR (CDCl$_3$): δ 11.73 (br, 1H), 7.93 (d, J=8.7 Hz, 2H), 7.34 (d, J=2.7 Hz, 1H), 7.12 (d, J=8.3 Hz, 1H), 6.98 (dd, J=8.3, 2.7 Hz, 1H), 6.94 (d, J=8.7 Hz, 2H), 6.25 (s, 1H), 3.88 (s, 3H), 3.86 (s, 3H), 2.82 (s, 2H), 1.34 (s, 6H).

EXAMPLE 60(5)

(Z)-2-(7-methoxy-3,3-dimethyl-3,4-dihydro-(2H)-isoquinolin-1-ylidene)-1-(4-bromophenyl)ethan-1-one TLC: Rf0.62 (hexane:ethyl acetate=2:1); NMR (CDCl$_3$): δ 11.83 (br, 1H), 7.81 (d, J=8.4 Hz, 2H), 7.56 (d, J=8.4 Hz, 2H), 7.32 (d, J=2.5 Hz, 1H), 7.14 (d, J=8.3 Hz, 1H), 7.00 (dd, J=8.3, 2.5 Hz, 1H), 6.21 (s, 1H), 3.88 (s, 3H), 2.83 (s, 2H), 1.35 (s, 6H).

EXAMPLE 60(6)

(Z)-2-(7-methoxy-3,3-dimethyl-3,4-dihydro-(2H)-isoquinolin-1-ylidene)-1-(4-nitrophenyl)ethan-1-one TLC: Rf0.53 (hexane:ethyl acetate=2:1); NMR (CDCl$_3$): δ 11.99 (br, 1H), 8.28 (d, J=8.7 Hz, 2H), 8.06 (d, J=8.7 Hz, 2H), 7.33 (d, J=2.6 Hz, 1H), 7.16 (d, J=8.5 Hz, 1H), 7.02 (dd, J=8.5, 2.6 Hz, 1H), 6.24 (s, 1H), 3.89 (s, 3H), 2.86 (s, 2H), 1.38 (s, 6H).

EXAMPLE 60(7)

(Z)-2-(6-methoxy-3,3-dimethyl-3,4-dihydro-(2H)-isoquinolin-1-ylidene)-1-(2-methoxyphenyl)ethan-1-one TLC: Rf0.59 (hexane:ethyl acetate=1:1); NMR (CDCl$_3$): δ 11.69 (br, 1H), 7.68 (d, J=8.8 Hz, 1H), 7.66 (dd, J=7.5, 2.1 Hz, 1H), 7.34 (m, 1H), 7.02-6.93 (m, 2H), 6.81 (dd, J=8.8, 2.7 Hz, 1H), 6.70 (d, J=2.7 Hz, 1H), 6.17 (s, 1H), 3.91 (s, 3H), 3.85 (s, 3H), 2.85 (s, 2H), 1.35 (s, 6H).

EXAMPLE 60(8)

(Z)-2-(6-chloro-3,3-dimethyl-3,4-dihydro-(2H)-isoquinolin-1-ylidene)-1-(2-nitrophenyl)ethan-1-one TLC: Rf0.55 (hexane:ethyl acetate=2:1); NMR (CDCl$_3$): δ 11.35 (br, 1H), 7.86 (m, 1H), 7.64-7.59 (m, 3H), 7.54-7.47 (m, 1H), 7.27 (m, 1H), 7.22 (m, 1H), 5.80 (s, 1H), 2.89 (s, 2H), 1.37 (s, 6H).

EXAMPLE 60(9)

(Z)-2-(7-methoxy-3,3-dimethyl-3,4-dihydro-(2H)-isoquinolin-1-ylidene)-1-(4-benzoyloxyphenyl)ethan-1-one TLC: Rf0.36 (hexane:ethyl acetate=2:1); NMR (CDCl$_3$): δ 11.81 (br, 1H), 8.24-8.20 (m, 2H), 8.02 (d, J=9.0 Hz, 2H), 7.66 (m, 1H), 7.56-7.50 (m, 2H), 7.34 (d, J=2.6 Hz, 1H), 7.30 (d, J=9.0 Hz, 2H), 7.14 (d, J=8.3 Hz, 1H), 7.00 (dd, J=8.3, 2.6 Hz, 1H), 6.27 (s, 1H), 3.89 (s, 3H), 2.84 (s, 2H), 1.36 (s, 6H).

EXAMPLE 60(10)

(Z)-2-(6-bromo-3,3-dimethyl-3,4-dihydro-(2H)-isoquinolin-1-ylidene)-1-(2-methoxyphenyl)ethan-1-one TLC: Rf0.41 (hexane:ethyl acetate=2:1); NMR (CDCl$_3$): δ 11.69 (br, 1H), 7.66 (dd, J=7.7, 2.0 Hz, 1H), 7.60 (d, J=8.3 Hz, 1H), 7.43 (dd, J=8.3, 2.0 Hz, 1H), 7.40-7.33 (m, 2H), 7.04-6.94 (m, 2H), 6.23 (s, 1H), 3.91 (s, 3H), 2.68 (s, 2H), 1.35 (s, 6H).

EXAMPLE 60(11)

(Z)-2-(7-fluoro-3,3-dimethyl-3,4-dihydro-(2H)-isoquinolin-1-ylidene)-1-(2-nitrophenyl)ethan-1-one TLC: Rf0.45 (hexane:ethyl acetate=2:1); NMR (CDCl$_3$): δ 11.34 (br, 1H), 7.87 (d, J=8.1 Hz, 1H), 7.64-7.60 (m, 2H), 7.51 (m, 1H), 7.38 (dd, J=9.6, 2.7 Hz, 1H), 7.22-7.10 (m, 2H), 5.78 (s, 1H), 2.88 (s, 2H), 1.37 (s, 6H).

EXAMPLE 60(12)

(Z)-2-(6-methylamino-3,3-dimethyl-3,4-dihydro-(2H)-isoquinolin-1-ylidene)-1-(2-methoxyphenyl)ethan-1-one TLC: Rf0.46 (hexane:ethyl acetate=2:3); NMR (CDCl$_3$): δ 11.69 (br, 1H), 7.66 (dd, J=7.7, 1.7 Hz, 1H), 7.56 (d, J=8.6 Hz, 1H), 7.33 (m, 1H), 7.01-6.93 (m, 2H), 6.47 (dd, J=8.6, 2.4 Hz, 1H), 6.34 (d, J=2.4 Hz, 1H), 6.10 (s, 1H), 4.10 (m, 1H), 3.90 (s, 3H), 2.89 (d, J=3.0 Hz, 3H), 2.79 (s, 2H), 1.35 (s, 6H).

EXAMPLE 60(13)

(Z)-2-(7-methoxy-3,3-dimethyl-4-oxa-3,4-dihydro-(2H)-isoquinolin-1-ylidene)-1-(2-nitrophenyl)ethan-1-one TLC: Rf0.39 (hexane:ethyl acetate=2:1); NMR (CDCl$_3$): δ 11.19 (br, 1H), 7.89 (m, 1H), 7.66-7.59 (m, 2H), 7.52 (m, 1H), 7.06-6.99 (m, 2H), 6.90 (d, J=8.4 Hz, 1H), 5.79 (s, 1H), 3.80 (s, 3H), 1.66 (s, 6H).

EXAMPLE 60(14)

(Z)-2-(7-fluoro-3,3-dimethyl-3,4-dihydro-(2H)-isoquinolin-1-ylidene)-1-(2-methylphenyl)ethan-1-one TLC: Rf0.55 (hexane:ethyl acetate=3:1); NMR (CDCl$_3$): δ 11.51 (br, 1H), 7.48-7.45 (m, 1H), 7.39 (dd, J=9.6, 2.7 Hz, 1H), 7.31-7.07 (m, 5H), 5.83 (s, 1H), 2.87 (s, 2H), 2.51 (s, 3H), 1.37 (s, 6H).

EXAMPLE 60(15)

(Z)-2-(6-chloro-3,3-dimethyl-3,4-dihydro-(2H)-isoquinolin-1-ylidene)-1-(2-methylphenyl)ethan-1-one TLC: Rf0.61 (hexane:ethyl acetate=4:1); NMR (CDCl$_3$): δ 11.51 (br, 1H), 7.63 (d, J=8.4 Hz, 1H), 7.46 (m, 1H), 7.30-7.17 (m, 5H), 5.85 (s, 1H), 2.88 (s, 2H), 2.50 (s, 3H), 1.37 (s, 6H).

EXAMPLE 60(16)

(Z)-2-(7-methoxy-3,3-dimethyl-4-oxa-3,4-dihydro-(2H)-isoquinolin-1-ylidene)-1-(2-methylphenyl)ethan-1-one TLC: Rf0.55 (hexane:ethyl acetate=3:1); NMR (CDCl$_3$): δ 11.38 (br, 1H), 7.49-7.45 (m, 1H), 7.32-7.19 (m, 3H), 7.07 (d, J=2.9 Hz, 1H), 6.99 (dd, J=9.0, 2.9 Hz, 1H), 6.89 (d, J=9.0 Hz, 1H), 5.85 (s, 1H), 3.80 (s, 3H), 2.49 (s, 3H), 1.66 (s, 6H).

EXAMPLE 60(17)

(Z)-2-(7-methoxy-3,3-dimethyl-4-oxa-3,4-dihydro-(2H)-isoquinolin-1-ylidene)-1-(2-ethoxyphenyl)ethan-1-one TLC: Rf0.59 (hexane:ethyl acetate=3:1); NMR (CDCl$_3$): δ 11.51 (br, 1H), 7.79 (dd, J=7.5, 1.8 Hz, 1H), 7.36 (m, 1H), 7.14 (d, J=3.0 Hz, 1H), 7.05-6.93 (m, 3H), 6.88 (d, J=9.0 Hz, 1H), 6.51 (s, 1H), 4.15 (q, J=7.0 Hz, 2H), 3.81 (s, 3H), 1.65 (s, 6H), 1.51 (t, J=7.0 Hz, 3H).

EXAMPLE 60(18)

(Z)-2-(7-fluoro-3,3-dimethyl-3,4-dihydro-(2H)-isoquinolin-1-ylidene)-1-(2-ethoxyphenyl)ethan-1-one TLC: Rf0.60 (hexane:ethyl acetate=2:1); NMR (CDCl$_3$): δ 11.60 (br, 1H), 7.82 (dd, J=7.7, 1.7 Hz, 1H), 7.46 (dd, J=9.9, 2.4 Hz, 1H), 7.35 (m, 1H), 7.19-7.06 (m, 2H), 7.01 (m, 1H), 6.95 (m, 1H), 6.52 (s, 1H), 4.16 (q, J=7.0 Hz, 2H), 2.86 (s, 2H), 1.52 (t, J=7.0 Hz, 3H), 1.35 (s, 6H).

EXAMPLE 60(19)

(Z)-2-(6,7-dimethoxy-3,3-dimethyl-3,4-dihydro-(2H)-isoquinolin-1-ylidene)-1-(4-cyanophenyl)ethan-1-one TLC: Rf0.55 (hexane:ethyl acetate=1:1); NMR (DMSO-d$_6$): δ 12.04 (s, 1H), 8.15 (d, J=8.1 Hz, 2H), 7.91 (d, J=8.1 Hz, 2H), 7.49 (s, 1H), 6.93 (s, 1H), 6.42 (s, 1H), 3.88 (s, 3H), 3.84 (s, 3H), 2.85 (s, 2H), 1.29 (s, 6H).

EXAMPLE 60(20)

(Z)-2-(6,7-dimethoxy-3,3-dimethyl-3,4-dihydro-(2H)-isoquinolin-1-ylidene)-1-(2-methoxyphenyl)ethan-1-one TLC: Rf0.50 (hexane:ethyl acetate=1:1); NMR (CDCl$_3$) δ 11.64 (br s, 1H), 7.66 (dd, J=7.5, 1.8 Hz, 1H), 7.39-7.33 (m, 1H), 7.20 (s, 1H), 7.04-6.95 (m, 2H), 6.66 (s, 1H), 6.13 (s, 1H), 3.93 (s, 3H), 3.91 (s, 6H), 2.82 (s, 2H), 1.36 (s, 6H).

EXAMPLE 60(21)

(Z)-2-(7-cyclopentyloxy-6-methoxy-3,3-dimethyl-3,4-dihydro-(2H)-isoquinolin-1-ylidene)-1-(4-cyanophenyl)ethan-1-one TLC: Rf0.70 (hexane:ethyl acetate=1:1); NMR (DMSO-d$_6$): δ 12.05 (s, 1H), 8.13 (d, J=8.1 Hz, 2H), 7.91 (d, J=8.1 Hz, 2H), 7.49 (s, 1H), 6.92 (s, 1H), 6.36 (s, 1H), 5.05-5.00 (m, 1H), 3.82 (s, 3H), 2.85 (s, 2H), 1.89-1.57 (m, 8H), 1.29 (s, 6H).

EXAMPLE 60(22)

(Z)-2-(7-cyclopentyloxy-6-methoxy-3,3-dimethyl-3,4-dihydro-(2H)-isoquinolin-1-ylidene)-1-(2-methoxyphenyl)ethan-1-one TLC: Rf0.60 (hexane:ethyl acetate=1:1); NMR (DMSO-d$_6$): δ 11.51 (s, 1H), 7.56 (d, J=7.8 Hz, 1H), 7.37 (t, J=7.8 Hz, 1H), 7.18 (s, 1H), 7.08 (d, J=7.8 Hz, 1H), 6.95 (t, J=7.8 Hz, 1H), 6.90 (s, 1H), 6.19 (s, 1H), 4.86-4.82 (m, 1H), 3.84 (s, 3H), 3.81 (s, 3H), 2.82 (s, 2H), 1.89-1.57 (m, 8H), 1.27 (s, 6H).

EXAMPLE 60(23)

(Z)-2-(7-fluoro-3,3-dimethyl-3,4-dihydro-(2H)-isoquinolin-1-ylidene)-1-(2-methoxycarbonylphenyl)ethan-1-one TLC: Rf0.44 (hexane:ethyl acetate=2:1); NMR (CDCl$_3$): δ 11.36 (br, 1H), 7.73 (m, 1H), 7.59 (m, 1H), 7.54-7.38 (m, 3H), 7.20-7.08 (m, 2H), 5.86 (s, 1H), 3.86 (s, 3H), 2.87 (s, 2H), 1.36 (s, 6H).

EXAMPLE 60(24)

(Z)-2-(6-cyclopentyloxy-7-methoxy-3,3-dimethyl-3,4-dihydro-(2H)-isoquinolin-1-ylidene)-1-(4-cyanophenyl)ethan-1-one TLC: Rf0.48 (hexane:ethyl acetate=2:1); NMR (CDCl$_3$): δ 11.94 (br, 1H), 8.00 (d, J=8.4 Hz, 2H), 7.72 (d, J=8.4 Hz, 2H), 7.23 (s, 1H), 6.68 (s, 1H), 6.12 (s, 1H), 4.85 (m, 1H), 3.93 (s, 3H), 2.83 (s, 2H), 2.05-1.78 (m, 6H), 1.73-1.60 (m, 2H), 1.38 (s, 6H).

EXAMPLE 60(25)

(Z)-2-(6-cyclopentyloxy-7-methoxy-3,3-dimethyl-3,4-dihydro-(2H)-isoquinolin-1-ylidene)-1-(2-methoxyphenyl)ethan-1-one TLC: Rf0.44 (hexane:ethyl acetate=1:1); NMR (CDCl$_3$): δ 11.64 (br, 1H), 7.66 (dd, J=7.7, 2.0 Hz, 1H), 7.35 (m, 1H), 7.20 (s, 1H), 7.03-7.94 (m, 2H), 6.64 (s, 1H), 6.12 (s, 1H), 4.83 (m, 1H), 3.90 (s, 3H), 3.86 (s, 3H), 2.80 (s, 2H), 2.05-1.77 (m, 6H), 1.70-1.56 (m, 2H), 1.35 (s, 6H).

EXAMPLE 60(26)

(Z)-2-(7-methoxy-3,3-dimethyl-3,4-dihydro-(2H)-isoquinolin-1-ylidene)-1-(2-nitrophenyl)ethan-1-one TLC: Rf0.40 (hexane:ethyl acetate=2:1); NMR (DMSO-d$_6$): δ 11.38 (s, 1H), 7.87-7.83 (m, 2H), 7.73-7.60 (m, 2H), 7.44 (d, J=1.5 Hz, 1H), 7.25 (d, J=8.4 Hz, 1H), 7.10 (dd, J=8.4, 1.5 Hz, 1H), 6.16 (s, 1H), 3.81 (s, 3H), 2.86 (s, 2H), 1.27 (s, 6H).

EXAMPLE 60(27)

(Z)-2-(7-methoxy-3,3-dimethyl-3,4-dihydro-(2H)-isoquinolin-1-ylidene)-1-(3-nitrophenyl)ethan-1-one TLC: Rf0.50 (hexane:ethyl acetate=2:1); NMR (CDCl$_3$): δ 11.95 (s, 1H), 8.76 (m, 1H), 8.31-8.25 (m, 2H), 7.61 (t, J=8.1 Hz, 1H), 7.35 (d, J=2.4 Hz, 1H), 7.16 (d, J=8.4 Hz, 1H), 7.02 (dd, J=8.4, 2.4 Hz, 1H), 6.25 (s, 1H), 3.90 (s, 3H), 2.86 (s, 2H), 1.38 (s, 6H).

EXAMPLE 60(28)

(Z)-2-(7-methoxy-3,3-dimethyl-3,4-dihydro-(2H)-isoquinolin-1-ylidene)-1-(3-cyanophenyl)ethan-1-one TLC: Rf0.48 (hexane:ethyl acetate=2:1); NMR (CDCl$_3$): δ 11.90 (br, 1H), 8.21 (m, 1H), 8.16 (m, 1H), 7.72 (m, 1H), 7.55 (t, J=7.7 Hz, 1H), 7.32 (d, J=2.4 Hz, 1H), 7.16 (d, J=8.2 Hz, 1H), 7.02 (dd, J=8.2, 2.4 Hz, 1H), 6.19 (s, 1H), 3.90 (s, 3H), 2.85 (s, 2H), 1.37 (s, 6H).

EXAMPLE 60(29)

(Z)-2-(7-methoxy-3,3-dimethyl-3,4-dihydro-(2H)-isoquinolin-1-ylidene)-1-(2-methoxycarbonylphenyl)ethan-1-one TLC: Rf0.60 (hexane:ethyl acetate=1:1); NMR (CDCl$_3$): δ 11.42 (br, 1H), 7.72 (m, 1H), 7.61 (m, 1H), 7.50 (m, 1H), 7.43 (m, 1H), 7.23 (d, J=2.6 Hz, 1H), 7.12 (d, J=8.3 Hz, 1H), 6.97 (dd, J=8.3, 2.6 Hz, 1H), 5.88 (s, 1H), 3.85 (s, 3H), 3.83 (s, 3H), 2.83 (s, 2H), 1.35 (s, 6H).

EXAMPLE 61

EXAMPLE 61(2)

By the same procedure as described in example 1 using a corresponding derivative in place of the compound prepared in reference example 1 and a corresponding derivative in place of 2-methyl-1-phenylpropan-2-ol, the following compounds of the present invention were given.

EXAMPLE 61

(Z)-2-(6-fluoro-3,3-dimethyl-3,4-dihydro-(2H-isoquinolin-1-ylidene)-1-(2-methoxyphenyl)ethan-1-one TLC: Rf0.50 (hexane:ethyl acetate=2:1); NMR (CDCl$_3$): δ 11.67 (br, 1H), 7.73 (dd, J=8.7, 5.7 Hz, 1H), 7.67 (d, J=7.8, 1.8 Hz, 1H), 7.36 (m, 1H), 7.03-6.94 (m, 3H), 6.91 (dd, J=8.7, 2.7 Hz, 1H), 6.21 (s, 1H), 3.91 (s, 3H), 2.88 (s, 2H), 1.36 (s, 6H).

EXAMPLE 61(1)

(Z)-2-(6-chloro-3,3-dimethyl-3,4-dihydro-(2H)-isoquinolin-1-ylidene)-1-(2-ethoxyphenyl)ethan-1-one TLC: Rf0.67 (hexane:ethyl acetate=2:1); NMR (CDCl$_3$): δ 11.62 (br, 1H), 7.80 (dd, J=7.5, 1.8 Hz, 1H), 7.69 (d, J=8.3 Hz, 1H), 7.35 (ddd, J=8.4, 7.5, 1.8 Hz, 1H), 7.28 (dd, J=8.3, 2.4 Hz, 1H), 7.20 (d, J=2.4 Hz, 1H), 7.01 (ddd, J=7.5, 7.5, 0.9 Hz, 1H), 6.94 (dd, J=8.4, 0.9 Hz, 1H), 6.51 (s, 1H), 4.14 (q, J=7.0 Hz, 2H), 2.87 (s, 2H), 1.48 (t, J=7.0 Hz, 3H), 1.36 (s, 6H).

EXAMPLE 61(2)

(Z)-2-(7-methoxy-3,3,4,4-tetramethyl-3,4-dihydro-(2H)-isoquinolin-1-ylidene)-1-(4-methoxycarbonylphenyl)ethan-1-one (compound A) and (Z)-2-(7-methoxy-3,3,4,4-tetramethyl-3,4-dihydro-(2H)-isoquinolin-1-ylidene)-1-(4-carboxyphenyl)ethan-1-one (compound B)

Compound A
TLC: Rf0.43 (hexane:ethyl acetate=2:1); NMR (CDCl$_3$): δ 11.91 (br, 1H), 8.09 (d, J=8.6 Hz, 2H), 7.99 (d, J=8.6 Hz, 2H), 7.78 (d, J=8.6 Hz, 1H), 6.95 (d, J=2.7 Hz, 1H), 6.84 (dd, J=8.6, 2.7 Hz, 1H), 6.23 (s, 1H), 3.94 (s, 3H), 3.89 (s, 3H), 1.29 (br, 12H).

Compound B
TLC: Rf0.49 (hexane:ethyl acetate=1:1); NMR (CDCl$_3$): δ 11.89 (br, 1H), 8.09 (d, J=8.4 Hz, 2H), 7.98 (d, J=8.4 Hz, 2H), 7.72 (d, J=8.5 Hz, 1H), 6.90 (d, J=2.4 Hz, 1H), 6.78 (dd, J=8.5, 2.4 Hz, 1H), 6.21 (s, 1H), 5.89 (br, 1H), 3.94 (s, 3H), 1.27 (br, 12H).

EXAMPLE 62

EXAMPLE 62(5)

By the same procedure as described in example 14 using the compound prepared in example 60(6), 60(8), 60(13), 60(11), 60(26) or 60(27), the following compounds of the present invention were given.

EXAMPLE 62

(Z)-2-(7-methoxy-3,3-dimethyl-3,4-dihydro-(2H)-isoquinolin-1-ylidene)-1-(4-aminophenyl)ethan-1-one TLC: Rf0.70 (hexane:ethyl acetate=1:1); NMR (CDCl$_3$): δ 11.66 (br, 1H), 7.82 (d, J=9.0 Hz, 2H), 7.33 (d, J=2.6 Hz, 1H), 7.12 (d, J=8.3 Hz, 1H), 6.96 (dd, J=8.3, 2.6 Hz, 1H), 6.69 (d, J=9.0 Hz, 2H), 6.23 (s, 1H), 3.92 (br, 2H), 3.88 (s, 3H), 2.81 (s, 2H), 1.33 (s, 6H).

EXAMPLE 62(1)

(Z)-2-(6-chloro-3,3-dimethyl-3,4-dihydro-(2H)-isoquinolin-1-ylidene)-1-(2-aminophenyl)ethan-1-one TLC: Rf0.43 (chloroform:methanol=10:1); NMR (DMSO-$d_6$): δ 8.11 (m, 1H), 7.72-7.55 (m, 3H), 7.72-7.00 (br, 1H), 7.49-7.44 (m, 2H), 7.30 (m, 1H), 6.01 (s, 1H), 3.32 (br, 2H), 2.71 (s, 2H), 1.22 (s, 6H).

EXAMPLE 62(2)

(Z)-2-(7-methoxy-3,3-dimethyl-4-oxa-3,4-dihydro-(2H)-isoquinolin-1-ylidene)-1-(2-aminophenyl)ethan-1-one TLC: Rf0.53 (hexane:ethyl acetate=3:1); NMR (CDCl$_3$): δ 11.30 (br, 1H), 7.68 (m, 1H), 7.19 (m, 1H), 7.17 (d, J=2.8 Hz, 1H), 6.99 (dd, J=8.8, 2.8 Hz, 1H), 6.88 (d, J=8.8 Hz, 1H), 6.71-6.64 (m, 2H), 6.19 (s, 1H), 5.81 (br, 2H), 3.85 (s, 3H), 1.64 (s, 6H).

EXAMPLE 62(3)

(Z)-2-(7-fluoro-3,3-dimethyl-3,4-dihydro-(2H)-isoquinolin-1-ylidene)-1-(2-aminophenyl)ethan-1-one TLC: Rf0.47 (chloroform:methanol=5:1); NMR (CD$_3$OD): δ 8.29 (m, 1H), 7.80-7.67 (m, 2H), 7.49-7.40 (m, 2H), 7.35 (dd, J=8.7, 2.8 Hz, 1H), 7.26 (dt, J=8.7, 2.8 Hz, 1H), 6.37 (s, 1H), 2.82 (s, 2H), 1.29 (s, 6H).

EXAMPLE 62(4)

(Z)-2-(7-methoxy-3,3-dimethyl-3,4-dihydro-(2H)-isoquinolin-1-ylidene)-1-(2-aminophenyl)ethan-1-one TLC: Rf0.28 (chloroform:methanol=5:1); NMR (CDCl$_3$): δ 8.43 (dd, J=8.4, 1.2 Hz, 1H), 7.58 (m, 1H), 7.47 (m, 1H), 7.34 (m, 1H), 7.24 (d, J=8.4 Hz, 1H), 7.11 (d, J=3.0 Hz, 1H), 7.00 (dd, J=8.4, 3.0 Hz, 1H), 6.36 (s, 1H), 3.84 (s, 3H), 2.74 (br s, 2H), 1.80-1.40 (m, 3H), 1.40 (s, 6H).

EXAMPLE 62(5)

(Z)-2-(7-methoxy-3,3-dimethyl-3,4-dihydro-(2H)-isoquinolin-1-ylidene)-1-(3-aminophenyl)ethan-1-one TLC: Rf0.50 (hexane:ethyl acetate=1:2); NMR (CDCl$_3$): δ 11.79 (br s, 1H), 7.33-7.26 (m, 3H), 7.21 (t, J=7.8 Hz, 1H), 7.12 (d, J=7.8 Hz, 1H), 6.98 (dd, J=7.8, 2.7 Hz, 1H), 6.77 (m, 1H), 6.23 (s, 1H), 3.87 (s, 3H), 3.80 (br s, 2H), 2.82 (s, 2H), 1.34 (s, 6H).

EXAMPLE 63

(Z)-2-(7-methoxy-3,3-dimethyl-3,4-dihydro-(2H)-isoquinolin-1-ylidene)-1-(4-acetylaminophenyl)ethan-1-one To a solution of the compound prepared in example 62 (0.33 g) in pyridine (0.25 ml) was added acetic anhydride (0.15 ml) at 0° C. and the mixture was stirred for 1 hour at 0° C. To the reaction mixture was added water and was extracted with ethyl acetate. The extract was washed with 1N hydrochloric acid, water and brine, dried over anhydrous magnesium sulfate and concentrated. The residue was purified by column chromatography on silica gel (hexane:ethyl acetate=3:1→1:1) to give the compound of the present invention (0.23 g) having the following physical data.

TLC: Rf0.35 (hexane:ethyl acetate=1:2); NMR (CDCl$_3$): δ 11.79 (br, 1H), 7.93 (d, J=8.9 Hz, 2H), 7.57 (d, J=8.9 Hz, 2H), 7.33 (d, J=2.5 Hz, 1H), 7.13 (d, J=8.3 Hz, 1H), 6.99 (dd, J=8.3, 2.5 Hz, 1H), 6.25 (s, 1H), 3.88 (s, 3H), 2.83 (s, 2H), 2.21 (s, 3H), 1.56 (br, 1H), 1.34 (s, 6H).

EXAMPLE 63(1)-EXAMPLE 63(37)

By the same procedure as described in example 63 using the compound prepared in example 62, or the compound prepared in 62(4) or 62(5) instead, and acetic anhydride or a corresponding acid anhydride or sulfonyl halide, optionally followed by converting to a corresponding salt by a conventional method, the following compounds of the present invention were given.

EXAMPLE 63(1)

(Z)-2-(7-methoxy-3,3-dimethyl-3,4-dihydro-(2H)-isoquinolin-1-ylidene)-1-(4-((cyclohexylcarbonyl)amino)phenyl)ethan-1-one TLC: Rf0.64 (hexane:ethyl acetate=1:1); NMR (CDCl$_3$): δ 11.79 (br, 1H), 7.93 (d, J=9.0 Hz, 2H), 7.60 (d, J=9.0 Hz, 2H), 7.34 (d, J=2.6 Hz, 1H), 7.24 (br, 1H), 7.13 (d, J=8.4 Hz, 1H), 6.98 (dd, J=8.4, 2.6 Hz, 1H), 6.26 (s, 1H), 3.88 (s, 3H), 2.82 (s, 2H), 2.25 (m, 1H), 2.02-1.94 (m, 2H), 1.90-1.82 (m, 2H), 1.75-1.67 (m, 1H), 1.64-1.49 (m, 3H), 1.34 (s, 6H), 1.40-1.25 (m, 2H).

EXAMPLE 63(2)

(Z)-2-(7-methoxy-3,3-dimethyl-3,4-dihydro-(2H)-isoquinolin-1-ylidene)-1-(4-((methoxycarbonyl)amino)phenyl)ethan-1-one TLC: Rf0.50 (hexane:ethyl acetate=1:1); NMR (CDCl$_3$): δ 11.78 (br s, 1H), 7.93 (d, J=8.7 Hz, 2H), 7.45 (d, J=8.7 Hz, 2H), 7.34 (d, J=2.7 Hz, 1H), 7.13 (d, J=8.4 Hz, 1H), 6.98 (dd, J=8.4, 2.7 Hz, 1H), 6.73 (s, 1H), 6.25 (s, 1H), 3.88 (s, 3H), 3.80 (s, 3H), 2.83 (s, 2H), 1.34 (s, 6H).

EXAMPLE 63(3)

(Z)-2-(7-methoxy-3,3-dimethyl-3,4-dihydro-(2H)-isoquinolin-1-ylidene)-1-(4-mesylaminophenyl)ethan-1-one free compound:
TLC: Rf0.35 (hexane:ethyl acetate=1:1); NMR (CDCl$_3$): δ 11.80 (br s, 1H), 7.95 (d, J=8.7 Hz, 2H), 7.32 (d, J=2.7 Hz, 1H), 7.25 (d, J=8.7 Hz, 2H), 7.14 (d, J=8.1 Hz, 1H), 7.00 (dd, J=8.1, 2.7 Hz, 1H), 6.60 (s, 1H), 6.22 (s, 1H), 3.88 (s, 3H), 3.06 (s, 3H), 2.83 (s, 2H), 1.35 (s, 6H).

Sodium Salt:
TLC: Rf0.35 (hexane:ethyl acetate=1:1); NMR (DMSO-$d_6$): δ 11.62 (s, 1H), 7.68 (d, J=8.7 Hz, 2H), 7.44 (d, J=2.7 Hz, 1H), 7.19 (d, J=8.4 Hz, 1H), 7.02 (dd, J=8.4, 2.7 Hz, 1H), 6.76 (d, J=8.7 Hz, 2H), 6.30 (s, 1H), 3.84 (s, 3H), 2.78 (s, 2H), 2.57 (s, 3H), 1.23 (s, 6H).

EXAMPLE 63(4)

(Z)-2-(7-methoxy-3,3-dimethyl-3,4-dihydro-(2H)-isoquinolin-1-ylidene)-1-(2-acetylaminophenyl)ethan-1-one TLC: Rf0.62 (chloroform:methanol=5:1); NMR (DMSO-$d_6$): δ 11.80 (s, 1H), 8.10 (d, J=8.1 Hz, 1H), 7.68-7.58 (m, 2H), 7.32 (m, 1H), 7.24-7.20 (m, 2H), 7.05 (dd, J=8.7, 2.7 Hz, 1H), 6.97 (d, J=2.7 Hz, 1H), 5.97 (s, 1H), 3.78 (s, 3H), 3.09 (s, 2H), 1.71 (s, 3H), 0.96 (s, 6H).

EXAMPLE 63(5)

(Z)-2-(7-methoxy-3,3-dimethyl-3,4-dihydro-(2H)-isoquinolin-1-ylidene)-1-(3-acetylaminophenyl)ethan-1-one TLC: Rf0.45 (ethyl acetate); NMR (CDCl$_3$): δ 11.81 (br s, 1H), 7.91 (d, J=8.4 Hz, 1H), 7.80 (s, 1H), 7.66 (d, J=7.5 Hz, 1H), 7.42-7.37 (m, 2H), 7.33 (d, J=2.7 Hz, 1H), 7.13 (d, J=8.4 Hz, 1H), 6.99 (dd, J=8.4, 2.7 Hz, 1H), 6.24 (s, 1H), 3.88 (s, 3H), 2.83 (s, 2H), 2.20 (s, 3H), 1.35 (s, 6H).

EXAMPLE 63(6)

(Z)-2-(7-methoxy-3,3-dimethyl-3,4-dihydro-(2H)-isoquinolin-1-ylidene)-1-(4-formylaminophenyl)ethan-1-one TLC: Rf0.44 (hexane:ethyl acetate=1:2); NMR (CDCl$_3$): δ 11.81 (br, 1H), 8.80 (d, J=11.6 Hz, 1H*1:2), 8.43 (d, J=1.8 Hz, 1H*1:2), 7.96 (d, J=9.0 Hz, 2H*1:2), 7.95 (d, J=9.0 Hz, 2H*1:2), 7.62 (d, J=9.0 Hz, 2H*1:2), 7.43 (d, J=11.6 Hz, 1H*1:2), 7.33 (d, J=2.4 Hz, 1H), 7.22 (br, 1H*1:2), 7.16-7.10 (m, 1H+2H*1:2), 6.99 (m, 1H), 6.25 & 6.27 (s, 1H), 3.88 (s, 3H), 2.83 (s, 2H), 1.36 & 1.35 (s, 6H).

EXAMPLE 63(7)

(Z)-2-(7-methoxy-3,3-dimethyl-3,4-dihydro-(2H)-isoquinolin-1-ylidene)-1-(2-((2-carboxybenzoyl)amino)phenyl)ethan-1-one TLC: Rf0.28 (chloroform:methanol=5:1); NMR (DMSO-$d_6$): δ 11.85 (s, 1H), 8.10 (d, J=8.1 Hz, 1H), 7.75-7.71 (m, 2H), 7.65-7.63 (m, 2H), 7.58-7.44 (m, 3H), 7.36-7.31 (m, 2H), 7.09 (dd, J=8.4, 2.7 Hz, 1H), 6.99 (d, J=2.7 Hz, 1H), 6.00 (s, 1H), 3.87 (s, 3H), 3.31 (m, 1H), 3.23 (s, 2H), 1.04 (s, 6H).

EXAMPLE 63(8)

(Z)-2-(7-methoxy-3,3-dimethyl-3,4-dihydro-(2H)-isoquinolin-1-ylidene)-1-(3-((2-carboxybenzoyl)amino)phenyl)ethan-1-one TLC: Rf0.45 (chloroform:methanol=5:1); NMR (DMSO-$d_6$): δ 11.83 (s, 1H), 10.42 (s, 1H), 8.22 (s, 1H), 7.89-7.83 (m, 2H), 7.75-7.56 (m, 4H), 7.45-7.38 (m, 2H), 7.25 (d, J=8.4 Hz, 1H), 7.10 (dd, J=8.4, 2.4 Hz, 1H), 6.35 (s, 1H), 3.83 (s, 3H), 3.32 (m, 1H), 2.85 (s, 2H), 1.28 (s, 6H).

EXAMPLE 63(9)

(Z)-2-(7-methoxy-3,3-dimethyl-3,4-dihydro-(2H)-isoquinolin-1-ylidene)-1-(4-((2-carboxybenzoyl)amino)phenyl)ethan-1-one TLC: Rf0.42 (chloroform:methanol=5:1); NMR (DMSO-$d_6$): δ 11.86 (s, 1H), 10.53 (s, 1H), 8.01 (d, J=8.7 Hz, 2H), 7.89 (m, 1H), 7.76 (d, J=8.7 Hz, 2H), 7.69-7.53 (m, 4H), 7.24 (d, J=8.4 Hz, 1H), 7.08 (dd, J=8.4, 2.7 Hz, 1H), 6.43 (s, 1H), 3.86 (s, 3H), 3.32 (m, 1H), 2.83 (s, 2H), 1.27 (s, 6H).

EXAMPLE 63(10)

(Z)-2-(7-methoxy-3,3-dimethyl-3,4-dihydro-(2H)-isoquinolin-1-ylidene)-1-(3-((furan-2-ylcarbonyl)amino)phenyl)ethan-1-one TLC: Rf0.57 (hexane:ethyl acetate=2:3); NMR (CDCl$_3$): δ 11.86 (br, 1H), 8.18 (br, 1H), 8.08 (m, 1H), 7.92 (t, J=1.8 Hz, 1H), 7.71 (dt, J=7.8, 1.8 Hz, 1H), 7.54 (dd, J=1.9, 0.9 Hz, 1H), 7.45 (t, J=7.8 Hz, 1H), 7.36 (d, J=2.7 Hz, 1H), 7.26 (dd, J=3.4, 0.9 Hz, 1H), 7.14 (d, J=8.1 Hz, 1H), 7.00 (dd, J=8.1, 2.7 Hz, 1H), 6.58 (dd, J=3.4, 1.9 Hz, 1H), 6.28 (s, 1H), 3.89 (s, 3H), 2.84 (s, 2H), 1.36 (s, 6H).

EXAMPLE 63(11)

(Z)-2-(7-methoxy-3,3-dimethyl-3,4-dihydro-(2H)-isoquinolin-1-ylidene)-1-(3-(3,4-dimethoxybenzoylamino)phenyl)ethan-1-one TLC: Rf0.53 (hexane:ethyl acetate=1:2); NMR (CDCl$_3$): δ 11.86 (br, 1H), 8.14 (m, 1H), 7.97 (br, 1H), 7.91 (t, J=1.8 Hz, 1H), 7.71 (dt, J=8.1, 1.8 Hz, 1H), 7.51 (d, J=1.9 Hz, 1H), 7.46 (t, J=8.1 Hz, 1H), 7.42 (dd, J=8.2, 1.9 Hz, 1H), 7.35 (d, J=2.7 Hz, 1H), 7.14 (d, J=8.5 Hz, 1H), 6.99 (dd, J=8.5, 2.7 Hz, 1H), 6.93 (d, J=8.2 Hz, 1H), 6.29 (s, 1H), 3.97 (s, 3H), 3.94 (s, 3H), 3.88 (s, 3H), 2.83 (s, 2H), 1.35 (s, 6H).

EXAMPLE 63(12)

(Z)-2-(7-methoxy-3,3-dimethyl-3,4-dihydro-(2H)-isoquinolin-1-ylidene)-1-(3-((2-methoxyacetyl)amino)phenyl)ethan-1-one TLC: Rf0.36 (hexane:ethyl acetate=1:2); NMR (CDCl$_3$): δ 11.86 (br, 1H), 8.37 (br, 1H), 7.99 (m, 1H), 7.86 (t, J=1.8 Hz, 1H), 7.69 (dt, J=7.9, 1.8 Hz, 1H), 7.42 (t, J=7.9 Hz, 1H), 7.35 (d, J=2.5 Hz, 1H), 7.14 (d, J=8.5 Hz, 1H), 6.99 (dd, J=8.5, 2.5 Hz, 1H), 6.26 (s, 1H), 4.04 (s, 2H), 3.86 (s, 3H), 3.53 (s, 3H), 2.84 (s, 2H), 1.36 (s, 6H).

EXAMPLE 63(13)

(Z)-2-(7-methoxy-3,3-dimethyl-3,4-dihydro-(2H)-isoquinolin-1-ylidene)-1-(4-((furan-2-ylcarbonyl)amino)phenyl)ethan-1-one TLC: Rf0.63 (hexane:ethyl acetate=1:2); NMR (CDCl$_3$): δ 11.81 (br, 1H), 8.18 (br, 1H), 7.98 (d, J=8.7 Hz, 2H), 7.74 (d, J=8.7 Hz, 2H), 7.54 (dd, J=1.7, 0.8 Hz, 1H), 7.35 (d, J=2.6 Hz, 1H), 7.27 (dd, J=3.5, 0.8 Hz, 1H), 7.14 (d, J=8.3 Hz, 1H), 6.99 (dd, J=8.3, 2.6 Hz, 1H), 6.58 (dd, J=3.5, 1.7 Hz, 1H), 6.28 (s, 1H), 3.89 (s, 3H), 2.83 (s, 2H), 1.35 (s, 6H).

EXAMPLE 63(14)

(Z)-2-(7-methoxy-3,3-dimethyl-3,4-dihydro-(2H)-isoquinolin-1-ylidene)-1-(4-(3,4-dimethoxybenzoylamino)phenyl)ethan-1-one TLC: Rf0.38 (hexane:ethyl acetate=1:2); NMR (CDCl$_3$): δ 11.82 (br, 1H), 7.99 (d, J=8.6 Hz, 2H), 7.88 (br, 1H), 7.72 (d, J=8.6 Hz, 2H), 7.52 (d, J=2.0 Hz, 1H), 7.41 (dd, J=8.4, 2.0 Hz, 1H), 7.36 (d, J=2.5 Hz, 1H), 7.14 (d, J=8.6 Hz, 1H), 6.99 (dd, J=8.6, 2.5 Hz, 1H), 6.93 (d, J=8.4 Hz, 1H), 6.29 (s, 1H), 3.98 (s, 3H), 3.96 (s, 3H), 3.89 (s, 3H), 2.84 (s, 2H), 1.35 (s, 6H).

EXAMPLE 63(15)

(Z)-2-(7-methoxy-3,3-dimethyl-3,4-dihydro-(2H)-isoquinolin-1-ylidene)-1-(4-((2-(4-methoxyphenyl)acetyl)amino)phenyl)ethan-1-one TLC: Rf0.57 (hexane:ethyl acetate=1:2); NMR (CDCl$_3$): δ 11.79 (br, 1H), 7.89 (d, J=8.9 Hz, 2H), 7.49 (d, J=8.9 Hz, 2H), 7.32 (d, J=2.4 Hz, 1H), 7.26 (d, J=8.6 Hz, 2H), 7.17 (br, 1H), 7.12 (d, J=8.4 Hz, 1H), 6.98 (dd, J=8.4, 2.4 Hz, 1H), 6.95 (d, J=8.6 Hz, 2H), 6.23 (s, 1H), 3.88 (s, 3H), 3.84 (s, 3H), 3.71 (s, 2H), 2.82 (s, 2H), 1.33 (s, 6H).

EXAMPLE 63(16)

(Z)-2-(7-methoxy-3,3-dimethyl-3,4-dihydro-(2H)-isoquinolin-1-ylidene)-1-(4-((2-methoxyacetyl)amino)phenyl)ethan-1-one TLC: Rf0.40 (hexane:ethyl acetate=1:2); NMR (CDCl$_3$): δ 11.81 (br, 1H), 8.36 (br, 1H), 7.95 (d, J=8.7 Hz, 2H), 7.66 (d, J=8.7 Hz, 2H), 7.34 (d, J=2.5 Hz, 1H), 7.13 (d, J=8.2 Hz, 1H), 6.99 (d, J=8.2, 2.5 Hz, 1H), 6.26 (s, 1H), 4.04 (s, 2H), 3.89 (s, 3H), 3.52 (s, 3H), 2.83 (s, 2H), 1.35 (s, 6H).

EXAMPLE 63(17)

(Z)-2-(7-methoxy-3,3-dimethyl-3,4-dihydro-(2H)-isoquinolin-1-ylidene)-1-(4-(3,5-dimethoxybenzoylamino)phenyl)ethan-1-one TLC: Rf0.57 (hexane:ethyl acetate=2:3); NMR (CDCl$_3$): δ 11.82 (br, s, 1H), 7.99 (d, J=8.7 Hz, 2H), 7.90 (br, s, 1H), 7.72 (d, J=8.7 Hz, 2H), 7.35 (d, J=2.4 Hz, 1H), 7.14 (d, J=8.1 Hz, 1H), 7.05-6.90 (m, 3H), 6.63 (t, J=2.1 Hz, 1H), 6.28 (s, 1H), 3.89 (s, 3H), 3.86 (s, 6H), 2.83 (s, 2H), 1.35 (s, 6H).

EXAMPLE 63(18)

(Z)-2-(7-methoxy-3,3-dimethyl-3,4-dihydro-(2H)-isoquinolin-1-ylidene)-1-(4-((5-methyl-3-(2-chlorophenyl)isooxazol-4-ylcarbonyl)amino)phenyl)ethan-1-one TLC: Rf0.70 (hexane:ethyl acetate=2:3); NMR (CDCl$_3$): δ 11.76 (br, s, 1H), 7.84 (d, J=8.7 Hz, 2H), 7.70-7.50 (m, 4H), 7.30 (d, J=2.7 Hz, 1H), 7.20 (d, J=8.7 Hz, 2H), 7.13 (d, J=8.4 Hz, 1H), 7.03 (br, s, 1H), 6.98 (dd, J=8.4, 2.7 Hz, 1H), 6.20 (s, 1H), 3.87 (s, 3H), 2.86 (s, 3H), 2.82 (s, 2H), 1.33 (s, 6H).

EXAMPLE 63(19)

(Z)-2-(7-methoxy-3,3-dimethyl-3,4-dihydro-(2H)-isoquinolin-1-ylidene)-1-(4-((2-(4-chlorophenoxy)pyridin-3-ylcarbonyl)amino)phenyl)ethan-1-one TLC: Rf0.58 (hexane:ethyl acetate=2:3); NMR (CDCl$_3$): δ 11.83 (br, s, 1H), 9.82 (br, s, 1H), 8.72 (dd, J=7.5, 2.1 Hz, 1H), 8.26 (dd, J=4.5, 2.1 Hz, 1H), 7.98 (d, J=8.7 Hz, 2H), 7.75 (d, J=8.7 Hz, 2H), 7.47 (d, J=9.0 Hz, 2H), 7.34 (d, J=2.4 Hz, 1H), 7.30-7.15 (m, 1H), 7.21 (d, J=9.0 Hz, 2H), 7.13 (d, J=8.4 Hz, 1H), 6.99 (dd, J=8.4, 2.4 Hz, 1H), 6.28 (s, 1H), 3.89 (s, 3H), 2.83 (s, 2H), 1.35 (s, 6H).

EXAMPLE 63(20)

(Z)-2-(7-methoxy-3,3-dimethyl-3,4-dihydro-(2H)-isoquinolin-1-ylidene)-1-(4-((3-methylbutanoyl)amino)phenyl)ethan-1-one TLC: Rf0.59 (hexane:ethyl acetate=2:3); NMR (CDCl$_3$): δ 11.79 (br, s, 1H), 7.93 (d, J=8.7 Hz, 2H), 7.60 (d, J=8.7 Hz, 2H), 7.33 (d, J=3.0 Hz, 1H), 7.28 (br, s, 1H), 7.13 (d, J=8.4 Hz, 1H), 6.98 (dd, J=8.4, 3.0 Hz, 1H), 6.25 (s, 1H), 3.88 (s, 3H), 2.82 (s, 2H), 2.28-2.20 (m, 3H), 1.34 (s, 6H), 1.03 (d, J=6.6 Hz, 6H).

EXAMPLE 63(21)

(Z)-2-(7-methoxy-3,3-dimethyl-3,4-dihydro-(2H)-isoquinolin-1-ylidene)-1-(4-((3-methylthiopropanoyl)amino)phenyl)ethan-1-one TLC: Rf0.59 (hexane:ethyl acetate=1:2); NMR (CDCl$_3$): δ 11.80 (br, 1H), 7.94 (d, J=8.3 Hz, 2H), 7.69 (br, 1H), 7.60 (d, J=8.3 Hz, 2H), 7.33 (d, J=2.4 Hz, 1H), 7.13 (d, J=8.0 Hz, 1H), 6.99 (dd, J=8.0, 2.4 Hz, 1H), 6.25 (s, 1H), 3.88 (s, 3H), 2.91 (t, J=7.0 Hz, 2H), 2.83 (s, 2H), 2.68 (t, J=7.0 Hz, 2H), 2.18 (s, 3H), 1.34 (s, 6H).

EXAMPLE 63(22)

(Z)-2-(7-methoxy-3,3-dimethyl-3,4-dihydro-(2H)-isoquinolin-1-ylidene)-1-(3-(3,5-dimethoxybenzoylamino)phenyl)ethan-1-one TLC: Rf0.59 (hexane:ethyl acetate=2:3); NMR (CDCl$_3$): δ 11.86 (br, s, 1H), 8.09 (m, 1H), 7.94 (br, s, 1H), 7.91 (t, J=2.1 Hz, 1H), 7.72 (m, 1H), 7.46 (t, J=8.1 Hz, 1H), 7.35 (d, J=2.4 Hz, 1H), 7.14 (d, J=8.7 Hz, 1H), 7.05-6.95 (m, 1H), 7.01 (d, J=2.4 Hz, 2H), 6.63 (t, J=2.4 Hz, 1H), 6.27 (s, 1H), 3.88 (s, 3H), 3.86 (s, 6H), 2.83 (s, 2H), 1.35 (s, 6H).

EXAMPLE 63(23)

(Z)-2-(7-methoxy-3,3-dimethyl-3,4-dihydro-(2H)-isoquinolin-1-ylidene)-1-(3-((5-methyl-3-(2-chlorophenyl)isooxazol-4-ylcarbonyl)amino)phenyl)ethan-1-one TLC: Rf0.64 (hexane:ethyl acetate=2:3); NMR (CDCl$_3$): δ 11.73 (br, s, 1H), 7.70-7.50 (m, 6H), 7.40-7.30 (m, 2H), 7.33 (d, J=2.1 Hz, 1H), 7.15 (d, J=8.1 Hz, 1H), 7.01 (dd, J=8.1, 2.1 Hz, 1H), 7.00-6.95 (br, 1H), 6.13 (s, 1H), 3.90 (s, 3H), 2.85 (s, 3H), 2.83 (s, 2H), 1.35 (s, 6H).

EXAMPLE 63(24)

(Z)-2-(7-methoxy-3,3-dimethyl-3,4-dihydro-(2H)-isoquinolin-1-ylidene)-1-(3-((2-(4-chlorophenoxy)pyridin-3-ylcarbonyl)amino)phenyl)ethan-1-one TLC: Rf0.63 (hexane:ethyl acetate=2:3); NMR (CDCl$_3$): δ 11.81 (br, s, 1H), 9.75 (br, s, 1H), 8.73 (dd, J=7.8, 1.8 Hz, 1H), 8.26 (dd, J=4.5, 1.8 Hz, 1H), 8.16 (m, 1H), 7.90 (t, J=1.8 Hz, 1H), 7.71 (dt, J=7.5, 1.8 Hz, 1H), 7.50-7.40 (m, 1H), 7.46 (d, J=9.0 Hz, 2H), 7.32 (d, J=2.7 Hz, 1H), 7.30-7.10 (m, 1H), 7.19 (d, J=9.0 Hz, 2H), 7.14 (d, J=8.1 Hz, 1H), 6.99 (dd, J=8.1, 2.7 Hz, 1H), 6.26 (s, 1H), 3.87 (s, 3H), 2.83 (s, 2H), 1.34 (s, 6H).

EXAMPLE 63(25)

(Z)-2-(7-methoxy-3,3-dimethyl-3,4-dihydro-(2H)-isoquinolin-1-ylidene)-1-(3-((3-methylbutanoyl)amino)phenyl)ethan-1-one TLC: Rf0.70 (hexane:ethyl acetate=2:3); NMR (CDCl$_3$): δ 11.82 (br, s, 1H), 7.96 (m, 1H), 7.79 (t, J=1.8 Hz, 1H), 7.66 (m, 1H), 7.40 (t, J=8.1 Hz, 1H), 7.34 (d, J=2.4 Hz, 1H), 7.26 (br, s, 1H), 7.14 (d, J=8.1 Hz, 1H), 6.99 (dd, J=8.1, 2.4 Hz, 1H), 6.25 (s, 1H), 3.88 (s, 3H), 2.83 (s, 2H), 2.30-2.20 (m, 3H), 1.35 (s, 6H), 1.03 (d, J=6.6 Hz, 6H).

EXAMPLE 63(26)

(Z)-2-(7-methoxy-3,3-dimethyl-3,4-dihydro-(2H)-isoquinolin-1-ylidene)-1-(3-((pyridin-2-ylcarbonyl)amino)phenyl)ethan-1-one TLC: Rf0.45 (hexane:ethyl acetate=1:1); NMR (CDCl$_3$): δ 11.88 (s, 1H), 10.17 (s, 1H), 8.65 (m, 1H), 8.32 (d, J=7.8 Hz, 1H), 8.19 (m, 1H), 8.08 (m, 1H), 7.92 (dt, J=1.5, 7.8 Hz, 1H), 7.72 (d, J=7.8 Hz, 1H), 7.52-7.45 (m, 2H), 7.38 (d, J=2.4 Hz, 1H), 7.14 (d, J=8.4 Hz, 1H), 7.00 (dd, J=8.4, 2.4 Hz, 1H), 6.30 (s, 1H), 3.90 (s, 3H), 2.84 (s, 2H), 1.37 (s, 6H).

EXAMPLE 63(27)

(Z)-2-(7-methoxy-3,3-dimethyl-3,4-dihydro-(2H)-isoquinolin-1-ylidene)-1-(3-((pyridin-3-ylcarbonyl)amino)phenyl)ethan-1-one TLC: Rf0.27 (ethyl acetate); NMR (CDCl$_3$): δ 11.79 (s, 1H), 9.18 (d, J=1.8 Hz, 1H), 8.76 (dd, J=4.5, 1.8 Hz, 1H), 8.58 (s, 1H), 8.25 (dt, J=8.1, 1.8 Hz, 1H), 8.14 (d, J=8.1 Hz, 1H), 7.97 (m, 1H), 7.74 (d, J=8.1 Hz, 1H), 7.50-7.43 (m, 2H), 7.31 (d, J=2.4 Hz, 1H), 7.12 (d, J=8.1 Hz, 1H), 6.99 (dd, J=8.1, 2.4 Hz, 1H), 6.24 (s, 1H), 3.87 (s, 3H), 2.77 (s, 2H), 1.27 (s, 6H).

EXAMPLE 63(28)

(Z)-2-(7-methoxy-3,3-dimethyl-3',4-dihydro-(2H)-isoquinolin-1-ylidene)-1-(3-((pyridin-4-ylcarbonyl)amino)phenyl)ethan-1-one TLC: Rf0.24 (ethyl acetate); NMR (CDCl$_3$): δ 11.81 (s, 1H), 8.79 (d, J=6.0 Hz, 2H), 8.30 (s, 1H), 8.11 (d, J=7.8 Hz, 1H), 8.01 (s, 1H), 7.75-7.71 (m, 3H), 7.47 (t, J=7.8 Hz, 1H), 7.34 (d, J=2.4 Hz, 1H), 7.14 (d, J=8.1 Hz, 1H), 7.00 (dd, J=8.1, 2.4 Hz, 1H), 6.27 (s, 1H), 3.88 (s, 3H), 2.81 (s, 2H), 1.31 (s, 6H).

EXAMPLE 63(29)

(Z)-2-(7-methoxy-3,3-dimethyl-3,4-dihydro-(2H)-isoquinolin-1-ylidene)-1-(3-((ethoxycarbonyl)amino)phenyl)ethan-1-one TLC: Rf0.62 (hexane:ethyl acetate=1:1); NMR (CDCl$_3$): δ 11.81 (s, 1H), 7.72 (m, 2H), 7.62 (d, J=8.1 Hz, 1H), 7.38 (t, J=8.1 Hz, 1H), 7.33 (d, J=2.4 Hz, 1H), 7.13 (d, J=8.1 Hz, 1H), 6.99 (dd, J=8.1, 2.4 Hz, 1H), 6.67 (s, 1H), 6.24 (s, 1H), 4.24 (q, J=7.2 Hz, 2H), 3.88 (s, 3H), 2.83 (s, 2H), 1.35 (s, 6H), 1.33 (t, J=7.2 Hz, 3H).

EXAMPLE 63(30)

(Z)-2-(7-methoxy-3,3-dimethyl-3,4-dihydro-(2H)-isoquinolin-1-ylidene)-1-(3-((isopropyloxycarbonyl)amino)phenyl)ethan-1-one TLC: Rf0.68 (hexane:ethyl acetate=1:1); NMR (CDCl$_3$): δ 11.80 (s, 1H), 7.72 (m, 2H), 7.61 (d, J=8.1 Hz, 1H), 7.38 (t, J=8.1 Hz, 1H), 7.33 (d, J=2.4 Hz, 1H), 7.13 (d, J=8.4 Hz, 1H), 6.99 (dd, J=8.4, 2.4 Hz, 1H), 6.60 (s, 1H), 6.24 (s, 1H), 5.03 (m, 1H), 3.88 (s, 3H), 2.83 (s, 2H), 1.35 (s, 6H), 1.31 (d, J=6.3 Hz, 6H).

EXAMPLE 63(31)

(Z)-2-(7-methoxy-3,3-dimethyl-3,4-dihydro-(2H)-isoquinolin-1-ylidene)-1-(4-((pyridin-2-ylcarbonyl)amino)phenyl)ethan-1-one TLC: Rf0.40 (hexane:ethyl acetate=1:1); NMR (CDCl$_3$): δ 11.83 (s, 1H), 10.17 (s, 1H), 8.64 (m, 1H), 8.32 (m, 1H), 8.01 (d, J=8.4 Hz, 2H), 7.93 (dt, J=1.5, 7.8 Hz, 1H), 7.87 (d, J=8.4 Hz, 2H), 7.50 (m, 1H), 7.36 (d, J=2.7 Hz, 1H), 7.14 (d, J=8.4 Hz, 1H), 6.99 (dd, J=8.4, 2.7 Hz, 1H), 6.30 (s, 1H), 3.90 (s, 3H), 2.84 (s, 2H), 1.36 (s, 6H).

EXAMPLE 63(32)

(Z)-2-(7-methoxy-3,3-dimethyl-3,4-dihydro-(2H)-isoquinolin-1-ylidene)-1-(4-((pyridin-3-ylcarbonyl)amino)phenyl)ethan-1-one TLC: Rf0.43 (chloroform:methanol=9:1); NMR (CDCl$_3$): δ 11.82 (s, 1H), 9.12 (d, J=1.8 Hz, 1H), 8.79 (dd, J=4.8, 1.8 Hz, 1H), 8.23 (dt, J=8.1, 1.8 Hz, 1H), 8.09 (s, 1H), 7.99 (d, J=9.0 Hz, 2H), 7.46 (dd, J=8.1, 4.8 Hz, 1H), 7.35 (d, J=2.4 Hz, 1H), 7.14 (d, J=8.4 Hz, 1H), 7.00 (dd, J=8.4, 2.4 Hz, 1H), 6.28 (s, 1H), 3.89 (s, 3H), 2.83 (s, 2H), 1.35 (s, 6H).

EXAMPLE 63(33)

(Z)-2-(7-methoxy-3,3-dimethyl-3,4-dihydro-(2H)-isoquinolin-1-ylidene)-1-(4-((ethoxycarbonyl)amino)phenyl)ethan-1-one TLC: Rf0.53 (hexane:ethyl acetate=1:1); NMR (CDCl$_3$): δ 11.78 (s, 1H), 7.92 (d, J=8.7 Hz, 2H), 7.45 (d, J=8.7 Hz, 2H), 7.33 (d, J=2.7 Hz, 1H), 7.13 (d, J=8.4 Hz, 1H), 6.98 (dd, J=8.4, 2.7 Hz, 1H), 6.72 (s, 1H), 6.25 (s, 1H), 4.25 (q, J=7.2 Hz, 1H), 3.88 (s, 3H), 2.82 (s, 2H), 1.34 (s, 6H), 1.32 (t, J=7.2 Hz, 3H).

EXAMPLE 63(34)

(Z)-2-(7-methoxy-3,3-dimethyl-3,4-dihydro-(2H)-isoquinolin-1-ylidene)-1-(4-((isopropyloxycarbonyl)amino)phenyl)ethan-1-one TLC: Rf0.58 (hexane:ethyl acetate=1:1); NMR (CDCl$_3$): δ 11.77 (s, 1H), 7.92 (d, J=8.7 Hz, 2H), 7.45 (d, J=8.7 Hz, 2H), 7.33 (d, J=2.4 Hz, 1H), 7.13 (d, J=8.4 Hz, 1H), 6.98 (dd, J=8.4, 2.4 Hz, 1H), 6.68 (s, 1H), 6.25 (s, 1H), 5.04 (m, 1H), 3.88 (s, 3H), 2.82 (s, 2H), 1.34 (s, 6H), 1.31 (d, J=6.0 Hz, 6H).

EXAMPLE 63(35)

(Z)-2-(7-methoxy-3,3-dimethyl-3,4-dihydro-(2H)-isoquinolin-1-ylidene)-1-(4-((pyridin-4-ylcarbonyl)amino)phenyl)ethan-1-one TLC: Rf0.48 (chloroform:methanol=9:1); NMR (CDCl$_3$): δ 11.83 (s, 1H), 8.82 (d, J=9.0 Hz, 2H), 8.01-7.99 (m, 3H), 7.75-7.72 (m, 4H), 7.35 (d, J=2.4 Hz, 1H), 7.14 (d, J=8.1 Hz, 1H), 7.00 (dd, J=8.1, 2.4 Hz, 1H), 6.28 (s, 1H), 3.89 (s, 3H), 2.84 (s, 2H), 1.35 (s, 6H).

EXAMPLE 63(36)

(Z)-2-(7-methoxy-3,3-dimethyl-3,4-dihydro-(2H)-isoquinolin-1-ylidene)-1-(3-(cyclopropylcarbonylamino)phenyl)ethan-1-one TLC: Rf0.38 (hexane:ethyl acetate=1:1); NMR (CDCl$_3$): δ 11.81 (s, 1H), 7.94 (m, 1H), 7.80 (m, 1H), 7.65 (m, 1H), 7.50 (m, 1H), 7.39 (t, J=8.1 Hz, 1H), 7.33 (d, J=2.7 Hz, 1H), 7.13 (d, J=8.1 Hz, 1H), 6.99 (dd, J=8.1, 2.7 Hz, 1H), 6.25 (s, 1H), 3.88 (s, 3H), 2.83 (s, 2H), 1.53 (m, 1H), 1.35 (s, 6H), 1.11 (m, 2H), 0.87 (m, 2H).

EXAMPLE 63(37)

(Z)-2-(7-methoxy-3,3-dimethyl-3,4-dihydro-(2H)-isoquinolin-1-ylidene)-1-(4-(cyclopropylcarbonylamino)phenyl)ethan-1-one TLC: Rf0.32 (hexane:ethyl acetate=1:1); NMR (CDCl$_3$): δ 11.79 (s, 1H), 7.93 (d, J=8.4 Hz, 2H), 7.59 (d, J=8.4 Hz, 2H), 7.49 (s, 1H), 7.34 (d, J=2.7 Hz, 1H), 7.13 (d, J=8.4 Hz, 1H), 6.98 (dd, J=8.4, 2.7 Hz, 1H), 6.26 (s, 1H), 3.88 (s, 3H), 2.82 (s, 2H), 1.54 (m, 1H), 1.34 (s, 6H), 1.12 (m, 2H), 0.88 (m, 2H).

EXAMPLE 64

(Z)-2-(7-methoxy-3,3-dimethyl-3,4-dihydro-(2H)-isoquinolin-1-ylidene)-1-(4-(N-cyclohexylcarbonyl-N-methylamino)phenyl)ethan-1-one To a solution of the compound prepared in example 63(1) (0.28 g) in N,N-dimethylformamide (3 ml) was added sodium hydride under cooling with ice, and the mixture was stirred for 1 hour. To the reaction mixture was added methyl iodide (97.1 μl) and the mixture was stirred overnight at room temperature. To the reaction mixture was added a saturated aqueous solution of ammonium chloride and was extracted with ethyl acetate. The extract was washed with water and a saturated aqueous solution of sodium chloride successively, dried over anhydrous magnesium sulfate and concentrated. The residue was purified by column chromatography on silica gel (hexane:ethyl acetate=3:1→2:1) to give the compound of the present invention (0.20 g) having the following physical data.

TLC: Rf0.51 (hexane:acetone=2:1); NMR (CDCl$_3$): δ 11.87 (br, 1H), 7.98 (d, J=8.3 Hz, 2H), 7.34 (d, J=2.6 Hz, 1H), 7.23 (d, J=8.3 Hz, 2H), 7.15 (d, J=8.2 Hz, 1H), 7.01 (dd, J=8.2, 2.6 Hz, 1H), 6.27 (s, 1H), 3.88 (s, 3H), 3.27 (s, 3H), 2.85 (s, 2H), 2.24 (m, 1H), 1.68-1.64 (m, 4H), 1.60-1.47 (m, 3H), 1.37 (s, 6H), 1.16 (m, 1H), 1.08-0.88 (m, 2H).

EXAMPLE 65-EXAMPLE 65(2)

By the same procedure as described in example 13 using the compound prepared in example 60, 60(5) or 60(10) in place of the compound prepared in example 12, the following compounds of the present invention were given.

EXAMPLE 65

(Z)-2-(7-formyl-3,3-dimethyl-3,4-dihydro-(2H)-isoquinolin-1-ylidene)-1-(2-methoxyphenyl)ethan-1-one TLC: Rf0.61 (hexane:ethyl acetate=1:1); NMR (CDCl$_3$): δ 11.62 (br, 1H), 10.03 (s, 1H), 8.25 (d, J=1.4 Hz, 1H), 7.92 (dd, J=7.8, 1.8 Hz, 1H), 7.68 (dd, J=7.7, 1.4 Hz, 1H), 7.39 (m, 1H), 7.38 (d, J=7.7 Hz, 1H), 7.05-6.97 (m, 2H), 6.38 (s, 1H), 3.93 (s, 3H), 2.98 (s, 2H), 1.37 (s, 6H).

EXAMPLE 65(1)

(Z)-2-(7-methoxy-3,3-dimethyl-3,4-dihydro-(2H)-isoquinolin-1-ylidene)-1-(4-formylphenyl)ethan-1-one TLC: Rf0.53 (hexane:ethyl acetate=1:1); NMR (CDCl$_3$): δ 11.97 (br, 1H), 10.08 (s, 1H), 8.07 (d, J=8.3 Hz, 2H), 7.95 (d, J=8.3 Hz, 2H), 7.34 (d, J=2.5 Hz, 1H), 7.16 (d, J=8.4 Hz, 1H), 7.01 (dd, J=8.4, 2.5 Hz, 1H), 6.28 (s, 1H), 3.89 (s, 3H), 2.85 (s, 2H), 1.37 (s, 6H).

EXAMPLE 65(2)

(Z)-2-(6-formyl-3,3-dimethyl-3,4-dihydro-(2H)-isoquinolin-1-ylidene)-1-(2-methoxyphenyl)ethan-1-one TLC: Rf0.41 (hexane:ethyl acetate=2:1); NMR (CDCl$_3$): δ 11.58 (br, 1H), 10.05 (s, 1H), 7.91 (d, J=8.0 Hz, 1H), 7.80 (dd, J=8.0, 1.7 Hz, 1H), 7.72 (d, J=1.7 Hz, 1H), 7.68 (dd, J=7.5, 1.8 Hz, 1H), 7.38 (m, 1H), 7.05-6.96 (m, 2H), 6.36 (s, 1H), 3.92 (s, 3H), 2.98 (s, 2H), 1.37 (s, 6H).

EXAMPLE 66-EXAMPLE 66(2)

By the same procedure as described in example 15 using the compound prepared in example 60, 60(5) or 60(10) in place of the compound prepared in example 12, the following compounds of the present invention were given.

EXAMPLE 66

(Z)-2-(7-carboxy-3,3-dimethyl-3,4-dihydro-(2H)-isoquinolin-1-ylidene)-1-(2-methoxyphenyl)ethan-1-one TLC: Rf0.55 (ethyl acetate:methanol=20:1); NMR (CDCl$_3$): δ 11.62 (br, 1H), 8.49 (d, J=1.8 Hz, 1H), 8.12 (dd, J=7.8, 1.8 Hz, 1H), 7.67 (dd, J=7.8, 1.5 Hz, 1H), 7.38 (m, 1H), 7.31 (d, J=7.8 Hz, 1H), 7.05-6.96 (m, 2H), 6.40 (s, 1H), 3.93 (s, 3H), 2.96 (s, 2H), 2.64 (br, 1H), 1.37 (s, 6H).

EXAMPLE 66(1)

(Z)-2-(7-methoxy-3,3-dimethyl-3,4-dihydro-(2H)-isoquinolin-1-ylidene)-1-(4-carboxyphenyl)ethan-1-one TLC: Rf0.39 (chloroform:methanol=10:1); NMR (CDCl$_3$): δ 11.96 (br, 1H), 8.17 (d, J=8.7 Hz, 2H), 8.01 (d, J=8.7 Hz, 2H), 7.34 (d, J=2.5 Hz, 1H), 7.15 (d, J=8.3 Hz, 1H), 7.01 (dd, J=8.3, 2.5 Hz, 1H), 6.28 (s, 1H), 3.89 (s, 3H), 3.12 (br, 1H), 2.85 (s, 2H), 1.37 (s, 6H).

EXAMPLE 66(2)

(Z)-2-(6-carboxy-3,3-dimethyl-3,4-dihydro-(2H)-isoquinolin-1-ylidene)-1-(2-methoxyphenyl)ethan-1-one TLC: Rf0.58 (ethyl acetate:methanol=20:1); NMR (CDCl$_3$): δ 11.61 (br, 1H), 8.03 (dd, J=8.3, 1.7 Hz, 1H), 7.94 (d, J=1.7, 1H), 7.84 (d, J=8.3 Hz, 1H), 7.69 (dd, J=7.5, 1.8 Hz, 1H), 7.38 (m, 1H), 7.05-6.96 (m, 2H), 6.35 (s, 1H), 5.03 (br, 1H), 3.92 (s, 3H), 2.96 (s, 2H), 1.37 (s, 6H).

EXAMPLE 67-EXAMPLE 67(1)

By the same procedure as described in example 4 using the compound prepared in example 60(23) or 60(29) in place of the compound prepared in example 1(1), the following compounds of the present invention were given.

EXAMPLE 67

(Z)-2-(7-fluoro-3,3-dimethyl-3,4-dihydro-(2H)-isoquinolin-1-ylidene)-1-(2-carboxyphenyl)ethan-1-one TLC: Rf0.74 (ethyl acetate:methanol=20:1); NMR (CDCl$_3$): δ 11.58 (br, 1H), 8.26 (m, 1H), 7.72 (m, 1H), 7.59-7.54 (m, 2H), 7.46 (dd, J=9.5, 2.3 Hz, 1H), 7.28-7.20 (m, 2H), 6.01 (s, 1H), 2.93 (s, 2H), 1.28 (s, 6H).

EXAMPLE 67(1)

(Z)-2-(7-methoxy-3,3-dimethyl-3,4-dihydro-(2H)-isoquinolin-1-ylidene)-1-(2-carboxyphenyl)ethan-1-one TLC: Rf0.54 (chloroform:methanol=10:1); NMR (CDCl$_3$): δ 11.64 (br, 1H), 8.27 (m, 1H), 7.72 (m, 1H), 7.60-7.50 (m, 2H), 7.26 (d, J=2.7 Hz, 1H), 7.18 (d, J=8.4 Hz, 1H), 7.05 (dd, J=8.4, 2.7 Hz, 1H), 6.04 (s, 1H), 3.86 (s, 3H), 2.87 (s, 2H), 1.55 (br, 1H), 1.40 (s, 6H).

EXAMPLE 68

(Z)-2-(7-methoxy-3,3-dimethyl-3,4-dihydro-(2H)-isoquinolin-1-ylidene)-1-(2-((2-hydroxy-1,1-dimethylethyl)carbamoyl)phenyl)ethan-1-one To a solution of the compound prepare in example 66(1) (0.3 g) in N,N-dimethylformamide (4.0 ml) were added 1-hydroxybenzotriazole (0.12 g), N-methylmorpholine (0.14 ml), 2-hydroxy-1,1-dimethylethylamine (0.12 ml) and 1-ethyl-3-(3-dimethylaminopropyl)carbodiimide hydrochloride (0.25 g) and the mixture was stirred for 4 hours at room temperature. To the reaction mixture was added water and was extracted with ethyl acetate. The extract was washed with 1N hydrochloric acid, a saturated aqueous solution of sodium bicarbonate and brine successively, dried over anhydrous magnesium sulfate and concentrated to give the compound of the present invention (0.35 g) having the following physical data.

TLC: Rf0.54 (chloroform:methanol=10:1); NMR (CDCl$_3$): δ 11.93 (br, 1H), 7.98 (d, J=8.3 Hz, 2H), 7.79 (d, J=8.3 Hz, 2H), 7.33 (d, J=2.6 Hz, 1H), 7.15 (d, J=8.3 Hz, 1H), 7.00 (dd, J=8.3, 2.6 Hz, 1H), 6.29 (br, 1H), 6.26 (s, 1H), 4.72 (br, 1H), 3.88 (s, 3H), 3.72 (s, 2H), 2.84 (s, 2H), 1.44 (s, 6H), 1.36 (s, 6H).

EXAMPLE 68(1)-EXAMPLE 68(9)

By the same procedure as described in example 68 using the compound prepared in example 66(1) or example 66, 66(2), 67 or 67(1) and a corresponding derivative in place of 2-hydroxy-1,1-dimethylethylamine, the following compounds of the present invention were given.

EXAMPLE 68(1)

(Z)-2-(7-carbamoyl-3,3-dimethyl-3,4-dihydro-(2H)-isoquinolin-1-ylidene)-1-(2-methoxyphenyl)ethan-1-one TLC: Rf0.73 (chloroform:methanol=10:1); NMR (CDCl$_3$): δ 11.61 (br, 1H), 8.20 (d, J=1.5 HZ, 1H), 7.83 (dd, J=7.8, 1.8 Hz, 1H), 7.65 (dd, J=7.5, 1.5 Hz, 1H), 7.37 (m, 1H), 7.30 (d, J=7.5 Hz, 1H), 7.04-6.95 (m, 2H), 6.31 (s, 1H), 6.20-5.50 (br, 2H), 3.92 (s, 3H), 2.95 (s, 2H), 1.36 (s, 6H).

EXAMPLE 68(2)

(Z)-2-(6-carbamoyl-3,3-dimethyl-3,4-dihydro-(2H)-isoquinolin-1-ylidene)-1-(2-methoxyphenyl)ethan-1-one TLC: Rf0.66 (ethyl acetate:methanol=20:1); NMR (CDCl$_3$): δ 11.59 (br, 1H), 7.81 (d, J=8.7 Hz, 1H), 7.71-7.65 (m, 3H), 7.38 (m, 1H), 7.05-6.95 (m, 2H), 6.31 (s, 1H), 6.10 (br, 1H), 5.70 (br, 1H), 3.92 (s, 3H), 2.94 (s, 2H), 1.36 (s, 6H).

EXAMPLE 68(3)

(Z)-2-(7-fluoro-3,3-dimethyl-3,4-dihydro-(2H)-isoquinolin-1-ylidene)-1-(2-carbamoylphenyl)ethan-1-one TLC: Rf0.45 (chloroform:methanol=10:1); NMR (CDCl$_3$): δ 11.50 (br, 1H), 7.79 (m, 1H), 7.56-7.38 (m, 4H), 7.22-7.10 (m, 2H), 7.04 (br, 1H), 5.88 (s, 1H), 5.63 (br, 1H), 2.88 (s, 2H), 1.37 (s, 6H).

EXAMPLE 68(4)

(Z)-2-(7-methoxy-3,3-dimethyl-3,4-dihydro-(2H)-isoquinolin-1-ylidene)-1-(4-cyclohexylcarbamoylphenyl)ethan-1-one TLC: Rf0.51 (hexane:ethyl acetate=1:1); NMR (CDCl$_3$): δ 11.92 (br, 1H), 7.98 (d, J=8.6 Hz, 2H), 7.81 (d, J=8.6 Hz, 2H), 7.33 (d, J=2.5 Hz, 1H), 7.15 (d, J=8.4 Hz, 1H), 7.00 (dd, J=8.4, 2.5 Hz, 1H), 6.27 (s, 1H), 6.00 (d, J=7.5 Hz, 1H), 4.00 (m, 1H), 3.89 (s, 3H), 2.84 (s, 2H), 2.10-2.03 (m, 2H), 1.82-1.72 (m, 2H), 1.72-1.60 (m, 1H), 1.60-1.15 (m, 5H), 1.36 (s, 6H).

EXAMPLE 68(5)

(Z)-2-(7-methoxy-3,3-dimethyl-3,4-dihydro-(2H)-isoquinolin-1-ylidene)-1-(4-(N-cyclohexyl-N-methylcarbamoyl)phenyl)ethan-1-one TLC: Rf0.49 (hexane:ethyl acetate=1:2); NMR (CDCl$_3$): δ 11.87 (br, 1H), 7.96 (d, J=7.8 Hz, 2H), 7.42 (d, J=7.8 Hz, 2H), 7.34 (d, J=2.5 Hz, 1H), 7.14 (d, J=8.3 Hz, 1H), 7.00 (dd, J=8.3, 2.5 Hz, 1H), 6.27 (s, 1H), 4.55 (m, 1*0.36H), 3.88 (s, 3H), 3.45 (m, 1*0.64H), 2.98 (s, 3*0.64H), 2.84 (s, 2H), 2.80 (s, 3*0.36H), 1.90-1.62 (m, 5H), 1.62-1.36 (m, 3H), 1.36 (s, 6H), 1.17-0.96 (m, 2H).

EXAMPLE 68(6)

(Z)-2-(7-methoxy-3,3-dimethyl-3,4-dihydro-(2H)-isoquinolin-1-ylidene)-1-(4-methylcarbamoylphenyl)ethan-1-one TLC: Rf0.54 (chloroform:methanol=10:1); NMR (CDCl$_3$): δ 11.91 (br, 1H), 7.98 (d, J=8.6 Hz, 2H), 7.82 (d, J=8.6 Hz, 2H), 7.34 (d, J=2.6 Hz, 1H), 7.15 (d, J=8.2 Hz, 1H), 7.00 (dd, J=8.2, 2.6 Hz, 1H), 6.27 (s, 1H), 6.21 (br, 1H), 3.89 (s, 3H), 3.04 (d, J=4.8 Hz, 3H), 2.84 (s, 2H), 1.36 (s, 6H).

EXAMPLE 68(7)

(Z)-2-(7-methoxy-3,3-dimethyl-3,4-dihydro-(2H)-isoquinolin-1-ylidene)-1-(4-hydrazinocarbonylphenyl)ethan-1-one TLC: Rf0.32 (chloroform:methanol=10:1); NMR (CDCl$_3$): δ 11.91 (br, 1H), 7.99 (d, J=8.1 Hz, 2H), 7.81 (d, J=8.1 Hz, 2H), 7.58 (br, 1H), 7.33 (d, J=2.2 Hz, 1H), 7.15 (d, J=8.4 Hz, 1H), 7.01 (dd, J=8.4, 2.2 Hz, 1H), 6.26 (s, 1H), 4.31 (br, 2H), 3.88 (s, 3H), 2.84 (s, 2H), 1.36 (s, 6H).

EXAMPLE 68(8)

(Z)-2-(7-methoxy-3,3-dimethyl-3,4-dihydro-(2H)-isoquinolin-1-ylidene)-1-(2-carbamoylphenyl)ethan-1-one TLC: Rf0.46 (chloroform:methanol=10:1); NMR (CDCl$_3$): δ 11.56 (br, 1H), 7.82 (m, 1H), 7.55-7.44 (m, 3H), 7.25 (br, 1H), 7.20 (d, J=2.6 Hz, 1H), 7.13 (d, J=8.3 Hz, 1H), 6.99 (dd, J=8.3, 2.6 Hz, 1H), 5.89 (s, 1H), 5.65 (br, 1H), 3.82 (s, 3H), 2.85 (s, 2H), 1.36 (s, 6H).

EXAMPLE 68(9)

(Z)-2-(7-methoxy-3,3-dimethyl-3,4-dihydro-(2H)-isoquinolin-1-ylidene)-1-(4-carbamoylphenyl)ethan-1-one TLC: Rf0.39 (chloroform:methanol=10:1); NMR (CDCl$_3$): δ 11.93 (br, 1H), 8.01 (d, J=8.7 Hz, 2H), 7.88 (d, J=8.7 Hz, 2H), 7.34 (d, J=2.5 Hz, 1H), 7.15 (d, J=8.3 Hz, 1H), 7.01 (dd, J=8.3, 2.5 Hz, 1H), 6.27 (s, 1H), 6.12 (br, 1H), 5.65 (br, 1H), 3.89 (s, 3H), 2.85 (s, 2H), 1.37 (s, 6H).

EXAMPLE 69

EXAMPLE 69(1)

By the same procedure as described in example 28 using the compound prepared in example 65 and example 65(1) in place of the compound prepared in example 13 the following compounds of the present invention were given.

EXAMPLE 69

(Z)-2-(7-hydroxymethyl-3,3-dimethyl-3,4-dihydro-(2H)-isoquinolin-1-ylidene)-1-(2-methoxyphenyl)ethan-1-one TLC: Rf0.58 (hexane:ethyl acetate=1:2); NMR (CDCl$_3$): δ 11.65 (br, 1H), 7.74 (d, J=1.7 Hz, 1H), 7.65 (dd, J=7.5, 1.7 Hz, 1H), 7.41 (dd, J=7.7, 1.7 Hz, 1H), 7.36 (m, 1H), 7.19 (d, J=7.7 Hz, 1H), 7.03-6.94 (m, 2H), 6.25 (s, 1H), 4.71 (d, J=4.8 Hz, 2H), 3.91 (s, 3H), 2.88 (s, 2H), 1.83 (t, J=4.8 Hz, 1H), 1.35 (s, 6H).

EXAMPLE 69(1)

(Z)-2-(7-methoxy-3,3-dimethyl-3,4-dihydro-(2H)-isoquinolin-1-ylidene)-1-(4-hydroxymethylphenyl)ethan-1-one TLC: Rf0.62 (hexane:ethyl acetate=1:2); NMR (CDCl$_3$): δ 11.83 (br, 1H), 7.94 (d, J=8.6 Hz, 2H), 7.43 (d, J=8.6 Hz, 2H), 7.34 (d, J=2.6 Hz, 1H), 7.14 (d, J=8.3 Hz, 1H), 6.99 (dd, J=8.3, 2.6 Hz, 1H), 6.27 (s, 1H), 4.76 (d, J=4.5 Hz, 2H), 3.88 (s, 3H), 2.83 (s, 2H), 1.74 (t, J=4.5 Hz, 1H), 1.35 (s, 6H).

EXAMPLE 70-EXAMPLE 70(1)

By the same procedure as described in example 45 using the compound prepared in example 68(2) or example 68(3) in place of the compound prepared in example 30(9), the following compounds of the present invention were given.

EXAMPLE 70

(Z)-2-(6-cyano-3,3-dimethyl-3,4-dihydro-(2H)-isoquinolin-1-ylidene)-1-(2-methoxyphenyl)ethan-1-one TLC: Rf0.44 (hexane:ethyl acetate=2:1); NMR (CDCl$_3$): δ 11.54 (br, 1H), 7.83 (d, J=8.2 Hz, 1H), 7.67 (dd, J=7.7, 1.7 Hz, 1H), 7.59 (dd, J=8.2, 1.7 Hz, 1H), 7.50 (d, J=1.7 Hz, 1H), 7.39 (m, 1H), 7.05-6.96 (m, 2H), 6.32 (s, 1H), 3.92 (s, 3H), 2.92 (s, 2H), 1.36 (s, 6H).

EXAMPLE 70(1)

(Z)-2-(7-fluoro-3,3-dimethyl-3,4-dihydro-(2H)-isoquinolin-1-ylidene)-1-(2-cyanophenyl)ethan-1-one TLC: Rf0.67 (hexane:ethyl acetate=1:1); NMR (CDCl$_3$): δ 11.69 (br, 1H), 7.83 (m, 1H), 7.77 (m, 1H), 7.63 (dt, J=1.3, 7.5 Hz, 1H), 7.54-7.47 (m, 2H), 7.23-7.11 (m, 2H), 6.11 (s, 1H), 2.89 (s, 2H), 1.38 (s, 6H).

EXAMPLE 71

(Z)-2-(7-methoxy-3,3-dimethyl-3,4-dihydro-(2H)-isoquinolin-1-ylidene)-1-(4-dimethylaminophenyl)ethan-1-one By the same procedure as described in example 41 using the compound prepared in example 62 in place of the compound prepared in example 38, the compound of the present invention having the following physical data was given.

TLC: Rf0.44 (hexane:ethyl acetate=2:1); NMR (CDCl₃): δ 11.64 (br, 1H), 7.90 (d, J=9.0 Hz, 2H), 7.35 (d, J=2.6 Hz, 1H), 7.11 (d, J=8.3 Hz, 1H), 6.96 (dd, J=8.3, 2.6 Hz, 1H), 6.71 (d, J=9.0 Hz, 2H), 6.27 (s, 1H), 3.88 (s, 3H), 3.04 (s, 6H), 2.81 (s, 2H), 1.33 (s, 6H).

EXAMPLE 72

(Z)-2-(7-methoxy-3,3-dimethyl-3,4-dihydro-(2H)-isoquinolin-1-ylidene)-1-(4-hydroxyphenyl)ethan-1-one To a solution of the compound prepared in example 60(9) (0.38 g) in benzene (4 ml) was added butylamine (0.89 ml) and the mixture was stirred for 4 hours at room temperature and overnight at 50° C. The mixture was cooled to room temperature and thereto was added a 1N aqueous solution of sodium hydroxide and the mixture was subjected to back extraction with ether. The extract was washed with water and brine successively, dried over anhydrous magnesium sulfate and concentrated. The residue was washed with ether to give the compound of the present invention (0.25 g) having the following physical data.

TLC: Rf0.45 (hexane:ethyl acetate=2:1); NMR (CDCl₃): δ 11.70 (br, 1H), 7.87 (d, J=9.0 Hz, 2H), 7.33 (d, J=2.6 Hz, 1H), 7.13 (d, J=8.2 Hz, 1H), 6.98 (dd, J=8.2, 2.6 Hz, 1H), 6.87 (d, J=9.0 Hz, 2H), 6.23 (s, 1H), 5.96 (br, 1H), 3.88 (s, 3H), 2.82 (s, 2H), 1.33 (s, 6H).

EXAMPLE 73

(Z)-2-(7-methoxy-3,3-dimethyl-3,4-dihydro-(2H)-isoquinolin-1-ylidene)-1-(4-((aminocarbonyl)amino)phenyl)ethan-1-one Under atmosphere of argon, a solution of the compound prepared in example 62 (150 mg) in tetrahydrofuran (2 ml) were added triethylamine (0.10 ml) and triphosgene (55 mg) at 0° C. for 30 minutes. To the reaction mixture was added ammonia water and the mixture was warmed to room temperature and thereto was added water and was extracted with ethyl acetate. The extract was washed with water and brine successively, dried over anhydrous magnesium sulfate and concentrated. The residue was recrystallized with a mixture of hexane and ethyl acetate to give the compound of the present invention (103 mg) having the following physical data.

TLC: Rf0.57 (ethyl acetate); NMR (CDCl₃): δ 11.75 (br s, 1H), 7.90 (d, J=8.7 Hz, 2H), 7.38 (d, J=8.7 Hz, 2H), 7.33 (d, J=2.7 Hz, 1H), 7.13 (d, J=8.1 Hz, 1H), 6.99 (dd, J=8.1, 2.7 Hz, 1H), 6.90 (s, 1H), 6.24 (s, 1H), 4.78 (s, 2H), 3.88 (s, 3H), 2.82 (s, 2H), 1.34 (s, 6H).

EXAMPLE 74-EXAMPLE 74(1)

By the same procedure as described in example 34 using the compound prepared in example 66(1) or example 66 in place of the compound prepared in example 33, the following compounds of the present invention were given.

EXAMPLE 74

(Z)-2-(7-methoxy-3,3-dimethyl-3,4-dihydro-(2H)-isoquinolin-1-ylidene)-1-(4-methoxycarbonylphenyl)ethan-1-one TLC: Rf0.53 (hexane:ethyl acetate=2:1); NMR (CDCl₃): δ 11.94 (br, 1H), 8.10 (d, J=8.4 Hz, 2H), 7.98 (d, J=8.4 Hz, 2H), 7.34 (d, J=2.6 Hz, 1H), 7.15 (d, J=8.4 Hz, 1H), 7.00 (dd, J=8.4, 2.6 Hz, 1H), 6.27 (s, 1H), 3.94 (s, 3H), 3.88 (s, 3H), 2.84 (s, 2), 1.36 (s, 6H).

EXAMPLE 74(1)

(Z)-2-(7-methoxycarbonyl-3,3-dimethyl-3,4-dihydro-(2H)-isoquinolin-1-ylidene)-1-(2-methoxyphenyl)ethan-1-one TLC: Rf0.44 (hexane:ethyl acetate=2:1); NMR (CDCl₃): δ 11.61 (br, 1H), 8.43 (d, J=1.8 Hz, 1H), 8.06 (dd, J=8.0, 1.7 Hz, 1H), 7.68 (dd, J=7.5, 1.8 Hz, 1H), 7.38 (m, 1H), 7.28 (d, J=7.5 Hz, 1H), 7.05-6.96 (m, 2H), 6.37 (s, 1H), 3.94 (s, 3H), 3.94 (s, 3H), 2.95 (s, 2H), 1.36 (s, 6H).

EXAMPLE 75

(Z)-2-(7-(pyridin-3-yl)-3,3-dimethyl-3,4-dihydro-(2H)-isoquinolin-1-ylidene)-1-(2-methoxyphenyl)ethan-1-one By the same procedure as described in example 9 using the compound prepared in example 60 in place of the compound prepared in example 1(68) and 3-(diethylboryl)pyridine in place of benzeneboronic acid, the compound of the present invention having the following physical data was given.

TLC: Rf0.50 (hexane:ethyl acetate=1:2); NMR (CDCl₃): δ 11.68 (br, 1H), 8.86 (m, 1H), 8.62 (dd, J=5.0, 1.7 Hz, 1H), 7.93 (d, J=1.8 Hz, 1H), 7.89 (d, J=8.0, 2.4, 1.7 Hz, 1H), 7.67 (dd, J=7.5, 1.8 Hz, 1H), 7.62 (dd, J=7.8, 1.8 Hz, 1H), 7.41-7.31 (m, 3H), 7.04-6.95 (m, 2H), 6.33 (s, 1H), 3.91 (s, 3H), 2.95 (s, 2H), 1.40 (s, 6H).

EXAMPLE 76

(Z)-2-(7-methoxy-3,3-dimethyl-3,4-dihydro-(2H)-isoquinolin-1-ylidene)-1-(4-(1,3,4-oxadiazol-2-yl)phenyl)ethan-1-one To a solution of the compound prepared in example 68(7) (0.20 g) in methyl orthoformate (1.2 ml) was added p-toluenesulfonic acid monohydrate (1 mg) and the mixture was refluxed for 30 minutes. The mixture was cooled to room temperature and thereto was added water, and extracted with ethyl acetate. The extract was washed with a saturated aqueous solution of sodium bicarbonate, water and brine successively, dried over anhydrous magnesium sulfate and concentrated. The residue was washed with a mixture of hexane and ethyl acetate (1/1) to give the compound of the present invention (0.11 g) having the following physical data.

TLC: Rf0.56 (hexane:ethyl acetate=1:2); NMR (CDCl₃): δ 11.95 (br, 1H), 8.50 (s, 1H), 8.16 (d, J=8.4 Hz, 2H), 8.08 (d, J=8.4 Hz, 2H), 7.35 (d, J=2.5 Hz, 1H), 7.16 (d, J=8.2 Hz, 1H), 7.00 (dd, J=8.2, 2.5 Hz, 1H), 6.29 (s, 1H), 3.89 (s, 3H), 2.86 (s, 2H), 1.38 (s, 6H).

EXAMPLE 77

(Z)-2-(7-methoxy-3,3-dimethyl-3,4-dihydro-(2H)-isoquinolin-1-ylidene)-1-(4-(4,4-dimethyl-4,5-dihydro-1,3-oxazol-2-yl)phenyl)ethan-1-one To a solution of the compound prepared in example 68 (0.35 g) in methylene chloride (28 ml) were added methanesulfonyl chloride (96 μl) and methanesulfonic acid (0.27 ml) and the mixture was refluxed overnight. The reaction mixture was cooled to room temperature and thereto was added water and the mixture was extracted with methylene chloride. The aqueous layer was extracted with ethyl acetate. The combined organic layer was dried over anhydrous magnesium sulfate and concentrated. The residue was purified by column chromatography on silica gel (hexane:ethyl acetate=2:1) to give the compound of the present invention (79.7 mg) having the following physical data.

TLC: Rf0.60 (chloroform:methanol=10:1); NMR (CDCl$_3$): δ 11.94 (br, 1H), 8.01 (d, J=8.7 Hz, 2H), 7.96 (d, J=8.7 Hz, 2H), 7.35 (d, J=2.4 Hz, 1H), 7.14 (d, J=8.1 Hz, 1H), 7.00 (d, J=8.1, 2.4 Hz, 1H), 6.28 (s, 1H), 4.13 (s, 2H), 3.89 (s, 3H), 2.84 (s, 2H), 1.40 (s, 6H), 1.36 (s, 6H).

EXAMPLE 78

(Z)-2-(7-fluoro-3,3-dimethyl-3,4-dihydro-(2H)-isoquinolin-1-ylidene)-1-(2-hydroxyphenyl)ethan-1-one By the same procedure as described in example 5 using the compound prepared in example 11(42) in place of the compound prepared in example 1(18), the compound of the present invention was given.

TLC: Rf0.50 (hexane:ethyl acetate=4:1); NMR (CDCl$_3$): δ 11.28 (br, 1H), 7.76 (dd, J=8.1, 1.8 Hz, 1H), 7.51 (dd, J=9.6, 2.4 Hz, 1H), 7.34 (m, 1H), 7.23-7.12 (m, 2H), 6.94 (dd, J=8.4, 1.2 Hz, 1H), 6.85 (m, 1H), 6.25 (s, 1H), 2.87 (s, 2H), 1.55 (s, 1H), 1.37 (s, 6H).

EXAMPLE 79

(Z)-2-(7-methoxy-3,3-dimethyl-3,4-dihydro-(2H)-isoquinolin-1-ylidene)-1-(3-carboxyphenyl)ethan-1-one To acetic acid (75 ml) was added the compound prepared in example 60(28) (4.29 g) was added concentrated hydrochloric acid (75 ml) and the mixture was stirred for 1 day at 80° C. The reaction mixture was cooled with ice, and it was added to sodium hydroxide (90 g) slowly to alkalify the mixture. The aqueous layer was subjected to back extraction with ether and acidified with a 2N hydrochloric acid and the mixture was extracted. The extract was washed with water and brine successively, dried over anhydrous magnesium sulfate and concentrated to give the compound of the present invention (2.79 g) having the following physical data.

TLC: Rf0.49 (chloroform:methanol=10:1); NMR (CDCl$_3$): δ 11.93 (br, 1H), 8.65 (t, J=1.7 Hz, 1H), 8.22-8.16 (m, 2H), 7.56 (t, J=7.8 Hz, 1H), 7.37 (d, J=2.6 Hz, 1H), 7.15 (d, J=8.3 Hz, 1H), 7.01 (dd, J=8.3, 2.6 Hz, 1H), 6.30 (s, 1H), 3.90 (s, 3H), 2.85 (s, 2H), 2.20-1.20 (br, 1H), 1.37 (s, 6H).

EXAMPLE 80-EXAMPLE 80(2)

By the same procedure as described in example 68 using the compound prepared in example 60(29) or 79 in place of the compound prepared in example 66(1), the compounds of the present invention were given.

EXAMPLE 80

(Z)-2-(7-methoxy-3,3-dimethyl-3,4-dihydro-(2H)-isoquinolin-1-ylidene)-1-(3-carbamoylphenyl)ethan-1-one TLC: Rf0.47 (chloroform:methanol=10:1); NMR (CDCl$_3$): δ 11.91 (br, 1H), 8.34 (t, J=1.5 Hz, 1H), 8.09 (dt, J=7.7, 1.5 Hz, 1H), 7.98 (m, 1H), 7.54 (t, J=7.7 Hz, 1H), 7.35 (d, J=2.5 Hz, 1H), 7.15 (d, J=8.3 Hz, 1H), 7.01 (dd, J=8.3, 2.5 Hz, 1H), 6.29 (s, 1H), 6.28 (br, 1H), 5.66 (br, 1H), 3.89 (s, 3H), 2.85 (s, 2H), 1.37 (s, 6H).

EXAMPLE 80(1)

(Z)-2-(7-methoxy-3,3-dimethyl-3,4-dihydro-(2H)-isoquinolin-1-ylidene)-1-(2-(methylcarbamoyl)phenyl)ethan-1-one TLC: Rf0.63 (chloroform:methanol=10:1); NMR (CDCl$_3$): δ 11.49 (br, 1H), 7.73 (m, 1H), 7.54 (m, 1H), 7.48-7.40 (m, 2H), 7.22 (d, J=2.4 Hz, 1H), 7.12 (d, J=8.2 Hz, 1H), 6.98 (dd, J=8.2, 2.4 Hz, 1H), 6.92 (m, 1H), 5.89 (s, 1H), 3.84 (s, 3H), 2.92 (d, J=5.1 Hz, 3H), 2.84 (s, 2H), 1.36 (s, 6H).

EXAMPLE 80(2)

(Z)-2-(7-methoxy-3,3-dimethyl-3,4-dihydro-(2H)-isoquinolin-1-ylidene)-1-(3-(methylcarbamoyl)phenyl)ethan-1-one TLC: Rf0.43 (chloroform:methanol=10:1); NMR (CDCl$_3$): δ 11.92 (br, 1H), 8.27 (t, J=1.7 Hz, 1H), 8.06 (dt, J=7.7, 1.5 Hz, 1H), 7.93 (m, 1H), 7.51 (t, J=7.7 Hz, 1H), 7.35 (d, J=2.6 Hz, 1H), 7.15 (d, J=8.3 Hz, 1H), 7.00 (dd, J=8.3, 2.6 Hz, 1H), 6.31 (br, 1H), 6.29 (s, 1H), 3.89 (s, 3H), 3.04 (d, J=4.8 Hz, 3H), 2.84 (s, 2H), 1.36 (s, 6H).

EXAMPLE 81

(Z)-2-(7-methoxy-3,3-dimethyl-3,4-dihydro-(2H)-isoquinolin-1-ylidene)-1-(4-(aminocarbonothioyl)phenyl)ethan-1-one To a solution of the compound prepared in example 11(35) (0.3 g) in N,N-dimethylformamide (3 ml) were added magnesium chloride (0.13 g) and sodium hydrosulfide (0.11 g) under cooling with ice, and the mixture was stirred for 3 hours at room temperature. To the reaction mixture was added water and the mixture was extracted with a mixture of ethyl acetate and tetrahydrofuran. The extract was washed with water and brine successively, dried over anhydrous magnesium sulfate and concentrated to give the compound of the present invention (0.33 g) having the following physical data. The given compound was used in the next reaction without subjecting to purification.

TLC: Rf0.29 (hexane:ethyl acetate=1:1); NMR (CDCl$_3$): δ 11.92 (br, 1H), 8.02-7.54 (m, 4H), 7.67 (br, 1H), 7.34 (br, 1H), 7.33 (d, J=2.5 Hz, 1H), 7.15 (d, J=8.3 Hz, 1H), 7.01 (dd, J=8.3, 2.5 Hz, 1H), 6.25 (s, 1H), 3.88 (s, 3H), 2.85 (s, 2H), 1.36 (s, 6H).

EXAMPLE 82

(Z)-2-(7-methoxy-3,3-dimethyl-3,4-dihydro-(2H)-isoquinolin-1-ylidene)-1-(4-(4-hydroxy-4-methyl-4,5-dihydro-1,3-thiazol-2-yl)phenyl)ethan-1-one To a solution of the compound prepared in example 81 (0.33 g) in ethanol (18 ml) were added sodium bicarbonate (0.13 g) and bromoacetone (0.11 g) and the mixture was stirred overnight at 70° C. The reaction mixture was cooled to room temperature, and thereto was added water and the mixture was extracted with ethyl acetate. The extract was washed with water and brine successively, dried over anhydrous magnesium sulfate and concentrated. The residue was purified by column chromatography on silica gel (hexane: ethyl acetate=1:1) to give the compound of the present invention (0.30 g) having the following physical data.

TLC: Rf0.48 (hexane:ethyl acetate=1:2); NMR (CDCl$_3$): δ 11.94 (br, 1H), 7.98 (d, J=8.3 Hz, 2H), 7.92 (d, J=8.3 Hz, 2H), 7.34 (d, J=2.5 Hz, 1H), 7.15 (d, J=8.3 Hz, 1H), 7.00 (dd, J=8.3, 2.5 Hz, 1H), 6.28 (s, 1H), 3.89 (s, 3H), 3.52 (d, J=11.9 Hz, 1H), 3.44 (dd, J=11.9 Hz, 1H), 2.96 (s, 1H), 2.84 (s, 2H), 1.75 (s, 3H), 1.36 (s, 6H).

EXAMPLE 83

(Z)-2-(7-methoxy-3,3-dimethyl-3,4-dihydro-(2H)-isoquinolin-1-ylidene)-1-(4-(4-methyl-1,3-thiazol-2-yl)phenyl)ethan-1-one To a solution of the compound prepared in example 82 (0.29 g) in dioxane (3.5 ml) was added a 4N solution of hydrogen chloride in dioxane (1.7 ml) and the mixture was stirred for 2 hours at room temperature. The reaction mixture was neutralized with a 1N aqueous solution of sodium hydroxide and the mixture was extracted with ethyl acetate. The extract was washed with water and brine successively, dried over anhydrous magnesium sulfate, and concentrated to give the compound of the present invention (0.20 g) having the following physical data.

TLC: Rf0.41 (hexane:ethyl acetate=2:1); NMR (CDCl$_3$): δ 11.92 (br, 1H), 8.00 (s, 4H), 7.36 (d, J=2.5 Hz, 1H), 7.15 (d, J=8.2 Hz, 1H), 7.00 (dd, J=8.2, 2.5 Hz, 1H), 6.92 (m, 1H), 6.30 (s, 1H), 3.89 (s, 3H), 2.84 (s, 2H), 2.53 (d, J=0.9 Hz, 3H), 1.36 (s, 6H).

EXAMPLE 84-EXAMPLE 84(444)

The compounds of example 84-example 84(444) were prepared according to the following method.

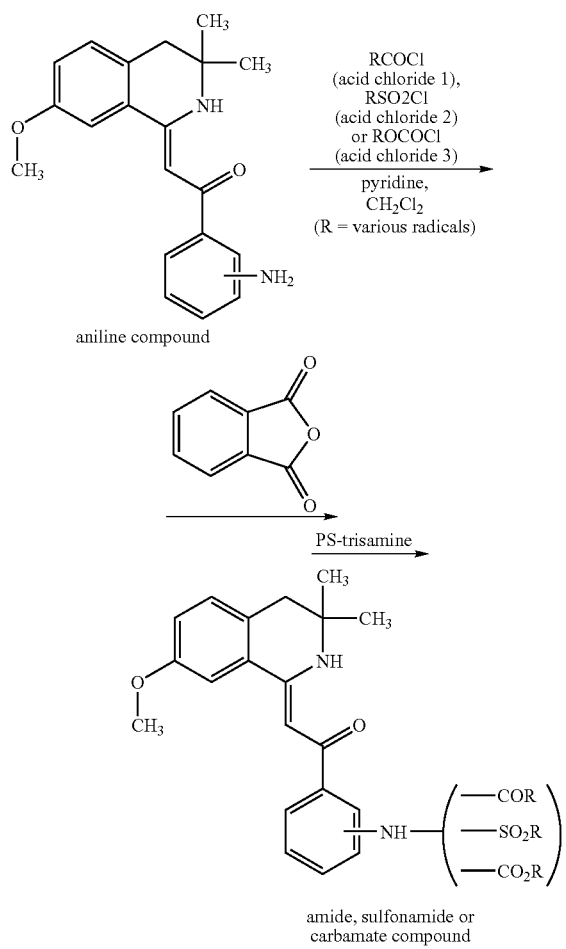

The Method for the Preparation of Example 84-84(306) (Amide Compound)

To a solution of an aniline compound (30 μmol) in pyridine (60 μl) was added a solution of acid chloride 1 (30 μmol) in methylene chloride (60 μl), and the mixture was stirred overnight at room temperature. To the reaction mixture was added phthalic anhydride (15 μmol) in tetrahydrofuran (15 μl) and 2 hours later to the mixture was added PS-trisamine (ca. 50 mg, tris-(2-aminoethyl)amine polystylene (resin)). 1 hour later thereto was added methylene chloride (1 ml) and the resin was filtered and was washed with methylene chloride (1 ml). The filtrate was concentrated to give an amide compound.

The method for the preparation of example 84(307)-84 (417) (sulfonamide compound) or example 84(418)-84(444) (carbamate compound)

To a solution of an aniline compound (30 μmol) in pyridine (60 μl) were added a solution of acid chloride 2 or acid chloride 3 (60 μmol) in methylene chloride (60 μl), and the mixture was stirred overnight at room temperature. To the reaction mixture was added phthalic anhydride (15 μmol) in tetrahydrofuran (15 μl) and 2 hours later was added PS-trisamine (ca. 50 mg). 1 hour later thereto was added methylene chloride (1 ml) and the resin was filtered and was washed with methylene chloride (1 ml). The filtrate was concentrated to give a sulfonamide or carbamate compound.

The condition under which HPLC was measured is as follows.
Column:XTerra C18, 4.6×50 mm (5 em),
Rate of flow: 3 ml/min,
Solvent
Solvent A: a 0.1% aqueous solution of trifluoroacetic acid,
Solvent B: a 0.1% solution of trifluoroacetic acid in acetonitrile
Ratio of Solvent:
At first, the ratio of solvent A/solvent B was fixed to 95/5 for first 0.5 minute. Next the ratio was changed to 0/100 linearly in 2.5 minutes and the ratio was fixed to 0/100 for 0.5 minute. Afterwards, the ratio was changed to 95/5 in 0.01 minute and the ratio was fixed to 95/5 for 1.49 minutes.

EXAMPLE 84

(Z)-2-(7-methoxy-3,3-dimethyl-3,4-dihydro-(2H)-isoquinolin-1-ylidene)-1-(3-((naphthalen-1-ylcarbonyl)amino)phenyl)ethan-1-one HPLC retention time (min.): 4.21; Mass (ESI, Pos. 20V): m/z 477 (M+H)$^+$.

EXAMPLE 84(1)

(Z)-2-(7-methoxy-3,3-dimethyl-3,4-dihydro-(2H)-isoquinolin-1-ylidene)-1-(3-(pivaloylamino)phenyl) ethan-1-one HPLC retention time (min.): 4.05; Mass (ESI, Pos. 20V): m/z 407 (M+H)$^+$.

EXAMPLE 84(2)

(Z)-2-(7-methoxy-3,3-dimethyl-3,4-dihydro-(2H)-isoquinolin-1-ylidene)-1-(3-((2-phenylacetyl)amino) phenyl)ethan-1-one HPLC retention time (min.): 4.04; Mass (ESI, Pos. 20V): m/z 441 (M+H)$^+$.

EXAMPLE 84(3)

(Z)-2-(7-methoxy-3,3-dimethyl-3,4-dihydro-(2H)-isoquinolin-1-ylidene)-1-(3-(hexanoylamino)phenyl)ethan-1-one HPLC retention time (min.): 4.16; Mass (ESI, Pos. 20V): m/z 421 (M+H)$^+$.

EXAMPLE 84(4)

(Z)-2-(7-methoxy-3,3-dimethyl-3,4-dihydro-(2H)-isoquinolin-1-ylidene)-1-(3-(cyclohexylcarbonylamino)phenyl)ethan-1-one HPLC retention time (min.): 4.17; Mass (ESI, Pos. 20V): m/z 433 (M+H)$^+$.

EXAMPLE 84(5)

(Z)-2-(7-methoxy-3,3-dimethyl-3,4-dihydro-(2H)-isoquinolin-1-ylidene)-1-(3-(benzoylamino)phenyl)ethan-1-one HPLC retention time (min.): 4.06; Mass (ESI, Pos. 20V): m/z 427 (M+H)$^+$.

EXAMPLE 84(6)

(Z)-2-(7-methoxy-3,3-dimethyl-3,4-dihydro-(2H)-isoquinolin-1-ylidene)-1-(3-((furan-2-ylcarbonyl)amino)phenyl)ethan-1-one HPLC retention time (min.): 3.93; Mass (ESI, Pos. 20V): m/z 417 (M+H)$^+$.

EXAMPLE 84(7)

(Z)-2-(7-methoxy-3,3-dimethyl-3,4-dihydro-(2H)-isoquinolin-1-ylidene)-1-(3-(acetylamino)phenyl)ethan-1-one HPLC retention time (min.): 3.71; Mass (ESI, Pos. 20V): m/z 365 (M+H)$^+$.

EXAMPLE 84(8)

(Z)-2-(7-methoxy-3,3-dimethyl-3,4-dihydro-(2H)-isoquinolin-1-ylidene)-1-(3-(cyclopropylcarbonylamino)phenyl)ethan-1-one HPLC retention time (min.): 3.90; Mass (ESI, Pos. 20V): m/z 391 (M+H)$^+$.

EXAMPLE 84(9)

(Z)-2-(7-methoxy-3,3-dimethyl-3,4-dihydro-(2H)-isoquinolin-1-ylidene)-1-(3-(4-phenylbenzoylamino)phenyl)ethan-1-one HPLC retention time (min.): 4.36; Mass (ESI, Pos. 20V): m/z 503 (M+H)$^+$.

EXAMPLE 84(10)

(Z)-2-(7-methoxy-3,3-dimethyl-3,4-dihydro-(2H)-isoquinolin-1-ylidene)-1-(3-(4-trifluoromethylbenzoylamino)phenyl)ethan-1-one HPLC retention time (min.): 4.28; Mass (ESI, Pos. 20V): m/z 495 (M+H)$^+$.

EXAMPLE 84(11)

(Z)-2-(7-methoxy-3,3-dimethyl-3,4-dihydro-(2H)-isoquinolin-1-ylidene)-1-(3-(3-trifluoromethylbenzoylamino)phenyl)ethan-1-one HPLC retention time (min.): 4.27; Mass (ESI, Pos. 20V): m/z 495 (M+H)$^+$.

EXAMPLE 84(12)

(Z)-2-(7-methoxy-3,3-dimethyl-3,4-dihydro-(2H)-isoquinolin-1-ylidene)-1-(3-(2,6-dichlorobenzoylamino)phenyl)ethan-1-one HPLC retention time (min.): 4.16; Mass (ESI, Pos. 20V): m/z 495 (M+H)$^+$.

EXAMPLE 84(13)

(Z)-2-(7-methoxy-3,3-dimethyl-3,4-dihydro-(2H)-isoquinolin-1-ylidene)-1-(3-(2-trifluoromethylbenzoylamino)phenyl)ethan-1-one HPLC retention time (min.): 4.12; Mass (ESI, Pos. 20V): m/z 495 (M+H)$^+$.

EXAMPLE 84(14)

(Z)-2-(7-methoxy-3,3-dimethyl-3,4-dihydro-(2H)-isoquinolin-1-ylidene)-1-(3-(3,5-ditrifluoromethylbenzoylamino)phenyl)ethan-1-one HPLC retention time (min.): 4.46; Mass (ESI, Pos. 20V): m/z 563 (M+H)$^+$.

EXAMPLE 84(15)

(Z)-2-(7-methoxy-3,3-dimethyl-3,4-dihydro-(2H)-isoquinolin-1-ylidene)-1-(3-(4-hexylbenzoylamino)phenyl)ethan-1-one HPLC retention time (min.): 4.68; Mass (ESI, Pos. 20V): m/z 511 (M+H)$^+$.

EXAMPLE 84(16)

(Z)-2-(7-methoxy-3,3-dimethyl-3,4-dihydro-(2H)-isoquinolin-1-ylidene)-1-(3-(2-chloro-5-nitrobenzoylamino)phenyl)ethan-1-one HPLC retention time (min.): 4.13; Mass (ESI, Pos. 20V): m/z 506 (M+H)$^+$.

EXAMPLE 84(17)

(Z)-2-(7-methoxy-3,3-dimethyl-3,4-dihydro-(2H)-isoquinolin-1-ylidene)-1-(3-(2,4-dichlorobenzoylamino)phenyl)ethan-1-one HPLC retention time (min.): 4.23; Mass (ESI, Pos. 20V): m/z 495 (M+H)$^+$.

EXAMPLE 84(18)

(Z)-2-(7-methoxy-3,3-dimethyl-3,4-dihydro-(2H)-isoquinolin-1-ylidene)-1-(3-(4-butylbenzoylamino)phenyl)ethan-1-one HPLC retention time (min.): 4.48; Mass (ESI, Pos. 20V): m/z 483 (M+H)$^+$.

EXAMPLE 84(19)

(Z)-2-(7-methoxy-3,3-dimethyl-3,4-dihydro-(2H)-isoquinolin-1-ylidene)-1-(3-(2,4,6-trichlorobenzoylamino)phenyl)ethan-1-one HPLC retention time (min.): 4.30; Mass (ESI, Pos. 20V): m/z 529 (M+H)$^+$, 531 (M+2H)$^+$.

EXAMPLE 84(20)

(Z)-2-(7-methoxy-3,3-dimethyl-3,4-dihydro-(2H)-isoquinolin-1-ylidene)-1-(3-((3-chlorobenzothiophen-2-ylcarbonyl)amino)phenyl)ethan-1-one HPLC retention time (min.): 4.51; Mass (ESI, Pos. 20V): m/z 517 (M+H)$^+$.

EXAMPLE 84(21)

(Z)-2-(7-methoxy-3,3-dimethyl-3,4-dihydro-(2H)-isoquinolin-1-ylidene)-1-(3-(2-chloro-4-nitrobenzoylamino)phenyl)ethan-1-one HPLC retention time (min.): 4.16; Mass (ESI, Pos. 20V): m/z 506 (M+H)$^+$.

EXAMPLE 84(22)

(Z)-2-(7-methoxy-3,3-dimethyl-3,4-dihydro-(2H)-isoquinolin-1-ylidene)-1-(3-(3,5-dichlorobenzoylamino)phenyl)ethan-1-one HPLC retention time (min.): 4.45; Mass (ESI, Pos. 20V): m/z 495 (M+H)$^+$.

EXAMPLE 84(23)

(Z)-2-(7-methoxy-3,3-dimethyl-3,4-dihydro-(2H)-isoquinolin-1-ylidene)-1-(3-(3,4-dichlorobenzoylamino)phenyl)ethan-1-one HPLC retention time (min.): 4.37; Mass (ESI, Pos. 20V): m/z 495 (M+H)$^+$.

EXAMPLE 84(24)

(Z)-2-(7-methoxy-3,3-dimethyl-3,4-dihydro-(2H)-isoquinolin-1-ylidene)-1-(3-(4-hexyloxybenzoylamino)phenyl)ethan-1-one HPLC retention time (min.): 4.60; Mass (ESI, Pos. 20V): m/z 527 (M+H)$^+$.

EXAMPLE 84(25)

(Z)-2-(7-methoxy-3,3-dimethyl-3,4-dihydro-(2H)-isoquinolin-1-ylidene)-1-(3-(3,4-dimethoxybenzoylamino)phenyl)ethan-1-one HPLC retention time (min.): 3.98; Mass (ESI, Pos. 20V): m/z 487 (M+H)$^+$.

EXAMPLE 84(26)

(Z)-2-(7-methoxy-3,3-dimethyl-3,4-dihydro-(2H)-isoquinolin-1-ylidene)-1-(3-(4-butoxybenzoylamino)phenyl)ethan-1-one HPLC retention time (min.): 4.39; Mass (ESI, Pos. 20V): m/z 499 (M+H)$^+$.

EXAMPLE 84(27)

(Z)-2-(7-methoxy-3,3-dimethyl-3,4-dihydro-(2H)-isoquinolin-1-ylidene)-1-(3-(2,3-difluorobenzoylamino)phenyl)ethan-1-one HPLC retention time (min.): 4.15; Mass (ESI, Pos. 20V): m/z 463 (M+H)$^+$.

EXAMPLE 84(28)

(Z)-2-(7-methoxy-3,3-dimethyl-3,4-dihydro-(2H)-isoquinolin-1-ylidene)-1-(3-(4-trifluoromethoxybenzoylamino)phenyl)ethan-1-one HPLC retention time (min.): 4.29; Mass (ESI, Pos. 20V): m/z 511 (M+H)$^+$.

EXAMPLE 84(29)

(Z)-2-(7-methoxy-3,3-dimethyl-3,4-dihydro-(2H)-isoquinolin-1-ylidene)-1-(3-(3,5-dimethoxybenzoylamino)phenyl)ethan-1-one HPLC retention time (min.): 4.16; Mass (ESI, Pos. 20V): m/z 487 (M+H)$^+$.

EXAMPLE 84(30)

(Z)-2-(7-methoxy-3,3-dimethyl-3,4-dihydro-(2H)-isoquinolin-1-ylidene)-1-(3-((5-methyl-3-(2-chloro-6-fluorophenyl)isoxazol-4-ylcarbonyl)amino)phenyl)ethan-1-one HPLC retention time (min.): 4.19; Mass (ESI, Pos. 20V): m/z 560 (M+H)$^+$.

EXAMPLE 84(31)

(Z)-2-(7-methoxy-3,3-dimethyl-3,4-dihydro-(2H)-isoquinolin-1-ylidene)-1-(3-((5-methyl-3-(2-chlorophenyl)isoxazol-4-ylcarbonyl)amino)phenyl)ethan-1-one HPLC retention time (min.): 4.20; Mass (ESI, Pos. 20V): m/z 542 (M+H)$^+$.

EXAMPLE 84(32)

(Z)-2-(7-methoxy-3,3-dimethyl-3,4-dihydro-(2H)-isoquinolin-1-ylidene)-1-(3-((5-methyl-3-(2,6-dichlorophenyl)isoxazol-4-ylcarbonyl)amino)phenyl)ethan-1-one HPLC retention time (min.): 4.27; Mass (ESI, Pos. 20V): m/z 576 (M+H)$^+$.

EXAMPLE 84(33)

(Z)-2-(7-methoxy-3,3-dimethyl-3,4-dihydro-(2H)-isoquinolin-1-ylidene)-1-(3-(3-trifluoromethoxybenzoylamino)phenyl)ethan-1-one HPLC retention time (min.): 4.31; Mass (ESI, Pos. 20V): m/z 511 (M+H)$^+$.

EXAMPLE 84(34)

(Z)-2-(7-methoxy-3,3-dimethyl-3,4-dihydro-(2H)-isoquinolin-1-ylidene)-1-(3-(5-fluoro-2-trifluoromethylbenzoylamino)phenyl)ethan-1-one HPLC retention time (min.): 4.16; Mass (ESI, Pos. 20V): m/z 513 (M+H)$^+$.

EXAMPLE 84(35)

(Z)-2-(7-methoxy-3,3-dimethyl-3,4-dihydro-(2H)-isoquinolin-1-ylidene)-1-(3-(4-hexyloxybenzoylamino)phenyl)ethan-1-one HPLC retention time (min.): 4.49; Mass (ESI, Pos. 20V): m/z 513 (M+H)$^+$.

EXAMPLE 84(36)

(Z)-2-(7-methoxy-3,3-dimethyl-3,4-dihydro-(2H)-isoquinolin-1-ylidene)-1-(3-(2,5-ditrifluoromethylbenzoylamino)phenyl)ethan-1-one HPLC retention time (min.): 4.28; Mass (ESI, Pos. 20V): m/z 563 (M+H)$^+$.

EXAMPLE 84(37)

(Z)-2-(7-methoxy-3,3-dimethyl-3,4-dihydro-(2H)-isoquinolin-1-ylidene)-1-(3-(2,4-dichloro-5-fluorobenzoylamino)phenyl)ethan-1-one HPLC retention time (min.): 4.28; Mass (ESI, Pos. 20V): m/z 513 (M+H)$^+$.

EXAMPLE 84(38)

(Z)-2-(7-methoxy-3,3-dimethyl-3,4-dihydro-(2H)-isoquinolin-1-ylidene)-1-(3-(4-pentylbenzoylamino)phenyl)ethan-1-one HPLC retention time (min.): 4.57; Mass (ESI, Pos. 20V): m/z 497 (M+H)$^+$.

EXAMPLE 84(39)

(Z)-2-(7-methoxy-3,3-dimethyl-3,4-dihydro-(2H)-isoquinolin-1-ylidene)-1-(3-(4-fluorobenzoylamino)phenyl)ethan-1-one HPLC retention time (min.): 4.11; Mass (ESI, Pos. 20V): m/z 445 (M+H)$^+$.

EXAMPLE 84(40)

(Z)-2-(7-methoxy-3,3-dimethyl-3,4-dihydro-(2H)-isoquinolin-1-ylidene)-1-(3-(3-fluorobenzoylamino)phenyl)ethan-1-one HPLC retention time (min.): 4.14; Mass (ESI, Pos. 20V): m/z 445 (M+H)$^+$.

EXAMPLE 84(41)

(Z)-2-(7-methoxy-3,3-dimethyl-3,4-dihydro-(2H)-isoquinolin-1-ylidene)-1-(3-(2-fluorobenzoylamino)phenyl)ethan-1-one HPLC retention time (min.): 4.11; Mass (ESI, Pos. 20V): m/z 445 (M+H)$^+$.

EXAMPLE 84(42)

(Z)-2-(7-methoxy-3,3-dimethyl-3,4-dihydro-(2H)-isoquinolin-1-ylidene)-1-(3-(cyclopentylcarbonylamino)phenyl)ethan-1-one HPLC retention time (min.): 4.09; Mass (ESI, Pos. 20V): m/z 419 (M+H)$^+$.

EXAMPLE 84(43)

(Z)-2-(7-methoxy-3,3-dimethyl-3,4-dihydro-(2H)-isoquinolin-1-ylidene)-1-(3-(2,4-difluorobenzoylamino)phenyl)ethan-1-one HPLC retention time (min.): 4.14; Mass (ESI, Pos. 20V): m/z 463 (M+H)$^+$.

EXAMPLE 84(44)

(Z)-2-(7-methoxy-3,3-dimethyl-3,4-dihydro-(2H)-isoquinolin-1-ylidene)-1-(3-(3-methylbenzoylamino)phenyl)ethan-1-one HPLC retention time (min.): 4.18; Mass (ESI, Pos. 20V): m/z 441 (M+H)$^+$.

EXAMPLE 84(45)

(Z)-2-(7-methoxy-3,3-dimethyl-3,4-dihydro-(2H)-isoquinolin-1-ylidene)-1-(3-(4-ethylbenzoylamino)phenyl)ethan-1-one HPLC retention time (min.): 4.26; Mass (ESI, Pos. 20V): m/z 455 (M+H)$^+$.

EXAMPLE 84(46)

(Z)-2-(7-methoxy-3,3-dimethyl-3,4-dihydro-(2H)-isoquinolin-1-ylidene)-1-(3-(4-propylbenzoylamino)phenyl)ethan-1-one HPLC retention time (min.): 4.36; Mass (ESI, Pos. 20V): m/z 469 (M+H)$^+$.

EXAMPLE 84(47)

(Z)-2-(7-methoxy-3,3-dimethyl-3,4-dihydro-(2H)-isoquinolin-1-ylidene)-1-(3-(2,6-difluorobenzoylamino)phenyl)ethan-1-one HPLC retention time (min.): 4.06; Mass (ESI, Pos. 20V): m/z 463 (M+H)$^+$.

EXAMPLE 84(48)

(Z)-2-(7-methoxy-3,3-dimethyl-3,4-dihydro-(2H)-isoquinolin-1-ylidene)-1-(3-(3-nitrobenzoylamino)phenyl)ethan-1-one HPLC retention time (min.): 4.14; Mass (ESI, Pos. 20V): m/z 472 (M+H)$^+$.

EXAMPLE 84(49)

(Z)-2-(7-methoxy-3,3-dimethyl-3,4-dihydro-(2H)-isoquinolin-1-ylidene)-1-(3-(3-methoxybenzoylamino)phenyl)ethan-1-one HPLC retention time (min.): 4.10; Mass (ESI, Pos. 20V): m/z 457 (M+H)$^+$.

EXAMPLE 84(50)

(Z)-2-(7-methoxy-3,3-dimethyl-3,4-dihydro-(2H)-isoquinolin-1-ylidene)-1-(3-((pyridin-3-ylcarbonyl)amino)phenyl)ethan-1-one HPLC retention time (min.): 3.47; Mass (ESI, Pos. 20V): m/z 428 (M+H)$^+$.

EXAMPLE 84(51)

(Z)-2-(7-methoxy-3,3-dimethyl-3,4-dihydro-(2H)-isoquinolin-1-ylidene)-1-(3-((pyridin-4-ylcarbonyl)amino)phenyl)ethan-1-one HPLC retention time (min.): 3.46; Mass (ESI, Pos. 20V): m/z 428 (M+H)$^+$.

EXAMPLE 84(52)

(Z)-2-(7-methoxy-3,3-dimethyl-3,4-dihydro-(2H)-isoquinolin-1-ylidene)-1-(3-((3-phenylpropanoyl)amino)phenyl)ethan-1-one HPLC retention time (min.): 4.14; Mass (ESI, Pos. 20V): m/z 455 (M+H)$^+$.

EXAMPLE 84(53)

(Z)-2-(7-methoxy-3,3-dimethyl-3,4-dihydro-(2H)-isoquinolin-1-ylidene)-1-(3-((2-phenoxyacetyl)amino)phenyl)ethan-1-one HPLC retention time (min.): 4.13; Mass (ESI, Pos. 20V): m/z 457 (M+H)$^+$.

EXAMPLE 84(54)

(Z)-2-(7-methoxy-3,3-dimethyl-3,4-dihydro-(2H)-isoquinolin-1-ylidene)-1-(3-((2-phenylthiopyridin-3-ylcarbonyl)amino)phenyl)ethan-1-one HPLC retention time (min.): 4.19; Mass (ESI, Pos. 20V): m/z 536 (M+H)$^+$.

EXAMPLE 84(55)

(Z)-2-(7-methoxy-3,3-dimethyl-3,4-dihydro-(2H)-isoquinolin-1-ylidene)-1-(3-((2-(4-methylphenyl)thiopyridin-3-ylcarbonyl)amino)phenyl)ethan-1-one HPLC retention time (min.): 4.26; Mass (ESI, Pos. 20V): m/z 550 (M+H)$^+$.

EXAMPLE 84(56)

(Z)-2-(7-methoxy-3,3-dimethyl-3,4-dihydro-(2H)-isoquinolin-1-ylidene)-1-(3-(2-chlorobenzoylamino)phenyl)ethan-1-one HPLC retention time (min.): 4.10; Mass (ESI, Pos. 20V): m/z 461 (M+H)$^+$.

EXAMPLE 84(57)

(Z)-2-(7-methoxy-3,3-dimethyl-3,4-dihydro-(2H)-isoquinolin-1-ylidene)-1-(3-(2-methoxybenzoylamino)phenyl)ethan-1-one HPLC retention time (min.): 4.20; Mass (ESI, Pos. 20V): m/z 457 (M+H)$^+$.

EXAMPLE 84(58)

(Z)-2-(7-methoxy-3,3-dimethyl-3,4-dihydro-(2H)-isoquinolin-1-ylidene)-1-(3-((2-(thiophen-2-yl)acetyl)amino)phenyl)ethan-1-one HPLC retention time (min.): 4.04; Mass (ESI, Pos. 20V): m/z 447 (M+H)$^+$.

EXAMPLE 84(59)

(Z)-2-(7-methoxy-3,3-dimethyl-3,4-dihydro-(2H)-isoquinolin-1-ylidene)-1-(3-((5-chloropentanoyl)amino)phenyl)ethan-1-one HPLC retention time (min.): 4.05; Mass (ESI, Pos. 20V): m/z 441 (M+H)$^+$.

EXAMPLE 84(60)

(Z)-2-(7-methoxy-3,3-dimethyl-3,4-dihydro-(2H)-isoquinolin-1-ylidene)-1-(3-(4-methylbenzoylamino)phenyl)ethan-1-one HPLC retention time (min.): 4.18; Mass (ESI, Pos. 20V): m/z 441 (M+H)$^+$.

EXAMPLE 84(61)

(Z)-2-(7-methoxy-3,3-dimethyl-3,4-dihydro-(2H)-isoquinolin-1-ylidene)-1-(3-(isobutyrylamino)phenyl)ethan-1-one HPLC retention time (min.): 3.95; Mass (ESI, Pos. 20V): m/z 393 (M+H)$^+$.

EXAMPLE 84(62)

(Z)-2-(7-methoxy-3,3-dimethyl-3,4-dihydro-(2H)-isoquinolin-1-ylidene)-1-(3-((3-cyclopentylpropanoyl)amino)phenyl)ethan-1-one HPLC retention time (min.): 4.33; Mass (ESI, Pos. 20V): m/z 447 (M+H)$^+$.

EXAMPLE 84(63)

(Z)-2-(7-methoxy-3,3-dimethyl-3,4-dihydro-(2H)-isoquinolin-1-ylidene)-1-(3-(octanoylamino)phenyl)ethan-1-one HPLC retention time (min.): 4.42; Mass (ESI, Pos. 20V): m/z 449 (M+H)$^+$.

EXAMPLE 84(64)

(Z)-2-(7-methoxy-3,3-dimethyl-3,4-dihydro-(2H)-isoquinolin-1-ylidene)-1-(3-(nonanoylamino)phenyl)ethan-1-one HPLC retention time (min.): 4.52; Mass (ESI, Pos. 20V): m/z 463 (M+H)$^+$.

EXAMPLE 84(65)

(Z)-2-(7-methoxy-3,3-dimethyl-3,4-dihydro-(2H)-isoquinolin-1-ylidene)-1-(3-(3-chlorobenzoylamino)phenyl)ethan-1-one HPLC retention time (min.): 4.25; Mass (ESI, Pos. 20V): m/z 461 (M+H)$^+$.

EXAMPLE 84(66)

(Z)-2-(7-methoxy-3,3-dimethyl-3,4-dihydro-(2H)-isoquinolin-1-ylidene)-1-(3-(2-methylbenzoylamino)phenyl)ethan-1-one HPLC retention time (min.): 4.13; Mass (ESI, Pos. 20V): m/z 441 (M+H)$^+$.

EXAMPLE 84(67)

(Z)-2-(7-methoxy-3,3-dimethyl-3,4-dihydro-(2H)-isoquinolin-1-ylidene)-1-(3-((3-chloropropanoyl)amino)phenyl)ethan-1-one HPLC retention time (min.): 3.93; Mass (ESI, Pos. 20V): m/z 413 (M+H)$^+$.

EXAMPLE 84(68)

(Z)-2-(7-methoxy-3,3-dimethyl-3,4-dihydro-(2H)-isoquinolin-1-ylidene)-1-(3-((4-chlorobutanoyl)amino)phenyl)ethan-1-one HPLC retention time (min.): 4.01; Mass (ESI, Pos. 20V): m/z 427 (M+H)$^+$.

EXAMPLE 84(69)

(Z)-2-(7-methoxy-3,3-dimethyl-3,4-dihydro-(2H)-isoquinolin-1-ylidene)-1-(3-(2-butenoylamino)phenyl)ethan-1-one HPLC retention time (min.): 3.91; Mass (ESI, Pos. 20V): m/z 391 (M+H)$^+$.

EXAMPLE 84(70)

(Z)-2-(7-methoxy-3,3-dimethyl-3,4-dihydro-(2H)-isoquinolin-1-ylidene)-1-(3-((3-methyl-2-butenoyl)amino)phenyl)ethan-1-one HPLC retention time (min.): 4.06; Mass (ESI, Pos. 20V): m/z 405 (M+H)$^+$.

EXAMPLE 84(71)

(Z)-2-(7-methoxy-3,3-dimethyl-3,4-dihydro-(2H)-isoquinolin-1-ylidene)-1-(3-((2-ethylhexanoyl)amino)phenyl)ethan-1-one HPLC retention time (min.): 4.33; Mass (ESI, Pos. 20V): m/z 449 (M+H)$^+$.

EXAMPLE 84(72)

(Z)-2-(7-methoxy-3,3-dimethyl-3,4-dihydro-(2H)-isoquinolin-1-ylidene)-1-(3-((3,3-dimethylbutanoyl)amino)phenyl)ethan-1-one HPLC retention time (min.): 4.16; Mass (ESI, Pos. 20V): m/z 421 (M+H)$^+$.

EXAMPLE 84(73)

(Z)-2-(7-methoxy-3,3-dimethyl-3,4-dihydro-(2H)-isoquinolin-1-ylidene)-1-(3-(4-nitrobenzoylamino)phenyl)ethan-1-one HPLC retention time (min.): 4.13; Mass (ESI, Pos. 20V): m/z 472 (M+H)$^+$.

EXAMPLE 84(74)

(Z)-2-(7-methoxy-3,3-dimethyl-3,4-dihydro-(2H)-isoquinolin-1-ylidene)-1-(3-((thiophen-2-ylcarbonyl)amino)phenyl)ethan-1-one HPLC retention time (min.): 4.06; Mass (ESI, Pos. 20V): m/z 433 (M+H)$^+$.

EXAMPLE 84(75)

(Z)-2-(7-methoxy-3,3-dimethyl-3,4-dihydro-(2H)-isoquinolin-1-ylidene)-1-(3-((2-(1,4-benzodioxan-2-yl)thiazol-4-ylcarbonyl)amino)phenyl)ethan-1-one HPLC retention time (min.): 4.37; Mass (ESI, Pos. 20V): m/z 568 (M+H)$^+$.

EXAMPLE 84(76)

(Z)-2-(7-methoxy-3,3-dimethyl-3,4-dihydro-(2H)-isoquinolin-1-ylidene)-1-(3-(4-chlorobenzoylamino)phenyl)ethan-1-one HPLC retention time (min.): 4.23; Mass (ESI, Pos. 20V): m/z 461 (M+H)$^+$.

EXAMPLE 84(77)

(Z)-2-(7-methoxy-3,3-dimethyl-3,4-dihydro-(2H)-isoquinolin-1-ylidene)-1-(3-((1-methylcyclohexylcarbonyl)amino)phenyl)ethan-1-one HPLC retention time (min.): 4.30; Mass (ESI, Pos. 20V): m/z 447 (M+H)$^+$.

EXAMPLE 84(78)

(Z)-2-(7-methoxy-3,3-dimethyl-3,4-dihydro-(2H)-isoquinolin-1-ylidene)-1-(3-((2,6,6-trimethyl-1-cyclohexen-1-ylcarbonyl)amino)phenyl)ethan-1-one HPLC retention time (min.): 4.35; Mass (ESI, Pos. 20V): m/z 473 (M+H)$^+$.

EXAMPLE 84(79)

(Z)-2-(7-methoxy-3,3-dimethyl-3,4-dihydro-(2H)-isoquinolin-1-ylidene)-1-(3-(2-trifluoromethoxybenzoylamino)phenyl)ethan-1-one HPLC retention time (min.): 4.20; Mass (ESI, Pos. 20V): m/z 511 (M+H)$^+$.

EXAMPLE 84(80)

(Z)-2-(7-methoxy-3,3-dimethyl-3,4-dihydro-(2H)-isoquinolin-1-ylidene)-1-(3-(2,4-trifluoromethylbenzoylamino)phenyl)ethan-1-one HPLC retention time (min.): 4.29; Mass (ESI, Pos. 20V): m/z 563 (M+H)$^+$.

EXAMPLE 84(81)

(Z)-2-(7-methoxy-3,3-dimethyl-3,4-dihydro-(2H)-isoquinolin-1-ylidene)-1-(3-5-fluoro-2-methylbenzoylamino)phenyl)ethan-1-one HPLC retention time (min.): 4.17; Mass (ESI, Pos. 20V): m/z 459 (M+H)$^+$.

EXAMPLE 84(82)

(Z)-2-(7-methoxy-3,3-dimethyl-3,4-dihydro-(2H)-isoquinolin-1-ylidene)-1-(3-((2-ethoxy-2-oxoacetyl)amino)phenyl)ethan-1-one HPLC retention time (min.): 3.98; Mass (ESI, Pos. 20V): m/z 423 (M+H)$^+$.

EXAMPLE 84(83)

(Z)-2-(7-methoxy-3,3-dimethyl-3,4-dihydro-(2H)-isoquinolin-1-ylidene)-1-(3-((5-methyl-3-phenyl-isoxazol-4-ylcarbonyl)amino)phenyl)ethan-1-one HPLC retention time (min.): 4.18; Mass (ESI, Pos. 20V): m/z 508 (M+H)$^+$.

EXAMPLE 84(84)

(Z)-2-(7-methoxy-3,3-dimethyl-3,4-dihydro-(2H)-isoquinolin-1-ylidene)-1-(3-((3-chlorothiophen-2-ylcarbonyl)amino)phenyl)ethan-1-one HPLC retention time (min.): 4.26; Mass (ESI, Pos. 20V): m/z 467 (M+H)$^+$.

EXAMPLE 84(85)

(Z)-2-(7-methoxy-3,3-dimethyl-3,4-dihydro-(2H)-isoquinolin-1-ylidene)-1-(3-((2-(4-chlorophenylthio)pyridin-3-ylcarbonyl)amino)phenyl)ethan-1-one HPLC retention time (min.): 4.34; Mass (ESI, Pos. 20V): m/z 570 (M+H)$^+$.

EXAMPLE 84(86)

(Z)-2-(7-methoxy-3,3-dimethyl-3,4-dihydro-(2H)-isoquinolin-1-ylidene)-1-(3-((5,6-dichloropyridin-3-ylcarbonyl)amino)phenyl)ethan-1-one HPLC retention time (min.): 4.26; Mass (ESI, Pos. 20V): m/z 496 (M+H)$^+$.

EXAMPLE 84(87)

(Z)-2-(7-methoxy-3,3-dimethyl-3,4-dihydro-(2H)-isoquinolin-1-ylidene)-1-(3-((5-methyl-2-phenyl-2H-1,2,3-triazol-4-ylcarbonyl)amino)phenyl)ethan-1-one HPLC retention time (min.): 4.53; Mass (ESI, Pos. 20V): m/z 508 (M+H)$^+$.

EXAMPLE 84(88)

(Z)-2-(7-methoxy-3,3-dimethyl-3,4-dihydro-(2H)-isoquinolin-1-ylidene)-1-(3-(2,6-dimethylbenzoylamino)phenyl)ethan-1-one HPLC retention time (min.): 4.16; Mass (ESI, Pos. 20V): m/z 455 (M+H)$^+$.

EXAMPLE 84(89)

(Z)-2-(7-methoxy-3,3-dimethyl-3,4-dihydro-(2H)-isoquinolin-1-ylidene)-1-(3-((2,5-dichlorothiophen-3-ylcarbonyl)amino)phenyl)ethan-1-one HPLC retention time (min.): 4.37; Mass (ESI, Pos. 20V): m/z 501 (M+H)$^+$.

EXAMPLE 84(90)

(Z)-2-(7-methoxy-3,3-dimethyl-3,4-dihydro-(2H)-isoquinolin-1-ylidene)-1-(3-((2-propylpentanoyl)amino)phenyl)ethan-1-one HPLC retention time (min.): 4.33; Mass (ESI, Pos. 20V): m/z 449 (M+H)$^+$.

EXAMPLE 84(91)

(Z)-2-(7-methoxy-3,3-dimethyl-3,4-dihydro-(2H)-isoquinolin-1-ylidene)-1-(3-((6-chloropyridin-3-ylcarbonyl)amino)phenyl)ethan-1-one HPLC retention time (min.): 4.06; Mass (ESI, Pos. 20V): m/z 462 (M+H)$^+$.

EXAMPLE 84(92)

(Z)-2-(7-methoxy-3,3-dimethyl-3,4-dihydro-(2H)-isoquinolin-1-ylidene)-1-(3-((naphthalen-2-ylcarbonyl)amino)phenyl)ethan-1-one HPLC retention time (min.): 4.29; Mass (ESI, Pos. 20V): m/z 477 (M+H)$^+$.

EXAMPLE 84(93)

(Z)-2-(7-methoxy-3,3-dimethyl-3,4-dihydro-(2H)-isoquinolin-1-ylidene)-1-(3-((2-benzyloxyacetyl)amino)phenyl)ethan-1-one HPLC retention time (min.): 4.15; Mass (ESI, Pos. 20V): m/z 471 (M+H)$^+$.

EXAMPLE 84(94)

(Z)-2-(7-methoxy-3,3-dimethyl-3,4-dihydro-(2H)-isoquinolin-1-ylidene)-1-(3-(cyclobutylcarbonylamino)phenyl)ethan-1-one HPLC retention time (min.): 4.01; Mass (ESI, Pos. 20V): m/z 405 (M+H)$^+$.

EXAMPLE 84(95)

(Z)-2-(7-methoxy-3,3-dimethyl-3,4-dihydro-(2H)-isoquinolin-1-ylidene)-1-(3-(2,4,5-trifluorobenzoylamino)phenyl)ethan-1-one HPLC retention time (min.): 4.20; Mass (ESI, Pos. 20V): m/z 481 (M+H)$^+$.

EXAMPLE 84(96)

(Z)-2-(7-methoxy-3,3-dimethyl-3,4-dihydro-(2H)-isoquinolin-1-ylidene)-1-(3-(2,3,4-trifluorobenzoylamino)phenyl)ethan-1-one HPLC retention time (min.): 4.19; Mass (ESI, Pos. 20V): m/z 481 (M+H)$^+$.

EXAMPLE 84(97)

(Z)-2-(7-methoxy-3,3-dimethyl-3,4-dihydro-(2H)-isoquinolin-1-ylidene)-1-(3-((benzothiophen-2-ylcarbonyl)amino)phenyl)ethan-1-one HPLC retention time (min.): 4.31; Mass (ESI, Pos. 20V): m/z 483 (M+H)$^+$.

EXAMPLE 84(98)

(Z)-2-(7-methoxy-3,3-dimethyl-3,4-dihydro-(2H)-isoquinolin-1-ylidene)-1-(3-((3-chloro-2,2,3,3-tetrafluoropropanoyl)amino)phenyl)ethan-1-one HPLC retention time (min.): 4.23; Mass (ESI, Pos. 20V): m/z 485 (M+H)$^+$.

EXAMPLE 84(99)

(Z)-2-(7-methoxy-3,3-dimethyl-3,4-dihydro-(2H)-isoquinolin-1-ylidene)-1-(3-((2,2,3,3-tetrafluoropropanoyl)amino)phenyl)ethan-1-one HPLC retention time (min.): 4.09; Mass (ESI, Pos. 20V): m/z 451 (M+H)$^+$.

EXAMPLE 84(100)

(Z)-2-(7-methoxy-3,3-dimethyl-3,4-dihydro-(2H)-isoquinolin-1-ylidene)-1-(3-((2-(4-methoxyphenyl)acetyl)amino)phenyl)ethan-1-one HPLC retention time (min.): 4.04; Mass (ESI, Pos. 20V): m/z 471 (M+H)$^+$.

EXAMPLE 84(101)

(Z)-2-(7-methoxy-3,3-dimethyl-3,4-dihydro-(2H)-isoquinolin-1-ylidene)-1-(3-((2,2,2-trichloroacetyl)amino)phenyl)ethan-1-one HPLC retention time (min.): 4.23; Mass (ESI, Pos. 20V): m/z 467 (M+H)$^+$, 469 (M+2+H)$^+$.

EXAMPLE 84(102)

(Z)-2-(7-methoxy-3,3-dimethyl-3,4-dihydro-(2H)-isoquinolin-1-ylidene)-1-(3-((2-chloropropanoyl)amino)phenyl)ethan-1-one HPLC retention time (min.): 4.00; Mass (ESI, Pos. 20V): m/z 413 (M+H)$^+$.

EXAMPLE 84(103)

(Z)-2-(7-methoxy-3,3-dimethyl-3,4-dihydro-(2H)-isoquinolin-1-ylidene)-1-(3-(2-nitrobenzoylamino)phenyl)ethan-1-one HPLC retention time (min.): 3.99; Mass (ESI, Pos. 20V): m/z 472 (M+H)$^+$.

EXAMPLE 84(104)

(Z)-2-(7-methoxy-3,3-dimethyl-3,4-dihydro-(2H)-isoquinolin-1-ylidene)-1-(3-(4-cyanobenzoylamino)phenyl)ethan-1-one HPLC retention time (min.): 4.06; Mass (ESI, Pos. 20V): m/z 452 (M+H)$^+$.

EXAMPLE 84(105)

(Z)-2-(7-methoxy-3,3-dimethyl-3,4-dihydro-(2H)-isoquinolin-1-ylidene)-1-(3-((2-(4-chlorophenoxy)pyridin-3-ylcarbonyl)amino)phenyl)ethan-1-one HPLC retention time (min.): 4.41; Mass (ESI, Pos. 20V): m/z 554 (M+H)$^+$.

EXAMPLE 84(106)

(Z)-2-(7-methoxy-3,3-dimethyl-3,4-dihydro-(2H)-isoquinolin-1-ylidene)-1-(3-((2-(4-methylphenoxy)pyridin-3-ylcarbonyl)amino)phenyl)ethan-1-one HPLC retention time (min.): 4.40; Mass (ESI, Pos. 20V): m/z 534 (M+H)$^+$.

EXAMPLE 84(107)

(Z)-2-(7-methoxy-3,3-dimethyl-3,4-dihydro-(2H)-isoquinolin-1-ylidene)-1-(3-((1-(4-chlorophenyl)-5-propylisoimidazol-4-ylcarbonyl)amino)phenyl)ethan-1-one HPLC retention time (min.): 4.46; Mass (ESI, Pos. 20V): m/z 569 (M+H)$^+$.

EXAMPLE 84(108)

(Z)-2-(7-methoxy-3,3-dimethyl-3,4-dihydro-(2H)-isoquinolin-1-ylidene)-1-(3-((2-propylthiopyridin-3-ylcarbonyl)amino)phenyl)ethan-1-one HPLC retention time (min.): 4.25; Mass (ESI, Pos. 20V): m/z 502 (M+H)$^+$.

EXAMPLE 84(109)

(Z)-2-(7-methoxy-3,3-dimethyl-3,4-dihydro-(2H)-isoquinolin-1-ylidene)-1-(3-(4-chloro-3-nitrobenzoylamino)phenyl)ethan-1-one HPLC retention time (min.): 4.26; Mass (ESI, Pos. 20V): m/z 506 (M+H)$^+$.

EXAMPLE 84(110)

(Z)-2-(7-methoxy-3,3-dimethyl-3,4-dihydro-(2H)-isoquinolin-1-ylidene)-1-(3-(3-nitro-4-methylbenzoylamino)phenyl)ethan-1-one HPLC retention time (min.): 4.21; Mass (ESI, Pos. 20V): m/z 486 (M+H)$^+$.

EXAMPLE 84(111)

(Z)-2-(7-methoxy-3,3-dimethyl-3,4-dihydra-(2H)-isoquinolin-1-ylidene)-1-(3-((2-(4-chlorophenoxy)acetyl)amino)phenyl)ethan-1-one HPLC retention time (min.): 4.26; Mass (ESI, Pos. 20V): m/z 491 (M+H)$^+$.

EXAMPLE 84(112)

(Z)-2-(7-methoxy-3,3-dimethyl-3,4-dihydro-(2H)-isoquinolin-1-ylidene)-1-(3-(4-ethoxybenzoylamino)phenyl)ethan-1-one HPLC retention time (min.): 4.18; Mass (ESI, Pos. 20V): m/z 471 (M+H)$^+$.

EXAMPLE 84(113)

(Z)-2-(7-methoxy-3,3-dimethyl-3,4-dihydro-(2H)-isoquinolin-1-ylidene)-1-(3-(2-ethoxybenzoylamino)phenyl)ethan-1-one HPLC retention time (min.): 4.33; Mass (ESI, Pos. 20V): m/z 471 (M+H)$^+$.

EXAMPLE 84(114)

(Z)-2-(7-methoxy-3,3-dimethyl-3,4-dihydro-(2H)-isoquinolin-1-ylidene)-1-(3-((2-methylbutanoyl)amino)phenyl)ethan-1-one HPLC retention time (min.): 4.03; Mass (ESI, Pos. 20V): m/z 407 (M+H)$^+$.

EXAMPLE 84(115)

(Z)-2-(7-methoxy-3,3-dimethyl-3,4-dihydro-(2H)-isoquinolin-1-ylidene)-1-(3-((4-methylpentanoyl)amino)phenyl)ethan-1-one HPLC retention time (min.): 4.18; Mass (ESI, Pos. 20V): m/z 421 (M+H)$^+$.

EXAMPLE 84(116)

(Z)-2-(7-methoxy-3,3-dimethyl-3,4-dihydro-(2H)-isoquinolin-1-ylidene)-1-(3-((2-methoxyacetyl)amino)phenyl)ethan-1-one HPLC retention time (min.): 3.81; Mass (ESI, Pos. 20V): m/z 395 (M+H)$^+$.

EXAMPLE 84(117)

(Z)-2-(7-methoxy-3,3-dimethyl-3,4-dihydro-(2H)-isoquinolin-1-ylidene)-1-(3-((3-methylthiopropanoyl)amino)phenyl)ethan-1-one HPLC retention time (min.): 3.94; Mass (ESI, Pos. 20V): m/z 425 (M+H)$^+$.

EXAMPLE 84(118)

(Z)-2-(7-methoxy-3,3-dimethyl-3,4-dihydro-(2H)-isoquinolin-1-ylidene)-1-(3-((2-((1R,2S,5R)-2-isopropyl-5-methylcyclohexyloxy)acetyl)amino)phenyl)ethan-1-one HPLC retention time (min.): 4.78; Mass (ESI, Pos. 20V): m/z 519 (M+H)$^+$.

EXAMPLE 84(119)

(Z)-2-(7-methoxy-3,3-dimethyl-3,4-dihydro-(2H)-isoquinolin-1-ylidene)-1-(3-((2-cyclopentylacetyl)amino)phenyl)ethan-1-one HPLC retention time (min.): 4.19; Mass (ESI, Pos. 20V): m/z 433 (M+H)$^+$.

EXAMPLE 84(120)

(Z)-2-(7-methoxy-3,3-dimethyl-3,4-dihydro-(2H)-isoquinolin-1-ylidene)-1-(3-((2-methylthiopyridin-3-ylcarbonyl)amino)phenyl)ethan-1-one HPLC retention time (min.): 4.03; Mass (ESI, Pos. 20V): m/z 474 (M+H)$^+$.

EXAMPLE 84(121)

(Z)-2-(7-methoxy-3,3-dimethyl-3,4-dihydro-(2H)-isoquinolin-1-ylidene)-1-(3-((2-phenoxybutanoyl)amino)phenyl)ethan-1-one HPLC retention time (min.): 4.27; Mass (ESI, Pos. 20V): m/z 485 (M+H)$^+$.

EXAMPLE 84(122)

(Z)-2-(7-methoxy-3,3-dimethyl-3,4-dihydro-(2H)-isoquinolin-1-ylidene)-1-(3-((2-(4-chlorophenyl)acetyl)amino)phenyl)ethan-1-one HPLC retention time (min.): 4.21; Mass (ESI, Pos. 20V): m/z 475 (M+H)$^+$.

EXAMPLE 84(123)

(Z)-2-(7-methoxy-3,3-dimethyl-3,4-dihydro-(2H)-isoquinolin-1-ylidene)-1-(3-((2-methylpentanoyl)amino)phenyl)ethan-1-one HPLC retention time (min.): 4.16; Mass (ESI, Pos. 20V): m/z 421 (M+H)$^+$.

EXAMPLE 84(124)

(Z)-2-(7-methoxy-3,3-dimethyl-3,4-dihydro-(2H)-isoquinolin-1-ylidene)-1-(3-((4-nitro-4-methylhexanoyl)amino)phenyl)ethan-1-one HPLC retention time (min.): 4.13; Mass (ESI, Pos. 20V): m/z 480 (M+H)$^+$.

EXAMPLE 84(125)

(Z)-2-(7-methoxy-3,3-dimethyl-3,4-dihydro-(2H)-isoquinolin-1-ylidene)-1-(3-(pentanoylamino)phenyl)ethan-1-one HPLC retention time (min.): 4.07; Mass (ESI, Pos. 20V): m/z 407 (M+H)$^+$.

EXAMPLE 84(126)

(Z)-2-(7-methoxy-3,3-dimethyl-3,4-dihydro-(2H)-isoquinolin-1-ylidene)-1-(3-((3-methylbutanoyl)amino)phenyl)ethan-1-one HPLC retention time (min.): 4.05; Mass (ESI, Pos. 20V): m/z 407 (M+H)$^+$.

EXAMPLE 84(127)

(Z)-2-(7-methoxy-3,3-dimethyl-3,4-dihydro-(2H)-isoquinolin-1-ylidene)-1-(3-((2,5-dimethylfuran-3-ylcarbonyl)amino)phenyl)ethan-1-one HPLC retention time (min.): 4.17; Mass (ESI, Pos. 20V): m/z 445 (M+H)$^+$.

EXAMPLE 84(128)

(Z)-2-(7-methoxy-3,3-dimethyl-3,4-dihydro-(2H)-isoquinolin-1-ylidene)-1-(3-(2,3,6-trifluorobenzoylamino)phenyl)ethan-1-one HPLC retention time (min.): 4.13; Mass (ESI, Pos. 20V): m/z 481 (M+H)$^+$.

EXAMPLE 84(129)

(Z)-2-(7-methoxy-3,3-dimethyl-3,4-dihydro-(2H)-isoquinolin-1-ylidene)-1-(3-((2-phenylbutanoyl)amino)phenyl)ethan-1-one HPLC retention time (min.): 4.26; Mass (ESI, Pos. 20V): m/z 469 (M+H)$^+$.

EXAMPLE 84(130)

(Z)-2-(7-methoxy-3,3-dimethyl-3,4-dihydro-(2H)-isoquinolin-1-ylidene)-1-(3-((3-chloro-4-mesylthiophen-2-ylcarbonyl)amino)phenyl)ethan-1-one HPLC retention time (min.): 4.01; Mass (ESI, Pos. 20V): m/z 545 (M+H)$^+$.

EXAMPLE 84(131)

(Z)-2-(7-methoxy-3,3-dimethyl-3,4-dihydro-(2H)-isoquinolin-1-ylidene)-1-(3-((3,5-dimethylthioisoxazol-4-ylcarbonyl)amino)phenyl)ethan-1-one HPLC retention time (min.): 4.32; Mass (ESI, Pos. 20V): m/z 526 (M+H)$^+$.

EXAMPLE 84(132)

(Z)-2-(7-methoxy-3,3-dimethyl-3,4-dihydro-(2H)-isoquinolin-1-ylidene)-1-(3-((2-ethylthiopyridin-3-ylcarbonyl)amino)phenyl)ethan-1-one HPLC retention time (min.): 4.14; Mass (ESI, Pos. 20V): m/z 488 (M+H)$^+$.

EXAMPLE 84(133)

(Z)-2-(7-methoxy-3,3-dimethyl-3,4-dihydro-(2H)-isoquinolin-1-ylidene)-1-(3-((4-isopropylsulfonyl-3-chlorothiophen-2-ylcarbonyl)amino)phenyl)ethan-1-one HPLC retention time (min.): 4.18; Mass (ESI, Pos. 20V): m/z 573 (M+H)$^+$.

EXAMPLE 84(134)

(Z)-2-(7-methoxy-3,3-dimethyl-3,4-dihydro-(2H)-isoquinolin-1-ylidene)-1-(3-((5-(4-chlorophenyl)-2-methylfuran-3-ylcarbonyl)amino)phenyl)ethan-1-one HPLC retention time (min.): 4.64; Mass (ESI, Pos. 20V): m/z 541 (M+H)$^+$.

EXAMPLE 84(135)

(Z)-2-(7-methoxy-3,3-dimethyl-3,4-dihydro-(2H)-isoquinolin-1-ylidene)-1-(3-((2,5-dichloropyridin-3-ylcarbonyl)amino)phenyl)ethan-1-one HPLC retention time (min.): 4.14; Mass (ESI, Pos. 20V): m/z 496 (M+H)$^+$.

EXAMPLE 84(136)

(Z)-2-(7-methoxy-3,3-dimethyl-3,4-dihydro-(2H)-isoquinolin-1-ylidene)-1-(3-((1-benzyl-3-t-butyl-isoimidazol-5-ylcarbonyl)amino)phenyl)ethan-1-one HPLC retention time (min.): 4.57; Mass (ESI, Pos. 20V): m/z 563 (M+H)$^+$.

EXAMPLE 84(137)

(Z)-2-(7-methoxy-3,3-dimethyl-3,4-dihydro-(2H)-isoquinolin-1-ylidene)-1-(3-((3-t-butyl-1-methyl-isoimidazol-5-ylcarbonyl)amino)phenyl)ethan-1-one HPLC retention time (min.): 4.31; Mass (ESI, Pos. 20V): m/z 487 (M+H)$^+$.

EXAMPLE 84(138)

(Z)-2-(7-methoxy-3,3-dimethyl-3,4-dihydro-(2H)-isoquinolin-1-ylidene)-1-(3-((2-chlorobutanoyl)amino)phenyl)ethan-1-one HPLC retention time (min.): 4.10; Mass (ESI, Pos. 20V): m/z 427 (M+H)$^+$.

EXAMPLE 84(139)

(Z)-2-(7-methoxy-3,3-dimethyl-3,4-dihydro-(2H)-isoquinolin-1-ylidene)-1-(3-(4-fluoro-2-trifluoromethylbenzoylamino)phenyl)ethan-1-one HPLC retention time (min.): 4.18; Mass (ESI, Pos. 20V): m/z 513 (M+H)$^+$.

EXAMPLE 84(140)

(Z)-2-(7-methoxy-3,3-dimethyl-3,4-dihydro-(2H)-isoquinolin-1-ylidene)-1-(3-(butanoylamino)phenyl)ethan-1-one HPLC retention time (min.): 3.98; Mass (ESI, Pos. 20V): m/z 393 (M+H)$^+$.

EXAMPLE 84(141)

(Z)-2-(7-methoxy-3,3-dimethyl-3,4-dihydro-(2H)-isoquinolin-1-ylidene)-1-(3-((5,5-dimethyl-3-methylhexanoyl)amino)phenyl)ethan-1-one HPLC retention time (min.): 4.43; Mass (ESI, Pos. 20V): m/z 463 (M+H)$^+$.

EXAMPLE 84(142)

(Z)-2-(7-methoxy-3,3-dimethyl-3,4-dihydro-(2H)-isoquinolin-1-ylidene)-1-(3-(propanoylamino)phenyl)ethan-1-one HPLC retention time (min.): 3.86; Mass (ESI, Pos. 20V): m/z 379 (M+H)$^+$.

EXAMPLE 84(143)

(Z)-2-(7-methoxy-3,3-dimethyl-3,4-dihydro-(2H)-isoquinolin-1-ylidene)-1-(3-((5-methyl-2-trifluoromethylfuran-3-ylcarbonyl)amino)phenyl)ethan-1-one HPLC retention time (min.): 4.23; Mass (ESI, Pos. 20V): m/z 499 (M+H)$^+$.

EXAMPLE 84(144)

(Z)-2-(7-methoxy-3,3-dimethyl-3,4-dihydro-(2H)-isoquinolin-1-ylidene)-1-(3-((5-t-butyl-2-methylfuran-3-ylcarbonyl)amino)phenyl)ethan-1-one HPLC retention time (min.): 4.51; Mass (ESI, Pos. 20V): m/z 487 (M+H)$^+$.

EXAMPLE 84(145)

(Z)-2-(7-methoxy-3,3-dimethyl-3,4-dihydro-(2H)-isoquinolin-1-ylidene)-1-(3-(3,4,5-trifluorobenzoylamino)phenyl)ethan-1-one HPLC retention time (min.): 4.29; Mass (ESI, Pos. 20V): m/z 481 (M+H)$^+$.

EXAMPLE 84(146)

(Z)-2-(7-methoxy-3,3-dimethyl-3,4-dihydro-(2H)-isoquinolin-1-ylidene)-1-(3-((2-ethylbutanoyl)amino)phenyl)ethan-1-one HPLC retention time (min.): 4.13; Mass (ESI, Pos. 20V): m/z 421 (M+H)$^+$.

EXAMPLE 84(147)

(Z)-2-(7-methoxy-3,3-dimethyl-3,4-dihydro-(2H)-isoquinolin-1-ylidene)-1-(3-(2,3,5-trifluorobenzoylamino)phenyl)ethan-1-one HPLC retention time (min.): 4.21; Mass (ESI, Pos. 20V): m/z 481 (M+H)$^+$.

EXAMPLE 84(148)

(Z)-2-(7-methoxy-3,3-dimethyl-3,4-dihydro-(2H)-isoquinolin-1-ylidene)-1-(3-(2,3-dimethylbenzoylamino)phenyl)ethan-1-one HPLC retention time (min.): 4.21; Mass (ESI, Pos. 20V): m/z 455 (M+H)$^+$.

EXAMPLE 84(149)

(Z)-2-(7-methoxy-3,3-dimethyl-3,4-dihydro-(2H)-isoquinolin-1-ylidene)-1-(3-(2-chloro-6-fluorobenzoylamino)phenyl)ethan-1-one HPLC retention time (min.): 4.13; Mass (ESI, Pos. 20V): m/z 479 (M+H)$^+$.

EXAMPLE 84(150)

(Z)-2-(7-methoxy-3,3-dimethyl-3,4-dihydro-(2H)-isoquinolin-1-ylidene)-1-(3-((2-chloro-6-methylpyridin-4-ylcarbonyl)amino)phenyl)ethan-1-one HPLC retention time (min.): 4.19; Mass (ESI, Pos. 20V): m/z 476 (M+H)$^+$.

EXAMPLE 84(151)

(Z)-2-(7-methoxy-3,3-dimethyl-3,4-dihydro-(2H)-isoquinolin-1-ylidene)-1-(3-(3-(4-trifluoromethoxyphenyl)-2-propenoylamino)phenyl)ethan-1-one HPLC retention time (min.): 4.39; Mass (ESI, Pos. 20V): m/z 537 (M+H)$^+$.

EXAMPLE 84(152)

(Z)-2-(7-methoxy-3,3-dimethyl-3,4-dihydro-(2H)-isoquinolin-1-ylidene)-1-(3-(4-methoxycarbonylbenzoylamino)phenyl)ethan-1-one HPLC retention time (min.): 4.14; Mass (ESI, Pos. 20V): m/z 485 (M+H)$^+$.

EXAMPLE 84(153)

(Z)-2-(7-methoxy-3,3-dimethyl-3,4-dihydro-(2H)-isoquinolin-1-ylidene)-1-(3-((4-ethoxycarbonylbutanoyl)amino)phenyl)ethan-1-one HPLC retention time (min.): 3.97; Mass (ESI, Pos. 20V): m/z 465 (M+H)$^+$.

EXAMPLE 84(154)

(Z)-2-(7-methoxy-3,3-dimethyl-3,4-dihydro-(2H)-isoquinolin-1-ylidene)-1-(4-((naphthalen-1-ylcarbonyl)amino)phenyl)ethan-1-one HPLC retention time (min.): 4.18; Mass (ESI, Pos. 20V): m/z 477 (M+H)$^+$.

EXAMPLE 84(155)

(Z)-2-(7-methoxy-3,3-dimethyl-3,4-dihydro-(2H)-isoquinolin-1-ylidene)-1-(4-(pivaloylamino)phenyl)ethan-1-one HPLC retention time (min.): 4.01; Mass (ESI, Pos. 20V): m/z 407 (M+H)$^+$.

EXAMPLE 84(156)

(Z)-2-(7-methoxy-3,3-dimethyl-3,4-dihydro-(2H)-isoquinolin-1-ylidene)-1-(4-((2-phenylacetyl)amino)phenyl)ethan-1-one HPLC retention time (min.): 4.01; Mass (ESI, Pos. 20V): m/z 441 (M+H)$^+$.

EXAMPLE 84(157)

(Z)-2-(7-methoxy-3,3-dimethyl-3,4-dihydro-(2H)-isoquinolin-1-ylidene)-1-(4-(hexanoylamino)phenyl)ethan-1-one HPLC retention time (min.): 4.13; Mass (ESI, Pos. 20V): m/z 421 (M+H)$^+$.

EXAMPLE 84(158)

(Z)-2-(7-methoxy-3,3-dimethyl-3,4-dihydro-(2H)-isoquinolin-1-ylidene)-1-(4-(cyclohexylcarbonylamino)phenyl)ethan-1-one HPLC retention time (min.): 4.13; Mass (ESI, Pos. 20V): m/z 433 (M+H)$^+$.

EXAMPLE 84(159)

(Z)-2-(7-methoxy-3,3-dimethyl-3,4-dihydro-(2H)-isoquinolin-1-ylidene)-1-(4-(benzoylamino)phenyl)ethan-1-one HPLC retention time (min.): 4.03; Mass (ESI, Pos. 20V): m/z 427 (M+H)$^+$.

EXAMPLE 84(160)

(Z)-2-(7-methoxy-3,3-dimethyl-3,4-dihydro-(2H)-isoquinolin-1-ylidene)-1-(4-((furan-2-ylcarbonyl)amino)phenyl)ethan-1-one HPLC retention time (min.): 3.90; Mass (ESI, Pos. 20V): m/z 417 (M+H)$^+$.

EXAMPLE 84(161)

(Z)-2-(7-methoxy-3,3-dimethyl-3,4-dihydro-(2H)-isoquinolin-1-ylidene)-1-(4-(acetylamino)phenyl)ethan-1-one HPLC retention time (min.): 3.67; Mass (ESI, Pos. 20V): m/z 365 (M+H)$^+$.

EXAMPLE 84(162)

(Z)-2-(7-methoxy-3,3-dimethyl-3,4-dihydro-(2H)-isoquinolin-1-ylidene)-1-(4-(cyclopropylcarbonylamino)phenyl)ethan-1-one HPLC retention time (min.): 3.84; Mass (ESI, Pos. 20V): m/z 391 (M+H)$^+$.

EXAMPLE 84(163)

(Z)-2-(7-methoxy-3,3-dimethyl-3,4-dihydro-(2H)-isoquinolin-1-ylidene)-1-(4-(4-phenylbenzoylamino)phenyl)ethan-1-one HPLC retention time (min.): 4.33; Mass (ESI, Pos. 20V): m/z 503 (M+H)$^+$.

EXAMPLE 84(164)

(Z)-2-(7-methoxy-3,3-dimethyl-3,4-dihydro-(2H)-isoquinolin-1-ylidene)-1-(4-(4-trifluoromethylbenzoylamino)phenyl)ethan-1-one HPLC retention time (min.): 4.23; Mass (ESI, Pos. 20V): m/z 495 (M+H)$^+$.

EXAMPLE 84(165)

(Z)-2-(7-methoxy-3,3-dimethyl-3,4-dihydro-(2H)-isoquinolin-1-ylidene)-1-(4-(3-trifluoromethylbenzoylamino)phenyl)ethan-1-one HPLC retention time (min.): 4.24; Mass (ESI, Pos. 20V): m/z 495 (M+H)$^+$.

EXAMPLE 84(166)

(Z)-2-(7-methoxy-3,3-dimethyl-3,4-dihydro-(2H)-isoquinolin-1-ylidene)-1-(4-(2,6-dichlorobenzoylamino)phenyl)ethan-1-one HPLC retention time (min.): 4.14; Mass (ESI, Pos. 20V): m/z 495 (M+H)$^+$.

EXAMPLE 84(167)

(Z)-2-(7-methoxy-3,3-dimethyl-3,4-dihydro-(2H)-isoquinolin-1-ylidene)-1-(4-(2-trifluoromethylbenzoylamino)phenyl)ethan-1-one HPLC retention time (min.): 4.09; Mass (ESI, Pos. 20V): m/z 495 (M+H)$^+$.

EXAMPLE 84(168)

(Z)-2-(7-methoxy-3,3-dimethyl-3,4-dihydro-(2H)-isoquinolin-1-ylidene)-1-(4-(3,5-ditrifluoromethylbenzoylamino)phenyl)ethan-1-one HPLC retention time (min.): 4.44; Mass (ESI, Pos. 20V): m/z 563 (M+H)$^+$.

EXAMPLE 84(169)

(Z)-2-(7-methoxy-3,3-dimethyl-3,4-dihydro-(2H)-isoquinolin-1-ylidene)-1-(4-(4-hexylbenzoylamino)phenyl)ethan-1-one HPLC retention time (min.): 4.65; Mass (ESI, Pos. 20V): m/z 511 (M+H)$^+$.

EXAMPLE 84(170)

(Z)-2-(7-methoxy-3,3-dimethyl-3,4-dihydro-(2H)-isoquinolin-1-ylidene)-1-(4-(2-chloro-5-nitrobenzoylamino)phenyl)ethan-1-one HPLC retention time (min.): 4.11; Mass (ESI, Pos. 20V): m/z 506 (M+H)$^+$.

EXAMPLE 84(171)

(Z)-2-(7-methoxy-3,3-dimethyl-3,4-dihydro-(2H)-isoquinolin-1-ylidene)-1-(4-(2,4-dichlorobenzoylamino)phenyl)ethan-1-one HPLC retention time (min.): 4.21; Mass (ESI, Pos. 20V): m/z 495 (M+H)$^+$.

EXAMPLE 84(172)

(Z)-2-(7-methoxy-3,3-dimethyl-3,4-dihydro-(2H)-isoquinolin-1-ylidene)-1-(4-(4-butylbenzoylamino)phenyl)ethan-1-one HPLC retention time (min.): 4.43; Mass (ESI, Pos. 20V): m/z 483 (M+H)$^+$.

EXAMPLE 84(173)

(Z)-2-(7-methoxy-3,3-dimethyl-3,4-dihydro-(2H)-isoquinolin-1-ylidene)-1-(4-((3-chlorobenzothiophen-2-ylcarbonyl)amino)phenyl)ethan-1-one HPLC retention time (min.): 4.48; Mass (ESI, Pos. 20V): m/z 517 (M+H)$^+$.

EXAMPLE 84(174)

(Z)-2-(7-methoxy-3,3-dimethyl-3,4-dihydro-(2H)-isoquinolin-1-ylidene)-1-(4-(2-chloro-4-nitrobenzoylamino)phenyl)ethan-1-one HPLC retention time (min.): 4.11; Mass (ESI, Pos. 20V): m/z 506 (M+H)$^+$.

EXAMPLE 84(175)

(Z)-2-(7-methoxy-3,3-dimethyl-3,4-dihydro-(2H)-isoquinolin-1-ylidene)-1-(4-(3,5-dichlorobenzoylamino)phenyl)ethan-1-one HPLC retention time (min.): 4.42; Mass (ESI, Pos. 20V): m/z 495 (M+H)$^+$.

EXAMPLE 84(176)

(Z)-2-(7-methoxy-3,3-dimethyl-3,4-dihydro-(2H)-isoquinolin-1-ylidene)-1-(4-(3,4-dichlorobenzoylamino)phenyl)ethan-1-one HPLC retention time (min.): 4.34; Mass (ESI, Pos. 20V): m/z 495 (M+H)$^+$.

EXAMPLE 84(177)

(Z)-2-(7-methoxy-3,3-dimethyl-3,4-dihydro-(2H)-isoquinolin-1-ylidene)-1-(4-(4-hexyloxybenzoylamino)phenyl)ethan-1-one HPLC retention time (min.): 4.56; Mass (ESI, Pos. 20V): m/z 527 (M+H)$^+$.

EXAMPLE 84(178)

(Z)-2-(7-methoxy-3,3-dimethyl-3,4-dihydro-(2H)-isoquinolin-1-ylidene)-1-(4-(3,4-dimethoxybenzoylamino)phenyl)ethan-1-one HPLC retention time (min.): 3.96; Mass (ESI, Pos. 20V): m/z 487 (M+H)$^+$.

EXAMPLE 84(179)

(Z)-2-(7-methoxy-3,3-dimethyl-3,4-dihydro-(2H)-isoquinolin-1-ylidene)-1-(4-(4-butoxybenzoylamino)phenyl)ethan-1-one HPLC retention time (min.): 4.34; Mass (ESI, Pos. 20V): m/z 499 (M+H)$^+$.

EXAMPLE 84(180)

(Z)-2-(7-methoxy-3,3-dimethyl-3,4-dihydro-(2H)-isoquinolin-1-ylidene)-1-(4-(2,3-difluorobenzoylamino)phenyl)ethan-1-one HPLC retention time (min.): 4.12; Mass (ESI, Pos. 20V): m/z 463 (M+H)$^+$.

EXAMPLE 84(181)

(Z)-2-(7-methoxy-3,3-dimethyl-3,4-dihydro-(2H)-isoquinolin-1-ylidene)-1-(4-(4-trifluoromethoxybenzoylamino)phenyl)ethan-1-one HPLC retention time (min.): 4.26; Mass (ESI, Pos. 20V): m/z 511 (M+H)$^+$.

EXAMPLE 84(182)

(Z)-2-(7-methoxy-3,3-dimethyl-3,4-dihydro-(2H)-isoquinolin-1-ylidene)-1-(4-(3,5-dimethoxybenzoylamino)phenyl)ethan-1-one HPLC retention time (min.): 4.11; Mass (ESI, Pos. 20V): m/z 487 (M+H)$^+$.

EXAMPLE 84(183)

(Z)-2-(7-methoxy-3,3-dimethyl-3,4-dihydro-(2H)-isoquinolin-1-ylidene)-1-(4-((5-methyl-3-(2-chloro-6-fluorophenyl)isoxazol-4-ylcarbonyl)amino)phenyl)ethan-1-one HPLC retention time (min.): 4.17; Mass (ESI, Pos. 20V): m/z 560 (M+H)$^+$.

EXAMPLE 84(184)

(Z)-2-(7-methoxy-3,3-dimethyl-3,4-dihydro-(2H)-isoquinolin-1-ylidene)-1-(4-((5-methyl-3-(2-chlorophenyl)isoxazol-4-ylcarbonyl)amino)phenyl)ethan-1-one HPLC retention time (min.): 4.18; Mass (ESI, Pos. 20V): m/z 542 (M+H)$^+$.

EXAMPLE 84(185)

(Z)-2-(7-methoxy-3,3-dimethyl-3,4-dihydro-(2H)-isoquinolin-1-ylidene)-1-(4-((5-methyl-3-(2,6-dichlorophenyl)isoxazol-4-ylcarbonyl)amino)phenyl)ethan-1-one HPLC retention time (min.): 4.23; Mass (ESI, Pos. 20V): m/z 576 (M+H)$^+$.

EXAMPLE 84(186)

(Z)-2-(7-methoxy-3,3-dimethyl-3,4-dihydro-(2H)-isoquinolin-1-ylidene)-1-(4-(3-trifluoromethoxybenzoylamino)phenyl)ethan-1-one HPLC retention time (min.): 4.28; Mass (ESI, Pos. 20V): m/z 511 (M+H)$^+$.

EXAMPLE 84(187)

(Z)-2-(7-methoxy-3,3-dimethyl-3,4-dihydro-(2H)-isoquinolin-1-ylidene)-1-(4-(5-fluoro-2-trifluoromethylbenzoylamino)phenyl)ethan-1-one HPLC retention time (min.): 4.13; Mass (ESI, Pos. 20V): m/z 513 (M+H)$^+$.

EXAMPLE 84(188)

(Z)-2-(7-methoxy-3,3-dimethyl-3,4-dihydro-(2H)-isoquinolin-1-ylidene)-1-(4-(4-pentyloxybenzoylamino)phenyl)ethan-1-one HPLC retention time (min.): 4.46; Mass (ESI, Pos. 20V): m/z 513 (M+H)$^+$.

EXAMPLE 84(189)

(Z)-2-(7-methoxy-3,3-dimethyl-3,4-dihydro-(2H)-isoquinolin-1-ylidene)-1-(4-(2,5-ditrifluoromethylbenzoylamino)phenyl)ethan-1-one HPLC retention time (min.): 4.26; Mass (ESI, Pos. 20V): m/z 563 (M+H)$^+$.

EXAMPLE 84(190)

(Z)-2-(7-methoxy-3,3-dimethyl-3,4-dihydro-(2H)-isoquinolin-1-ylidene)-1-(4-(2,4-dichloro-5-fluorobenzoylamino)phenyl)ethan-1-one HPLC retention time (min.): 4.25; Mass (ESI, Pos. 20V): m/z 513 (M+H)$^+$.

EXAMPLE 84(191)

(Z)-2-(7-methoxy-3,3-dimethyl-3,4-dihydro-(2H)-isoquinolin-1-ylidene)-1-(4-(4-pentylbenzoylamino)phenyl)ethan-1-one HPLC retention time (min.): 4.53; Mass (ESI, Pos. 20V): m/z 497 (M+H)$^+$.

EXAMPLE 84(192)

(Z)-2-(7-methoxy-3,3-dimethyl-3,4-dihydro-(2H)-isoquinolin-1-ylidene)-1-(4-(4-fluorobenzoylamino)phenyl)ethan-1-one HPLC retention time (min.): 4.08; Mass (ESI, Pos. 20V): m/z 445 (M+H)$^+$.

EXAMPLE 84(193)

(Z)-2-(7-methoxy-3,3-dimethyl-3,4-dihydro-(2H)-isoquinolin-1-ylidene)-1-(4-(3-fluorobenzoylamino)phenyl)ethan-1-one HPLC retention time (min.): 4.09; Mass (ESI, Pos. 20V): m/z 445 (M+H)$^+$.

EXAMPLE 84(194)

(Z)-2-(7-methoxy-3,3-dimethyl-3,4-dihydro-(2H)-isoquinolin-1-ylidene)-1-(4-(2-fluorobenzoylamino)phenyl)ethan-1-one HPLC retention time (min.): 4.07; Mass (ESI, Pos. 20V): m/z 445 (M+H)$^+$.

EXAMPLE 84(195)

(Z)-2-(7-methoxy-3,3-dimethyl-3,4-dihydro-(2H)-isoquinolin-1-ylidene)-1-(4-(cyclopentylcarbonylamino)phenyl)ethan-1-one HPLC retention time (min.): 4.06; Mass (ESI, Pos. 20V): m/z 419 (M+H)$^+$.

EXAMPLE 84(196)

(Z)-2-(7-methoxy-3,3-dimethyl-3,4-dihydro-(2H)-isoquinolin-1-ylidene)-1-(4-(2,4-difluorobenzoylamino)phenyl)ethan-1-one HPLC retention time (min.): 4.11; Mass (ESI, Pos. 20V): m/z 463 (M+H)$^+$.

EXAMPLE 84(197)

(Z)-2-(7-methoxy-3,3-dimethyl-3,4-dihydro-(2H)-isoquinolin-1-ylidene)-1-(4-(3-methylbenzoylamino)phenyl)ethan-1-one HPLC retention time (min.): 4.16; Mass (ESI, Pos. 20V): m/z 441 (M+H)$^+$.

EXAMPLE 84(198)

(Z)-2-(7-methoxy-3,3-dimethyl-3,4-dihydro-(2H)-isoquinolin-1-ylidene)-1-(4-(4-ethylbenzoylamino)phenyl)ethan-1-one HPLC retention time (min.): 4.23; Mass (ESI, Pos. 20V): m/z 455 (M+H)$^+$.

EXAMPLE 84(199)

(Z)-2-(7-methoxy-3,3-dimethyl-3,4-dihydro-(2H)-isoquinolin-1-ylidene)-1-(4-(4-propylbenzoylamino)phenyl)ethan-1-one HPLC retention time (min.): 4.33; Mass (ESI, Pos. 20V): m/z 469 (M+H)$^+$.

EXAMPLE 84(200)

(Z)-2-(7-methoxy-3,3-dimethyl-3,4-dihydro-(2H)-isoquinolin-1-ylidene)-1-(4-(2,6-difluorobenzoylamino)phenyl)ethan-1-one HPLC retention time (min.): 4.05; Mass (ESI, Pos. 20V): m/z 463 (M+H)$^+$.

EXAMPLE 84(201)

(Z)-2-(7-methoxy-3,3-dimethyl-3,4-dihydro-(2H)-isoquinolin-1-ylidene)-1-(4-(3-nitrobenzoylamino)phenyl)ethan-1-one HPLC retention time (min.): 4.10; Mass (ESI, Pos. 20V): m/z 472 (M+H)$^+$.

EXAMPLE 84(202)

(Z)-2-(7-methoxy-3,3-dimethyl-3,4-dihydro-(2H)-isoquinolin-1-ylidene)-1-(4-(3-methoxybenzoylamino)phenyl)ethan-1-one HPLC retention time (min.): 4.07; Mass (ESI, Pos. 20V): m/z 457 (M+H)$^+$.

EXAMPLE 84(203)

(Z)-2-(7-methoxy-3,3-dimethyl-3,4-dihydro-(2H)-isoquinolin-1-ylidene)-1-(4-((pyridin-3-ylcarbonyl)amino)phenyl)ethan-1-one HPLC retention time (min.): 3.46; Mass (ESI, Pos. 20V): m/z 428 (M+H)$^+$.

EXAMPLE 84(204)

(Z)-2-(7-methoxy-3,3-dimethyl-3,4-dihydro-(2H)-isoquinolin-1-ylidene)-1-(4-((pyridin-4-ylcarbonyl)amino)phenyl)ethan-1-one HPLC retention time (min.): 3.43; Mass (ESI, Pos. 20V): m/z 428 (M+H)$^+$.

EXAMPLE 84(205)

(Z)-2-(7-methoxy-3,3-dimethyl-3,4-dihydro-(2H)-isoquinolin-1-ylidene)-1-(4-((3-phenylpropanoyl)amino)phenyl)ethan-1-one HPLC retention time (min.): 4.11; Mass (ESI, Pos. 20V): m/z 455 (M+H)$^+$.

EXAMPLE 84(206)

(Z)-2-(7-methoxy-3,3-dimethyl-3,4-dihydro-(2H)-isoquinolin-1-ylidene)-1-(4-((2-phenoxyacetyl)amino)phenyl)ethan-1-one HPLC retention time (min.): 4.09; Mass (ESI, Pos. 20V): m/z 457 (M+H)$^+$.

EXAMPLE 84(207)

(Z)-2-(7-methoxy-3,3-dimethyl-3,4-dihydro-(2H)-isoquinolin-1-ylidene)-1-(4-((2-phenylthiopyridin-3-ylcarbonyl)amino)phenyl)ethan-1-one HPLC retention time (min.): 4.15; Mass (ESI, Pos. 20V): m/z 536 (M+H)$^+$.

EXAMPLE 84(208)

(Z)-2-(7-methoxy-3,3-dimethyl-3,4-dihydro-(2H)-isoquinolin-1-ylidene)-1-(4-((2-(4-methylphenyl)thiopyridin-3-ylcarbonyl)amino)phenyl)ethan-1-one HPLC retention time (min.): 4.22; Mass (ESI, Pos. 20V): m/z 550 (M+H)$^+$.

EXAMPLE 84(209)

(Z)-2-(7-methoxy-3,3-dimethyl-3,4-dihydro-(2H)-isoquinolin-1-ylidene)-1-(4-(2-chlorobenzoylamino)phenyl)ethan-1-one HPLC retention time (min.): 4.07; Mass (ESI, Pos. 20V): m/z 461 (M+H)$^+$.

EXAMPLE 84(210)

(Z)-2-(7-methoxy-3,3-dimethyl-3,4-dihydro-(2H)-isoquinolin-1-ylidene)-1-(4-(2-methoxybenzoylamino)phenyl)ethan-1-one HPLC retention time (min.): 4.16; Mass (ESI, Pos. 20V): m/z 457 (M+H)$^+$.

EXAMPLE 84(211)

(Z)-2-(7-methoxy-3,3-dimethyl-3,4-dihydro-(2H)-isoquinolin-1-ylidene)-1-(4-((2-(thiophen-2-yl)acetyl)amino)phenyl)ethan-1-one HPLC retention time (min.): 3.99; Mass (ESI, Pos. 20V): m/z 447 (M+H)$^+$.

EXAMPLE 84(212)

(Z)-2-(7-methoxy-3,3-dimethyl-3,4-dihydro-(2H)-isoquinolin-1-ylidene)-1-(4-((5-chloropentanoyl)amino)phenyl)ethan-1-one HPLC retention time (min.): 4.02; Mass (ESI, Pos. 20V): m/z 441 (M+H)$^+$.

EXAMPLE 84(213)

(Z)-2-(7-methoxy-3,3-dimethyl-3,4-dihydro-(2H)-isoquinolin-1-ylidene)-1-(4-(4-methylbenzoylamino)phenyl)ethan-1-one HPLC retention time (min.): 4.12; Mass (ESI, Pos. 20V): m/z 441 (M+H)$^+$.

EXAMPLE 84(214)

(Z)-2-(7-methoxy-3,3-dimethyl-3,4-dihydro-(2H)-isoquinolin-1-ylidene)-1-(4-(isobutyrylamino)phenyl)ethan-1-one HPLC retention time (min.): 3.91; Mass (ESI, Pos. 20V): m/z 393 (M+H)$^+$.

EXAMPLE 84(215)

(Z)-2-(7-methoxy-3,3-dimethyl-3,4-dihydro-(2H)-isoquinolin-1-ylidene)-1-(4-((3-cyclopentylpropanoyl)amino)phenyl)ethan-1-one HPLC retention time (min.): 4.27; Mass (ESI, Pos. 20V): m/z 447 (M+H)$^+$.

EXAMPLE 84(216)

(Z)-2-(7-methoxy-3,3-dimethyl-3,4-dihydro-(2H)-isoquinolin-1-ylidene)-1-(4-(octanoylamino)phenyl)ethan-1-one HPLC retention time (min.): 4.37; Mass (ESI, Pos. 20V): m/z 449 (M+H)$^+$.

EXAMPLE 84(217)

(Z)-2-(7-methoxy-3,3-dimethyl-3,4-dihydro-(2H)-isoquinolin-1-ylidene)-1-(4-(nonanoylamino)phenyl)ethan-1-one HPLC retention time (min.): 4.48; Mass (ESI, Pos. 20V): m/z 463 (M+H)$^+$.

EXAMPLE 84(218)

(Z)-2-(7-methoxy-3,3-dimethyl-3,4-dihydro-(2H)-isoquinolin-1-ylidene)-1-(4-(3-chlorobenzoylamino)phenyl)ethan-1-one HPLC retention time (min.): 4.21; Mass (ESI, Pos. 20V): m/z 461 (M+H)$^+$.

EXAMPLE 84(219)

(Z)-2-(7-methoxy-3,3-dimethyl-3,4-dihydro-(2H)-isoquinolin-1-ylidene)-1-(4-(2-methylbenzoylamino)phenyl)ethan-1-one HPLC retention time (min.): 4.09; Mass (ESI, Pos. 20V): m/z 441 (M+H)$^+$.

EXAMPLE 84(220)

(Z)-2-(7-methoxy-3,3-dimethyl-3,4-dihydro-(2H)-isoquinolin-1-ylidene)-1-(4-((3-chloropropanoyl)amino)phenyl)ethan-1-one HPLC retention time (min.): 3.88; Mass (ESI, Pos. 20V): m/z 413 (M+H)$^+$.

EXAMPLE 84(221)

(Z)-2-(7-methoxy-3,3-dimethyl-3,4-dihydro-(2H)-isoquinolin-1-ylidene)-1-(4-((4-chlorobutanoyl)amino)phenyl)ethan-1-one HPLC retention time (min.): 3.97; Mass (ESI, Pos. 20V): m/z 427 (M+H)$^+$.

EXAMPLE 84(222)

(Z)-2-(7-methoxy-3,3-dimethyl-3,4-dihydro-(2H)-isoquinolin-1-ylidene)-1-(4-(2-butenoylamino)phenyl)ethan-1-one HPLC retention time (min.): 3.87; Mass (ESI, Pos. 20V): m/z 391 (M+H)$^+$.

EXAMPLE 84(223)

(Z)-2-(7-methoxy-3,3-dimethyl-3,4-dihydro-(2H)-isoquinolin-1-ylidene)-1-(4-((3-methyl-2-butenoyl)amino)phenyl)ethan-1-one HPLC retention time (min.): 4.01; Mass (ESI, Pos. 20V): m/z 405 (M+H)$^+$.

EXAMPLE 84(224)

(Z)-2-(7-methoxy-3,3-dimethyl-3,4-dihydro-(2H)-isoquinolin-1-ylidene)-1-(4-((2-ethylhexanoyl)amino)phenyl)ethan-1-one HPLC retention time (min.): 4.29; Mass (ESI, Pos. 20V): m/z 449 (M+H)$^+$.

EXAMPLE 84(225)

(Z)-2-(7-methoxy-3,3-dimethyl-3,4-dihydro-(2H)-isoquinolin-1-ylidene)-1-(4-((3,3-dimethylbutanoyl)amino)phenyl)ethan-1-one HPLC retention time (min.): 4.11; Mass (ESI, Pos. 20V): m/z 421 (M+H)$^+$.

EXAMPLE 84(226)

(Z)-2-(7-methoxy-3,3-dimethyl-3,4-dihydro-(2H)-isoquinolin-1-ylidene)-1-(4-(4-nitrobenzoylamino)phenyl)ethan-1-one HPLC retention time (min.): 4.08; Mass (ESI, Pos. 20V): m/z 472 (M+H)$^+$.

EXAMPLE 84(227)

(Z)-2-(7-methoxy-3,3-dimethyl-3,4-dihydro-(2H)-isoquinolin-1-ylidene)-1-(4-((thiophen-2-ylcarbonyl)amino)phenyl)ethan-1-one HPLC retention time (min.): 4.01; Mass (ESI, Pos. 20V): m/z 433 (M+H)$^+$.

EXAMPLE 84(228) -benzodioxan-2-yl)thiazol-4-ylcarbonyl)amino)phenyl)ethan-1-one HPLC retention time (min.): 4.35; Mass (ESI, Pos. 20V): m/z 568 (M+H)$^+$.

EXAMPLE 84(229)

(Z)-2-(7-methoxy-3,3-dimethyl-3,4-dihydro-(2H)-isoquinolin-1-ylidene)-1-(4-(4-chlorobenzoylamino)phenyl)ethan-1-one HPLC retention time (min.): 4.20; Mass (ESI, Pos. 20V): m/z 461 (M+1H)$^+$.

EXAMPLE 84(230)

(Z)-2-(7-methoxy-3,3-dimethyl-3,4-dihydro-(2H)-isoquinolin-1-ylidene)-1-(4-((1-methylcyclohexyl-carbonyl)amino)phenyl)ethan-1-one HPLC retention time (min.): 4.27; Mass (ESI, Pos. 20V): m/z 447 (M+H)$^+$.

EXAMPLE 84(231)

(Z)-2-(7-methoxy-3,3-dimethyl-3,4-dihydro-(2H)-isoquinolin-1-ylidene)-1-(4-((2,6,6-trimethyl-1-cyclohexen-1-ylcarbonyl)amino)phenyl)ethan-1-one HPLC retention time (min.): 4.31; Mass (ESI, Pos. 20V): m/z 473 (M+H)$^+$.

EXAMPLE 84(232)

(Z)-2-(7-methoxy-3,3-dimethyl-3,4-dihydro-(2H)-isoquinolin-1-ylidene)-1-(4-(2-trifluoromethoxybenzoylamino)phenyl)ethan-1-one HPLC retention time (min.): 4.16; Mass (ESI, Pos. 20V): m/z 511 (M+H)$^+$.

EXAMPLE 84(233)

(Z)-2-(7-methoxy-3,3-dimethyl-3,4-dihydro-(2H)-isoquinolin-1-ylidene)-1-(4-(2,4-ditrifluoromethyl-benzoylamino)phenyl)ethan-1-one HPLC retention time (min.): 4.26; Mass (ESI, Pos. 20V): m/z 563 (M+H)$^+$.

EXAMPLE 84(234)

(Z)-2-(7-methoxy-3,3-dimethyl-3,4-dihydro-(2H)-isoquinolin-1-ylidene)-1-(4-(5-fluoro-2-methylbenzoylamino)phenyl)ethan-1-one HPLC retention time (min.): 4.13; Mass (ESI, Pos. 20V): m/z 459 (M+H)$^+$.

EXAMPLE 84(235)

(Z)-2-(7-methoxy-3,3-dimethyl-3,4-dihydro-(2H)-isoquinolin-1-ylidene)-1-(4-((2-ethoxy-2-oxoacetyl)amino)phenyl)ethan-1-one HPLC retention time (min.): 3.94; Mass (ESI, Pos. 20V): m/z 423 (M+H)$^+$.

EXAMPLE 84(236)

(Z)-2-(7-methoxy-3,3-dimethyl-3,4-dihydro-(2H)-isoquinolin-1-ylidene)-1-(4-((5-methyl-3-phenyl-isoxazol-4-ylcarbonyl)amino)phenyl)ethan-1-one HPLC retention time (min.): 4.16; Mass (ESI, Pos. 20V): m/z 508 (M+H)$^+$.

EXAMPLE 84(237)

(Z)-2-(7-methoxy-3,3-dimethyl-3,4-dihydro-(2H)-isoquinolin-1-ylidene)-1-(4-((3-chlorothiophen-2-ylcarbonyl)amino)phenyl)ethan-1-one HPLC retention time (min.): 4.22; Mass (ESI, Pos. 20V): m/z 467 (M+H)$^+$.

EXAMPLE 84(238)

(Z)-2-(7-methoxy-3,3-dimethyl-3,4-dihydro-(2H)-isoquinolin-1-ylidene)-1-(4-((2-(4-chlorophenylthio)pyridin-3-ylcarbonyl)amino)phenyl)ethan-1-one HPLC retention time (min.): 4.29; Mass (ESI, Pos. 20V): m/z 570 (M+H)$^+$.

EXAMPLE 84(239)

(Z)-2-(7-methoxy-3,3-dimethyl-3,4-dihydro-(2H)-isoquinolin-1-ylidene)-1-(4-((5,6-dichloropyridin-3-ylcarbonyl)amino)phenyl)ethan-1-one HPLC retention time (min.): 4.22; Mass (ESI, Pos. 20V): m/z 496 (M+H)$^+$.

EXAMPLE 84(240)

(Z)-2-(7-methoxy-3,3-dimethyl-3,4-dihydro-(2H)-isoquinolin-1-ylidene)-1-(4-((5-methyl-2-phenyl-2H-1,2,3-triazol-4-ylcarbonyl)amino)phenyl)ethan-1-one HPLC retention time (min.): 4.48; Mass (ESI, Pos. 20V): m/z 508 (M+H)$^+$.

EXAMPLE 84(241)

(Z)-2-(7-methoxy-3,3-dimethyl-3,4-dihydro-(2H)-isoquinolin-1-ylidene)-1-(4-(2,6-dimethylbenzoylamino)phenyl)ethan-1-one HPLC retention time (min.): 4.13; Mass (ESI, Pos. 20V): m/z 455 (M+H)$^+$.

EXAMPLE 84(242)

(Z)-2-(7-methoxy-3,3-dimethyl-3,4-dihydro-(2H)-isoquinolin-1-ylidene)-1-(4-((2,5-dichlorothiophen-3-ylcarbonyl)amino)phenyl)ethan-1-one HPLC retention time (min.): 4.33; Mass (ESI, Pos. 20V): m/z 501 (M+H)$^+$.

EXAMPLE 84(243)

(Z)-2-(7-methoxy-3,3-dimethyl-3,4-dihydro-(2H)-isoquinolin-1-ylidene)-1-(4-((2-propylpentanoyl)amino)phenyl)ethan-1-one HPLC retention time (min.): 4.29; Mass (ESI, Pos. 20V): m/z 449 (M+H)$^+$.

EXAMPLE 84(244)

(Z)-2-(7-methoxy-3,3-dimethyl-3,4-dihydro-(2H)-isoquinolin-1-ylidene)-1-(4-((6-chloropyridin-3-ylcarbonyl)amino)phenyl)ethan-1-one HPLC retention time (min.): 4.01; Mass (ESI, Pos. 20V): m/z 462 (M+H)$^+$.

EXAMPLE 84(245)

(Z)-2-(7-methoxy-3,3-dimethyl-3,4-dihydro-(2H)-isoquinolin-1-ylidene)-1-(4-((naphthalen-2-ylcarbonyl)amino)phenyl)ethan-1-one HPLC retention time (min.): 4.25; Mass (ESI, Pos. 20V): m/z 477 (M+H)$^+$.

EXAMPLE 84(246)

(Z)-2-(7-methoxy-3,3-dimethyl-3,4-dihydro-(2H)-isoquinolin-1-ylidene)-1-(4-((2-benzyloxyacetyl)amino)phenyl)ethan-1-one HPLC retention time (min.): 4.14; Mass (ESI, Pos. 20V): m/z 471 (M+H)$^+$.

EXAMPLE 84(247)

(Z)-2-(7-methoxy-3,3-dimethyl-3,4-dihydro-(2H)-isoquinolin-1-ylidene)-1-(4-(cyclobutylcarbonylamino)phenyl)ethan-1-one HPLC retention time (min.): 3.96; Mass (ESI, Pos. 20V): m/z 405 (M+H)$^+$.

EXAMPLE 84(248)

(Z)-2-(7-methoxy-3,3-dimethyl-3,4-dihydro-(2H)-isoquinolin-1-ylidene)-1-(4-(2,4,5-trifluorobenzoylamino)phenyl)ethan-1-one HPLC retention time (min.): 4.18; Mass (ESI, Pos. 20V): m/z 481 (M+H)$^+$.

EXAMPLE 84(249)

(Z)-2-(7-methoxy-3,3-dimethyl-3,4-dihydro-(2H)-isoquinolin-1-ylidene)-1-(4-(2,3,4-trifluorobenzoylamino)phenyl)ethan-1-one HPLC retention time (min.): 4.15; Mass (ESI, Pos. 20V): m/z 481 (M+H)$^+$.

EXAMPLE 84(250)

(Z)-2-(7-methoxy-3,3-dimethyl-3,4-dihydro-(2H)-isoquinolin-1-ylidene)-1-(4-((benzothiophen-2-ylcarbonyl)amino)phenyl)ethan-1-one HPLC retention time (min.): 4.28; Mass (ESI, Pos. 20V): m/z 483 (M+H)$^+$.

EXAMPLE 84(251)

(Z)-2-(7-methoxy-3,3-dimethyl-3,4-dihydro-(2H)-isoquinolin-1-ylidene)-1-(4-((3-chloro-2,2,3,3-tetrafluoropropanoyl)amino)phenyl)ethan-1-one HPLC retention time (min.): 4.21; Mass (ESI, Pos. 20V): m/z 485 (M+H)$^+$.

EXAMPLE 84(252)

(Z)-2-(7-methoxy-3,3-dimethyl-3,4-dihydro-(2H)-isoquinolin-1-ylidene)-1-(4-((2,2,3,3-tetrafluoropropanoyl)amino)phenyl)ethan-1-one HPLC retention time (min.): 4.08; Mass (ESI, Pos. 20V): m/z 451 (M+H)$^+$.

EXAMPLE 84(253)

(Z)-2-(7-methoxy-3,3-dimethyl-3,4-dihydro-(2H)-isoquinolin-1-ylidene)-1-(4-((2-(4-methoxyphenyl)acetyl)amino)phenyl)ethan-1-one HPLC retention time (min.): 4.00; Mass (ESI, Pos. 20V): m/z 471 (M+H)$^+$.

EXAMPLE 84(254)

(Z)-2-(7-methoxy-3,3-dimethyl-3,4-dihydro-(2H)-isoquinolin-1-ylidene)-1-(4-((2,2,2-trichloroacetyl)amino)phenyl)ethan-1-one HPLC retention time (min.): 4.20; Mass (ESI, Pos. 20V): m/z 467 (M+H)$^+$, 469 (M+2+H)$^+$.

EXAMPLE 84(255)

(Z)-2-(7-methoxy-3,3-dimethyl-3,4-dihydro-(2H)-isoquinolin-1-ylidene)-1-(4-((2-chloropropanoyl)amino)phenyl)ethan-1-one HPLC retention time (min.): 3.97; Mass (ESI, Pos. 20V): m/z 413 (M+H)$^+$.

EXAMPLE 84(256)

(Z)-2-(7-methoxy-3,3-dimethyl-3,4-dihydro-(2H)-isoquinolin-1-ylidene)-1-(4-(2-nitrobenzoylamino)phenyl)ethan-1-one HPLC retention time (min.): 3.96; Mass (ESI, Pos. 20V): m/z 472 (M+H)$^+$.

EXAMPLE 84(257)

(Z)-2-(7-methoxy-3,3-dimethyl-3,4-dihydro-(2H)-isoquinolin-1-ylidene)-1-(4-(4-cyanobenzoylamino)phenyl)ethan-1-one HPLC retention time (min.): 4.03; Mass (ESI, Pos. 20V): m/z 452 (M+H)$^+$.

EXAMPLE 84(258)

(Z)-2-(7-methoxy-3,3-dimethyl-3,4-dihydro-(2H)-isoquinolin-1-ylidene)-1-(4-((2-(4-chlorophenoxy)pyridin-3-ylcarbonyl)amino)phenyl)ethan-1-one HPLC retention time (min.): 4.38; Mass (ESI, Pos. 20V): m/z 554 (M+H)$^+$.

EXAMPLE 84(259)

(Z)-2-(7-methoxy-3,3-dimethyl-3,4-dihydro-(2H)-isoquinolin-1-ylidene)-1-(4-((2-(4-methylphenoxy)pyridin-3-ylcarbonyl)amino)phenyl)ethan-1-one HPLC retention time (min.): 4.37; Mass (ESI, Pos. 20V): m/z 534 (M+H)$^+$.

EXAMPLE 84(260)

(Z)-2-(7-methoxy-3,3-dimethyl-3,4-dihydro-(2H)-isoquinolin-1-ylidene)-1-(4-((1-(4-chlorophenyl)-5-propylisoimidazol-4-ylcarbonyl)amino)phenyl)ethan-1-one HPLC retention time (min.): 4.43; Mass (ESI, Pos. 20V): m/z 569 (M+H)$^+$.

EXAMPLE 84(261)

(Z)-2-(7-methoxy-3,3-dimethyl-3,4-dihydro-(2H)-isoquinolin-1-ylidene)-1-(4-((2-propylthiopyridin-3-ylcarbonyl)amino)phenyl)ethan-1-one HPLC retention time (min.): 4.19; Mass (ESI, Pos. 20V): m/z 502 (M+H)$^+$.

EXAMPLE 84(262)

(Z)-2-(7-methoxy-3,3-dimethyl-3,4-dihydro-(2H)-isoquinolin-1-ylidene)-1-(4-(4-chloro-3-nitrobenzoylamino)phenyl)ethan-1-one HPLC retention time (min.): 4.22; Mass (ESI, Pos. 20V): m/z 506 (M+H)$^+$.

EXAMPLE 84(263)

(Z)-2-(7-methoxy-3,3-dimethyl-3,4-dihydro-(2H)-isoquinolin-1-ylidene)-1-(4-(3-nitro-4-methylbenzoylamino)phenyl)ethan-1-one HPLC retention time (min.): 4.18; Mass (ESI, Pos. 20V): m/z 486 (M+H)$^+$.

EXAMPLE 84(264)

(Z)-2-(7-methoxy-3,3-dimethyl-3,4-dihydro-(2H)-isoquinolin-1-ylidene)-1-(4-((2-(4-chlorophenoxy)pyridin-3-ylcarbonyl)amino)phenyl)ethan-1-one HPLC retention time (min.): 4.22; Mass (ESI, Pos. 20V): m/z 491 (M+H)$^+$.

EXAMPLE 84(265)

(Z)-2-(7-methoxy-3,3-dimethyl-3,4-dihydro-(2H)-isoquinolin-1-ylidene)-1-(4-4-ethoxybenzoylamino)phenyl)ethan-1-one HPLC retention time (min.): 4.13; Mass (ESI, Pos. 20V): m/z 471 (M+H)$^+$.

EXAMPLE 84(266)

(Z)-2-(7-methoxy-3,3-dimethyl-3,4-dihydro-(2H)-isoquinolin-1-ylidene)-1-(4-(2-ethoxybenzoylamino)phenyl)ethan-1-one HPLC retention time (min.): 4.30; Mass (ESI, Pos. 20V): m/z 471 (M+H)$^+$.

EXAMPLE 84(267)

(Z)-2-(7-methoxy-3,3-dimethyl-3,4-dihydro-(2H)-isoquinolin-1-ylidene)-1-(4-((2-methylbutanoyl)amino)phenyl)ethan-1-one HPLC retention time (min.): 3.98; Mass (ESI, Pos. 20V): m/z 407 (M+H)$^+$.

EXAMPLE 84(268)

(Z)-2-(7-methoxy-3,3-dimethyl-3,4-dihydro-(2H)-isoquinolin-1-ylidene)-1-(4-((4-methylpentanoyl)amino)phenyl)ethan-1-one HPLC retention time (min.): 4.13; Mass (ESI, Pos. 20V): m/z 421 (M+H)$^+$.

EXAMPLE 84(269)

(Z)-2-(7-methoxy-3,3-dimethyl-3,4-dihydro-(2H)-isoquinolin-1-ylidene)-1-(4-((2-methoxyacetyl)amino)phenyl)ethan-1-one HPLC retention time (min.): 3.76; Mass (ESI, Pos. 20V): m/z 395 (M+H)$^+$.

EXAMPLE 84(270)

(Z)-2-(7-methoxy-3,3-dimethyl-3,4-dihydro-(2H)-isoquinolin-1-ylidene)-1-(4-((3-methylthiopropanoyl)amino)phenyl)ethan-1-one HPLC retention time (min.): 3.88; Mass (ESI, Pos. 20V): m/z 425 (M+H)$^+$.

EXAMPLE 84(271)

(Z)-2-(7-methoxy-3,3-dimethyl-3,4-dihydro-(2H)-isoquinolin-1-ylidene)-1-(4-((2-(((1R,2S,5R)-2-isopropyl-5-methylcyclohexyloxy)acetyl)amino)phenyl)ethan-1-one HPLC retention time (min.): 4.75; Mass (ESI, Pos. 20V): m/z 519 (M+H)$^+$.

EXAMPLE 84(272)

(Z)-2-(7-methoxy-3,3-dimethyl-3,4-dihydro-(2H)-isoquinolin-1-ylidene)-1-(4-((2-cyclopentylacetyl)amino)phenyl)ethan-1-one HPLC retention time (min.): 4.14; Mass (ESI, Pos. 20V): m/z 433 (M+H)$^+$.

EXAMPLE 84(273)

(Z)-2-(7-methoxy-3,3-dimethyl-3,4-dihydro-(2H)-isoquinolin-1-ylidene)-1-(4-((2-methylthiopyridin-3-ylcarbonyl)amino)phenyl)ethan-1-one HPLC retention time (min.): 3.99; Mass (ESI, Pos. 20V): m/z 474 (M+H)$^+$.

EXAMPLE 84(274)

(Z)-2-(7-methoxy-3,3-dimethyl-3,4-dihydro-(2H)-isoquinolin-1-ylidene)-1-(4-((2-phenoxybutanoyl)amino)phenyl)ethan-1-one HPLC retention time (min.): 4.23; Mass (ESI, Pos. 20V): m/z 485 (M+H)$^+$.

EXAMPLE 84(275)

(Z)-2-(7-methoxy-3,3-dimethyl-3,4-dihydro-(2H)-isoquinolin-1-ylidene)-1-(4-((2-(4-chlorophenyl)acetyl)amino)phenyl)ethan-1-one HPLC retention time (min.): 4.15; Mass (ESI, Pos. 20V): m/z 475 (M+H)$^+$.

EXAMPLE 84(276)

(Z)-2-(7-methoxy-3,3-dimethyl-3,4-dihydro-(2H)-isoquinolin-1-ylidene)-1-(4-((2-methylpentanoyl)amino)phenyl)ethan-1-one HPLC retention time (min.): 4.11; Mass (ESI, Pos. 20V): m/z 421 (M+H)$^+$.

EXAMPLE 84(277)

(Z)-2-(7-methoxy-3,3-dimethyl-3,4-dihydro-(2H)-isoquinolin-1-ylidene)-1-(4-((4-nitro-4-methylhexanoyl)amino)phenyl)ethan-1-one HPLC retention time (min.): 4.07; Mass (ESI, Pos. 20V): m/z 480 (M+H)$^+$.

EXAMPLE 84(278)

(Z)-2-(7-methoxy-3,3-dimethyl-3,4-dihydro-(2H)-isoquinolin-1-ylidene)-1-(4-(pentanoylamino)phenyl)ethan-1-one HPLC retention time (min.): 4.03; Mass (ESI, Pos. 20V): m/z 407 (M+H)$^+$.

EXAMPLE 84(279)

(Z)-2-(7-methoxy-3,3-dimethyl-3,4-dihydro-(2H)-isoquinolin-1-ylidene)-1-(4-((3-methylbutanoyl)amino)phenyl)ethan-1'-one HPLC retention time (min.): 4.00; Mass (ESI, Pos. 20V) m/z 407 (M+H)$^+$.

EXAMPLE 84(280)

(Z)-2-(7-methoxy-3,3-dimethyl-3,4-dihydro-(2H)-isoquinolin-1-ylidene)-1-(4-((2,5-dimethylfuran-3-ylcarbonyl)amino)phenyl)ethan-1-one HPLC retention time (min.): 4.13; Mass (ESI, Pos. 20V): m/z 445 (M+H)$^+$.

EXAMPLE 84(281)

(Z)-2-(7-methoxy-3,3-dimethyl-3,4-dihydro-(2H)-isoquinolin-1-ylidene)-1-(4-(2,3,6-trifluorobenzoylamino)phenyl)ethan-1-one HPLC retention time (min.): 4.09; Mass (ESI, Pos. 20V): m/z 481 (M+H)$^+$.

EXAMPLE 84(282)

(Z)-2-(7-methoxy-3,3-dimethyl-3,4-dihydro-(2H)-isoquinolin-1-ylidene)-1-(4-((2-phenylbutanoyl)amino)phenyl)ethan-1-one HPLC retention time (min.): 4.22; Mass (ESI, Pos. 20V): m/z 469 (M+H)$^+$.

EXAMPLE 84(283)

(Z)-2-(7-methoxy-3,3-dimethyl-3,4-dihydro-(2H)-isoquinolin-1-ylidene)-1-(4-((3-chloro-4-mesylthiophen-2-ylcarbonyl)amino)phenyl)ethan-1-one HPLC retention time (min.): 4.00; Mass (ESI, Pos. 20V): m/z 545 (M+H)$^+$.

EXAMPLE 84(284)

(Z)-2-(7-methoxy-3,3-dimethyl-3,4-dihydro-(2H)-isoquinolin-1-ylidene)-1-(4-((3,5-dimethylthioisoxazol0-4-ylcarbonyl)amino)phenyl)ethan-1-one HPLC retention time (min.): 4.28; Mass (ESI, Pos. 20V): m/z 526 (M+H)$^+$.

EXAMPLE 84(285)

(Z)-2-(7-methoxy-3,3-dimethyl-3,4-dihydro-(2H)-isoquinolin-1-ylidene)-1-(4-((2-ethylthiopyridin-3-ylcarbonyl)amino)phenyl)ethan-1-one HPLC retention time (min.): 4.10; Mass (ESI, Pos. 20V): m/z 488 (M+H)$^+$.

EXAMPLE 84(286)

(Z)-2-(7-methoxy-3,3-dimethyl-3,4-dihydro-(2H)-isoquinolin-1-ylidene)-1-(4-((4-isopropylsulfonyl-3-chlorothiophen-2-ylcarbonyl)amino)phenyl)ethan-1-one HPLC retention time (min.): 4.15; Mass (ESI, Pos. 20V): m/z 573 (M+H)$^+$.

EXAMPLE 84(287)

(Z)-2-(7-methoxy-3,3-dimethyl-3,4-dihydro-(2H)-isoquinolin-1-ylidene)-1-(4-((5-(4-chlorophenyl)-2-methylfuran-3-ylcarbonyl)amino)phenyl)ethan-1-one HPLC retention time (min.): 4.60; Mass (ESI, Pos. 20V): m/z 541 (M+H)$^+$.

EXAMPLE 84(288)

(Z)-2-(7-methoxy-3,3-dimethyl-3,4-dihydro-(2H)-isoquinolin-1-ylidene)-1-(4-((2,5-dichloropyridin-3-ylcarbonyl)amino)phenyl)ethan-1-one HPLC retention time (min.): 4.11; Mass (ESI, Pos. 20V): m/z 496 (M+H)$^+$.

EXAMPLE 84(289)

(Z)-2-(7-methoxy-3,3-dimethyl-3,4-dihydro-(2H)-isoquinolin-1-ylidene)-1-(4-((1-benzyl-3-t-butyl-isoimidazolisoimidazol-5-ylcarbonyl)amino)phenyl)ethan-1-one HPLC retention time (min.): 4.56; Mass (ESI, Pos. 20V): m/z 563 (M+H)$^+$.

EXAMPLE 84(290)

(Z)-2-(7-methoxy-3,3-dimethyl-3,4-dihydro-(2H)-isoquinolin-1-ylidene)-1-(4-((3-t-butyl-1-methyl-isoimidazol-5-ylcarbonyl)amino)phenyl)ethan-1-one HPLC retention time (min.): 4.27; Mass (ESI, Pos. 20V): m/z 487 (M+H)$^+$.

EXAMPLE 84(291)

(Z)-2-(7-methoxy-3,3-dimethyl-3,4-dihydro-(2H)-isoquinolin-1-ylidene)-1-(4-((2-chlorobutanoyl)amino)phenyl)ethan-1-one HPLC retention time (min.): 4.06; Mass (ESI, Pos. 20V): m/z 427 (M+H)$^+$.

EXAMPLE 84(292)

(Z)-2-(7-methoxy-3,3-dimethyl-3,4-dihydro-(2H)-isoquinolin-1-ylidene)-1-(4-(4-fluoro-2-trifluoromethylbenzoylamino)phenyl)ethan-1-one HPLC retention time (min.): 4.15; Mass (ESI, Pos. 20V): m/z 513 (M+H)$^+$.

EXAMPLE 84(293)

(Z)-2-(7-methoxy-3,3-dimethyl-3,4-dihydro-(2H)-isoquinolin-1-ylidene)-1-(4-(butanoylamino)phenyl)ethan-1-one HPLC retention time (min.): 3.93; Mass (ESI, Pos. 20V): m/z 393 (M+H)$^+$.

EXAMPLE 84(294)

(Z)-2-(7-methoxy-3,3-dimethyl-3,4-dihydro-(2H)-isoquinolin-1-ylidene)-1-(4-((5,5-dimethyl-3-methylhexanoyl)amino)phenyl)ethan-1-one HPLC retention time (min.): 4.39; Mass (ESI, Pos. 20V): m/z 463 (M+H)$^+$.

EXAMPLE 84(295)

(Z)-2-(7-methoxy-3,3-dimethyl-3,4-dihydro-(2H)-isoquinolin-1-ylidene)-1-(4-(propanoylamino)phenyl)ethan-1-one HPLC retention time (min.): 3.81; Mass (ESI, Pos. 20V): m/z 379 (M+H)$^+$.

EXAMPLE 84(296)

(Z)-2-(7-methoxy-3,3-dimethyl-3,4-dihydro-(2H)-isoquinolin-1-ylidene)-1-(4-((5-methyl-2-trifluoromethylfuran-3-ylcarbonyl)amino)phenyl)ethan-1-one HPLC retention time (min.): 4.21; Mass (ESI, Pos. 20V): m/z 499 (M+H)$^+$.

EXAMPLE 84(297)

(Z)-2-(7-methoxy-3,3-dimethyl-3,4-dihydro-(2H)-isoquinolin-1-ylidene)-1-(4-((5-t-butyl-2-methylfuran-3-ylcarbonyl)amino)phenyl)ethan-1-one HPLC retention time (min.): 4.47; Mass (ESI, Pos. 20V): m/z 487 (M+H)$^+$.

EXAMPLE 84(298)

(Z)-2-(7-methoxy-3,3-dimethyl-3,4-dihydro-(2H)-isoquinolin-1-ylidene)-1-(4-(3,4,5-trifluorobenzoylamino)phenyl)ethan-1-one HPLC retention time (min.): 4.24; Mass (ESI, Pos. 20V): m/z 481 (M+H)$^+$.

EXAMPLE 84(299)

(Z)-2-(7-methoxy-3,3-dimethyl-3,4-dihydro-(2H)-isoquinolin-1-ylidene)-1-(4-((2-ethylbutanoyl)amino)phenyl)ethan-1-one HPLC retention time (min.): 4.08; Mass (ESI, Pos. 20V): m/z 421 (M+H)$^+$.

EXAMPLE 84(300)

(Z)-2-(7-methoxy-3,3-dimethyl-3,4-dihydro-(2H)-isoquinolin-1-ylidene)-1-(4-(2,3,5-trifluorobenzoylamino)phenyl)ethan-1-one HPLC retention time (min.): 4.19; Mass (ESI, Pos. 20V): m/z 481 (M+H)$^+$.

EXAMPLE 84(301)

(Z)-2-(7-methoxy-3,3-dimethyl-3,4-dihydro-(2H)-isoquinolin-1-ylidene)-1-(4-(2,3-dimethylbenzoylamino)phenyl)ethan-1-one HPLC retention time (min.): 4.17; Mass (ESI, Pos. 20V): m/z 455 (M+H)$^+$.

EXAMPLE 84(302)

(Z)-2-(7-methoxy-3,3-dimethyl-3,4-dihydro-(2H)-isoquinolin-1-ylidene)-1-(4-(2-chloro-6-fluorobenzoylamino)phenyl)ethan-1-one HPLC retention time (min.): 4.10; Mass (ESI, Pos. 20V): m/z 479 (M+H)$^+$.

EXAMPLE 84(303)

(Z)-2-(7-methoxy-3,3-dimethyl-3,4-dihydro-(2H)-isoquinolin-1-ylidene)-1-(4-((2-chloro-6-methylpyridin-4-ylcarbonyl)amino)phenyl)ethan-1-one HPLC retention time (min.): 4.13; Mass (ESI, Pos. 20V): m/z 476 (M+H)$^+$.

EXAMPLE 84(304)

(Z)-2-(7-methoxy-3,3-dimethyl-3,4-dihydro-(2H)-isoquinolin-1-ylidene)-1-(4-(3-(4-trifluoromethoxyphenyl)-2-propenoylamino)phenyl)ethan-1-one HPLC retention time (min.): 4.35; Mass (ESI, Pos. 20V): m/z 537 (M+H)$^+$.

EXAMPLE 84(305)

(Z)-2-(7-methoxy-3,3-dimethyl-3,4-dihydro-(2H)-isoquinolin-1-ylidene)-1-(4-(4-methoxycarbonylbenzoylamino)phenyl)ethan-1-one HPLC retention time (min.): 4.10; Mass (ESI, Pos. 20V): m/z 485 (M+H)$^+$.

EXAMPLE 84(306)

(Z)-2-(7-methoxy-3,3-dimethyl-3,4-dihydro-(2H)-isoquinolin-1-ylidene)-1-(4-((4-ethoxycarbonylbutanoyl)amino)phenyl)ethan-1-one HPLC retention time (min.): 3.93; Mass (ESI, Pos. 20V): m/z 465 (M+H)$^+$.

EXAMPLE 84(307)

(Z)-2-(7-methoxy-3,3-dimethyl-3,4-dihydro-(2H)-isoquinolin-1-ylidene)-1-(3-(mesylamino)phenyl)ethan-1-one HPLC retention time (min.): 3.79; Mass (ESI, Pos. 20V): m/z 401 (M+H)$^+$.

EXAMPLE 84(308)

(Z)-2-(7-methoxy-3,3-dimethyl-3,4-dihydro-(2H)-isoquinolin-1-ylidene)-1-(3-((pentylsulfonyl)amino)phenyl)ethan-1-one HPLC retention time (min.): 4.17; Mass (ESI, Pos. 20V): m/z 457 (M+H)$^+$.

EXAMPLE 84(309)

(Z)-2-(7-methoxy-3,3-dimethyl-3,4-dihydro-(2H)-isoquinolin-1-ylidene)-1-(3-((isopropylsulfonyl)amino)phenyl)ethan-1-one HPLC retention time (min.): 3.96; Mass (ESI, Pos. 20V): m/z 429 (M+H)$^+$.

EXAMPLE 84(310)

(Z)-2-(7-methoxy-3,3-dimethyl-3,4-dihydro-(2H)-isoquinolin-1-ylidene)-1-(3-((4-chlorophenylsulfonyl)amino)phenyl)ethan-1-one HPLC retention time (min.): 4.20; Mass (ESI, Pos. 20V): m/z 497 (M+H)$^+$.

EXAMPLE 84(311)

(Z)-2-(7-methoxy-3,3-dimethyl-3,4-dihydro-(2H)-isoquinolin-1-ylidene)-1-(3-((2-iodophenylsulfonyl)amino)phenyl)ethan-1-one HPLC retention time (min.): 4.16; Mass (ESI, Pos. 20V): m/z 589 (M+H)$^+$.

EXAMPLE 84(312)

(Z)-2-(7-methoxy-3,3-dimethyl-3,4-dihydro-(2H)-isoquinolin-1-ylidene)-1-(3-((4-nitrophenylsulfonyl)amino)phenyl)ethan-1-one HPLC retention time (min.): 4.09; Mass (ESI, Pos. 20V): m/z 508 (M+H)$^+$.

EXAMPLE 84(313)

(Z)-2-(7-methoxy-3,3-dimethyl-3,4-dihydro-(2H)-isoquinolin-1-ylidene)-1-(3-((4-mesylphenylsulfonyl)amino)phenyl)ethan-1-one HPLC retention time (min.): 3.90; Mass (ESI, Pos. 20V): m/z 541 (M+H)$^+$.

EXAMPLE 84(314)

(Z)-2-(7-methoxy-3,3-dimethyl-3,4-dihydro-(2H)-isoquinolin-1-ylidene)-1-(3-((4-trifluoromethylphenylsulfonyl)amino)phenyl)ethan-1-one HPLC retention time (min.): 4.21; Mass (ESI, Pos. 20V): m/z 531 (M+H)$^+$.

EXAMPLE 84(315)

(Z)-2-(7-methoxy-3,3-dimethyl-3,4-dihydro-(2H)-isoquinolin-1-ylidene)-1-(3-((4-phenylphenylsulfonyl)amino)phenyl)ethan-1-one HPLC retention time (min.): 4.31; Mass (ESI, Pos. 20V): m/z 539 (M+H)$^+$.

EXAMPLE 84(316)

(Z)-2-(7-methoxy-3,3-dimethyl-3,4-dihydro-(2H)-isoquinolin-1-ylidene)-1-(3-((2-phenylphenylsulfonyl)amino)phenyl)ethan-1-one HPLC retention time (min.): 4.30; Mass (ESI, Pos. 20V): m/z 539 (M+H)$^+$.

EXAMPLE 84(317)

(Z)-2-(7-methoxy-3,3-dimethyl-3,4-dihydro-(2H)-isoquinolin-1-ylidene)-1-(3-((2,6-difluorophenylsulfonyl)amino)phenyl)ethan-1-one HPLC retention time (min.): 4.05; Mass (ESI, Pos. 20V): m/z 499 (M+H)$^+$.

EXAMPLE 84(318)

(Z)-2-(7-methoxy-3,3-dimethyl-3,4-dihydro-(2H)-isoquinolin-1-ylidene)-1-(3-((2,5-difluorophenylsulfonyl)amino)phenyl)ethan-1-one HPLC retention time (min.): 4.10; Mass (ESI, Pos. 20V): m/z 499 (M+H)$^+$.

EXAMPLE 84(319)

(Z)-2-(7-methoxy-3,3-dimethyl-3,4-dihydro-(2H)-isoquinolin-1-ylidene)-1-(3-((2,5-dimethoxyphenylsulfonyl)amino)phenyl)ethan-1-one HPLC retention time (min.): 4.04; Mass (ESI, Pos. 20V): m/z 523 (M+H)$^+$.

EXAMPLE 84(320)

(Z)-2-(7-methoxy-3,3-dimethyl-3,4-dihydro-(2H)-isoquinolin-1-ylidene)-1-(3-((naphthalen-2-ylsulfonyl)amino)phenyl)ethan-1-one HPLC retention time (min.): 4.20; Mass (ESI, Pos. 20V): m/z 513 (M+H)$^+$.

EXAMPLE 84(321)

(Z)-2-(7-methoxy-3,3-dimethyl-3,4-dihydro-(2H)-isoquinolin-1-ylidene)-1-(3-((2-(naphthalen-1-yl)ethylsulfonyl)amino)phenyl)ethan-1-one HPLC retention time (min.): 4.31; Mass (ESI, Pos. 20V): m/z 541 (M+H)$^+$.

EXAMPLE 84(322)

(Z)-2-(7-methoxy-3,3-dimethyl-3,4-dihydro-(2H)-isoquinolin-1-ylidene)-1-(3-((2-phenylethenyl sulfonyl)amino)phenyl)ethan-1-one HPLC retention time (min.): 4.15; Mass (ESI, Pos. 20V): m/z 489 (M+H)$^+$.

EXAMPLE 84(323)

(Z)-2-(7-methoxy-3,3-dimethyl-3,4-dihydro-(2H)-isoquinolin-1-ylidene)-1-(3-((furan-2-ylsulfonyl)amino)phenyl)ethan-1-one HPLC retention time (min.): 3.98; Mass (ESI, Pos. 20V): m/z 453 (M+H)$^+$.

EXAMPLE 84(324)

(Z)-2-(7-methoxy-3,3-dimethyl-3,4-dihydro-(2H)-isoquinolin-1-ylidene)-1-(3-((thiophen-2-ylsulfonyl)amino)phenyl)ethan-1-one HPLC retention time (min.): 4.02; Mass (ESI, Pos. 20V): m/z 469 (M+H)$^+$.

EXAMPLE 84(325)

(Z)-2-(7-methoxy-3,3-dimethyl-3,4-dihydro-(2H)-isoquinolin-1-ylidene)-1-(3-((4-bromo-2,5-dichlorothiophen-3-ylsulfonyl)amino)phenyl)ethan-1-one HPLC retention time (min.): 4.40; Mass (ESI, Pos. 20V): m/z 617 (M+H)$^+$.

EXAMPLE 84(326)

(Z)-2-(7-methoxy-3,3-dimethyl-3,4-dihydro-(2H)-isoquinolin-1-ylidene)-1-(3-((5-phenylsulfonylthiophen-2-ylsulfonyl)amino)phenyl)ethan-1-one HPLC retention time (min.): 4.18; Mass (ESI, Pos. 20V): m/z 609 (M+H)$^+$.

EXAMPLE 84(327)

(Z)-2-(7-methoxy-3,3-dimethyl-3,4-dihydro-(2H)-isoquinolin-1-ylidene)-1-(3-(7-chloro-2,1,3-benzoxadiazol-4-ylsulfonyl)amino)phenyl)ethan-1-one HPLC retention time (min.): 4.17; Mass (ESI, Pos. 20V): m/z 539 (M+H)$^+$.

EXAMPLE 84(328)

(Z)-2-(7-methoxy-3,3-dimethyl-3,4-dihydro-(2H)-isoquinolin-1-ylidene)-1-(3-(2-acetylamino-4-methylthioazol-5-ylsulfonyl)amino)phenyl)ethan-1-one HPLC retention time (min.): 3.82; Mass (ESI, Pos. 20V): m/z 541 (M+H)$^+$.

EXAMPLE 84(329)

(Z)-2-(7-methoxy-3,3-dimethyl-3,4-dihydro-(2H)-isoquinolin-1-ylidene)-1-(3-(2-methoxydibenzo[b,d]furan-3-ylsulfonyl)amino)phenyl)ethan-1-one HPLC retention time (min.): 4.34; Mass (ESI, Pos. 20V): m/z 583 (M+H)$^+$.

EXAMPLE 84(330)

(Z)-2-(7-methoxy-3,3-dimethyl-3,4-dihydro-(2H)-isoquinolin-1-ylidene)-1-(3-(3,4-dichlorophenylsulfonyl)amino)phenyl)ethan-1-one HPLC retention time (min.): 4.33; Mass (ESI, Pos. 20V): m/z 531 (M+H)$^+$.

EXAMPLE 84(331)

(Z)-2-(7-methoxy-3,3-dimethyl-3,4-dihydro-(2H)-isoquinolin-1-ylidene)-1-(3-(4-methoxyphenylsulfonyl)amino)phenyl)ethan-1-one HPLC retention time (min.): 4.05; Mass (ESI, Pos. 20V): m/z 493 (M+H)$^+$.

EXAMPLE 84(332)

(Z)-2-(7-methoxy-3,3-dimethyl-3,4-dihydro-(2H)-isoquinolin-1-ylidene)-1-(3-(benzylsulfonyl)amino)phenyl)ethan-1-one HPLC retention time (min.): 4.07; Mass (ESI, Pos. 20V): m/z 477 (M+H)$^+$.

EXAMPLE 84(333)

(Z)-2-(7-methoxy-3,3-dimethyl-3,4-dihydro-(2H)-isoquinolin-1-ylidene)-1-(3-(phenylsulfonyl)amino)phenyl)ethan-1-one HPLC retention time (min.): 4.04; Mass (ESI, Pos. 20V): m/z 463 (M+H)$^+$.

EXAMPLE 84(334)

(Z)-2-(7-methoxy-3,3-dimethyl-3,4-dihydro-(2H)-isoquinolin-1-ylidene)-1-(3-(4-methylphenylsulfonyl)amino)phenyl)ethan-1-one HPLC retention time (min.): 4:1; Mass (ESI, Pos. 20V): m/z 477 (M+H)$^+$.

EXAMPLE 84(335)

(Z)-2-(7-methoxy-3,3-dimethyl-3,4-dihydro-(2H)-isoquinolin-1-ylidene)-1-(3-(3-methylphenylsulfonyl)amino)phenyl)ethan-1-one HPLC retention time (min.): 4.12; Mass (ESI, Pos. 20V): m/z 477 (M+H)$^+$.

EXAMPLE 84(336)

(Z)-2-(7-methoxy-3,3-dimethyl-3,4-dihydro-(2H)-isoquinolin-1-ylidene)-1-(3-(2-fluorophenylsulfonyl)amino)phenyl)ethan-1-one HPLC retention time (min.): 4.05; Mass (ESI, Pos. 20V): m/z 481 (M+H)$^+$.

EXAMPLE 84(337)

(Z)-2-(7-methoxy-3,3-dimethyl-3,4-dihydro-(2H)-isoquinolin-1-ylidene)-1-(3-(4-cyanophenylsulfonyl)amino)phenyl)ethan-1-one HPLC retention time (min.): 4.03; Mass (ESI, Pos. 20V): m/z 488 (M+H)$^+$.

EXAMPLE 84(338)

(Z)-2-(7-methoxy-3,3-dimethyl-3,4-dihydro-(2H)-isoquinolin-1-ylidene)-1-(3-(2-cyanophenylsulfonyl)amino)phenyl)ethan-1-one HPLC retention time (min.): 3.99; Mass (ESI, Pos. 20V): m/z 488 (M+H)$^+$.

EXAMPLE 84(339)

(Z)-2-(7-methoxy-3,3-dimethyl-3,4-dihydro-(2H)-isoquinolin-1-ylidene)-1-(3-(4-ethenylphenylsulfonyl)amino)phenyl)ethan-1-one HPLC retention time (min.): 4.16; Mass (ESI, Pos. 20V): m/z 489 (M+H)$^+$.

EXAMPLE 84(340)

(Z)-2-(7-methoxy-3,3-dimethyl-3,4-dihydro-(2H)-isoquinolin-1-ylidene)-1-(3-(quinolin-8-ylsulfonyl)amino)phenyl)ethan-1-one HPLC retention time (min.): 4.06; Mass (ESI, Pos. 20V): m/z 514 (M+H)$^+$.

EXAMPLE 84(341)

(Z)-2-(7-methoxy-3,3-dimethyl-3,4-dihydro-(2H)-isoquinolin-1-ylidene)-1-(3-(4-acetylaminophenylsulfonyl)amino)phenyl)ethan-1-one HPLC retention time (min.): 3.81; Mass (ESI, Pos. 20V): m/z 520 (M+H)$^+$.

EXAMPLE 84(342)

(Z)-2-(7-methoxy-3,3-dimethyl-3,4-dihydro-(2H)-isoquinolin-1-ylidene)-1-(3-(2-chloro-4-cyanophenylsulfonyl)amino)phenyl)ethan-1-one HPLC retention time (min.): 4.09; Mass (ESI, Pos. 20V): m/z 522 (M+H)$^+$.

EXAMPLE 84(343)

(Z)-2-(7-methoxy-3,3-dimethyl-3,4-dihydro-(2H)-isoquinolin-1-ylidene)-1-(3-(3-methoxyphenylsulfonyl)amino)phenyl)ethan-1-one HPLC retention time (min.): 4.06; Mass (ESI, Pos. 20V): m/z 493 (M+H)$^+$.

EXAMPLE 84(344)

(Z)-2-(7-methoxy-3,3-dimethyl-3,4-dihydro-(2H)-isoquinolin-1-ylidene)-1-(3-(2-nitro-4-methoxyphenylsulfonyl)amino)phenyl)ethan-1-one HPLC retention time (min.): 4.11; Mass (ESI, Pos. 20V): m/z 538 (M+H)$^+$.

EXAMPLE 84(345)

(Z)-2-(7-methoxy-3,3-dimethyl-3,4-dihydro-(2H)-isoquinolin-1-ylidene)-1-(3-(2-methoxy-5-methylphenyl sulfonyl)amino)phenyl)ethan-1-one HPLC retention time (min.): 4.13; Mass (ESI, Pos. 20V): m/z 507 (M+H)$^+$.

EXAMPLE 84(346)

(Z)-2-(7-methoxy-3,3-dimethyl-3,4-dihydro-(2H)-isoquinolin-1-ylidene)-1-(3-(2,4,6-trimethylphenylsulfonyl)amino)phenyl)ethan-1-one HPLC retention time (min.): 4.28; Mass (ESI, Pos. 20V): m/z 505 (M+H)$^+$.

EXAMPLE 84(347)

(Z)-2-(7-methoxy-3,3-dimethyl-3,4-dihydro-(2H)-isoquinolin-1-ylidene)-1-(3-(4-butoxyphenylsulfonyl)amino)phenyl)ethan-1-one HPLC retention time (min.): 4.36; Mass (ESI, Pos. 20V): m/z 535 (M+H)$^+$.

EXAMPLE 84(348)

(Z)-2-(7-methoxy-3,3-dimethyl-3,4-dihydro-(2H)-isoquinolin-1-ylidene)-1-(3-(4-fluorophenylsulfonyl)amino)phenyl)ethan-1-one HPLC retention time (min.): 4.09; Mass (ESI, Pos. 20V): m/z 481 (M+H)$^+$.

EXAMPLE 84(349)

(Z)-2-(7-methoxy-3,3-dimethyl-3,4-dihydro-(2H)-isoquinolin-1-ylidene)-1-(3-(2-methylphenylsulfonyl)amino)phenyl)ethan-1-one HPLC retention time (min.): 4.12; Mass (ESI, Pos. 20V): m/z 477 (M+H)$^+$.

EXAMPLE 84(350)

(Z)-2-(7-methoxy-3,3-dimethyl-3,4-dihydro-(2H)-isoquinolin-1-ylidene)-1-(3-(3-chloro-4-methylphenylsulfonyl)amino)phenyl)ethan-1-one HPLC retention time (min.): 4.29; Mass (ESI, Pos. 20V): m/z 511 (M+H)$^+$.

EXAMPLE 84(351)

(Z)-2-(7-methoxy-3,3-dimethyl-3,4-dihydro-(2H)-isoquinolin-1-ylidene)-1-(3-(2-chloro-6-methylphenylsulfonyl)amino)phenyl)ethan-1-one HPLC retention time (min.): 4.18; Mass (ESI, Pos. 20V): m/z 511 (M+H)$^+$.

EXAMPLE 84(352)

(Z)-2-(7-methoxy-3,3-dimethyl-3,4-dihydro-(2H)-isoquinolin-1-ylidene)-1-(3-(3-nitro-4-methylphenylsulfonyl)amino)phenyl)ethan-1-one HPLC retention time (min.): 4.15; Mass (ESI, Pos. 20V): m/z 522 (M+H)$^+$.

EXAMPLE 84(353)

(Z)-2-(7-methoxy-3,3-dimethyl-3,4-dihydro-(2H)-isoquinolin-1-ylidene)-1-(3-(2-trifluoromethylphenylsulfonyl)amino)phenyl)ethan-1-one HPLC retention time (min.): 4.16; Mass (ESI, Pos. 20V): m/z 531 (M+H)$^+$.

EXAMPLE 84(354)

(Z)-2-(7-methoxy-3,3-dimethyl-3,4-dihydro-(2H)-isoquinolin-1-ylidene)-1-(3-(3-trifluoromethylphenylsulfonyl)amino)phenyl)ethan-1-one HPLC retention time (min.): 4.21; Mass (ESI, Pos. 20V): m/z 531 (M+H)$^+$.

EXAMPLE 84(355)

(Z)-2-(7-methoxy-3,3-dimethyl-3,4-dihydro-(2H)-isoquinolin-1-ylidene)-1-(3-(5-bromo-2-methoxyphenylsulfonyl)amino)phenyl)ethan-1-one HPLC retention time (min.): 4.22; Mass (ESI, Pos. 20V): m/z 571 (M+H)$^+$, 573 (M+2+H)$^+$.

EXAMPLE 84(356)

(Z)-2-(7-methoxy-3,3-dimethyl-3,4-dihydro-(2H)-isoquinolin-1-ylidene)-1-(3-(2-nitro-4-trifluoromethylphenylsulfonyl)amino)phenyl)ethan-1-one HPLC retention time (min.): 4.22; Mass (ESI, Pos. 20V): m/z 576 (M+H)$^+$.

EXAMPLE 84(357)

(Z)-2-(7-methoxy-3,3-dimethyl-3,4-dihydro-(2H)-isoquinolin-1-ylidene)-1-(3-(4-bromo-2-trifluoromethoxyphenylsulfonyl)amino)phenyl)ethan-1-one HPLC retention time (min.): 4.38; Mass (ESI, Pos. 20V): m/z 625 (M+H)$^+$, 627 (M+2+H)$^+$.

EXAMPLE 84(358)

(Z)-2-(7-methoxy-3,3-dimethyl-3,4-dihydro-(2H)-isoquinolin-1-ylidene)-1-(3-(4-isopropylphenylsulfonyl)amino)phenyl)ethan-1-one HPLC retention time (min.): 4.29; Mass (ESI, Pos. 20V): m/z 505 (M+H)$^+$.

EXAMPLE 84(359)

(Z)-2-(7-methoxy-3,3-dimethyl-3,4-dihydro-(2H)-isoquinolin-1-ylidene)-1-(3-(naphthalen-1-ylsulfonyl)amino)phenyl)ethan-1-one HPLC retention time (min.): 4.20; Mass (ESI, Pos. 20V): m/z 513 (M+H)$^+$.

EXAMPLE 84(360)

(Z)-2-(7-methoxy-3,3-dimethyl-3,4-dihydro-(2H)-isoquinolin-1-ylidene)-1-(3-(4-t-butylphenylsulfonyl)amino)phenyl)ethan-1-one HPLC retention time (min.): 4.33; Mass (ESI, Pos. 20V): m/z 519 (M+H)$^+$.

EXAMPLE 84(361)

(Z)-2-(7-methoxy-3,3-dimethyl-3,4-dihydro-(2H)-isoquinolin 1-ylidene)-1-(3-(5-dimethylaminonaphthalen-1-ylsulfonyl)amino)phenyl)ethan-1-one HPLC retention time (min.): 3.95; Mass (ESI, Pos. 20V): m/z 556 (M+H)$^+$.

EXAMPLE 84(362)

(Z)-2-(7-methoxy-3,3-dimethyl-3,4-dihydro-(2H)-isoquinolin-1-ylidene)-1-(3-(5-((phenylcarbonyl)aminomethyl)thiophen-2-ylsulfonyl)amino)phenyl)ethan-1-one HPLC retention time (min.): 4.02; Mass (ESI, Pos. 20V): m/z 602 (M+H)$^+$.

EXAMPLE 84(363)

(Z)-2-(7-methoxy-3,3-dimethyl-3,4-dihydro-(2H)-isoquinolin-1-ylidene)-1-(4-(mesylamino)phenyl)ethan-1-one HPLC retention time (min.): 3.75; Mass (ESI, Pos. 20V): m/z 401 (M+H)$^+$.

EXAMPLE 84(364)

(Z)-2-(7-methoxy-3,3-dimethyl-3,4-dihydro-(2H)-isoquinolin-1-ylidene)-1-(4-((pentylsulfonyl)amino)phenyl)ethan-1-one HPLC retention time (min.): 4.13; Mass (ESI, Pos. 20V): m/z 457 (M+H)$^+$.

EXAMPLE 84(365)

(Z)-2-(7-methoxy-3,3-dimethyl-3,4-dihydro-(2H)-isoquinolin-1-ylidene)-1-(4-((isopropylsulfonyl)amino)phenyl)ethan-1-one HPLC retention time (min.): 3.91; Mass (ESI, Pos. 20V): m/z 429 (M+H)$^+$.

EXAMPLE 84(366)

(Z)-2-(7-methoxy-3,3-dimethyl-3,4-dihydro-(2H)-isoquinolin-1-ylidene)-1-(4-((4-chlorophenyl sulfonyl)amino)phenyl)ethan-1-one HPLC retention time (min.): 4.16; Mass (ESI, Pos. 20V): m/z 497 (M+H)$^+$.

EXAMPLE 84(367)

(Z)-2-(7-methoxy-3,3-dimethyl-3,4-dihydro-(2H)-isoquinolin-1-ylidene)-1-(4-((2-iodophenylsulfonyl)amino)phenyl)ethan-1-one HPLC retention time (min.): 4.11; Mass (ESI, Pos. 20V): m/z 589 (M+H)$^+$.

EXAMPLE 84(368)

(Z)-2-(7-methoxy-3,3-dimethyl-3,4-dihydro-(2H)-isoquinolin-1-ylidene)-1-(4-((4-nitrophenylsulfonyl)amino)phenyl)ethan-1-one HPLC retention time (min.): 4.06; Mass (ESI, Pos. 20V): m/z 508 (M+H)$^+$.

EXAMPLE 84(369)

(Z)-2-(7-methoxy-3,3-dimethyl-3,4-dihydro-(2H)-isoquinolin-1-ylidene)-1-(4-((4-mesylphenylsulfonyl)amino)phenyl)ethan-1-one HPLC retention time (min.): 3.86; Mass (ESI, Pos. 20V): m/z 541 (M+H)$^+$.

EXAMPLE 84(370)

(Z)-2-(7-methoxy-3,3-dimethyl-3,4-dihydro-(2H)-isoquinolin-1-ylidene)-1-(4-((4-trifluoromethylphenylsulfonyl)amino)phenyl)ethan-1-one HPLC retention time (min.): 4.21; Mass (ESI, Pos. 20V): m/z 531 (M+H)$^+$.

EXAMPLE 84(371)

(Z)-2-(7-methoxy-3,3-dimethyl-3,4-dihydro-(2H)-isoquinolin-1-ylidene)-1-(4-((4-phenylphenyl sulfonyl)amino)phenyl)ethan-1-one HPLC retention time (min.): 4.28; Mass (ESI, Pos. 20V): m/z 539 (M+H)$^+$.

EXAMPLE 84(372)

(Z)-2-(7-methoxy-3,3-dimethyl-3,4-dihydro-(2H)-isoquinolin-1-ylidene)-1-(4-((2-phenylphenylsulfonyl)amino)phenyl)ethan-1-one HPLC retention time (min.): 4.25; Mass (ESI, Pos. 20V): m/z 539 (M+H)$^+$.

EXAMPLE 84(373)

(Z)-2-(7-methoxy-3,3-dimethyl-3,4-dihydro-(2H)-isoquinolin-1-ylidene)-1-(4-((2,6-difluorophenylsulfonyl)amino)phenyl)ethan-1-one HPLC retention time (min.): 4.02; Mass (ESI, Pos. 20V): m/z 499 (M+H)$^+$.

EXAMPLE 84(374)

(Z)-2-(7-methoxy-3,3-dimethyl-3,4-dihydro-(2H)-isoquinolin-1-ylidene)-1-(4-((2,5-difluorophenylsulfonyl)amino)phenyl)ethan-1-one HPLC retention time (min.): 4.07; Mass (ESI, Pos. 20V): m/z 499 (M+H)$^+$.

EXAMPLE 84(375)

(Z)-2-(7-methoxy-3,3-dimethyl-3,4-dihydro-(2H)-isoquinolin-1-ylidene)-1-(4-((2,5-dimethoxyphenylsulfonyl)amino)phenyl)ethan-1-one HPLC retention time (min.): 4.01; Mass (ESI, Pos. 20V): m/z 523 (M+H)$^+$.

EXAMPLE 84(376)

(Z)-2-(7-methoxy-3,3-dimethyl-3,4-dihydro-(2H)-isoquinolin-1-ylidene)-1-(4-((naphthalen-2-ylsulfonyl)amino)phenyl)ethan-1-one HPLC retention time (min.): 4.17; Mass (ESI, Pos. 20V): m/z 513 (M+H)$^+$.

EXAMPLE 84(377)

(Z)-2-(7-methoxy-3,3-dimethyl-3,4-dihydro-(2H)-isoquinolin-1-ylidene)-1-(4-((2-(naphthalen-1-yl)ethyl sulfonyl)amino)phenyl)ethan-1-one HPLC retention time (min.): 4.27; Mass (ESI, Pos. 20V): m/z 541 (M+H)$^+$.

EXAMPLE 84(378)

(Z)-2-(7-methoxy-3,3-dimethyl-3,4-dihydro-(2H)-isoquinolin-1-ylidene)-1-(4-((2-phenylethenylsulfonyl)amino)phenyl)ethan-1-one HPLC retention time (min.): 4.10; Mass (ESI, Pos. 20V): m/z 489 (M+H)$^+$.

EXAMPLE 84(379)

(Z)-2-(7-methoxy-3,3-dimethyl-3,4-dihydro-(2H)-isoquinolin-1-ylidene)-1-(4-((furan-2-ylsulfonyl)amino)phenyl)ethan-1-one HPLC retention time (min.): 3.94; Mass (ESI, Pos. 20V): m/z 453 (M+H)$^+$.

EXAMPLE 84(380)

(Z)-2-(7-methoxy-3,3-dimethyl-3,4-dihydro-(2H)-isoquinolin-1-ylidene)-1-(4-((thiophen-2-ylsulfonyl)amino)phenyl)ethan-1-one HPLC retention time (min.): 3.98; Mass (ESI, Pos. 20V): m/z 469 (M+H)$^+$.

EXAMPLE 84(381)

(Z)-2-(7-methoxy-3,3-dimethyl-3,4-dihydro-(2H)-isoquinolin-1-ylidene)-1-(4-((4-bromo-2,5-dichlorothiophen-3-ylsulfonyl)amino)phenyl)ethan-1-one HPLC retention time (min.): 4.36; Mass (ESI, Pos. 20V): m/z 617 (M+H)$^+$.

EXAMPLE 84(382)

(Z)-2-(7-methoxy-3,3-dimethyl-3,4-dihydro-(2H)-isoquinolin-1-ylidene)-1-(4-((5-phenylsulfonylthiophen-2-ylsulfonyl)amino)phenyl)ethan-1-one HPLC retention time (min.): 4.16; Mass (ESI, Pos. 20V): m/z 609 (M+H)$^+$.

EXAMPLE 84(383)

(Z)-2-(7-methoxy-3,3-dimethyl-3,4-dihydro-(2H)-isoquinolin-1-ylidene)-1-(4-(7-chloro-2,1,3-benzoxadiazol-4-ylsulfonyl)amino)phenyl)ethan-1-one HPLC retention time (min.): 4.15; Mass (ESI, Pos. 20V): m/z 539 (M+H)$^+$.

EXAMPLE 84(384)

(Z)-2-(7-methoxy-3,3-dimethyl-3,4-dihydro-(2H)-isoquinolin-1-ylidene)-1-(4-(2-acetylamino-4-methylthiazol-5-ylsulfonyl)amino)phenyl)ethan-1-one HPLC retention time (min.): 3.81; Mass (ESI, Pos. 20V): m/z 541 (M+H)$^+$.

EXAMPLE 84(385)

(Z)-2-(7-methoxy-3,3-dimethyl-3,4-dihydro-(2H)-isoquinolin-1-ylidene)-1-(4-(2-methoxydibenzo[b,d]furan-3-ylsulfonyl)amino)phenyl)ethan-1-one HPLC retention time (min.): 4.29; Mass (ESI, Pos. 20V): m/z 583 (M+H)$^+$.

EXAMPLE 84(386)

(Z)-2-(7-methoxy-3,3-dimethyl-3,4-dihydro-(2H)-isoquinolin-1-ylidene)-1-(4-(3,4-dichlorophenylsulfonyl)amino)phenyl)ethan-1-one HPLC retention time (min.): 4.28; Mass (ESI, Pos. 20V): m/z 531 (M+H)$^+$.

EXAMPLE 84(387)

(Z)-2-(7-methoxy-3,3-dimethyl-3,4-dihydro-(2H)-isoquinolin-1-ylidene)-1-(4-(4-methoxyphenylsulfonyl)amino)phenyl)ethan-1-one HPLC retention time (min.): 4.01; Mass (ESI, Pos. 20V): m/z 493 (M+H)$^+$.

EXAMPLE 84(388)

(Z)-2-(7-methoxy-3,3-dimethyl-3,4-dihydro-(2H)-isoquinolin-1-ylidene)-1-(4-(benzylsulfonyl)amino)phenyl)ethan-1-one HPLC retention time (min.): 4.04; Mass (ESI, Pos. 20V): m/z 477 (M+H)$^+$.

EXAMPLE 84(389)

(Z)-2-(7-methoxy-3,3-dimethyl-3,4-dihydro-(2H)-isoquinolin-1-ylidene)-1-(4-(phenylsulfonyl)amino)phenyl)ethan-1-one HPLC retention time (min.): 4.01; Mass (ESI, Pos. 20V): m/z 463 (M+H)$^+$.

EXAMPLE 84(390)

(Z)-2-(7-methoxy-3,3-dimethyl-3,4-dihydro-(2H)-isoquinolin-1-ylidene)-1-(4-(4-methylphenylsulfonyl)amino)phenyl)ethan-1-one HPLC retention time (min.): 4.08; Mass (ESI, Pos. 20V): m/z 477 (M+H)$^+$.

EXAMPLE 84(391)

(Z)-2-(7-methoxy-3,3-dimethyl-3,4-dihydro-(2H)-isoquinolin-1-ylidene)-1-(4-(3-methylphenylsulfonyl)amino)phenyl)ethan-1-one HPLC retention time (min.): 4.10; Mass (ESI, Pos. 20V): m/z 477 (M+H)$^+$.

EXAMPLE 84(392)

(Z)-2-(7-methoxy-3,3-dimethyl-3,4-dihydro-(2H)-isoquinolin-1-ylidene)-1-(4-(2-fluorophenylsulfonyl)amino)phenyl)ethan-1-one HPLC retention time (min.): 4.01; Mass (ESI, Pos. 20V): m/z 481 (M+H)$^+$.

EXAMPLE 84(393)

(Z)-2-(7-methoxy-3,3-dimethyl-3,4-dihydro-(2H)-isoquinolin-1-ylidene)-1-(4-(4-cyanophenylsulfonyl)amino)phenyl)ethan-1-one HPLC retention time (min.): 4.00; Mass (ESI, Pos. 20V): m/z 488 (M+H)$^+$.

EXAMPLE 84(394)

(Z)-2-(7-methoxy-3,3-dimethyl-3,4-dihydro-(2H)-isoquinolin-1-ylidene)-1-(4-(2-cyanophenylsulfonyl)amino)phenyl)ethan-1-one HPLC retention time (min.): 3.96; Mass (ESI, Pos. 20V): m/z 488 (M+H)$^+$.

EXAMPLE 84(395)

(Z)-2-(7-methoxy-3,3-dimethyl-3,4-dihydro-(2H)-isoquinolin-1-ylidene)-1-(4-(4-ethenylphenylsulfonyl)amino)phenyl)ethan-1-one HPLC retention time (min.): 4.14; Mass (ESI, Pos. 20V): m/z 489 (M+H)$^+$.

EXAMPLE 84(396)

(Z)-2-(7-methoxy-3,3-dimethyl-3,4-dihydro-(2H)-isoquinolin-1-ylidene)-1-(4-(quinolin-8-ylsulfonyl)amino)phenyl)ethan-1-one HPLC retention time (min.): 4.03; Mass (ESI, Pos. 20V): m/z 514 (M+H)$^+$.

EXAMPLE 84(397)

(Z)-2-(7-methoxy-3,3-dimethyl-3,4-dihydro-(2H)-isoquinolin-1-ylidene)-1-(4-(4-acetylaminophenylsulfonyl)amino)phenyl)ethan-1-one HPLC retention time (min.): 3.79; Mass (ESI, Pos. 20V): m/z 520 (M+H)$^+$.

EXAMPLE 84(398)

(Z)-2-(7-methoxy-3,3-dimethyl-3,4-dihydro-(2H)-isoquinolin-1-ylidene)-1-(4-(2-chloro-4-cyanophenylsulfonyl)amino)phenyl)ethan-1-one HPLC retention time (min.): 4.07; Mass (ESI, Pos. 20V): m/z 522 (M+H)$^+$.

EXAMPLE 84(399)

(Z)-2-(7-methoxy-3,3-dimethyl-3,4-dihydro-(2H)-isoquinolin-1-ylidene)-1-(4-(3-methoxyphenylsulfonyl)amino)phenyl)ethan-1-one HPLC retention time (min.): 4.04; Mass (ESI, Pos. 20V): m/z 493 (M+H)$^+$.

EXAMPLE 84(400)

(Z)-2-(7-methoxy-3,3-dimethyl-3,4-dihydro-(2H)-isoquinolin-1-ylidene)-1-(4-(2-nitro-4-methoxyphenylsulfonyl)amino)phenyl)ethan-1-one HPLC retention time (min.): 4.08; Mass (ESI, Pos. 20V): m/z 538 (M+H)$^+$.

EXAMPLE 84(401)

(Z)-2-(7-methoxy-3,3-dimethyl-3,4-dihydro-(2H)-isoquinolin-1-ylidene)-1-(4-(2-methoxy-5-methylphenylsulfonyl)amino)phenyl)ethan-1-one HPLC retention time (min.): 4.08; Mass (ESI, Pos. 20V): m/z 507 (M+H)$^+$.

EXAMPLE 84(402)

(Z)-2-(7-methoxy-3,3-dimethyl-3,4-dihydro-(2H)-isoquinolin-1-ylidene)-1-(4-(2,4,6-trimethylphenylsulfonyl)amino)phenyl)ethan-1-one HPLC retention time (min.): 4.25; Mass (ESI, Pos. 20V): m/z 505 (M+H)$^+$.

EXAMPLE 84(403)

(Z)-2-(7-methoxy-3,3-dimethyl-3,4-dihydro-(2H)-isoquinolin-1-ylidene)-1-(4-(4-butoxyphenylsulfonyl)amino)phenyl)ethan-1-one HPLC retention time (min.): 4.33; Mass (ESI, Pos. 20V): m/z 535 (M+H)$^+$.

EXAMPLE 84(404)

(Z)-2-(7-methoxy-3,3-dimethyl-3,4-dihydro-(2H)-isoquinolin-1-ylidene)-1-(4-(4-fluorophenylsulfonyl)amino)phenyl)ethan-1-one HPLC retention time (min.): 4.06; Mass (ESI, Pos. 20V): m/z 481 (M+H)$^+$.

EXAMPLE 84(405)

(Z)-2-(7-methoxy-3,3-dimethyl-3,4-dihydro-(2H)-isoquinolin-1-ylidene)-1-(4-(2-methylphenylsulfonyl)amino)phenyl)ethan-1-one HPLC retention time (min.): 4.08; Mass (ESI, Pos. 20V): m/z 477 (M+H)$^+$.

EXAMPLE 84(406)

(Z)-2-(7-methoxy-3,3-dimethyl-3,4-dihydro-(2H)-isoquinolin-1-ylidene)-1-(4-(3-chloro-4-methylphenylsulfonyl)amino)phenyl)ethan-1-one HPLC retention time (min.): 4.24; Mass (ESI, Pos. 20V): m/z 511 (M+H)$^+$.

EXAMPLE 84(407)

(Z)-2-(7-methoxy-3,3-dimethyl-3,4-dihydro-(2H)-isoquinolin-1-ylidene)-1-(4-(2-chloro-6-methylphenylsulfonyl)amino)phenyl)ethan-1-one HPLC retention time (min.): 4.15; Mass (ESI, Pos. 20V): m/z 511 (M+H)$^+$.

EXAMPLE 84(408)

(Z)-2-(7-methoxy-3,3-dimethyl-3,4-dihydro-(2H)-isoquinolin-1-ylidene)-1-(4-(3-nitro-4-methylphenylsulfonyl)amino)phenyl)ethan-1-one HPLC retention time (min.): 4.11; Mass (ESI, Pos. 20V): m/z 522 (M+H)$^+$.

EXAMPLE 84(409)

(Z)-2-(7-methoxy-3,3-dimethyl-3,4-dihydro-(2H)-isoquinolin-1-ylidene)-1-(4-(2-trifluoromethylphenylsulfonyl)amino)phenyl)ethan-1-one HPLC retention time (min.): 4.13; Mass (ESI, Pos. 20V): m/z 531 (M+H)$^+$.

EXAMPLE 84(410)

(Z)-2-(7-methoxy-3,3-dimethyl-3,4-dihydro-(2H)-isoquinolin-1-ylidene)-1-(4-(3-trifluoromethylphenylsulfonyl)amino)phenyl)ethan-1-one HPLC retention time (min.): 4.19; Mass (ESI, Pos. 20V): m/z 531 (M+H)$^+$.

EXAMPLE 84(411)

(Z)-2-(7-methoxy-3,3-dimethyl-3,4-dihydro-(2H)-isoquinolin-1-ylidene)-1-(4-(5-bromo-2-methoxyphenylsulfonyl)amino)phenyl)ethan-1-one HPLC retention time (min.): 4.18; Mass (ESI, Pos. 20V): m/z 571 (M+H)$^+$, 573 (M+2H)$^+$.

EXAMPLE 84(412)

(Z)-2-(7-methoxy-3,3-dimethyl-3,4-dihydro-(2H)-isoquinolin-1-ylidene)-1-(4-(4-bromo-2-trifluoromethoxyphenylsulfonyl)amino)phenyl)ethan-1-one HPLC retention time (min.): 4.34; Mass (ESI, Pos. 20V): m/z 625 (M+1H)$^+$, 627 (M+2H)$^+$.

EXAMPLE 84(413)

(Z)-2-(7-methoxy-3,3-dimethyl-3,4-dihydro-(2H)-isoquinolin-1-ylidene)-1-(4-(4-isopropylphenylsulfonyl)amino)phenyl)ethan-1-one HPLC retention time (min.): 4.25; Mass (ESI, Pos. 20V): m/z 505 (M+H)$^+$.

EXAMPLE 84(414)

(Z)-2-(7-methoxy-3,3-dimethyl-3,4-dihydro-(2H)-isoquinolin-1-ylidene)-1-(4-(naphthalen-1-ylsulfonyl)amino)phenyl)ethan-1-one HPLC retention time (min.): 4.16; Mass (ESI, Pos. 20V): m/z 513 (M+H)$^+$.

EXAMPLE 84(415)

(Z)-2-(7-methoxy-3,3-dimethyl-3,4-dihydro-(2H)-isoquinolin-1-ylidene)-1-(4-(4-t-butylphenylsulfonyl)amino)phenyl)ethan-1-one HPLC retention time (min.): 4.31; Mass (ESI, Pos. 20V): m/z 519 (M+H)$^+$.

EXAMPLE 84(416)

(Z)-2-(7-methoxy-3,3-dimethyl-3,4-dihydro-(2H)-isoquinolin-1-ylidene)-1-(4-(5-dimethylaminonaphthalen-1-ylsulfonyl)amino)phenyl)ethan-1-one HPLC retention time (min.): 3.91; Mass (ESI, Pos. 20V): m/z 556 (M+H)$^+$.

EXAMPLE 84(417)

(Z)-2-(7-methoxy-3,3-dimethyl-3,4-dihydro-(2H)-isoquinolin-1-ylidene)-1-(4-(5-((phenylcarbonyl)aminomethyl)thiophen-2-yl sulfonyl)amino)phenyl)ethan-1-one HPLC retention time (min.): 3.99; Mass (ESI, Pos. 20V): m/z 602 (M+H)$^+$.

EXAMPLE 84(418)

(Z)-2-(7-methoxy-3,3-dimethyl-3,4-dihydro-(2H)-isoquinolin-1-ylidene)-1-(3-((isobutyloxycarbonyl)amino)phenyl)ethan-1-one HPLC retention time (min.): 4.24; Mass (ESI, Pos. 20V): m/z 423 (M+H)$^+$.

EXAMPLE 84(419)

(Z)-2-(7-methoxy-3,3-dimethyl-3,4-dihydro-(2H)-isoquinolin-1-ylidene)-1-(3-((2-ethylhexyloxycarbonyl)amino)phenyl)ethan-1-one HPLC retention time (min.): 4.66; Mass (ESI, Pos. 20V): m/z 479 (M+H)$^+$.

EXAMPLE 84(420)

(Z)-2-(7-methoxy-3,3-dimethyl-3,4-dihydro-(2H)-isoquinolin-1-ylidene)-1-(3-((ethoxycarbonyl)amino)phenyl)ethan-1-one HPLC retention time (min.): 4.02; Mass (ESI, Pos. 20V): m/z 395 (M+H)$^+$.

EXAMPLE 84(421)

(Z)-2-(7-methoxy-3,3-dimethyl-3,4-dihydro-(2H)-isoquinolin-1-ylidene)-1-(3-((2-propenyloxycarbonyl)amino)phenyl)ethan-1-one HPLC retention time (min.): 4.07; Mass (ESI, Pos. 20V): m/z 407 (M+H)$^+$.

EXAMPLE 84(422)

(Z)-2-(7-methoxy-3,3-dimethyl-3,4-dihydro-(2H)-isoquinolin-1-ylidene)-1-(3'-((propoxycarbonyl)amino)phenyl)ethan-1-one HPLC retention time (min.): 4.15; Mass (ESI, Pos. 20V): m/z 409 (M+H)$^+$.

EXAMPLE 84(423)

(Z)-2-(7-methoxy-3,3-dimethyl-3,4-dihydro-(2H)-isoquinolin-1-ylidene)-1-(3-((butoxycarbonyl)amino)phenyl)ethan-1-one HPLC retention time (min.): 4.26; Mass (ESI, Pos. 20V): m/z 423 (M+H)$^+$.

EXAMPLE 84(424)

(Z)-2-(7-methoxy-3,3-dimethyl-3,4-dihydro-(2H)-isoquinolin-1-ylidene)-1-(3-((hexyloxycarbonyl)amino)phenyl)ethan-1-one HPLC retention time (min.): 4.48; Mass (ESI, Pos. 20V): m/z 451 (M+H)$^+$.

EXAMPLE 84(425)

(Z)-2-(7-methoxy-3,3-dimethyl-3,4-dihydro-(2H)-isoquinolin-1-ylidene)-1-(3-((2,2,2,-trichloroethoxycarbonyl)amino)phenyl)ethan-1-one HPLC retention time (min.): 4.32; Mass (ESI, Pos. 20V): m/z 497 (M+H)$^+$, 499 (M+2+H)$^+$.

EXAMPLE 84(426)

(Z)-2-(7-methoxy-3,3-dimethyl-3,4-dihydro-(2H)-isoquinolin-1-ylidene)-1-(3-(((1R,2S,5R)-2-isopropyl-5-methylcyclohexyloxycarbonyl)amino)phenyl)ethan-1-one HPLC retention time (min.): 4.74; Mass (ESI, Pos. 20V): m/z 505 (M+H)$^+$.

EXAMPLE 84(427)

(Z)-2-(7-methoxy-3,3-dimethyl-3,4-dihydro-(2H)-isoquinolin-1-ylidene)-1-(3-((isopropyloxycarbonyl)amino)phenyl)ethan-1-one HPLC retention time (min.): 4.13; Mass (ESI, Pos. 20V): m/z 409 (M+H)$^+$.

EXAMPLE 84(428)

(Z)-2-(7-methoxy-3,3-dimethyl-3,4-dihydro-(2H)-isoquinolin-1-ylidene)-1-(3-((3-butenyloxycarbonyl)amino)phenyl)ethan-1-one HPLC retention time (min.): 4.16; Mass (ESI, Pos. 20V): m/z 421 (M+H)$^+$.

EXAMPLE 84(429)

(Z)-2-(7-methoxy-3,3-dimethyl-3,4-dihydro-(2H)-isoquinolin-1-ylidene)-1-(3-(((1S,2R,5 S)-2-isopropyl-5-methylcyclohexyloxycarbonyl)amino)phenyl)ethan-1-one HPLC retention time (min.): 4.73; Mass (ESI, Pos. 20V): m/z 505 (M+H)$^+$.

EXAMPLE 84(430)

(Z)-2-(7-methoxy-3,3-dimethyl-3,4-dihydro-(2H)-isoquinolin-1-ylidene)-1-(3-((t-butoxycarbonyl)amino)phenyl)ethan-1-one HPLC retention time (min.): 4.25; Mass (ESI, Pos. 20V): m/z 423 (M+H)$^+$.

EXAMPLE 84(431)

(Z)-2-(7-methoxy-3,3-dimethyl-3,4-dihydro-(2H)-isoquinolin-1-ylidene)-1-(3-((benzyloxycarbonyl)amino)phenyl)ethan-1-one HPLC retention time (min.): 4.25; Mass (ESI, Pos. 20V): m/z 457 (M+H)$^+$.

EXAMPLE 84(432)

(Z)-2-(7-methoxy-3,3-dimethyl-3,4-dihydro-(2H)-isoquinolin-1-ylidene)-1-(4-((isobutyloxycarbonyl)amino)phenyl)ethan-1-one HPLC retention time (min.): 4.20; Mass (ESI, Pos. 20V): m/z 423 (M+H)$^+$.

EXAMPLE 84(433)

(Z)-2-(7-methoxy-3,3-dimethyl-3,4-dihydro-(2H)-isoquinolin-1-ylidene)-1-(4-((2-ethylhexyloxycarbonyl)amino)phenyl)ethan-1-one HPLC retention time (min.): 4.59; Mass (ESI, Pos. 20V): m/z 479 (M+H)$^+$.

EXAMPLE 84(434)

(Z)-2-(7-methoxy-3,3-dimethyl-3,4-dihydro-(2H)-isoquinolin-1-ylidene)-1-(4-((ethoxycarbonyl)amino)phenyl)ethan-1-one HPLC retention time (min.): 3.96; Mass (ESI, Pos. 20V): m/z 395 (M+H)$^+$.

EXAMPLE 84(435)

(Z)-2-(7-methoxy-3,3-dimethyl-3,4-dihydro-(2H)-isoquinolin-1-ylidene)-1-(4-((2-propenyloxycarbonyl)amino)phenyl)ethan-1-one HPLC retention time (min.): 4.03; Mass (ESI, Pos. 20V): m/z 407 (M+H)$^+$.

EXAMPLE 84(436)

(Z)-2-(7-methoxy-3,3-dimethyl-3,4-dihydro-(2H)-isoquinolin-1-ylidene)-1-(4-((propoxycarbonyl)amino)phenyl)ethan-1-one HPLC retention time (min.): 4.08; Mass (ESI, Pos. 20V): m/z 409 (M+H)$^+$.

EXAMPLE 84(437)

(Z)-2-(7-methoxy-3,3-dimethyl-3,4-dihydro-(2H)-isoquinolin-1-ylidene)-1-(4-((butoxycarbonyl)amino)phenyl)ethan-1-one HPLC retention time (min.): 4.19; Mass (ESI, Pos. 20V): m/z 423 (M+H)$^+$.

EXAMPLE 84(438)

(Z)-2-(7-methoxy-3,3-dimethyl-3,4-dihydro-(2H)-isoquinolin-1-ylidene)-1-(4-((hexyloxycarbonyl)amino)phenyl)ethan-1-one HPLC retention time (min.): 4.43; Mass (ESI, Pos. 20V): m/z 451 (M+H)$^+$.

EXAMPLE 84(439)

(Z)-2-(7-methoxy-3,3-dimethyl-3,4-dihydro-(2H)-isoquinolin-1-ylidene)-1-(4-((2,2,2,-trichloroethoxycarbonyl)amino)phenyl)ethan-1-one HPLC retention time (min.): 4.28; Mass (ESI, Pos. 20V): m/z 497 (M+H)$^+$.

EXAMPLE 84(440)

(Z)-2-(7-methoxy-3,3-dimethyl-3,4-dihydro-(2H)-isoquinolin-1-ylidene)-1-(4-(((1R,2S,5R)-2-isopropyl-5-methylcyclohexyloxycarbonyl)amino)phenyl)ethan-1-one HPLC retention time (min.): 4.68; Mass (ESI, Pos. 20V): m/z 505 (M+H)$^+$.

EXAMPLE 84(441)

(Z)-2-(7-methoxy-3,3-dimethyl-3,4-dihydro-(2H)-isoquinolin-1-ylidene)-1-(4-((isopropyloxycarbonyl)amino)phenyl)ethan-1-one HPLC retention time (min.): 4.07; Mass (ESI, Pos. 20V): m/z 409 (M+H)$^+$.

EXAMPLE 84(442)

(Z)-2-(7-methoxy-3,3-dimethyl-3,4-dihydro-(2H)-isoquinolin-1-ylidene)-1-(4-((3-ブテ@ルoxycarbonyl)amino)phenyl)ethan-1-one HPLC retention time (min.): 4.11; Mass (ESI, Pos. 20V): m/z 421 (M+H)$^+$.

EXAMPLE 84(443)

(Z)-2-(7-methoxy-3,3-dimethyl-3,4-dihydro-(2H)-isoquinolin-1-ylidene)-1-(4-(((1S,2R,5 S)-2-isopropyl-5-methylcyclohexyloxycarbonyl)amino)phenyl)ethan-1-one HPLC retention time (min.): 4.69; Mass (ESI, Pos. 20V): m/z 505 (M+H)$^+$.

EXAMPLE 84(444)

(Z)-2-(7-methoxy-3,3-dimethyl-3,4-dihydro-(2H)-isoquinolin-1-ylidene)-1-(4-((benzyloxycarbonyl)amino)phenyl)ethan-1-one HPLC retention time (min.): 4.18; Mass (ESI, Pos. 20V): m/z 457 (M+H)$^+$.

EXAMPLE 85

(Z)-2-(7-methoxy-3,3-dimethyl-3,4-dihydro-(2H)-isoquinolin-1-ylidene)-1-(4-hydroxycarbamoylphenyl)ethan-1-one To a solution of the compound prepared in example 66(1) (0.15 g) in tetrahydrofuran (2 ml) were added triethylamine (89 µl) and chloroethylformate (61 µl) and the mixture was stirred for 1 hour at 0° C. To the reaction mixture was added a 50% aqueous solution of hydroxylamine (0.1 ml) and the mixture was stirred for 1 hour at room temperature. To the reaction mixture was added water and the mixture was extracted with ethyl acetate. The extract was washed with a saturated aqueous solution of sodium bicarbonate, water and brine successively, dried over anhydrous magnesium sulfate and concentrated. The residue was washed with a mixture of hexane and ethyl acetate to give the compound of the present invention (69.8 mg) having the following physical data.

TLC: Rf0.35 (chloroform:methanol=10:1); NMR (DMSO-d$_6$): δ 11.98 (s, 1H), 11.30 (br, 1H), 9.11 (br, 1H), 8.07 (d, J=8.1 Hz, 2H), 7.80 (d, J=8.1 Hz, 2H), 7.57 (d, J=2.6 Hz, 1H), 7.25 (d, J=8.4 Hz, 1H), 7.10 (dd, J=8.4, 2.6 Hz, 1H), 6.47 (s, 1H), 3.85 (s, 3H), 2.85 (s, 2H), 1.28 (s, 6H).

EXAMPLE 86-EXAMPLE 86(27)

By the same procedure as described in example 56 using the compound prepared in reference example 17 or a corresponding derivative and 4-nitrophenacyl bromide or a corresponding derivative, the following compounds of the present invention were given.

EXAMPLE 86

(Z)-2-(6-difluoromethoxy-3,3-dimethyl-2,3-dihydro-(2H)-isoindol-1-ylidene)-1-(4-cyanophenyl)ethan-1-one TLC: Rf0.29 (hexane:ethyl acetate=2:1); NMR (CDCl$_3$): δ 10.54 (br, s, 1H), 8.06 (d, J=9.0 Hz, 2H), 7.75 (d, J=9.0 Hz, 2H), 7.50 (d, J=1.5 Hz, 1H), 7.43 (d, J=8.4 Hz, 1H), 7.34 (dd, J=8.4, 1.5 Hz, 1H), 6.58 (t, J=73.5 Hz, 1H), 6.29 (s, 1H), 1.61 (s, 6H).

EXAMPLE 86(1)

(Z)-2-(6-difluoromethoxy-3,3-dimethyl-2,3-dihydro-(2H)-isoindol-1-ylidene)-1-(4-methoxyphenyl)ethan-1-one TLC: Rf0.30 (hexane:ethyl acetate=2:1); NMR (CDCl$_3$): δ 10.31 (br, s, 1H), 7.99 (d, J=9.0 Hz, 2H), 7.48 (d, J=1.8 Hz, 1H), 7.39 (d, J=8.1 Hz, 1H), 7.29 (dd, J=8.1, 1.8 Hz, 1H), 6.96 (d, J=9.0 Hz, 2H), 6.57 (t, J=73.5 Hz, 1H), 6.30 (s, 1H), 3.88 (s, 3H), 1.58 (s, 6H).

EXAMPLE 86(2)

(Z)-2-(6-methoxy-3,3-diethyl-2,3-dihydro-(2H)-isoindol-1-ylidene)-1-(4-methoxyphenyl)ethan-1-one TLC: Rf0.43 (hexane:ethyl acetate=2:1); NMR (CDCl$_3$): δ 10.20 (br, s, 1H), 8.01 (d, J=9.0 Hz, 2H), 7.22 (d, J=2.4 Hz, 1H), 7.20 (d, J=8.4 Hz, 1H), 7.07 (dd, J=8.4, 2.4 Hz, 1H), 6.96 (d, J=9.0 Hz, 2H), 6.30 (s, 1H), 3.91 (s, 3H), 3.87 (s, 3H), 2.05-1.80 (m, 4H), 0.65 (t, J=7.5 Hz, 6H).

EXAMPLE 86(3)

(Z)-2-(6-methoxy-3,3-diethyl-2,3-dihydro-(2H)-isoindol-1-ylidene)-1-(4-cyanophenyl)ethan-1-one TLC: Rf0.49 (hexane:ethyl acetate=2:1); NMR (CDCl$_3$): δ 10.42 (br, s, 1H), 8.08 (d, J=8.7 Hz, 2H), 7.75 (d, J=8.7 Hz, 2H), 7.24 (d, J=8.4 Hz, 1H), 7.22 (d, J=1.8 Hz, 1H), 7.11 (dd, J=8.4, 1.8 Hz, 1H), 6.29 (s, 1H), 3.91 (s, 3H), 2.10-1.80 (m, 4H), 0.65 (t, J=7.5 Hz, 6H).

EXAMPLE 86(4)

(Z)-2-(6-methoxy-3,3-diethyl-2,3-dihydro-(2H)-isoindol-1-ylidene)-1-(4-nitrophenyl)ethan-1-one TLC: Rf0.57 (hexane:ethyl acetate=2:1); NMR (CDCl$_3$): δ 10.46 (br, s, 1H), 8.30 (d, J=9.0 Hz, 2H), 8.14 (d, J=9.0 Hz, 2H), 7.30-7.20 (m, 2H), 7.12 (dd, J=7.8, 1.8 Hz, 1H), 6.32 (s, 1H), 3.92 (s, 3H), 2.10-1.85 (m, 4H), 0.66 (t, J=7.5 Hz, 6H).

EXAMPLE 86(5)

(Z)-2-(6-methoxy-3,3-diethyl-2,3-dihydro-(2H)-isoindol-1-ylidene)-1-(3-nitrophenyl)ethan-1-one TLC: Rf0.55 (hexane:ethyl acetate=2:1); NMR (CDCl$_3$): δ 10.50-10.35 (br, 1H), 8.83 (t, J=2.1 Hz, 1H), 8.40-8.25 (m, 2H), 7.64 (t, J=7.8 Hz, 1H), 7.30-7.20 (m, 2H), 7.13 (dd, J=8.4, 2.4 Hz, 1H), 6.34 (s, 1H), 3.94 (s, 3H), 2.10-1.85 (m, 4H), 0.66 (t, J=7.5 Hz, 6H).

EXAMPLE 86(6)

(Z)-2-(6-methoxy-2,2-dimethyl-2,3-dihydro-(4H)-1,3-benzothiazin-4-ylidene)-1-(4-cyanophenyl)ethan-1-one TLC: Rf0.40 (hexane:ethyl acetate=3:1); NMR (CDCl$_3$): δ 12.49 (s, 1H), 7.99 (d, J=8.4 Hz, 2H), 7.73 (d, J=8.4 Hz, 2H), 7.33 (d, J=2.7 Hz, 1H), 7.30 (d, J=8.4 Hz, 1H), 7.03 (dd, J=8.4, 2.7 Hz, 1H), 6.15 (s, 1H), 3.89 (s, 3H), 1.74 (s, 6H).

EXAMPLE 86(7)

(Z)-2-(6-methoxy-2,2-dimethyl-2,3-dihydro-(4H)-1,3-benzothiazin-4-ylidene)-1-(4-methoxyphenyl)ethan-1-one TLC: Rf0.38 (hexane:ethyl acetate=3:1); NMR (CDCl$_3$): δ 12.28 (s, 1H), 7.92 (d, J=8.7 Hz, 2H), 7.34 (d, J=2.7 Hz, 1H), 7.27 (d, J=8.7 Hz, 1H), 6.99 (dd, J=8.7, 2.7 Hz, 1H), 6.94 (d, J=8.7 Hz, 2H), 6.18 (s, 1H), 3.89 (s, 3H), 3.87 (s, 3H), 1.71 (s, 6H).

EXAMPLE 86(8)

(Z)-2-(6-methoxy-2,2-dimethyl-2,3-dihydro-(4H)-1,3-benzothiazin-4-ylidene)-1-(4-nitrophenyl)ethan-1-one TLC: Rf0.40 (hexane:ethyl acetate=3:1); NMR (CDCl$_3$): δ 1.75 (s, 6H) 3.90 (s, 3H) 6.18 (s, 1H) 7.03 (dd, J=8.55, 2.75 Hz, 1H) 7.30 (d, J=8.55 Hz, 1H) 7.34 (d, J=2.75 Hz, 1H) 8.05 (d, J=8.85 Hz, 2H) 8.29 (d, J=8.55 Hz, 2H) 12.54 (s, 1H).

EXAMPLE 86(9)

(Z)-2-(7-methoxy-3,3-diethyl-3,4-dihydro-(2H)-isoquinolin-1-ylidene)-1-(4-nitrophenyl)ethan-1-one TLC: Rf0.49 (hexane:ethyl acetate=2:1); NMR (CDCl$_3$): δ 12.14 (br, 1H), 8.28 (d, J=9.0 Hz, 2H), 8.07 (d, J=9.0 Hz, 2H), 7.32 (d, J=2.4 Hz, 1H), 7.16 (d, J=8.6 Hz, 1H), 7.01 (dd, J=8.6, 2.4 Hz, 1H), 6.26 (s, 1H), 3.88 (s, 3H), 2.85 (s, 2H), 1.73-1.57 (m, 4H), 0.95 (t, J=7.5 Hz, 6H).

EXAMPLE 86(10)

(Z)-2-(7-methoxy-3,3-dimethyl-3,4-dihydro-(2H)-isoquinolin-1-ylidene)-1-(2-dimethylamino-3-bromopyridin-5-yl)ethan-1-one TLC: Rf0.56 (hexane:ethyl acetate=2:1); NMR (CDCl$_3$): δ 11.69 (br, 1H), 8.74 (d, J=2.0 Hz, 1H), 8.32 (d, J=2.0 Hz, 1H), 7.29 (d, J=2.8 Hz, 1H), 7.13 (d, J=8.3 Hz, 1H), 6.99 (dd, J=8.3, 2.8 Hz, 1H), 6.13 (s, 1H), 3.88 (s, 3H), 3.11 (s, 6H), 2.83 (s, 2H), 1.34 (s, 6H).

EXAMPLE 86(11)

(Z)-2-(7-methoxy-3,3-dimethyl-3,4-dihydro-(2H)-isoquinolin-1-ylidene)-1-(2-dimethylaminopyridin-5-yl)ethan-1-one TLC: Rf0.47 (hexane:ethyl acetate=1:2); NMR (CDCl$_3$): δ 11.59 (br, 1H), 8.83 (d, J=2.4 Hz, 1H), 8.07 (dd, J=8.8, 2.4 Hz, 1H), 7.30 (d, J=2.8 Hz, 1H), 7.11 (d, J=8.3 Hz, 1H), 6.97 (dd, J=8.3, 2.8 Hz, 1H), 6.54 (d, J=8.8 Hz, 1H), 6.21 (s, 1H), 3.87 (s, 3H), 3.17 (s, 6H), 2.81 (s, 2H), 1.33 (s, 6H).

EXAMPLE 86(12)

(Z)-2-(6-methoxy-3,3-dimethyl-2,3-dihydro-(2H)-isoindol-1-ylidene)-1-(3-nitrophenyl)ethan-1-one TLC: Rf0.47 (hexane:ethyl acetate=2:1); NMR (CDCl$_3$): δ 10.57 (s, 1H), 8.82 (t, J=1.8 Hz, 1H), 8.36-8.30 (m, 2H), 7.64 (t, J=8.1 Hz, 1H), 7.33 (d, J=8.4 Hz, 1H), 7.26 (m, 1H), 7.13 (dd, J=8.4, 2.4 Hz, 1H), 6.33 (s, 1H), 3.94 (s, 3H), 1.60 (s, 6H).

EXAMPLE 86(13)

(Z)-2-(7-methoxy-3,3-diethyl-3,4-dihydro-(2H)-isoquinolin-1-ylidene)-1-(3-nitrophenyl)ethan-1-one TLC: Rf0.38 (hexane:ethyl acetate=3:1); NMR (CDCl$_3$): δ 12.10 (br, 1H), 8.77 (t, J=2.0 Hz, 1H), 8.31-8.26 (m, 2H), 7.61 (t, J=8.0 Hz, 1H), 7.34 (d, J=2.5 Hz, 1H), 7.16 (d, J=8.3 Hz, 1H), 7.01 (dd, J=8.3, 2.5 Hz, 1H), 6.27 (s, 1H), 3.89 (s, 3H), 2.86 (s, 2H), 1.75-1.55 (m, 4H), 0.96 (t, J=7.5 Hz, 6H).

EXAMPLE 86(14)

(Z)-2-(7-methoxy-3,3-dimethyl-3,4-dihydro-(2H)-isoquinolin-1-ylidene)-1-(2-methoxypyridin-5-yl)ethan-1-one TLC: Rf0.44 (hexane:ethyl acetate=2:1); NMR (CDCl$_3$): δ 11.71 (br, 1H), 8.78 (d, J=2.4 Hz, 1H), 8.15 (dd, J=8.6, 2.4 Hz, 1H), 7.30 (d, J=2.8 Hz, 1H), 7.13 (d, J=8.3 Hz, 1H), 6.99 (dd, J=8.3, 2.8 Hz, 1H), 6.79 (d, J=8.6 Hz, 1H), 6.19 (s, 1H), 4.00 (s, 3H), 3.88 (s, 3H), 2.83 (s, 2H), 1.35 (s, 6H).

EXAMPLE 86(15)

(Z)-2-(7-methoxy-3,3-dimethyl-3,4-dihydro-(2H)-isoquinolin-1-ylidene)-1-(pyridin-2-yl)ethan-1-one TLC: Rf0.46 (hexane:ethyl acetate=1:2); NMR (CDCl$_3$): δ 11.94 (br, 1H), 8.66 (m, 1H), 8.14 (dt, J=7.8, 1.5 Hz, 1H), 7.82 (dt, J=1.5, 7.8 Hz, 1H), 7.49 (d, J=2.6 Hz, 1H), 7.35 (m, 1H), 7.12 (d, J=8.3 Hz, 1H), 7.08 (s, 1H), 6.99 (dd, J=8.3, 2.6 Hz, 1H), 3.89 (s, 3H), 2.85 (s, 2H), 1.37 (s, 6H).

EXAMPLE 86(16)

(Z)-2-(7-methoxy-3,3-dimethyl-3,4-dihydro-(2H)-isoquinolin-1-ylidene)-1-(pyridin-3-yl)ethan-1-one TLC: Rf0.38 (hexane:ethyl acetate=1:4); NMR (CDCl$_3$): δ 11.87 (br, 1H), 9.15 (d, J=1.9 Hz, 1H), 8.67 (dd, J=4.8, 1.9 Hz, 1H), 8.21 (dt, J=7.8, 1.9 Hz, 1H), 7.38 (dd, J=7.8, 4.8 Hz, 1H), 7.32 (d, J=2.7 Hz, 1H), 7.15 (d, J=8.5 Hz, 1H), 7.01 (d d, J=8.5, 2.7 Hz, 1H), 6.23 (s, 1H), 3.88 (s, 3H), 2.85 (s 2H), 1.37 (s, 6H).

EXAMPLE 86(17)

(Z)-2-(7-methoxy-3,3-dimethyl-3,4-dihydro-(2H)-isoquinolin-1-ylidene)-1-(3-iodophenyl)ethan-1-one TLC: Rf0.52 (hexane:ethyl acetate=3:1); NMR (CDCl$_3$): δ 1.35 (s, 6H) 2.84 (s, 2H) 3.89 (s, 3H) 6.17 (s, 1H) 7.00 (dd, J=8.24, 2.75 Hz, 1H) 7.14 (d, J=8.52 Hz, 1H) 7.17 (t, J=7.69 Hz, 1H) 7.32 (d, J=2.47 Hz, 1H) 7.77 (dt, J=7.97, 1.37 Hz, 1H) 7.88 (dt, J=7.76, 1.34 Hz, 1H) 8.26 (t, J=1.65 Hz, 1H) 11.85 (s, 1H).

EXAMPLE 86(18)

(Z)-2-(7-methoxy-3,3-diethyl-3,4-dihydro-(2H)-isoquinolin-1-ylidene)-1-(4-cyanophenyl)ethan-1-one TLC: Rf0.55 (hexane:ethyl acetate=2:1); NMR (CDCl$_3$): δ 12.10 (br, 1H), 8.02 (d, J=8.7 Hz, 2H), 7.72 (d, J=8.7 Hz, 2H), 7.31 (d, J=2.6 Hz, 1H), 7.15 (d, J=8.3 Hz, 1H), 7.01 (dd, J=8.3, 2.6 Hz, 1H), 6.23 (s, 1H), 3.88 (s, 3H), 2.85 (s, 2H), 1.72-1.56 (m, 4H), 0.95 (t, J=7.7 Hz, 6H).

EXAMPLE 86(19)

(Z)-2-(7-methoxy-3,3-dimethyl-3,4-dihydro-(2H)-isoquinolin-1-ylidene)-1-(pyridin-4-yl)ethan-1-one TLC: Rf0.53 (hexane:ethyl acetate=1:5); NMR (CDCl$_3$): δ 11.98 (br, 1H), 8.72 (dd, J=4.5, 1.5 Hz, 2H), 7.74 (dd, J=4.5, 1.5 Hz, 2H), 7.32 (d, J=2.7 Hz, 1H), 7.16 (d, J=8.3 Hz, 1H), 7.02 (dd, J=8.3, 2.7 Hz, 1H), 6.23 (s, 1H), 3.89 (s, 3H), 2.85 (s, 2H), 1.37 (s, 6H).

EXAMPLE 86(20)

(Z)-2-(7-methoxy-3,3-diethyl-3,4-dihydro-(2H)-isoquinolin-1-ylidene)-1-(3-cyanophenyl)ethan-1-one TLC: Rf0.55 (hexane:ethyl acetate=2:1); NMR (CDCl$_3$): δ 12.06 (br, 1H), 8.22 (t, J=1.7 Hz, 1H), 8.17 (dt, J=8.0, 1.7 Hz, 1H), 7.71 (dt, J=8.0, 1.7 Hz, 1H), 7.54 (t, J=8.0 Hz, 1H), 7.31 (d, J=2.7 Hz, 1H), 7.15 (d, J=8.3 Hz, 1H), 7.01 (dd, J=8.3, 2.7 Hz, 1H), 6.21 (s, 1H), 3.89 (s, 3H), 2.85 (s, 2H), 1.75-1.55 (m, 4H), 0.95 (t, J=7.5 Hz, 6H).

EXAMPLE 86(21)

(Z)-2-(6-methoxy-3,3-diethyl-2,3-dihydro-(2H)-isoindol-1-ylidene)-1-(3-cyanophenyl)ethan-1-one TLC: Rf0.31 (hexane:ethyl acetate=3:1); NMR (CDCl$_3$): δ 0.65 (t, J=7.2 Hz, 6H), 1.96 (m, 4H), 3.93 (s, 3H), 6.27 (s, 1H), 7.12 (dd, J=8.4, 2.4 Hz, 1H), 7.24 (d, J=2.4 Hz, 1H), 7.23 (d, J=8.4 Hz, 1H), 7.57 (t, J=7.5 Hz, 1H), 7.74 (dt, J=7.5, 1.8 Hz, 1H), 8.24 (dt, J=7.5, 1.8 Hz, 1H), 8.29 (t, J=1.8 Hz, 1H), 10.35 (s, 1H).

EXAMPLE 86(22)

(Z)-2-(6-methoxy-3,3-dimethyl-2,3-dihydro-(2H)-isoindol-1-ylidene)-1-(4-(pyrrolidin-1-yl)phenyl)ethan-1-one TLC: Rf0.19 (hexane:ethyl acetate=3:1); NMR (CDCl$_3$): δ 1.55 (s, 6H), 2.03 (m, 4H), 3.38 (t, J=6.6 Hz, 4H), 3.90 (s, 3H), 6.31 (s, 1H), 6.57 (d, J=8.7 Hz, 2H), 7.05 (dd, J=8.4, 2.4 Hz, 1H), 7.21 (d, J=2.4 Hz, 1H), 7.28 (d, J=8.4 Hz, 1H), 7.96 (d, J=8.7 Hz, 2H), 10.22 (s, 1H).

EXAMPLE 86(23)

(Z)-2-(6-methoxy-3,3-dimethyl-2,3-dihydro-(2H)-isoindol-1-ylidene)-1-(3-cyanophenyl)ethan-1-one TLC: Rf0.21 (hexane:ethyl acetate=3:1); NMR (CDCl$_3$): δ 1.59 (s, 6H), 3.93 (s, 3H), 6.26 (s, 1H), 7.12 (dd, J=8.4, 2.4 Hz, 1H), 7.23 (d, J=2.4 Hz, 1H), 7.32 (d, J=8.4 Hz, 1H), 7.57 (t, J=7.5 Hz, 1H), 7.74 (dt, J=7.5, 1.5 Hz, 1H), 8.22 (dt, J=7.5, 1.5 Hz, 1H), 8.28 (t, J=1.5 Hz, 1H), 10.49 (s, 1H).

EXAMPLE 86(24)

(Z)-2-(7-methoxy-3,3,5-trimethyl-3,4-dihydro-(2H)-isoquinolin-1-ylidene)-1-(4-cyanophenyl)ethan-1-one TLC: Rf0.27 (hexane:ethyl acetate=4:1); NMR (CDCl$_3$): δ 1.37 (s, 6H) 2.31 (s, 3H) 2.78 (s, 2H) 3.87 (s, 3H) 6.20 (s, 1H) 6.92 (d, J=2.20 Hz, 1H) 7.18 (d, J=2.20 Hz, 1H) 7.72 (d, J=8.24 Hz, 2H) 8.00 (d, J=8.24 Hz, 2H) 12.03 (s, 1H).

EXAMPLE 86(25)

(Z)-2-(7-methoxy-3,3,5-trimethyl-3,4-dihydro-(2H)-isoquinolin-1-ylidene)-1-(4-methoxyphenyl)ethan-1-one TLC: Rf0.27 (hexane:ethyl acetate=4:1); NMR (CDCl$_3$): δ 1.35 (s, 6H) 2.30 (s, 3H) 2.75 (s, 2H) 3.86 (s, 3H) 3.87 (s, 3H) 6.23 (s, 1H) 6.88 (d, J=2.75 Hz, 1H) 6.93 (d, J=9.07 Hz, 2H) 7.21 (d, J=2.75 Hz, 1H) 7.93 (d, J=9.07 Hz, 2H) 11.82 (s, 1H).

EXAMPLE 86(26)

(Z)-2-(6-methoxy-3,3-dimethyl-2,3-dihydro-(2H)-isoindol-1-ylidene)-1-(4-dimethylaminophenyl)ethan-1-one TLC: Rf0.45 (hexane:ethyl acetate=1:1); NMR (CDCl$_3$): δ 1.55 (s, 6H), 3.05 (s, 6H), 3.90 (s, 3H), 6.30 (s, 1H), 6.73 (d, J=8.7 Hz, 2H), 7.06 (dd, J=8.7, 2.4 Hz, 1H), 7.21 (d, J=2.4 Hz, 1H), 7.28 (d, J=8.7 Hz, 1H), 7.96 (d, J=8.7 Hz, 2H), 10.24 (s, 1H).

EXAMPLE 86(27)

(Z)-2-(7-methoxy-3,3,5-trimethyl-3,4-dihydro-(2H)-isoquinolin-1-ylidene)-1-(4-nitrophenyl)ethan-1-one TLC: Rf0.44 (hexane:ethyl acetate=4:1); NMR (CDCl$_3$): δ 1.38 (s, 6H) 2.32 (s, 3H) 2.79 (s, 2H) 3.88 (s, 3H) 6.22 (s, 1H) 6.93 (d, J=2.75 Hz, 1H) 7.20 (d, J=2.75 Hz, 1H) 8.06 (d, J=8.79 Hz, 2H) 8.28 (d, J=8.79 Hz, 2H) 12.07 (s, 1H).

EXAMPLE 87-EXAMPLE 87(6)

By the same procedure as described in example 58 using the compound prepared in example 86(8), 86(4), 86(5), 86(12), 86(9)$_m$ $_{86}$(13) or 86(27) in place of the compound prepared in example 56, the following compounds of the present invention were given.

EXAMPLE 87

(Z)-2-(6-methoxy-2,2-dimethyl-2,3-dihydro-(4H)-1,3-benzothiazin-4-ylidene)-1-(4-aminophenyl)ethan-1-one TLC: Rf0.45 (hexane:ethyl acetate=1:2); NMR (CDCl$_3$): δ 12.21 (s, 1H), 7.80 (d, J=8.7 Hz, 2H), 7.33 (d, J=2.7 Hz, 1H), 7.26 (d, J=8.7 Hz, 1H), 6.97 (dd, J=8.7, 2.7 Hz, 1H), 6.68 (d, J=8.7 Hz, 2H), 6.16 (s, 1H), 3.96 (br s, 2H), 3.89 (s, 3H), 1.71 (s, 6H).

EXAMPLE 87(1)

(Z)-2-(6-methoxy-3,3-diethyl-2,3-dihydro-(2H)-isoindol-1-ylidene)-1-(4-aminophenyl)ethan-1-one TLC: Rf0.44 (hexane:ethyl acetate=1:1); NMR (CDCl$_3$): δ 10.13 (br, s, 1H), 7.89 (d, J=9.0 Hz, 2H), 7.21 (d, J=2.1 Hz, 1H), 7.19 (d, J=8.7 Hz, 1H), 7.06 (dd, J=8.7, 2.1 Hz, 1H), 6.71 (d, J=9.0 Hz, 2H), 6.28 (s, 1H), 3.93 (br, s, 2H), 3.90 (s, 3H), 2.05-1.80 (m, 4H), 0.64 (t, J=7.5 Hz, 6H).

EXAMPLE 87(2)

(Z)-2-(6-methoxy-3,3-diethyl-2,3-dihydro-(2H)-isoindol-1-ylidene)-1-(3-aminophenyl)ethan-1-one TLC: Rf0.40 (hexane:ethyl acetate=1:1); NMR (CDCl$_3$): δ 10.24 (br, s, 1H), 7.40 (m, 1H), 7.35 (m, 1H), 7.30-7.15 (m, 3H), 7.07 (dd, J=8.7, 2.1 Hz, 1H), 6.79 (m, 1H), 6.29 (s, 1H), 3.90 (s, 3H), 3.76 (br, s, 2H), 2.05-1.80 (m, 4H), 0.65 (t, J=7.5 Hz, 6H).

EXAMPLE 87(3)

(Z)-2-(6-methoxy-3,3-dimethyl-2,3-dihydro-(2H)-isoindol-1-ylidene)-1-(3-aminophenyl)ethan-1-one TLC: Rf0.58 (hexane:ethyl acetate=1:2); NMR (CDCl$_3$): δ 10.37 (br, s, 1H), 7.38 (m, 1H), 7.33 (m, 1H), 7.29 (d, J=8.4 Hz, 1H), 7.23 (t, J=7.5 Hz, 1H), 7.20 (d, J=2.1 Hz, 1H), 7.08 (dd, J=8.4, 2.1 Hz, 1H), 6.79 (ddd, J=7.5, 2.4, 1.5 Hz, 1H), 6.28 (s, 1H), 3.90 (s, 3H), 3.77 (br, s, 2H), 1.56 (s, 6H).

EXAMPLE 87(4)

(Z)-2-(7-methoxy-3,3-diethyl-3,4-dihydro-(2H)-isoquinolin-1-ylidene)-1-(4-aminophenyl)ethan-1-one TLC: Rf0.61 (hexane:ethyl acetate=1:2); NMR (CDCl$_3$): δ 11.80 (br, 1H), 7.83 (d, J=8.6 Hz, 2H), 7.33 (d, J=2.6 Hz, 1H), 7.11 (d, J=8.4 Hz, 1H), 6.95 (dd, J=8.4, 2.6 Hz, 1H), 6.69 (d, J=8.6 Hz, 2H), 6.25 (s, 1H), 3.91 (s, 2H), 3.87 (s, 3H), 2.80 (s, 2H), 1.70-1.50 (m, 4H), 0.92 (t, J=7.5 Hz, 6H).

EXAMPLE 87(5)

(Z)-2-(7-methoxy-3,3-diethyl-3,4-dihydro-(2H)-isoquinolin-1-ylidene)-1-(3-aminophenyl)ethan-1-one TLC: Rf0.63 (hexane:ethyl acetate=1:2); NMR (CDCl$_3$): δ 11.95 (br, 1H), 7.35-7.28 (m, 3H), 7.21 (t, J=7.7 Hz, 1H), 7.12 (d, J=8.5 Hz, 1H), 6.97 (dd, J=8.5, 2.6 Hz, 1H), 6.77 (m, 1H), 6.26 (s, 1H), 3.87 (s, 3H), 3.74 (br, 2H), 2.82 (s, 2H), 1.70-1.53 (m, 4H), 0.93 (t, J=7.5 Hz, 6H).

EXAMPLE 87(6)

(Z)-2-(7-methoxy-3,3,5-trimethyl-3,4-dihydro-(2H)-isoquinolin-1-ylidene)-1-(4-aminophenyl)ethan-1-one TLC: Rf0.32 (hexane:ethyl acetate=1:1); NMR (CDCl$_3$): δ 1.32 (s, 6H) 2.28 (s, 3H) 2.72 (s, 2H) 3.85 (s, 3H) 3.89 (s, 2H) 6.20 (s, H) 6.67 (d, J=8.79 Hz, 2H) 6.85 (d, J=2.75 Hz, 1H) 7.19 (d, J=2.75 Hz, 1H) 7.80 (d, J=8.79 Hz, 2H) 11.73 (s, 1H).

EXAMPLE 88-EXAMPLE 88(1)

By the same procedure as described in example 79 using the compound prepared in example 86(24) and example 56(1) in place of the compound prepared in example 79, the compounds of the present invention having the following physical data were given.

EXAMPLE 88

(Z)-2-(7-methoxy-3,3,5-trimethyl-3,4-dihydro-(2H)-isoquinolin-1-ylidene)-1-(4-carboxyphenyl)ethan-1-one TLC: Rf0.47 (chloroform:methanol=10:1); NMR (DMSO-d$_6$): δ 1.29 (s, 6H) 2.28 (s, 3H) 2.78 (s, 2H) 3.84 (s, 3H) 6.44 (s, 1H) 7.03 (d, J=2.47 Hz, 1H) 7.40 (d, J=2.47 Hz, 1H) 7.99 (m, 3H) 8.09 (d, J=8.79 Hz, 2H) 12.08 (s, 1H).

EXAMPLE 88(1)

(Z)-2-(6-methoxy-3,3-dimethyl-2,3-dihydro-(2H)-isoindol-1-ylidene)-1-(4-carboxyphenyl)ethan-1-one TLC: Rf0.52 (ethyl acetate); NMR (DMSO-d$_6$): δ 1.52 (s, 6H), 3.86 (s, 3H), 6.64 (s, 1H), 7.14 (dd, J=8.39, 2.35 Hz, 1H), 7.51 (d, J=8.39 Hz, 1H), 7.65 (d, J=2.35 Hz, 1H), 8.02 (d, J=8.06 Hz, 2H), 8.13 (d, J=8.06 Hz, 2H), 10.49 (s, 1H), 13.09 (s, 1H).

EXAMPLE 89-EXAMPLE 89(26)

By the same procedure as described in example 68 using the compound prepared in example 66(1) or a corresponding derivative instead, and a corresponding derivative in place of 2-hydroxy-1,1-dimethylethylamine, the compounds of the present invention having the following physical data were given.

EXAMPLE 89

(Z)-2-(7-methoxy-3,3-dimethyl-3,4-dihydro-(2H)-isoquinolin-1-ylidene)-1-(3-(1,1-dioxotetrahydrothiophen-3-ylcarbamoyl)phenyl)ethan-1-one TLC: Rf0.57 (chloroform:methanol=10:1); NMR (CDCl$_3$): δ 11.92 (br, 1H), 8.28 (m, 1H), 8.09 (m, 1H), 7.91 (m, 1H), 7.53 (t, J=7.7 Hz, 1H), 7.34 (d, J=2.6 Hz, 1H), 7.14 (d, J=8.3 Hz, 1H), 7.01 (dd, J=8.3, 2.6 Hz, 1H), 6.82 (d, J=7.8 Hz, 1H), 6.27 (s, 1H), 5.00 (m, 1H), 3.89 (s, 3H), 3.52 (dd, J=13.8, 7.2 Hz, 1H), 3.32 (m, 1H), 3.24-3.08 (m, 2H), 2.85 (s, 2H), 2.65 (m, 1H), 2.42 (m, 1H), 1.37 (s, 6H).

EXAMPLE 89(1)

(Z)-2-(7-methoxy-3,3-dimethyl-3,4-dihydro-(2H)-isoquinolin-1-ylidene)-1-(4-(1,1-dioxotetrahydrothiophen-3-ylcarbamoyl)phenyl)ethan-1-one TLC: Rf0.52 (chloroform:methanol=10:1); NMR (CDCl$_3$): δ 11.94 (br, 1H), 8.00 (d, J=8.1 Hz, 2H), 7.83 (d, J=8.1 Hz, 2H), 7.33 (d, J=2.6 Hz, 1H), 7.15 (d, J=8.5 Hz, 1H), 7.01 (dd, J=8.5, 2.6 Hz, 1H), 6.80 (d, J=7.8 Hz, 1H), 6.26 (s, 1H), 5.04 (m, 1H), 3.89 (s, 3H), 3.47 (dd, J=13.8, 6.9 Hz, 1H), 3.37-3.10 (m, 3H), 2.85 (s, 2H), 2.64 (m, 1H), 2.46 (m, 1H), 1.36 (s, 6H).

EXAMPLE 89(2)

(Z)-2-(7-methoxy-3,3-dimethyl-3,4-dihydro-(2H)-isoquinolin-1-ylidene)-1-(3-((2-(morpholin-4-yl)ethyl)carbamoyl)phenyl)ethan-1-one TLC: Rf0.47 (chloroform:methanol=10:1); NMR (CDCl$_3$): δ 11.90 (br, s, 1H), 8.31 (m, 1H), 8.07 (m, 1H), 7.91 (m, 1H), 7.52 (t, J=7.8 Hz, 1H), 7.35 (d, J=2.4 Hz, 1H), 7.15 (d, J=8.1 Hz, 1H), 7.00 (dd, J=8.1, 2.4 Hz, 1H), 6.81 (m, 1H), 6.29 (s, 1H), 3.88 (s, 3H), 3.78-3.66 (m, 4H), 3.62-3.56 (m, 2H), 2.85 (s, 2H), 2.64-2.58 (m, 2H), 2.56-2.44 (m, 4H), 1.37 (s, 6H).

EXAMPLE 89(3)

(Z)-2-(7-methoxy-3,3-dimethyl-3,4-dihydro-(2H)-isoquinolin-1-ylidene)-1-(3-(pyridin-4-ylcarbamoyl)phenyl)ethan-1-one TLC: Rf0.46 (chloroform:methanol=10:1); NMR (CDCl$_3$): δ 11.93 (br, s, 1H), 8.60-8.52 (m, 2H), 8.44-8.36 (m, 2H), 8.12-8.00 (m, 2H), 7.72-7.62 (m, 2H), 7.56 (t, J=8.1 Hz, 1H), 7.34 (d, J=2.4 Hz, 1H), 7.15 (d, J=8.1 Hz, 1H), 7.01 (dd, J=8.1, 2.4 Hz, 1H), 6.28 (s, 1H), 3.88 (s, 3H), 2.83 (s, 2H), 1.36 (s, 6H).

EXAMPLE 89(4)

(Z)-2-(7-methoxy-3,3-dimethyl-3,4-dihydro-(2H)-isoquinolin-1-ylidene)-1-(3-((2-(2-hydroxyethoxy)ethyl)carbamoyl)phenyl)ethan-1-one TLC: Rf0.46 (chloroform:methanol=10:1); NMR (CDCl$_3$): δ 11.89 (br, s, 1H), 8.34 (m, 1H), 8.04 (m, 1H), 7.97 (m, 1H), 7.50 (t, J=8.4 Hz, 1H), 7.35 (d, J=2.4 Hz, 1H), 7.14 (d, J=8.4 Hz, 1H), 7.00 (dd, J=8.4, 2.4 Hz, 1H), 6.97 (m, 1H), 6.29 (s, 1H), 3.88 (s, 3H), 3.82-3.76 (m, 2H), 3.76-3.60 (m, 6H), 2.84 (s, 2H), 2.60 (br, s, 1H), 1.36 (s, 6H).

EXAMPLE 89(5)

(Z)-2-(7-methoxy-3,3-dimethyl-3,4-dihydro-(2H)-isoquinolin-1-ylidene)-1-(3-((tetrahydrofuran-2-ylmethyl)carbamoyl)phenyl)ethan-1-one TLC: Rf0.58 (chloroform:methanol=10:1); NMR (CDCl$_3$): δ 11.90 (br, s, 1H), 8.32 (m, 1H), 8.06 (m, 1H), 7.94 (m, 1H), 7.51 (t, J=8.4 Hz, 1H), 7.34 (d, J=2.4 Hz, 1H), 7.14 (d, J=8.4 Hz, 1H), 7.00 (dd, J=8.4, 2.4 Hz, 1H), 6.63 (m, 1H), 6.29 (s, 1H), 4.08 (m, 1H), 3.96-3.74 (m, 3H), 3.88 (s, 3H), 3.38 (m, 1H), 2.84 (s, 2H), 2.10-1.84 (m, 3H), 1.62 (m, 1H), 1.36 (s, 6H).

EXAMPLE 89(6)

(Z)-2-(7-methoxy-3,3-dimethyl-3,4-dihydro-(2H)-isoquinolin-1-ylidene)-1-(3-((1-ethoxycarbonylpiperidin-4-yl)carbamoyl)phenyl)ethan-1-one TLC: Rf0.53 (chloroform:methanol=10:1); NMR (CDCl$_3$): δ 11.92 (br, s, 1H), 8.25 (m, 1H), 8.04 (m, 1H), 7.96 (m, 1H), 7.52 (t, J=8.4 Hz, 1H), 7.34 (d, J=2.4 Hz, 1H), 7.15 (d, J=8.4 Hz, 1H), 7.01 (dd, J=8.4, 2.4 Hz, 1H), 6.28 (s, 1H), 6.16 (d, J=8.1 Hz, 1H), 4.15 (m, 1H), 4.15 (q, J=7.2 Hz, 2H), 3.89 (s, 3H), 3.02-2.86 (m, 2H), 2.85 (s, 2H), 2.12-1.98 (m, 2H), 1.54-1.38 (m, 4H), 1.37 (s, 6H), 1.28 (t, J=7.2 Hz, 3H).

EXAMPLE 89(7)

(Z)-2-(7-methoxy-3,3-dimethyl-3,4-dihydro-(2H)-isoquinolin-1-ylidene)-1-(3-((2-methoxyethyl)carbamoyl)phenyl)ethan-1-one TLC: Rf0.44 (chloroform:methanol=10:1); NMR (CDCl$_3$): δ 11.91 (br, s, 1H), 8.32 (m, 1H), 8.06 (m, 1H), 7.95 (m, 1H), 7.51 (t, J=8.4 Hz, 1H), 7.34 (d, J=2.4 Hz, 1H), 7.14 (d, J=8.4 Hz, 1H), 7.00 (dd, J=8.4, 2.4 Hz, 1H), 6.64 (m, 1H), 6.29 (s, 1H), 3.88 (s, 3H), 3.72-3.62 (m, 2H), 3.60-3.52 (m, 2H), 3.39 (s, 3H), 2.85 (s, 2H), 1.37 (s, 6H).

EXAMPLE 89(8)

(Z)-2-(7-methoxy-3,3-dimethyl-3,4-dihydro-(2H)-isoquinolin-1-ylidene)-1-(3-(4-methylpiperazin-1-ylcarbonyl)phenyl)ethan-1-one TLC: Rf0.49 (chloroform:methanol=10:1); NMR (CDCl$_3$): δ 11.86 (br, s, 1H), 8.04-7.88 (m, 2H), 7.56-7.42 (m, 2H), 7.32 (d, J=2.4 Hz, 1H), 7.14 (d, J=8.7 Hz, 1H), 7.00 (dd, J=8.7, 2.4 Hz, 1H), 6.25 (s, 1H), 3.94-3.70 (m, 2H), 3.88 (s, 3H), 3.56-3.36 (m, 2H), 2.84 (s, 2H), 2.60-2.18 (m, 4H), 2.32 (s, 3H), 1.36 (s, 6H).

EXAMPLE 89(9)

(Z)-2-(7-methoxy-3,3-dimethyl-3,4-dihydro-(2H)-isoquinolin-1-ylidene)-1-(3-((pyridin-2-ylmethyl)carbamoyl)phenyl)ethan-1-one TLC: Rf0.54 (chloroform:methanol=10:1); NMR (CDCl$_3$): δ 11.90 (br, s, 1H), 8.59 (m, 1H), 8.42 (m, 1H), 8.08 (m, 1H), 8.00 (m, 1H), 7.69 (m, 1H), 7.63 (br, s, 1H), 7.56 (t, J=8.4 Hz, 1H), 7.40-7.31 (m, 2H), 7.22 (m, 1H), 7.14 (d, J=8.4 Hz, 1H), 7.00 (dd, J=8.4, 2.4 Hz, 1H), 6.31 (s, 1H), 4.80 (d, J=5.1 Hz, 2H), 3.88 (s, 3H), 2.84 (s, 2H), 1.36 (s, 6H).

EXAMPLE 89(10)

(Z)-2-(7-methoxy-3,3-dimethyl-3,4-dihydro-(2H)-isoquinolin-1-ylidene)-1-(3-((2-(piperidin-1-yl)ethyl)carbamoyl)phenyl)ethan-1-one TLC: Rf0.19 (chloroform:methanol=10:1); NMR (CDCl$_3$): δ 11.90 (br, s, 1H), 8.33 (m, 1H), 8.07 (m, 1H), 7.90 (m, 1H), 7.51 (t, J=8.4 Hz, 1H), 7.35 (d, J=2.4 Hz, 1H), 7.14 (d, J=8.4 Hz, 1H), 7.00 (dd, J=8.4, 2.4 Hz, 1H), 7.00 (m, 1H), 6.31 (s, 1H), 3.88 (s, 3H), 3.57 (q, J=6.0 Hz, 2H), 2.84 (s, 2H), 2.57 (t, J=6.0 Hz, 2H), 2.52-2.36 (m, 4H), 1.76-1.50 (m, 4H), 1.50-1.38 (m, 2H), 1.37 (s, 6H).

EXAMPLE 89(11)

(Z)-2-(7-methoxy-3,3-dimethyl-3,4-dihydro-(2H)-isoquinolin-1-ylidene)-1-(3-((1-oxidopyridin-2-yl)carbamoyl)phenyl)ethan-1-one TLC: Rf0.59 (chloroform:methanol=10:1); NMR (CDCl$_3$): δ 11.92 (br, s, 1H), 10.97 (br, s, 1H), 8.64 (dd, J=8.7, 2.1 Hz, 1H), 8.56 (m, 1H), 8.31 (dd, J=6.9, 1.5 Hz, 1H), 8.19 (m, 1H), 8.06 (m, 1H), 7.61 (t, J=8.4 Hz, 1H), 7.40 (m, 1H), 7.36 (d, J=2.4 Hz, 1H), 7.14 (d, J=8.4 Hz, 1H), 7.08-6.98 (m, 2H), 6.31 (s, 1H), 3.90 (s, 3H), 2.85 (s, 2H), 1.37 (s, 6H).

EXAMPLE 89(12)

(Z)-2-(7-methoxy-3,3-dimethyl-3,4-dihydro-(2H)-isoquinolin-1-ylidene)-1-(3-(ethylcarbamoyl)phenyl)ethan-1-one TLC: Rf0.43 (chloroform:methanol=10:1); NMR (CDCl$_3$): δ 1.27 (t, J=7.2 Hz, 3H), 1.36 (s, 6H), 2.85 (s, 2H), 3.53 (m, 2H), 3.89 (s, 3H), 6.25 (m, 1H), 6.29 (s, 1H), 7.00 (dd, J=8.4, 2.4 Hz, 1H), 7.15 (d, J=8.4 Hz, 1H), 7.35 (d, J=2.4 Hz, 1H), 7.51 (t, J=8.4 Hz, 1H), 7.93 (m, 1H), 8.04 (m, 1H), 8.28 (m, 1H), 11.92 (s, 1H).

EXAMPLE 89(13)

(Z)-2-(7-methoxy-3,3-dimethyl-3,4-dihydro-(2H)-isoquinolin-1-ylidene)-1-(3-(((1S)-1-hydroxymethyl-3-methylthiopropyl)carbamoyl)phenyl)ethan-1-one TLC: Rf0.31 (chloroform:methanol=10:1); NMR (CDCl$_3$): δ 1.36 (s, 6H), 1.99 (m, 2H), 2.13 (s, 3H), 2.63 (t, J=7.2 Hz, 2H), 2.74 (t, J=5.4 Hz, 1H), 2.84 (s, 2H), 3.80 (m, 2H), 3.88 (s, 3H), 4.32 (m, 1H), 6.28 (s, 1H), 6.77 (d, J=7.8 Hz, 1H), 7.00 (d d, J=8.7, 2.7 Hz, 1H), 7.14 (d, J=8.7 Hz, 1H), 7.34 (d, J=2.7 Hz, 1H), 7.51 (t, J=8.7 Hz, 1H), 7.95 (m, 1H), 8.06 (m, 1H), 8.32 (m, 1H), 11.90 (s, 1H).

EXAMPLE 89(14)

(Z)-2-(7-methoxy-3,3-dimethyl-3,4-dihydro-(2H)-isoquinolin-1-ylidene)-1-(4-((1-oxidopyridin-2-yl)carbamoyl)phenyl)ethan-1-one TLC: Rf0.50 (chloroform:methanol=10:1); NMR (CDCl$_3$): δ 1.38 (s, 6H), 2.86 (s, 2H), 3.89 (s, 3H), 6.29 (s, 1H), 7.04 (m, 2H), 7.15 (d, J=8.4 Hz, 1H), 7.35 (d, J=3.0 Hz, 1H), 7.42 (m, 1H), 8.08 (s, 4H), 8.32 (m, 1H), 8.64 (m, 1H), 10.99 (s, 1H), 11.97 (s, 1H).

EXAMPLE 89(15)

(Z)-2-(7-methoxy-3,3-dimethyl-3,4-dihydro-(2H)-isoquinolin-1-ylidene)-1-(3-((2-dimethylaminoethyl)carbamoyl)phenyl)ethan-1-one TLC: Rf0.15 (chloroform:methanol=10:1); NMR (CDCl$_3$): δ 1.37 (s, 6H), 2.27 (s, 6H), 2.53 (t, J=5.7 Hz, 2H), 2.85 (s, 2H), 3.55 (m, 2H), 3.88 (s, 3H), 6.30 (s, 1H), 6.90 (m, 1H), 7.00 (dd, J=8.4, 2.4 Hz, 1H), 7.14 (d, J=8.4 Hz, 1H), 7.35 (d, J=2.4 Hz, 1H), 7.51 (t, J=7.8 Hz, 1H), 7.94 (m, 1H), 8.06 (m, 1H), 8.33 (m, 1H), 11.89 (s, 1H).

EXAMPLE 89(16)

(Z)-2-(7-methoxy-3,3-dimethyl-3,4-dihydro-(2H)-isoquinolin-1-ylidene)-1-(3-((2-(acetylamino)ethyl)carbamoyl)phenyl)ethan-1-one TLC: Rf0.50 (chloroform:methanol=10:1); NMR (CDCl$_3$): δ 1.36 (s, 6H), 2.01 (s, 3H), 2.84 (s, 2H), 3.52 (m, 2H), 3.62 (m, 2H), 3.87 (s, 3H), 6.29 (m, 1H), 6.36 (s, 1H), 6.99 (dd, J=8.4, 2.4 Hz, 1H), 7.14 (d, J=8.4 Hz, 1H), 7.30 (m, 1H), 7.44 (d, J=2.4 Hz, 1H), 7.52 (t, J=7.8 Hz, 1H), 7.93 (dt, J=7.8, 1.6 Hz, 1H), 8.09 (dt, J=7.8, 1.6 Hz, 1H), 8.35 (t, J=1.6 Hz, 1H), 11.94 (s, 1H).

EXAMPLE 89(17)

(Z)-2-(7-methoxy-3,3-dimethyl-3,4-dihydro-(2H)-isoquinolin-1-ylidene)-1-(3-(4-(2-hydroxyethyl)piperazin-1-ylcarbonyl)phenyl)ethan-1-one TLC: Rf0.48 (chloroform:methanol=10:1); NMR (CDCl$_3$): δ 1.36 (s, 6H), 2.51 (m, 5H), 2.60 (t, J=5.4 Hz, 2H), 2.84 (s, 2H), 3.48 (m, 2H), 3.65 (t, J=5.4 Hz, 2H), 3.84 (m, 2H), 3.88 (s, 3H), 6.24 (s, 1H), 7.00 (dd, J=8.7, 2.4 Hz, 1H), 7.14 (d, J=8.7 Hz, 1H), 7.32 (d, J=2.4 Hz, 1H), 7.49 (m, 2H), 7.94 (m, 1H), 7.99 (m, 1H), 11.86 (s, 1H).

EXAMPLE 89(18)

(Z)-2-(7-methoxy-3,3-dimethyl-3,4-dihydro-(2H)-isoquinolin-1-ylidene)-1-(3-((pyridin-3-ylmethyl)carbamoyl)phenyl)ethan-1-one TLC: Rf0.11 (ethyl acetate); NMR (CDCl$_3$): δ 1.35 (s, 6H), 2.84 (s, 2H), 3.88 (s, 3H), 4.69 (d, J=6.0 Hz, 2H), 6.28 (s, 1H), 6.71 (t, J=6.0 Hz, 1H), 7.00 (dd, J=8.4, 2.4 Hz, 1H), 7.15 (d, J=8.4 Hz, 1H), 7.29 (m, 1H), 7.33 (d, J=2.4 Hz, 1H), 7.53 (t, J=7.8 Hz, 1H), 7.73 (m, 1H), 7.98 (dt, J=7.8, 1.8 Hz, 1H), 8.07 (dt, J=7.8, 1.8 Hz, 1H), 8.30 (t, J=1.8 Hz, 1H), 8.55 (m, 1H), 8.63 (m, 1H), 11.91 (s, 1H).

EXAMPLE 89(19)

(Z)-2-(7-methoxy-3,3-dimethyl-3,4-dihydro-(2H)-isoquinolin-1-ylidene)-1-(3-((3-dimethylaminopropyl)carbamoyl)phenyl)ethan-1-one TLC: Rf0.21 (ethyl acetate:methanol:ammonia water=50: 10:1); NMR (CDCl$_3$): δ 1.36 (s, 6H), 1.78 (m, 2H), 2.31 (s, 6H), 2.50 (m, 2H), 2.84 (s, 2H), 3.59 (m, 2H), 3.88 (s, 3H), 6.30 (s, 1H), 7.00 (dd, J=8.4, 2.4 Hz, 1H), 7.14 (d, J=8.4 Hz, 1H), 7.34 (d, J=2.4 Hz, 1H), 7.50 (t, J=7.8 Hz, 1H), 7.89 (dt, J=7.8, 1.8 Hz, 1H), 8.06 (dt, J=7.8, 1.8 Hz, 1H), 8.33 (t, J=1.8 Hz, 1H), 8.40 (m, 1H), 11.90 (s, 1H).

EXAMPLE 89(20)

(Z)-2-(7-methoxy-3,3-dimethyl-3,4-dihydro-(2H)-isoquinolin-1-ylidene)-1-(3-((2R)-2-hydroxymethylpyrrolidin-1-ylcarbonyl)phenyl)ethan-1-one TLC: Rf0.19 (ethyl acetate); NMR (CDCl$_3$): δ 1.36 (s, 6H), 1.74 (m, 3H), 2.19 (m, 1H), 2.84 (s, 2H), 3.52 (m, 2H), 3.80 (m, 2H), 3.89 (s, 3H), 4.42 (m, 1H), 4.93 (m, 1H), 6.25 (s, 1H), 7.00 (dd, J=8.4, 2.7 Hz, 1H), 7.15 (d, J=8.4 Hz, 1H), 7.34 (d, J=2.7 Hz, 1H), 7.50 (t, J=7.8 Hz, 1H), 7.60 (m, 1H), 8.01 (m, 1H), 8.06 (m, 1H), 11.89 (s, 1H).

EXAMPLE 89(21)

(Z)-2-(7-methoxy-3,3-dimethyl-3,4-dihydro-(2H)-isoquinolin-1-ylidene)-1-(3-(2,6-dimethylmorpholin-1-ylcarbonyl)phenyl)ethan-1-one TLC: Rf0.56 (ethyl acetate); NMR (CDCl$_3$): δ 1.09 (s, 3H), 1.25 (s, 3H), 1.36 (s, 3H), 2.58 (m, 1H), 2.83 (s, 2H), 2.83 (m, 1H), 3.60 (m, 3H), 3.88 (s, 3H), 4.61 (m, 1H), 6.24 (s, 1H), 7.00 (dd, J=8.4, 2.4 Hz, 1H), 7.14 (d, J=8.4 Hz, 1H), 7.32 (d, J=2.4 Hz, 1H), 7.49 (m, 2H), 7.92 (m, 1H), 8.00 (m, 1H), 11.87 (s, 1H).

EXAMPLE 89(22)

(Z)-2-(7-methoxy-3,3-dimethyl-3,4-dihydro-(2H)-isoquinolin-1-ylidene)-1-(3-((1-ethylpyrrolidin-2-ylmethyl)carbamoyl)phenyl)ethan-1-one TLC: Rf0.48 (ethyl acetate:methanol:ammonia water=50: 10:1); NMR (CDCl$_3$): δ 1.14 (t, J=7.2 Hz, 3H), 1.37 (s, 6H), 1.72 (m, 3H), 1.93 (m, 1H), 2.26 (m, 2H), 2.71 (m, 1H), 2.84 (s, 2H), 2.86 (m, 1H), 3.22 (m, 1H), 3.34 (m, 1H), 3.76 (m, 1H), 3.88 (s, 3H), 6.31 (s, 1H), 6.91 (m, 1H), 7.00 (dd, J=8.4, 2.4 Hz, 1H), 7.14 (d, J=8.4 Hz, 1H), 7.35 (d, J=2.4 Hz, 1H), 7.52 (t, J=7.8 Hz, 1H), 7.90 (m, 1H), 8.08 (m, 1H), 8.33 (m, 1H), 11.90 (s, 1H).

EXAMPLE 89(23)

(Z)-2-(7-methoxy-3,3-dimethyl-3,4-dihydro-(2H)-isoquinolin-1-ylidene)-1-(4-((pyridin-2-yl)carbamoyl)phenyl)ethan-1-one TLC: Rf0.24 (hexane:ethyl acetate=1:1); NMR (CDCl$_3$): δ 1.37 (s, 6H), 2.85 (s, 2H), 3.89 (s, 3H), 6.29 (s, 1H), 7.01 (dd, J=8.4, 2.4 Hz, 1H), 7.09 (m, 1H), 7.15 (d, J=8.4 Hz, 1H), 7.35 (d, J=2.4 Hz, 1H), 7.78 (m, 1H), 7.99 (d, J=8.1 Hz, 2H), 8.06 (d, J=8.1 Hz, 2H), 8.33 (m, 1H), 8.41 (m, 1H), 8.61 (s, 1H), 11.96 (s, 1H).

EXAMPLE 89(24)

(Z)-2-(6-methoxy-3,3-dimethyl-2,3-dihydro-(2H)-isoindol-1-ylidene)-1-(4-((2-(morpholin-4-yl)ethyl)carbamoyl)phenyl)ethan-1-one TLC: Rf0.26 (ethyl acetate:methanol=10:1); NMR (CDCl$_3$): δ 1.58 (s, 6H), 2.52 (m, 4H), 2.63 (m, 2H), 3.58 (m, 2H), 3.75 (m, 4H), 3.91 (s, 3H), 6.33 (s, 1H), 6.83 (m, 1H), 7.11 (dd, J=8.24, 2.47 Hz, 1H), 7.22 (d, J=2.47 Hz, 1H), 7.32 (d, J=8.24 Hz, 1H), 7.86 (d, J=8.24 Hz, 2H), 8.06 (d, J=8.24 Hz, 2H), 10.51 (s, 1H).

EXAMPLE 89(25)

(Z)-2-(6-methoxy-3,3-dimethyl-2,3-dihydro-(2H)-isoindol-1-ylidene)-1-(4-((1-oxidopyridin-2-yl)carbamoyl)phenyl)ethan-1-one TLC: Rf0.24 (ethyl acetate); NMR (CDCl$_3$): δ 1.58 (s, 6H), 3.92 (s, 3H), 6.35 (s, 1H), 7.05 (m, 1H), 7.12 (dd, J=8.24, 2.47 Hz, 1H), 7.24 (d, J=2.47 Hz, 1H), 7.32 (d, J=8.24 Hz, 1H), 7.42 (m, 1H), 8.12 (m, 4H), 8.32 (m, 1H), 8.64 (dd, J=8.52, 1.92 Hz, 1H), 10.56 (s, 1H), 11.00 (s, 1H).

EXAMPLE 89(26)

(Z)-2-(6-methoxy-3,3-dimethyl-2,3-dihydro-(2H)-isoindol-1-ylidene)-1-(4-((pyridin-4-yl)carbamoyl)phenyl)ethan-1-one TLC: Rf0.30 (ethyl acetate); NMR (CDCl$_3$): δ 1.58 (s, 6H), 3.91 (s, 3H), 6.32 (s, 1H), 7.12 (dd, J=8.24, 2.20 Hz, 1H), 7.23 (d, J=2.20 Hz, 1H), 7.33 (d, J=8.24 Hz, 1H), 7.66 (m, 2H), 7.94 (d, J=8.52 Hz, 2H), 8.08 (d, J=8.52 Hz, 2H), 8.21 (s, 1H), 8.58 (m, 2H), 10.53 (s, 1H).

EXAMPLE 90-EXAMPLE 90(16)

By the same procedure as described in example 63 using a corresponding derivative in place of the compound prepared in example 62 and the acetic anhydride or a corresponding acid anhydride, acid halide or sulfonyl halide instead, optionally followed by converting to a corresponding salt, the following compounds of the present invention were given.

EXAMPLE 90

(Z)-2-(7-methoxy-3,3-dimethyl-3,4-dihydro-(2H)-isoquinolin-1-ylidene)-1-(3-((3-methylthiopropanoyl)amino)phenyl)ethan-1-one TLC: Rf0.61 (hexane:ethyl acetate=1:2); NMR (CDCl$_3$): δ 11.82 (br, 1H), 7.94 (m, 1H), 7.80 (m, 1H), 7.69-7.65 (m, 2H), 7.40 (t, J=7.0 Hz, 1H), 7.34 (d, J=2.5 Hz, 1H), 7.14 (d, J=8.3 Hz, 1H), 6.99 (dd, J=8.3, 2.5 Hz, 1H), 6.25 (s, 1H), 3.88 (s, 3H), 2.91 (t, J=7.0 Hz, 2H), 2.83 (s, 2H), 2.68 (t, J=7.0 Hz, 2H), 2.18 (s, 3H), 1.35 (s, 6H).

EXAMPLE 90(1)

(Z)-2-(7-methoxy-3,3-dimethyl-3,4-dihydro-(2H)-isoquinolin-1-ylidene)-1-(3-((2-(4-methoxyphenyl)acetyl)amino)phenyl)ethan-1-one TLC: Rf0.61 (hexane:ethyl acetate=1:2); NMR (CDCl$_3$): δ 11.82 (br, 1H), 7.98 (m, 1H), 7.62 (m, 1H), 7.54 (m, 1H), 7.37 (t, J=8.0 Hz, 1H), 7.31 (d, J=2.5 Hz, 1H), 7.25 (d, J=8.4 Hz, 2H), 7.13 (d, J=8.4 Hz, 1H), 7.13 (br, 1H), 6.99 (dd, J=8.4, 2.5 Hz, 1H), 6.94 (d, J=8.4 Hz, 2H), 6.22 (s, 1H), 3.88 (s, 3H), 3.85 (s, 3H), 3.71 (s, 2H), 2.82 (s, 2H), 1.33 (s, 6H).

EXAMPLE 90(2)

(Z)-2-(6-methoxy-2,2-dimethyl-2,3-dihydro-(4H)-1,3-benzothiazin-4-ylidene)-1-(4-(acetylamino)phenyl)ethan-1-one TLC: Rf0.58 (ethyl acetate); NMR (CDCl$_3$): δ 12.34 (s, 1H), 7.91 (d, J=8.7 Hz, 2H), 7.58 (d, J=8.7 Hz, 2H), 7.34 (d, J=2.7 Hz, 1H), 7.27 (d, J=8.7 Hz, 1H), 7.26 (m, 1H), 7.00 (dd, J=8.7, 2.7 Hz, 1H), 6.19 (s, 1H), 3.89 (s, 3H), 2.21 (s, 3H), 1.72 (s, 6H).

EXAMPLE 90(3)

(Z)-2-(6-methoxy-3,3-diethyl-2,3-dihydro-(2H)-isoindol-1-ylidene)-1-(3-((pyridin-4-ylcarbonyl)amino)phenyl)ethan-1-one hydrochloride TLC: Rf0.35 (ethyl acetate); NMR (DMSO-d$_6$): δ 10.87 (br s, 1H), 10.17 (s, 1H), 8.94 (m, 2H), 8.36 (s, 1H), 8.18 (m, 2H), 7.97 (d, J=7.8 Hz, 1H), 7.87 (d, J=7.8 Hz, 1H), 7.59 (d, J=2.1 Hz, 1H), 7.50 (t, J=7.8 Hz, 1H), 7.40 (d, J=8.4 Hz, 1H), 7.14 (dd, J=8.4, 2.1 Hz, 1H), 6.56 (s, 1H), 6.00-4.00 (br s, 1H), 3.86 (s, 3H), 2.10-1.85 (m, 4H), 0.48 (t, J=7.2 Hz, 6H).

EXAMPLE 90(4)

(Z)-2-(6-methoxy-3,3-diethyl-2,3-dihydro-(2H)-isoindol-1-ylidene)-1-(4-((pyridin-4-ylcarbonyl)amino)phenyl)ethan-1-one TLC: Rf0.35 (ethyl acetate); NMR (CDCl$_3$): δ 10.29 (s, 1H), 8.83 (d, J=5.4 Hz, 2H), 8.07 (d, J=8.1 Hz, 2H), 8.02 (s, 1H), 7.77-7.73 (m, 4H), 7.24-7.20 (m, 2H), 7.09 (dd, J=8.7, 2.4 Hz, 1H), 6.34 (s, 1H), 3.92 (s, 3H), 2.01-1.84 (m, 4H), 0.65 (t, J=7.2 Hz, 6H).

EXAMPLE 90(5)

(Z)-2-(6-methoxy-3,3-diethyl-2,3-dihydro-(2H)-isoindol-1-ylidene)-1-(4-((2-methoxyacetyl)amino)phenyl)ethan-1-one TLC: Rf0.24 (hexane:ethyl acetate=1:1); NMR (CDCl$_3$): δ 10.27 (br, s, 1H), 8.38 (br, s, 1H), 8.02 (d, J=8.7 Hz, 2H), 7.68 (d, J=8.7 Hz, 2H), 7.23 (d, J=2.7 Hz, 1H), 7.21 (d, J=8.1 Hz, 1H), 7.08 (dd, J=8.1, 2.7 Hz, 1H), 6.32 (s, 1H), 4.04 (s, 2H), 3.91 (s, 3H), 3.53 (s, 3H), 2.05-1.80 (m, 4H), 0.65 (t, J=7.5 Hz, 6H).

EXAMPLE 90(6)

(Z)-2-(6-methoxy-3,3-diethyl-2,3-dihydro-(2H)-isoindol-1-ylidene)-1-(3-((2-methoxyacetyl)amino)phenyl)ethan-1-one TLC: Rf0.40 (hexane:ethyl acetate=1:1); NMR (CDCl$_3$): δ 10.32 (br, 1H), 8.38 (br, s, 1H), 8.00-7.90 (m, 2H), 7.77 (m, 1H), 7.44 (t, J=8.1 Hz, 1H), 7.30-7.15 (m, 2H), 7.09 (dd, J=8.4, 2.1 Hz, 1H), 6.31 (s, 1H), 4.05 (s, 2H), 3.91 (s, 3H), 3.53 (s, 3H), 2.05-1.80 (m, 4H), 0.66 (t, J=7.4 Hz, 6H).

EXAMPLE 90(7)

(Z)-2-(6-methoxy-3,3-dimethyl-2,3-dihydro-(2H)-isoindol-1-ylidene)-1-(4-((pyridin-4-ylcarbonyl)amino)phenyl)ethan-1-one TLC: Rf0.26 (ethyl acetate); NMR (CDCl$_3$): δ 10.42 (br, s, 1H), 8.82 (d, J=6.0 Hz, 2H), 8.07 (br, s, 1H), 8.06 (d, J=8.7 Hz, 2H), 7.76 (d, J=8.7 Hz, 2H), 7.74 (d, J=6.0 Hz, 2H), 7.31 (d, J=8.1 Hz, 1H), 7.23 (d, J=2.4 Hz, 1H), 7.10 (dd, J=8.1, 2.4 Hz, 1H), 6.33 (s, 1H), 3.91 (s, 3H), 1.57 (s, 6H).

EXAMPLE 90(8)

(Z)-2-(6-methoxy-3,3-dimethyl-2,3-dihydro-(2H)-isoindol-1-ylidene)-1-(4-((2-methoxyacetyl)amino)phenyl)ethan-1-one TLC: Rf0.35 (hexane:ethyl acetate=1:2); NMR (CDCl$_3$): δ 10.40 (br, s, 1H), 8.38 (br, s, 1H), 8.01 (d, J=8.7 Hz, 2H), 7.68 (d, J=8.7 Hz, 2H), 7.30 (d, J=8.1 Hz, 1H), 7.22 (d, J=2.7 Hz, 1H), 7.09 (dd, J=8.1, 2.7 Hz, 1H), 6.31 (s, 1H), 4.04 (s, 2H), 3.91 (s, 3H), 3.53 (s, 3H), 1.57 (s, 6H).

EXAMPLE 90(9)

(Z)-2-(6-methoxy-3,3-dimethyl-2,3-dihydro-(2H)-isoindol-1-ylidene)-1-(3-((pyridin-4-ylcarbonyl)amino)phenyl)ethan-1-one TLC: Rf0.26 (ethyl acetate); NMR (CDCl$_3$): δ 1.57 (s, 6H) 3.91 (s, 3H) 6.33 (s, 1H) 7.10 (dd, J=8.52, 2.47 Hz, 1H) 7.23 (d, J=2.47 Hz, 1H) 7.31 (d, J=8.52 Hz, 1H) 7.50 (t, J=8.24 Hz, 1H) 7.74 (d, J=5.22 Hz, 2H) 7.82 (m, 1H) 8.05 (m, 3H) 8.82 (d, J=5.22 Hz, 2H) 10.44 (s, 1H).

EXAMPLE 90(10)

(Z)-2-(6-methoxy-3,3-dimethyl-2,3-dihydro-(2H)-isoindol-1-ylidene)-1-(3-((2-methoxyacetyl)amino)phenyl)ethan-1-one TLC: Rf0.45 (hexane:ethyl acetate=1:2); NMR (CDCl$_3$): δ 1.58 (s, 6H) 3.54 (s, 3H) 3.91 (s, 3H) 4.05 (s, 2H) 6.31 (s, 1H) 7.09 (dd, J=8.24, 2.47 Hz, 1H) 7.23 (d, J=2.47 Hz, 1H) 7.30 (d, J=8.24 Hz, 1H) 7.44 (t, J=7.69 Hz, 1H) 7.76 (m, 1H) 7.95 (m, 2H) 8.38 (s, 1H) 10.44 (s, 1H).

EXAMPLE 90(11)

(Z)-2-(6-methoxy-3,3-dimethyl-2,3-dihydro-(2H)-isoindol-1-ylidene)-1-(3-acetylaminophenyl)ethan-1-one TLC: Rf0.25 (chloroform:methanol=10:1); NMR (CDCl$_3$): δ 1.57 (s, 6H), 2.21 (s, 3H), 3.90 (s, 3H), 6.30 (s, 1H), 7.09 (dd, J=8.4, 2.4 Hz, 1H), 7.22 (d, J=2.4 Hz, 1H), 7.30 (d, J=8.4 Hz, 1H), 7.39 (s, 1H), 7.42 (t, J=7.8 Hz, 1H), 7.73 (m, 1H), 7.89 (m, 2H), 10.43 (s, 1H).

EXAMPLE 90(12)

(Z)-2-(7-methoxy-3,3-diethyl-3,4-dihydro-(2H)-isoquinolin-1-ylidene)-1-(3-((pyridin-4-ylcarbonyl)amino)phenyl)ethan-1-one TLC: Rf0.28 (ethyl acetate); NMR (CDCl$_3$): δ 0.94 (t, J=7.2 Hz, 6H), 1.64 (m, 4H), 2.84 (s, 2H), 3.88 (s, 3H), 6.29 (s, 1H), 6.99 (dd, J=8.4, 2.4 Hz, 1H), 7.14 (d, J=8.4 Hz, 1H), 7.35 (d, J=2.4 Hz, 1H), 7.48 (t, J=8.1 Hz, 1H), 7.74 (m, 3H), 7.95 (m, 2H), 8.08 (m, 1H), 8.83 (m, 2H), 12.03 (s, 1H).

EXAMPLE 90(13)

(Z)-2-(7-methoxy-3,3-diethyl-3,4-dihydro-(2H)-isoquinolin-1-ylidene)-1-(4-((pyridin-4-ylcarbonyl)amino)phenyl)ethan-1-one TLC: Rf0.22 (ethyl acetate); NMR (CDCl$_3$): δ 0.94 (t, J=7.2 Hz, 6H), 1.64 (m, 4H), 2.83 (s, 2H), 3.89 (s, 3H), 6.29 (s, 1H), 6.99 (dd, J=8.4, 2.4 Hz, 1H), 7.14 (d, J=8.4 Hz, 1H), 7.34 (d, J=2.4 Hz, 1H), 7.74 (m, 4H), 7.96 (m, 1H), 8.02 (m, 2H), 8.83 (m, 2H), 11.98 (s, 1H).

EXAMPLE 90(14)

(Z)-2-(7-methoxy-3,3-diethyl-3,4-dihydro-(2H)-isoquinolin-1-ylidene)-1-(3-((2-methoxyacetyl)amino)phenyl)ethan-1-one TLC: Rf0.27 (hexane:ethyl acetate=1:1); NMR (CDCl$_3$): δ 0.94 (t, J=7.5 Hz, 6H), 1.63 (m, 4H), 2.83 (s, 2H), 3.52 (s, 3H), 3.88 (s, 3H), 4.03 (s, 2H), 6.28 (s, 1H), 6.98 (dd, J=8.4, 2.4 Hz, 1H), 7.13 (d, J=8.4 Hz, 1H), 7.34 (d, J=2.4 Hz, 1H), 7.42 (t, J=7.8 Hz, 1H), 7.70 (dt, J=7.8, 1.8 Hz, 1H), 7.86 (t, J=1.8 Hz, 1H), 8.02 (dt, J=7.8, 1.8 Hz, 1H), 8.38 (s, 1H), 12.03 (s, 1H).

EXAMPLE 90(15)

(Z)-2-(7-methoxy-3,3-diethyl-3,4-dihydro-(2H)-isoquinolin-1-ylidene)-1-(4-((2-methoxyacetyl)amino)phenyl)ethan-1-one TLC: Rf0.22 (hexane:ethyl acetate=1:1); NMR (CDCl$_3$): δ 0.92 (t, J=7.2 Hz, 6H), 1.62 (m, 4H), 2.82 (s, 2H), 3.52 (s, 3H), 3.88 (s, 3H), 4.03 (s, 2H), 6.28 (s, 1H), 6.98 (dd, J=8.4, 2.4 Hz, 1H), 7.12 (d, J=8.4 Hz, 1H), 7.33 (d, J=2.4 Hz, 1H), 7.66 (d, J=8.4 Hz, 2H), 7.96 (d, J=8.4 Hz, 2H), 8.37 (s, 1H), 11.94 (s, 1H).

EXAMPLE 90(16)

(Z)-2-(6-methoxy-3,3-dimethyl-2,3-dihydro-(2H)-isoindol-1-ylidene)-1-(4-mesylaminophenyl)ethan-1-one TLC: Rf0.39 (hexane:ethyl acetate=1:1); NMR (CDCl$_3$): δ 1.57 (s, 6H) 3.07 (s, 3H) 3.91 (s, 3H) 6.27 (s, 1H) 6.58 (s, 1H) 7.10 (dd, J=8.38, 2.34 Hz, 1H) 7.21 (d, J=2.34 Hz, 1H) 7.27 (d, J=8.79 Hz, 2H) 7.31 (d, J=8.38 Hz, 1H) 8.01 (d, J=8.79 Hz, 2H) 10.41 (s, 1H).

EXAMPLE 91

(Z)-2-(6-methoxy-3,3-diethyl-2,3-dihydro-(2H)-isoindol-1-ylidene)-1-(4-dimethylaminophenyl)ethan-1-one By the same procedure as described in example 41 using the compound prepared in example 87(1) in place of the compound prepared in example 38, the compound of the present invention having the following physical data was given.

TLC: Rf0.19 (hexane:ethyl acetate=3:1); NMR (CDCl$_3$): δ 0.65 (t, J=7.5 Hz, 6H), 1.91 (m, 4H), 3.05 (s, 6H), 3.91 (s, 3H), 6.31 (s, 1H), 6.73 (d, J=8.7 Hz, 2H), 7.05 (dd, J=8.4, 2.4 Hz, 1H), 7.19 (d, J=8.4 Hz, 1H), 7.22 (d, J=2.4 Hz, 1H), 7.97 (d, J=8.7 Hz, 2H), 10.11 (s, 1H).

EXAMPLE 92

(Z)-2-(7-methoxy-3,3-dimethyl-3,4-dihydro-(2H)-isoquinolin-1-ylidene)-1-(3-(2-(pyridin-4-yl)ethynyl)phenyl)ethan-1-one To triethylamine (3 ml) was suspended the compound prepared in example 86(17) (0.51 g) and the atmosphere was substituted with argon, thereto were added bis(triphenylphosphine)palladium(II) chloride (0.07 g) and copper bromide(I) (0.02 g) and the atmosphere was again substituted with argon, thereto was added 4-ethynylpyridine (0.13 g) and the mixture was stirred for 1 hour at 60° C. and for 4 hours at 90° C. The reaction mixture was azeotroped with toluene. To the residue was added water and ethyl acetate and was filtered. The filtrate was washed with water and brine, dried over anhydrous magnesium sulfate and concentrated. The residue was purified by column chromatography on silica gel (hexane:ethyl acetate=1:1) to give the compound of the present invention (0.44 g) having the following physical data.

TLC: Rf0.49 (hexane:ethyl acetate=1:4); NMR (CDCl$_3$): δ 11.89 (br, 1H), 8.63 (br, 2H), 8.11 (t, J=1.5 Hz, 1H), 7.97 (dt, J=7.8, 1.5 Hz, 1H), 7.62 (dt, J=7.8, 1.5 Hz, 1H), 7.46 (t, J=7.8 Hz, 1H), 7.41 (br, 2H), 7.36 (d, J=2.6 Hz, 1H), 7.15 (d, J=8.4 Hz, 1H), 7.01 (dd, J=8.4, 2.6 Hz, 1H), 6.26 (s, 1H), 3.89 (s, 3H), 2.85 (s, 2H), 1.37 (s, 6H).

EXAMPLE 93

(Z)-2-(7-methoxy-3,3-dimethyl-3,4-dihydro-(2H)-isoquinolin-1-ylidene)-1-(3-(2-(pyridin-4-yl)ethyl)phenyl)ethan-1-one Under atmosphere of argon, to the compound prepared in example 92 (0.22 g) were added 10% palladium carbon (0.02 g) and methanol (10 ml). Under atmosphere of hydrogen the mixture was stirred for 6 hours at room temperature. The reaction mixture was filtered over celite. The filtrate was concentrated. The residue was purified by column chromatography on silica gel (ethyl acetate) to give the compound of the present invention having the following physical data.

TLC: Rf0.56 (ethyl acetate); NMR (CDCl$_3$): δ 11.88 (br, 1H), 8.49 (dd, J=4.5, 1.8 Hz, 2H), 7.81-7.75 (m, 2H), 7.34 (d, J=2.7 Hz, 1H), 7.34 (t, J=7.7 Hz, 1H), 7.21 (m, 1H), 7.14 (d, J=8.3 Hz, 1H), 7.10 (dd, J=4.5, 1.8 Hz, 2H), 6.99 (dd, J=8.3, 2.7 Hz, 1H), 6.24 (s, 1H), 3.89 (s, 3H), 3.05-2.92 (m, 4H), 2.84 (s, 2H), 1.36 (s, 6H).

EXAMPLE 94

(Z)-2-(7-methoxy-3,3-dimethyl-3,4-dihydro-(2H)-isoquinolin-1-ylidene)-1-(2-hydroxypyridin-5-yl)ethan-1-one To a solution of hexamethyldisilathiane (1 ml) in 1,3-dimethyl-2-imidazolidinone (5 ml) was added sodium methoxide (0.24 g) and the mixture was stirred for 1 hour at room temperature. To the reaction solution was added the compound prepared in example 86(14) (0.43 g) and the mixture was stirred for 1 hour at 150° C. The reaction mixture was allowed to cool to room temperature and thereto was added water and the mixture was extracted with ethyl acetate. The extract was washed with water and brine, dried over anhydrous magnesium sulfate and concentrated. The residue was purified by column chromatography on silica gel (ethyl acetate:methanol=1:0→50:1→40:1) and thus purified compound was sonicated to give the compound of the present invention (0.22 g) having the following physical data.

TLC: Rf0.64 (chloroform:methanol:water=10:2:0.1); NMR (CDCl$_3$): δ 12.44 (br, 1H), 11.62 (br, 1H), 8.11-8.06 (m, 2H), 7.26 (d, J=2.7 Hz, 1H), 7.13 (d, J=8.4 Hz, 1H), 7.00 (dd, J=8.4, 2.7 Hz, 1H), 6.63 (m, 1H), 5.98 (s, 1H), 3.90 (s, 3H), 2.82 (s, 2H), 1.34 (s, 6H).

EXAMPLE 95

(Z)-2-(7-methoxy-3,3-dimethyl-3,4-dihydro-(2H)-isoquinolin-1-ylidene)-1-(1-methyl-6-oxo-1,6-dihydropyridin-3-yl)ethan-1-one To a solution of the compound prepared in example 94 (0.72 g) in tetrahydrofuran (1 ml) and dimethylformamide (1 ml) were added potassium carbonate (46 mg) and methyl iodide (21 μl) and the mixture was stirred for 6 hours at room temperature. To the reaction mixture was added water and the mixture was extracted with ethyl acetate. The extract was washed with water and brine, dried over anhydrous magnesium sulfate and concentrated. The residue was purified by column chromatography on silica gel (ethyl acetate) to give the compound of the present invention (76 mg) having the following physical data.
TLC: Rf0.35 (ethyl acetate:methanol=40:1); NMR (CDCl$_3$): δ 11.67 (br, 1H), 8.11 (d, J=2.8 Hz, 1H), 7.88 (dd, J=8.5, 2.8 Hz, 1H), 7.29 (d, J=2.5 Hz, 1H), 7.14 (d, J=8.2 Hz, 1H), 7.00 (dd, J=8.2, 2.5 Hz, 1H), 6.57 (d, J=8.5 Hz, 1H), 5.98 (s, 1H), 3.88 (s, 3H), 3.63 (s, 3H), 2.83 (s, 2H), 1.34 (s, 6H).

EXAMPLE 96-EXAMPLE 96(2)

By the same procedure as described in reference example 11→reference example 6→example 11→example 42 using 7-methoxy-4-hydroxy-3,3-dimethyl-3,4-dihydro-(2H)-isoquinolin-1-one in place of the compound prepared in reference example 10 and a corresponding derivative in place of benzoylmethyl bromide, the following compounds of the present invention were given.

EXAMPLE 96

(Z)-2-(4-hydroxy-7-methoxy-3,3-dimethyl-3,4-dihydro-(2H)-isoquinolin-1-ylidene)-1-(4-cyanophenyl)ethan-1-one TLC: Rf0.48 (hexane:ethyl acetate=1:1); NMR (CDCl$_3$): δ 11.78 (br s, 1H), 7.99 (d, J=8.4 Hz, 2H), 7.72 (d, J=8.4 Hz, 2H), 7.46 (d, J=8.4 Hz, 1H), 7.31 (d, J=2.7 Hz, 1H), 7.09 (dd, J=8.4, 2.7 Hz, 1H), 6.24 (s, 1H), 4.48 (d, J=7.5 Hz, 1H), 3.90 (s, 3H), 1.96 (d, J=7.5 Hz, 1H), 1.43 (s, 3H), 1.28 (s, 3H).

EXAMPLE 96(1)

(Z)-2-(4-hydroxy-7-methoxy-3,3-dimethyl-3,4-dihydro-(2H)-isoquinolin-1-ylidene)-1-(4-methoxyphenyl)ethan-1-one TLC: Rf0.31 (hexane:ethyl acetate=1:1); NMR (CDCl$_3$): δ 1.22 (s, 3H) 1.43 (s, 3H) 2.92 (d, J=8.06 Hz, 1H) 3.85 (s, 6H) 4.40 (d, J=8.06 Hz, 1H) 6.17 (s, 1H) 6.87 (d, J=8.73 Hz, 2H) 7.02 (dd, J=8.39, 2.35 Hz, 1H) 7.18 (d, J=2.35 Hz, 1H) 7.42 (d, J=8.39 Hz, 1H) 7.83 (d, J=8.73 Hz, 2H) 11.50 (s, 1H).

EXAMPLE 96(2)

(Z)-2-(4-hydroxy-7-methoxy-3,3-dimethyl-3,4-dihydro-(2H)-isoquinolin-1-ylidene)-1-(4-nitrophenyl)ethan-1-one TLC: Rf0.41 (hexane:ethyl acetate=1:1); NMR (DMSO-d$_6$): δ 1.18 (s, 3H) 1.24 (s, 3H) 3.87 (s, 3H) 4.44 (d, J=5.71 Hz, 1H) 5.74 (d, J=5.71 Hz, 1H) 6.54 (s, 1H) 7.17 (dd, J=8.39, 2.52 Hz, 1H) 7.47 (d, J=8.39 Hz, 1H) 7.59 (d, J=2.52 Hz, 1H) 8.26 (s, 4H) 11.95 (s, 1H).

EXAMPLE 97

(Z)-2-(4-oxo-7-methoxy-3,3-dimethyl-3,4-dihydro-(2H)-isoquinolin-1-ylidene)-1-(4-cyanophenyl)ethan-1-one By the same procedure as described in example 43 using the compound prepared in example 96 in place of the compound prepared in example 42, the compound of the present invention having the following physical data was given.
TLC: Rf0.45 (hexane:ethyl acetate=2:1); NMR (CDCl$_3$): δ 12.44 (br s, 1H), 8.18 (d, J=8.7 Hz, 1H), 8.03 (d, J=8.4 Hz, 2H), 7.76 (d, J=8.4 Hz, 2H), 7.44 (d, J=2.4 Hz, 1H), 7.21 (dd, J=8.7, 2.4 Hz, 1H), 6.45 (s, 1H), 3.99 (s, 3H), 1.61 (s, 6H).

EXAMPLE 98

(Z)-2-(4-hydroxy-7-methoxy-3,3-dimethyl-3,4-dihydro-(2H)-isoquinolin-1-ylidene)-1-(4-aminophenyl)ethan-1-one By the same procedure as described in example 58 using the compound prepared in example 96(2) in place of the compound prepared in example 56, the compound of the present invention having the following physical data was given.
TLC: Rf0.70 (ethyl acetate); NMR (DMSO-d$_6$): δ 1.07 (s, 3H) 1.21 (s, 3H) 3.85 (s, 3H) 4.39 (d, J=5.88 Hz, 1H) 5.65 (m, 3H) 6.29 (s, 1H) 6.54 (d, J=8.73 Hz, 2H) 7.10 (dd, J=8.48, 2.27 Hz, 1H) 7.44 (m, 2H) 7.74 (d, J=8.73 Hz, 2H) 11.51 (s, 1H).

EXAMPLE 99-EXAMPLE 99(164)

The compounds of example 99 to example 99(164) were prepared according to the following method.

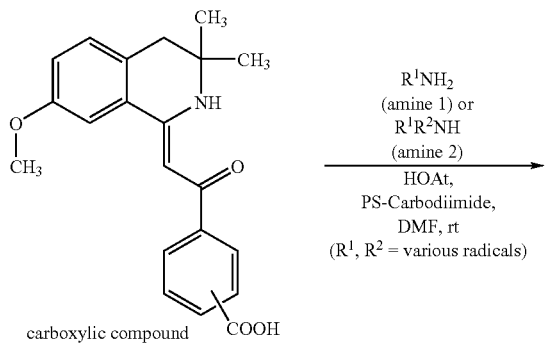
carboxylic compound

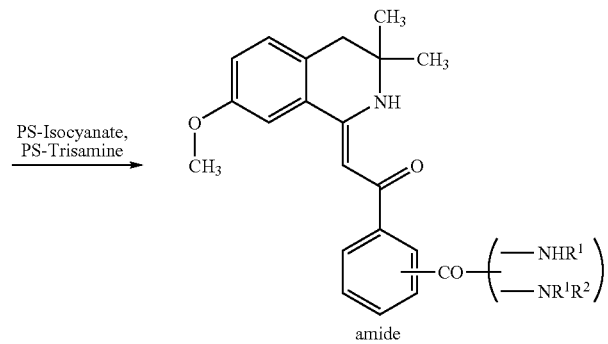
amide

To a solution of a carboxylic acid (15 μmol) in pyridine (30 μl) were added a solution of amine 1 or amine 2 (30 μmol) in N,N-dimethylformamide (120 μl), a solution of HOAt (30 mmol, 1-hydroxy-7-azabenzotriazole) in N,N-dimethylformamide (60 μl) and PS-Carbodiimide (ca. 45 mg, Argonaut Technologies Inc.) and the mixture was allowed to stand overnight at room temperature. To the mixture were added PS-Isocyanate (ca. 60 mg, Argonaut Technologies Inc.) and PS-Trisamine (ca. 25 mg, Argonaut Technologies Inc.) and the resin was filtered and was washed with methylene chloride (3 ml). The filtrate was concentrated to give an amide compound. The condition under which HPLC was measured is as follows.
Column: XTerra C18, 4.6×50 mm (5 um)
Rate of flow: 3 ml/min, μ
Solvent
Solvent A: a 0.1% aqueous solution of trifluoroacetic acid,
Solvent B: a 0.1% solution of trifluoroacetic acid in acetonitrile
Ratio of solvent:
At first, the ratio of solvent A/solvent B was fixed to 95/5 for first 0.5 minute. Next the ratio was changed to 0/100 linearly in 2.5 minutes and the ratio was fixed to 0/100 for 0.5 minute. Afterwards, the ratio was changed to 95/5 in 0.01 minute and the ratio was fixed to 95/5 for 1.49 minutes.

EXAMPLE 99

(Z)-2-(7-methoxy-3,3-dimethyl-3,4-dihydro-(2H)-isoquinolin-1-ylidene)-1-(3-(cyclobutylcarbamoyl)phenyl)ethan-1-one HPLC retention time (min.): 3.97; Mass (ESI, Pos. 20V): m/z 405 (M+H)$^+$.

EXAMPLE 99(1)

(Z)-2-(7-methoxy-3,3-dimethyl-3,4-dihydro-(2H)-isoquinolin-1-ylidene)-1-(3-(cyclopentylcarbamoyl)phenyl)ethan-1-one HPLC retention time (min.): 4.05; Mass (ESI, Pos. 20V): m/z 419 (M+H)$^+$.

EXAMPLE 99(2)

(Z)-2-(7-methoxy-3,3-dimethyl-3,4-dihydro-(2H)-isoquinolin-1-ylidene)-1-(3-((cyclohexylmethyl)carbamoyl)phenyl)ethan-1-one HPLC retention time (min.): 4.27; Mass (ESI, Pos. 20V): m/z 447 (M+H)$^+$.

EXAMPLE 99(3)

(Z)-2-(7-methoxy-3,3-dimethyl-3,4-dihydro-(2H)-isoquinolin-1-ylidene)-1-(3-(N-methyl-N-(2-hydroxyethyl)carbamoyl)phenyl)ethan-1-one HPLC retention time (min.): 3.52; Mass (ESI, Pos. 20V) m/z 409 (M+H)$^+$.

EXAMPLE 99(4)

(Z)-2-(7-methoxy-3,3-dimethyl-3,4-dihydro-(2H)-isoquinolin-1-ylidene)-1-(3-(1,3,4-thiadiazol-2-ylcarbamoyl)phenyl)ethan-1-one HPLC retention time (min.): 3.83; Mass (ESI, Pos. 20V): m/z 435 (M+H)$^+$.

EXAMPLE 99(5)

(Z)-2-(7-methoxy-3,3-dimethyl-3,4-dihydro-(2H)-isoquinolin-1-ylidene)-1-(3-((1-ethylpyrrolidin-2-ylmethyl)carbamoyl)phenyl)ethan-1-one HPLC retention time (min.): 3.40; Mass (ESI, Pos. 20V): m/z 462 (M+H)$^+$.

EXAMPLE 99(6)

(Z)-2-(7-methoxy-3,3-dimethyl-3,4-dihydro-(2H)-isoquinolin-1-ylidene)-1-(3-((furan-2-ylmethyl)carbamoyl)phenyl)ethan-1-one HPLC retention time (min.): 3.94; Mass (ESI, Pos. 20V): m/z 431 (M+H)$^+$.

EXAMPLE 99(7)

(Z)-2-(7-methoxy-3,3-dimethyl-3,4-dihydro-(2H)-isoquinolin-1-ylidene)-1-(3-(1,3-thiazolidin-3-ylcarbonyl)phenyl)ethan-1-one HPLC retention time (min.): 3.91; Mass (ESI, Pos. 20V): m/z 423 (M+H)$^+$.

EXAMPLE 99(8)

(Z)-2-(7-methoxy-3,3-dimethyl-3,4-dihydro-(2H)-isoquinolin 1-ylidene)-1-(3-(pyrrolidin-1-ylcarbonyl)phenyl)ethan-1-one HPLC retention time (min.): 3.86; Mass (ESI, Pos. 20V): m/z 405 (M+H)$^+$.

EXAMPLE 99(9)

(Z)-2-(7-methoxy-3,3-dimethyl-3,4-dihydro-(2H)-isoquinolin-1-ylidene)-1-(3-((tetrahydrofuran-2-ylmethyl)carbamoyl)phenyl)ethan-1-one HPLC retention time (min.): 3.82; Mass (ESI, Pos. 20V): m/z 435 (M+H)$^+$.

EXAMPLE 99(10)

(Z)-2-(7-methoxy-3,3-dimethyl-3,4-dihydro-(2H)-isoquinolin-1-ylidene)-1-(3-(4-methylpiperazin-1-ylcarbonyl)phenyl)ethan-1-one HPLC retention time (min.): 3.27; Mass (ESI, Pos. 20V): m/z 434 (M+H)$^+$.

EXAMPLE 99(11)

(Z)-2-(7-methoxy-3,3-dimethyl-3,4-dihydro-(2H)-isoquinolin-1-ylidene)-1-(3-(morpholin-4-ylcarbonyl)phenyl)ethan-1-one HPLC retention time (min.): 3.71; Mass (ESI, Pos. 20V): m/z 421 (M+H)$^+$.

EXAMPLE 99(12)

(Z)-2-(7-methoxy-3,3-dimethyl-3,4-dihydro-(2H)-isoquinolin-1-ylidene)-1-(3-(thiomorpholin-4-ylcarbonyl)phenyl)ethan-1-one HPLC retention time (min.): 3.94; Mass (ESI, Pos. 20V): m/z 437 (M+H)$^+$.

EXAMPLE 99(13)

(Z)-2-(7-methoxy-3,3-dimethyl-3,4-dihydro-(2H)-isoquinolin-1-ylidene)-1-(3-((2-(morpholin-4-yl)ethyl)carbamoyl)phenyl)ethan-1-one HPLC retention time (min.): 3.32; Mass (ESI, Pos. 20V): m/z 464 (M+H)$^+$.

EXAMPLE 99(14)

(Z)-2-(7-methoxy-3,3-dimethyl-3,4-dihydro-(2H)-isoquinolin-1-ylidene)-1-(3-((pyridin-2-ylmethyl)carbamoyl)phenyl)ethan-1-one HPLC retention time (min.): 3.35; Mass (ESI, Pos. 20V): m/z 442 (M+H)$^+$.

EXAMPLE 99(15)

(Z)-2-(7-methoxy-3,3-dimethyl-3,4-dihydro-(2H)-isoquinolin-1-ylidene)-1-(3-((2-(pyridin-2-yl)ethyl)carbamoyl)phenyl)ethan-1-one HPLC retention time (min.): 3.34; Mass (ESI, Pos. 20V): m/z 456 (M+H)$^+$.

EXAMPLE 99(16)

(Z)-2-(7-methoxy-3,3-dimethyl-3,4-dihydro-(2H)-isoquinolin-1-ylidene)-1-(3-(pyridin-3-ylcarbamoyl)phenyl)ethan-1-one HPLC retention time (min.): 3.40; Mass (ESI, Pos. 20V): m/z 428 (M+H)$^+$.

EXAMPLE 99(17)

(Z)-2-(7-methoxy-3,3-dimethyl-3,4-dihydro-(2H)-isoquinolin-1-ylidene)-1-(3-((pyridin-3-ylmethyl)carbamoyl)phenyl)ethan-1-one HPLC retention time (min.): 3.32; Mass (ESI, Pos. 20V): m/z 442 (M+H)$^+$.

EXAMPLE 99(18)

(Z)-2-(7-methoxy-3,3-dimethyl-3,4-dihydro-(2H)-isoquinolin-1-ylidene)-1-(3-(pyridin-4-ylcarbamoyl)phenyl)ethan-1-one HPLC retention time (min.): 3.43; Mass (ESI, Pos. 20V): m/z 428 (M+H)$^+$.

EXAMPLE 99(19)

(Z)-2-(7-methoxy-3,3-dimethyl-3,4-dihydro-(2H)-isoquinolin-1-ylidene)-1-(3-((1-ethoxycarbonylpiperidin-4-yl)carbamoyl)phenyl)ethan-1-one HPLC retention time (min.): 3.93; Mass (ESI, Pos. 20V): m/z 506 (M+H)$^+$.

EXAMPLE 99(20)

(Z)-2-(7-methoxy-3,3-dimethyl-3,4-dihydro-(2H)-isoquinolin-1-ylidene)-1-(3-((2-(piperidin-1-yl)ethyl)carbamoyl)phenyl)ethan-1-one HPLC retention time (min.): 3.40; Mass (ESI, Pos. 20V): m/z 462 (M+H)$^+$.

EXAMPLE 99(21)

(Z)-2-(7-methoxy-3,3-dimethyl-3,4-dihydro-(2H)-isoquinolin-1-ylidene)-1-(3-(phenylcarbamoyl)phenyl)ethan-1-one HPLC retention time (min.): 4.11; Mass (ESI, Pos. 20V): m/z 427 (M+H)$^+$.

EXAMPLE 99(22)

(Z)-2-(7-methoxy-3,3-dimethyl-3,4-dihydro-(2H)-isoquinolin-1-ylidene)-1-(3-((2-methoxyphenyl)carbamoyl)phenyl)ethan-1-one HPLC retention time (min.): 4.20; Mass (ESI, Pos. 20V): m/z 457 (M+H)$^+$.

EXAMPLE 99(23)

(Z)-2-(7-methoxy-3,3-dimethyl-3,4-dihydro-(2H)-isoquinolin-1-ylidene)-1-(3-((3-methoxyphenyl)carbamoyl)phenyl)ethan-1-one HPLC retention time (min.): 4.13; Mass (ESI, Pos. 20V): m/z 457 (M+H)$^+$.

EXAMPLE 99(24)

(Z)-2-(7-methoxy-3,3-dimethyl-3,4-dihydro-(2H)-isoquinolin-1-ylidene)-1-(3-(t-butylcarbamoyl)phenyl)ethan-1-one HPLC retention time (min.): 4.06; Mass (ESI, Pos. 20V): m/z 407 (M+H)$^+$.

EXAMPLE 99(25)

(Z)-2-(7-methoxy-3,3-dimethyl-3,4-dihydro-(2H)-isoquinolin-1-ylidene)-1-(3-(benzylcarbamoyl)phenyl)ethan-1-one HPLC retention time (min.): 4.06; Mass (ESI, Pos. 20V): m/z 441 (M+H)$^+$.

EXAMPLE 99(26)

(Z)-2-(7-methoxy-3,3-dimethyl-3,4-dihydro-(2H)-isoquinolin-1-ylidene)-1-(3-((4-chlorobenzyl)carbamoyl)phenyl)ethan-1-one HPLC retention time (min.): 4.18; Mass (ESI, Pos. 20V): m/z 475 (M+H)$^+$.

EXAMPLE 99(27)

(Z)-2-(7-methoxy-3,3-dimethyl-3,4-dihydro-(2H)-isoquinolin-1-ylidene)-1-(3-((4-methoxybenzyl)carbamoyl)phenyl)ethan-1-one HPLC retention time (min.): 4.03; Mass (ESI, Pos. 20V): m/z 471 (M+H)$^+$.

EXAMPLE 99(28)

(Z)-2-(7-methoxy-3,3-dimethyl-3,4-dihydro-(2H)-isoquinolin-1-ylidene)-1-(3-((2,2-dimethylpropyl)carbamoyl)phenyl)ethan-1-one HPLC retention time (min.): 4.12; Mass (ESI, Pos. 20V): m/z 421 (M+H)$^+$.

EXAMPLE 99(29)

(Z)-2-(7-methoxy-3,3-dimethyl-3,4-dihydro-(2H)-isoquinolin-1-ylidene)-1-(3-((2-methylpropyl)carbamoyl)phenyl)ethan-1-one HPLC retention time (min.): 4.02; Mass (ESI, Pos. 20V): m/z 407 (M+H)$^+$.

EXAMPLE 99(30)

(Z)-2-(7-methoxy-3,3-dimethyl-3,4-dihydro-(2H)-isoquinolin-1-ylidene)-1-(3-((2-(phenylamino)ethyl)carbamoyl)phenyl)ethan-1-one HPLC retention time (min.): 3.61; Mass (ESI, Pos. 20V): m/z 470 (M+H)$^+$.

EXAMPLE 99(31)

(Z)-2-(7-methoxy-3,3-dimethyl-3,4-dihydro-(2H)-isoquinolin-1-ylidene)-1-(3-((2-(acetylamino)ethyl)carbamoyl)phenyl)ethan-1-one HPLC retention time (min.): 3.51; Mass (ESI, Pos. 20V): m/z 436 (M+H)$^+$.

EXAMPLE 99(32)

(Z)-2-(7-methoxy-3,3-dimethyl-3,4-dihydro-(2H)-isoquinolin-1-ylidene)-1-(3-((2-methoxyethyl)carbamoyl)phenyl)ethan-1-one HPLC retention time (min.): 3.73; Mass (ESI, Pos. 20V): m/z 409 (M+H)$^+$.

EXAMPLE 99(33)

(Z)-2-(7-methoxy-3,3-dimethyl-3,4-dihydro-(2H)-isoquinolin-1-ylidene)-1-(3-((2-phenylethyl)carbamoyl)phenyl)ethan-1-one HPLC retention time (min.): 4.09; Mass (ESI, Pos. 20V): m/z 455 (M+H)$^+$.

EXAMPLE 99(34)

(Z)-2-(7-methoxy-3,3-dimethyl-3,4-dihydro-(2H)-isoquinolin-1-ylidene)-1-(3-(N-methyl-N-phenylcarbamoyl)phenyl)ethan-1-one HPLC retention time (min.): 4.06; Mass (ESI, Pos. 20V): m/z 441 (M+H)$^+$.

EXAMPLE 99(35)

(Z)-2-(7-methoxy-3,3-dimethyl-3,4-dilhydro-(2H)-isoquinolin-1-ylidene)-1-(3-(N,N-dimethylcarbamoyl)phenyl)ethan-1-one HPLC retention time (min.): 3.74; Mass (ESI, Pos. 20V): m/z 379 (M+H)$^+$.

EXAMPLE 99(36)

(Z)-2-(7-methoxy-3,3-dimethyl-3,4-dihydro-(2H)-isoquinolin-1-ylidene)-1-(3-(N-methyl-N-benzylcarbamoyl)phenyl)ethan-1-one HPLC retention time (min.): 4.13; Mass (ESI, Pos. 20V): m/z 455 (M+H)$^+$.

EXAMPLE 99(37)

(Z)-2-(7-methoxy-3,3-dimethyl-3,4-dihydro-(2H)-isoquinolin-1-ylidene)-1-(3-(N-methyl-N-phenethyl-carbamoyl)phenyl)ethan-1-one HPLC retention time (min.): 4.12; Mass (ESI, Pos. 20V): m/z 469 (M+H)$^+$.

EXAMPLE 99(38)

(Z)-2-(7-methoxy-3,3-dimethyl-3,4-dihydro-(2H)-isoquinolin-1-ylidene)-1-(3-((cyclopropylmethyl)carbamoyl)phenyl)ethan-1-one HPLC retention time (min.): 3.95; Mass (ESI, Pos. 20V): m/z 405 (M+H)$^+$.

EXAMPLE 99(39)

(Z)-2-(7-methoxy-3,3-dimethyl-3,4-dihydro-(2H)-isoquinolin-1-ylidene)-1-(3-(ethylcarbamoyl)phenyl)ethan-1-one HPLC retention time (min.): 3.80; Mass (ESI, Pos. 20V): m/z 379 (M+H)$^+$.

EXAMPLE 99(40)

(Z)-2-(7-methoxy-3,3-dimethyl-3,4-dihydro-(2H)-isoquinolin-1-ylidene)-1-(3-(3-hydroxypiperidin-1-ylcarbonyl)phenyl)ethan-1-one HPLC retention time (min.): 3.60; Mass (ESI, Pos. 20V): m/z 435 (M+H)$^+$.

EXAMPLE 99(41)

(Z)-2-(7-methoxy-3,3-dimethyl-3,4-dihydro-(2H)-isoquinolin-1-ylidene)-1-(3-(isopropylcarbamoyl)phenyl)ethan-1-one HPLC retention time (min.): 3.91; Mass (ESI, Pos. 20V): m/z 393 (M+H)$^+$.

EXAMPLE 99(42)

(Z)-2-(7-methoxy-3,3-dimethyl-3,4-dihydro-(2H)-isoquinolin-1-ylidene)-1-(3-((2-(thiophen-2-yl)ethyl)carbamoyl)phenyl)ethan-1-one HPLC retention time (min.): 4.06; Mass (ESI, Pos. 20V): m/z 461 (M+H)$^+$.

EXAMPLE 99(43)

(Z)-2-(7-methoxy-3,3-dimethyl-3,4-dihydro-(2H)-isoquinolin-1-ylidene)-1-(3-((5-methylfuran-2-ylmethyl)carbamoyl)phenyl)ethan-1-one HPLC retention time (min.): 4.03; Mass (ESI, Pos. 20V): m/z 445 (M+H)$^+$.

EXAMPLE 99(44)

(Z)-2-(7-methoxy-3,3-dimethyl-3,4-dihydro-(2H)-isoquinolin-1-ylidene)-1-(3-(((1S)-1-hydroxymethyl-3-methylthiopropyl)carbamoyl)phenyl)ethan-1-one HPLC retention time (min.): 3.74; Mass (ESI, Pos. 20V): m/z 469 (M+H)$^+$.

EXAMPLE 99(45)

(Z)-2-(7-methoxy-3,3-dimethyl-3,4-dihydro-(2H)-isoquinolin-1-ylidene)-1-(3-((1,3-dioxaindan-5-yl)carbamoyl)phenyl)ethan-1-one HPLC retention time (min.): 4.06; Mass (ESI, Pos. 20V): m/z 471 (M+H)$^+$.

EXAMPLE 99(46)

(Z)-2-(7-methoxy-3,3-dimethyl-3,4-dihydro-(2H)-isoquinolin-1-ylidene)-1-(3-(4-(2-hydroxyethyl)piperazin-1-ylcarbonyl)phenyl)ethan-1-one HPLC retention time (min.): 3.25; Mass (ESI, Pos. 20V): m/z 464 (M+H)$^+$.

EXAMPLE 99(47)

(Z)-2-(7-methoxy-3,3-dimethyl-3,4-dihydro-(2H)-isoquinolin-1-ylidene)-1-(3-((quinolin-5-yl)carbamoyl)phenyl)ethan-1-one HPLC retention time (min.): 3.45; Mass (ESI, Pos. 20V): m/z 478 (M+H)$^+$.

EXAMPLE 99(48)

(Z)-2-(7-methoxy-3,3-dimethyl-3,4-dihydro-(2H)-isoquinolin-1-ylidene)-1-(3-((quinolin-6-yl)carbamoyl)phenyl)ethan-1-one HPLC retention time (min.): 3.50; Mass (ESI, Pos. 20V): m/z 478 (M+H)$^+$.

EXAMPLE 99(49)

(Z)-2-(7-methoxy-3,3-dimethyl-3,4-dihydro-(2H)-isoquinolin-1-ylidene)-1-(3-((3-cyanophenyl)carbamoyl)phenyl)ethan-1-one HPLC retention time (min.): 4.13; Mass (ESI, Pos. 20V): m/z 452 (M+H)$^+$.

EXAMPLE 99(50)

(Z)-2-(7-methoxy-3,3-dimethyl-3,4-dihydro-(2H)-isoquinolin-1-ylidene)-1-(3-((3-hydroxyphenyl)carbamoyl)phenyl)ethan-1-one HPLC retention time (min.): 3.87; Mass (ESI, Pos. 20V): m/z 443 (M+H)$^+$.

EXAMPLE 99(51)

(Z)-2-(7-methoxy-3,3-dimethyl-3,4-dihydro-(2H)-isoquinolin-1-ylidene)-1-(3-((4-hydroxyphenyl)carbamoyl)phenyl)ethan-1-one HPLC retention time (min.): 3.81; Mass (ESI, Pos. 20V): m/z 443 (M+H)$^+$.

EXAMPLE 99(52)

(Z)-2-(7-methoxy-3,3-dimethyl-3,4-dihydro-(2H)-isoquinolin-1-ylidene)-1-(3-((2-dimethylaminoethyl)carbamoyl)phenyl)ethan-1-one HPLC retention time (min.): 3.31; Mass (ESI, Pos. 20V): m/z 422 (M+H)$^+$.

EXAMPLE 99(53)

(Z)-2-(7-methoxy-3,3-dimethyl-3,4-dihydro-(2H)-isoquinolin-1-ylidene)-1-(3-((2-(2-hydroxyethoxy)ethyl)carbamoyl)phenyl)ethan-1-one HPLC retention time (min.): 3.51; Mass (ESI, Pos. 20V): m/z 439 (M+H)$^+$.

EXAMPLE 99(54)

(Z)-2-(7-methoxy-3,3-dimethyl-3,4-dihydro-(2H)-isoquinolin-1-ylidene)-1-(3-((2-hydroxyethyl)carbamoyl)phenyl)ethan-1-one HPLC retention time (min.): 3.51; Mass (ESI, Pos. 20V): m/z 395 (M+H)$^+$.

EXAMPLE 99(55)

(Z)-2-(7-methoxy-3,3-dimethyl-3,4-dihydro-(2H)-isoquinolin-1-ylidene)-1-(3-(2-propynylcarbamoyl)phenyl)ethan-1-one HPLC retention time (min.): 3.83; Mass (ESI, Pos. 20V): m/z 389 (M+H)$^+$.

EXAMPLE 99(56)

(Z)-2-(7-methoxy-3,3-dimethyl-3,4-dihydro-(2H)-isoquinolin-1-ylidene)-1-(3-(2-propenylcarbamoyl)phenyl)ethan-1-one HPLC retention time (min.): 3.86; Mass (ESI, Pos. 20V): m/z 391 (M+H)$^+$.

EXAMPLE 99(57)

(Z)-2-(7-methoxy-3,3-dimethyl-3,4-dihydro-(2H)-isoquinolin-1-ylidene)-1-(3-((3-methylbutyl)carbamoyl)phenyl)ethan-1-one HPLC retention time (min.): 4.13; Mass (ESI, Pos. 20V): m/z 421 (M+H)$^+$.

EXAMPLE 99(58)

(Z)-2-(7-methoxy-3,3-dimethyl-3,4-dihydro-(2H)-isoquinolin-1-ylidene)-1-(3-((3-dimethylaminopropyl)carbamoyl)phenyl)ethan-1-one HPLC retention time (min.): 3.32; Mass (ESI, Pos. 20V): m/z 436 (M+H)$^+$.

EXAMPLE 99(59)

(Z)-2-(7-methoxy-3,3-dimethyl-3,4-dihydro-(2H)-isoquinolin-1-ylidene)-1-(3-((3-ethoxypropyl)carbamoyl)phenyl)ethan-1-one HPLC retention time (min.): 3.90; Mass (ESI, Pos. 20V): m/z 437 (M+H)$^+$.

EXAMPLE 99(60)

(Z)-2-(7-methoxy-3,3-dimethyl-3,4-dihydro-(2H)-isoquinolin-1-ylidene)-(3-(N-methyl-N-(2,2-dimethoxyethyl)carbamoyl)phenyl)ethan-1-one HPLC retention time (min.): 3.84; Mass (ESI, Pos. 20V): m/z 453 (M+H)$^+$.

EXAMPLE 99(61)

(Z)-2-(7-methoxy-3,3-dimethyl-3,4-dihydro-(2H)-isoquinolin-1-ylidene)-1-(3-((N-methyl-N-hydroxycarbamoyl)phenyl)ethan-1-one HPLC retention time (min.): 3.61; Mass (ESI, Pos. 20V): m/z 381 (M+H)$^+$.

EXAMPLE 99(62)

(Z)-2-(7-methoxy-3,3-dimethyl-3,4-dihydro-(2H)-isoquinolin-1-ylidene)-1-(3-(bis(2-methoxyethyl)carbamoyl)phenyl)ethan-1-one HPLC retention time (min.): 3.84; Mass (ESI, Pos. 20V): m/z 467 (M+H)$^+$.

EXAMPLE 99(63)

(Z)-2-(7-methoxy-3,3-dimethyl-3,4-dihydro-(2H)-isoquinolin-1-ylidene)-1-(3-((3-chlorobenzyl)carbamoyl)phenyl)ethan-1-one HPLC retention time (min.): 4.18; Mass (ESI, Pos. 20V): m/z 475 (M+H)$^+$.

EXAMPLE 99(64)

(Z)-2-(7-methoxy-3,3-dimethyl-3,4-dihydro-(2H)-isoquinolin-1-ylidene)-1-(3-((4-acetylpiperazin-1-yl)carbonyl)phenyl)ethan-1-one HPLC retention time (min.): 3.54; Mass (ESI, Pos. 20V): m/z 462 (M+H)$^+$.

EXAMPLE 99(65)

(Z)-2-(7-methoxy-3,3-dimethyl-3,4-dihydro-(2H)-isoquinolin-1-ylidene)-1-(3-((2R)-2-hydroxymethylpyrrolidin-1-ylcarbonyl)phenyl)ethan-1-one HPLC retention time (min.): 3.68; Mass (ESI, Pos. 20V): m/z 435 (M+H)$^+$.

EXAMPLE 99(66)

(Z)-2-(7-methoxy-3,3-dimethyl-3,4-dihydro-(2H)-isoquinolin-1-ylidene)-1-(3-(2,6-dimethylmorpholin-1-ylcarbonyl)phenyl)ethan-1-one HPLC retention time (min.): 3.93; Mass (ESI, Pos. 20V): m/z 449 (M+H)$^+$.

EXAMPLE 99(67)

(Z)-2-(7-methoxy-3,3-dimethyl-3,4-dihydro-(2H)-isoquinolin-1-ylidene)-1-(3-(N-methyl-N-(2-(pyridin-2-yl)ethyl)carbamoyl)phenyl)ethan-1-one HPLC retention time (min.): 3.33; Mass (ESI, Pos. 20V): m/z 470 (M+H)$^+$.

EXAMPLE 99(68)

(Z)-2-(7-methoxy-3,3-dimethyl-3,4-dihydro-(2H)-isoquinolin-1-ylidene)-1-(3-(((2,2,2-trifluoroethyl)amino)carbamoyl)phenyl)ethan-1-one HPLC retention time (min.): 3.90; Mass (ESI, Pos. 20V): m/z 448 (M+H)$^+$.

EXAMPLE 99(69)

(Z)-2-(7-methoxy-3,3-dimethyl-3,4-dihydro-(2H)-isoquinolin-1-ylidene)-1-(3-((1,1-diethyl-2-propynyl)carbamoyl)phenyl)ethan-1-one HPLC retention time (min.): 4.17; Mass (ESI, Pos. 20V): m/z 445 (M+H)$^+$.

EXAMPLE 99(70)

(Z)-2-(7-methoxy-3,3-dimethyl-3,4-dihydro-(2H)-isoquinolin-1-ylidene)-1-(3-((pyridin-2-yl)carbamoyl)phenyl)ethan-1-one HPLC retention time (min.): 3.53; Mass (ESI, Pos. 20V): m/z 428 (M+H)$^+$.

EXAMPLE 99(71)

(Z)-2-(7-methoxy-3,3-dimethyl-3,4-dihydro-(2H)-isoquinolin-1-ylidene)-1-(3-((4-methoxyphenyl)carbamoyl)phenyl)ethan-1-one HPLC retention time (min.): 4.07; Mass (ESI, Pos. 20V): m/z 457 (M+H)$^+$.

EXAMPLE 99(72)

(Z)-2-(7-methoxy-3,3-dimethyl-3,4-dihydro-(2H)-isoquinolin-1-ylidene)-1-(3-((1H-indazol-5-yl)carbamoyl)phenyl)ethan-1-one HPLC retention time (min.): 3.81; Mass (ESI, Pos. 20V): m/z 467 (M+H)$^+$.

EXAMPLE 99(73)

(Z)-2-(7-methoxy-3,3-dimethyl-3,4-dihydro-(2H)-isoquinolin-1-ylidene)-1-(3-((1-oxidopyridin-2-yl)carbamoyl)phenyl)ethan-1-one HPLC retention time (min.): 3.86; Mass (ESI, Pos. 20V): m/z 444 (M+H)$^+$.

EXAMPLE 99(74)

(Z)-2-(7-methoxy-3,3-dimethyl-3,4-dihydro-(2H)-isoquinolin-1-ylidene)-1-(3-((thiophen-2-ylmethyl)carbamoyl)phenyl)ethan-1-one HPLC retention time (min.): 4.03; Mass (ESI, Pos. 20V): m/z 447 (M+H)$^+$.

EXAMPLE 99(75)

(Z)-2-(7-methoxy-3,3-dimethyl-3,4-dihydro-(2H)-isoquinolin-1-ylidene)-1-(3-((2-ethylthioethyl)carbamoyl)phenyl)ethan-1-one HPLC retention time (min.): 4.01; Mass (ESI, Pos. 20V): m/z 439 (M+H)$^+$.

EXAMPLE 99(76)

(Z)-2-(7-methoxy-3,3-dimethyl-3,4-dihydro-(2H)-isoquinolin-1-ylidene)-1-(3-((2,2,2-trifluoroethyl)carbamoyl)phenyl)ethan-1-one HPLC retention time (min.): 3.97; Mass (ESI, Pos. 20V): m/z 433 (M+H)$^+$.

EXAMPLE 99(77)

(Z)-2-(7-methoxy-3,3-dimethyl-3,4-dihydro-(2H)-isoquinolin-1-ylidene)-1-(3-(N-methyl-N-(furan-2-ylmethyl)carbamoyl)phenyl)ethan-1-one HPLC retention time (min.): 4.01; Mass (ESI, Pos. 20V): m/z 445 (M+H)$^+$.

EXAMPLE 99(78)

(Z)-2-(7-methoxy-3,3-dimethyl-3,4-dihydro-(2H)-isoquinolin-1-ylidene)-1-(3-(N-propyl-N-(2-hydroxyethyl)carbamoyl)phenyl)ethan-1-one HPLC retention time (min.): 3.73; Mass (ESI, Pos. 20V): m/z 437 (M+H)$^+$.

EXAMPLE 99(79)

(Z)-2-(7-methoxy-3,3-dimethyl-3,4-dihydro-(2H)-isoquinolin-1-ylidene)-1-(3-(N-methyl-N-(2-methoxyethyl)carbamoyl)phenyl)ethan-1-one HPLC retention time (min.): 3.78; Mass (ESI, Pos. 20V): m/z 423 (M+H)$^+$.

EXAMPLE 99(80)

(Z)-2-(7-methoxy-3,3-dimethyl-3,4-dihydro-(2H)-isoquinolin-1-ylidene)-1-(3-((2-mercaptoethyl)carbamoyl)phenyl)ethan-1-one HPLC retention time (min.): 4.37; Mass (ESI, Pos. 20V): m/z 411 (M+H)$^+$.

EXAMPLE 99(81)

(Z)-2-(7-methoxy-3,3-dimethyl-3,4-dihydro-(2H)-isoquinolin-1-ylidene)-1-(3-(methylcarbamoyl)phenyl)ethan-1-one HPLC retention time (min.): 3.68; Mass (ESI, Pos. 20V): m/z 365 (M+H)$^+$.

EXAMPLE 99(82)

(Z)-2-(7-methoxy-3,3-dimethyl-3,4-dihydro-(2H)-isoquinolin-1-ylidene)-1-(4-(cyclobutylcarbamoyl)phenyl)ethan-1-one HPLC retention time (min.): 3.95; Mass (ESI, Pos. 20V): m/z 405 (M+H)$^+$.

EXAMPLE 99(83)

(Z)-2-(7-methoxy-3,3-dimethyl-3,4-dihydro-(2H)-isoquinolin-1-ylidene)-1-(4-(cyclopentylcarbamoyl)phenyl)ethan-1-one HPLC retention time (min.): 4.02; Mass (ESI, Pos. 20V): m/z 419 (M+H)$^+$.

EXAMPLE 99(84)

(Z)-2-(7-methoxy-3,3-dimethyl-3,4-dihydro-(2H)-isoquinolin-1-ylidene)-1-(4-((cyclohexylmethyl)carbamoyl)phenyl)ethan-1-one HPLC retention time (min.): 4.25; Mass (ESI, Pos. 20V): m/z 447 (M+H)$^+$.

EXAMPLE 99(85)

(Z)-2-(7-methoxy-3,3-dimethyl-3,4-dihydro-(2H)-isoquinolin-1-ylidene)-1-(4-(N-methyl-N-(2-hydroxyethyl)carbamoyl)phenyl)ethan-1-one HPLC retention time (min.): 3.51; Mass (ESI, Pos. 20V): m/z 409 (M+H)$^+$.

EXAMPLE 99(86)

(Z)-2-(7-methoxy-3,3-dimethyl-3,4-dihydro-(2H)-isoquinolin-1-ylidene)-1-(4-(1,3,4-thiadiazol-2-ylcarbamoyl)phenyl)ethan-1-one HPLC retention time (min.): 3.83; Mass (ESI, Pos. 20V): m/z 435 (M+H)$^+$.

EXAMPLE 99(87)

(Z)-2-(7-methoxy-3,3-dimethyl-3,4-dihydro-(2H)-isoquinolin-1-ylidene)-1-(4-((1-ethylpyrrolidin-2-ylmethyl)carbamoyl)phenyl)ethan-1-one HPLC retention time (min.): 3.41; Mass (ESI, Pos. 20V): m/z 462 (M+H)$^+$.

EXAMPLE 99(88)

(Z)-2-(7-methoxy-3,3-dimethyl-3,4-dihydro-(2H)-isoquinolin-1-ylidene)-1-(4-((furan-2-ylmethyl)carbamoyl)phenyl)ethan-1-one HPLC retention time (min.): 3.93; Mass (ESI, Pos. 20V): m/z 431 (M+H)$^+$.

EXAMPLE 99(89)

(Z)-2-(7-methoxy-3,3-dimethyl-3,4-dihydro-(2H)-isoquinolin-1-ylidene)-1-(4-(1,3'-thiazolidin-3-ylcarbonyl)phenyl)ethan-1-one HPLC retention time (min.): 3.91; Mass (ESI, Pos. 20V): m/z 423 (M+H)$^+$.

EXAMPLE 99(90)

(Z)-2-(7-methoxy-3,3-dimethyl-3,4-dihydro-(2H)-isoquinolin-1-ylidene)-1-(4-(pyrrolidin-1-ylcarbonyl)phenyl)ethan-1-one HPLC retention time (min.): 3.86; Mass (ESI, Pos. 20V): m/z 405 (M+H)$^+$.

EXAMPLE 99(91)

(Z)-2-(7-methoxy-3,3-dimethyl-3,4-dihydro-(2H)-isoquinolin-1-ylidene)-1-(4-((4,5-dihydro-1,3-thiazol-2-yl)carbamoyl)phenyl)ethan-1-one HPLC retention time (min.): 3.74; Mass (ESI, Pos. 20V): m/z 436 (M+H)$^+$.

EXAMPLE 99(92)

(Z)-2-(7-methoxy-3,3-dimethyl-3,4-dihydro-(2H)-isoquinolin-1-ylidene)-1-(4-((tetrahydrofuran-2-ylmethyl)carbamoyl)phenyl)ethan-1-one HPLC retention time (min.): 3.78; Mass (ESI, Pos. 20V): m/z 435 (M+H)$^+$.

EXAMPLE 99(93)

(Z)-2-(7-methoxy-3,3-dimethyl-3,4-dihydro-(2H)-isoquinolin-1-ylidene)-1-(4-(4-methylpiperazin-1-ylcarbonyl)phenyl)ethan-1-one HPLC retention time (min.): 3.26; Mass (ESI, Pos. 20V): m/z 434 (M+H)$^+$.

EXAMPLE 99(94)

(Z)-2-(7-methoxy-3,3-dimethyl-3,4-dihydro-(2H)-isoquinolin-1-ylidene)-1-(4-(morpholin-4-ylcarbonyl)phenyl)ethan-1-one HPLC retention time (min.): 3.72; Mass (ESI, Pos. 20V): m/z 421 (M+H)$^+$.

EXAMPLE 99(95)

(Z)-2-(7-methoxy-3,3-dimethyl-3,4-dihydro-(2H)-isoquinolin-1-ylidene)-1-(4-(thiomorpholin-4-ylcarbonyl)phenyl)ethan-1-one HPLC retention time (min.): 3.94; Mass (ESI, Pos. 20V): m/z 437 (M+H)$^+$.

EXAMPLE 99(96)

(Z)-2-(7-methoxy-3,3-dimethyl-3,4-dihydro-(2H)-isoquinolin-1-ylidene)-1-(4-((2-(morpholin-4-yl)ethyl)carbamoyl)phenyl)ethan-1-one HPLC retention time (min.): 3.33; Mass (ESI, Pos. 20V): m/z 464 (M+H)$^+$.

EXAMPLE 99(97)

(Z)-2-(7-methoxy-3,3-dimethyl-3,4-dihydro-(2H)-isoquinolin-1-ylidene)-1-(4-((pyridin-2-ylmethyl)carbamoyl)phenyl)ethan-1-one HPLC retention time (min.): 3.34; Mass (ESI, Pos. 20V): m/z 442 (M+H)$^+$.

EXAMPLE 99(98)

(Z)-2-(7-methoxy-3,3-dimethyl-3,4-dihydro-(2H)-isoquinolin-1-ylidene)-1-(4-((2-(pyridin-2-yl)ethyl)carbamoyl)phenyl)ethan-1-one HPLC retention time (min.): 3.34; Mass (ESI, Pos. 20V): m/z 456 (M+H)$^+$.

EXAMPLE 99(99)

(Z)-2-(7-methoxy-3,3-dimethyl-3,4-dihydro-(2H)-isoquinolin-1-ylidene)-1-(4-(pyridin-3-ylcarbamoyl)phenyl)ethan-1-one HPLC retention time (min.): 3.41; Mass (ESI, Pos. 20V): m/z 428 (M+H)$^+$.

EXAMPLE 99(100)

(Z)-2-(7-methoxy-3,3-dimethyl-3,4-dihydro-(2H)-isoquinolin-1-ylidene)-1-(4-((pyridin-3-ylmethyl)carbamoyl)phenyl)ethan-1-one HPLC retention time (min.): 3.32; Mass (ESI, Pos. 20V): m/z 442 (M+H)$^+$.

EXAMPLE 99(101)

(Z)-2-(7-methoxy-3,3-dimethyl-3,4-dihydro-(2H)-isoquinolin-1-ylidene)-1-(4-(pyridin-4-ylcarbamoyl)phenyl)ethan-1-one HPLC retention time (min.): 3.44; Mass (ESI, Pos. 20V): m/z 428 (M+H)$^+$.

EXAMPLE 99(102)

(Z)-2-(7-methoxy-3,3-dimethyl-3,4-dihydro-(2H)-isoquinolin-1-ylidene)-1-(4-((1-ethoxycarbonylpiperidin-4-yl)carbamoyl)phenyl)ethan-1-one HPLC retention time (min.): 3.90; Mass (ESI, Pos. 20V): m/z 506 (M+H)$^+$.

EXAMPLE 99(103)

(Z)-2-(7-methoxy-3,3-dimethyl-3,4-dihydro-(2H)-isoquinolin-1-ylidene)-1-(4-((2-(piperidin-1-yl)ethyl)carbamoyl)phenyl)ethan-1-one HPLC retention time (min.): 3.39; Mass (ESI, Pos. 20V): m/z 462 (M+H)$^+$.

EXAMPLE 99(104)

(Z)-2-(7-methoxy-3,3-dimethyl-3,4-dihydro-(2H)-isoquinolin-1-ylidene)-1-(4-(phenylcarbamoyl)phenyl)ethan-1-one HPLC retention time (min.): 4.10; Mass (ESI, Pos. 20V): m/z 427 (M+H)$^+$.

EXAMPLE 99(105)

(Z)-2-(7-methoxy-3,3-dimethyl-3,4-dihydro-(2H)-isoquinolin-1-ylidene)-1-(4-((2-methoxyphenyl)carbamoyl)phenyl)ethan-1-one HPLC retention time (min.): 4.22; Mass (ESI, Pos. 20V): m/z 457 (M+H)$^+$.

EXAMPLE 99(106)

(Z)-2-(7-methoxy-3,3-dimethyl-3,4-dihydro-(2H)-isoquinolin-1-ylidene)-1-(4-((3-methoxyphenyl)carbamoyl)phenyl)ethan-1-one HPLC retention time (min.): 4.12; Mass (ESI, Pos. 20V): m/z 457 (M+H)$^+$.

EXAMPLE 99(107)

(Z)-2-(7-methoxy-3,3-dimethyl-3,4-dihydro-(2H)-isoquinolin-1-ylidene)-1-(4-(t-butylcarbamoyl)phenyl)ethan-1-one HPLC retention time (min.): 4.05; Mass (ESI, Pos. 20V): m/z 407 (M+H)$^+$.

EXAMPLE 99(108)

(Z)-2-(7-methoxy-3,3-dimethyl-3,4-dihydro-(2H)-isoquinolin-1-ylidene)-1-(4-(benzylcarbamoyl)phenyl)ethan-1-one HPLC retention time (min.): 4.05; Mass (ESI, Pos. 20V): m/z 441 (M+H)$^+$.

EXAMPLE 99(109)

(Z)-2-(7-methoxy-3,3-dimethyl-3,4-dihydro-(2H)-isoquinolin-1-ylidene)-1-(4-((4-chlorobenzyl)carbamoyl)phenyl)ethan-1-one HPLC retention time (min.): 4.16; Mass (ESI, Pos. 20V): m/z 475 (M+H)$^+$.

EXAMPLE 99(110)

(Z)-2-(7-methoxy-3,3-dimethyl-3,4-dihydro-(2H)-isoquinolin-1-ylidene)-1-(4-((4-methoxybenzyl)carbamoyl)phenyl)ethan-1-one HPLC retention time (min.): 4.03; Mass (ESI, Pos. 20V): m/z 471 (M+H)$^+$.

EXAMPLE 99(111)

(Z)-2-(7-methoxy-3,3-dimethyl-3,4-dihydro-(2H)-isoquinolin-1-ylidene)-1-(4-((2,2-dimethylpropyl)carbamoyl)phenyl)ethan-1-one HPLC retention time (min.): 4.10; Mass (ESI, Pos. 20V): m/z 421 (M+H)$^+$.

EXAMPLE 99(112)

(Z)-2-(7-methoxy-3,3-dimethyl-3,4-dihydro-(2H)-isoquinolin-1-ylidene)-1-(4-((2-methylpropyl)carbamoyl)phenyl)ethan-1-one HPLC retention time (min.): 3.98; Mass (ESI, Pos. 20V): m/z 407 (M+H)$^+$.

EXAMPLE 99(113)

(Z)-2-(7-methoxy-3,3-dimethyl-3,4-dihydro-(2H)-isoquinolin-1-ylidene)-1-(4-((2-(phenylamino)ethyl)carbamoyl)phenyl)ethan-1-one HPLC retention time (min.): 3.59; Mass (ESI, Pos. 20V): m/z 470 (M+H)$^+$.

EXAMPLE 99(114)

(Z)-2-(7-methoxy-3,3-dimethyl-3,4-dihydro-(2H)-isoquinolin-1-ylidene)-1-(4-((2-(acetylamino)ethyl)carbamoyl)phenyl)ethan-1-one HPLC retention time (min.): 3.49; Mass (ESI, Pos. 20V): m/z 436 (M+H)$^+$.

EXAMPLE 99(115)

(Z)-2-(7-methoxy-3,3-dimethyl-3,4-dihydro-(2H)-isoquinolin-1-ylidene)-1-(4-((2-methoxyethyl)carbamoyl)phenyl)ethan-1-one HPLC retention time (min.): 3.72; Mass (ESI, Pos. 20V) m/z 409 (M+H)$^+$.

EXAMPLE 99(116)

(Z)-2-(7-methoxy-3,3-dimethyl-3,4-dihydro-(2H)-isoquinolin-1-ylidene)-1-(4-((2-phenylethyl)carbamoyl)phenyl)ethan-1-one HPLC retention time (min.): 4.08; Mass (ESI, Pos. 20V): m/z 455 (M+H)$^+$.

EXAMPLE 99(117)

(Z)-2-(7-methoxy-3,3-dimethyl-3,4-dihydro-(2H)-isoquinolin-1-ylidene)-1-(4-(N-methyl-N-phenylcarbamoyl)phenyl)ethan-1-one HPLC retention time (min.): 4.06; Mass (ESI, Pos. 20V): m/z 441 (M+H)$^+$.

EXAMPLE 99(118)

(Z)-2-(7-methoxy-3,3-dimethyl-3,4-dihydro-(2H)-isoquinolin-1-ylidene)-1-(4-(N,N-dimethylcarbamoyl)phenyl)ethan-1-one HPLC retention time (min.): 3.73; Mass (ESI, Pos. 20V): m/z 379 (M+H)$^+$.

EXAMPLE 99(119)

(Z)-2-(7-methoxy-3,3-dimethyl-3,4-dihydro-(2H)-isoquinolin-1-ylidene)-1-(4-(N-methyl-N-benzylcarbamoyl)phenyl)ethan-1-one HPLC retention time (min.): 4.12; Mass (ESI, Pos. 20V): m/z 455 (M+H)$^+$.

EXAMPLE 99(120)

(Z)-2-(7-methoxy-3,3-dimethyl-3,4-dihydro-(2H)-isoquinolin-1-ylidene)-1-(4-(N-methyl-N-phenethylcarbamoyl)phenyl)ethan-1-one HPLC retention time (min.): 4.13; Mass (ESI, Pos. 20V): m/z 469 (M+H)$^+$.

EXAMPLE 99(121)

(Z)-2-(7-methoxy-3,3-dimethyl-3,4-dihydro-(2H)-isoquinolin-1-ylidene)-1-(4-((cyclopropylmethyl)carbamoyl)phenyl)ethan-1-one HPLC retention time (min.): 3.93; Mass (ESI, Pos. 20V): m/z 405 (M+H)$^+$.

EXAMPLE 99(122)

(Z)-2-(7-methoxy-3,3-dimethyl-3,4-dihydro-(2H)-isoquinolin-1-ylidene)-1-(4-(ethylcarbamoyl)phenyl)ethan-1-one HPLC retention time (min.): 3.77; Mass (ESI, Pos. 20V): m/z 379 (M+H)$^+$.

EXAMPLE 99(123)

(Z)-2-(7-methoxy-3,3-dimethyl-3,4-dihydro-(2H)-isoquinolin-1-ylidene)-1-(4-(3-hydroxypiperidin-1-ylcarbonyl)phenyl)ethan-1-one HPLC retention time (min.): 3.62; Mass (ESI, Pos. 20V): m/z 435 (M+H)$^+$.

EXAMPLE 99(124)

(Z)-2-(7-methoxy-3,3-dimethyl-3,4-dihydro-(2H)-isoquinolin-1-ylidene)-1-(4-(isopropylcarbamoyl)phenyl)ethan-1-one HPLC retention time (min.): 3.88; Mass (ESI, Pos. 20V): m/z 393 (M+H)$^+$.

EXAMPLE 99(125)

(Z)-2-(7-methoxy-3,3-dimethyl-3,4-dihydro-(2H)-isoquinolin-1-ylidene)-1-(4-((2-(thiophen-2-yl)ethyl)carbamoyl)phenyl)ethan-1-one HPLC retention time (min.): 4.04; Mass (ESI, Pos. 20V): m/z 461 (M+H)$^+$.

EXAMPLE 99(126)

(Z)-2-(7-methoxy-3,3-dimethyl-3,4-dihydro-(2H)-isoquinolin-1-ylidene)-1-(4-((5-methylfuran-2-ylmethyl)carbamoyl)phenyl)ethan-1-one HPLC retention time (min.): 4.01; Mass (ESI, Pos. 20V): m/z 445 (M+H)$^+$.

EXAMPLE 99(127)

(Z)-2-(7-methoxy-3,3-dimethyl-3,4-dihydro-(2H)-isoquinolin-1-ylidene)-1-(4-(((1S)-1-hydroxymethyl-3-methylthiopropyl)carbamoyl)phenyl)ethan-1-one HPLC retention time (min.): 3.72; Mass (ESI, Pos. 20V): m/z 469 (M+H)$^+$.

EXAMPLE 99(128)

(Z)-2-(7-methoxy-3,3-dimethyl-3,4-dihydro-(2H)-isoquinolin-1-ylidene)-1-(4-((1,3-dioxaindan-5-yl)carbamoyl)phenyl)ethan-1-one HPLC retention time (min.): 4.05; Mass (ESI, Pos. 20V): m/z 471 (M+H)$^+$.

EXAMPLE 99(129)

(Z)-2-(7-methoxy-3,3-dimethyl-3,4-dihydro-(2H)-isoquinolin-1-ylidene)-1-(4-(4-(2-hydroxyethyl)piperazin-1-ylcarbonyl)phenyl)ethan-1-one HPLC retention time (min.): 3.24; Mass (ESI, Pos. 20V): m/z 464 (M+H)$^+$.

EXAMPLE 99(130)

(Z)-2-(7-methoxy-3,3-dimethyl-3,4-dihydro-(2H)-isoquinolin-1-ylidene)-1-(4-((quinolin-5-yl)carbamoyl)phenyl)ethan-1-one HPLC retention time (min.): 3.43; Mass (ESI, Pos. 20V): m/z 478 (M+H)$^+$.

EXAMPLE 99(131)

(Z)-2-(7-methoxy-3,3-dimethyl-3,4-dihydro-(2H)-isoquinolin-1-ylidene)-1-(4-((quinolin-6-yl)carbamoyl)phenyl)ethan-1-one HPLC retention time (min.): 3.52; Mass (ESI, Pos. 20V): m/z 478 (M+H)$^+$.

EXAMPLE 99(132)

(Z)-2-(7-methoxy-3,3-dimethyl-3,4-dihydro-(2H)-isoquinolin-1-ylidene)-1-(4-((3-cyanophenyl)carbamoyl)phenyl)ethan-1-one HPLC retention time (min.): 4.10; Mass (ESI, Pos. 20V): m/z 452 (M+H)$^+$.

EXAMPLE 99(133)

(Z)-2-(7-methoxy-3,3-dimethyl-3,4-dihydro-(2H)-isoquinolin-1-ylidene)-1-(4-((3-hydroxyphenyl)carbamoyl)phenyl)ethan-1-one HPLC retention time (min.): 3.85; Mass (ESI, Pos. 20V): m/z 443 (M+H)$^+$.

EXAMPLE 99(134)

(Z)-2-(7-methoxy-3,3-dimethyl-3,4-dihydro-(2H)-isoquinolin-1-ylidene)-1-(4-((4-hydroxyphenyl)carbamoyl)phenyl)ethan-1-one HPLC retention time (min.): 3.81; Mass (ESI, Pos. 20V): m/z 443 (M+H)$^+$.

EXAMPLE 99(135)

(Z)-2-(7-methoxy-3,3-dimethyl-3,4-dihydro-(2H)-isoquinolin-1-ylidene)-1-(4-((2-dimethylaminoethyl)carbamoyl)phenyl)ethan-1-one HPLC retention time (min.): 3.31; Mass (ESI, Pos. 20V): m/z 422 (M+H)$^+$.

EXAMPLE 99(136)

(Z)-2-(7-methoxy-3,3-dimethyl-3,4-dihydro-(2H)-isoquinolin-1-ylidene)-1-(4-((2-(2-hydroxyethoxy)ethyl)carbamoyl)phenyl)ethan-1-one HPLC retention time (min.): 3.50; Mass (ESI, Pos. 20V): m/z 439 (M+H)$^+$.

EXAMPLE 99(137)

(Z)-2-(7-methoxy-3,3-dimethyl-3,4-dihydro-(2H)-isoquinolin-1-ylidene)-1-(4-((2-hydroxyethyl)carbamoyl)phenyl)ethan-1-one HPLC retention time (min.): 3.50; Mass (ESI, Pos. 20V): m/z 395 (M+H)$^+$.

EXAMPLE 99(138)

(Z)-2-(7-methoxy-3,3-dimethyl-3,4-dihydro-(2H)-isoquinolin-1-ylidene)-1-(4-(2-propynylcarbamoyl)phenyl)ethan-1-one HPLC retention time (min.): 3.80; Mass (ESI, Pos. 20V): m/z 389 (M+H)$^+$.

EXAMPLE 99(139)

(Z)-2-(7-methoxy-3,3-dimethyl-3,4-dihydro-(2H)-isoquinolin-1-ylidene)-1-(4-(2-propenylcarbamoyl)phenyl)ethan-1-one HPLC retention time (min.): 3.84; Mass (ESI, Pos. 20V): m/z 391 (M+H)$^+$.

EXAMPLE 99(140)

(Z)-2-(7-methoxy-3,3-dimethyl-3,4-dihydro-(2H)-isoquinolin-1-ylidene)-1-(4-((3-methylbutyl)carbamoyl)phenyl)ethan-1-one HPLC retention time (min.): 4.11; Mass (ESI, Pos. 20V): m/z 421 (M+H)$^+$.

EXAMPLE 99(141)

(Z)-2-(7-methoxy-3,3-dimethyl-3,4-dihydro-(2H)-isoquinolin-1-ylidene)-1-(4-((3-dimethylaminopropyl)carbamoyl)phenyl)ethan-1-one HPLC retention time (min.): 3.32; Mass (ESI, Pos. 20V): m/z 436 (M+H)$^+$.

EXAMPLE 99(142)

(Z)-2-(7-methoxy-3,3-dimethyl-3,4-dihydro-(2H)-isoquinolin-1-ylidene)-1-(4-((3-ethoxypropyl)carbamoyl)phenyl)ethan-1-one HPLC retention time (min.): 3.88; Mass (ESI, Pos. 20V): m/z 437 (M+H)$^+$.

EXAMPLE 99(143)

(Z)-2-(7-methoxy-3,3-dimethyl-3,4-dihydro-(2H)-isoquinolin-1-ylidene)-1-(4-(N-methyl-N-(2,2-dimethoxyethyl)carbamoyl)phenyl)ethan-1-one HPLC retention time (min.): 3.83; Mass (ESI, Pos. 20V): m/z 453 (M+H)$^+$.

EXAMPLE 99(144)

(Z)-2-(7-methoxy-3,3-dimethyl-3,4-dihydro-(2H)-isoquinolin-1-ylidene)-1-(4-((N-methyl-N-hydroxycarbamoyl)phenyl)ethan-1-one HPLC retention time (min.): 3.73; Mass (ESI, Pos. 20V): m/z 381 (M+H)$^+$.

EXAMPLE 99(145)

(Z)-2-(7-methoxy-3,3-dimethyl-3,4-dihydro-(2H)-isoquinolin-1-ylidene)-1-(4-(bis(2-methoxyethyl)carbamoyl)phenyl)ethan-1-one HPLC retention time (min.): 3.84; Mass (ESI, Pos. 20V): m/z 467 (M+H)$^+$.

EXAMPLE 99(146)

(Z)-2-(7-methoxy-3,3-dimethyl-3,4-dihydro-(2H)-isoquinolin-1-ylidene)-1-(4-((3-chlorobenzyl)carbamoyl)phenyl)ethan-1-one HPLC retention time (min.): 4.16; Mass (ESI, Pos. 20V): m/z 475 (M+H)$^+$.

EXAMPLE 99(147)

(Z)-2-(7-methoxy-3,3-dimethyl-3,4-dihydro-(2H)-isoquinolin-1-ylidene)-1-(4-((4-acetylpiperazin-1-yl)carbonyl)phenyl)ethan-1-one HPLC retention time (min.): 3.56; Mass (ESI, Pos. 20V): m/z 462 (M+H)$^+$.

EXAMPLE 99(148)

(Z)-2-(7-methoxy-3,3-dimethyl-3,4-dihydro-(2H)-isoquinolin-1-ylidene)-1-(4-((2R)-2-hydroxymethylpyrrolidin-1-ylcarbonyl)phenyl)ethan-1-one HPLC retention time (min.): 3.66; Mass (ESI, Pos. 20V): m/z 435 (M+H)$^+$.

EXAMPLE 99(149)

(Z)-2-(7-methoxy-3,3-dimethyl-3,4-dihydro-(2H)-isoquinolin-1-ylidene)-1-(4-(2,6-dimethylmorpholin-1-ylcarbonyl)phenyl)ethan-1-one HPLC retention time (min.): 3.91; Mass (ESI, Pos. 20V): m/z 449 (M+H)$^+$.

EXAMPLE 99(150)

(Z)-2-(7-methoxy-3,3-dimethyl-3,4-dihydro-(2H)-isoquinolin-1-ylidene)-1-(4-(N-methyl-N-(2-(pyridin-2-yl)ethyl)carbamoyl)phenyl)ethan-1-one HPLC retention time (min.): 3.32; Mass (ESI, Pos. 20V): m/z 470 (M+H)$^+$.

EXAMPLE 99(151)

(Z)-2-(7-methoxy-3,3-dimethyl-3,4-dihydro-(2H)-isoquinolin-1-ylidene)-1-(4-(((2,2,2-trifluoroethyl)amino)carbamoyl)phenyl)ethan-1-one HPLC retention time (min.): 3.89; Mass (ESI, Pos. 20V): m/z 448 (M+H)$^+$.

EXAMPLE 99(152)

(Z)-2-(7-methoxy-3,3-dimethyl-3,4-dihydro-(2H)-isoquinolin-1-ylidene)-1-(4-((1,1-diethyl-2-propynyl)carbamoyl)phenyl)ethan-1-one HPLC retention time (min.): 4.16; Mass (ESI, Pos. 20V): m/z 445 (M+H)$^+$.

EXAMPLE 99(153)

(Z)-2-(7-methoxy-3,3-dimethyl-3,4-dihydro-(2H)-isoquinolin-1-ylidene)-1-(4-((pyridin-2-yl)carbamoyl)phenyl)ethan-1-one HPLC retention time (min.): 3.51; Mass (ESI, Pos. 20V): m/z 428 (M+H)$^+$.

EXAMPLE 99(154)

(Z)-2-(7-methoxy-3,3-dimethyl-3,4-dihydro-(2H)-isoquinolin-1-ylidene)-1-(4-((4-methoxyphenyl)carbamoyl)phenyl)ethan-1-one HPLC retention time (min.): 4.06; Mass (ESI, Pos. 20V): m/z 457 (M+H)$^+$.

EXAMPLE 99(155)

(Z)-2-(7-methoxy-3,3-dimethyl-3,4-dihydro-(2H)-isoquinolin-1-ylidene)-1-(4-((1H indazol-5-yl)carbamoyl)phenyl)ethan-1-one HPLC retention time (min.): 3.72; Mass (ESI, Pos. 20V): m/z 467 (M+H)$^+$.

EXAMPLE 99(156)

(Z)-2-(7-methoxy-3,3-dimethyl-3,4-dihydro-(2H)-isoquinolin-1-ylidene)-1-(4-((1-oxidopyridin-2-yl)carbamoyl)phenyl)ethan-1-one HPLC retention time (min.): 3.85; Mass (ESI, Pos. 20V): m/z 444 (M+H)$^+$.

EXAMPLE 99(157)

(Z)-2-(7-methoxy-3,3-dimethyl-3,4-dihydro-(2H)-isoquinolin-1-ylidene)-1-(4-((thiophen-2-ylmethyl)carbamoyl)phenyl)ethan-1-one HPLC retention time (min.): 4.01; Mass (ESI, Pos. 20V): m/z 447 (M+H)$^+$.

EXAMPLE 99(158)

(Z)-2-(7-methoxy-3,3-dimethyl-3,4-dihydro-(2H)-isoquinolin-1-ylidene)-1-(4-((2-ethylthioethyl)carbamoyl)phenyl)ethan-1-one HPLC retention time (min.): 4.00; Mass (ESI, Pos. 20V): m/z 439 (M+H)$^+$.

EXAMPLE 99(159)

(Z)-2-(7-methoxy-3,3-dimethyl-3,4-dihydro-(2H)-isoquinolin-1-ylidene)-1-(4-((2,2,2-trifluoroethyl)carbamoyl)phenyl)ethan-1-one HPLC retention time (min.): 3.95; Mass (ESI, Pos. 20V): m/z 433 (M+H)$^+$.

EXAMPLE 99(160)

(Z)-2-(7-methoxy-3,3-dimethyl-3,4-dihydro-(2H)-isoquinolin-1-ylidene)-1-(4-(N-methyl-N-(furan-2-ylmethyl)carbamoyl)phenyl)ethan-1-one HPLC retention time (min.): 3.99; Mass (ESI, Pos. 20V): m/z 445 (M+H)$^+$.

EXAMPLE 99(161)

(Z)-2-(7-methoxy-3,3-dimethyl-3,4-dihydro-(2H)-isoquinolin-1-ylidene)-1-(4-(N-propyl-N-(2-hydroxyethyl)carbamoyl)phenyl)ethan-1-one HPLC retention time (min.): 3.73; Mass (ESI, Pos. 20V): m/z 437 (M+H)$^+$.

EXAMPLE 99(162)

(Z)-2-(7-methoxy-3,3-dimethyl-3,4-dihydro-(2H)-isoquinolin-1-ylidene)-1-(4-(N-methyl-N-(2-methoxyethyl)carbamoyl)phenyl)ethan-1-one HPLC retention time (min.): 3.78; Mass (ESI, Pos. 20V): m/z 423 (M+H)$^+$.

EXAMPLE 99(163)

(Z)-2-(7-methoxy-3,3-dimethyl-3,4-dihydro-(2H)-isoquinolin-1-ylidene)-1-(4-((2-mercaptoethyl)carbamoyl)phenyl)ethan-1-one HPLC retention time (min.): 4.34; Mass (ESI, Pos. 20V): m/z 411 (M+H)$^+$.

EXAMPLE 99(164)

(Z)-2-(7-methoxy-3,3-dimethyl-3,4-dihydro-(2H)-isoquinolin-1-ylidene)-1-(4-(methylcarbamoyl)phenyl)ethan-1-one HPLC retention time (min.): 3.66; Mass (ESI, Pos. 20V): m/z 365 (M+H)$^+$.

FORMULATION EXAMPLES

FORMULATION EXAMPLE 1

The following components were admixed in a conventional method and punched out to obtain 100 tablets each containing 50 mg of the active ingredient.

| | |
|---|---|
| (Z)-2-(3,3-dimethyl-3,4-dihydro-(2H)-isoquinolin-1-ylidene)-1-cyclohexylethan-1-one | 5.0 g |
| Carboxymethyl cellulose calcium (disintegrating agent) | 0.2 g |
| Magnesium stearate (lubricant) | 0.1 g |
| Microcrystalline cellulose | 4.7 g |

FORMULATION EXAMPLE 2

The following components were admixed in a conventional method, and the solution was sterilized in a conventional method, placed at 5 ml into ampoules and freeze-dried

| | |
|---|---|
| (Z)-2-(3,3-dimethyl-3,4-dihydro-(2H)-isoquinolin-1-ylidene)-1-cyclohexylethan-1-one | 2.0 g |
| Mannitol | 20 g |
| Distilled water | 1000 ml | in a conventional method to thereby obtain 100 ampoules each containing 20 mg of the active ingredient.

The invention claimed is:

1. A compound of formula (I)

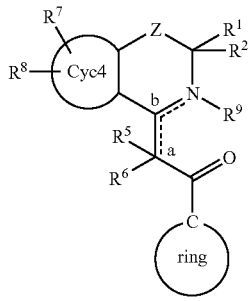

wherein $R^1$ and $R^2$ are each independently C1-8 alkyl;
Z is —$CR^3R^4$—;
$R^3$ and $R^4$ are each independently, (1) hydrogen atom, (2) C1-8 alkyl, (3) C1-8 alkoxy, or (4) hydroxy;
$R^5$ and $R^6$ are each independently, (1) hydrogen atom, or (2) C1-8 alkyl, or
$R^5$ and $R^6$ may be taken together with the carbon atom to which they are attached to form Cyc1;
Cyc1, which is represented by $R^1$ and $R^2$, $R^3$ and $R^4$, $R^5$ and $R^6$ is, each independently, (1) C3-10 cycloalkyl, or (2) 3-10 membered monocyclic heterorimg comprising 1-2 of heteroatom selected from oxygen, nitrogen and sulfur, and Cyc1 may be substituted with $R^{10}$;
$R^{10}$ is (1) C1-8 alkyl, (2) C1-8 alkoxy, (3) hydroxy, (4) —$COOR^{11}$, (5) oxo, (6) —$SO_2R^{12}$, or (7) —$COR^{13}$;
$R^{11}$ is hydrogen atom, or C1-8 alkyl;
$R^{12}$ and $R^{13}$ are (1) C1-8 alkyl, or (2) phenyl which may be substituted with C1-8 alkyl;
$R^7$ and $R^8$ are each independently, (1) hydrogen atom, (2) C1-8 alkyl, (3) C1-8 alkoxy, (4) hydroxy, (5) cyano, (6) halogen atom, (7) —$COOR^{14}$, (8) —$CONR^{15}R^{16}$, (9) Cyc2, (10) C2-8 alkenyl, (11) C2-8 alkynyl, (12) —$NR^{51}R^{52}$, (13) nitro, (14) formyl, (15) C2-8 acyl, (16) C1-8 alkyl substituted with hydroxy, C1-8 alkoxy, Cyc2, —$NR^{51}R^{52}$, or —$NR^{53}$-Cyc2, (17) —$NR^{54}COR^{55}$, (18) —$NR^{56}SO_2R^{57}$, (19) —$SO_2NR^{58}R^{59}$, (20) C2-8 alkenyl substituted with —$COOR^{14}$, (21) —CH=N—OH, (22) —(C1-8 alkylene)-$NR^{60}$—(C1-8 alkylene)-$R^{61}$, (23) C1-8 alkylthio, (24) C1-8 alkyl substituted with 1-3 of halogen atom, (25) C1-8 alkoxy substituted with 1-3 of halogen atom, (26) C1-8 alkoxy substituted with Cyc2, (27) —O-Cyc2, (28) —$OSO_2R^{65}$, or (29) —CH=N—$OR^{137}$;
$R^{14}$ is hydrogen atom, or C1-8 alkyl;
$R^{15}$ and $R^{16}$ are each independently hydrogen atom or C1-8 alkyl;
$R^{51}$ and $R^{52}$, $R^{58}$ and $R^{59}$ are each independently, hydrogen atom, or C1-8 alkyl;
$R^{53}$, $R^{54}$, $R^{56}$ and $R^{60}$ are each independently, hydrogen atom, or C1-8 alkyl;

$R^{55}$ is hydrogen atom, C1-8 alkyl, or C1-8 alkoxy;
$R^{57}$ is C1-8 alkyl;
$R^{61}$ is —$NR^{62}R^{63}$ or hydroxy;
$R^{62}$ and $R^{63}$ are each independently, hydrogen atom, or C1-8 alkyl;
$R^{65}$ is C1-8 alkyl;
$R^{137}$ is C1-8 alkyl;

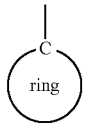

(hereinafter it is abbreviated as ring;) is Cyc2 wherein the group which attaches to carbonyl is carbon;
$R^7$ $R^8$ represented by ring are each independently (1) C3-15 mono-, bi- or tri-cyclic (fused or spiro) carboring, or (2) 3-15 membered mono-, bi- or tri-cyclic (fused or spiro) heterorimg comprising 1-4 of heteroatoms selected from oxygen, nitrogen, and sulfur, and Cyc2 represented by ring is C3-15 mono-, bi- or tri-cyclic (fused or spiro) carboring selected from the group consisting of cyclopropane, cyclobutane, cyclopentane, cyclohexane, cycloheptane, cyclooctane, cyclononane, cyclodecane, cycloundecane, cyclododecane, cyclotridodecane, bicyclo[3.3.0]octane, bicyclo[4.3.0]nonane, bicyclo[4.4.0]decane, spiro[4.4]nonane, spiro[4.5]decane, spiro[5.5]undecane, bicyclo[3.1.1]heptane, adamantan, noradamantan, and bicyclo[2.2.2]octane;
Cyc2 may be substituted with 1-5 of $R^{17}$ or $R^{17'}$;
$R^{17}$ is (1) C1-8 alkyl, (2) C2-8 alkenyl, (3) C2-8 alkynyl, (4) C1-8 alkoxy, (5) C1-8 alkylthio, (6) hydroxy, (7) halogen atom, (8) nitro, (9) oxo, (10) carboxy, (11) formyl, (12) cyano, (13) —$NR^{18}R^{19}$, (14) phenyl, phenoxy or phenylthio, which may be substituted with 1-5 of
$R^{20}$, (15) C1-8 alkyl, C2-8 alkenyl, C1-8 alkoxy or C1-8 alkylthio, which may be substituted with 1-5 of $R^{21}$ (16) —$OCOR^{22}$, (17) —$CONR^{23}R^{24}$, (18) —$SO_2NR^{25}R^{26}$ (19) —$COOR^{27}$, (20) —$COCOOR^{28}$, (21) —$COR^{29}$, (22) —$COCOR^{30}$, (23) —$NR^{31}COR^{32}$, (24) —$SO_2R^{33}$, (25) —$NR^{34}SO_2R^{35}$, or (26) —$SOR^{64}$;
$R^{18}$ and $R^{19}$, $R^{31}$ and $R^{34}$ are each independently, hydrogen atom, or C1-8 alkyl;
$R^{20}$ and $R^{21}$ are C1-8 alkyl, C1-8 alkoxy, hydroxy, halogen atom, nitro, or —$COOR^{36}$;
$R^{22}$ and $R^{64}$ are each independently C1-8 alkyl;
$R^{23}$, $R^{24}$, $R^{25}$ and $R^{26}$ are each independently hydrogen atom, C1-8 alkyl, or phenyl;
$R^{27}$, $R^{28}$, $R^{29}$, $R^{30}$, $R^{32}$, $R^{33}$ and $R^{35}$ are (1) C1-8 alkyl, (2) C2-8 alkenyl, (3) C1-8 alkyl substituted with 1-5 of $R^{37}$, (4) diphenylmethyl, (5) triphenylmethyl, (6) Cyc3, (7) C1-8 alkyl or C2-8 alkenyl substituted with Cyc3, (8) C1-8 alkyl substituted with —O-Cyc3, —S-Cyc3 or —$SO_2$-Cyc3;
$R^{36}$ is hydrogen atom, or C1-8 alkyl;
$R^{37}$ is C1-8 alkoxy, C1-8 alkylthio, benzyloxy, halogen atom, nitro or —$COOR^{38}$;
$R^{38}$ is hydrogen atom, C1-8 alkyl or C2-8 alkenyl;
Cyc3 is (1) C3-15 mono-, bi- or tri-cyclic (fused or spiro)carboring, or (2) 3-15 membered mono-, bi- or tri-cyclic (fused or spiro)heterorimg comprising 1-4 of heteroatom selected from oxygen, nitrogen and sulfur;

Cyc3 may be substituted with 1-5 of $R^{39}$;

$R^{39}$ is (1) C1-8 alkyl, (2) C2-8 alkenyl, (3) C2-8 alkynyl, (4) C1-8 alkoxy, (5) C1-8 alkylthio, (6) hydroxy, (7) halogen atom, (8) nitro, (9) oxo, (10) cyano, (11) benzyl, (12) benzyloxy, (13) C1-8 alkyl, C1-8 alkoxy or C1-8 alkylthio substituted with 1-5 of $R^{40}$, (14) phenyl, phenoxy, phenylthio, phenylsulfonyl or benzoyl which may be substituted with 1-5 of $R^{41}$, (15) —$OCOR^{42}$, (16) —$SO_2R^{43}$, (17) —$NR^{44}COR^{45}$, (18) —$SO_2NR^{46}R^{47}$, (19) —$COOR^{48}$, or (20) —$NR^{49}R^{50}$;

$R^{40}$ is halogen atom;

$R^{41}$ is C1-8 alkyl, C1-8 alkoxy, halogen atom, or nitro;

$R^{42}$, $R^{43}$ and $R^{45}$ are C1-8 alkyl;

$R^{44}$ and $R^{48}$ are hydrogen atom or C1-8 alkyl;

$R^{46}$ and $R^{47}$, $R^{49}$ and $R^{50}$ are each independently, hydrogen atom or C1-8 alkyl;

$R^{17'}$ is (1) SH, (2) —$NR^{66}CHO$, (3) Cyc5, (4) C1-8 alkyl, C2-8 alkenyl or C2-8 alkynyl substituted with Cyc5, (5) —CO—(NH-amino acid residue-CO)$_n$—OH, (6) —$NR^{67}CONR^{68}R^{69}$, (7) —$CONR^{70}NR^{71}R^{72}$, (8) —$CONR^{73}OR^{74}$, (9) —$CONR^{75}COR^{76}$, (10) —$C(S)NR^{77}R^{78}$, (11) —$CONR^{79}C(S)COOR^{80}$, (12) —$NR^{81}COCOOR^{82}$, (13) —$NR^{83}COOR^{84}$, (14) —$CONR^{85}C(S)R^{86}$, (15) —$OCOR^{87}$, (16) —$SOR^{88}$, (17) —$CONR^{89}R^{90}$, (18) —$SO_2NR^{91}R^{92}$, (19) —$COOR^{93}$, (20) —$COCOOR^{94}$, (21) —$COR^{95}$, (22) —$COCOR^{96}$, (23) —$NR^{97}COR^{98}$, (24) —$SO_2R^{99}$, (25) —$NR^{100}SO_2R^{101}$, or (26) —$NR^{102}R^{103}$;

n is an integer of 1 or 2;

$R^{66}$, $R^{73}$, $R^{75}$, $R^{77}$, $R^{79}$, $R^{81}$, $R^{83}$, $R^{85}$, $R^{97}$, $R^{100}$, and $R^{102}$ are hydrogen atom, or C1-8 alkyl;

$R^{67}$ and $R^{68}$, $R^{70}$ and $R^{71}$ are each independently, hydrogen atom, or C1-8 alkyl;

$R^{89}$ and $R^{91}$ are (1) hydrogen atom, (2) C1-8 alkyl, (3) phenyl, or (4) C1-8 alkyl substituted with cyano or C1-8 alkoxy;

$R^{103}$ is Cyc6;

$R^{69}$, $R^{72}$, $R^{74}$, $R^{76}$, $R^{78}$, $R^{80}$, $R^{82}$, $R^{84}$, $R^{86}$, $R^{87}$, $R^{88}$, $R^{90}$ and $R^{92}$ are (1) hydrogen atom, (2) C1-8 alkyl, (3) C2-8 alkenyl, (4) C2-8 alkynyl, (5) C1-8 alkyl substituted with 1-5 of $R^{104}$, (6) diphenylmethyl, (7) triphenylmethyl, (8) Cyc6, (9) C1-8 alkyl or C2-8 alkenyl substituted with Cyc6, or (10) C1-8 alkyl substituted with —O-Cyc6, —S-Cyc6 or —$SO_2$-Cyc6;

$R^{104}$ is (1) C1-8 alkoxy, (2) C1-8 alkylthio, (3) benzyloxy, (4) halogen atom, (5) nitro, (6) —$COOR^{105}$, (7) cyano, (8) —$NR^{106}R^{107}$, (9) —$NR^{108}COR^{109}$, (10) hydroxy, (11) SH, (12) —$SO_3H$, (13) —S(O)OH, (14) —$OSO_3H$, (15) C2-8 alkenyloxy, (16) C2-8 alkynyloxy, (17) —$COR^{110}$, (18) —$SO_2R^{111}$, or (19) C1-8 alkoxy or C1-8 alkylthio substituted with hydroxy;

$R^{105}$ is hydrogen atom, C1-8 alkyl, or C2-8 alkenyl;

$R^{106}$ and $R^{107}$ are each independently, hydrogen atom, or C1-8 alkyl;

$R^{108}$ is hydrogen atom, or C1-8 alkyl;

$R^{109}$ and $R^{111}$ are C1-8 alkyl;

$R^{110}$ is C1-8 alkyl, or halogen atom;

wherein $R^{82}$, $R^{84}$ and $R^{86}$ are not hydrogen atom;

wherein $R^{87}$ and $R^{88}$ are not hydrogen atom and C1-8 alkyl;

wherein $R^{90}$ and $R^{92}$ are not hydrogen atom, C1-8 alkyl or phenyl;

$R^{93}$, $R^{94}$, $R^{95}$, $R^{96}$, $R^{98}$, $R^{99}$ and $R^{101}$ are (1) C2-8 alkynyl, (2) C1-8 alkyl substituted with $R^{128}$ which may be substituted with 1-4 of $R^{129}$, (3) Cyc8, (4) C1-8 alkyl or C2-8 alkenyl substituted with Cyc8, or (5) C1-8 alkyl substituted with —O-Cyc8, —S-Cyc8 or —$SO_2$-Cyc8;

$R^{128}$ is (1) cyano, (2) —$NR^{106}R^{107}$, (3) —$NR^{108}COR^{109}$, (4) hydroxy, (5) SH, (6) —$SO_3H$, (7) —S(O)OH, (8) —$OSO_3H$, (9) C2-8 alkenyloxy, (10) C2-8 alkynyloxy, (11) —$COR^{110}$, (12) —$SO_2R^{111}$, or (13) C1-8 alkoxy or C1-8 alkylthio substituted with hydroxy;

$R^{129}$ has the same meaning as $R^{104}$;

Cyc5 and Cyc6 may be substituted with 1-5 of $R^{112}$;

$R^{112}$ is (1) C1-8 alkyl, (2) C2-8 alkenyl, (3) C2-8 alkynyl, (4) C1-8 alkoxy, (5) C1-8 alkylthio, (6) hydroxy, (7) halogen atom, (8) nitro, (9) oxo, (10) cyano, (11) benzyl, (12) benzyloxy, (13) C1-8 alkyl, C1-8 alkoxy or C1-8 alkylthio substituted with 1-5 of $R^{113}$, (14) phenyl, phenoxy, phenylthio or benzoyl, which may be substituted with 1-5 of $R^{114}$, (15) —$COR^{115}$, (16) —$SO_2R^{116}$, (17) —$NR^{117}COR^{118}$, (18) —$SO_2NR^{119}R^{120}$, (19) —$COOR^{121}$, (20) —$NR^{122}R^{123}$, (21) —$COR^{124}$, (22) —$CONR^{125}R^{126}$, (23) SH, (24) C1-8 alkyl substituted with hydroxy or —$NR^{127}$-benzoyl, or (25) Cyc7;

$R^{113}$ is halogen atom;

$R^{114}$ is C1-8 alkyl, C1-8 alkoxy, halogen atom, or nitro;

$R^{115}$, $R^{116}$ and $R^{118}$ are C1-8 alkyl;

$R^{117}$, $R^{121}$, $R^{124}$ and $R^{127}$ are hydrogen atom, or C1-8 alkyl;

$R^{119}$ and $R^{120}$, $R^{122}$ and $R^{123}$, $R^{125}$ and $R^{126}$ are each independently, hydrogen atom or C1-8 alkyl;

Cyc7 may be substituted with 1-5 group selected from (1) C1-8 alkyl, (2) C1-8 alkoxy, (3) halogen atom, or (4) nitro;

Cyc8 may be substituted with $R^{130}$, and it further may be substituted with 1-4 of $R^{131}$;

$R^{130}$ is (1) —$COR^{124}$, (2) —$CONR^{125}R^{126}$, (3) SH, (4) C1-8 alkyl substituted with hydroxy or —$NR^{127}$-benzoyl, or (5) Cyc7;

$R^{131}$ has the same meaning as $R^{112}$;

Cyc5, Cyc6, Cyc7 and Cyc8 are (1) C3-15 mono-, bi- or tri-cyclic (fused or spiro)carboring, or (2) 3-15 membered mono-, bi- or tri-cyclic (fused or spiro)heteroring comprising 1-4 of heteroatom selected from 1-4 of oxygen, nitrogen or sulfur;

wherein when $R^{17'}$ is Cyc5, Cyc5 is not phenyl which may be substituted with 1-5 selected from C1-8 alkyl, C1-8 alkoxy, hydroxy, halogen atom, nitro, —COOH, or —COO—(C1-8 alkyl);

wherein Cyc7 is not phenyl;

Cyc4 is benzo;

a
-----

(abbreviated as dashed line a hereafter;) and b
-----

(abbreviated as dashed line b hereafter;) are (1) a bond, or (2) a double bond;

$R^9$ (1) does not exist or (2) is hydrogen atom; wherein 1) when dashed line a is a bond, dashed line b is a double bond, and $R^9$ does not exist, 2) when dashed line a is a double bond, dashed line b is a bond, and $R^9$ is hydrogen atom and $R^6$ does not exist, and 3) 2-(3,3-dimethyl-3,4-dihydro-(2H)-isoquinolin-1-ylidene)-1-phenylethan-1-one is excluded, or a pharmacologically acceptable salt thereof.

2. The compound according to claim 1, in formula (I), wherein
(i) Z is —$CR^3R^4$— and at least either of $R^7$ or $R^8$ is (24) C1-8 alkyl substituted with 1-3 of halogen atom, (25) C1-8 alkoxy substituted with 1-3 of halogen atom, (26) C1-8 alkoxy substituted with Cyc2, (27) —O-Cyc2, (28) —$OSO_2R^{65}$, or (29) —CH=N—$OR^{137}$, or
(ii) Z is —$CR^3R^4$— and at least one Cyc2 which is represented by $R^7$, $R^8$ or ring is substituted with at least one $R^{17'}$ or a pharmacologically acceptable salt thereof.

3. The compound according to claim 1, which is represented by formula (I')

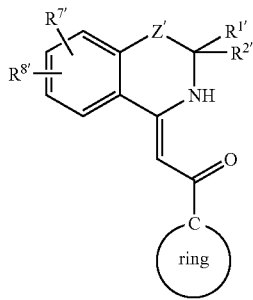

(I')

wherein, $R^1$ and $R^2$ are each independently, C1-8 alkyl, Z' is —$CR^{3'}R^{4'}$—, $R^{3'}$ and $R^{4'}$ are each independently, hydrogen atom, C1-8 alkyl, or hydroxy,
$R^{7'}$ and $R^{8'}$ are each independently, hydrogen atom, C1-8 alkyl, C1-8 alkoxy, hydroxy, cyano, halogen atom, —$COOR^{14}$, —$CONR^{15}R^{16}$, Cyc2, —$NR^{51}R^{52}$, formyl, hydroxy or C1-8 alkyl substituted with C1-8 alkoxy, or —$SO_2NR^{58}R^{59}$,
Cyc2 represented by

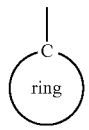

may be substituted with 1-5 of $R^{17''}$,
$R^{17''}$ is C1-8 alkyl, C1-8 alkoxy, hydroxy, halogen atom, nitro, oxo, (10) carboxy, (11) formyl, (12) cyano, (13) —$NR^{18}R^{19}$, (15) C1-8 alkyl substituted with 1-5 of $R^{21}$, (17) —$CONR^{23}R^{24}$, (19) —$COOR^{27}$, (21) —$COR^{29}$, (23) —$NR^{31}COR^{32}$, or (25) —$NR^{34}SO_2R^{35}$ and the other symbols have the same meaning as claim 1, or a pharmacologically acceptable salt thereof.

4. The compound according to claim 2, which is (Z)-2-(7-bromomethyl-3,3-dimethyl-3,4-dihydro-(2H)-isoquinolin-1-ylidene)-1-(adamantan-1-yl)ethan-1-one, or a pharmacologically acceptable salt thereof.

5. The compound according to claim 3, which is
(1) (Z)-2-(7-t-butylsulfamoyl-3,3-dimethyl-3,4-dihydro-(2H)-isoquinolin-1-ylidene)-1-(adamantan-1-yl)ethan-1-one,
(2) (Z)-2-(7-hydroxy-3,3-dimethyl-3,4-dihydro-(2H)-isoquinolin-1-ylidene)-1-cycloheptylethan-1-one,
(3) (Z)-2-(6-hydroxy-3,3-dimethyl-3,4-dihydro-(2H)-isoquinolin-1-ylidene)-1-cyclohexylethan-1-one,
(4) (Z)-2-(6-hydroxy-3,3-dimethyl-3,4-dihydro-(2H)-isoquinolin-1-ylidene)-1-cycloheptylethan-1-one,
(5) (Z)-2-(6-hydroxy-3,3-dimethyl-3,4-dihydro-(2H)-isoquinolin-1-ylidene)-1-(adamantan-1-yl)ethan-1-one,
(6) (Z)-2-(7-hydroxy-3,3,6-trimethyl-3,4-dihydro-(2H)-isoquinolin-1-ylidene)-1-(adamantan-1-yl)ethan-1-one,
(7) (Z)-2-(7-hydroxy-3,3,6-trimethyl-3,4-dihydro-(2H)-isoquinolin-1-ylidene)-1-cyclohexylethan-1-one,
(8) (Z)-2-(7-hydroxy-3,3,6-trimethyl-3,4-dihydro-(2H)-isoquinolin-1-ylidene)-1-cycloheptylethan-1-one,
(9) (Z)-2-(7-(1-hydroxy-1-methylethyl)-6-methoxy-3,3-dimethyl-3,4-dihydro-(2H)-isoquinolin-1-ylidene)-1-cycloheptylethan-1-one,
(10) (Z)-2-(7-(1-hydroxyethyl)-6-methoxy-3,3-dimethyl-3,4-dihydro-(2H)-isoquinolin-1-ylidene)-1-cycloheptylethan-1-one,
(11) (Z)-2-(7-methoxymethyl-3,3-dimethyl-3,4-dihydro-(2H)-isoquinolin-1-ylidene)-1-(adamantan-1-yl)ethan-1-one, or
(12) (Z)-2-(7-sulfamoyl-3,3-dimethyl-3,4-dihydro-(2H)-isoquinolin-1-ylidene)-1-(adamantan-1-yl)ethan-1-one, or a pharmacologically acceptable salt thereof.
or a pharmacologically acceptable salt thereof.

6. A pharmaceutical composition comprising the compound according to claim 1 or a pharmacologically acceptable salt thereof as active ingredient and a pharmaceutically acceptable carrier.

7. A pharmaceutical composition comprising the compound according to claim 2, or a pharmacologically acceptable salt as active ingredient and a pharmaceutically acceptable carrier.

8. A method for treating allergic diseases, rejection of an organ transplant, graft versus host disease (GVHD), osteoporosis, bone fracture, re-stenosis, arteriosclerosis, obesity, ischemic reperfusion injury, or depression, which comprises administering the compound according to claim 1 or a pharmacologically acceptable salt thereof.

9. A method for treating asthma, allergy rhinitis, atopic dermatitis, rheumatism, postoperative pain and/or carcinomatous pain, which comprises administering the compound according to claim 2, or a pharmacologically acceptable salt as active ingredient.

* * * * *